(12) United States Patent
Dorn, II et al.

(10) Patent No.: US 10,844,023 B2
(45) Date of Patent: Nov. 24, 2020

(54) SMALL MOLECULE REGULATORS OF MITOCHONDRIAL FUSION AND METHODS OF USE THEREOF

(71) Applicant: Washington University, St. Louis, MO (US)

(72) Inventors: Gerald W. Dorn, II, St. Louis, MO (US); James Janetka, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 0 days.

(21) Appl. No.: 16/152,172

(22) Filed: Oct. 4, 2018

(65) Prior Publication Data

US 2019/0169138 A1 Jun. 6, 2019

Related U.S. Application Data

(63) Continuation of application No. PCT/US2018/028514, filed on Apr. 20, 2018.

(60) Provisional application No. 62/488,787, filed on Apr. 23, 2017, provisional application No. 62/584,515, filed on Nov. 10, 2017.

(51) Int. Cl.
*A61K 31/4196* (2006.01)
*C07D 249/12* (2006.01)
*C07D 405/12* (2006.01)
*A61P 25/28* (2006.01)

(52) U.S. Cl.
CPC ............ *C07D 249/12* (2013.01); *A61P 25/28* (2018.01); *C07D 405/12* (2013.01)

(58) Field of Classification Search
CPC ............ A61K 31/4196; C07D 249/12; C07D 405/12
USPC ................. 514/384; 548/264.4, 267.6, 269.4
See application file for complete search history.

(56) References Cited

U.S. PATENT DOCUMENTS

| | | | |
|---|---|---|---|
| 5,707,804 | A | 1/1998 | Mathies et al. |
| 5,728,528 | A | 3/1998 | Mathies et al. |
| 5,853,992 | A | 12/1998 | Glazer et al. |
| 5,869,255 | A | 2/1999 | Mathies et al. |
| 9,708,411 | B2 | 7/2017 | Shi |
| 2007/0021606 | A1 | 1/2007 | Egle et al. |
| 2008/0267942 | A1 | 10/2008 | Boyle et al. |
| 2011/0275670 | A1 | 11/2011 | Chapman et al. |
| 2012/0141527 | A1 | 6/2012 | Walensky et al. |

FOREIGN PATENT DOCUMENTS

| | | | | |
|---|---|---|---|---|
| WO | WO-9118885 | A1 * | 12/1991 | ........... C07D 233/64 |
| WO | 2005051974 | A2 | 6/2005 | |
| WO | 2009114700 | A2 | 9/2009 | |
| WO | 2015121461 | A1 | 8/2015 | |
| WO | 2018057648 | A1 | 3/2018 | |
| WO | 2018200323 | A1 | 11/2018 | |

OTHER PUBLICATIONS

Cardullo, R. et al., "Detection of nucleic acid hybridization by nonradiative fluorescence resonance energy transfer," Proc. Natl. Acad. Sci. USA, Dec. 1988, pp. 8790-8794, vol. 85.
Dillon, C. et al., "RNAI as an Experimental and Therapeutic Tool to Study and Regulate Physiological and Disease Processes," Annu. Rev. Physiol., 2005, pp. 147-173, vol. 67.
Dykxhoorn, D. et al., "The Silent Revolution: RNA Interference as Basic Biology, Research Tool, and Therapeutic," Annu. Rev. Med., 2005, pp. 401-423, vol. 56.
Franco, A. et al., "Correcting mitochondrial fusion by manipulating mitofusin conformations," HHS Public Access, Author Manuscript, Feb. 17, 2017, pp. 1-26, published in final form as: Nature, Dec. 1, 2016, pp. 74-79, vol. 540, No. 7631.
Ghadessy, F. et al., "Directed evolution of polymerase function by compartmentalized self-replication," PNAS, Apr. 10, 2001, pp. 4552-4557, vol. 98, No. 8.
Helene, C. et al., "Control of Gene Expression by Triple Helix-Forming Oligonucleotides. The Antigene Strategy," Ann. N.Y. Acad. Sci., Oct. 1992, pp. 27-36, vol. 660, No. 1.
Huang, P. et al., "Control of Mitochondrial Morphology Through Differential Interactions of Mitochondrial Fusion and Fission Proteins," PLoS ONE, May 2011, pp. 1-14, vol. 6, No. 5, e20655.
International Search Report and Written Opinion dated Aug. 23, 2018, from related PCT Application No. PCT/US2018/028514; 12 pgs.
Irwin, J. et al., "Zinc—A Free Database of Commercially Available Compounds for Virtual Screening," J. Chem. Inf. Model., 2005, pp. 177-182, vol. 45.
Jager, M. et al., "Site-specific labeling of proteins for single-molecule FRET by combining chemical and enzymatic modification," Protein Sci., 2006, pp. 640-646, vol. 15, Cold Spring Harbor Laboratory Press.
Jager, M. et al., "Protein-protein interactions as a tool for site-specific labeling of proteins," Protein Sci., 2005, pp. 2059-2068, vol. 14, Cold Spring Harbor Laboratory Press.
Koshiba, T. et al., "Structural Basis of Mitochondrial Tethering by Mitofusin Complexes," Sci., Aug. 6, 2004, pp. 858-862, vol. 305, No. 5685.

(Continued)

*Primary Examiner* — Matthew P Coughlin
*Assistant Examiner* — Sagar Patel
(74) *Attorney, Agent, or Firm* — Polsinelli PC

(57) ABSTRACT

Compositions comprising small molecule mitofusin agonists are described. The mitofusin modulating agents are useful for treating diseases or disorders associated with a mitochondria-associated disease, disorder, or condition such as diseases or disorders associated with mitofusin 1 (Mfn1) and/or mitofusin 2 (Mfn2), or mitochondrial dysfunction. Methods of treatment, pharmaceutical formulations, and screening methods for identifying compounds that regulate mitochondrial function are also described.

4 Claims, 125 Drawing Sheets

Specification includes a Sequence Listing.

(56) References Cited

OTHER PUBLICATIONS

Lee, J. et al., "Aptamer therapeutics advance," Curr. Opin. Chem. Biol., Jun. 2006, pp. 282-289, vol. 10, No. 3.
Link, A. et al., "Beyond toothpicks: new methods for isolating mutant bacteria," Nat. Rev. Microbiol., Sep. 2007, pp. 680-688, vol. 5, No. 9.
Lipinski, C., "Drug-like properties and the causes of poor solubility and poor permeability," J. Pharm. Tox. Methods, 2000, pp. 235-249, vol. 44, Elsevier.
Low, H. et al., "A bacterial dynamin-like protein," Nature, Dec. 7, 2006, pp. 766-769, vol. 444, Nature Publishing Group.
Maher, L., "DNA Triple-Helix Formation: An Approach to Artificial Gene Repressors?," BioEssays, Dec. 1992, pp. 807-815, vol. 14, No. 12.
Mergny, J-L. et al., "Fluorescence energy transfer as a probe for nucleic acid structures and sequences," Nucleic Acid Res., 1994, pp. 920-928, vol. 22, No. 6, Oxford University Press.
Protein Data Bank ID No. 2J69, "Bacterial dynamin-like protein BDLP," Sep. 26, 2006; 4 pgs.
PubChem CID14434744, Feb. 9, 2007, pp. 1-14, retrieved from: https://pubchem.ncbi.nlm.nih.gov/compound/14434744.
PubChem CID21468123, Dec. 5, 2007, pp. 1-14, retrieved from: https://pubchem.ncbi.nlm.nih.gov/compound/21468123.
PubChem CID60645332, Oct. 18, 2012, pp. 1-14, retrieved from: https://pubchem.ncbi.nlm.nih.gov/compound/60645332.
PubChem CID8808146, Feb. 12, 2015, pp. 1-12, retrieved from: https://pubchem.ncbi.nlm.nih.gov/compound/8808146.
Reynolds, A. et al., "Rational siRNA design for RNA interference," Nat. Biotechnol., Mar. 2004, pp. 326-330, vol. 22, No. 3, Nature Publishing Group.
Rocha, A. et al., "MFN2 agonists reverse mitochondrial defects in preclinical models of Charco-Marie-Tooth disease type 2A," Sci., Apr. 20, 2018, pp. 336-341, vol. 360, No. 6386.
Sagner, G. et al., "Rapid filter assay for the detection of DNA polymerase activity: direct identification of the gene for the DNA polymerase from Thermus aquaticus," Gene, 1991, pp. 119-123, vol. 97, No. 1, Elsevier.
Studier, W., "Protein production by auto-induction in high-density cultures," Protein Expr. Purif., 2005, pp. 207-234, vol. 41, Elsevier Inc.
Zacharioudakis, E. et al., "Direct Small Molecule Activation Mitofusins," bioRxiv, The Preprint Server for Biology, Apr. 2018, pp. 1-30, doi: https://doi.org/10.1101/301713.
International Search Report and Written Opinion dated Mar. 18, 2019 from related PCT Application No. PCT/US2018/060177; 15 pgs.
PubChem, Substance Record for SID 345345044, Oct. 9, 2017, 5 pgs.

\* cited by examiner

Compound B from vendor

Compound B after purification

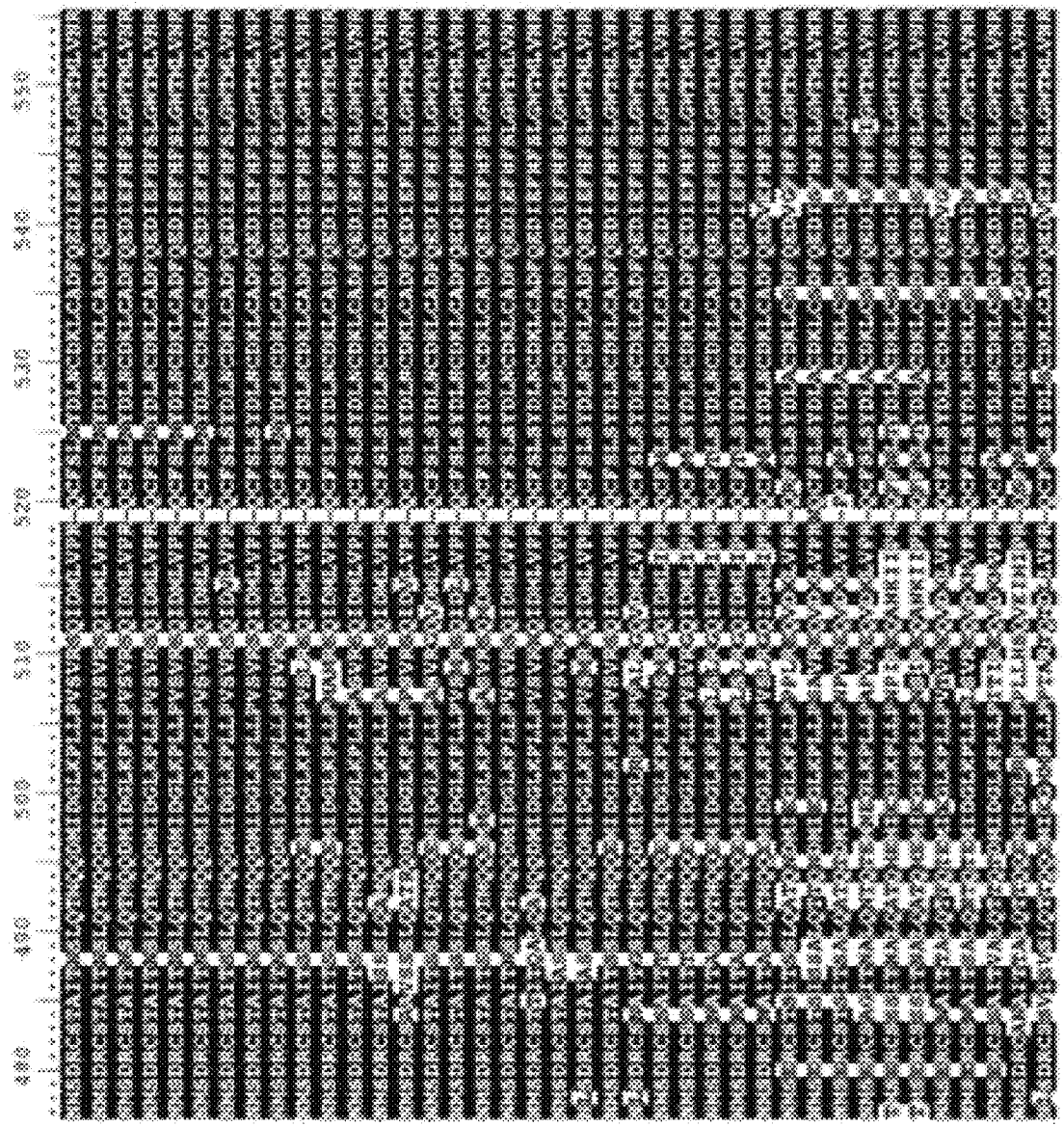

FIG. 13J

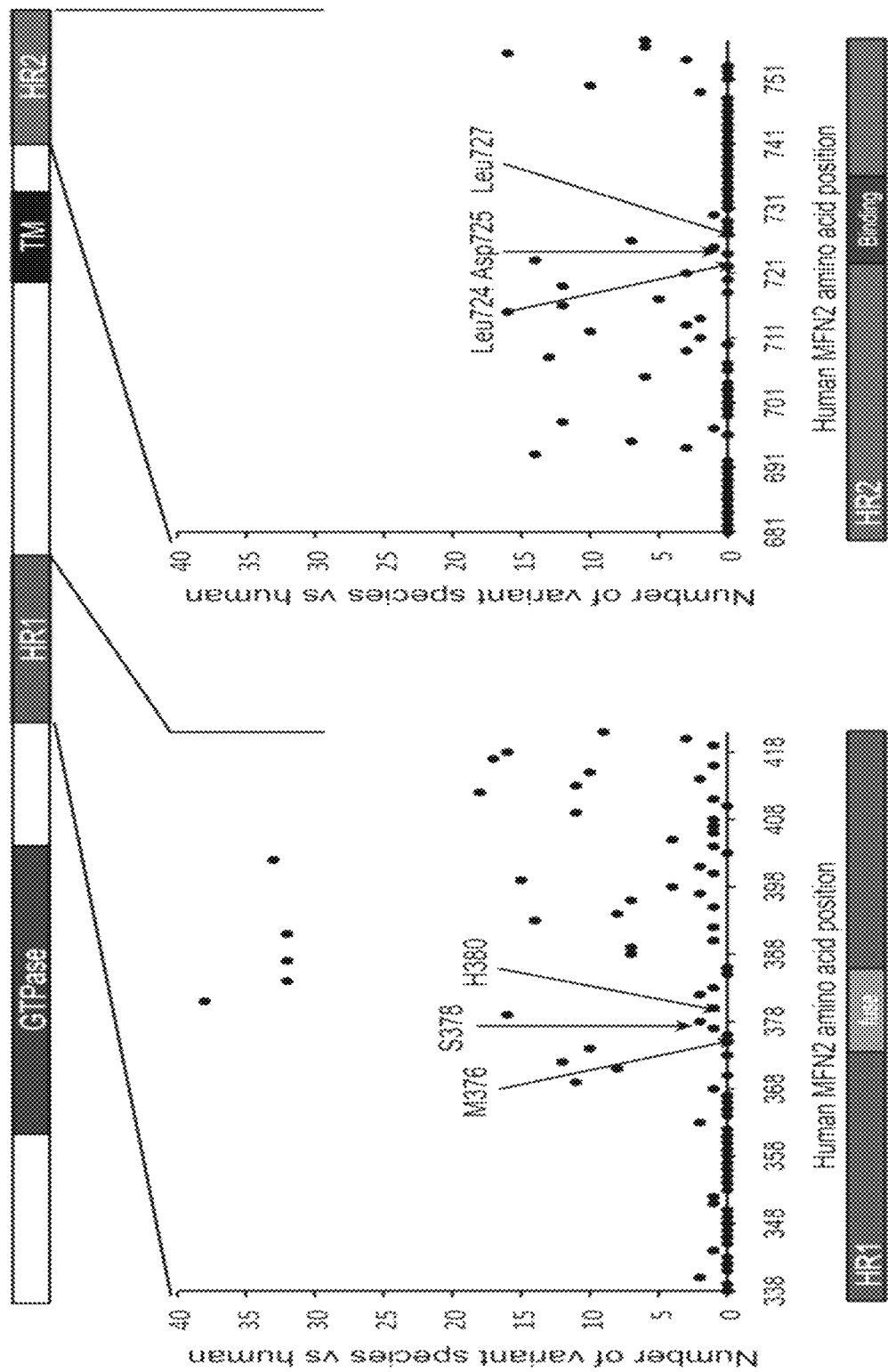

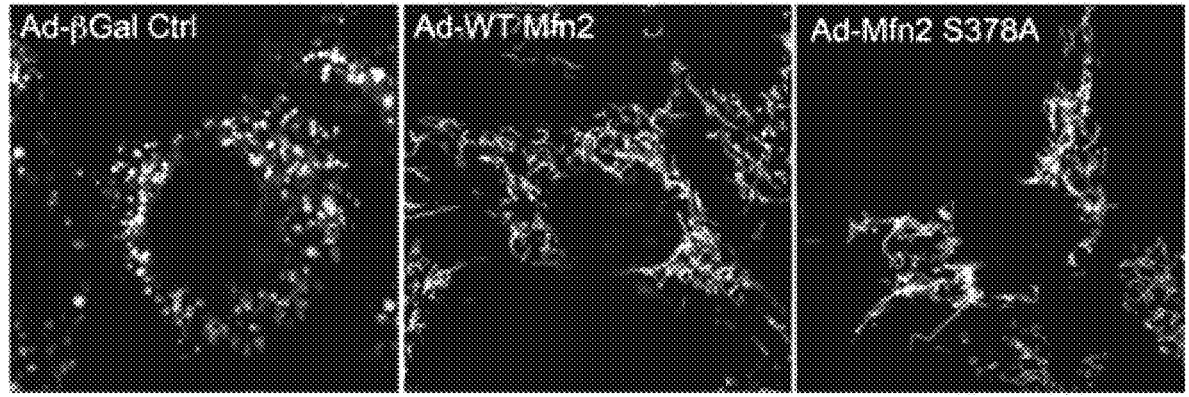
FIG. 18A  FIG. 18B  FIG. 18C
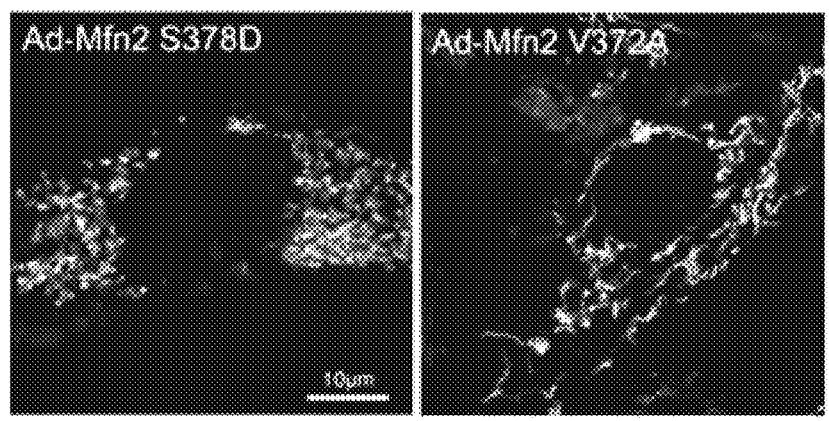
FIG. 18D  FIG. 18E

Regeneurin-S/Chimera B-A/I

| | Aug-17 | Nov-17 | Feb-18 |
|---|---|---|---|
| Molecular weight | 399.6 g/mol | | |
| Solubility | 157 µM | 67 µM | |
| Plasma protein binding | | | |
| human | 97.80% | 98.20% | 98.8% |
| CD-1 mouse | 93.80% | 92.10% | 96.2% |
| Plasma stability [120 min] | | | |
| human | 78.70% | 94.60% | 92.1% |
| mouse | 78% | 93.00% | 96.7% |
| Microsome stability (T1/2) | | | |
| human liver | 2.9 min | 3.1 min | 2.6 min |
| rat liver | | | 1.9 min |
| mouse liver | 0.8 min | 0.7 min | 1.2 min |

*Regeneurin* backbone S metabolites

Mitochondrial (m) fusion EC50
Liver (h) microsome T1/2
Plasma (h) protein % bound

*Regeneurin* synthetic backbone substitutions

Fusogenin series: 2 methyl, 3 phenyl triazol ring

Fusogenin-1
T1/2 43.2 min
87.5% bound

Fusogenin-3
T1/2 >145 min
26.8% bound

Fusogenin-4
T1/2 >145 min
45.0% bound

FIG. 55

SEQUENCE LISTING

<160> NUMBER OF SEQ ID NOS: 28

<210> SEQ ID NO 1
<211> LENGTH: 36
<212> TYPE: PRT
<213> ORGANISM: Artificial Sequence
<220> FEATURE:
<223> OTHER INFORMATION: Synthetic peptide

<400> SEQUENCE: 1

His His His His His His Gly Gly Gly Gly Ala Ala Met Asn Lys Lys
1               5                   10                  15

Ile Glu Val Leu Asp Ser Leu Gln Ser Lys Ala Lys Leu Leu Arg Asn
            20                  25                  30

Lys Ala Gly Gly
        35

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Gly Gly Gly Gly Ala Val Arg Gly Ile Met Asp Asp Leu His Met Ala
1               5                   10                  15

Ala Arg Gly Gly
        20

<210> SEQ ID NO 3
<211> LENGTH: 31
<212> TYPE: PRT
<213> ORGANISM: Artificial Sequence
<220> FEATURE:
<223> OTHER INFORMATION: Synthetic peptide

<400> SEQUENCE: 3

His His His His His His Gly Gly Gly Gly Leu His Ala Phe Thr Gly
1               5                   10                  15

Ser Leu Glu Gln Gln Val Gln His Ser Cys Asn Ser Gly Gly Gly
            20                  25                  30

<210> SEQ ID NO 4
<211> LENGTH: 22
<212> TYPE: PRT
<213> ORGANISM: Artificial Sequence
<220> FEATURE:
<223> OTHER INFORMATION: Synthetic peptide

<400> SEQUENCE: 4

Gly Gly Gly Gly Lys Gln Leu Glu Leu Leu Ala Gln Asp Tyr Lys Leu
1               5                   10                  15

Arg Ile Lys Gln Gly Gly
            20

<210> SEQ ID NO 5
<211> LENGTH: 741
<212> TYPE: PRT
<213> ORGANISM: Homo sapiens

<400> SEQUENCE: 5

Met Ala Glu Pro Val Ser Pro Leu Lys His Phe Val Leu Ala Lys Lys
1               5                   10                  15

```
Ala Ile Thr Ala Ile Phe Asp Gln Leu Leu Glu Phe Val Thr Glu Gly
            20                  25                  30

Ser His Phe Val Glu Ala Thr Tyr Lys Asn Pro Glu Leu Asp Arg Ile
        35                  40                  45

Ala Thr Glu Asp Asp Leu Val Glu Met Gln Gly Tyr Lys Asp Lys Leu
    50                  55                  60

Ser Ile Ile Gly Glu Val Leu Ser Arg Arg His Met Lys Val Ala Phe
65                  70                  75                  80

Phe Gly Arg Thr Ser Ser Gly Lys Ser Ser Val Ile Asn Ala Met Leu
                85                  90                  95

Trp Asp Lys Val Leu Pro Ser Gly Ile Gly His Ile Thr Asn Cys Phe
            100                 105                 110

Leu Ser Val Glu Gly Thr Asp Gly Asp Lys Ala Tyr Leu Met Thr Glu
        115                 120                 125

Gly Ser Asp Glu Lys Lys Ser Val Lys Thr Val Asn Gln Leu Ala His
    130                 135                 140

Ala Leu His Met Asp Lys Asp Leu Lys Ala Gly Cys Leu Val Arg Val
145                 150                 155                 160

Phe Trp Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ser Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Arg Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His
                245                 250                 255

Met Glu Arg Cys Leu His Phe Leu Val Glu Glu Leu Lys Val Val Asn
            260                 265                 270

Ala Leu Glu Ala Gln Asn Arg Ile Phe Phe Val Ser Ala Lys Glu Val
        275                 280                 285

Leu Ser Ala Arg Lys Gln Lys Ala Gln Gly Met Pro Glu Ser Gly Val
    290                 295                 300

Ala Leu Ala Glu Gly Phe His Ala Arg Leu Gln Glu Phe Gln Asn Phe
305                 310                 315                 320

Glu Gln Ile Phe Glu Glu Cys Ile Ser Gln Ser Ala Val Lys Thr Lys
                325                 330                 335

Phe Glu Gln His Thr Ile Arg Ala Lys Gln Ile Leu Ala Thr Val Lys
            340                 345                 350

Asn Ile Met Asp Ser Val Asn Leu Ala Ala Glu Asp Lys Arg His Tyr
        355                 360                 365

Ser Val Glu Glu Arg Glu Asp Gln Ile Asp Arg Leu Asp Phe Ile Arg
    370                 375                 380

Asn Gln Met Asn Leu Leu Thr Leu Asp Val Lys Lys Lys Ile Lys Glu
385                 390                 395                 400

Val Thr Glu Glu Val Ala Asn Lys Val Ser Cys Ala Met Thr Asp Glu
                405                 410                 415

Ile Cys Arg Leu Ser Val Leu Val Asp Glu Phe Cys Ser Glu Phe His
            420                 425                 430
```

Pro Asn Pro Asp Val Leu Lys Ile Tyr Lys Ser Glu Leu Asn Lys His
        435                 440                 445

Ile Glu Asp Gly Met Gly Arg Asn Leu Ala Asp Arg Cys Thr Asp Glu
    450                 455                 460

Val Asn Ala Leu Val Leu Gln Thr Gln Gln Glu Ile Ile Glu Asn Leu
465                 470                 475                 480

Lys Pro Leu Leu Pro Ala Gly Ile Gln Asp Lys Leu His Thr Leu Ile
                485                 490                 495

Pro Cys Lys Lys Phe Asp Leu Ser Tyr Asn Leu Asn Tyr His Lys Leu
            500                 505                 510

Cys Ser Asp Phe Gln Glu Asp Ile Val Phe Arg Phe Ser Leu Gly Trp
        515                 520                 525

Ser Ser Leu Val His Arg Phe Leu Gly Pro Arg Asn Ala Gln Arg Val
    530                 535                 540

Leu Leu Gly Leu Ser Glu Pro Ile Phe Gln Leu Pro Arg Ser Leu Ala
545                 550                 555                 560

Ser Thr Pro Thr Ala Pro Thr Thr Pro Ala Thr Pro Asp Asn Ala Ser
                565                 570                 575

Gln Glu Glu Leu Met Ile Thr Leu Val Thr Gly Leu Ala Ser Val Thr
            580                 585                 590

Ser Arg Thr Ser Met Gly Ile Ile Val Gly Gly Val Ile Trp Lys
        595                 600                 605

Thr Ile Gly Trp Lys Leu Leu Ser Val Ser Leu Thr Met Tyr Gly Ala
    610                 615                 620

Leu Tyr Leu Tyr Glu Arg Leu Ser Trp Thr Thr His Ala Lys Glu Arg
625                 630                 635                 640

Ala Phe Lys Gln Gln Phe Val Asn Tyr Ala Thr Glu Lys Leu Arg Met
                645                 650                 655

Ile Val Ser Ser Thr Ser Ala Asn Cys Ser His Gln Val Lys Gln Gln
            660                 665                 670

Ile Ala Thr Thr Phe Ala Arg Leu Cys Gln Gln Val Asp Ile Thr Gln
        675                 680                 685

Lys Gln Leu Glu Glu Glu Ile Ala Arg Leu Pro Lys Glu Ile Asp Gln
    690                 695                 700

Leu Glu Lys Ile Gln Asn Asn Ser Lys Leu Leu Arg Asn Lys Ala Val
705                 710                 715                 720

Gln Leu Glu Asn Glu Leu Glu Asn Phe Thr Lys Gln Phe Leu Pro Ser
                725                 730                 735

Ser Asn Glu Glu Ser
            740

<210> SEQ ID NO 6
<211> LENGTH: 757
<212> TYPE: PRT
<213> ORGANISM: Homo sapiens

<400> SEQUENCE: 6

Met Ser Leu Leu Phe Ser Arg Cys Asn Ser Ile Val Thr Val Lys Lys
1               5                   10                  15

Asn Lys Arg His Met Ala Glu Val Asn Ala Ser Pro Leu Lys His Phe
            20                  25                  30

Val Thr Ala Lys Lys Lys Ile Asn Gly Ile Phe Glu Gln Leu Gly Ala
        35                  40                  45

Tyr Ile Gln Glu Ser Ala Thr Phe Leu Glu Asp Thr Tyr Arg Asn Ala
    50                  55                  60

```
Glu Leu Asp Pro Val Thr Thr Glu Glu Gln Val Leu Asp Val Lys Gly
 65                  70                  75                  80

Tyr Leu Ser Lys Val Arg Gly Ile Ser Glu Val Leu Ala Arg Arg His
                 85                  90                  95

Met Lys Val Ala Phe Phe Gly Arg Thr Ser Asn Gly Lys Ser Thr Val
            100                 105                 110

Ile Asn Ala Met Leu Trp Asp Lys Val Leu Pro Ser Gly Ile Gly His
        115                 120                 125

Thr Thr Asn Cys Phe Leu Arg Val Glu Gly Thr Asp Gly His Glu Ala
130                 135                 140

Phe Leu Leu Thr Glu Gly Ser Glu Glu Lys Arg Ser Ala Lys Thr Val
145                 150                 155                 160

Asn Gln Leu Ala His Ala Leu His Gln Asp Lys Gln Leu His Ala Gly
                165                 170                 175

Ser Leu Val Ser Val Met Trp Pro Asn Ser Lys Cys Pro Leu Leu Lys
            180                 185                 190

Asp Asp Leu Val Leu Met Asp Ser Pro Gly Ile Asp Val Thr Thr Glu
        195                 200                 205

Leu Asp Ser Trp Ile Asp Lys Phe Cys Leu Asp Ala Asp Val Phe Val
210                 215                 220

Leu Val Ala Asn Ser Glu Ser Thr Leu Met Gln Thr Glu Lys His Phe
225                 230                 235                 240

Phe His Lys Val Ser Glu Arg Leu Ser Arg Pro Asn Ile Phe Ile Leu
                245                 250                 255

Asn Asn Arg Trp Asp Ala Ser Ala Ser Glu Pro Glu Tyr Met Glu Glu
            260                 265                 270

Val Arg Arg Gln His Met Glu Arg Cys Thr Ser Phe Leu Val Asp Glu
        275                 280                 285

Leu Gly Val Val Asp Arg Ser Gln Ala Gly Asp Arg Ile Phe Phe Val
290                 295                 300

Ser Ala Lys Glu Val Leu Asn Ala Arg Ile Gln Lys Ala Gln Gly Met
305                 310                 315                 320

Pro Glu Gly Gly Gly Ala Leu Ala Glu Gly Phe Gln Val Arg Met Phe
                325                 330                 335

Glu Phe Gln Asn Phe Glu Arg Arg Phe Glu Glu Cys Ile Ser Gln Ser
            340                 345                 350

Ala Val Lys Thr Lys Phe Glu Gln His Thr Val Arg Ala Lys Gln Ile
        355                 360                 365

Ala Glu Ala Val Arg Leu Ile Met Asp Ser Leu His Met Ala Ala Arg
370                 375                 380

Glu Gln Gln Val Tyr Cys Glu Glu Met Arg Glu Glu Arg Gln Asp Arg
385                 390                 395                 400

Leu Lys Phe Ile Asp Lys Gln Leu Glu Leu Leu Ala Gln Asp Tyr Lys
                405                 410                 415

Leu Arg Ile Lys Gln Ile Thr Glu Glu Val Glu Arg Gln Val Ser Thr
            420                 425                 430

Ala Met Ala Glu Glu Ile Arg Arg Leu Ser Val Leu Val Asp Asp Tyr
        435                 440                 445

Gln Met Asp Phe His Pro Ser Pro Val Val Leu Lys Val Tyr Lys Asn
450                 455                 460

Glu Leu His Arg His Ile Glu Glu Gly Leu Gly Arg Asn Met Ser Asp
465                 470                 475                 480
```

Arg Cys Ser Thr Ala Ile Thr Asn Ser Leu Gln Thr Met Gln Gln Asp
                485                 490                 495

Met Ile Asp Gly Leu Lys Pro Leu Leu Pro Val Ser Val Arg Ser Gln
            500                 505                 510

Ile Asp Met Leu Val Pro Arg Gln Cys Phe Ser Leu Asn Tyr Asp Leu
        515                 520                 525

Asn Cys Asp Lys Leu Cys Ala Asp Phe Gln Glu Asp Ile Glu Phe His
    530                 535                 540

Phe Ser Leu Gly Trp Thr Met Leu Val Asn Arg Phe Leu Gly Pro Lys
545                 550                 555                 560

Asn Ser Arg Arg Ala Leu Met Gly Tyr Asn Asp Gln Val Gln Arg Pro
                565                 570                 575

Ile Pro Leu Thr Pro Ala Asn Pro Ser Met Pro Pro Leu Pro Gln Gly
            580                 585                 590

Ser Leu Thr Gln Glu Glu Phe Met Val Ser Met Val Thr Gly Leu Ala
        595                 600                 605

Ser Leu Thr Ser Arg Thr Ser Met Gly Ile Leu Val Val Gly Gly Val
    610                 615                 620

Val Trp Lys Ala Val Gly Trp Arg Leu Ile Ala Leu Ser Phe Gly Leu
625                 630                 635                 640

Tyr Gly Leu Leu Tyr Val Tyr Glu Arg Leu Thr Trp Thr Thr Lys Ala
                645                 650                 655

Lys Glu Arg Ala Phe Lys Arg Gln Phe Val Glu His Ala Ser Glu Lys
            660                 665                 670

Leu Gln Leu Val Ile Ser Tyr Thr Gly Ser Asn Cys Ser His Gln Val
        675                 680                 685

Gln Gln Glu Leu Ser Gly Thr Phe Ala His Leu Cys Gln Gln Val Asp
    690                 695                 700

Val Thr Arg Glu Asn Leu Glu Gln Glu Ile Ala Ala Met Asn Lys Lys
705                 710                 715                 720

Ile Glu Val Leu Asp Ser Leu Gln Ser Lys Ala Lys Leu Leu Arg Asn
                725                 730                 735

Lys Ala Gly Trp Leu Asp Ser Glu Leu Asn Met Phe Thr His Gln Tyr
            740                 745                 750

Leu Gln Pro Ser Arg
        755

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 7
cgactcatca tggacgacct gcacatggcg gc                                    32

<210> SEQ ID NO 8
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 8
gccgccatgt gcaggtcgtc catgatgagt cg                                    32

```
<210> SEQ ID NO 9
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 9
gactcatcat ggacgccctg cacatggcg                                    29

<210> SEQ ID NO 10
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 10
cgccatgtgc agggcgtcca tgatgagtc                                    29

<210> SEQ ID NO 11
<211> LENGTH: 24
<212> TYPE: PRT
<213> ORGANISM: Artificial Sequence
<220> FEATURE:
<223> OTHER INFORMATION: Synthetic peptide

<400> SEQUENCE: 11

Gly Ile Ala Asp Ser Leu His Met Ala Ala Arg Gly Gly Tyr Gly Arg
1               5                   10                  15

Lys Lys Arg Arg Gln Arg Arg Arg
            20

<210> SEQ ID NO 12
<211> LENGTH: 24
<212> TYPE: PRT
<213> ORGANISM: Artificial Sequence
<220> FEATURE:
<223> OTHER INFORMATION: Synthetic peptide

<400> SEQUENCE: 12

Gly Ile Met Ala Ser Leu His Met Ala Ala Arg Gly Gly Tyr Gly Arg
1               5                   10                  15

Lys Lys Arg Arg Gln Arg Arg Arg
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic peptide

<400> SEQUENCE: 13

Gly Ile Met Asp Ala Leu His Met Ala Ala Arg Gly Gly Tyr Gly Arg
1               5                   10                  15

Lys Lys Arg Arg Gln Arg Arg Arg
            20

<210> SEQ ID NO 14
<211> LENGTH: 24
<212> TYPE: PRT
<213> ORGANISM: Artificial Sequence
<220> FEATURE:
<223> OTHER INFORMATION: Synthetic peptide
```

```
<400> SEQUENCE: 14

Gly Ile Met Asp Ser Ala His Met Ala Ala Arg Gly Gly Tyr Gly Arg
1               5                   10                  15

Lys Lys Arg Arg Gln Arg Arg Arg
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic peptide

<400> SEQUENCE: 15

Gly Ile Met Asp Ser Leu Ala Met Ala Ala Arg Gly Gly Tyr Gly Arg
1               5                   10                  15

Lys Lys Arg Arg Gln Arg Arg Arg
            20

<210> SEQ ID NO 16
<211> LENGTH: 24
<212> TYPE: PRT
<213> ORGANISM: Artificial Sequence
<220> FEATURE:
<223> OTHER INFORMATION: Synthetic peptide

<400> SEQUENCE: 16

Gly Ile Met Asp Ser Leu His Ala Ala Ala Arg Gly Gly Tyr Gly Arg
1               5                   10                  15

Lys Lys Arg Arg Gln Arg Arg Arg
            20

<210> SEQ ID NO 17
<211> LENGTH: 24
<212> TYPE: PRT
<213> ORGANISM: Artificial Sequence
<220> FEATURE:
<223> OTHER INFORMATION: Synthetic peptide

<400> SEQUENCE: 17

Gly Ile Met Asp Asp Leu His Met Ala Ala Arg Gly Gly Tyr Gly Arg
1               5                   10                  15

Lys Lys Arg Arg Gln Arg Arg Arg
            20

<210> SEQ ID NO 18
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa represents phosphorylation of serine

<400> SEQUENCE: 18

Gly Ile Met Asp Xaa Leu His Met Ala Ala Arg Gly Gly Tyr Gly Arg
1               5                   10                  15

Lys Lys Arg Arg Gln Arg Arg Arg
            20

<210> SEQ ID NO 19
<211> LENGTH: 24
```

-continued

```
<212> TYPE: PRT
<213> ORGANISM: Artificial Sequence
<220> FEATURE:
<223> OTHER INFORMATION: Synthetic peptide

<400> SEQUENCE: 19

Gly Ile Met Asp Gly Leu His Met Ala Ala Arg Gly Gly Tyr Gly Arg
1               5                   10                  15

Lys Lys Arg Arg Gln Arg Arg Arg
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic peptide

<400> SEQUENCE: 20

Gly Ile Met Asp Cys Leu His Met Ala Ala Arg Gly Gly Tyr Gly Arg
1               5                   10                  15

Lys Lys Arg Arg Gln Arg Arg Arg
            20

<210> SEQ ID NO 21
<211> LENGTH: 24
<212> TYPE: PRT
<213> ORGANISM: Artificial Sequence
<220> FEATURE:
<223> OTHER INFORMATION: Synthetic peptide

<400> SEQUENCE: 21

Gly Ile Met Asp Asn Leu His Met Ala Ala Arg Gly Gly Tyr Gly Arg
1               5                   10                  15

Lys Lys Arg Arg Gln Arg Arg Arg
            20

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide

<400> SEQUENCE: 22

Ala Val Arg Gly Ile Met Asp Ser Leu His Met Ala Ala Arg
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa represents phosphorylation of serine

<400> SEQUENCE: 23

Ala Val Arg Gly Ile Met Asp Xaa Leu His Met Ala Ala Arg
1               5                   10

<210> SEQ ID NO 24
<211> LENGTH: 36
<212> TYPE: PRT
```

<213> ORGANISM: Artificial Sequence
<220> FEATURE:
<223> OTHER INFORMATION: Synthetic peptide

<400> SEQUENCE: 24

```
His His His His His His Gly Gly Gly Gly Ala Ala Met Asn Lys Lys
1               5                   10                  15

Ile Glu Val Leu Asp Ser Leu Gln Ser Lys Ala Lys Leu Leu Arg Asn
            20                  25                  30

Lys Ala Gly Gly
        35
```

<210> SEQ ID NO 25
<211> LENGTH: 36
<212> TYPE: PRT
<213> ORGANISM: Artificial Sequence
<220> FEATURE:
<223> OTHER INFORMATION: Synthetic peptide

<400> SEQUENCE: 25

```
His His His His His His Gly Gly Gly Gly Ala Ala Met Asn Lys Lys
1               5                   10                  15

Ile Glu Val Ala Ala Ser Ala Gln Ser Lys Ala Lys Leu Leu Arg Asn
            20                  25                  30

Lys Ala Gly Gly
        35
```

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

```
Gly Gly Gly Gly Ala Val Arg Gly Ile Met Asp Ser Leu His Met Ala
1               5                   10                  15

Ala Arg Gly Gly
        20
```

<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

```
Gly Gly Gly Gly Ala Val Arg Gly Ile Met Asp Asp Leu His Met Ala
1               5                   10                  15

Ala Arg Gly Gly
        20
```

<210> SEQ ID NO 28
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 28

Gly Gly Gly Gly Ala Val Arg Gly Ile Met Asp Ala Leu His Met Ala
1               5                   10                  15

Ala Arg Gly Gly
            20
```

SMALL MOLECULE REGULATORS OF MITOCHONDRIAL FUSION AND METHODS OF USE THEREOF

CROSS-REFERENCE TO RELATED APPLICATIONS

This application is a continuation of PCT application number PCT/US2018/028514 filed on Apr. 20, 2018, which claims priority from U.S. Provisional Application Ser. No. 62/488,787 filed on 23 Apr. 2017 and U.S. Provisional Application Ser. No. 62/584,515 filed on 10 Nov. 2017, each of which are incorporated herein by reference in their entireties.

STATEMENT REGARDING FEDERALLY SPONSORED RESEARCH OR DEVELOPMENT

This invention was made with government support under grant number HL 135736 awarded by National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to compositions and methods for treating mitochondria-associated diseases, disorders, or conditions. Also provided are methods for screening compositions.

SUMMARY OF THE INVENTION

Among the various aspects of the present disclosure is the provision of a small molecule regulator of mitochondrial fusion and methods of use thereof.

One aspect of the present disclosure provides for a method of treating a mitochondria-associated disease, disorder, or condition. In some embodiments, the method comprises administering to a subject a therapeutically effective amount of a composition comprising one or more of a mitofusin modulating agent or a pharmaceutically acceptable salt thereof, wherein the mitofusin modulating agent is a mitofusin agonist; the mitofusin modulating agent regulates mitochondrial fusion; or the mitofusin modulating agent is not a compound of TABLE 4.

Another aspect of the present disclosure provides for a method of modulating mitofusin in a subject in need thereof. In some embodiments, the method comprises administering to a subject a composition comprising a mitofusin modulating agent or a pharmaceutically acceptable salt thereof; wherein, the mitofusin modulating agent is a mitofusin agonist; the mitofusin modulating agent regulates mitochondrial fusion; the subject has a mitochondria-associated disease, disorder, or condition; or the mitofusin modulating agent is not a compound of TABLE 4.

Another aspect of the present disclosure provides for a method of enhancing mitochondrial trafficking in nerve axons in a subject in need thereof. In some embodiments, the method comprises administering to a subject a composition comprising a mitofusin modulating agent or a pharmaceutically acceptable salt thereof; wherein, the mitofusin modulating agent is a mitofusin agonist; the mitofusin modulating agent regulates mitochondrial fusion; the subject has a mitochondria-associated disease, disorder, or condition; or the mitofusin modulating agent is not a compound of TABLE 4.

In some embodiments, the mitochondria-associated disease, disorder, or condition is selected from one or more of the group consisting of: a chronic neurodegenerative condition wherein mitochondrial fusion, fitness, or trafficking are impaired; a disease or disorder associated with mitofusin 1 (Mfn1) or mitofusin 2 (Mfn2) or mitochondrial dysfunction, fragmentation, or fusion; dysfunction in Mfn1 or Mfn2 unfolding; mitochondria dysfunction caused by mutations; a degenerative neurological condition, such as Alzheimer's, Parkinson's, Charcot Marie Tooth Disease, or Huntington's diseases; or hereditary motor and sensory neuropathy, autism, autosomal dominant optic atrophy (ADOA), muscular dystrophy, Lou Gehrig's disease, cancer, mitochondrial myopathy, Diabetes mellitus and deafness (DAD), Leber's hereditary optic neuropathy (LHON), Leigh syndrome, subacute sclerosing encephalopathy, Neuropathy, ataxia, retinitis pigmentosa, and ptosis (NARP), Myoneurogenic gastrointestinal encephalopathy (MNGIE), Myoclonic Epilepsy with Ragged Red Fibers (MERRF), Mitochondrial myopathy, encephalomyopathy, lactic acidosis, stroke-like symptoms (MELAS), mtDNA depletion, mitochondrial neurogastrointestinal encephalomyopathy (MNGIE), Dysautonomic Mitochondrial Myopathy, Mitochondrial Channelopathy, or pyruvate dehydrogenase complex deficiency (PDCD/PDH).

In some embodiments, the neurodegenerative condition is selected from Charcot Marie Tooth disease, Huntington's disease, Parkinson's disease, Alzheimer's disease, or amyotrophic lateral sclerosis (ALS).

In some embodiments, the mitofusin modulating agent is a small molecule mimetic of a Mfn2 peptide-peptide interface.

In some embodiments, the mitofusin modulating agent: has substantially similar functional potency and specificity of both 1-[2-(benzylsulfanyl)ethyl]-3-(2-methylcyclohexyl) urea (Cpd A) and 2-{2-[(5-cyclopropyl-4-phenyl-4H-1,2,4-triazol-3-yl)sulfanyl]propanamido}-4H,5H,6H-cyclopenta [b]thiophene-3-carboxamide (Cpd B); targets at least two phosphorylated forms of MFN; or stimulates mitofusin activity (e.g., fusion and trafficking).

In some embodiments, the mitofusin modulating agent: enhances mitochondrial trafficking in nerve axons; increases microsomal stability; corrects cell and organ dysfunction caused by primary abnormalities in mitochondrial fission or fusion; reverses mitochondrial defects (e.g., dysmorphometry); restores, activates, regulates, modulates, promotes, or enhances the fusion, function, tethering, transport, trafficking (e.g., axonal mitochondrial trafficking), mobility, or movement of mitochondria (in, optionally, a nerve or a neuron); enhances mitochondrial elongation or mitochondrial elongation aspect ratio; disrupts intramolecular restraints in Mfn2; allosterically activates Mfn2; corrects mitochondrial dysfunction and cellular dysfunction; repairs defects in neurons with mitochondrial mutations; or targets Mfn1 or Mfn2.

In some embodiments, the mitofusin modulating agent is selected from a compound of formula:

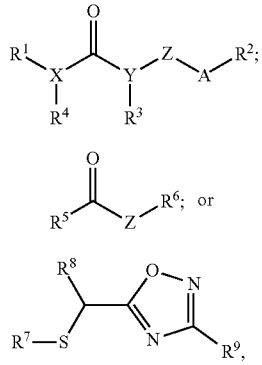

or a pharmaceutically acceptable salt, tautomer, or stereoisomer thereof wherein, $R^1$ is selected from the group consisting of $C_{1-8}$ alkyl, $C_{1-8}$ alkyl substituted with S, S, thiophene, $C_{3-8}$ cycloalkyl, $C_{3-8}$ heteroaryl, $C_{3-8}$ heterocyclyl, thiophene, and thiophene carboxamide; $R^2$ is selected from the group consisting of $C_{3-8}$ cycloalkyl, $C_{3-8}$ heteroaryl, $C_{3-8}$ heterocyclyl, imidazole, thiophene, thiophene carboxamide, and triazole; $R^3$ is selected from the group consisting of hydrogen (H) and $C_{1-8}$ alkyl; $R^4$ is selected form the group consisting of hydrogen (H) and $C_{1-8}$ alkyl; $R^5$ is selected from the group consisting of $C_{1-8}$ alkyl, $C_{1-8}$ alkyl substituted with S, S, thiophene, $C_{3-8}$ cycloalkyl, $C_{3-8}$ heteroaryl, $C_{3-8}$ heterocyclyl, thiophene, thiophene carboxamide, and triazole; $R^6$ is selected from the group consisting of bicyclononanone, pyrrole, benzimidizole, pyrrole substituted pyrrole, and substituted benzimidizole; $R^7$ is selected from the group consisting of $C_{1-8}$ alkyl, pyrrole, pyrrole substituted pyrrole, benzimidizole, and substituted benzimidizole; $R^8$ is selected from the group consisting of hydrogen (H); $R^9$ is selected from the group consisting of $C_{1-8}$ alkyl, pyrrole, substituted pyrrole, pyrrole substituted pyrrole, benzimidizole, and substituted benzimidizole; A is selected from the group consisting of a bond, S, C, O, and N; X is selected from the group consisting of O, C, and N;

Y is selected from the group consisting of O, C, and N; and Z is a linker group selected from the group consisting of a bond or $C_{1-6}$ alkyl; and optionally, $R^1$ and $R^2$ form a cyclic group, $R^1$ and $R^4$ form a cyclic group, $R^2$ and $R^3$ form a cyclic group, $R^4$ and $R^3$ form a cyclic group; or $R^8$ and $R^7$ form a cyclic group, wherein, the bicyclononanone optionally comprises one or more N atoms.

In some embodiments, the mitofusin modulating agent is selected from a compound of

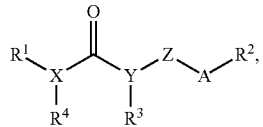

wherein, $R^1$ is selected from the group consisting of

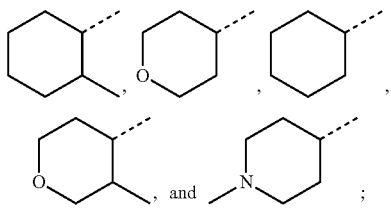

$R^2$ is selected from the group consisting of

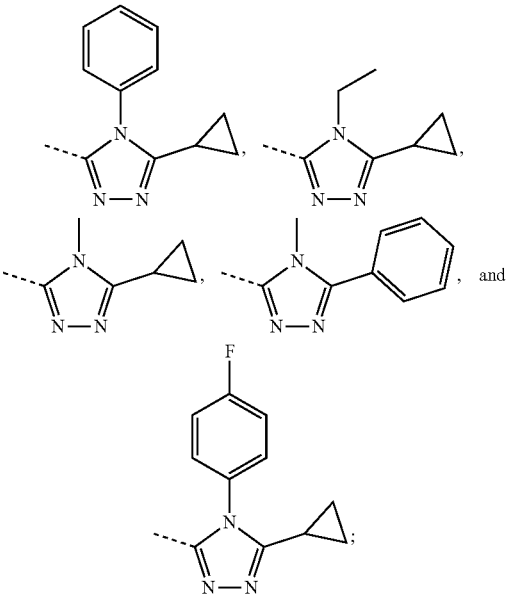

$R^3$ is selected from the group consisting of hydrogen (H) and $C_{1-8}$ alkyl; $R^4$ is selected form the group consisting of hydrogen (H) and $C_{1-8}$ alkyl; A is a bond, S, SO, $SO_2$, C, or O;

X is N; Y is N; and Z is a linker group selected from the group consisting of a bond or $C_{1-6}$ alkyl.

In some embodiments, $R^1$, $R^2$, $R^3$, or $R^4$ are optionally substituted by one or more of: acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene; and optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene; wherein, the alkyl, cycloalkyl, heteroaryl, heterocyclyl, indole, or phenyl, is optionally further substituted with one or more selected from the group consisting of acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene.

In some embodiments, the compound is selected from the group consisting of:

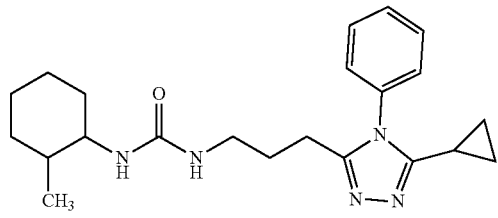

1-(3-(5-cyclopropyl-4-phenyl-4H-1,2,4-triazol-3-yl)propyl)-3-(2-methylcyclohexyl)urea;

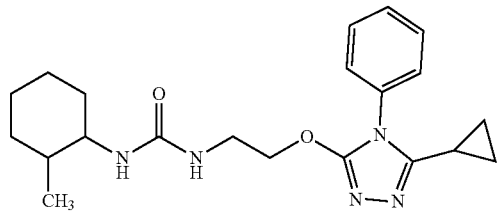

1-(2-((5-cyclopropyl-4-phenyl-4H-1,2,4-triazol-3-yl)oxy)ethyl)-3-(2-methylcyclohexyl)urea;

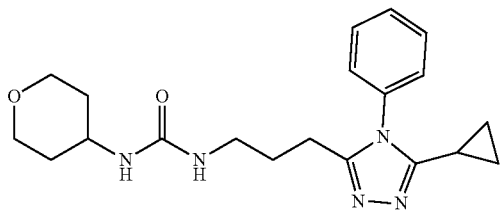

1-(3-(5-cyclopropyl-4-phenyl-4H-1,2,4-triazol-3-yl)propyl)-3-(2-tetrahydro-2H-pyran-4-yl)urea;

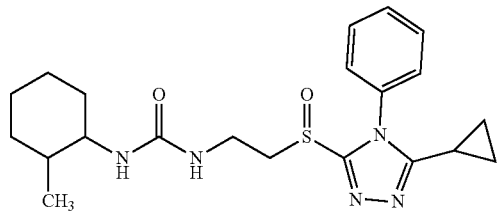

1-(2-((5-cyclopropyl-4-phenyl-4H-1,2,4-triazol-3-yl)sulfinyl)ethyl)-3-(2-methylcyclohexyl)urea;

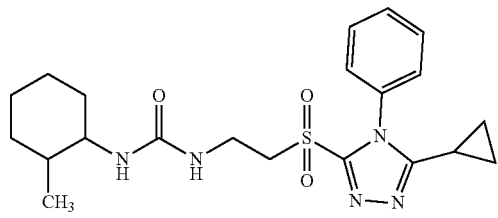

1-(2-((5-cyclopropyl-4-phenyl-4H-1,2,4-triazol-3-yl)sulfonyl)ethyl)-3-(2-methylcyclohexyl)urea;

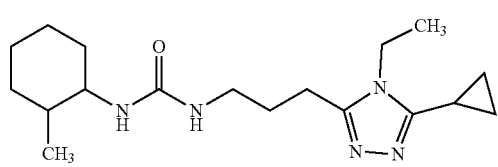

1-(3-(5-cyclopropyl-4-ethyl-4H-1,2,4-triazol-3-yl)propyl)ethyl)-3-(2-methylcyclohexyl)urea;

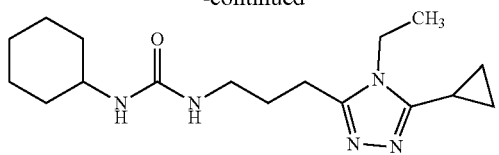

1-cyclohexyl-3-(3-(5-cyclopropyl)-4-ethyl-4H-1,2,4-triazol-3-yl)propyl)urea;

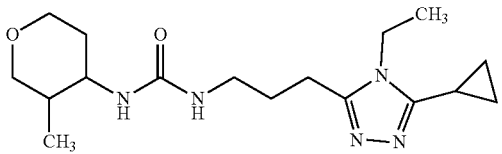

1-(3-(5-cyclopropyl-4-ethyl-4H-1,2,4-triazol-3-yl)propyl)-3-(3-methyltetrahydro-2H-pyran-4-yl)urea;

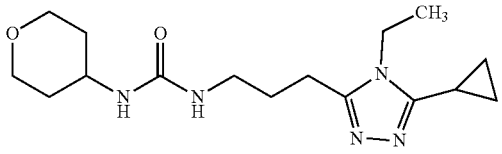

1-(3-(5-cyclopropyl-4-ethyl-4H-1,2,4-triazol-3-yl)propyl)-3-(tetrahydro-2H-pyran-4-yl)urea;

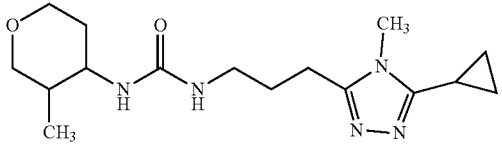

1-(3-(5-cyclopropyl-4-methyl-4H-1,2,4-triazol-3-yl)propyl)-3-(3-methyltetrahydro-2H-pyran-4-yl)urea;

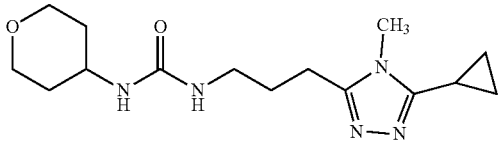

1-(3-(5-cyclopropyl-4-methyl-4H-1,2,4-triazol-3-yl)propyl)-3-(tetrahydro-2H-pyran-4-yl)urea;

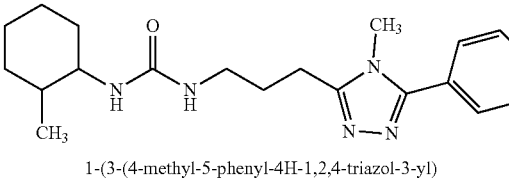

1-(3-(4-methyl-5-phenyl-4H-1,2,4-triazol-3-yl)propyl)-3-(2-methylcyclohexyl)urea;

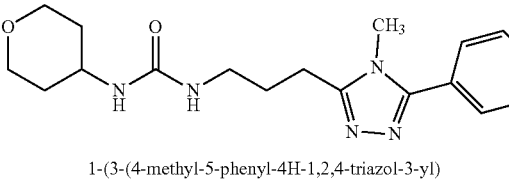

1-(3-(4-methyl-5-phenyl-4H-1,2,4-triazol-3-yl)propyl)-3-(tetrahydro-2H-pyran-4-yl)urea; or

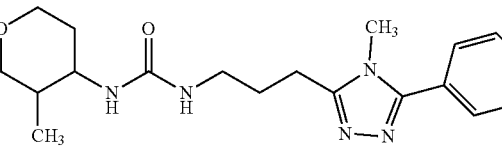

1-(3-(4-methyl-5-phenyl-4H-1,2,4-triazol-3-yl)propyl)-3-(3-methyltetrahydro-2H-pyran-4-yl)urea.

In some embodiments, the compound is selected from the group consisting of:

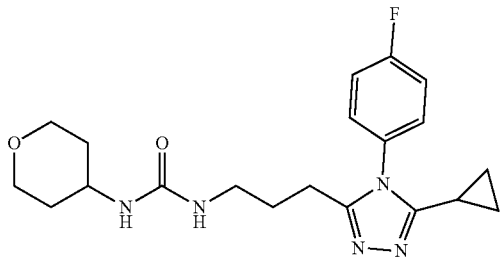

1-(3-(5-cyclopropyl-4-(4-fluorophenyl)-4H-1,2,4-triazol-3-yl)propyl)-3-(tetrahydro-2H-pyran-4-yl)urea;

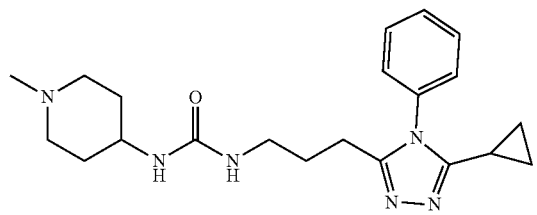

1-(3-(5-cyclopropyl-4-phenyl-4H-1,2,4-triazol-3-yl)propyl)-3-(1-methylpiperidin-4-yl)urea;

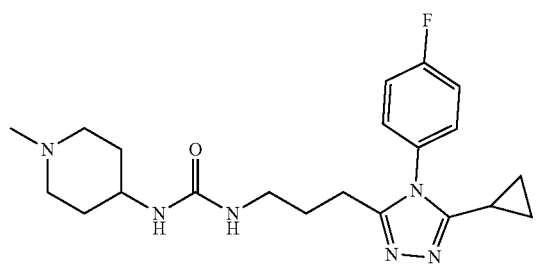

1-(3-(5-cyclopropyl-4-(4-fluorophenyl)-4H-1,2,4-triazol-3-yl)propyl)-3-(1-methylpiperidin-4-yl)urea;

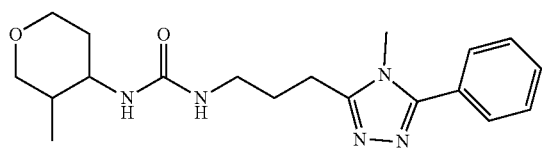

1-(3-(4-methyl-5-phenyl-4H-1,2,4-triazol-3-yl)propyl)-3-(3-methyltetrahydro-2H-pyran-4-yl)urea; and

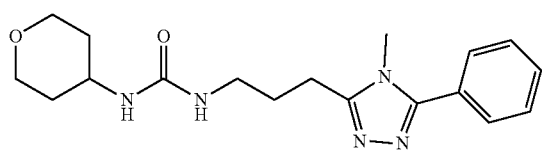

1-(3-(4-methyl-5-phenyl-4H-1,2,4-triazol-3-yl)propyl)-3-(tetrahydro-2H-pyran-4-yl)urea.

Yet another aspect of the present disclosure provides for a compound of formula:

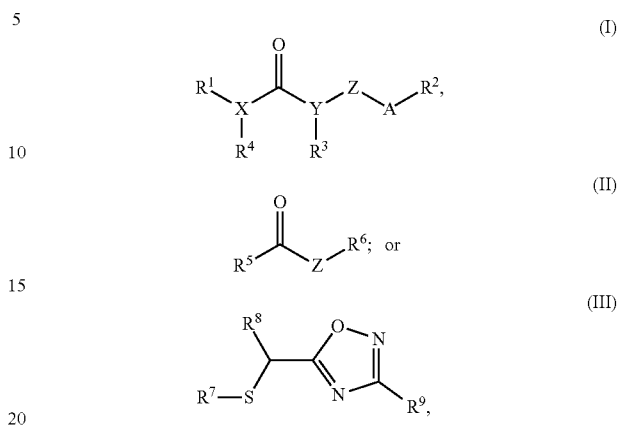

or a pharmaceutically acceptable salt, tautomer, or stereoisomer thereof wherein, $R^1$ is selected from the group consisting of $C_{1-8}$ alkyl, $C_{1-8}$ alkyl substituted with S, S, thiophene, $C_{3-8}$ cycloalkyl, $C_{3-8}$ heteroaryl, $C_{3-8}$ heterocyclyl, thiophene, and thiophene carboxamide; $R^2$ is selected from the group consisting of $C_{3-8}$ cycloalkyl, $C_{3-8}$ heteroaryl, $C_{3-8}$ heterocyclyl, imidazole, thiophene, thiophene carboxamide, and triazole; $R^3$ is selected from the group consisting of hydrogen (H) and $C_{1-8}$ alkyl; $R^4$ is selected form the group consisting of hydrogen (H) and $C_{1-8}$ alkyl; $R^5$ is selected from the group consisting of $C_{1-8}$ alkyl, $C_{1-8}$ alkyl substituted with S, S, thiophene, $C_{3-8}$ cycloalkyl, $C_{3-8}$ heteroaryl, $C_{3-8}$ heterocyclyl, thiophene, thiophene carboxamide, and triazole; $R^6$ is selected from the group consisting of bicyclononanone, pyrrole, benzimidizole, pyrrole substituted pyrrole, and substituted benzimidizole; $R^7$ is selected from the group consisting of $C_{1-8}$ alkyl, pyrrole, pyrrole substituted pyrrole, benzimidizole, and substituted benzimidizole; $R^8$ is selected from the group consisting of hydrogen (H); $R^9$ is selected from the group consisting of $C_{1-8}$ alkyl, pyrrole, substituted pyrrole, pyrrole substituted pyrrole, benzimidizole, and substituted benzimidizole; X is selected from the group consisting of O, C, and N; Y is selected from the group consisting of O, C, and N; or Z is a linker group selected from the group consisting of a bond or $C_{1-6}$ alkyl.

In some embodiments, $R^1$ and $R^2$ form a cyclic group, $R^1$ and $R^4$ form a cyclic group, $R^2$ and $R^3$ form a cyclic group, $R^4$ and $R^3$ form a cyclic group; or $R^8$ and $R^7$ form a cyclic group, wherein, the bicyclononanone optionally comprises one or more N atoms; or formula (I), (II), or (III) is not a compound of TABLE 4, TABLE 5, TABLE 7, or

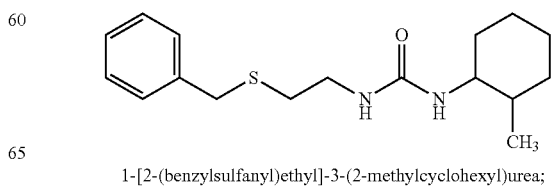

1-[2-(benzylsulfanyl)ethyl]-3-(2-methylcyclohexyl)urea;

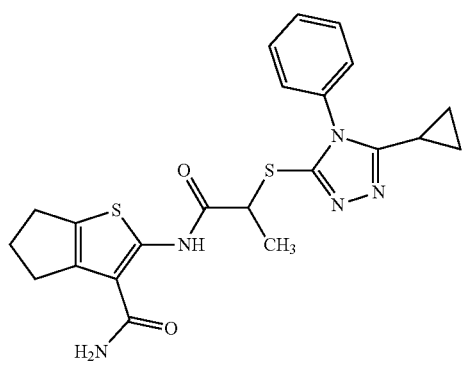

2-{2-[(5-cyclopropyl-4-phenyl-4H-1,2,4-triazol-3-yl)sulfanyl]propanamido}-4H,5H,6H-cyclopenta[b]thiophene-3-carboxamide;

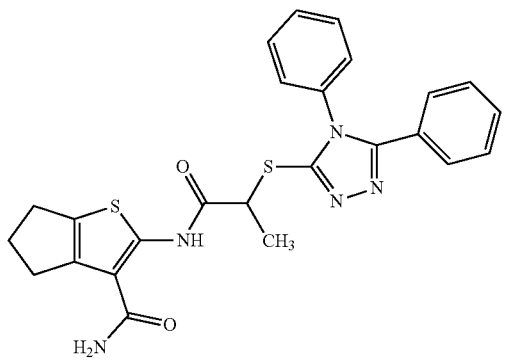

2-{2-[(diphenyl-4H-1,2,4-triazol-3-yl)sulfanyl]propanamido}-4H,5H,6H-cyclopenta[b]thiophene-3-carboxamide;

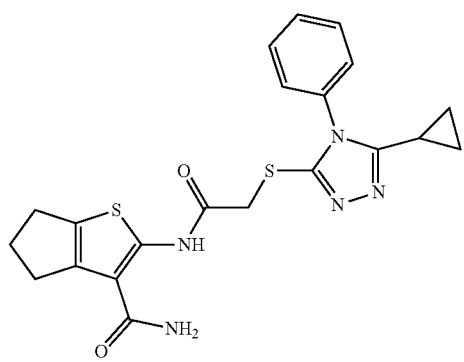

2-{2-[(5-cyclopropyl-4-phenyl-4H-1,2,4-triazol-3-yl)sulfanyl]acetamido}-4H,5H,6H-cyclopenta[b]thiophene-3-carboxamide;

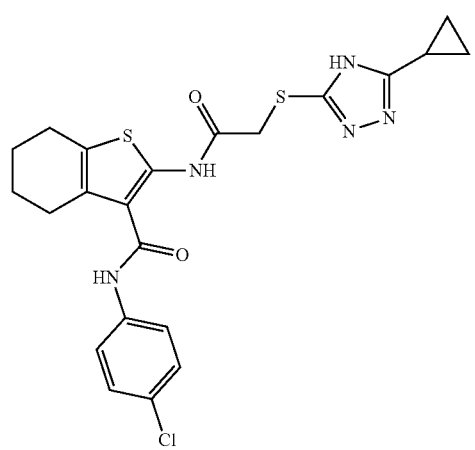

N-(4-chlorophenyl)-2-{2-[(5-cyclopropyl-4H-1,2,4-triazol-3-yl)sulfanyl]acetamido}-4,5,6,7-tetrahydro-1-benzothiophene-3-carboxamide;

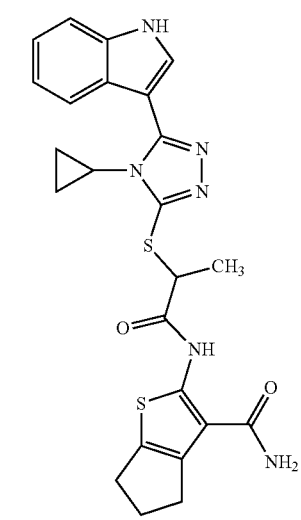

2-(2-{[4-cyclopropyl-5-(1H-indol-3-yl)-4H-1,2,4-triazol-3-yl]sulfanyl}propanamido)-4H,5H,6H-cyclopenta[b]thiophene-3-carboxamide;

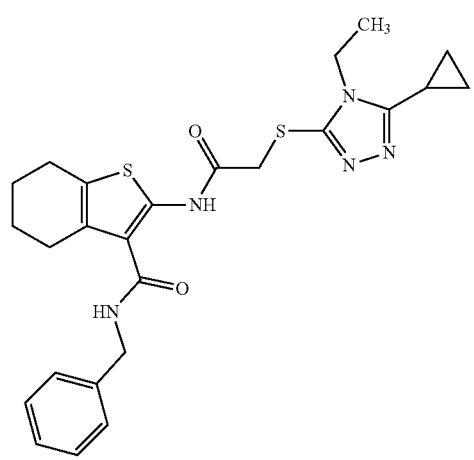

N-benzyl-2-{2-[(5-cyclopropyl-4-ethyl-4H-1,2,4-triazol-3-yl)sulfanyl]acetamido}-4,5,6,7-tetrahydro-1-benzothiophene-3-carboxamide;

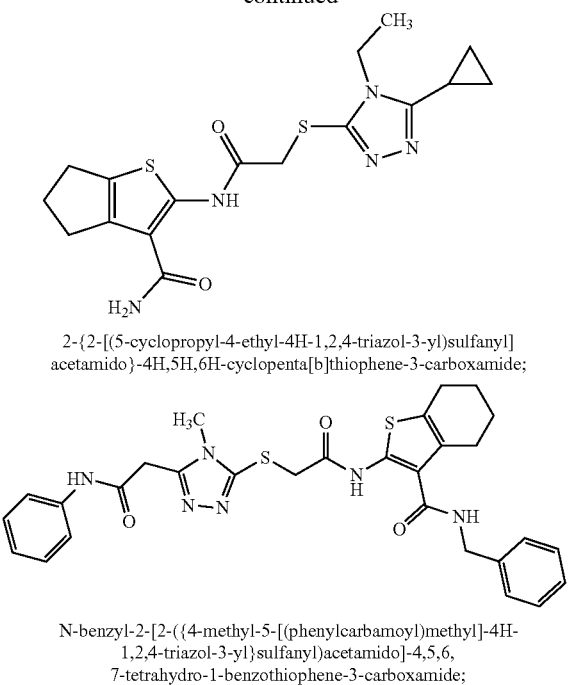

2-{2-[(5-cyclopropyl-4-ethyl-4H-1,2,4-triazol-3-yl)sulfanyl]
acetamido}-4H,5H,6H-cyclopenta[b]thiophene-3-carboxamide;

N-benzyl-2-[2-({4-methyl-5-[(phenylcarbamoyl)methyl]-4H-
1,2,4-triazol-3-yl}sulfanyl)acetamido]-4,5,6,
7-tetrahydro-1-benzothiophene-3-carboxamide;

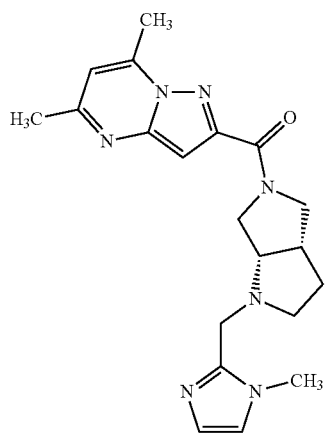

2-{[(3aS,6aS)-5-{5,7-dimethylpyrazolo[1,5-a]pyrimidine-2-carbonyl}-
octahydropyrrolo[3,4-b]pyrrol-1-yl]methyl}-1-methyl-1H-imidazole;

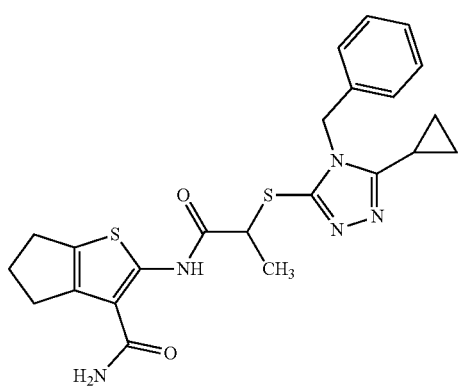

2-{2-[(4-benzyl-5-cyclopropyl-4H-1,2,4-triazol-3-yl)sulfanyl]
propanamido}-4H,5H,6H-cyclopenta[b]thiophene-3-carboxamide;

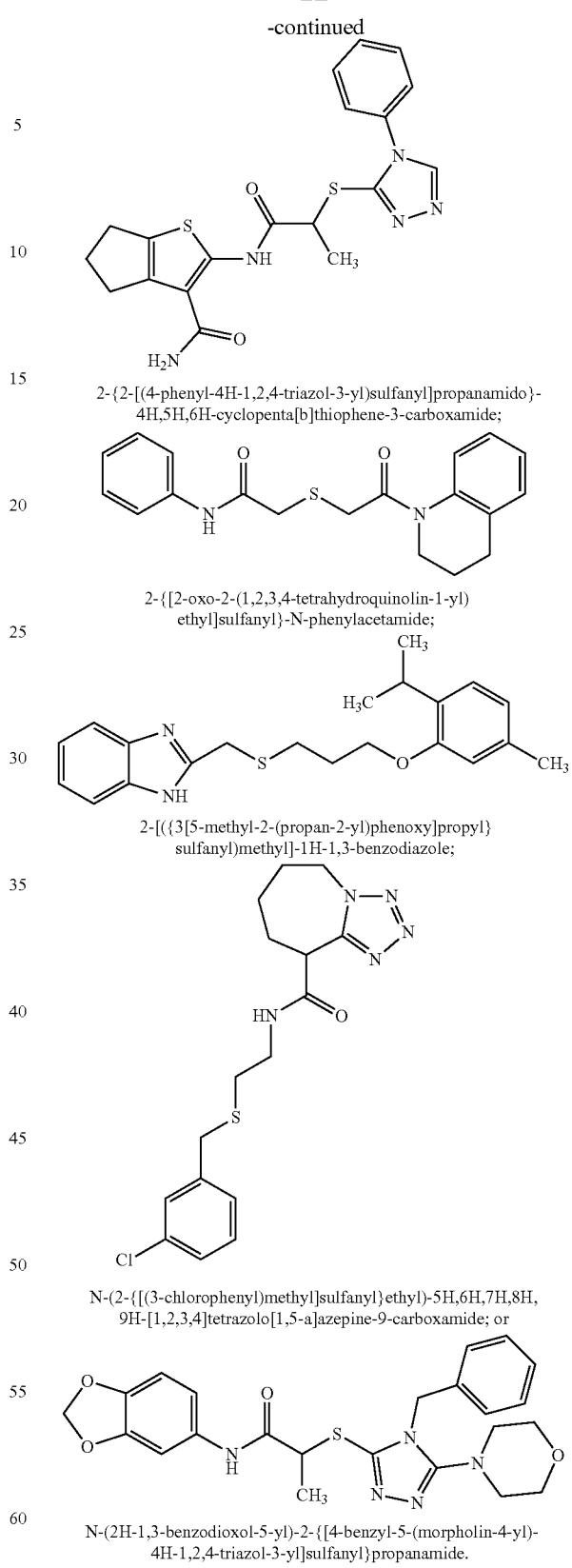

2-{2-[(4-phenyl-4H-1,2,4-triazol-3-yl)sulfanyl]propanamido}-
4H,5H,6H-cyclopenta[b]thiophene-3-carboxamide;

2-{[2-oxo-2-(1,2,3,4-tetrahydroquinolin-1-yl)
ethyl]sulfanyl}-N-phenylacetamide;

2-[({3[5-methyl-2-(propan-2-yl)phenoxy]propyl}
sulfanyl)methyl]-1H-1,3-benzodiazole;

N-(2-{[(3-chlorophenyl)methyl]sulfanyl}ethyl)-5H,6H,7H,8H,
9H-[1,2,3,4]tetrazolo[1,5-a]azepine-9-carboxamide; or N-(2H-1,3-benzodioxol-5-yl)-2-{[4-benzyl-5-(morpholin-4-yl)-
4H-1,2,4-triazol-3-yl]sulfanyl}propanamide.

In some embodiments, $R^1$, $R^2$, $R^3$, $R^4$, $R^5$, $R^6$, $R^7$, $R^8$, or $R^9$ are optionally substituted by one or more of: acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene; or optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene; wherein, the alkyl, cycloalkyl, heteroaryl, heterocyclyl, indole, or phenyl, is optionally further substituted with one or more selected from the group consisting of acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene.

In some embodiments, the compound is of formula

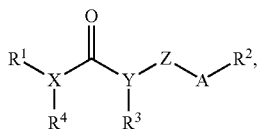
(I)

wherein, $R^1$ is selected from the group consisting of

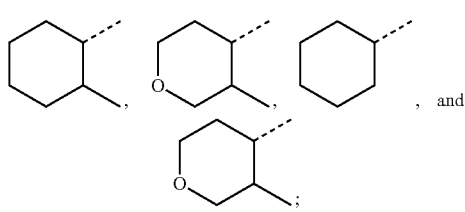

$R^2$ is selected from the group consisting of

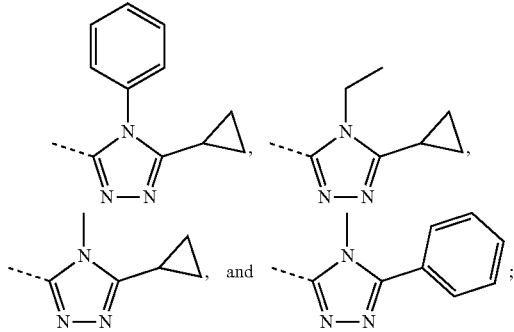

$R^3$ is selected from the group consisting of hydrogen (H) and $C_{1-8}$ alkyl; $R^4$ is selected form the group consisting of hydrogen (H) and $C_{1-8}$ alkyl; A is a bond, S, SO, $SO_2$, C, or O;

X is N; Y is N; or Z is a linker group selected from the group consisting of a bond or $C_{1-6}$ alkyl.

In some embodiments, $R^1$, $R^2$, $R^3$, or $R^4$ are optionally substituted by one or more of: acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene; and optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene; wherein, the alkyl, cycloalkyl, heteroaryl, heterocyclyl, indole, or phenyl, is optionally further substituted with one or more selected from the group consisting of acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene.

In some embodiments, the compound is selected from:

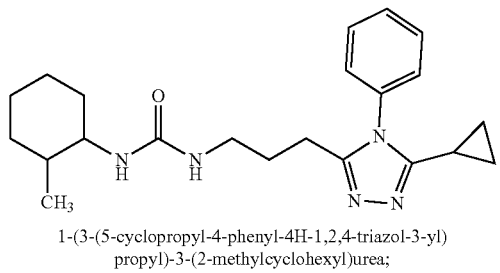

1-(3-(5-cyclopropyl-4-phenyl-4H-1,2,4-triazol-3-yl)propyl)-3-(2-methylcyclohexyl)urea;

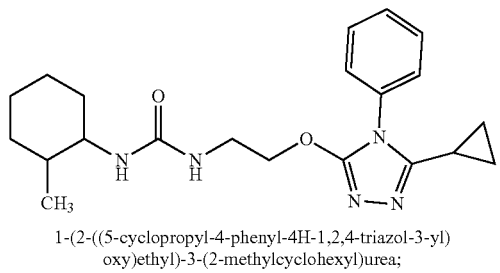

1-(2-((5-cyclopropyl-4-phenyl-4H-1,2,4-triazol-3-yl)oxy)ethyl)-3-(2-methylcyclohexyl)urea;

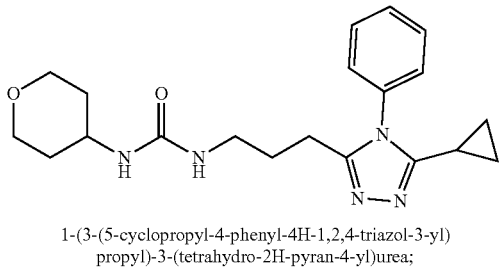

1-(3-(5-cyclopropyl-4-phenyl-4H-1,2,4-triazol-3-yl)propyl)-3-(tetrahydro-2H-pyran-4-yl)urea;

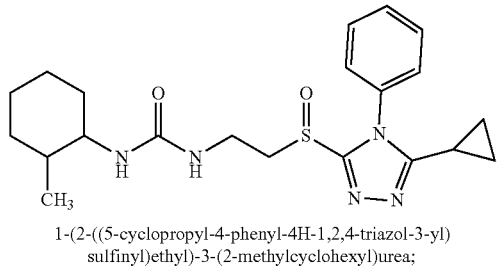

1-(2-((5-cyclopropyl-4-phenyl-4H-1,2,4-triazol-3-yl)sulfinyl)ethyl)-3-(2-methylcyclohexyl)urea;

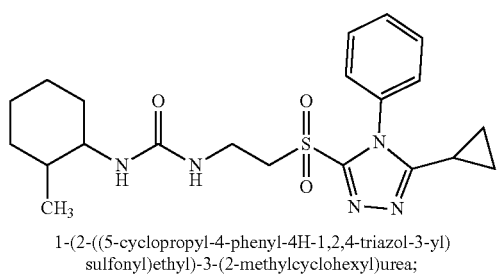

1-(2-((5-cyclopropyl-4-phenyl-4H-1,2,4-triazol-3-yl)sulfonyl)ethyl)-3-(2-methylcyclohexyl)urea;

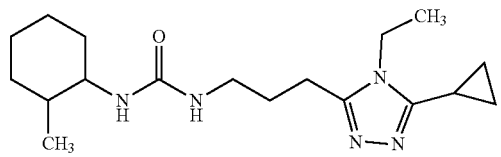

1-(3-(5-cyclopropyl-4-ethyl-4H-1,2,4-triazol-3-yl)
propyl)-3-(2-methylcyclohexyl)urea;

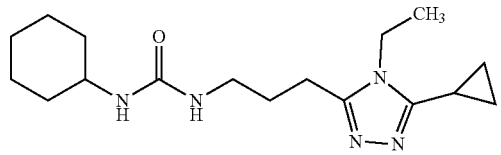

1-cyclohexyl-3-(3-(5-cyclopropyl)-4-
ethyl-4H-1,2,4-triazol-3-yl)propyl)urea;

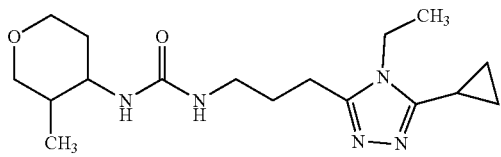

1-(3-(5-cyclopropyl-4-ethyl-4H-1,2,4-triazol-3-yl)
propyl)-3-(3-methyltetrahydro-2H-pyran-4-yl)urea;

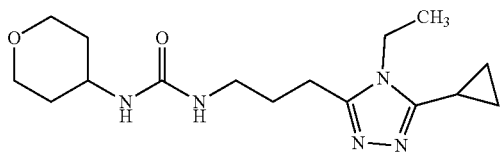

1-(3-(5-cyclopropyl-4-ethyl-4H-1,2,4-triazol-3-yl)
propyl)-3-(tetrahydro-2H-pyran-4-yl)urea;

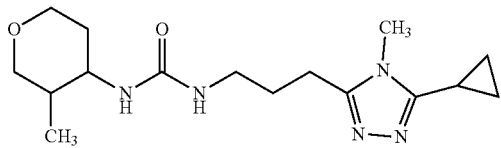

1-(3-(5-cyclopropyl-4-methyl-4H-1,2,4-triazol-3-yl)
propyl)-3-(methyltetrahydro-2H-pyran-4-yl)urea;

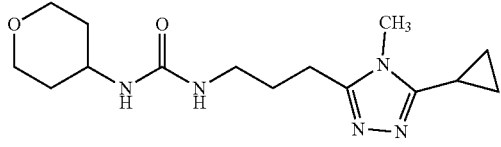

1-(3-(5-cyclopropyl-4-methyl-4H-1,2,4-triazol-3-yl)
propyl)-3-(tetrahydro-2H-pyran-4-yl)urea;

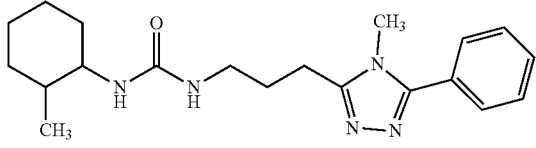

1-(3-(4-methyl-5-phenyl-4H-1,2,4-triazol-3-yl)
propyl)-3-(2-methylcyclohexyl)urea;

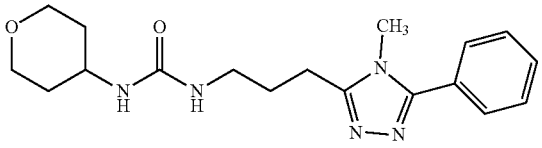

1-(3-(4-methyl-5-phenyl-4H-1,2,4-triazol-3-yl)
propyl)-3-(tetrahydro-2H-pyran-4-yl)urea; or

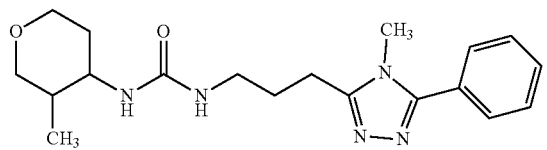

1-(3-(4-methyl-5-phenyl-4H-1,2,4-triazol-3-yl)
propyl)-3-(3-methyltetrahydro-2H-pyran-4-yl)urea.

In some embodiments, the compound is selected from:

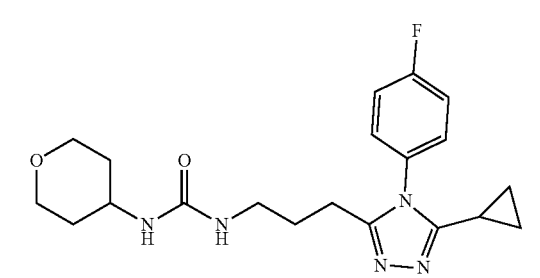

1-(3-(5-cyclopropyl-4-(4-fluorophenyl)-4H-1,2,4-triazol-3-yl)
propyl)-3-(tetrahydro-2H-pyran-4-yl)urea;

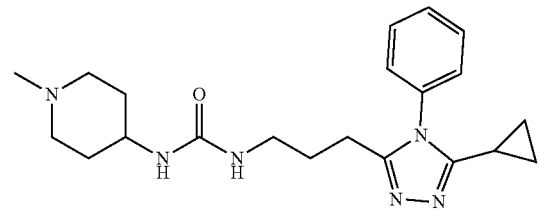

1-(3-(5-cyclopropyl-4-phenyl-4H-1,2,4-triazol-3-yl)
propyl)-3-(1-methylpiperidin-4-yl)urea;

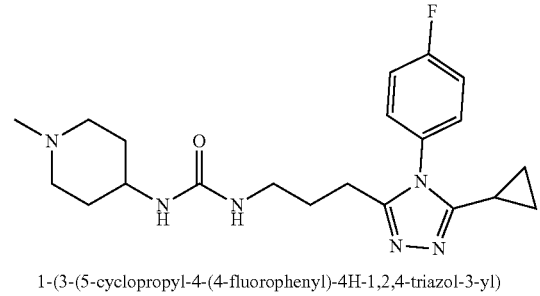

1-(3-(5-cyclopropyl-4-(4-fluorophenyl)-4H-1,2,4-triazol-3-yl)
propyl)-3-(1-methylpiperidin-4-yl)urea;

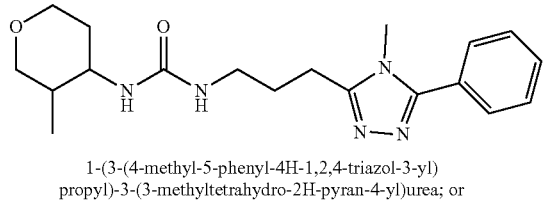

1-(3-(4-methyl-5-phenyl-4H-1,2,4-triazol-3-yl)
propyl)-3-(3-methyltetrahydro-2H-pyran-4-yl)urea; or

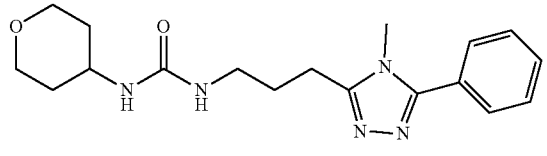

1-(3-(4-methyl-5-phenyl-4H-1,2,4-triazol-3-yl)
propyl)-3-(tetrahydro-2H-pyran-4-yl)urea.

In some embodiments, the compound is a small molecule mimetic of a Mfn2 peptide-peptide interface.

In some embodiments, the compound targets at least two phosphorylated forms of MFN; enhances mitochondrial trafficking in nerve axons; increases microsomal stability; corrects cell and organ dysfunction caused by primary abnormalities in mitochondrial fission or fusion; reverses mitochondrial defects (e.g., dysmorphometry); restores, activates, regulates, modulates, promotes, or enhances the fusion, function, tethering, transport, trafficking (e.g., axonal mitochondrial trafficking), mobility, or movement of mitochondria (in, optionally, a nerve or a neuron); enhances mitochondrial elongation or mitochondrial elongation aspect ratio; disrupts intramolecular restraints in Mfn2; allosterically activates Mfn2; corrects mitochondrial dysfunction and cellular dysfunction; repairs defects in neurons with mitochondrial mutations; or targets Mfn1 or Mfn2.

Yet another aspect of the present disclosure provides for a pharmaceutical composition comprising a compound of formula (I), (II), or (III), optionally in combination with one or more therapeutically acceptable diluents or carriers.

In some embodiments, the pharmaceutical composition comprises a pharmaceutically acceptable excipient.

In some embodiments, the pharmaceutical composition comprises a at least one compound selected from the group consisting of neuroprotectants, antiparkinsonian drugs, amyloid protein deposition inhibitors, beta amyloid synthesis inhibitors, antidepressants, anxiolytic drugs, antipsychotic drugs, anti-amyotrophic lateral sclerosis drugs, anti-Huntington's drugs, anti-Alzheimer's drugs, anti-epileptic drugs, or steroids.

Yet another aspect of the present disclosure provides for a method of treating a mitochondria-associated disease, disorder, or condition in a subject comprising administering to the subject a therapeutically effective amount of a mitofusin modulating agent comprising the compound of formula (I), (II), or (III).

In some embodiments, the subject is diagnosed with or is suspected of having a mitochondria-associated disease.

In some embodiments, the mitochondria-associate disease is selected from one or more of the group consisting of: a chronic neurodegenerative condition wherein mitochondrial fusion, fitness, or trafficking are impaired; a disease or disorder associated with mitofusin 1 (Mfn1) or mitofusin 2 (Mfn2) or mitochondrial dysfunction, fragmentation, or fusion; dysfunction in Mfn1 or Mfn2 unfolding; mitochondria dysfunction caused by mutations; a degenerative neurological condition, such as Alzheimer's, Parkinson's, Charcot Marie Tooth Disease, or Huntington's diseases; diabetes-induced neuropathy, or heart disease; or hereditary motor and sensory neuropathy, autism, autosomal dominant optic atrophy (ADOA), muscular dystrophy, Lou Gehrig's disease, cancer, mitochondrial myopathy, Diabetes mellitus and deafness (DAD), Leber's hereditary optic neuropathy (LHON), Leigh syndrome, subacute sclerosing encephalopathy, Neuropathy, ataxia, retinitis pigmentosa, and ptosis (NARP), Myoneurogenic gastrointestinal encephalopathy (MNGIE), Myoclonic Epilepsy with Ragged Red Fibers (MERRF), Mitochondrial myopathy, encephalomyopathy, lactic acidosis, stroke-like symptoms (MELAS), mtDNA depletion, mitochondrial neurogastrointestinal encephalomyopathy (MNGIE), Dysautonomic Mitochondrial Myopathy, Mitochondrial Channelopathy, or pyruvate dehydrogenase complex deficiency (PDCD/PDH).

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 4A shows 3D structures of 1-[2-(benzylsulfanyl)ethyl]-3-(2-methylcyclohexyl)urea, designated compound A, and 2-{2-[(5-cyclopropyl-4-phenyl-4H-1,2,4-triazol-3yl)sulfanyl]propanamido}-4H,5H,6H-cyclopenta[b]thiophene-3-carboxamide, designated compound B. FIG. 4B shows that mitochondrial elongation (increased mitochondrial aspect ratio) evoked by compounds A and B requires either Mfn1 or Mfn2 and each of compound A and compound B inhibited Mfn1 or Mfn2. Note that there was no effect on mitochondrial elongation when both Mfn1 and Mfn2 were absent (see e.g., Example 2). Black bars are compound-treated cells and white bars are vehicle (DMSO) treated. *=P<0.05 vs control (white).

FIG. 6A shows A+B synergism. More specifically, that the EC50 values of compounds A and B were each 100-200 nM. Note that when added in equal amounts, compounds A and B synergistically promoted mitochondrial elongation, with a combined EC50 of ~40 nM and a ~25% greater maximal increase in mitochondrial aspect ratio. FIG. 6B is a bar graph showing a negative charge conferred by Ser378 phosphorylation or Asp (D) substitution is essential for mini-peptide fusion promoting activity and shows how a S378D mutation, which mimics phosphorylation of this site, influenced Mfn2 conformation and function similarly to HR1 peptide 374-384 (see e.g., Example 2). FIG. 6C is a series of images showing representative confocal micrographs of cells treated with mini-peptides in compound B. FIG. 6D is a series of images showing the structural consequences of Ser378 phosphorylation on the Mfn2 HR1-HR2 interacting face; His 380 rotates out and Leu379 rotates in.

FIG. 11A, FIG. 11B, FIG. 11C, FIG. 11D, FIG. 11E, FIG. 11F, and FIG. 11G area series of images and graphs showing small molecule mimetics of MFN2 HR1 amino acid side chains that interact with HR2 are mitofusin agonists. (A) (top) Three dimensional representations of minipeptide conformations driven by Ser378 phosphorylation, and (bottom) their respective small molecule mimetics. (B) Dose-dependent mitofusin agonism by small molecule agonists (n=6 each). (C) Displacement of minipeptide 374-384 from its HR2 binding site by mitofusin agonists (n=3 each). (D) Restoration of MFN2 T105M-impaired mitochondrial fusion in MEFs by mitofusin agonists. (E) Selectivity of a class A, but not a class B, mitofusin agonist for $Ser^{378}$-phosphorylated MFN2. (F) Impaired basal function, but normal proportional agonist responsiveness, of MFN2 mutations altering HR1-HR2 interacting amino acids. (G) Change in FRET evoked by mitofusin agonists as a function of Ser378 mutant; decreased FRET reflects conformational opening.

FIG. 8 shows that HR1 and HR2 domain interaction can result in a folded conformation in which tethering to adjacent Mfn proteins is unfavorable. Disruption of HR1 and HR2 domains can result in an unfolded conformation in which tethering is favorable. FIG. 12A-FIG. 12B are illustrations of change in FRET signaling evoked by Mfn conformation. FIG. 12C is a graph of a representative experiment with changes in Δ80-275 Mfn2 FRET signal provoked by Mfn antagonist MP2 and agonist MP1. This novel Forster resonance energy transfer (FRET) assay screens compounds that induce unfolding of a fluorescently tagged Mfn2 construct. Note that both mini-peptides 1 and 2 influenced the FRET signal, suggesting that they induced Mfn2 conformational changes (see e.g., Example 4).

Figure 2A:
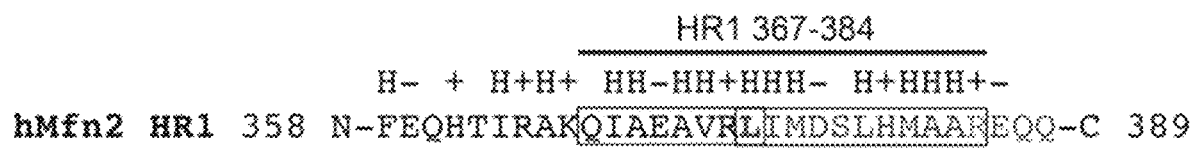
FIG. 2A, FIG. 2B, FIG. 2C, FIG. 2D, FIG. 2E, FIG. 2F, FIG. 2G and FIG. 2H are a series of images and graphs showing MFN2 $Ser^{378}$ phosphorylation by PINK1 regulates mitochondrial fusion. (A) Amino acid sequence surrounding fusion-promoting MFN2 peptide. Side chain characteristics (H, hydrophobic; +, basic; −, acidic) are above. (B) Mitochondrial fusion stimulated by N- and C-terminal minipeptides. Aspect ratio is mitochondrial long axis/short axis. Inset: Fusion in MFN1- and MFN2-null MEFs. (C) Alanine (A) scanning of minipeptide 374-384 fusion activity. (D) Ser378 substitution analysis of minipeptide 374-384 fusion activity. p values in D and E are vs parent minipeptide 374-384 (ANOVA). (E) Binding of minipeptides with Ser378 substitutions to HR2 target sequence (n=6). (F) Binding of Asp378 minipeptide to HR2 target sequence before (left) and after (right) Ala substitution for putative interacting amino acids. (G) Ion chromatograms from assigned MFN2 Ser378 phosphopeptide fragment ions after incubation with PINK1 kinase (top) and stable isotope-labeled synthetic counterpart (bottom); proportional intensities are in adjacent stack plots. (H) Mitochondrial fusion promoted by MFN2 Ser378 mutants with and without PINK1 kinase; immunoblot of protein expression at bottom. p values are by ANOVA.
Figure 2B:
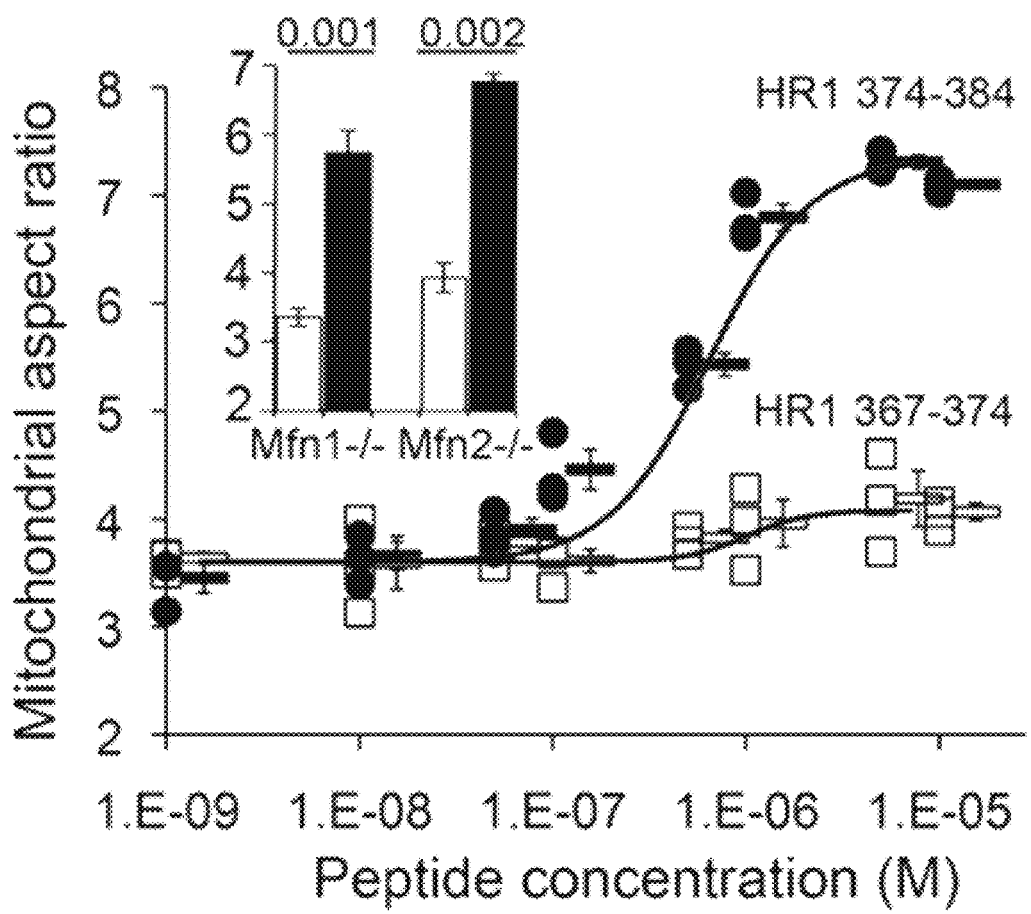
Figure 2C:
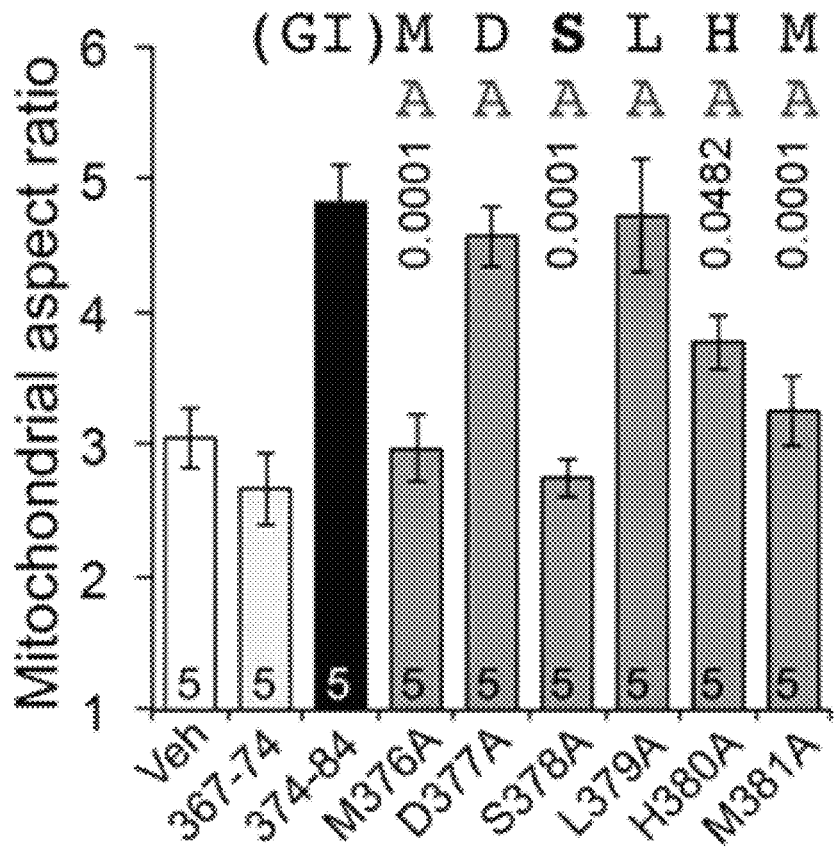
Figure 2D:
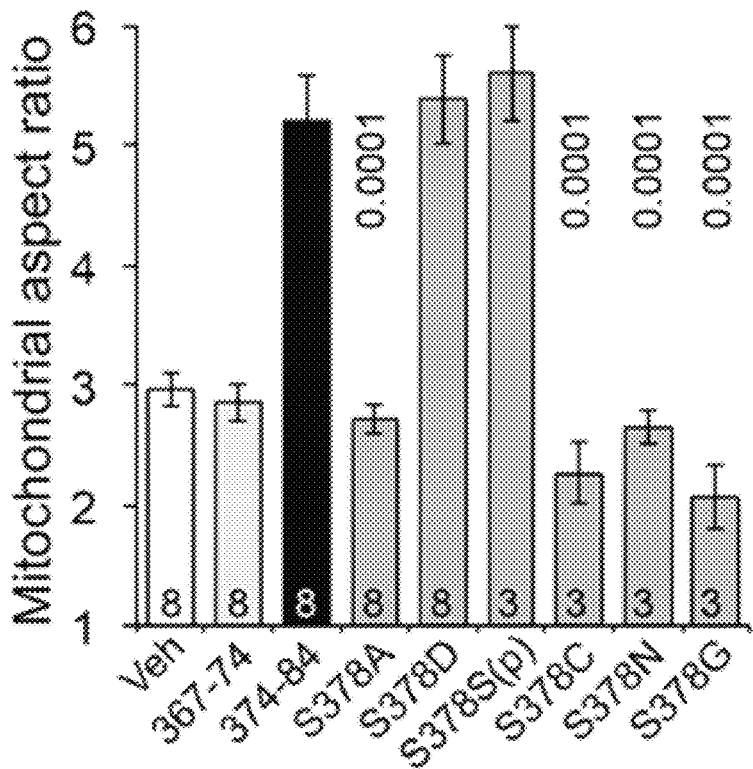

Group mean data from FIG. 2D are to the right; p values are by ANOVA with Tukey's post hoc comparison.

FIG. 16A, FIG. 16B, FIG. 16C and FIG. 16D are a series of NMR spectroscopy images and calculated structures. NMR spectroscopy suggests a structural mechanism for effects of Ser378 phosphorylation on HR1 372-384 minipeptide fusogenic function. (A) Amide proton regions of 2D NOESY spectra of Ala371 to Arg384 fragment of hMFN2. left—unphosphorylated Ser378 peptide; right—peptide synthesized with phosphorylated Ser-378. Sequential cross peaks between amide groups indicative of α-helical secondary structure are labeled. (B) Overlaid $^{15}N$-$^{1}H$ heteronuclear single quantum coherence spectra of minipeptide backbone amides (bold highlights on covalent wire-model to the left). Red is Ser378 peptide; green is (p)-Ser378 peptide. # marks the positions of Ser378 and (p)-Ser378. In addition to Ser378, the amide signals for amino acids 379-382 shifted down-field (i.e. to higher values) after phosphorylation, as observed when amides within peptides form or strengthen hydrogen bonds. Here, phosphorylation of Ser378 can induce hydrogen bonding for the amide of Leu379, stabilizing the downstream helix and evoking the observed down-field shifts for amides of His380 and Met381. (C) Ensembles of structures calculated from NMR restraints. Color coding is the same as in (B). (D) PepFold3 modeling of the HR1 minipeptide shows how different backbone structure provoked by Ser378 phosphorylation (see panel B) can alter Leu379 and His 380. * in (B) and (D) mark amino acids with the greatest changes between Ser378 and (p)-Ser378 peptides.

Figure 17A:
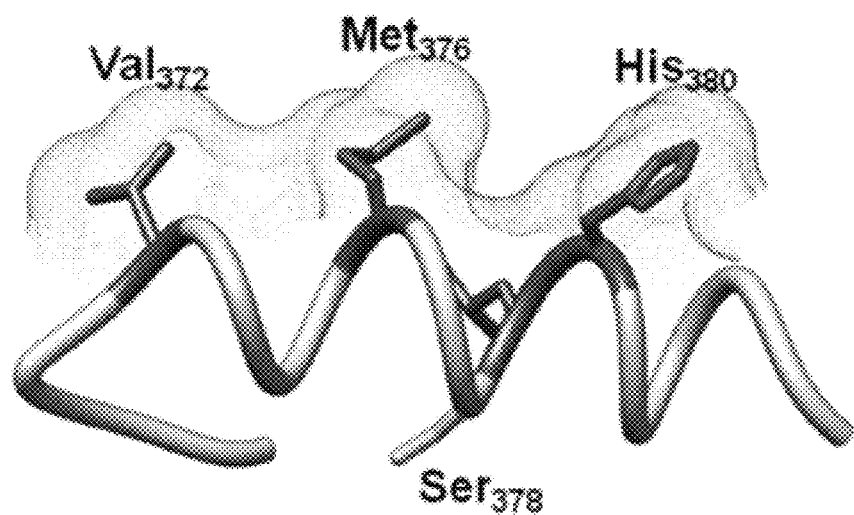
Figure 17B:
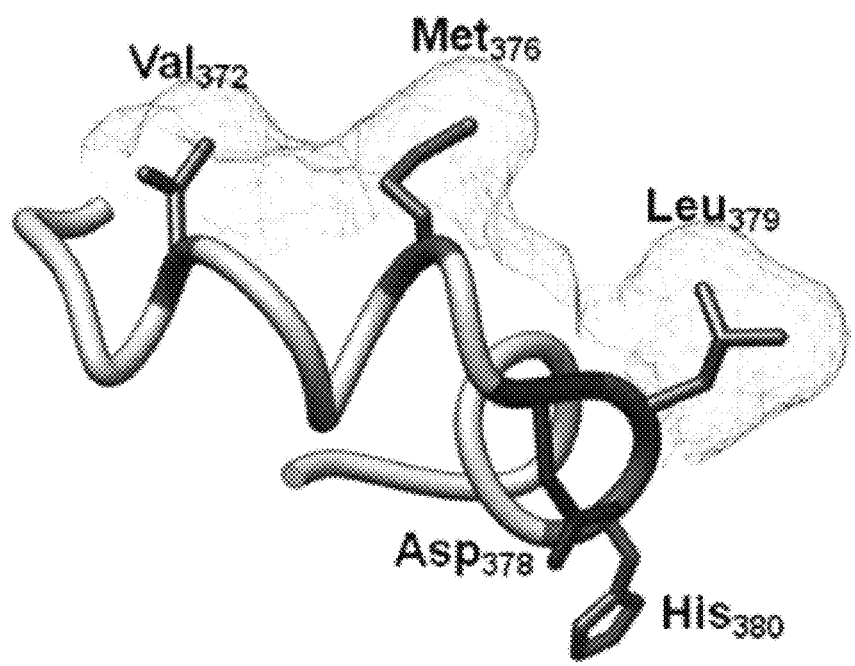

FIG. 17 show calculated structures from the modeling of HR1 MP374-384 conformation before (top) and after (bottom) S378 phosphorylation.

Figure 15A:
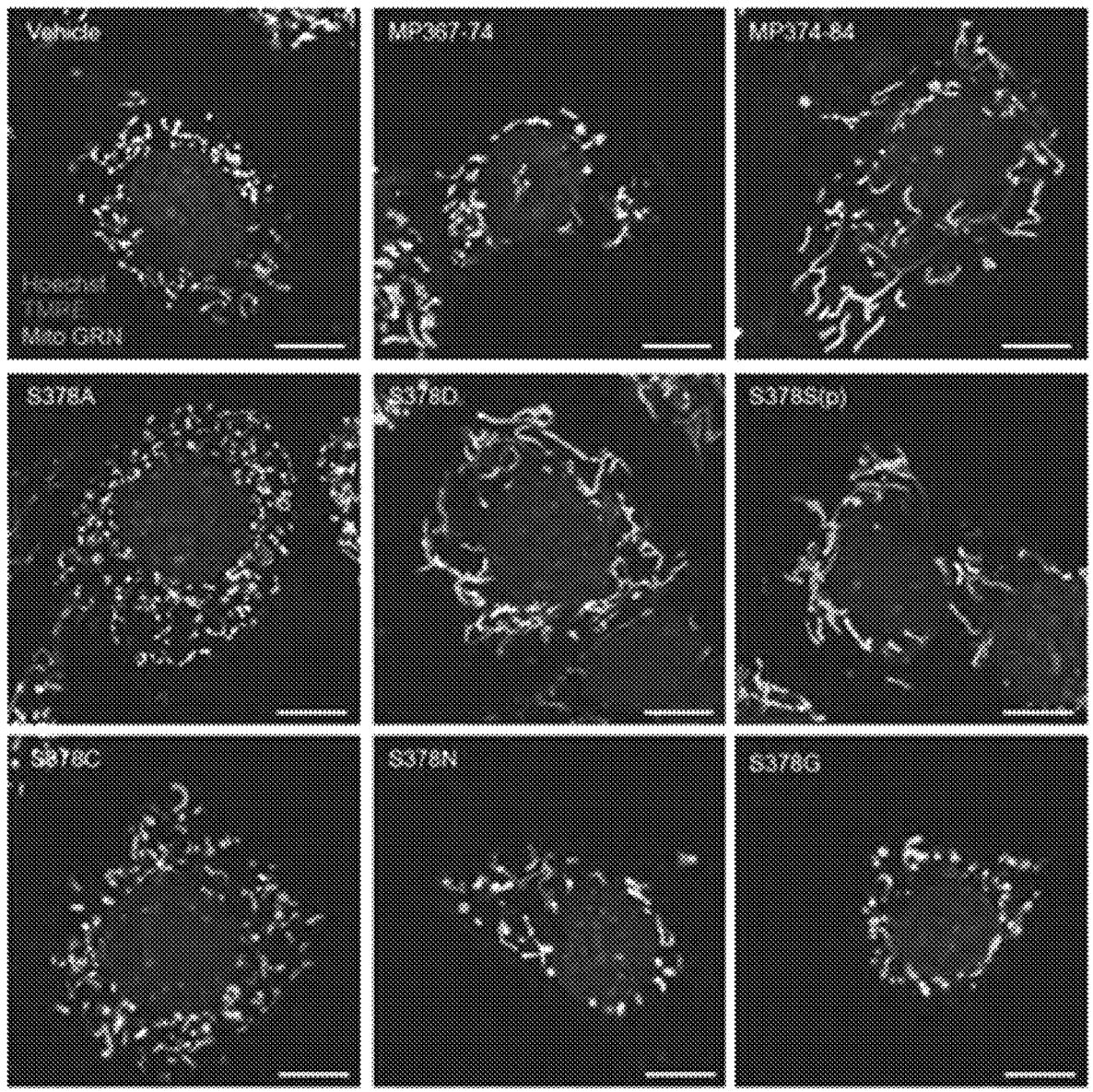
FIG. 15 is a series of images and a bar graph showing MFN2 Ser378 charge status determines fusion-promoting activity of HR1 MP374-384. Ser378 substitution analysis of mitochondrial fusion promoted by HR1 MP374-384. Representative confocal images of MitoTracker Green/TMRE (red) stained live cells are on the left; scale bars are 10 μm.
Figure 15B:
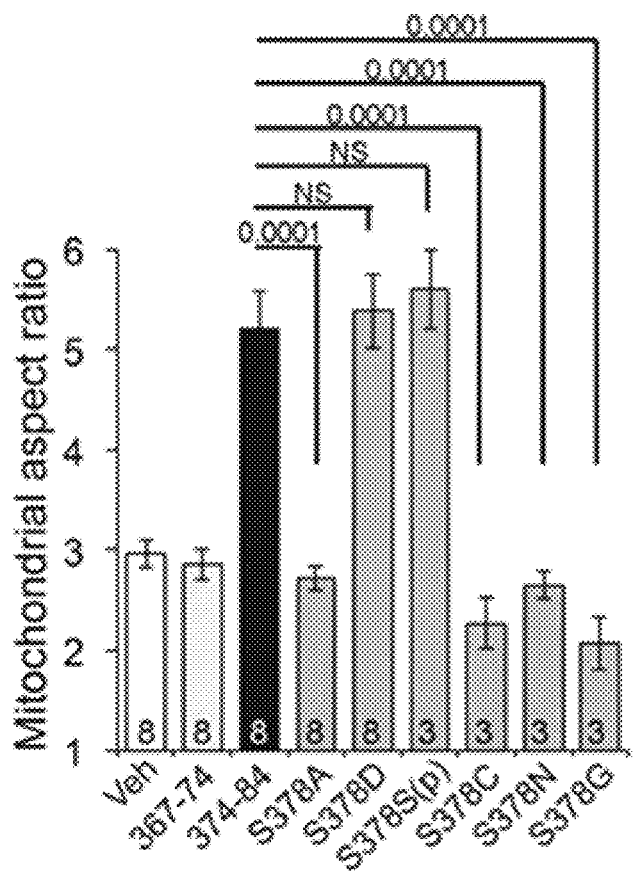
Figures 16A, 16B:
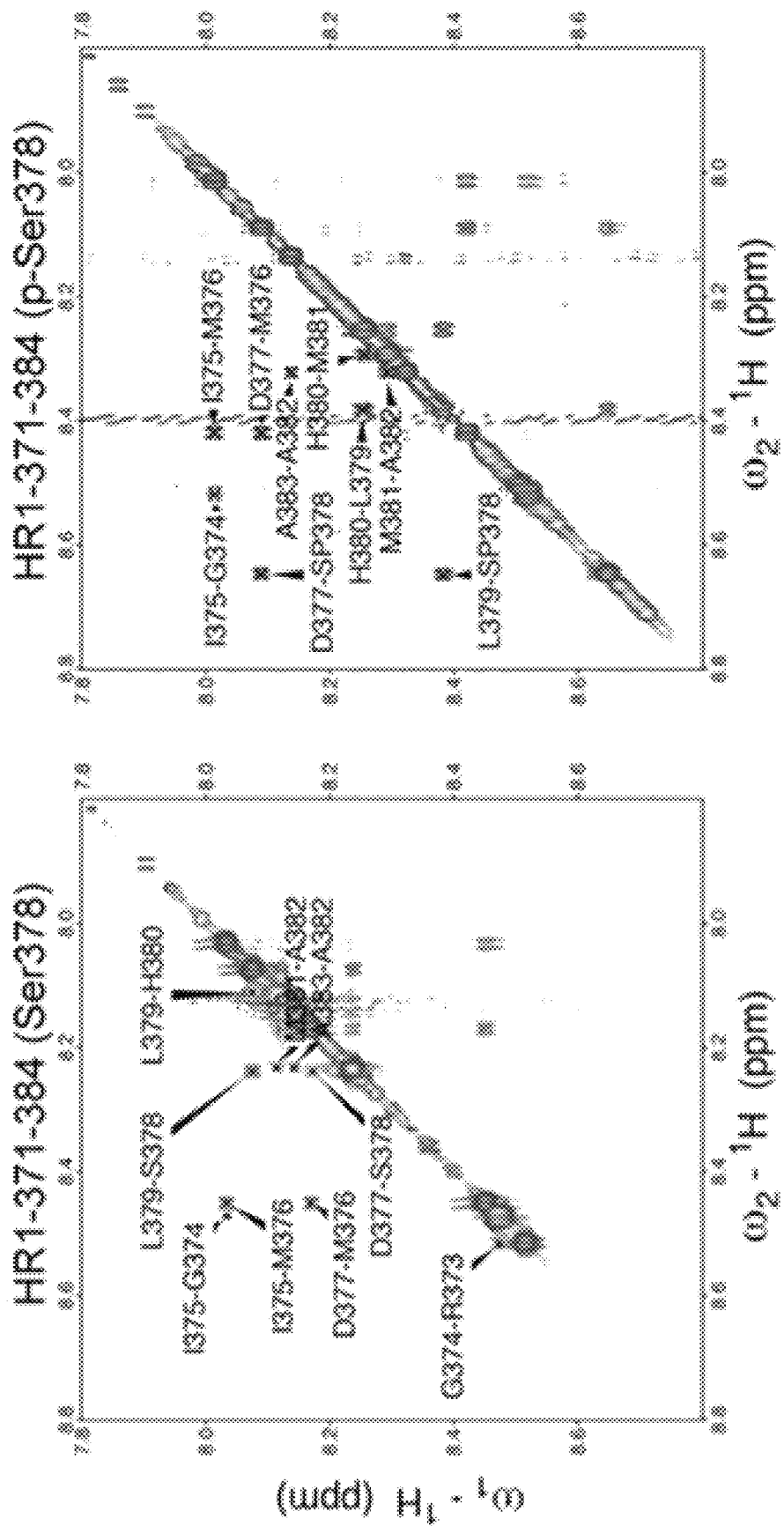
Figure 16C:
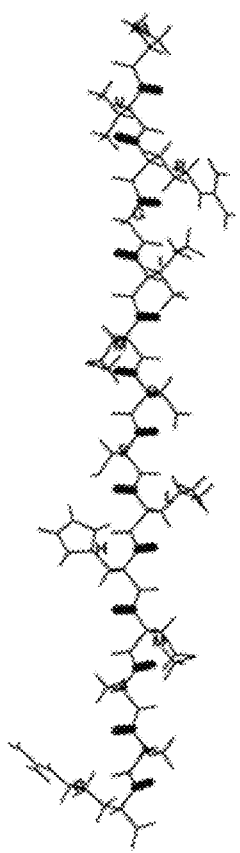
Figure 16D:
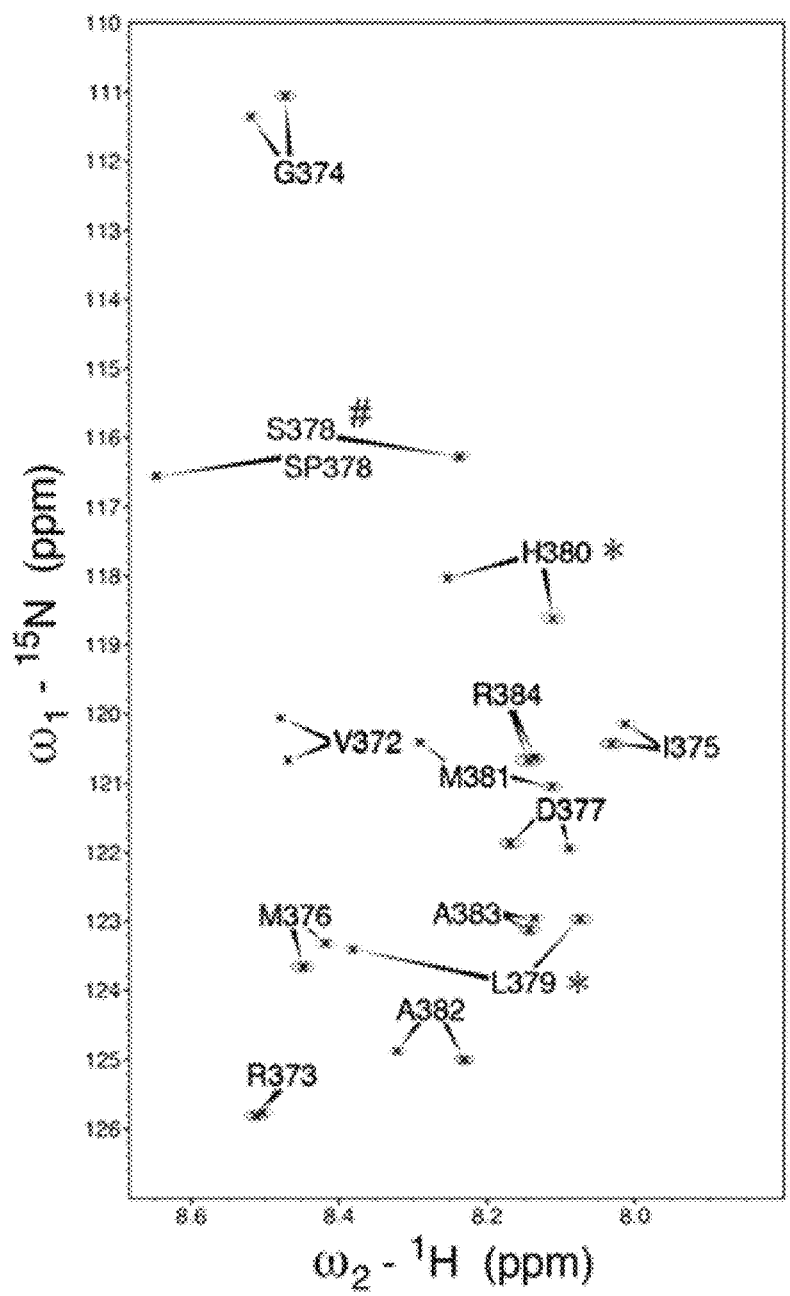
Figure 16E:
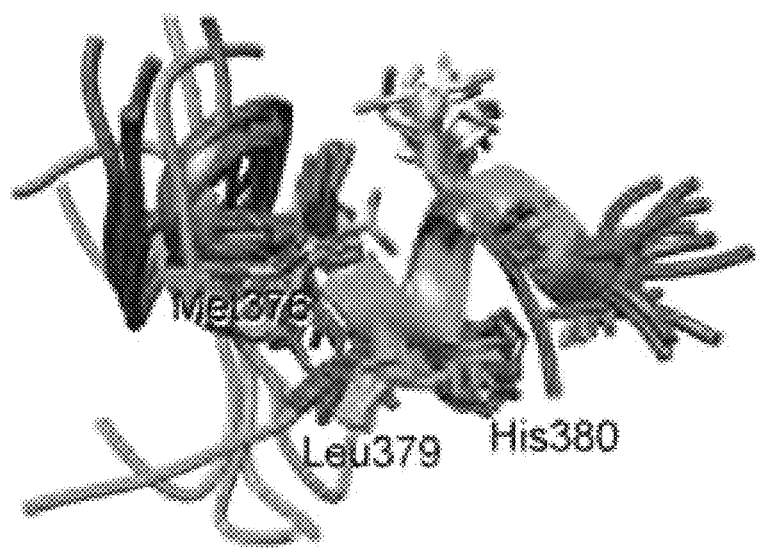
Figure 16F:
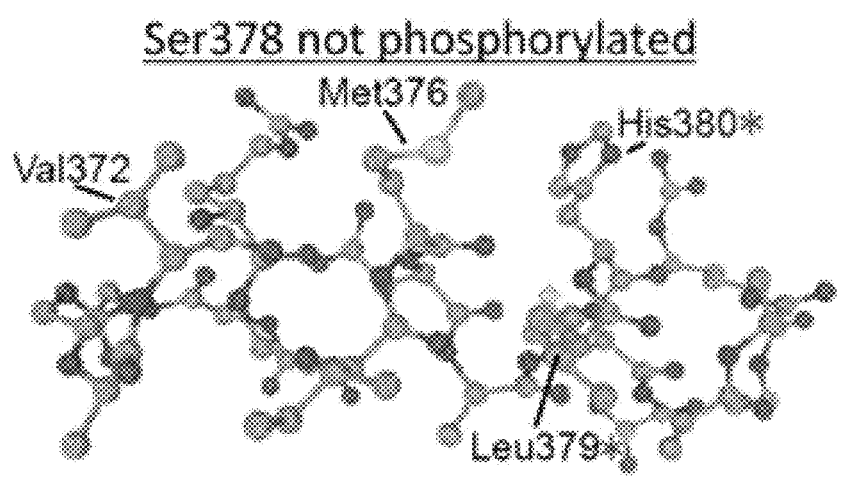
Figure 16G:
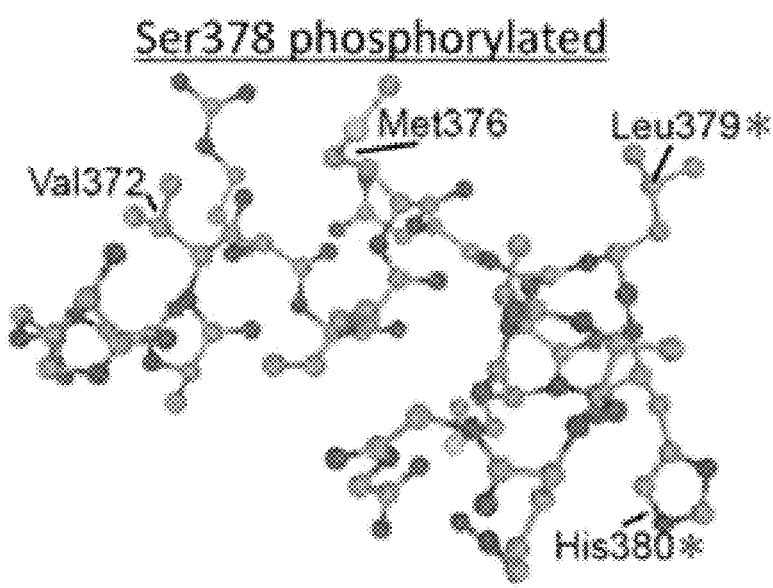
Figure 18F:
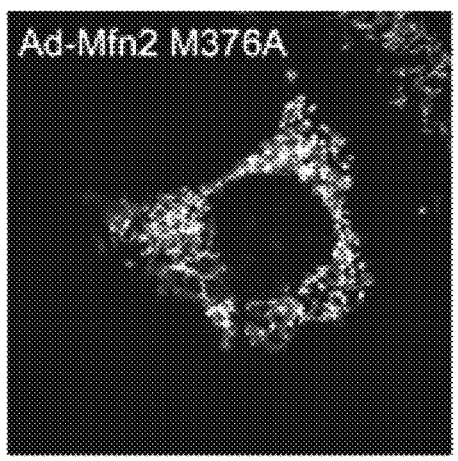
Figure 18G:
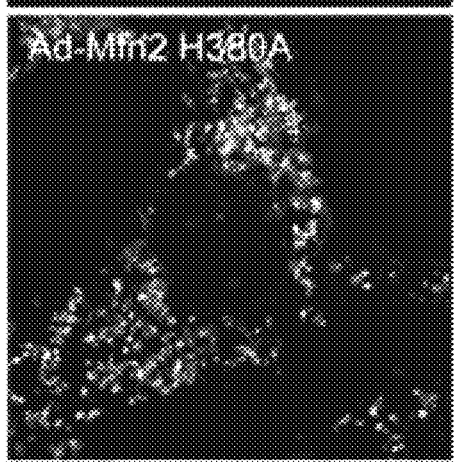
Figure 18H:
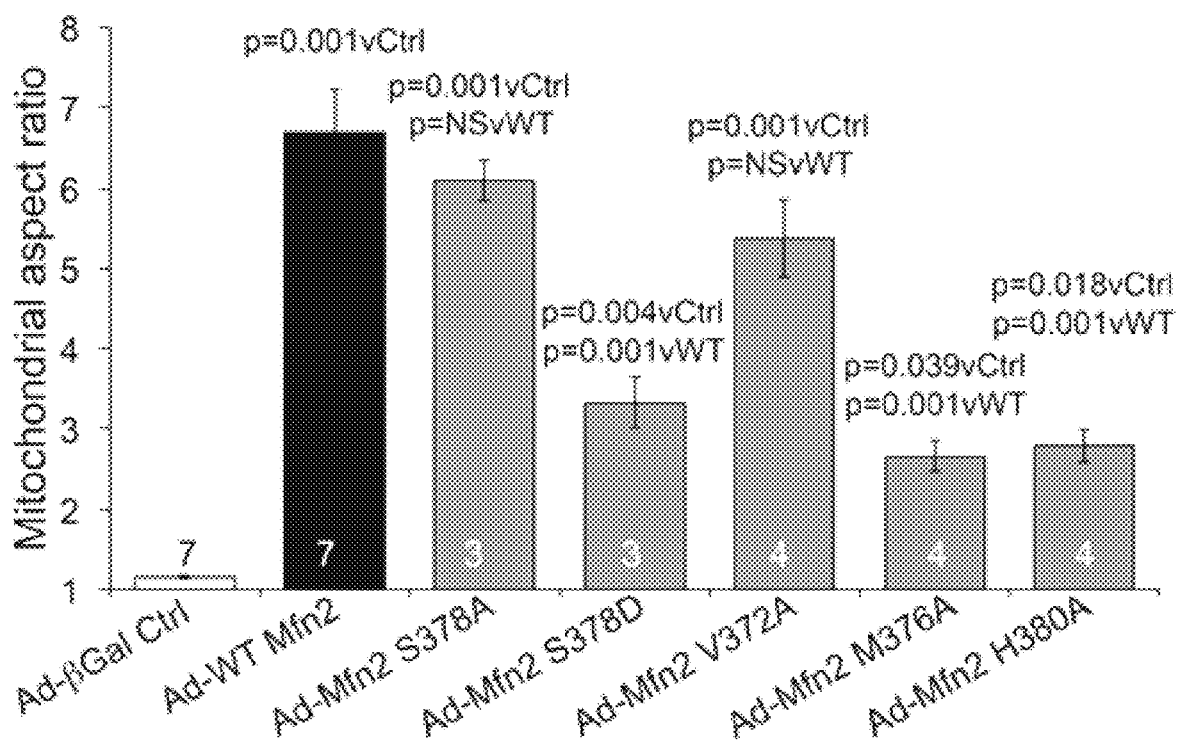
Figures 19A, 19B:
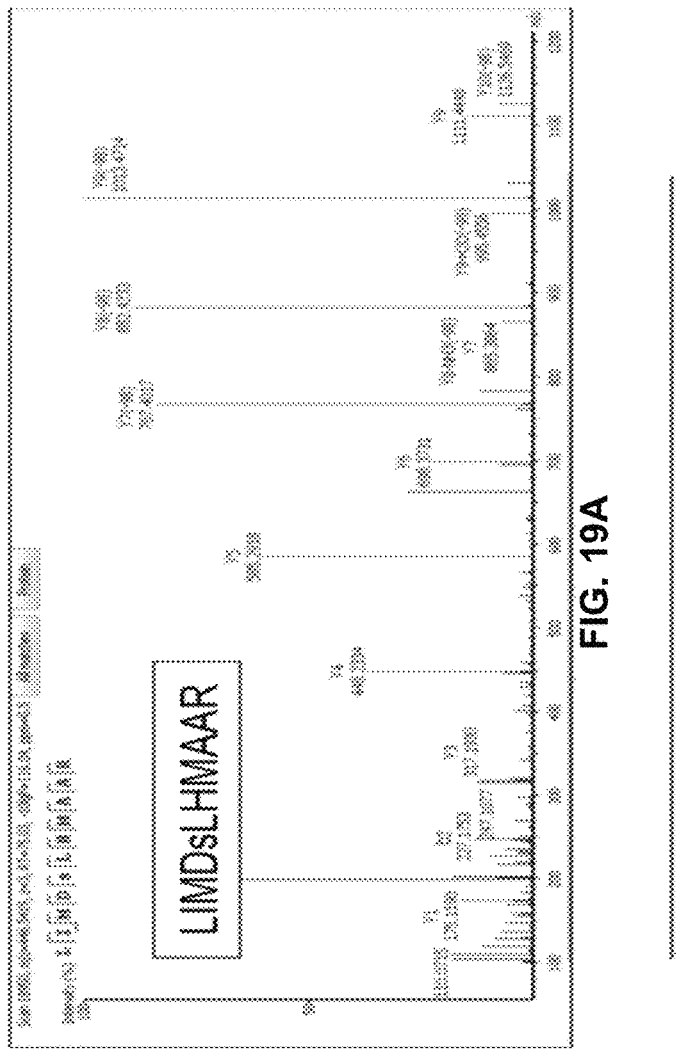
Figures 19C, 19D:
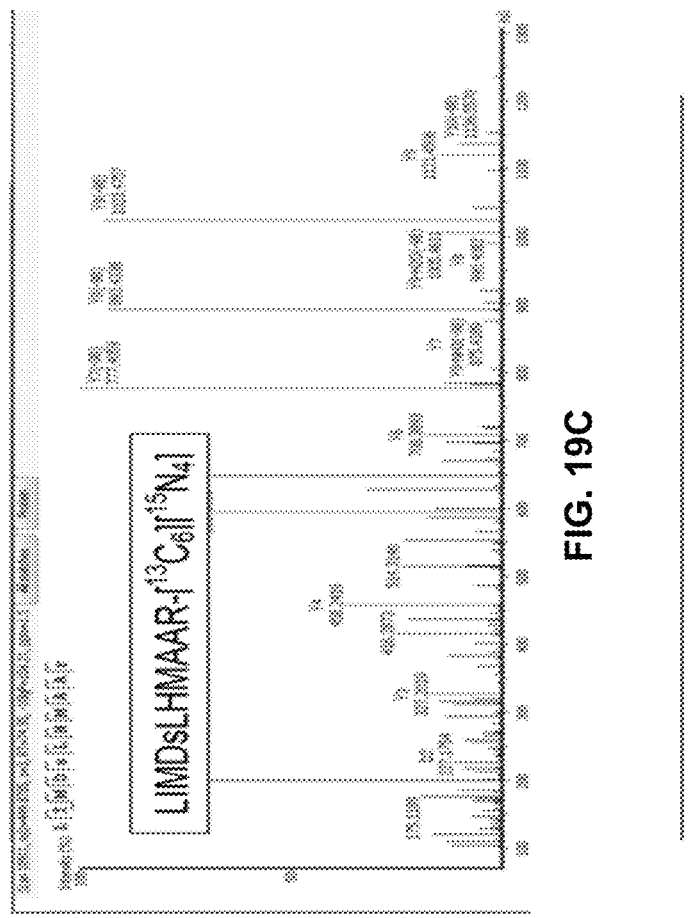
Figures 19E, 19F:
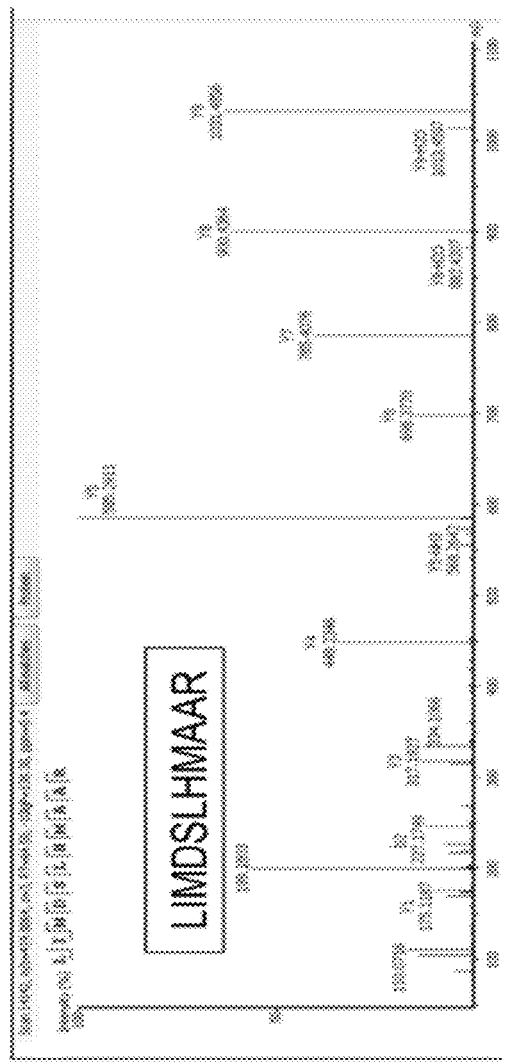
Figures 19G, 19H:
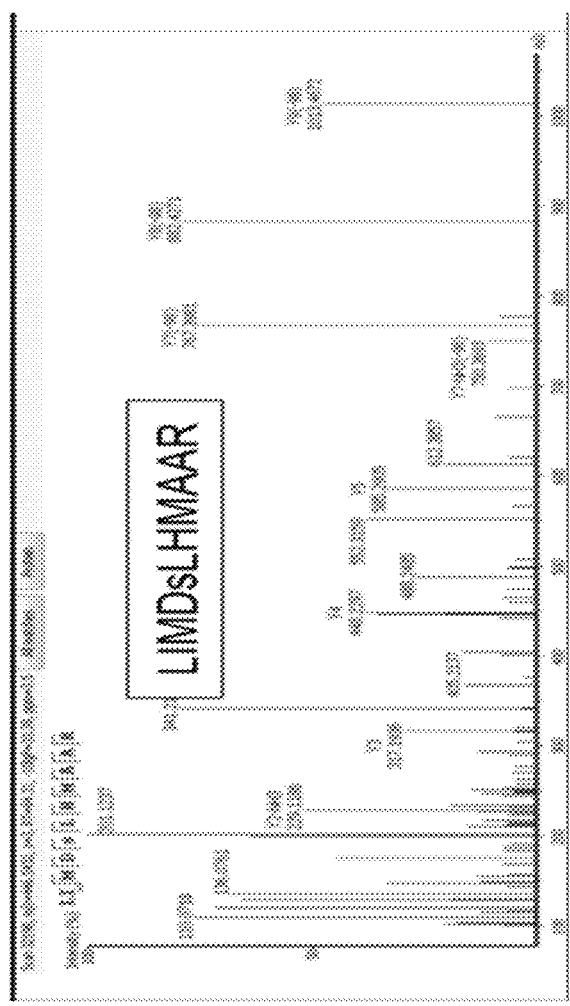
Figures 19I, 19J:
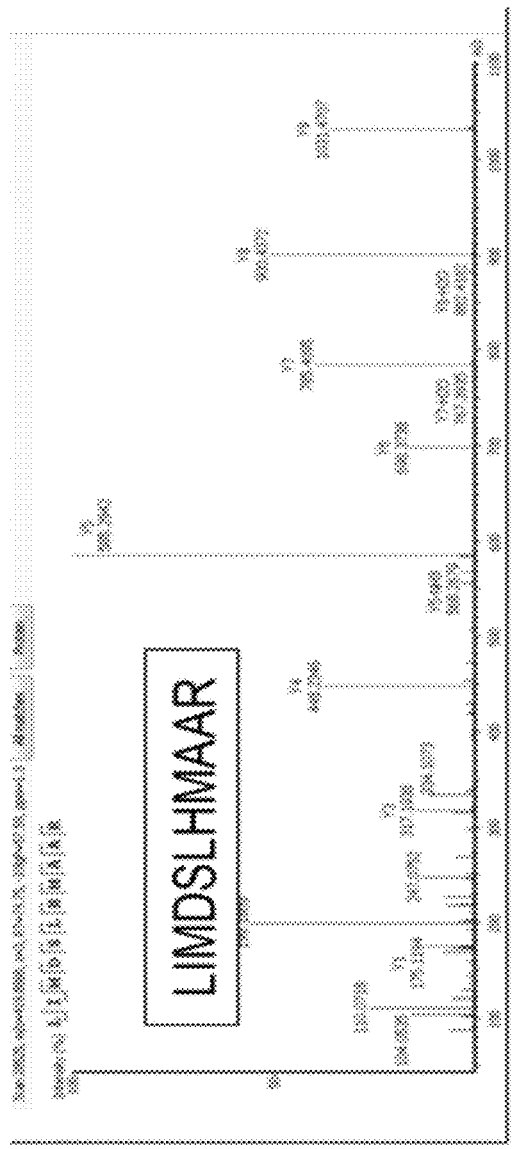

FIG. 18 shows mutagenesis analysis of MFN2-function based on Ser378 phosphorylation status and integrity of Met376 and His380 that are spatially regulated by Ser378 phosphorylation. Group data and representative confocal images showing mitochondrial aspect ratio in mitofusin deficient cells (MFN1−/−, MFN2−/− MEFs) infected with adnoviri expressing β-galactosidase (negative control), wild-type (WT) MFN2 (positive control), or different single amino acid MFN2 mutants. Fusogenic function was impaired in pseudo-phosphorylated MFN2 Ser378Asp (S378D) and alanine-substituted MFN2 Met376Ala (M376A) and His380Ala (H380A); non-phosphorylatable MFN2 Ser378Ala (S378A) and MFN2 Val372Ala (V372A), which is not in the HR1-HR2 interacting domain) retained full activity. p values are by ANOVA with Tukey's post hoc comparison. MEFs were stained as described in FIG. 15 legend. Scale bar is 10 μm.

FIG. 19A, FIG. 19B, FIG. 19C, FIG. 19D, and FIG. 19E are a series of high-resolution tandem mass spectra of peptides from a tryptic digest of PINK1-treated recombinant human MFN2. The spectra of the phosphopeptide with the Ser-378 phosphorylation site (A), a stable isotope-labeled synthetic phosphopeptide (B), and the non-phosphorylated peptide (C) are shown from a 4-hour in vitro PINK1 phosphorylation experiment. (D) and (E) are like (A) and (C) after an overnight period for PINK1 phosphorylation. The m/z values for the assigned ions are highlighted in the adjacent ion tables.

Figure 20A:
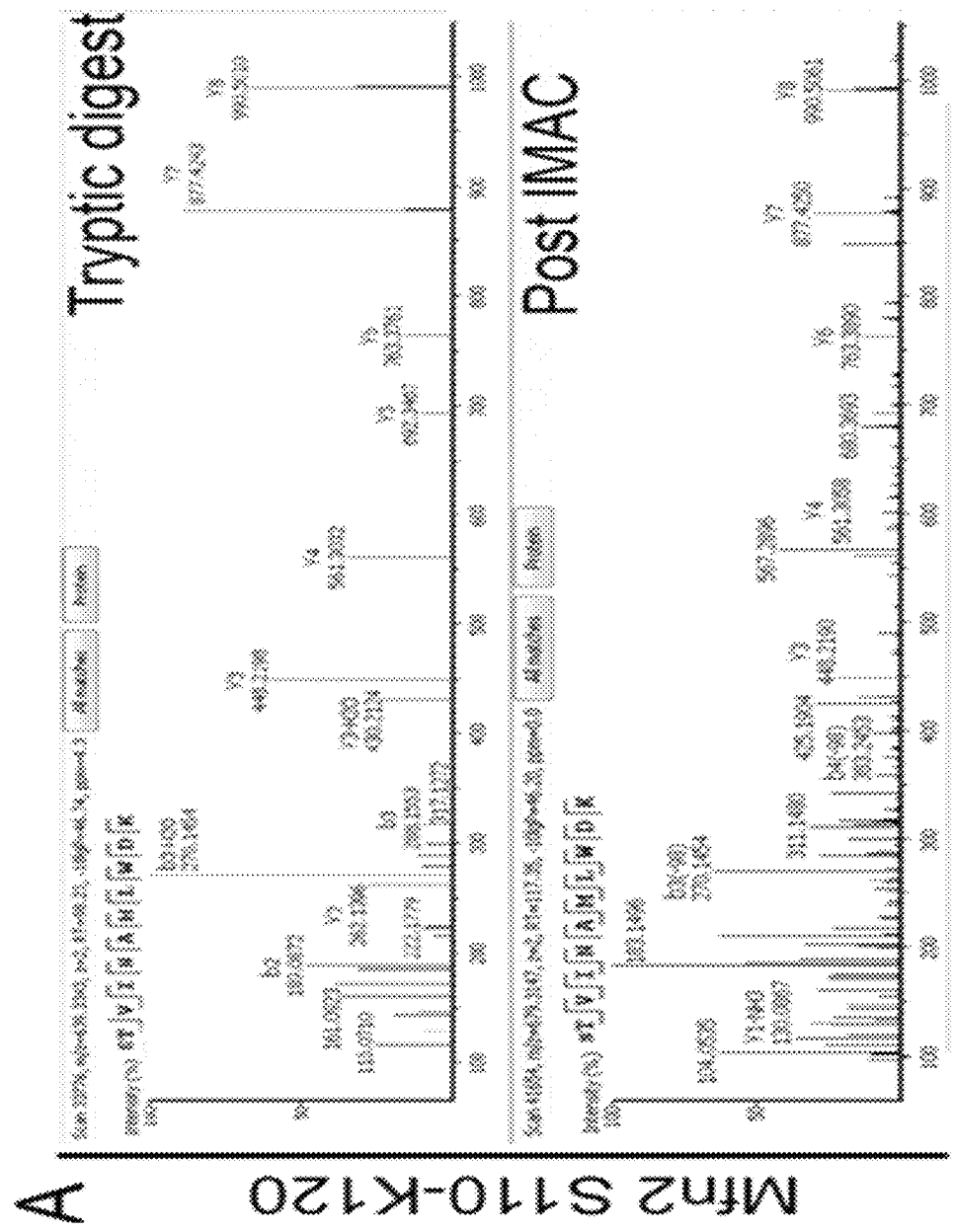
Figure 20B:
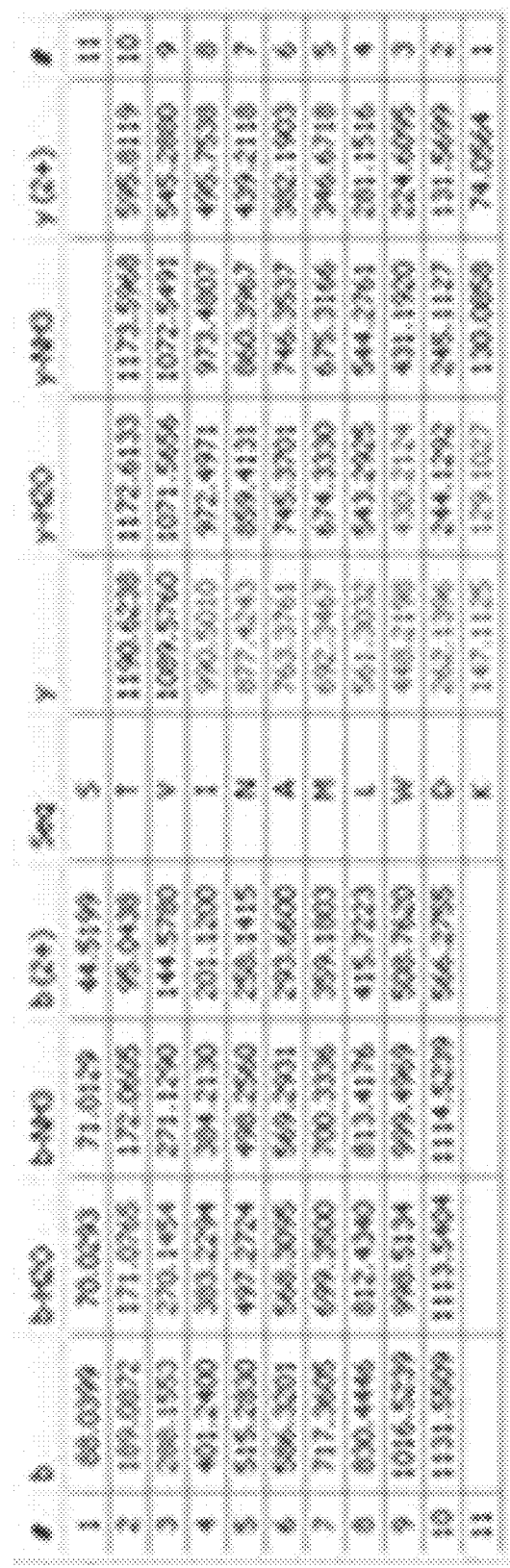
Figure 20B:
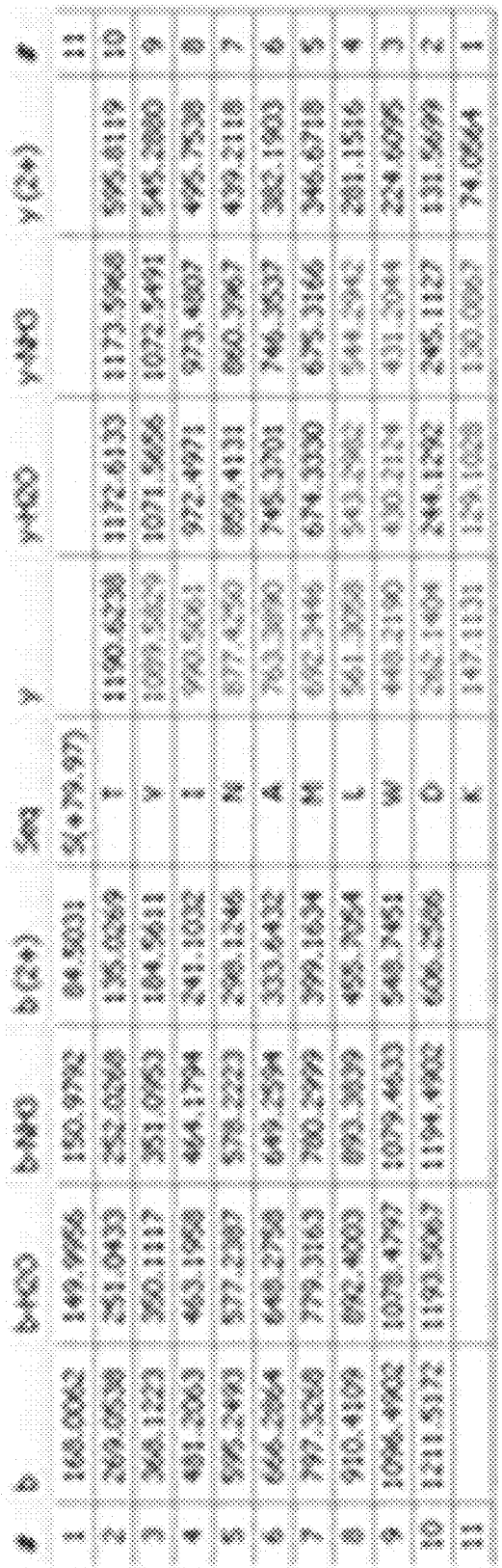
Figure 20C:
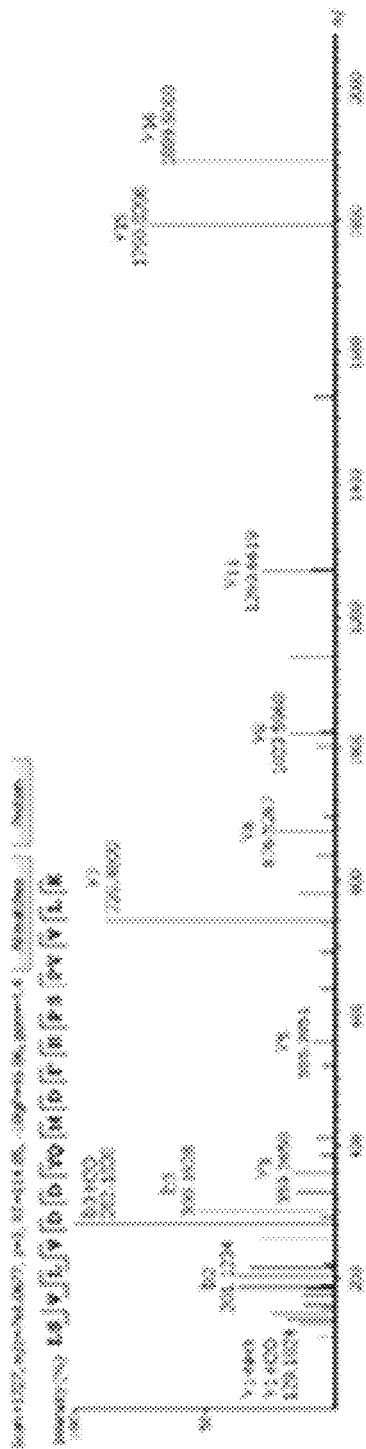
Figure 20C:
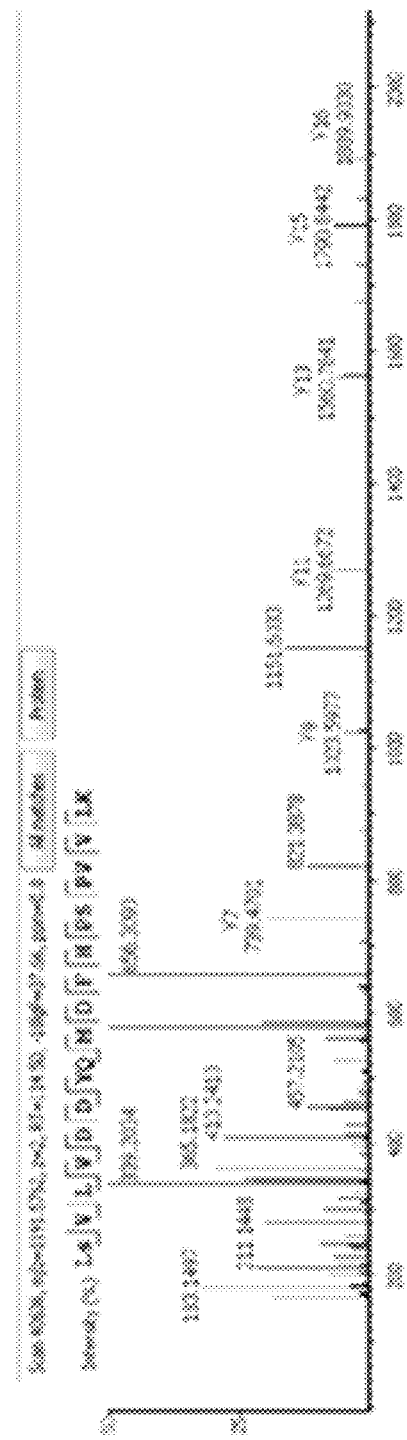
Figures 20D, 20E:
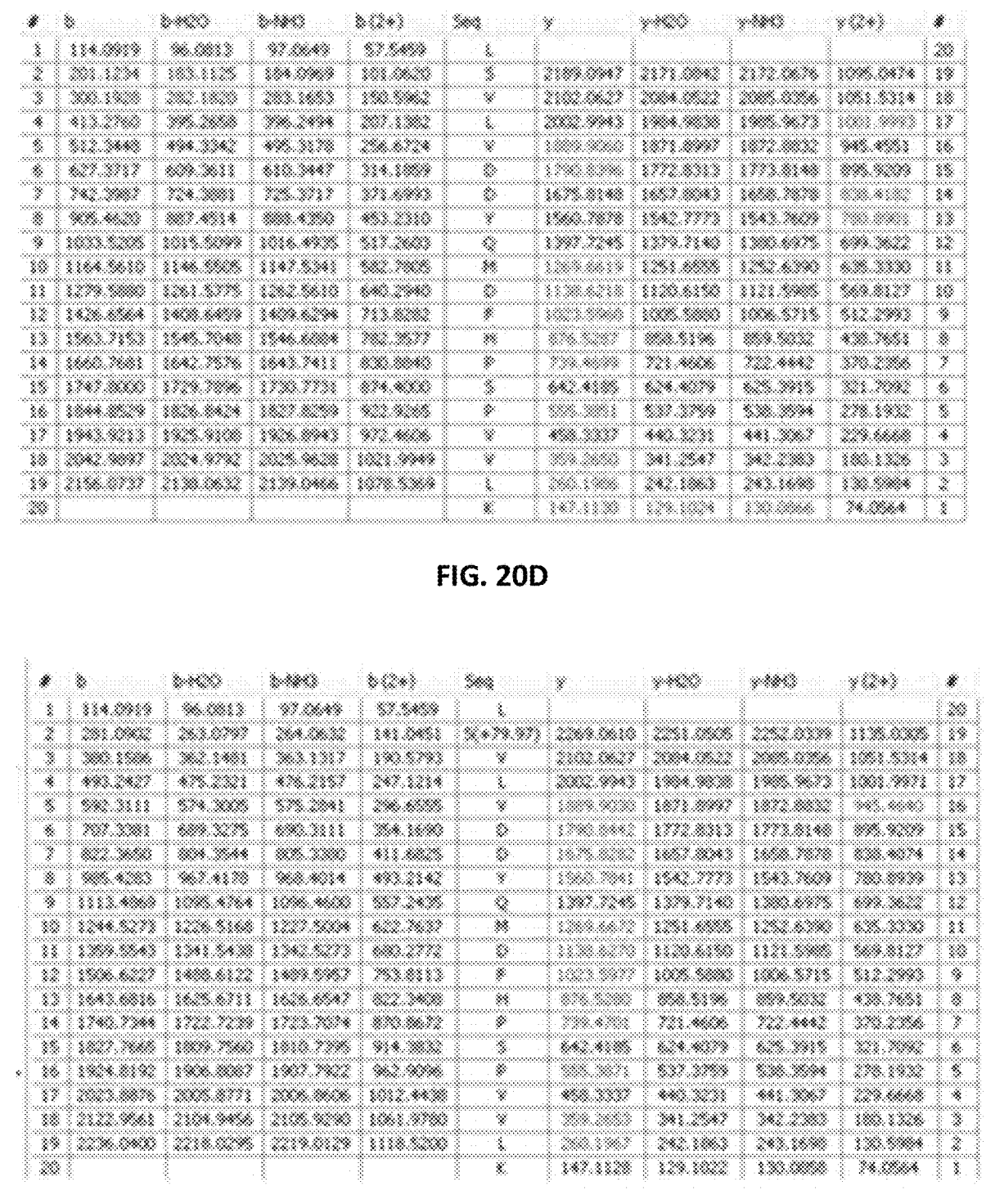

FIG. 20A and FIG. 20B are a series of high-resolution mass spectra of PINK1-phosphorylated recombinant human MFN2 demonstrating phosphorylation of Thrill (A) and Ser442 (B). These spectra were obtained in the study shown in FIGS. 19D and E. m/z values for assigned fragmentation ions are shown to the right.

Figure 21A:
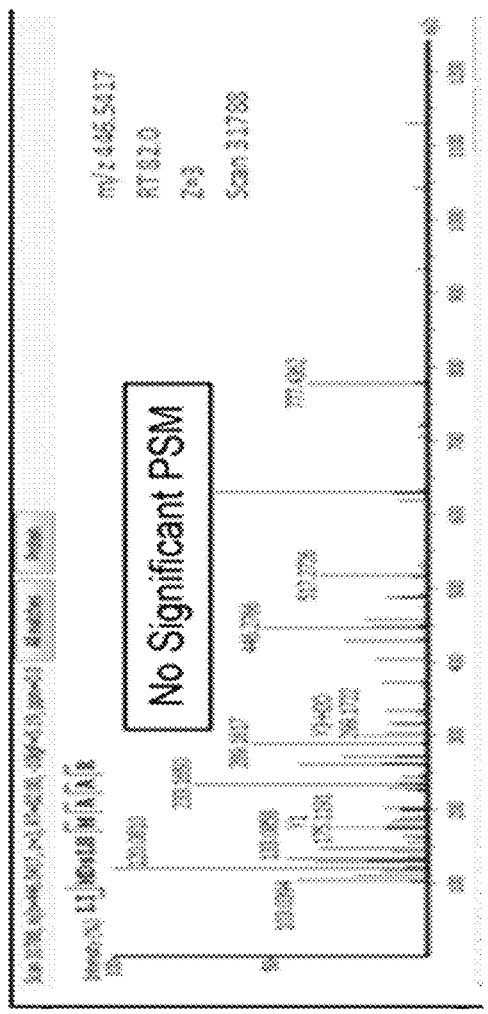
Figure 21B:
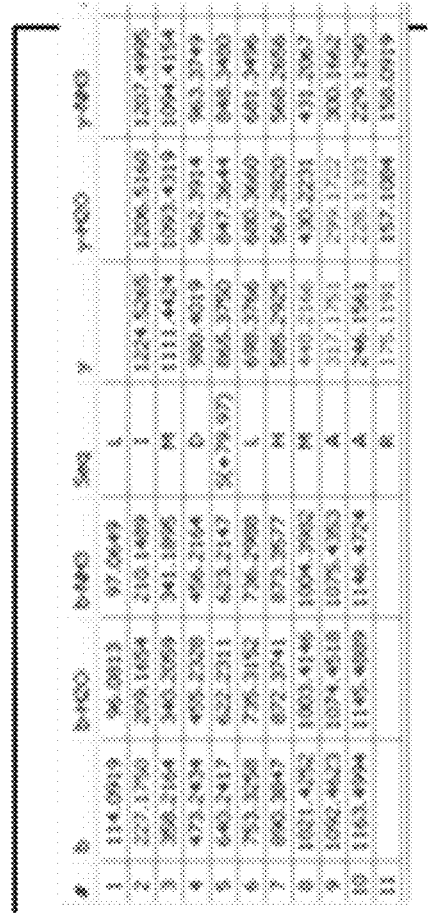
Figure 21C:
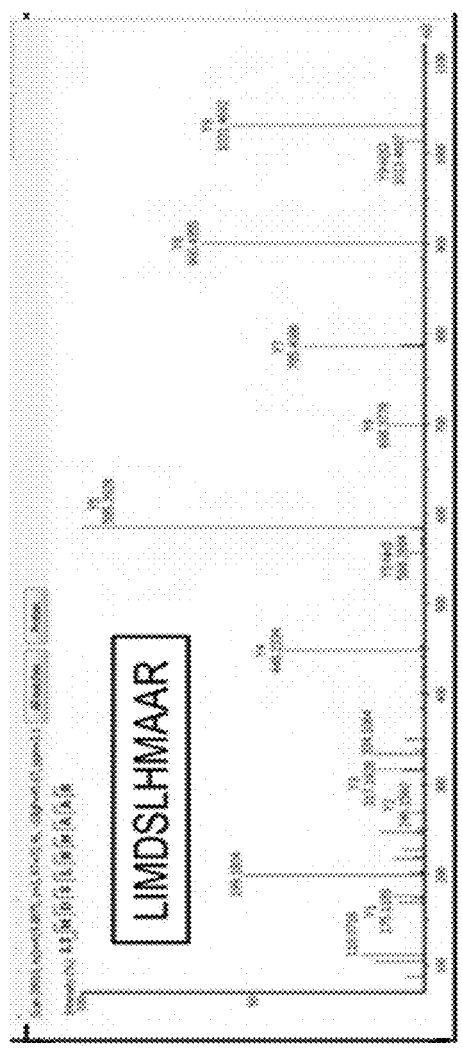
Figure 21D:
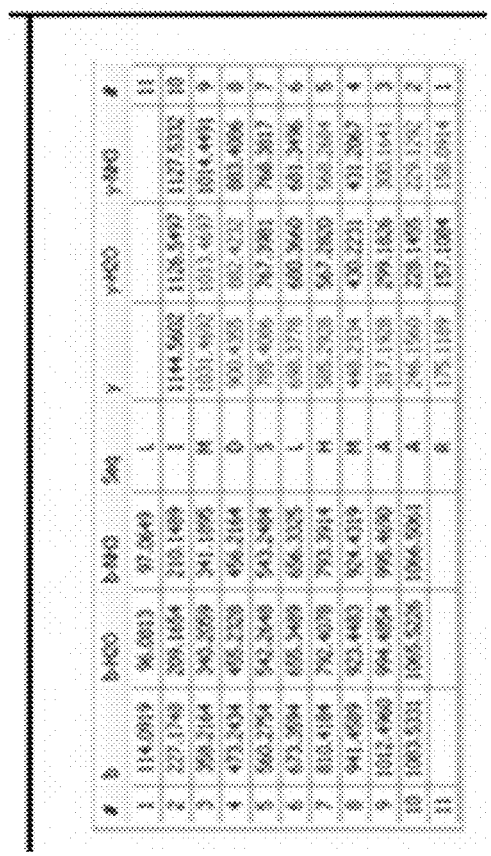
Figure 21E:
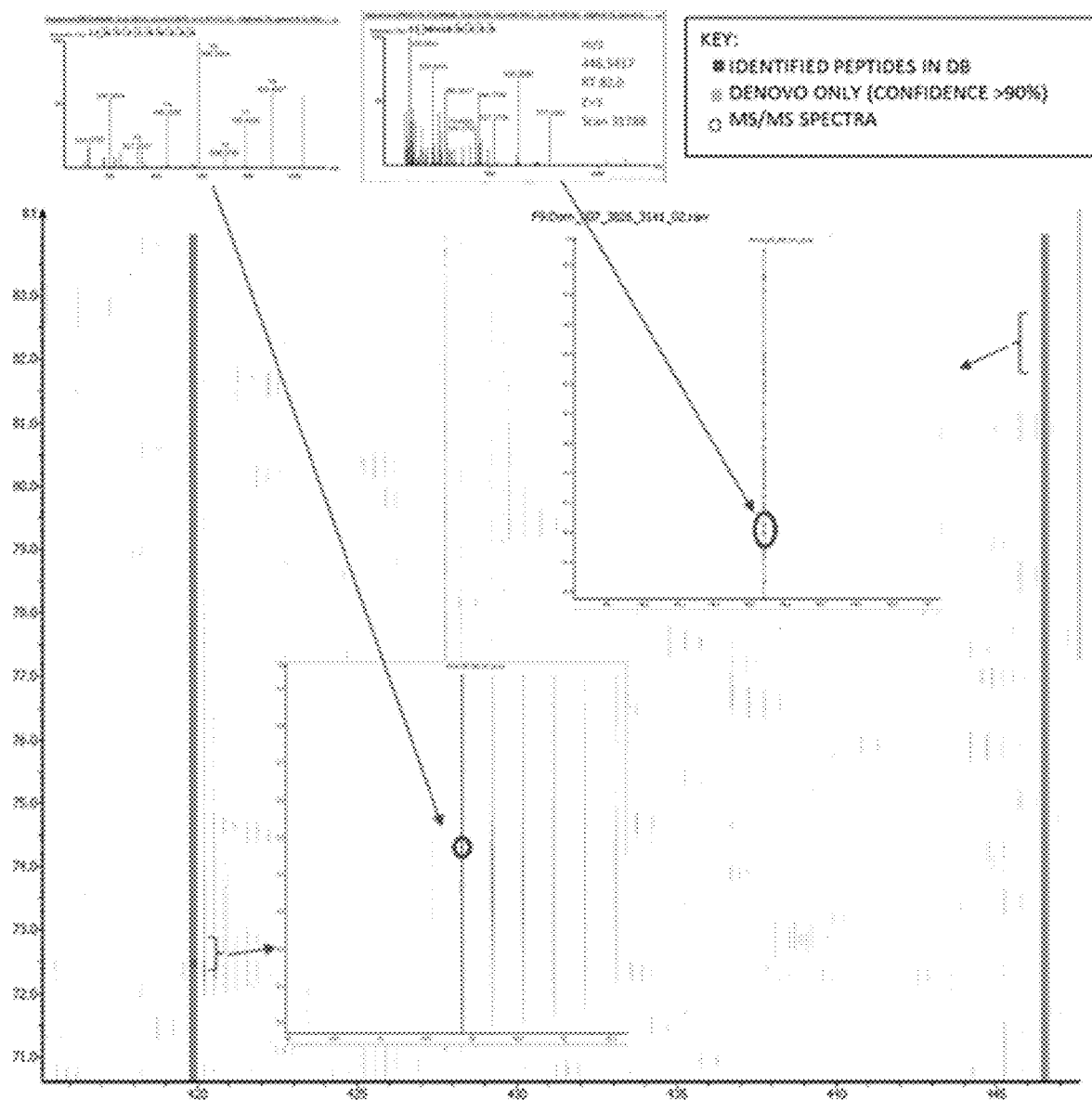

FIG. 21A, FIG. 21B, and FIG. 21C are a series of high-resolution tandem mass spectra of peptides from tryptic digest of GRK-treated recombinant human MFN2. (A) Representative non-matching spectrum from the elution window of the Ser-378 phosphopeptide. (B) Matching spectrum for the non-phosphorylated peptide from the GRK tryptic digest. The m/z values for the assigned ions are highlighted in the adjacent ion tables. (C) Retention time/m/z coordinates of tandem spectra that were analyzed by targeted LC-MS for phosphorylation of the Ser-378 containing peptide. The seven tandem spectra that were acquired at retention times between 82-83 min at m/z=446.542 showed no evidence of phosphorylation.

Figure 2E:
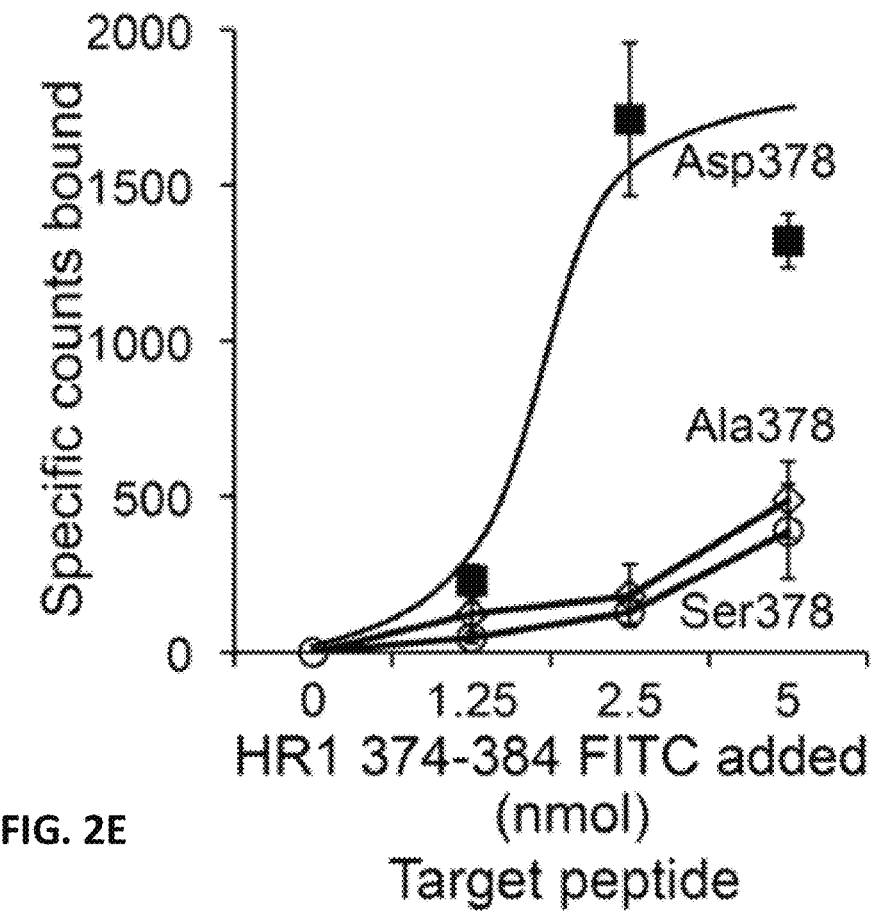
Figure 2F:
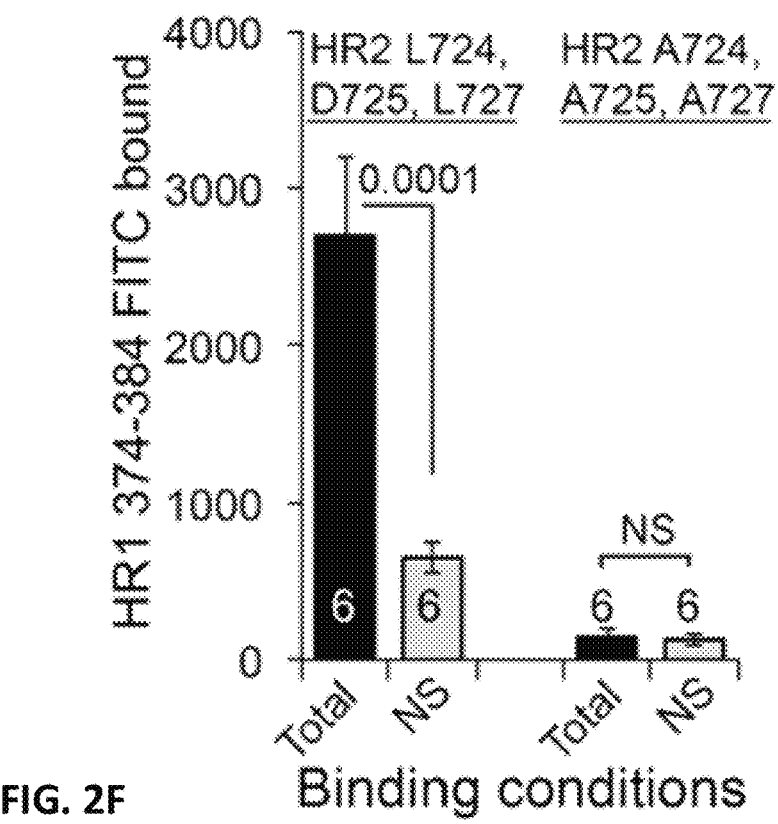
Figure 2G:
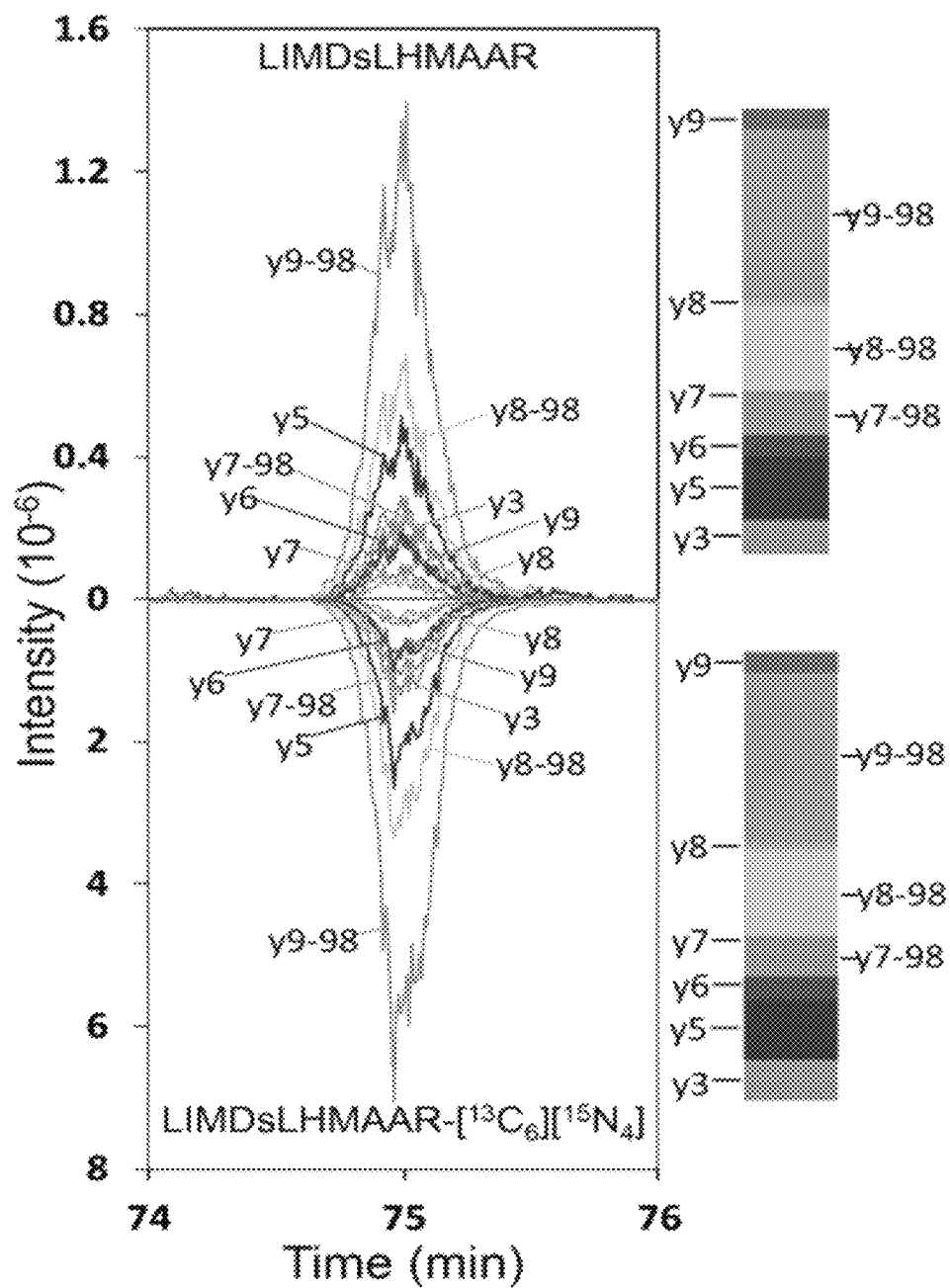
Figure 2H:
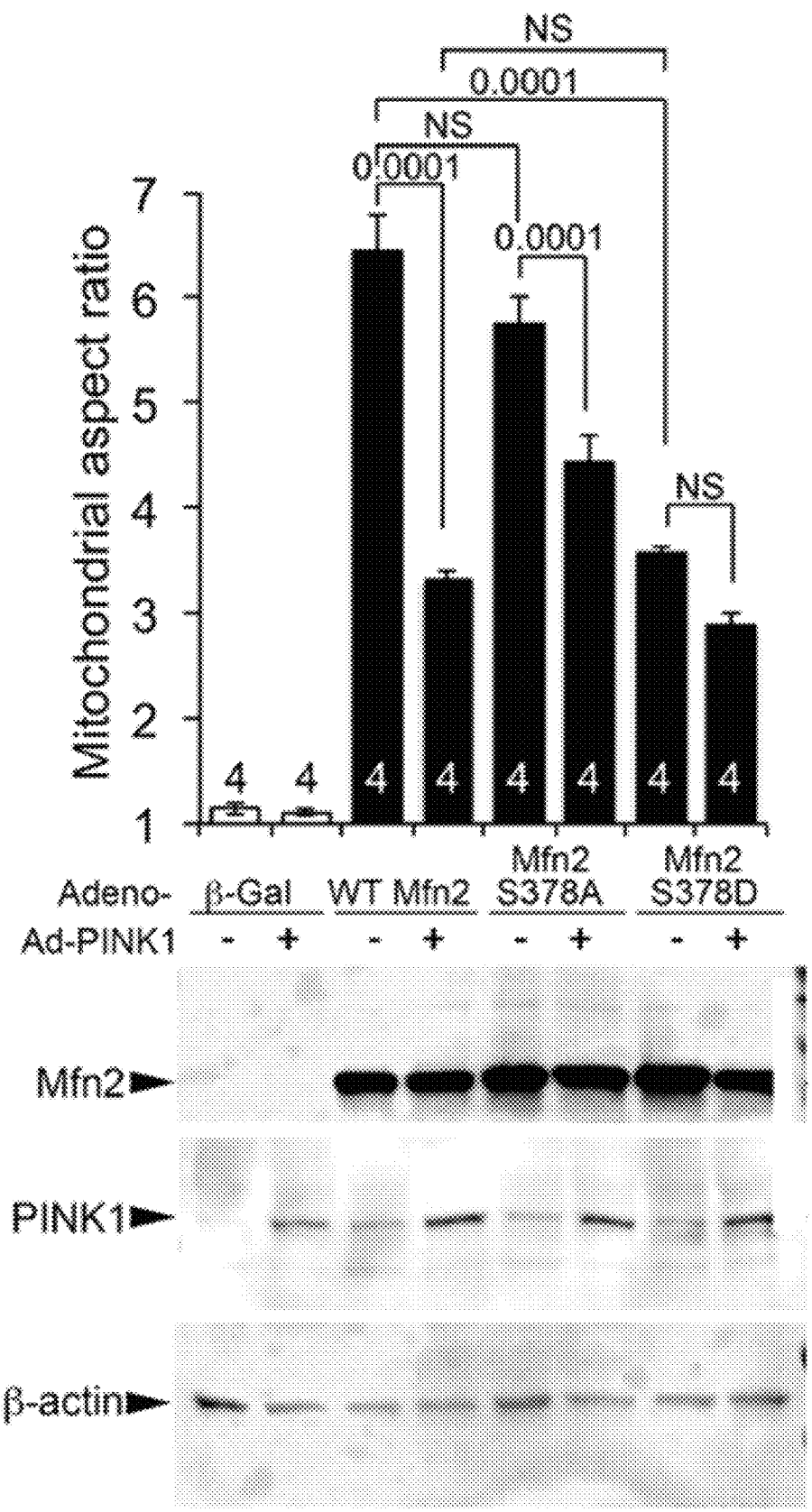
Figure 3A:
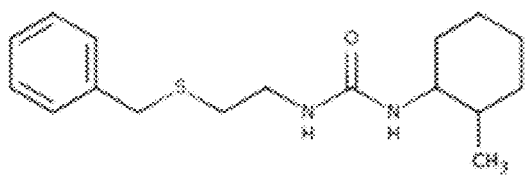
FIG. 3 shows the purification of mitofusin agonist compounds A and B. At the top are high performance liquid chromatography and mass spectra of compounds as they were obtained from the commercial vendor. On the bottom are spectra after in-house purification. Cpd A: expected m/z 306.18, exact mass found 307.3 $[M+H]^+$; Cpd B: expected m/z 453.15, exact mass found 454.3 $[M+H]^+$.
Figure 3A:
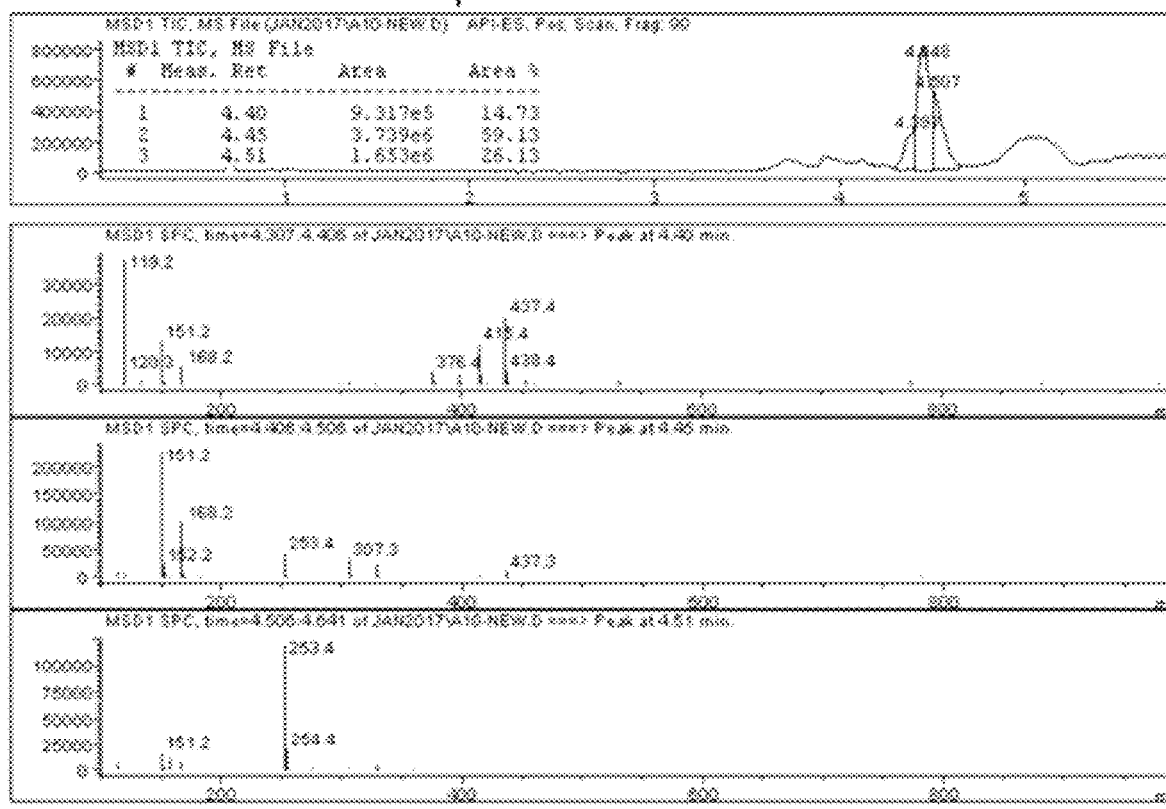
Figure 3A:
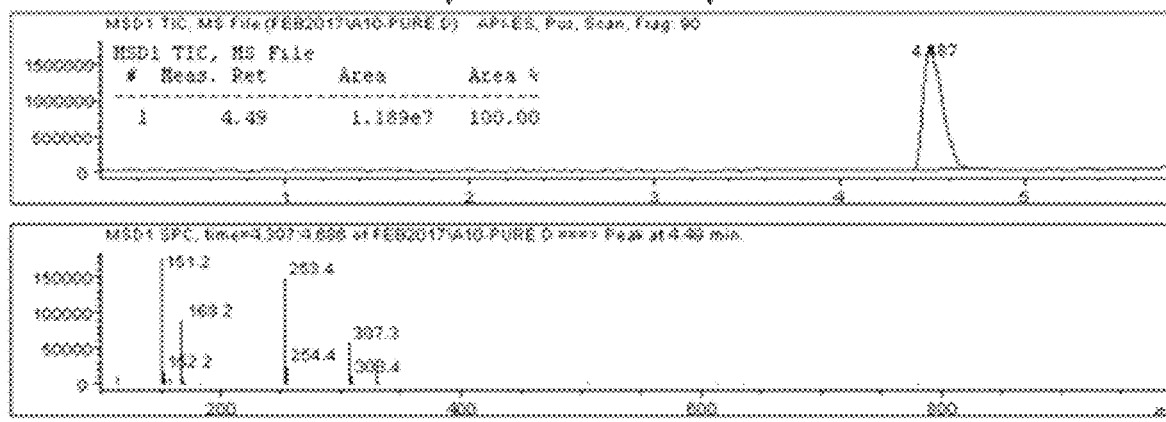
Figure 3B:
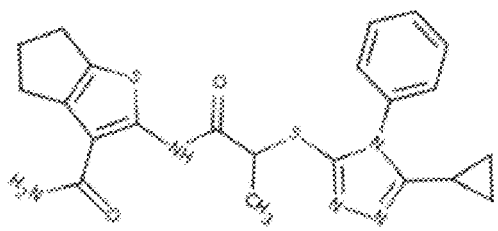
Figure 3B:
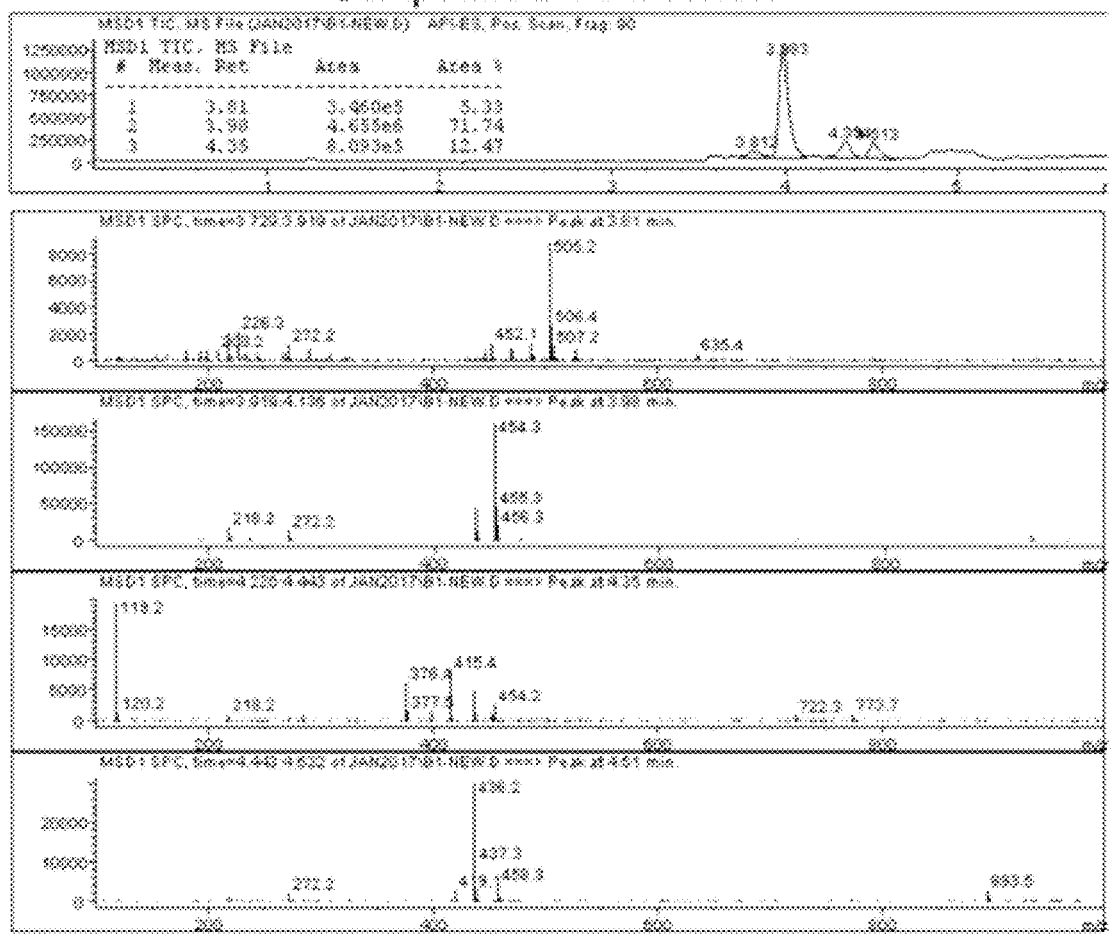
Figure 3B:
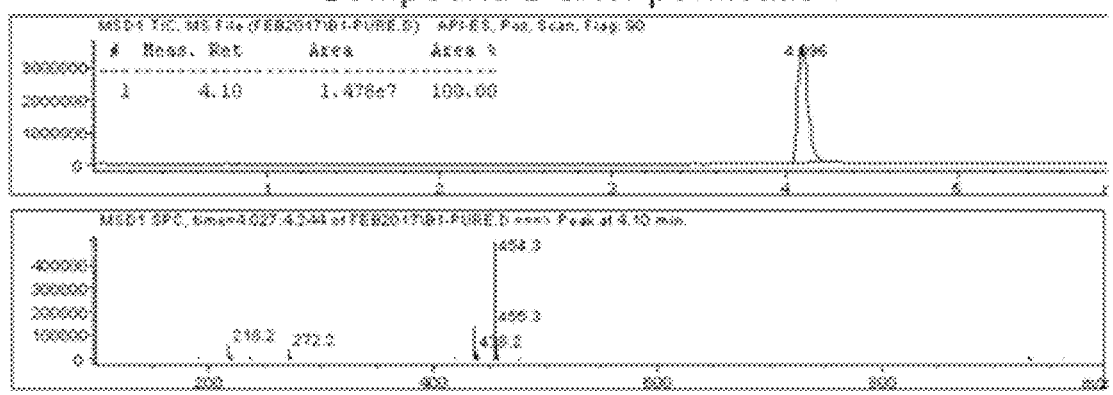
Figure 22:
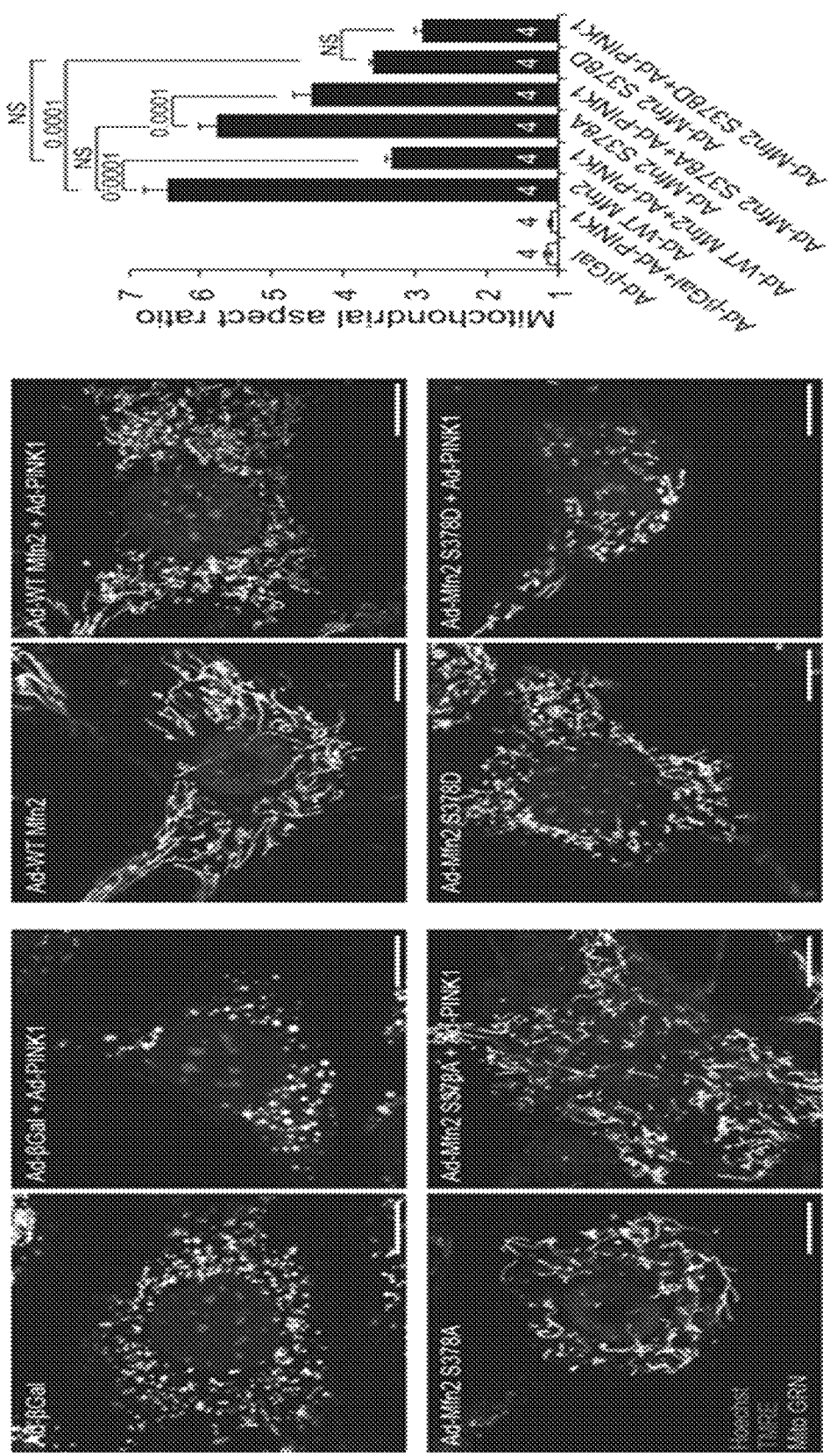

FIG. 22 is a series of representative live-cell confocal images and a bar graph from studies described in FIG. 2H. Mitochondria of MFN1−/−, MFN2−/− MEFs infected with adenoviri expressing MFN2 mutants with or without adenoPINK1 kinase were co-stained with MitoTracker Green (green) and TMRE (red); nuclei are stained blue with Hoechst. Scale bars are 10 μm. Quantitative group mean data to the right are reproduced from FIG. 2H for comparison.

Figure 23:
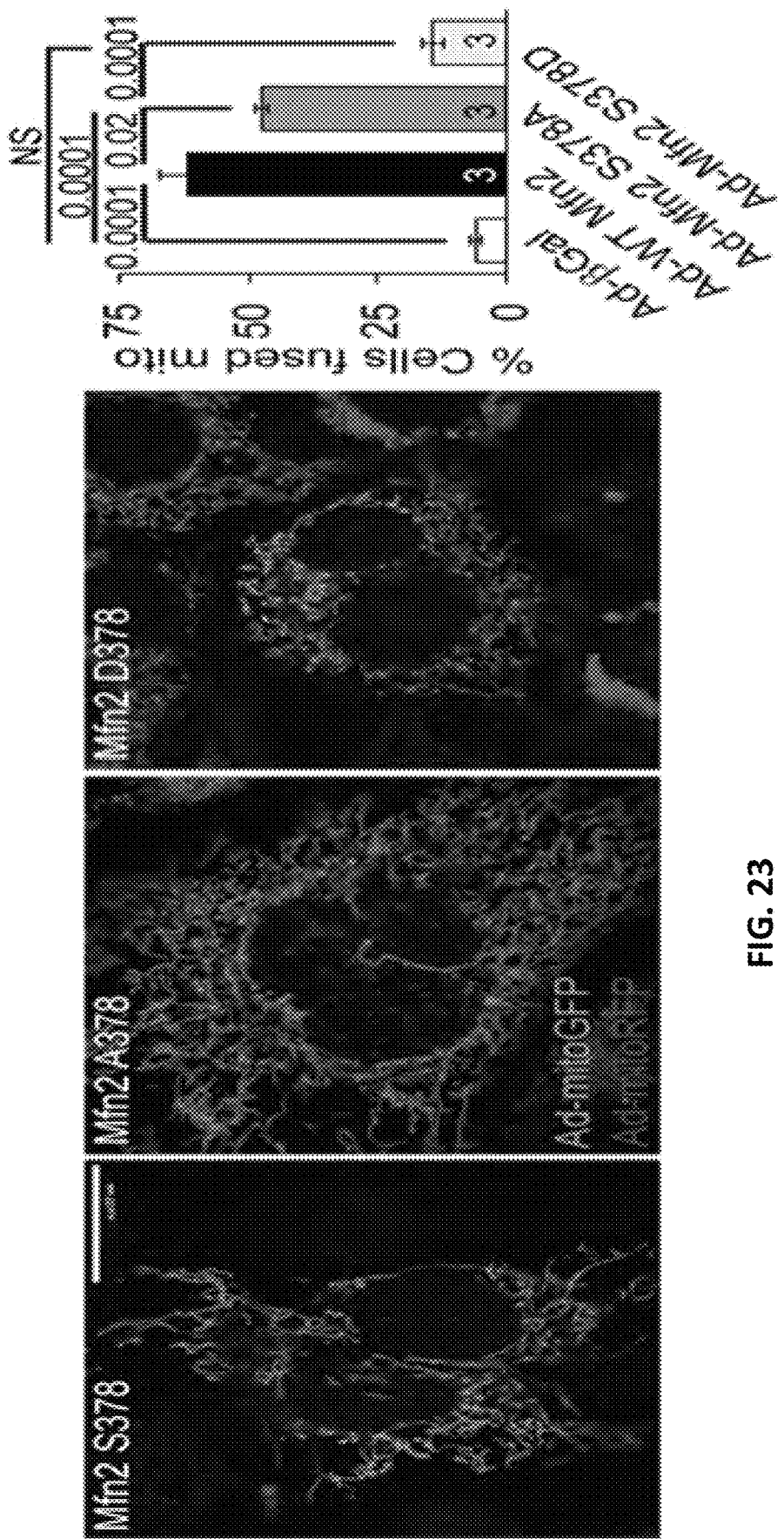

FIG. 23 is a series of images and a bar graph showing effects of MFN2 mutations that prevent or mimic Ser378 phosphorylation on mitochondrial fusion measured as content exchange. (left) Representative live cell confocal images showing mitochondrial fusion (red/green mixing) 3 hours after PEG treatment of MFN1−/−, MFN2−/− MEFs expressing MFN2 Ser378 mutants. Scale bar is 21 μm. N=3 independent studies; p values are by ANOVA with Tukey's post hoc comparison.

Figure 24A:
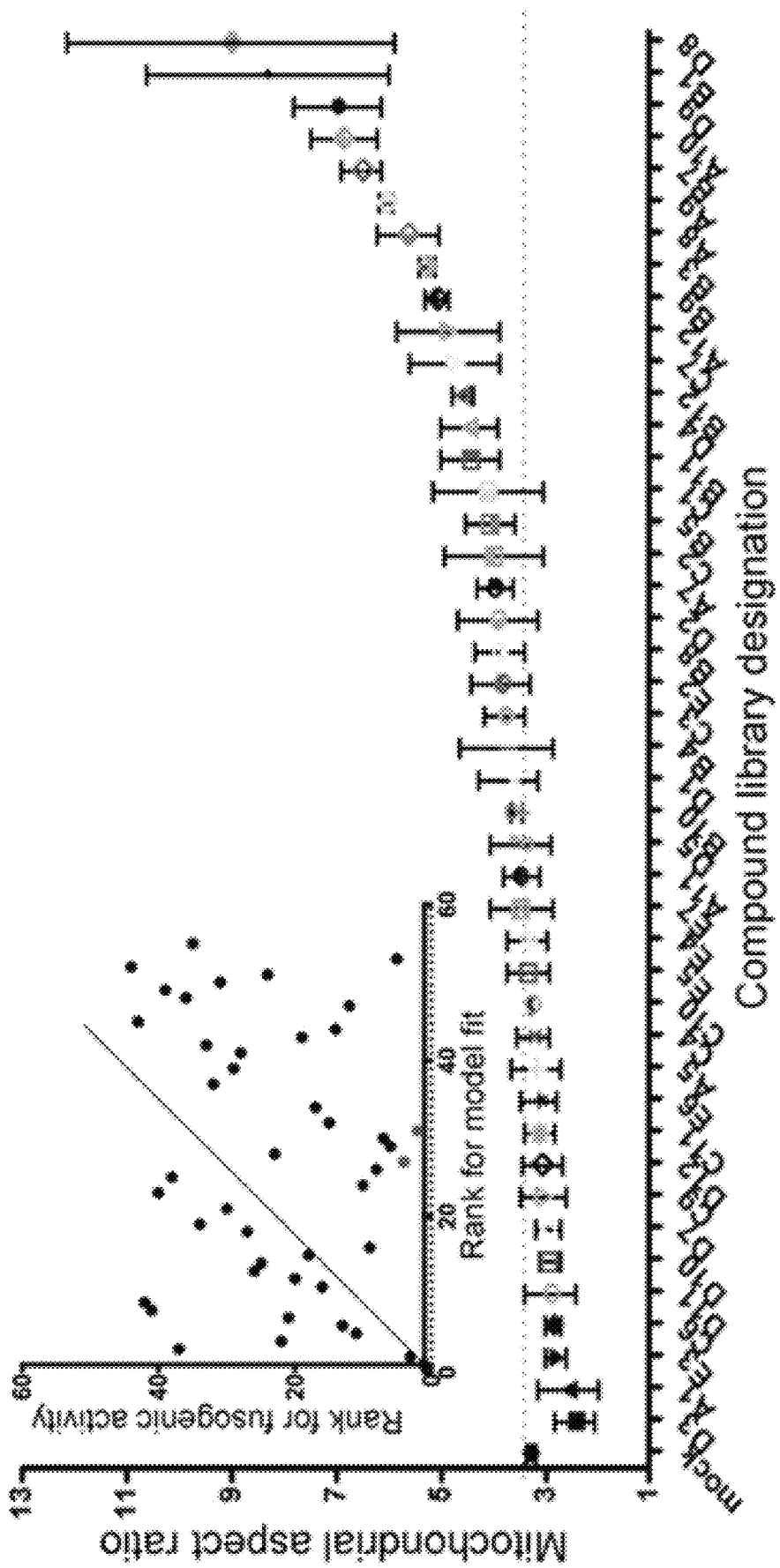
Figure 24B:
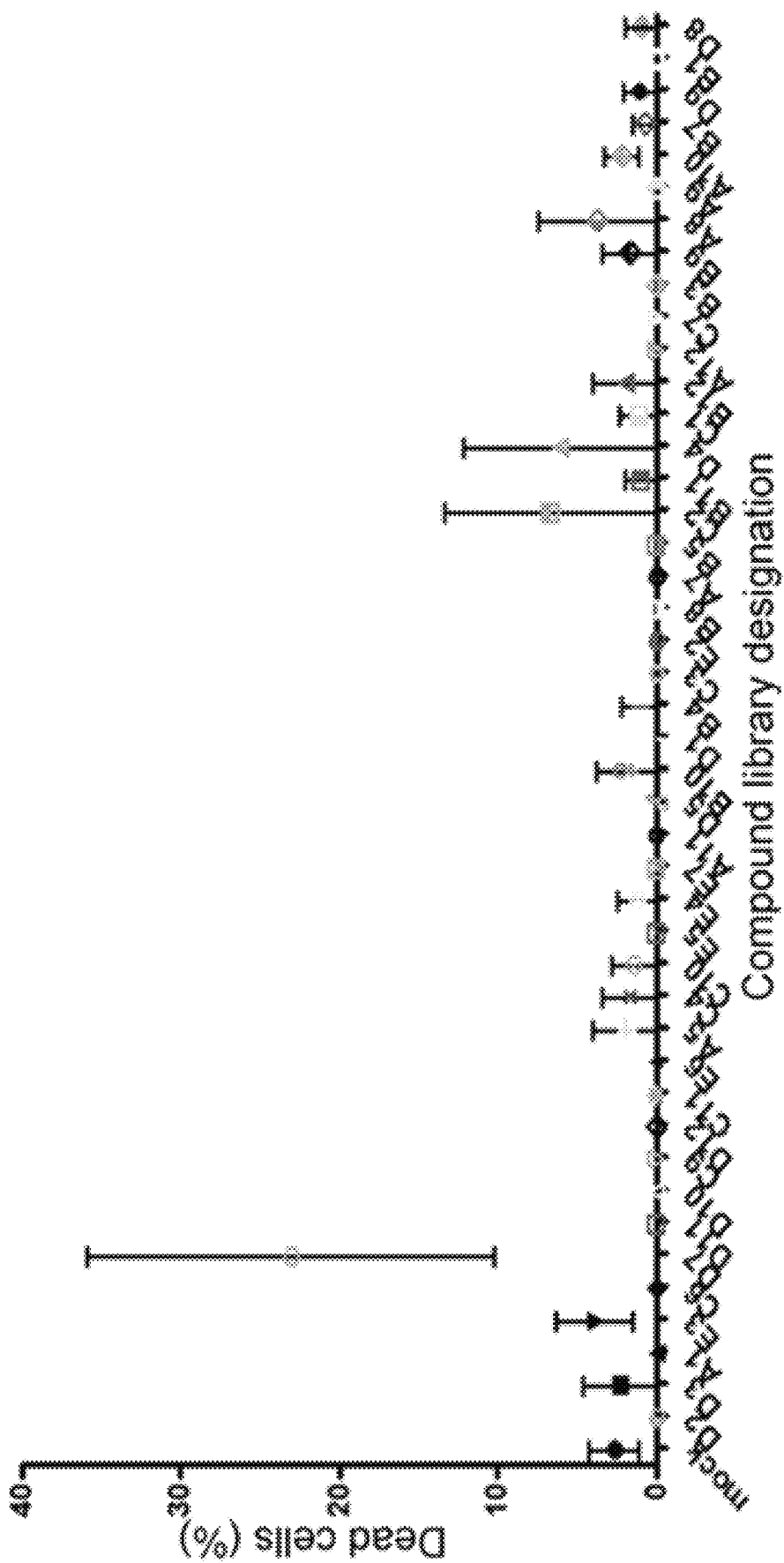

FIG. 24A and FIG. 24B show functional screening for fusogenic activity of mitofusin agonist pharmacophores. (A) Mitochondrial fusogenicity measured as aspect ratio of MFN2 null MEFs after overnight treatment with 1 mM indicated library compound. Chemical details, structures, and commercial sources of these compounds are in TABLE 4. Mock=DMSO vehicle control. Horizontal dotted line indicates baseline value. Cells treated with 5 mM mitofusin agonist peptide HR1 367-384 (positive control) had aspect ratios of ~6. Inset: correlation of rank order for initial model fit vs actual fusogenicity (r=0.214). Red dots are compounds A10 and B1 that ranked $4^{th}$ and $2^{nd}$ for fusogenicity, but $22^{nd}$ and $31^{st}$, respectively, for fit to the original pharmacophore model. (B) Cytotoxicity measured by live-dead assay. Compounds are ranked by fusogenicity as in A. Means±SEM of 3 independent experiments examining ~30 cells per experiment.

Figure 25A:
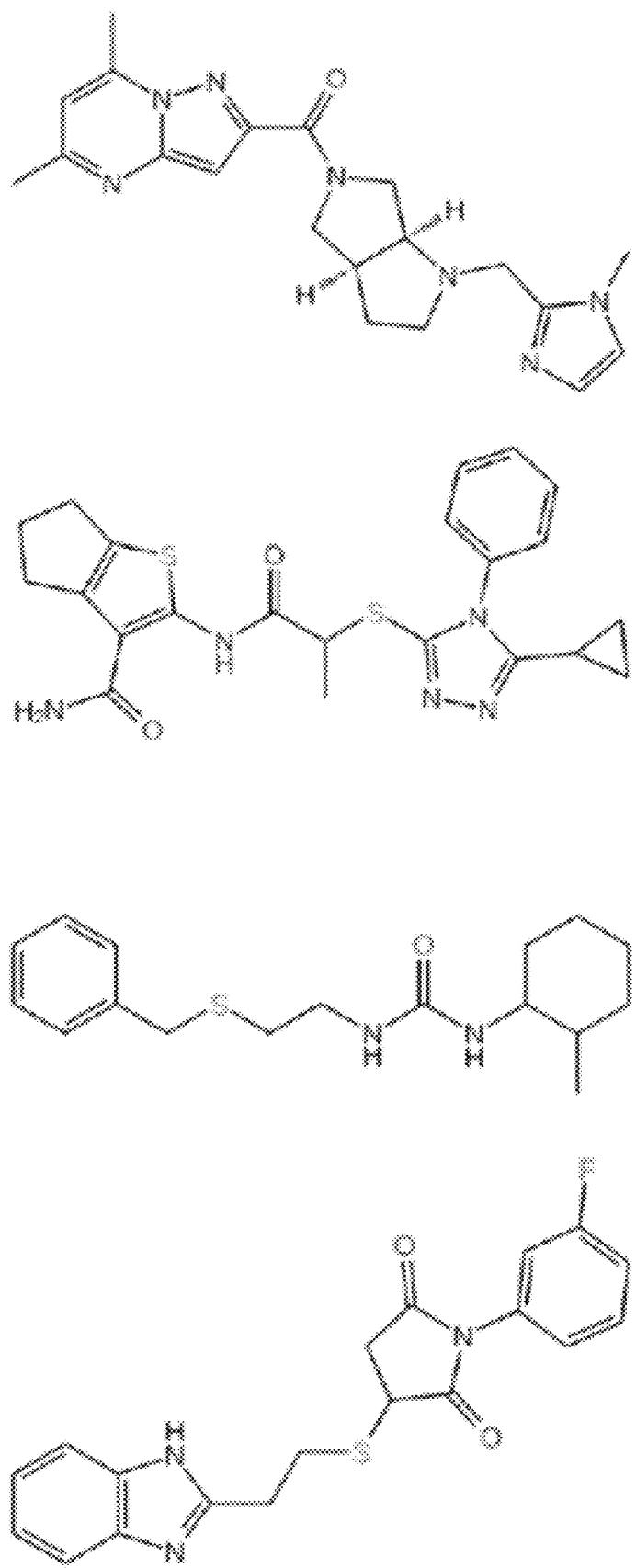
Figure 25B:
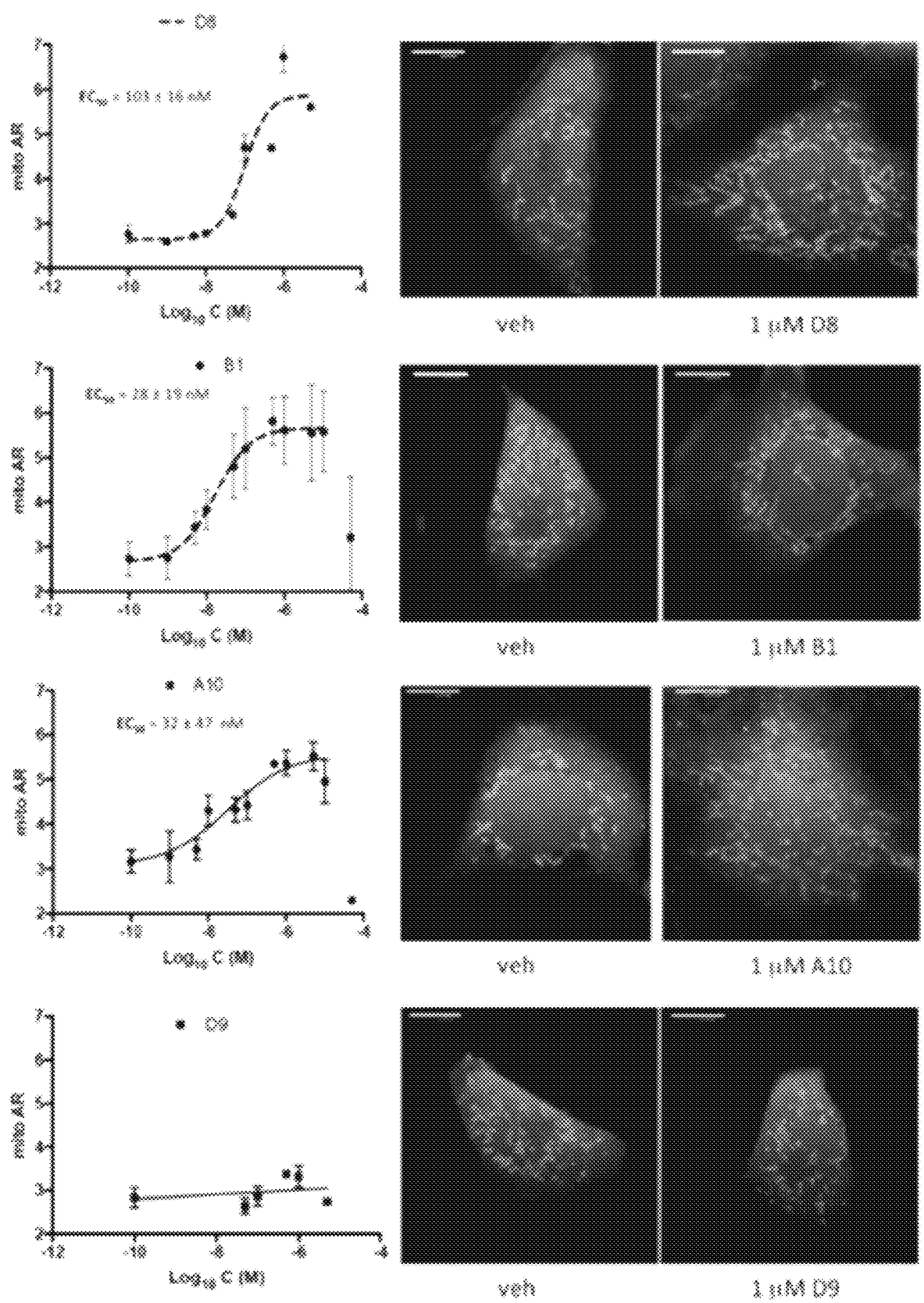
Figure 25C:
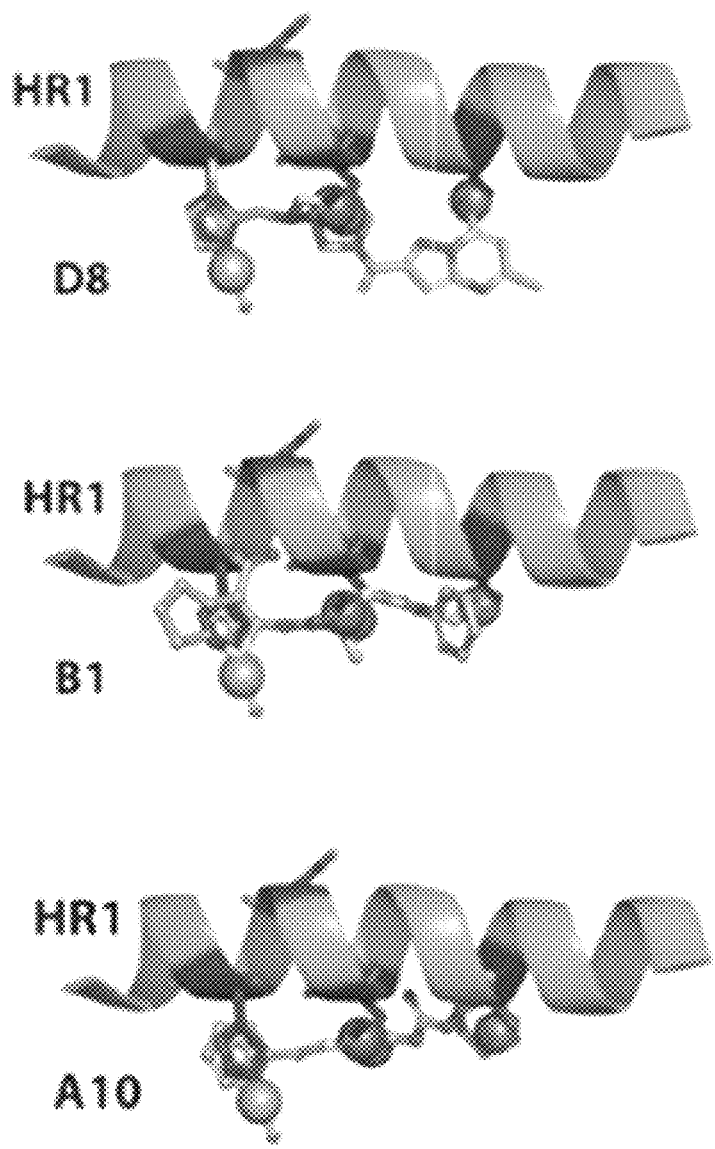
Figure 26A:
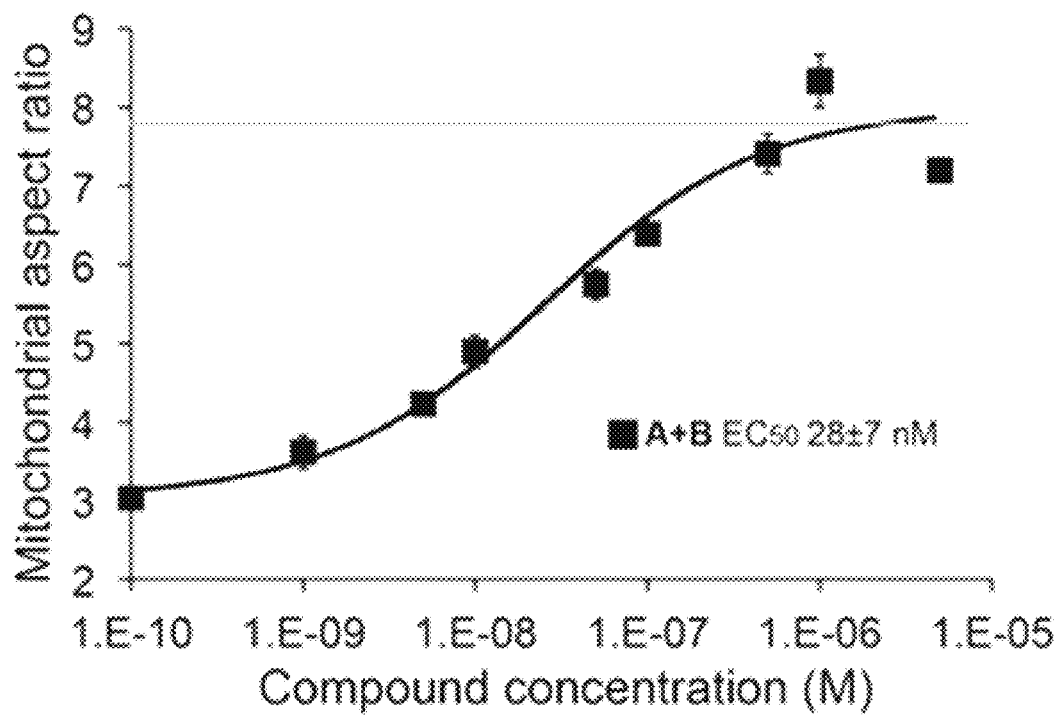
Figure 26B:
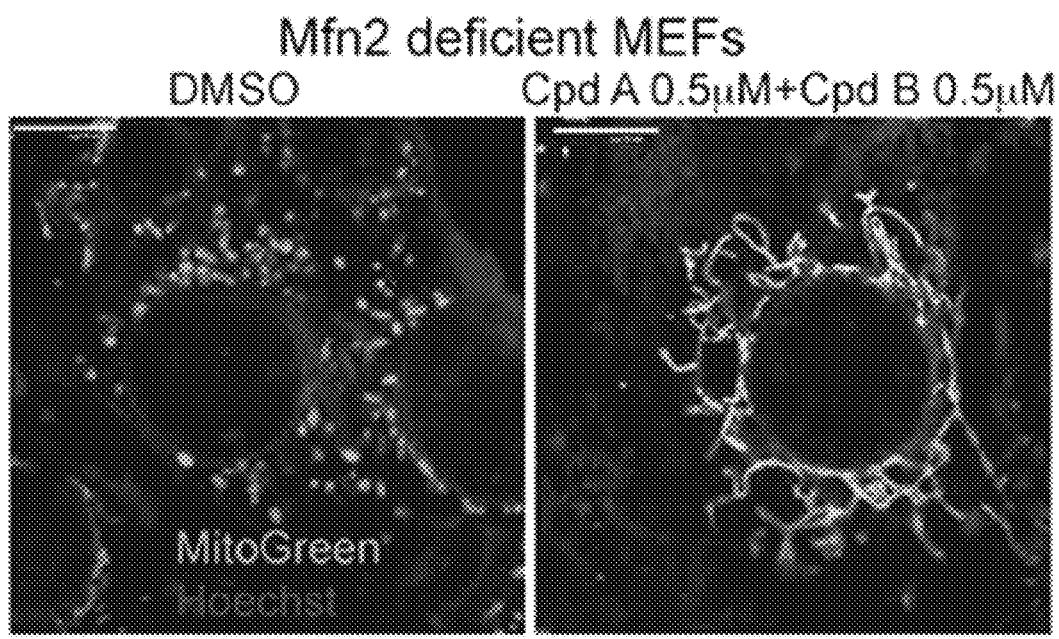
Figure 26C:
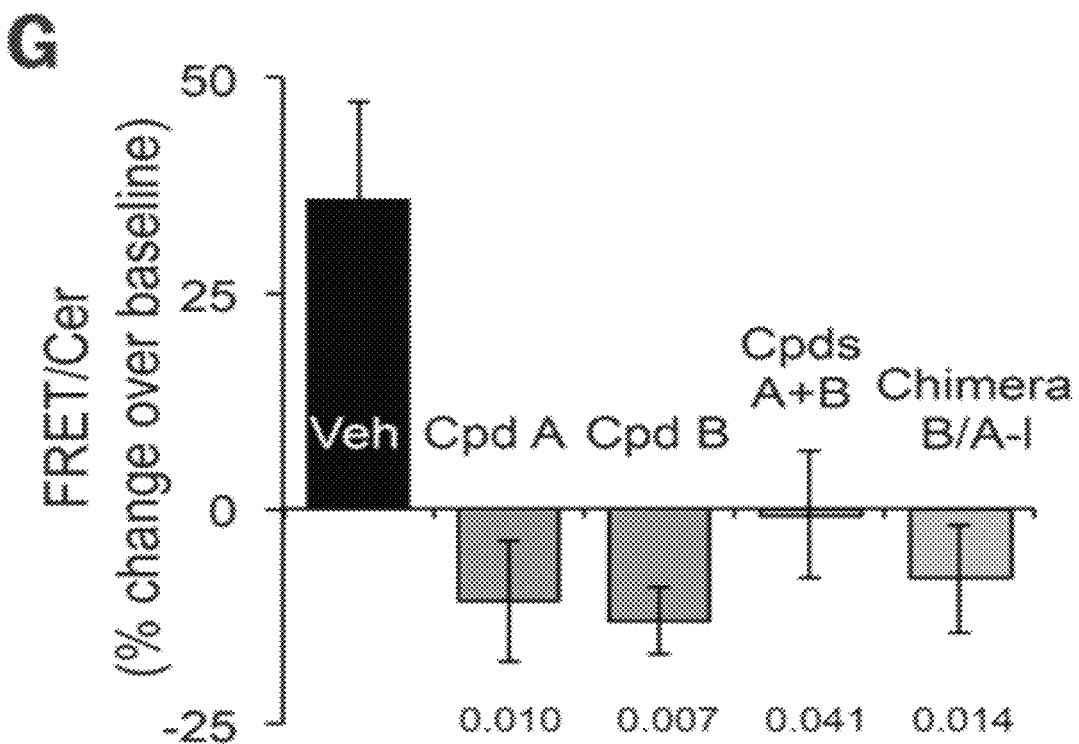
Figure 26D:
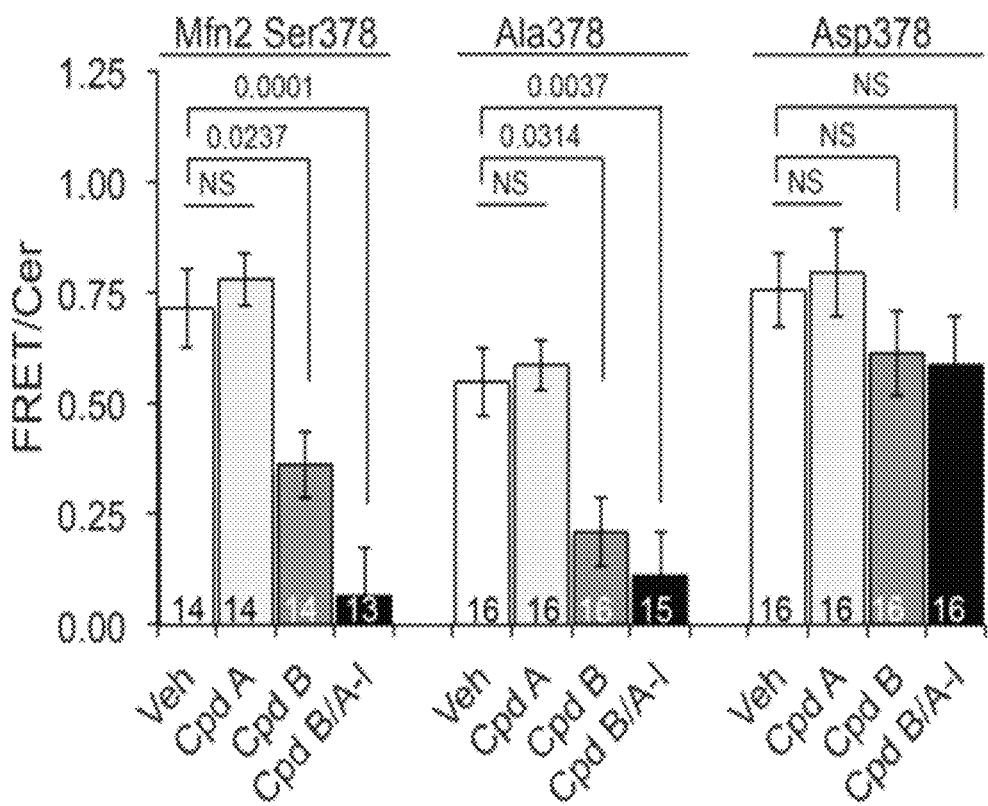

FIG. 25A, FIG. 25B, and FIG. 25C shows functional validation and dose-response relations of candidate fusogenic small molecules. (A) Chemical structures of 4 top candidate fusogenic compounds from initial screening (see e.g., FIG. 24). (B) Dose relations with representative images of vehicle and 1 mM treated Mfn2 null MEFs for each of the compounds, only 3 of which were true positives. Cells are stained with Mitotracker orange, calcein AM (green; alive) and ethidium homodimer (red nucleus; dead). There are no dead cells. $EC_{50}$ values are provided for true positives; D9 showed no true fusogenic activity. Scale bars are 10 microns. Dose-response curves are means±SEM of 3 independent experiments. (C) Schematic depiction of pharmacophore model fit for the 3 true positive fusogenic compounds.

FIG. 26 is a graph and image showing the synergistic effects of a class A and class B mitofusin agonist. Mitochondrial elongation (increase in aspect ratio) in MFN2-deficient MEFs stimulated by equimolar concentrations of mitofusin agonists A and B. Dose-response curve on the left is from 6 independent experiments. Peak aspect ratio achieved with A+B is ~25% greater than with either agonist alone (compare to SF10C). Representative live-cell confocal images are on right. Scale bar is 10 mm.

Figure 27A:
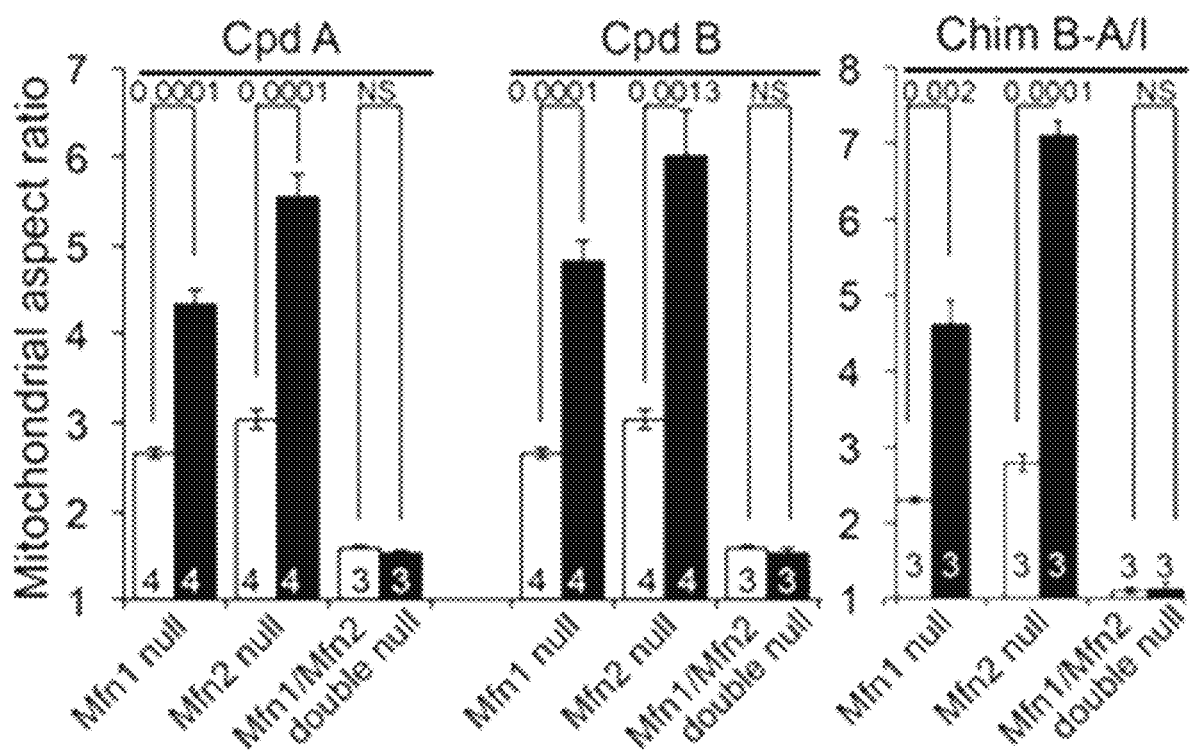
Figure 27B:
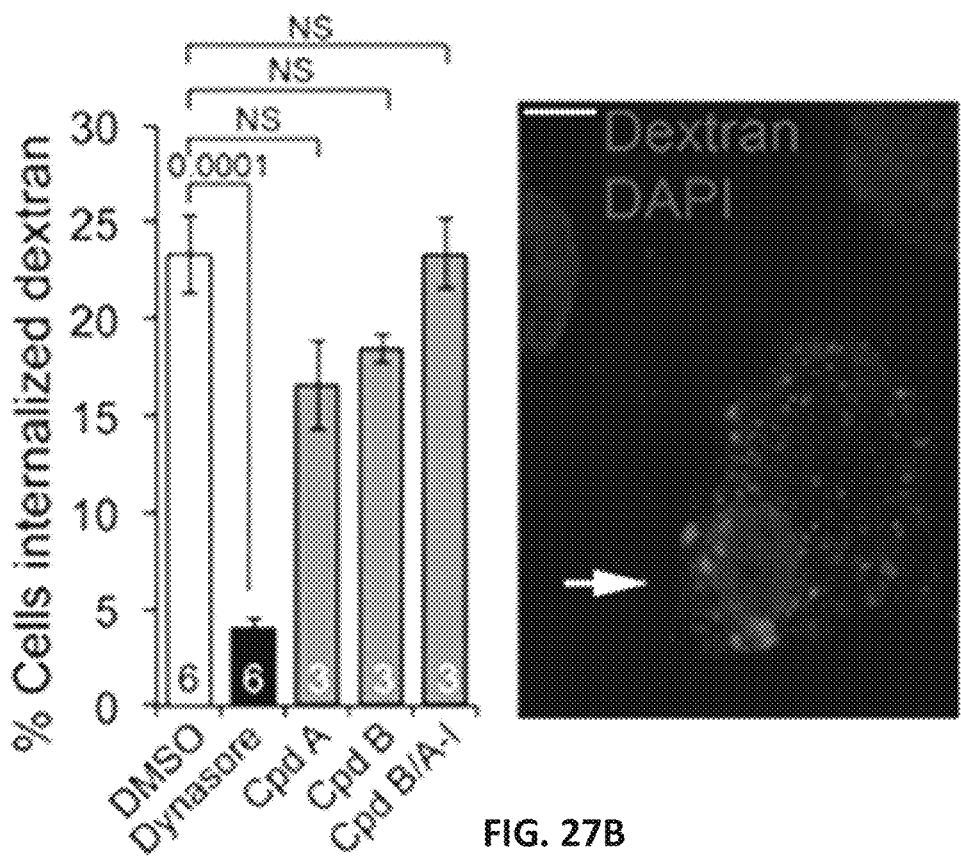
Figure 27C:
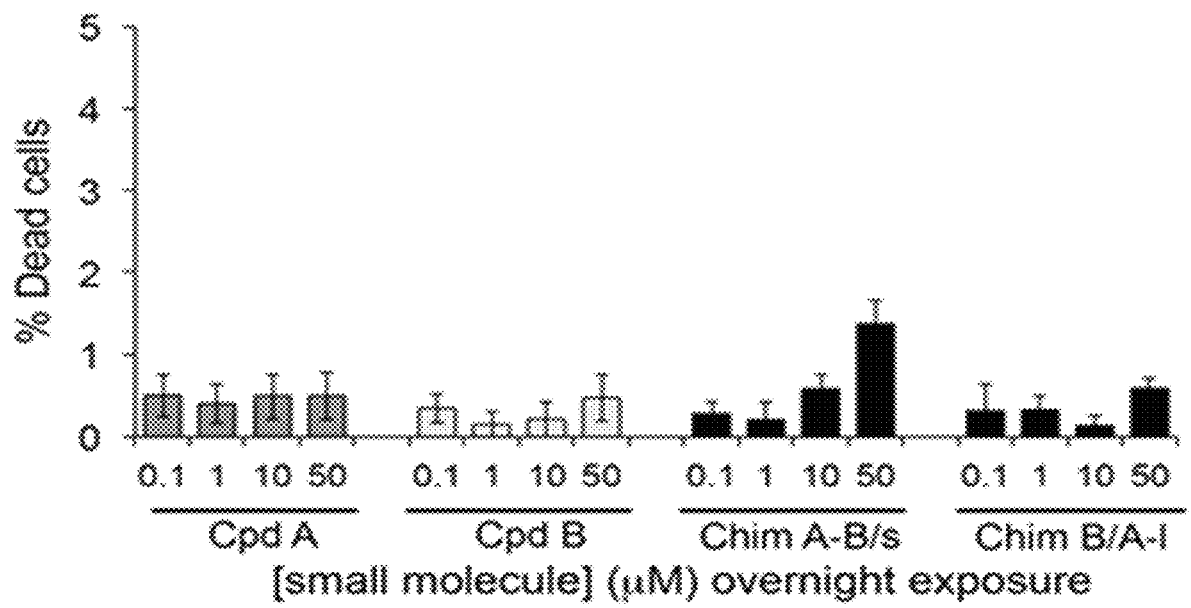
Figure 28A:
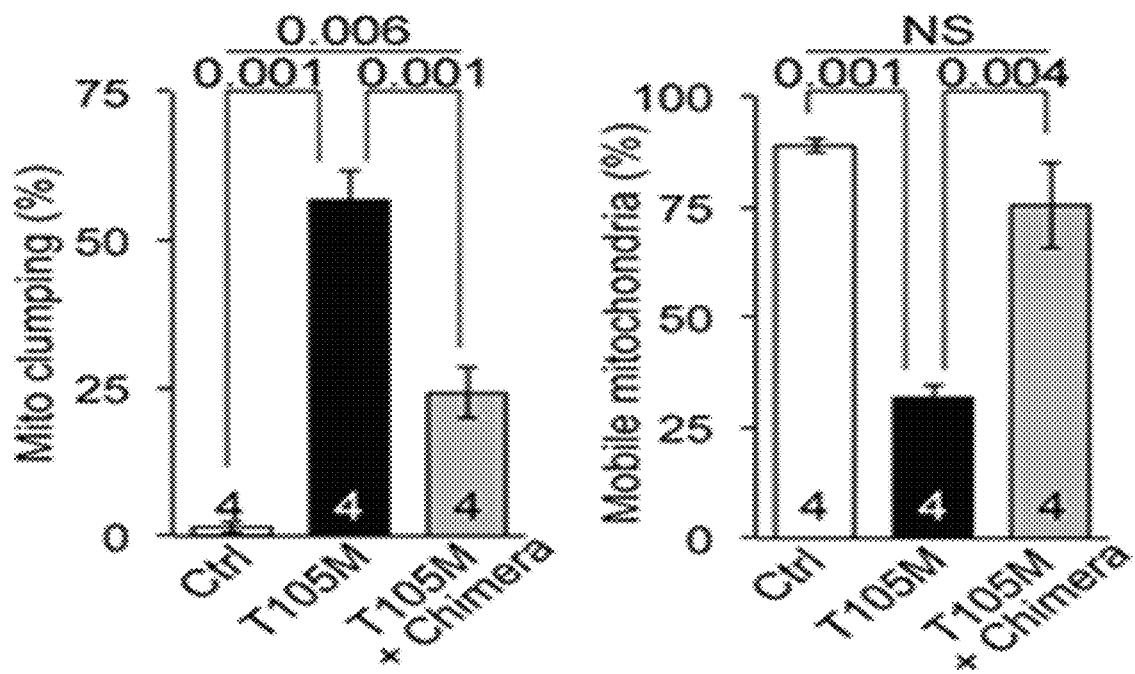
Figure 28B:
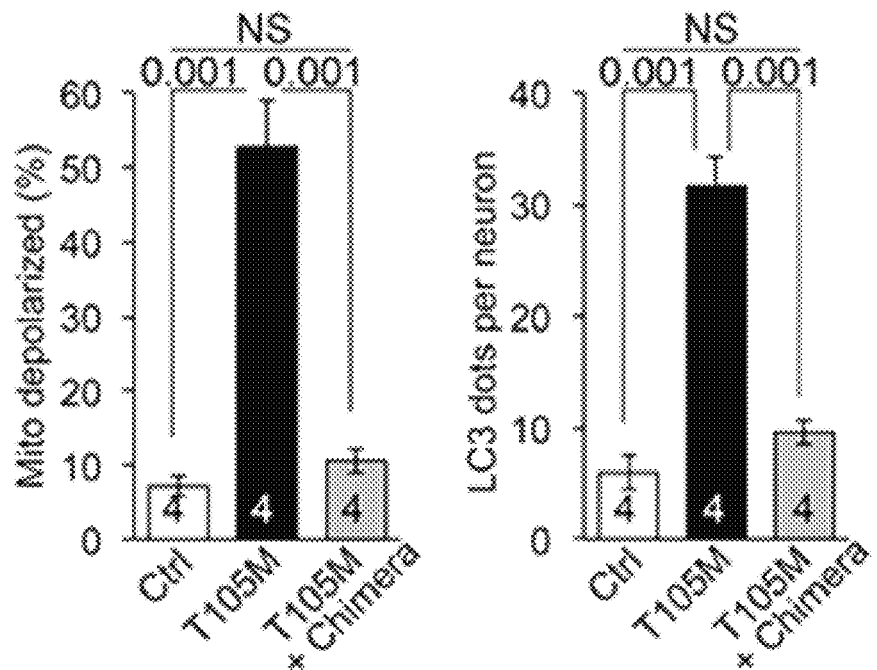
Figure 28C:
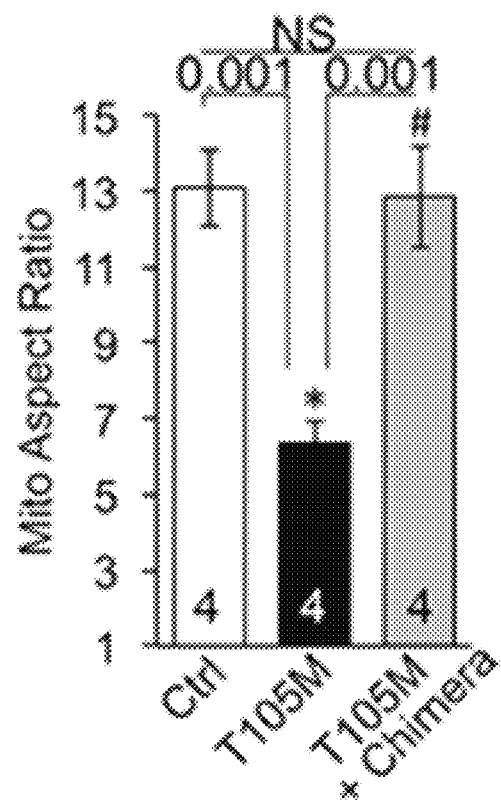
Figure 28D:
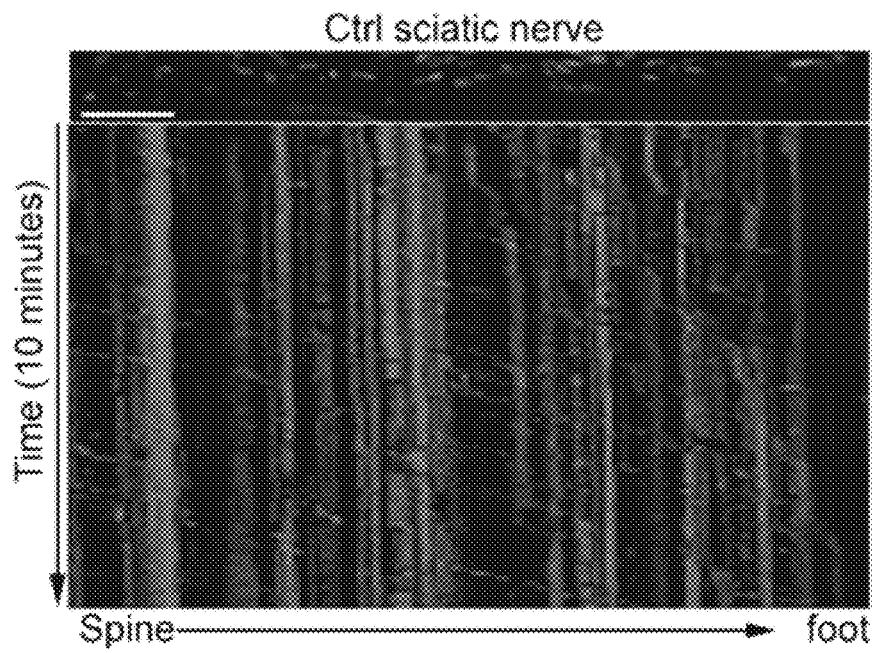
Figure 28E:
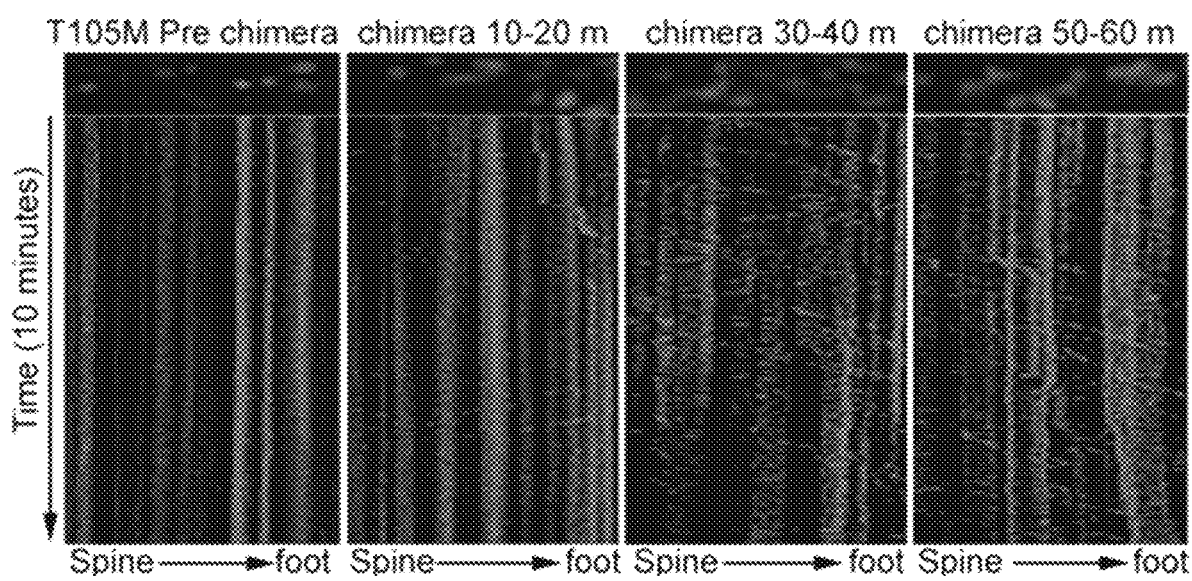
Figure 28F:
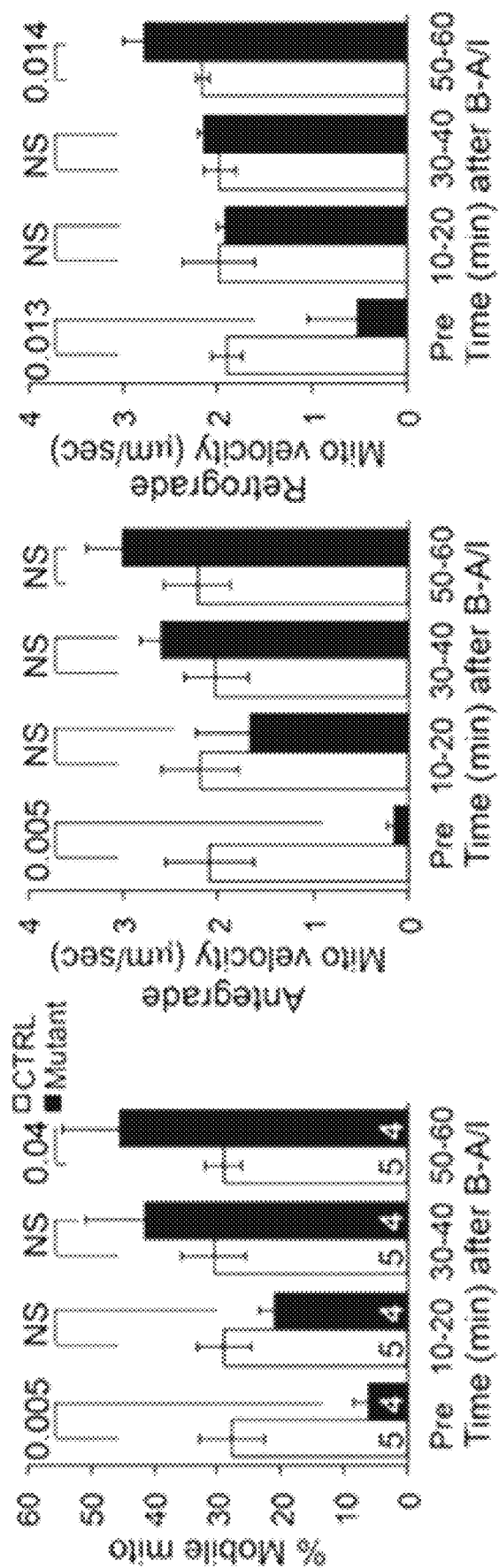
Figure 28G:
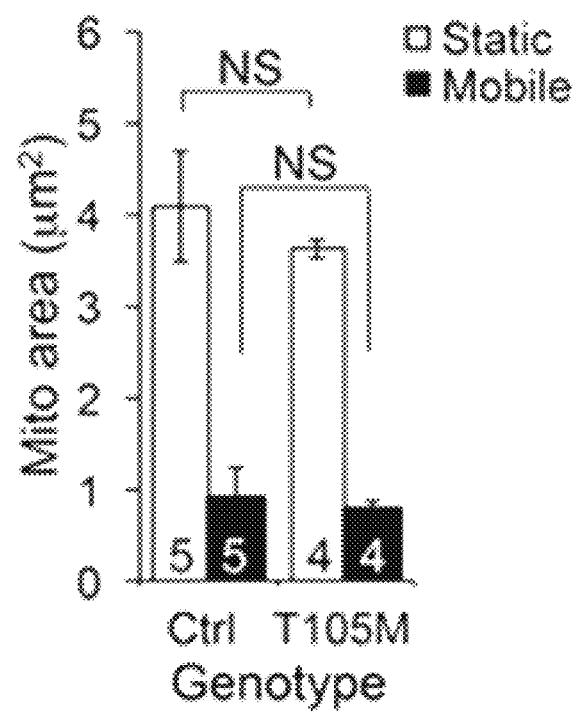

FIG. 27 is a series of graphs and an image showing the functional evaluation of structurally diverse mitofusin agonists. (A) Mitochondrial elongation stimulated by mitofusin agonists A and B or chimera B-A/I in cells having different MFN expression profiles. White bars are vehicle (DMSO) treated, black bars are 1 µM agonist overnight; *=p<0.05 vs vehicle (t-test). (B) Effects of cpds A and B or chimera B-A/I (1 µM) on dynamin-mediated endocytosis of Alexa-Fluor 594 Dextran. Dynasore is a dynamin inhibitor. (C) Cell viability assessed after overnight exposure to indicated concentrations of mitofusin agonist (n=4). Test compounds were not fully soluble at concentrations greater than 50 µM. p values are by ANOVA with Tukey's test.

FIG. 28A, FIG. 28B, FIG. 28C, FIG. 28D, FIG. 28E, FIG. 28F and FIG. 28G are a series of graphs and images showing mitofusin agonists restore axonal mitochondrial trafficking suppressed by CMT2A mutant MFN2 T105M. (A-C) Chimera B-A/I effects on mitochondrial mobility (A), function (B), and morphology (C) in cultured CMT2A MFN2 T105M mouse neurons. (D) Kymograph of mitochondrial trafficking in a Ctrl mouse sciatic nerve. (E) Serial kymographs of mitochondria in a MFN2 T105M mouse sciatic nerve before and after chimera B-A/I. (F) Quantitative data for sciatic nerve mitochondrial motility studies. (G) Size of motile and static mitochondria in Ctrl and B-A/I-treated (60 minutes) sciatic nerves. Data information: Mean, standard deviation, and P-values calculated using two-tailed t-test are shown. MitoSOX n=4, TMRM n=6, Mito Aspect ratio n=4.

Figure 29A:
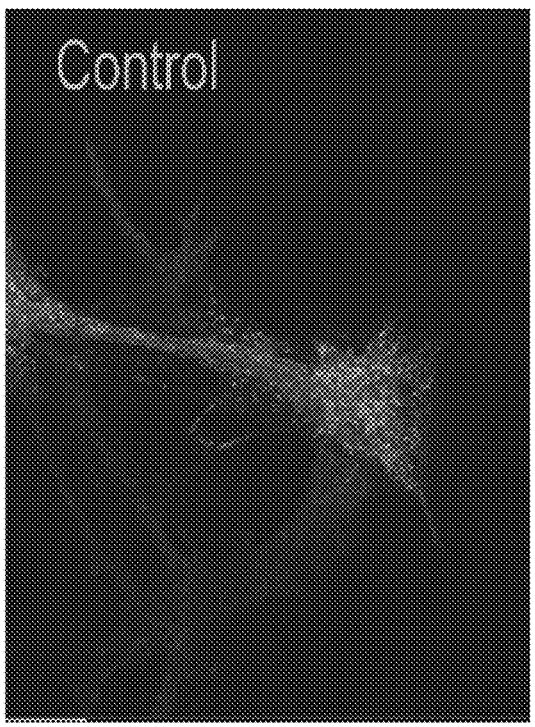
Figure 29B:
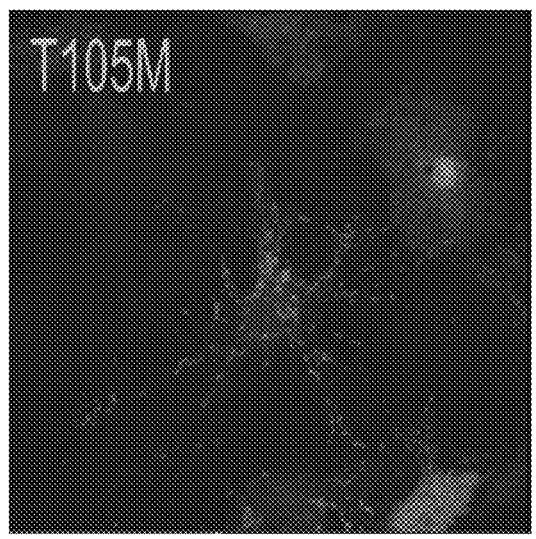
Figure 29C:
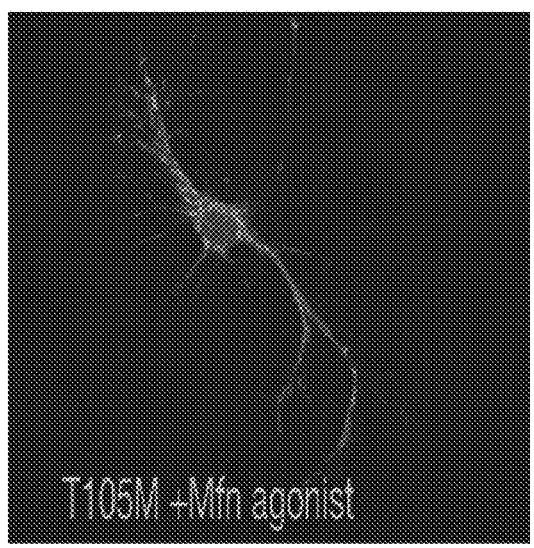

FIG. 29 shows in vitro mouse mitochondrial mobility in Ctrl neuron, MFN2 T105M neuron, and MFN2 T105M neuron treated with compounds A+B (24 hours).

Figure 30:
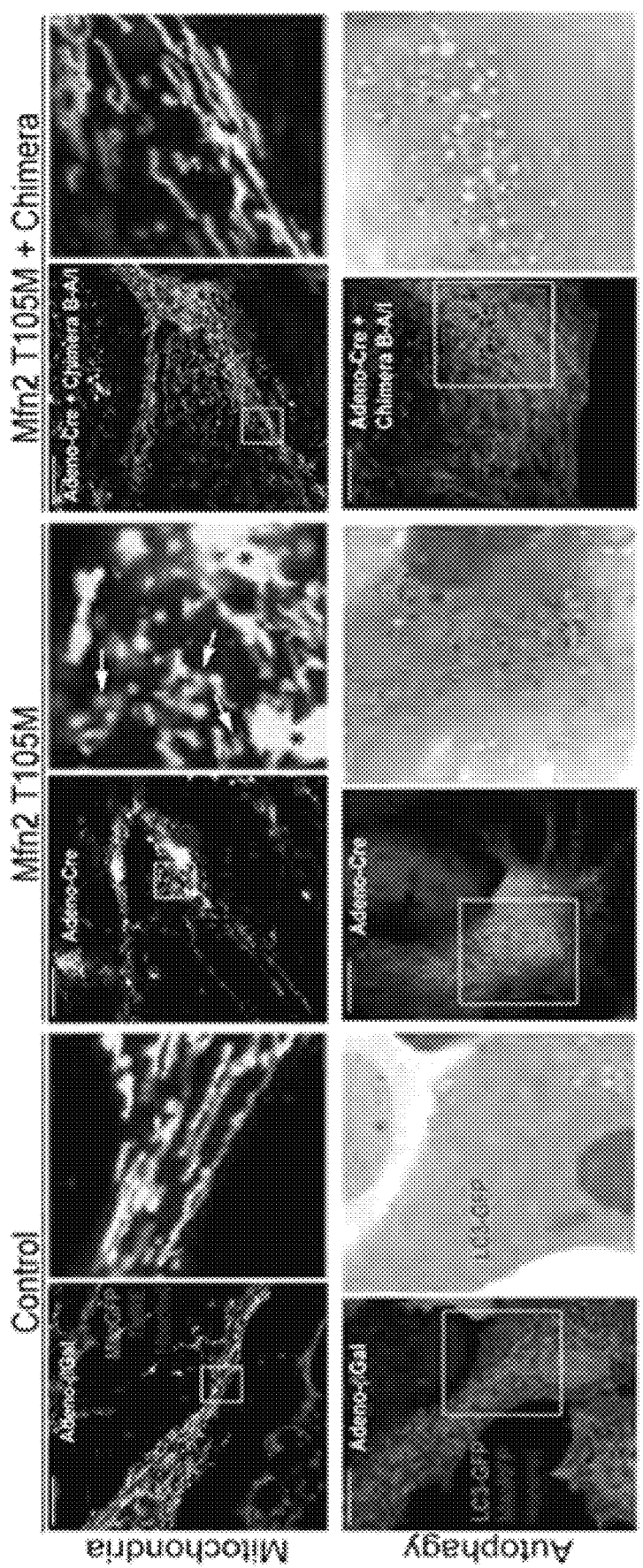

FIG. 30 is a series of images showing mitofusin agonist chimera B-A/I reverses mitochondrial abnormalities induced by CMT2A mutant MFN2 T105M in cultured mouse neurons. Representative confocal images of living mouse neurons expressing MitoGFP and stained with TMRE and Hoescht from experiments reported in FIG. 28B and FIG. 28C. Scale bars are 21 µm; expanded views are from white squares. MFN2 T105M was induced by addition of adeno-Cre.

Figure 31:
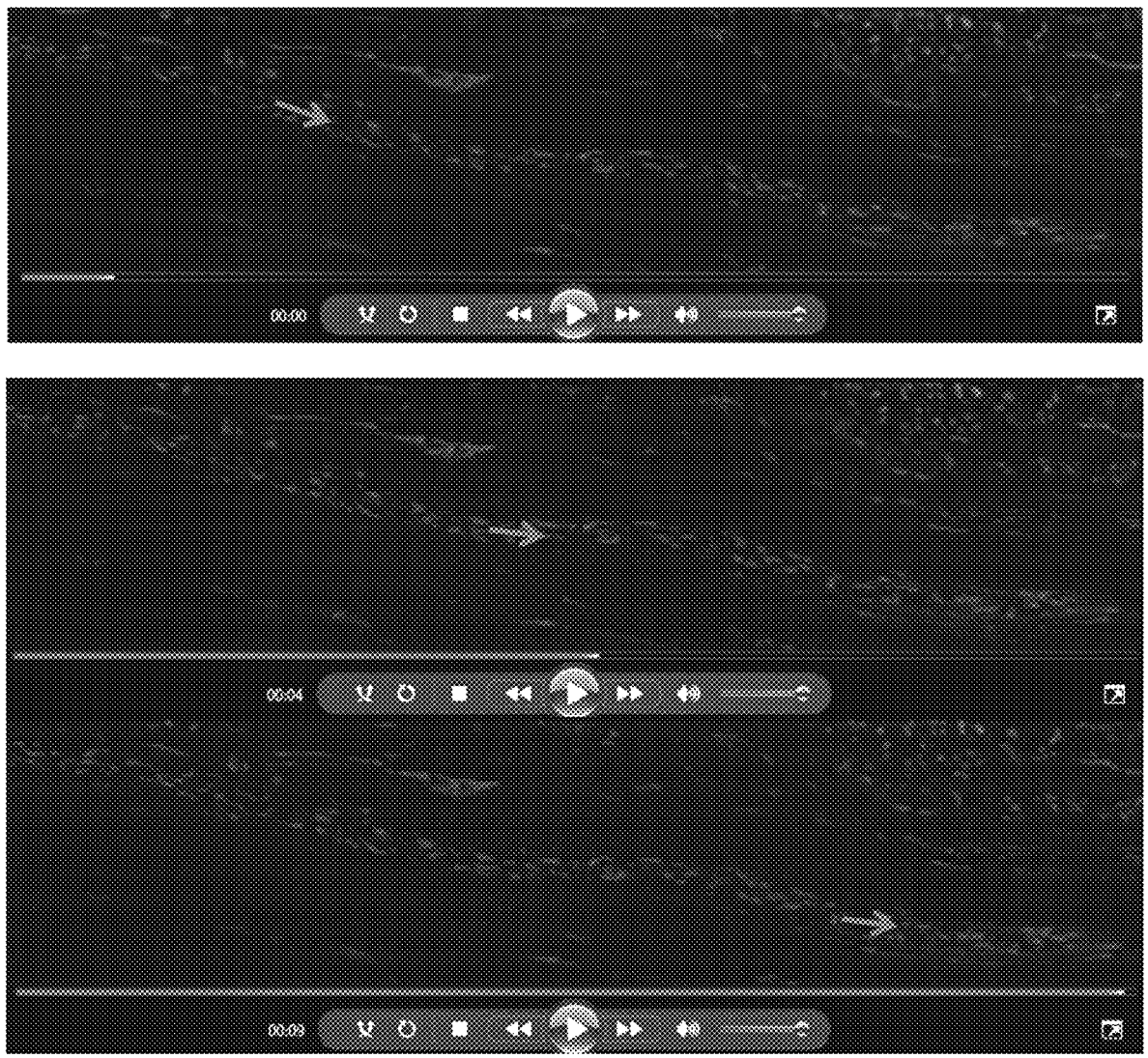

FIG. 31 shows mitochondrial mobility in a neuronal axon of a control mouse sciatic nerve. Blue arrows represent the mitochondrial transport in the nerve.

Figure 32A:
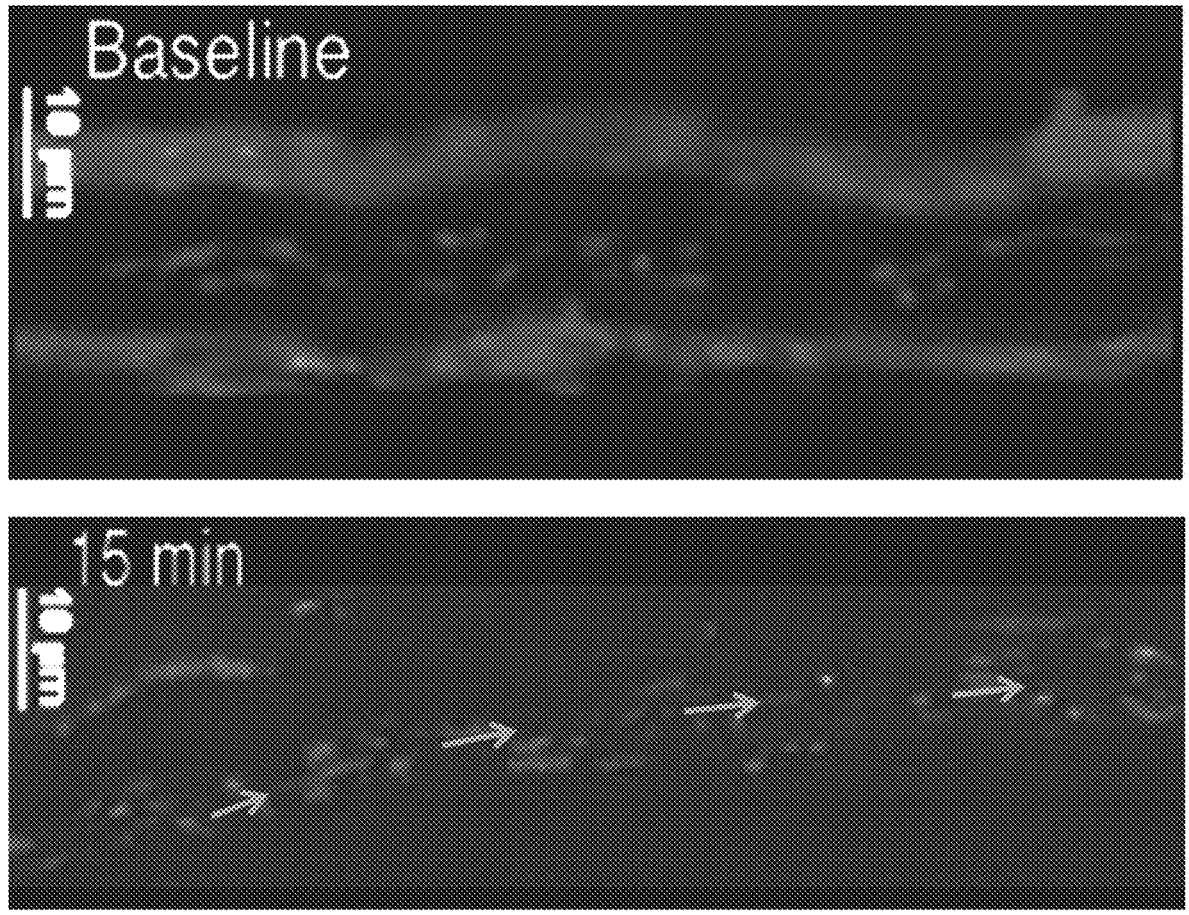
Figure 32B:
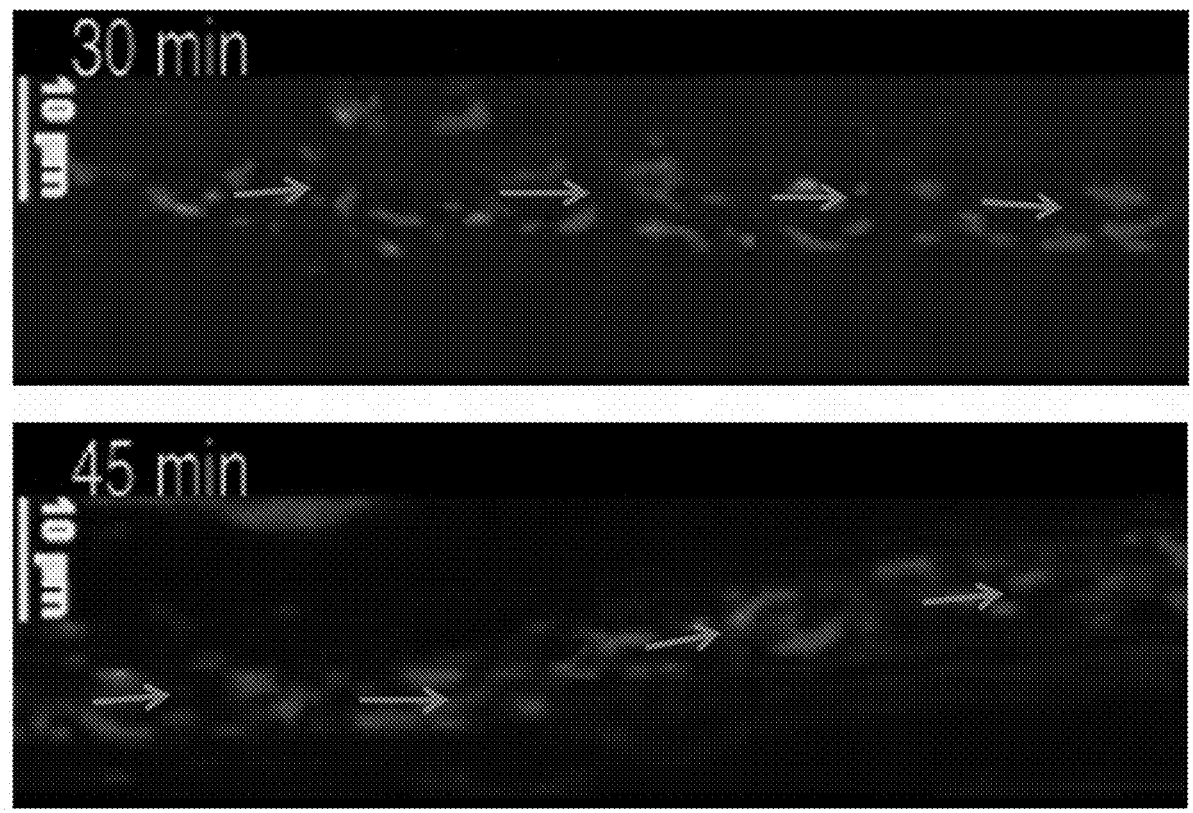

FIG. 32 shows mitochondrial mobility in axons of a MFN2 T105M mouse sciatic nerve before and at serial 15 minute periods after application of chimera B-A/I. Blue arrows represent the mitochondrial transport in the nerve.

Figure 33:
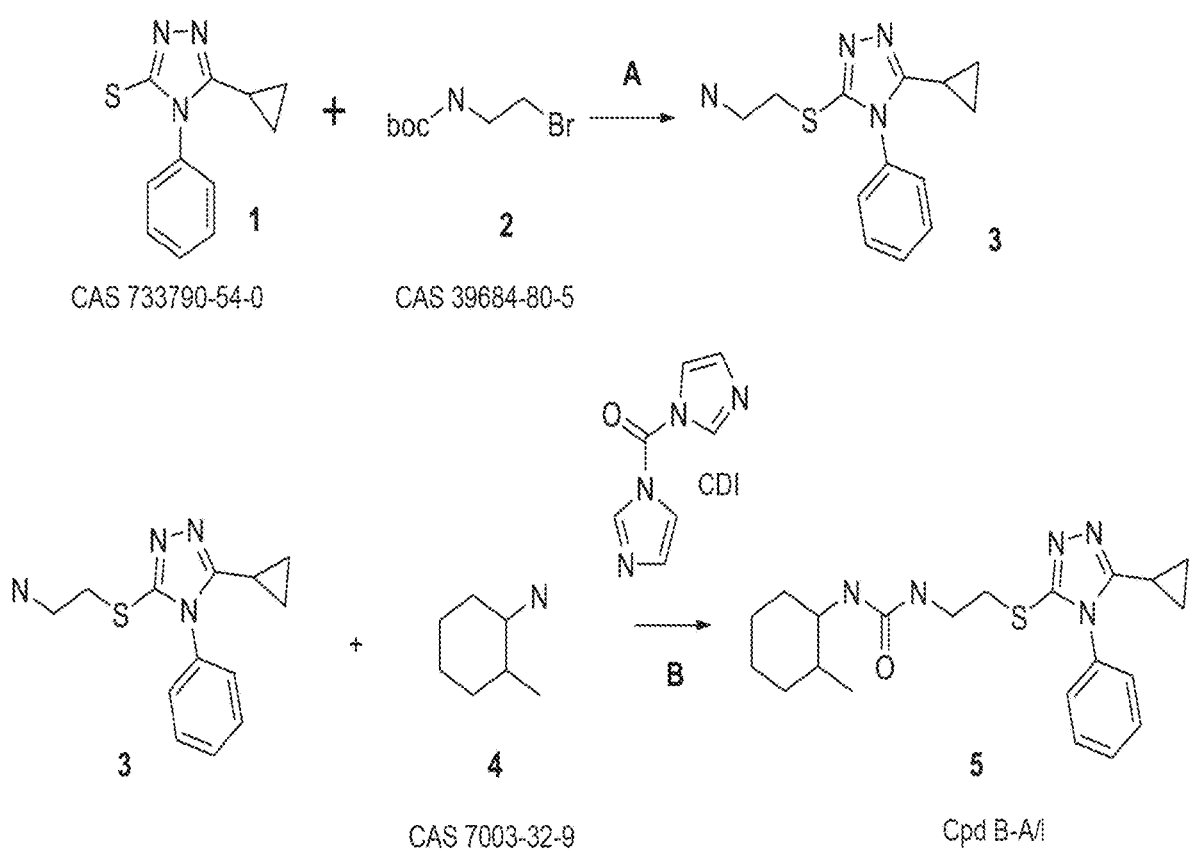

FIG. 33 shows the synthetic route for preparation of Chimera B-A/I (compound 5).

Figure 34A:
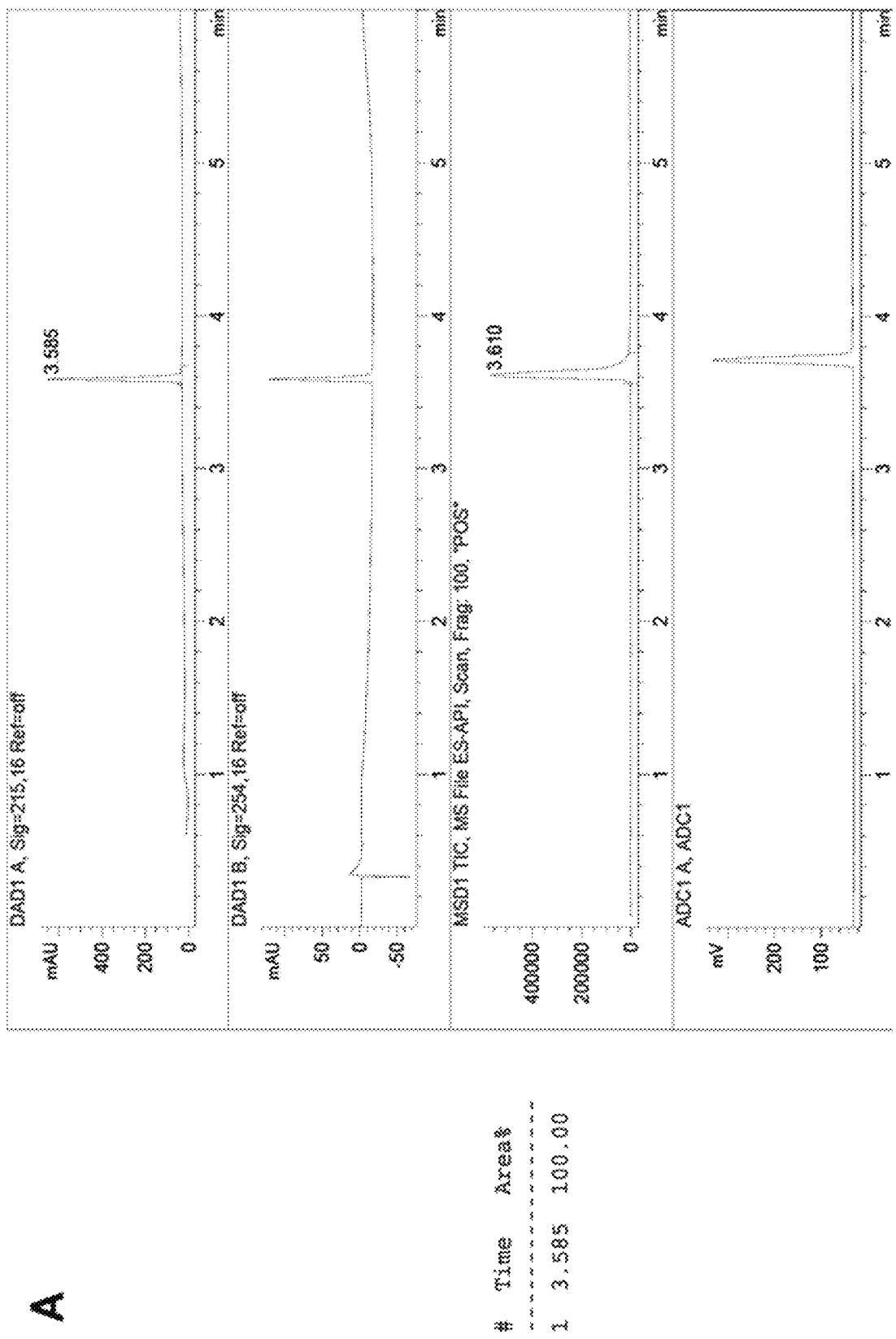
Figure 34B:
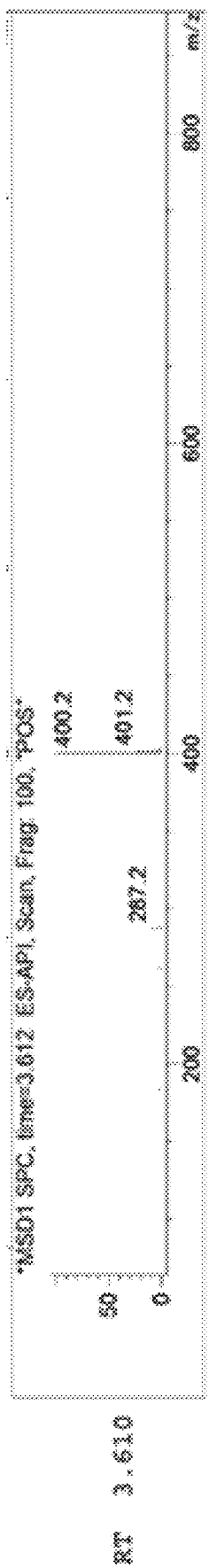

FIG. 34A and FIG. 34B show RP-HPLC and HRMS of newly synthesized chimera B-A/I. (A) HPLC spectrum of chimera B-A/I. From top to bottom: UV Absorbance at 215 nm; UV Absorbance at 254 nm; complete ionization mass selective detector (MSD) spectrum; evaporative light scattering detection spectrum. Chimera B-A/I was 99.99% pure. (B) HRMS chromatogram of compound B-A/I (C21H29N5OS) shows exact mass: $[M+H]^+$: 400.2.

Figure 35A:
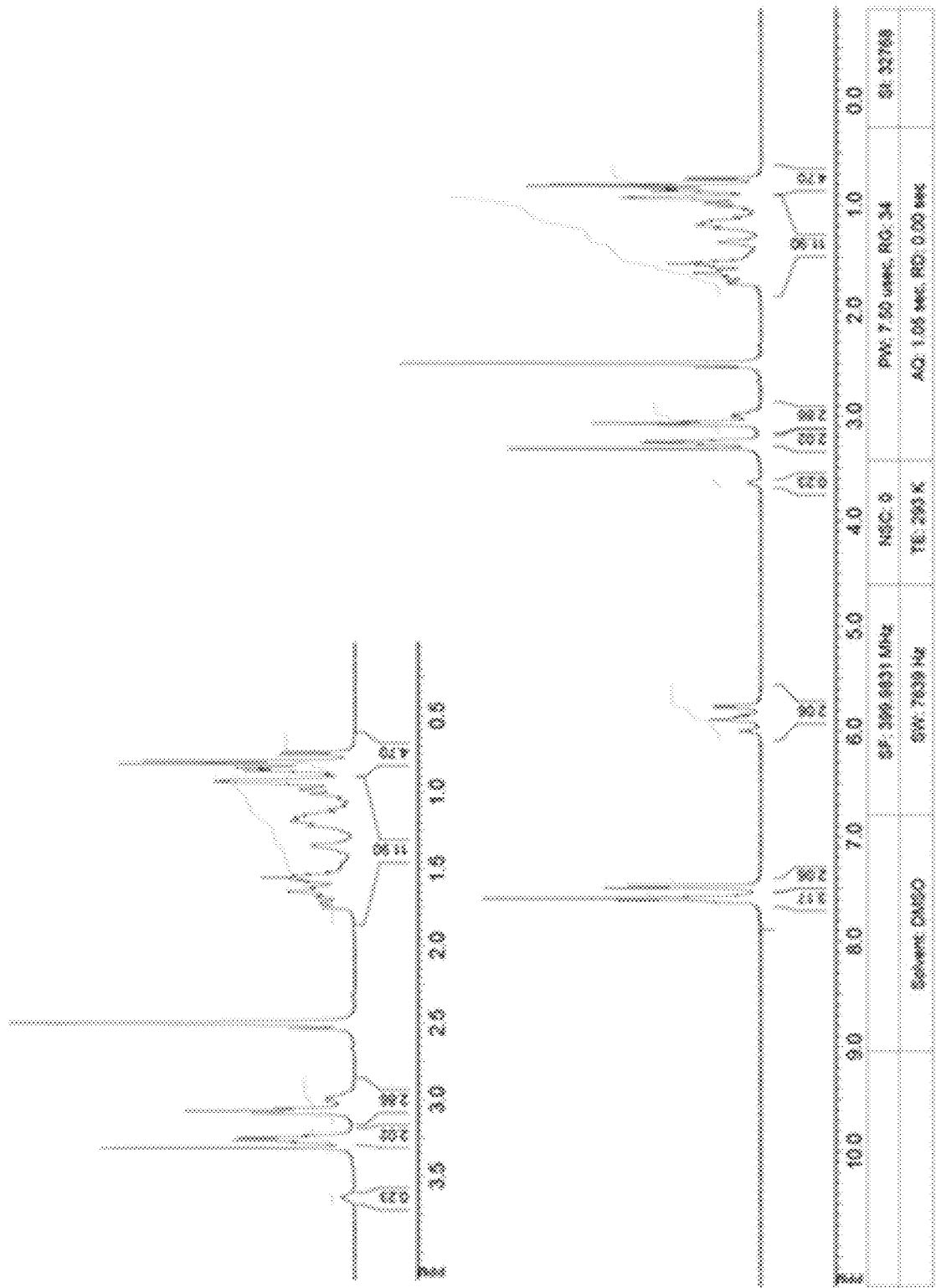
Figure 35B:
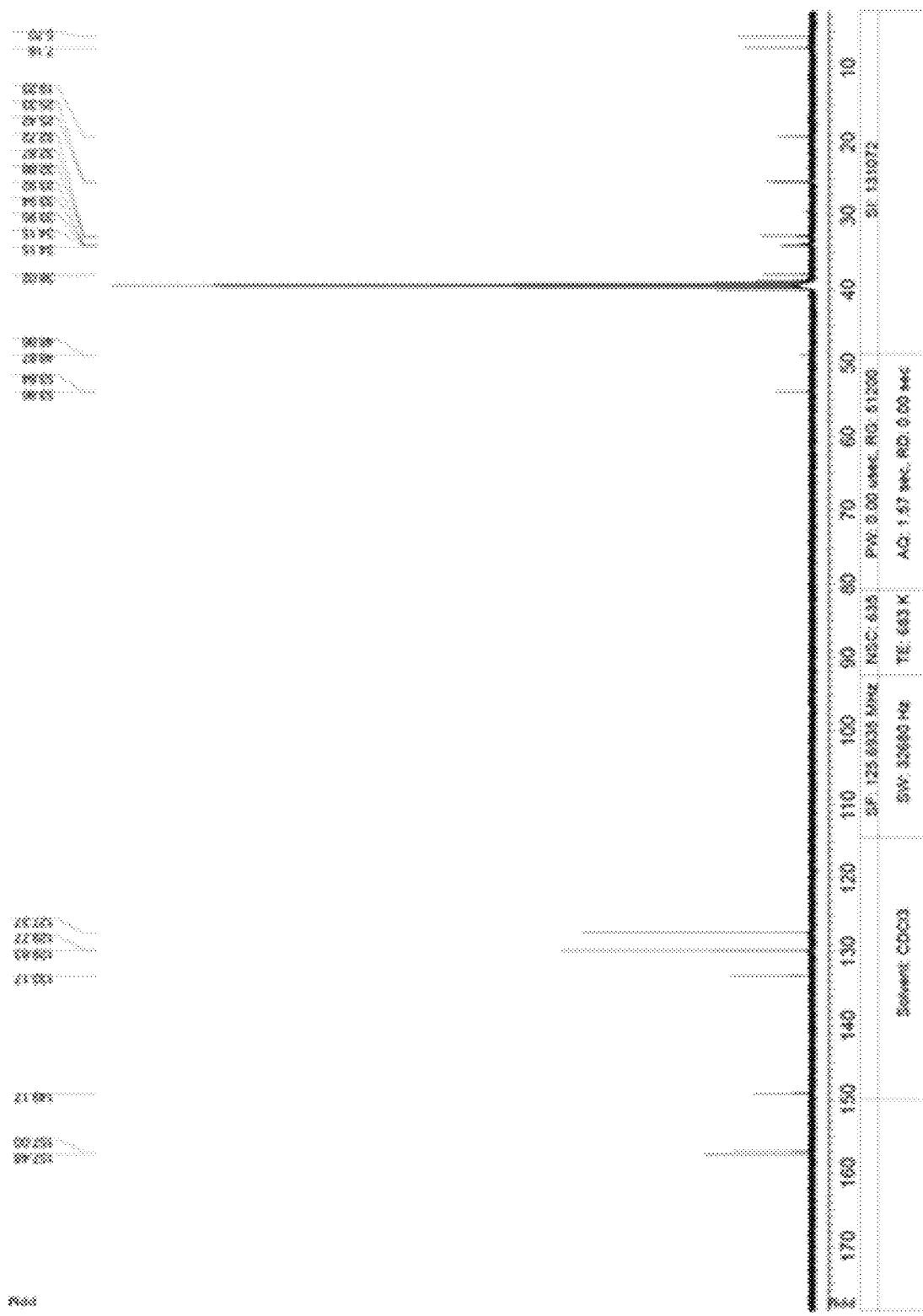

FIG. 35A and FIG. 35B show the proton and carbon-13 NMR of newly synthesized chimera B-A/I. (A) Full $^1$H NMR spectrum (400 MHz) of compound B-A/I (DMSO-$d_6$ solvent) and expanded view of region δ 0.0-4.0 PPM. (B) $^{13}$C NMR spectrum (126 MHz) of compound B-A/I (CDCl$_3$ solvent).

Figure 36:
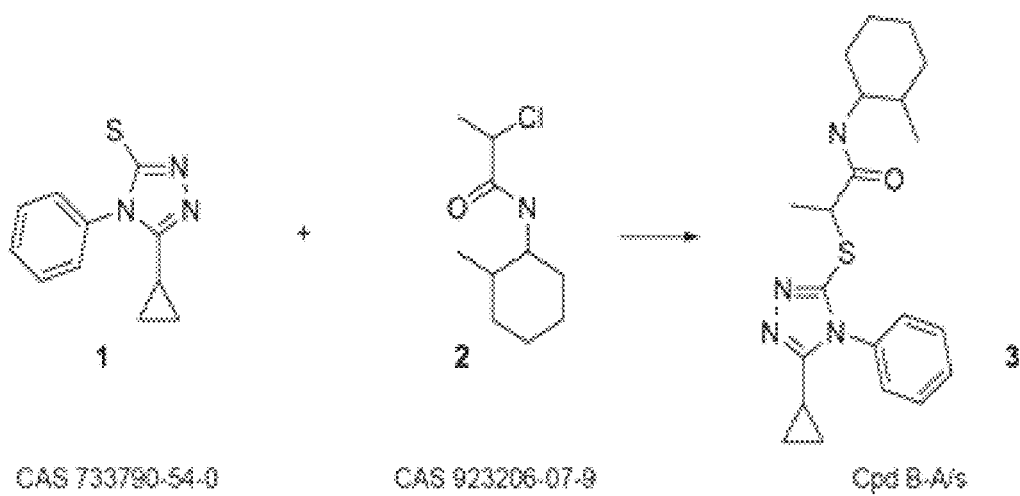

FIG. 36 shows the synthetic route for preparation of chimera B-A/s (compound 3).

Figure 37A:
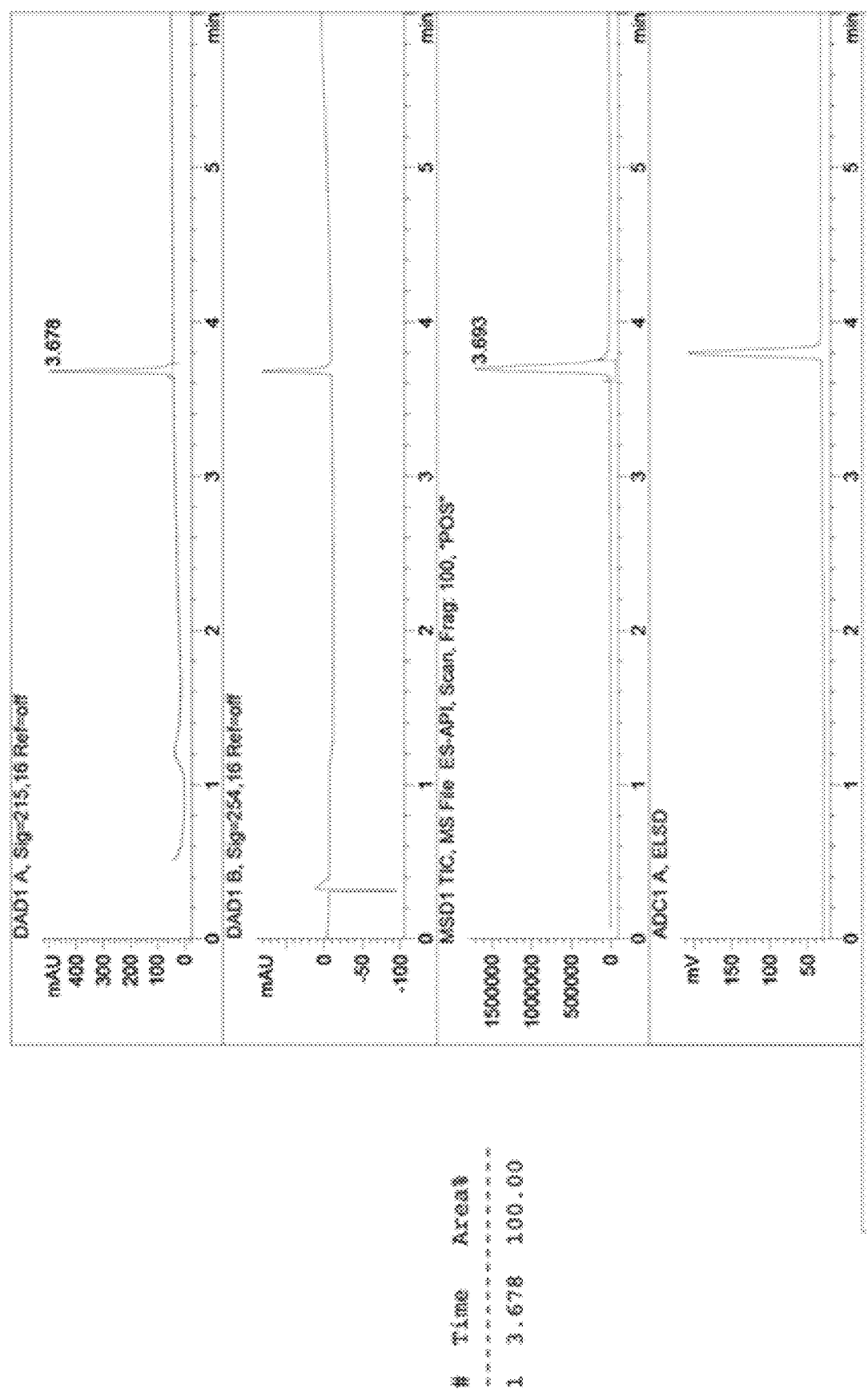
Figure 37B:
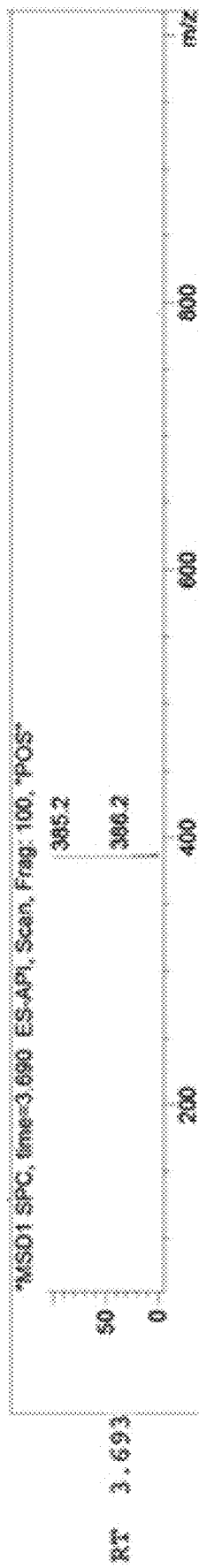

FIG. 37A and FIG. 37B show RP-HPLC and HRMS of newly synthesized chimera B-A/s. (A) HPLC spectrum of compound B-A/s. From top to bottom: UV Absorbance at 215 nm; UV Absorbance at 254 nm; complete ionization MSD spectrum; evaporative light scattering detection spectrum. Chimera B-A/s was 99.99% pure. (B) HRMS chromatogram of compound B-A/s (C21H28N4OS) shows exact mass found: $[M+H]^+$: 385.2.

Figure 38A:
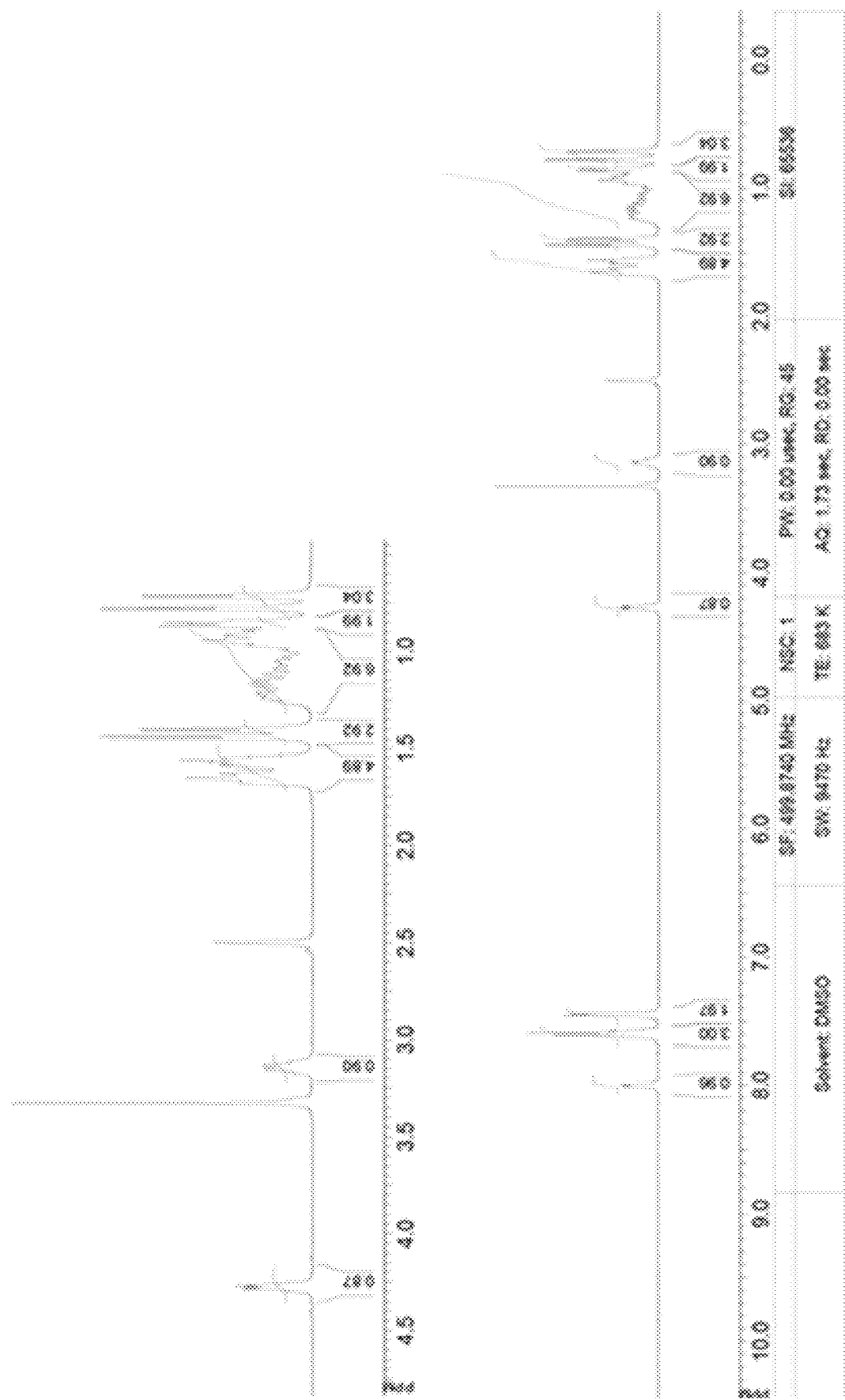
Figure 38B:
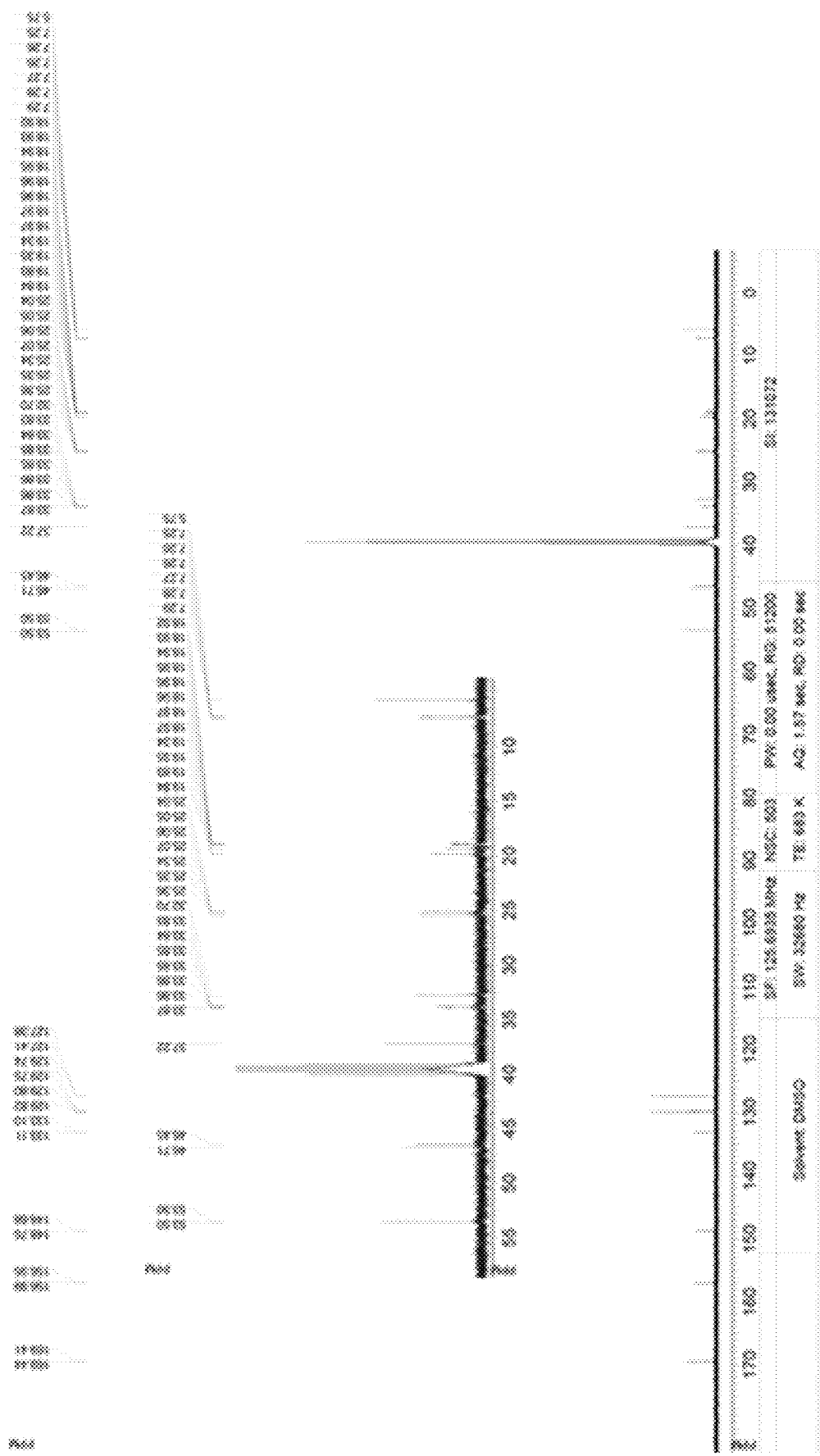

FIG. 38A and FIG. 38B show the proton and carbon-13 NMR of newly synthesized chimera B-A/s. (A) Full $^1$H NMR spectrum (500 MHz) of compound B-A/s (DMSO-$d_6$ solvent) and expanded view of region 60.5-4.8 PPM. (B) $^{13}$C NMR spectrum (126 MHz) of compound B-A/s (DMSO-$d_6$ solvent) and expanded view of region δ 5-60 PPM.

Figure 39:
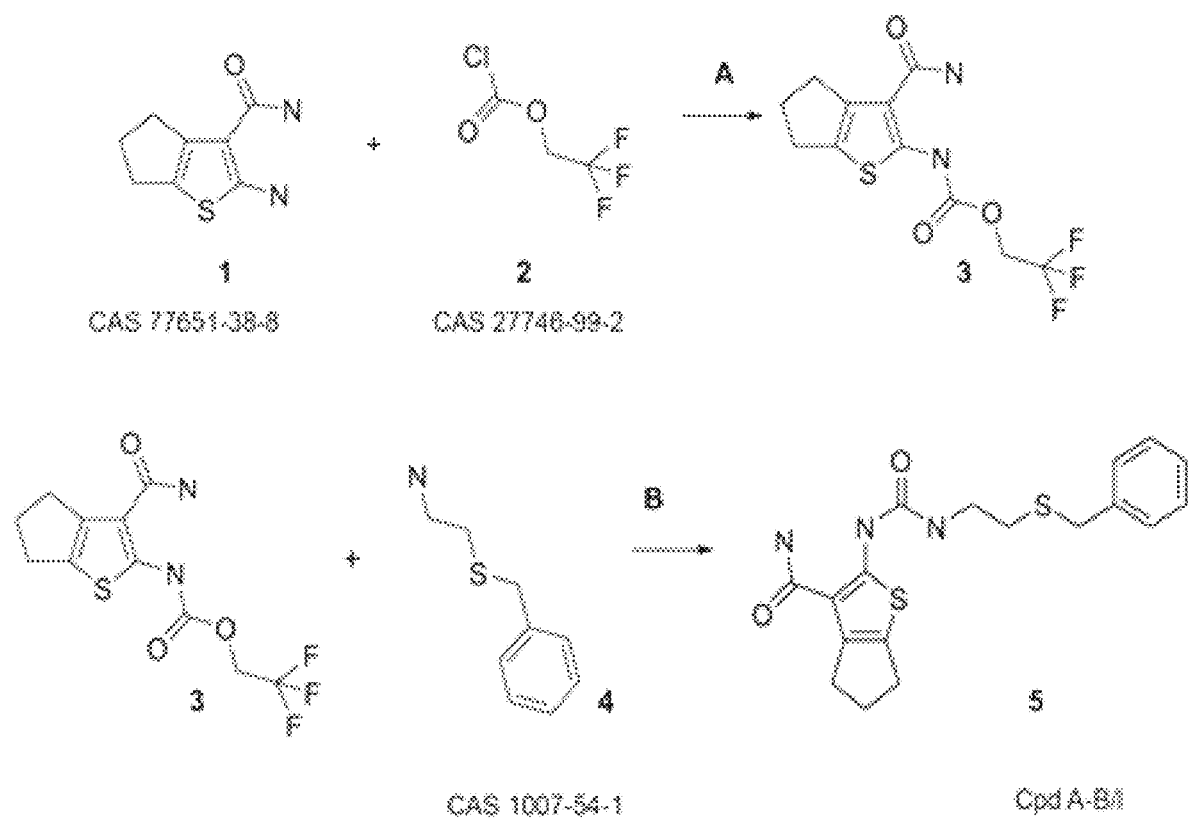

FIG. 39 shows the synthetic route for preparation of chimera A-B/I (compound 5).

Figure 40A:
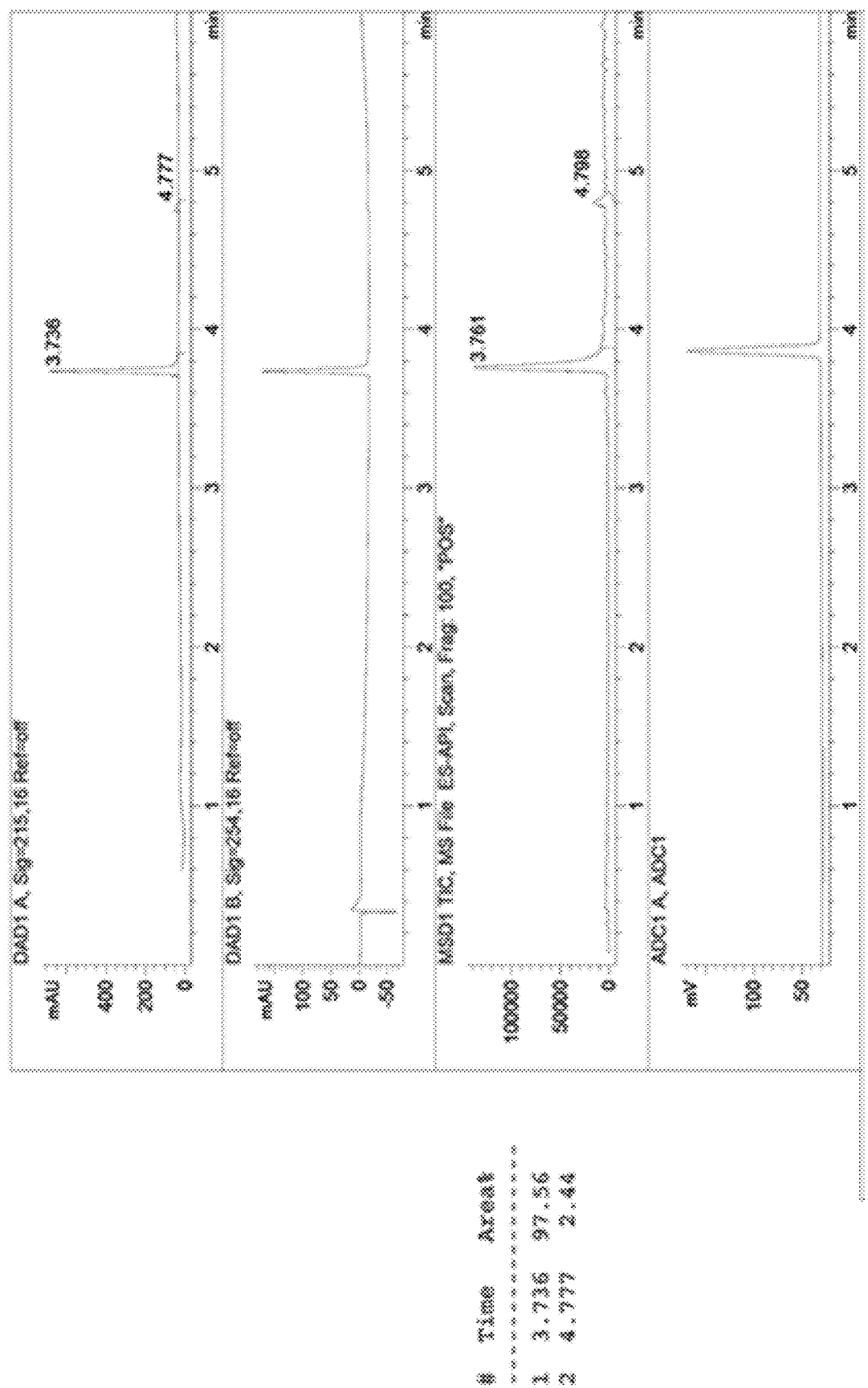
Figure 40B:
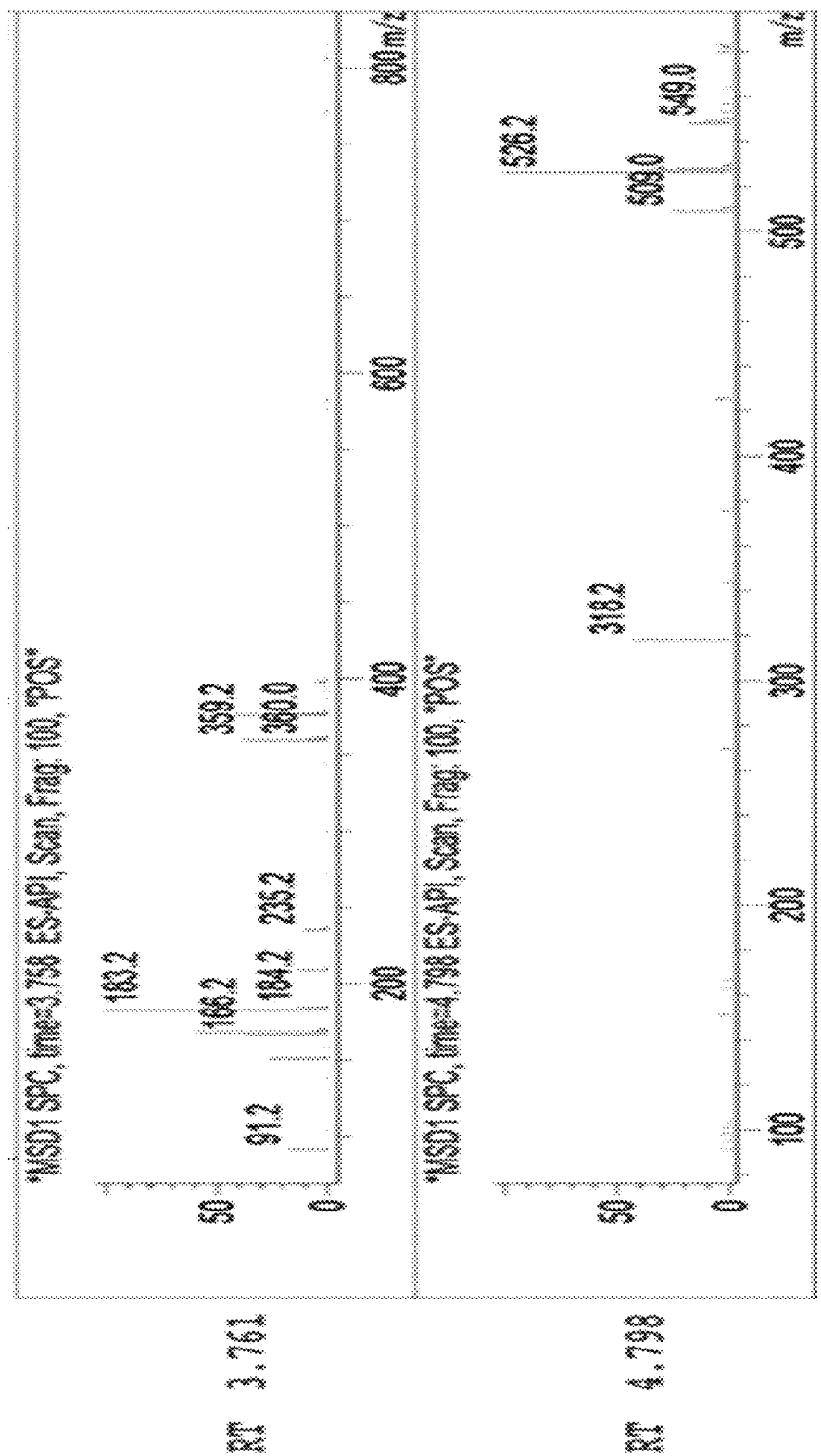

FIG. 40A and FIG. 40B show RP-HPLC and HRMS of newly synthesized chimera A-B/I. (A) HPLC spectrum of newly synthesized chimera A-B/I. From top to bottom: UV Absorbance at 215 nm; UV Absorbance at 254 nm; complete ionization MSD spectrum; evaporative light scattering detection spectrum. Chimera A-B/I was 97.56% pure. (B) HRMS chromatogram of compound A-B/I (C18H21N3O2S2) shows exact mass found: $[M+H]^+$: 376.0.

Figure 41A:
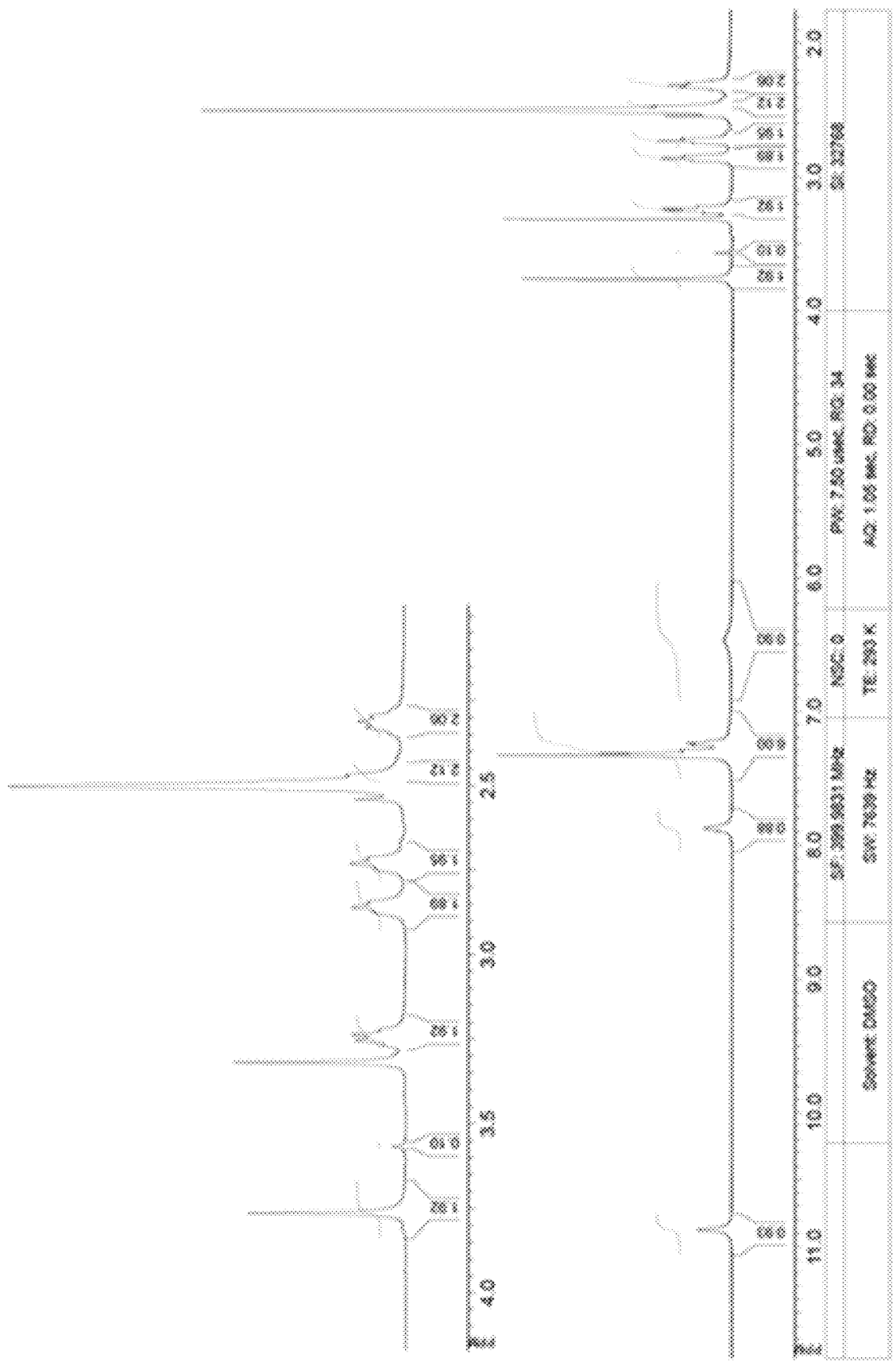
Figure 41B:
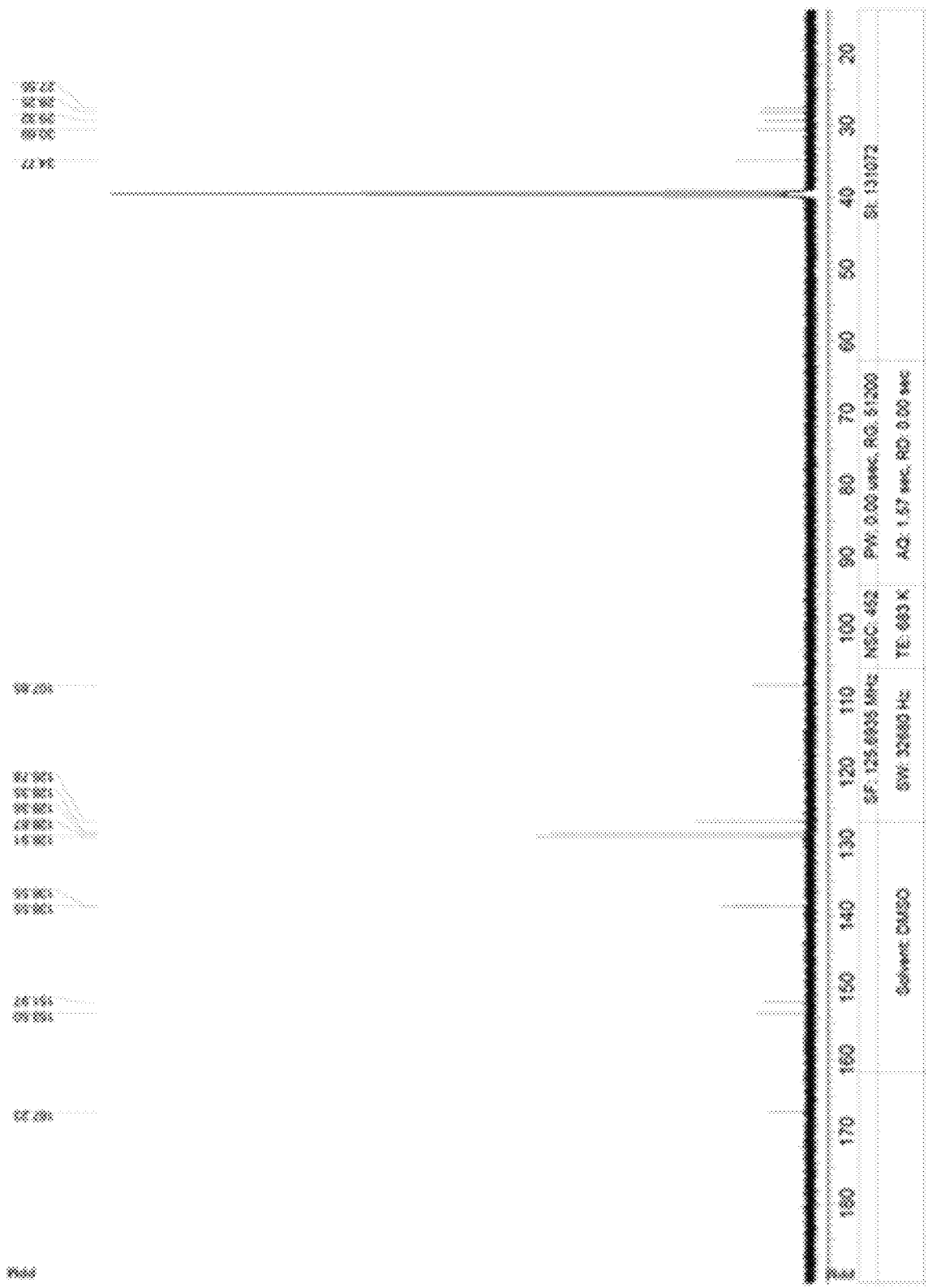

FIG. 41A and FIG. 41B show Proton and carbon-13 NMR of newly synthesized chimera A-B/I. (A) Full $^1$H NMR spectrum (400 MHz) of newly synthesized chimera A-B/I (DMSO-$d_6$ solvent) and expanded view of region δ 2.0-4.1 PPM. (B) $^{13}$C NMR spectrum (126 MHz) of chimera A-B/I (DMSO solvent).

Figure 42:
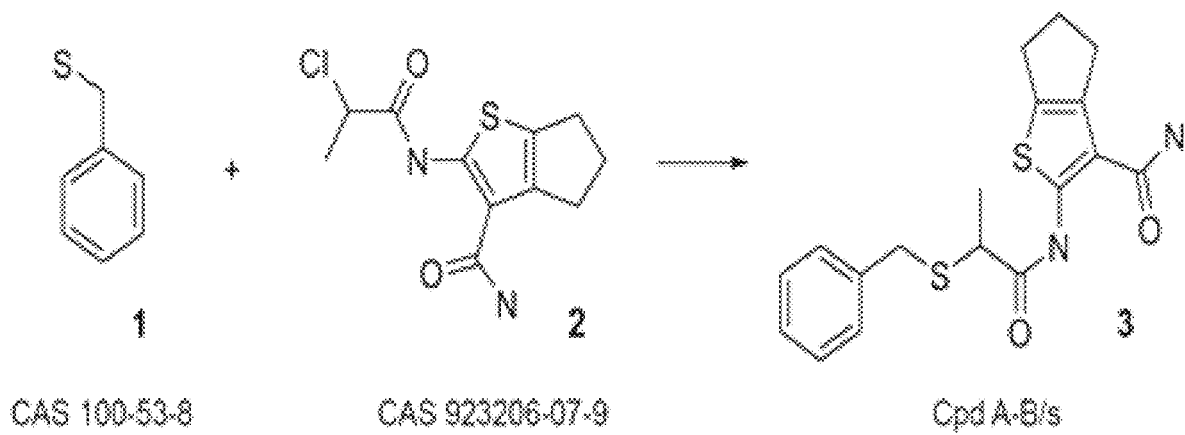

FIG. 42 is a schematic showing the synthetic route for preparation of chimera A-B/s (compound 3).

Figure 43A:
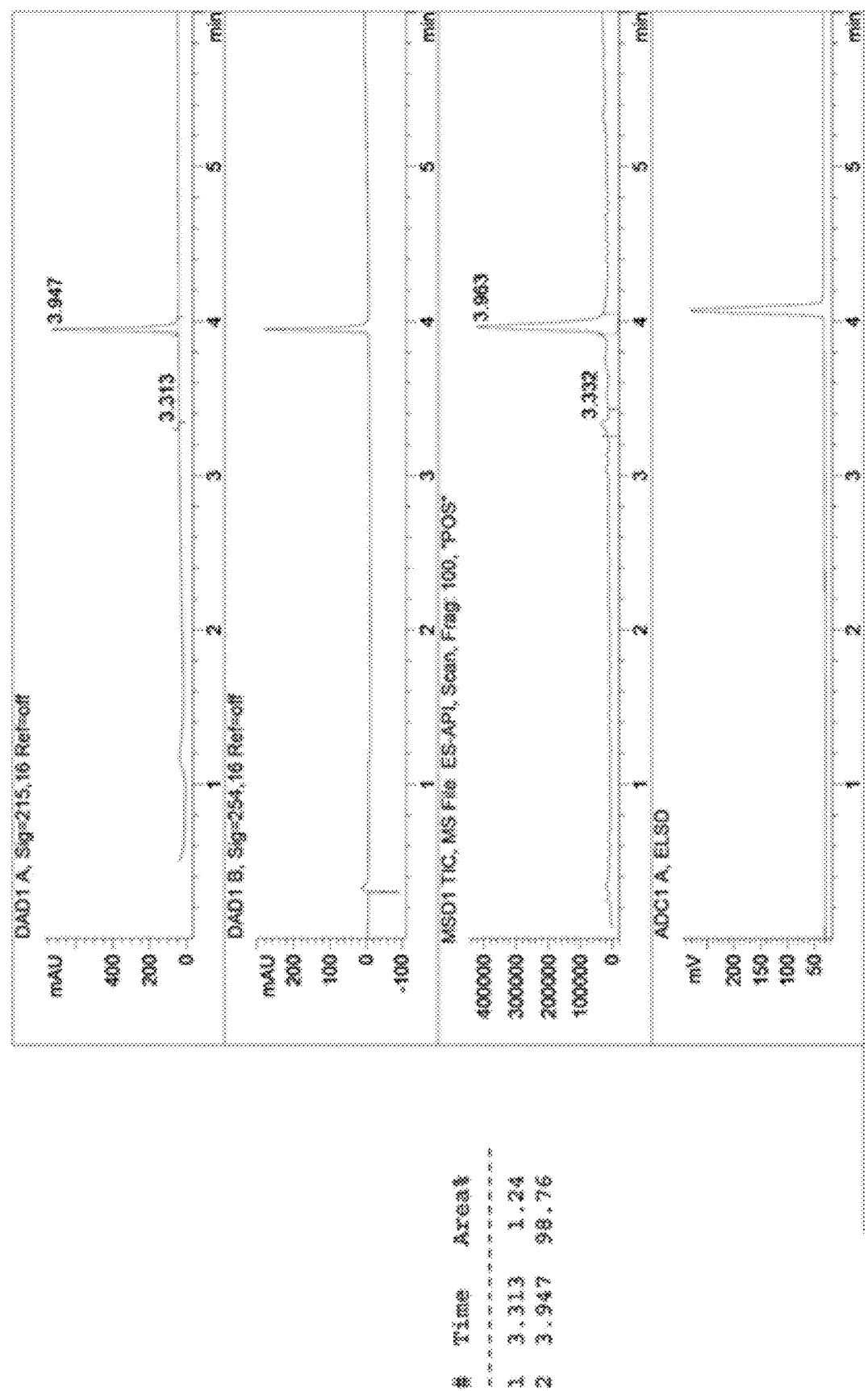
Figure 43B:
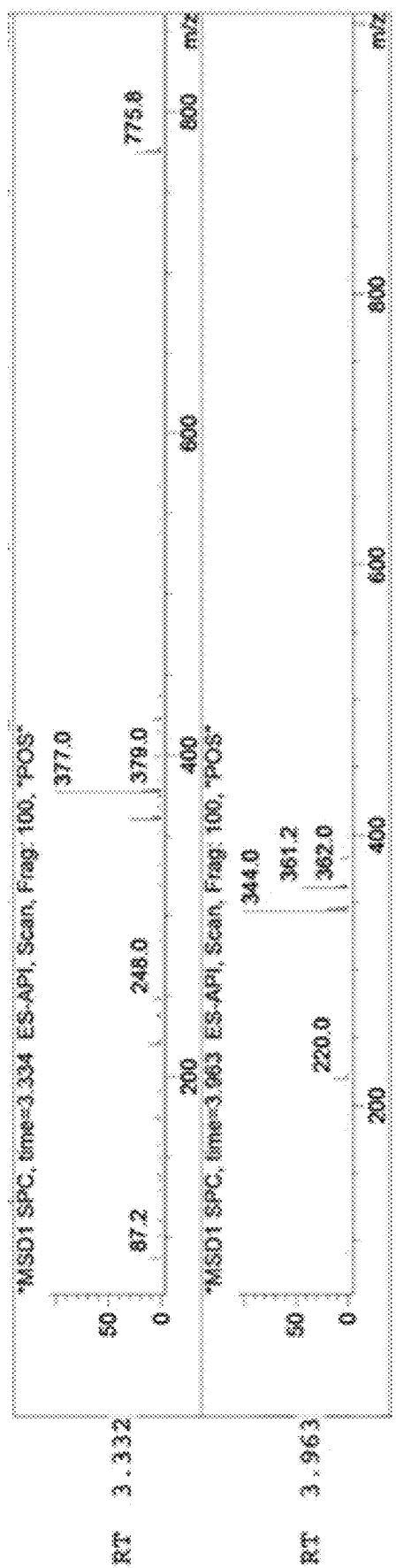

FIG. 43A and FIG. 43B show RP-HPLC and HRMS of newly synthesized chimera A-B/s. (A) HPLC spectrum of compound A-B/s. From top to bottom: UV Absorbance at 215 nm; UV Absorbance at 254 nm; complete ionization MSD spectrum; evaporative light scattering detection spectrum. Chimera A-B/s was 98.76% pure. (B) HRMS chromatogram of chimera A-B/s (C18H20N2O2S2) shows exact mass found: $[M+H]^+$: 361.2.

Figure 44A:
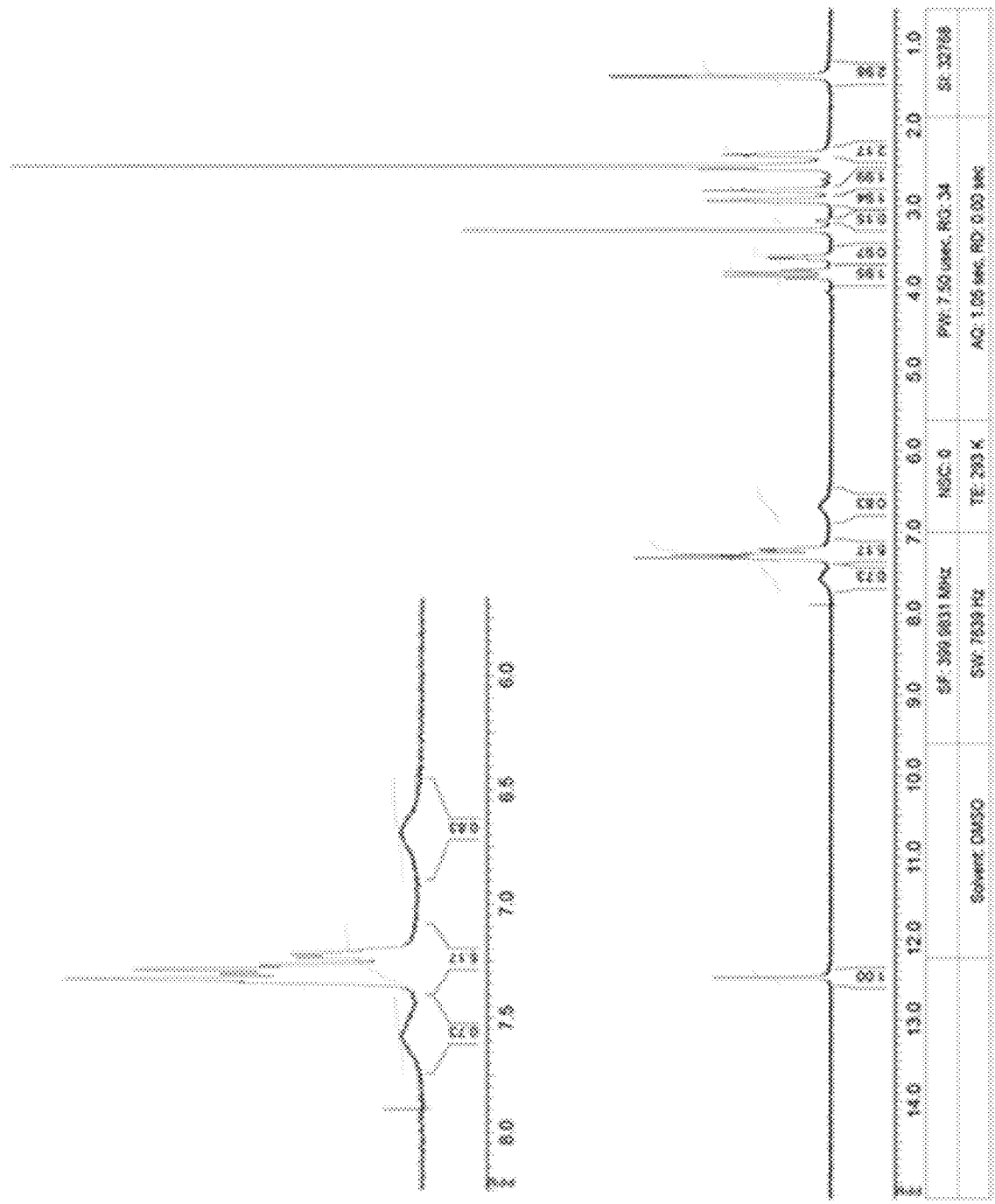
Figure 44B:
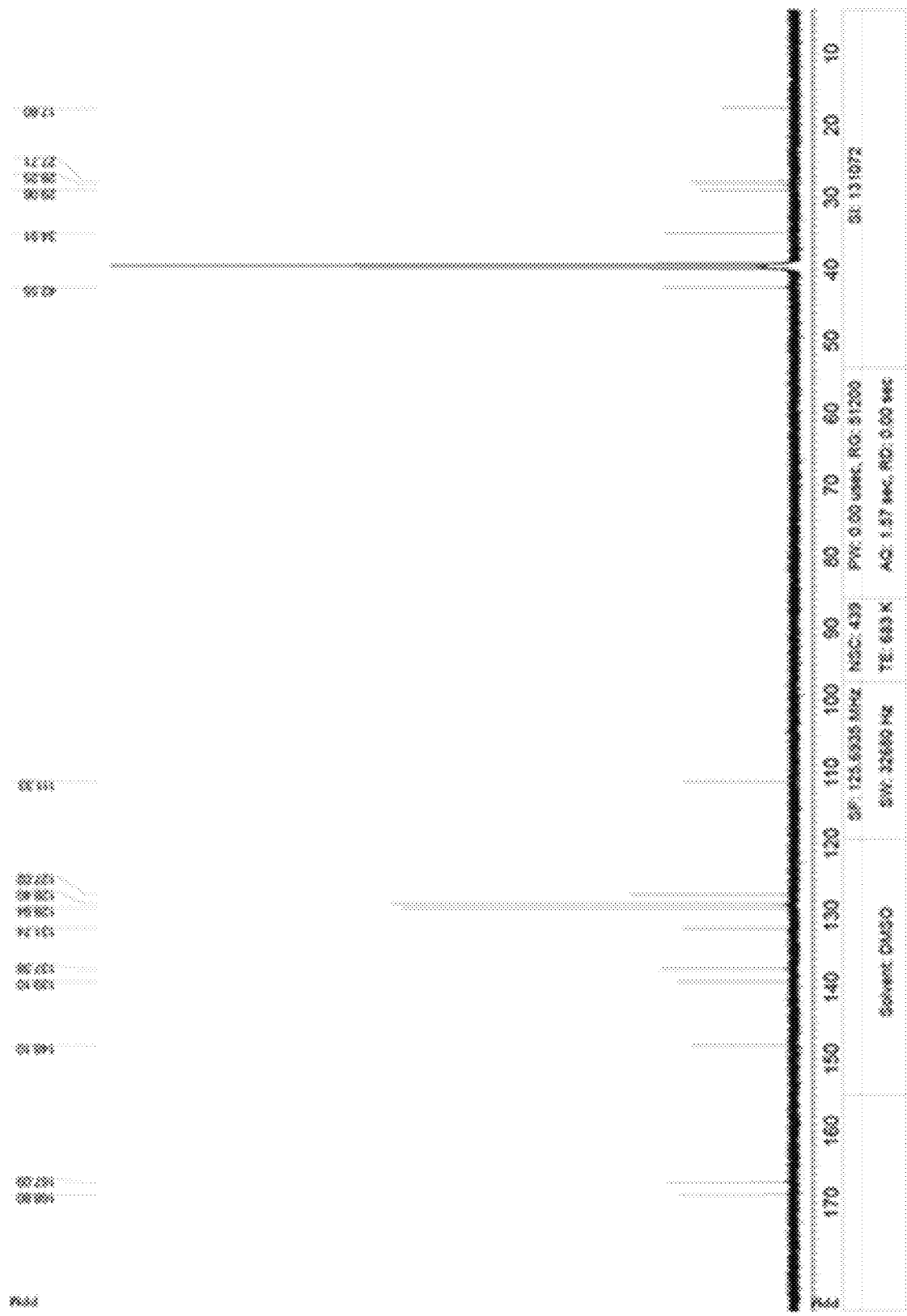

FIG. 44A and FIG. 44B show the proton and carbon-13 NMR spectra of newly synthesized chimera A-B/s. (A) Full $^1$H NMR spectrum (400 MHz) of chimera A-B/s (DMSO-$d_6$ solvent) and expanded view of region δ 5.7-8.2 PPM. (B) $^{13}$C NMR spectrum (126 MHz) of chimera A-B/s (DMSO-$d_6$ solvent).

Figure 45:
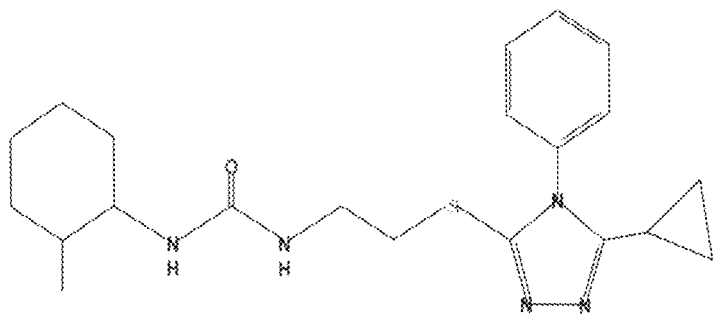

FIG. 45 shows the initial PK studies of Chimera B-A/I, a.k.a. Regeneurin-S. In vitro pharmacokinetic profiling of Regeneurin-S reveals rapid degradation by liver mcirosomes. Chimera B-A/I from Rocha, et al Science 2018 was designated Regeneurin-S. Shown is its chemical structure and results of three independent pharmacokinetic (PK) assays performed months apart.

Figure 46:
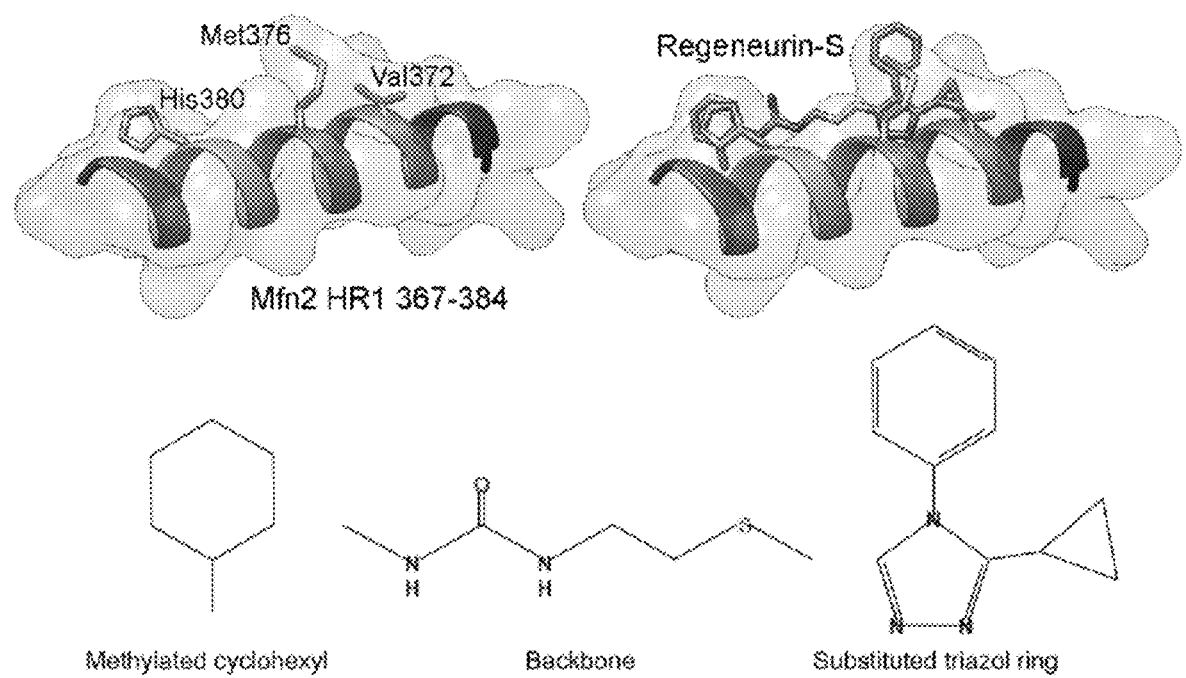

FIG. 46 is a series of structures showing structural considerations for chemical evolution of the lead mitofusin agonist. (top left) Structural model of human Mfn2 HR1 367-384 agonist peptide (ribbon) in context of Mfn2 HR1 domain from which it was derived (space-filling; from Franco Nature 2016); side chains of HR1-HR2 interacting amino acids Val372, Met376, and His380 are depicted. (top right) Structure of HR1 367-384 peptidomimetic Regeneurin-S (chimera B-A/I from Rocha Science 2018) is shown mimicking function-critical side chains from HR1 367-384. Modeled using Chimera UCSF. (bottom) Functional groups of Regeneurin-S are depicted as conceived for chemical engineering: methylated cyclohexyl corresponding to ring structure of His380; thioether backbone providing proper spacing; phenyl-, cyclopropyl-substituted triazol ring mimicking hydrophobicity of Met376 and Val372.

Figure 47:
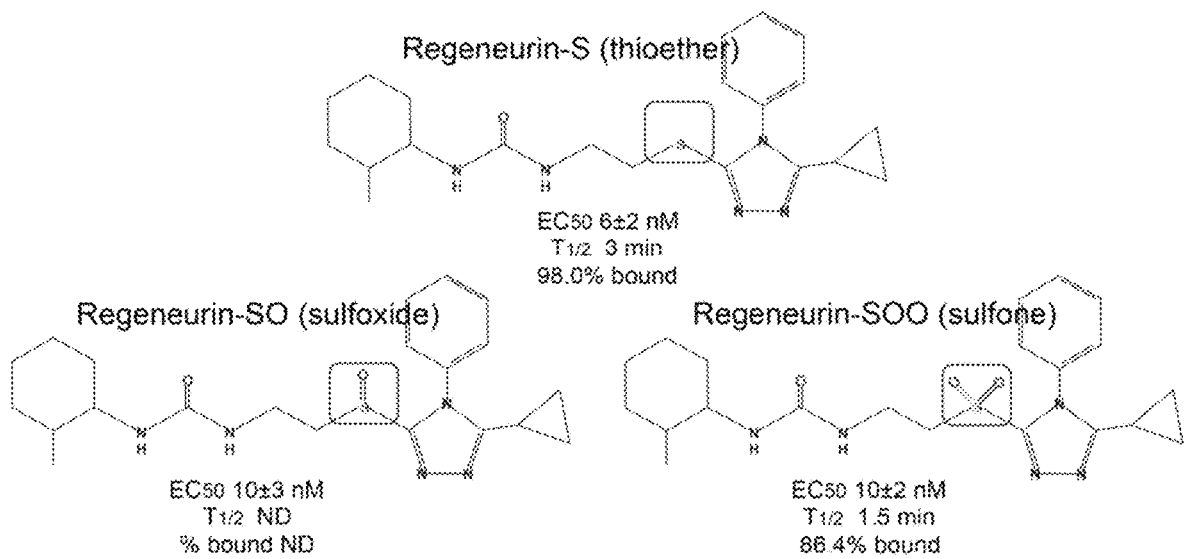
Figure 47:
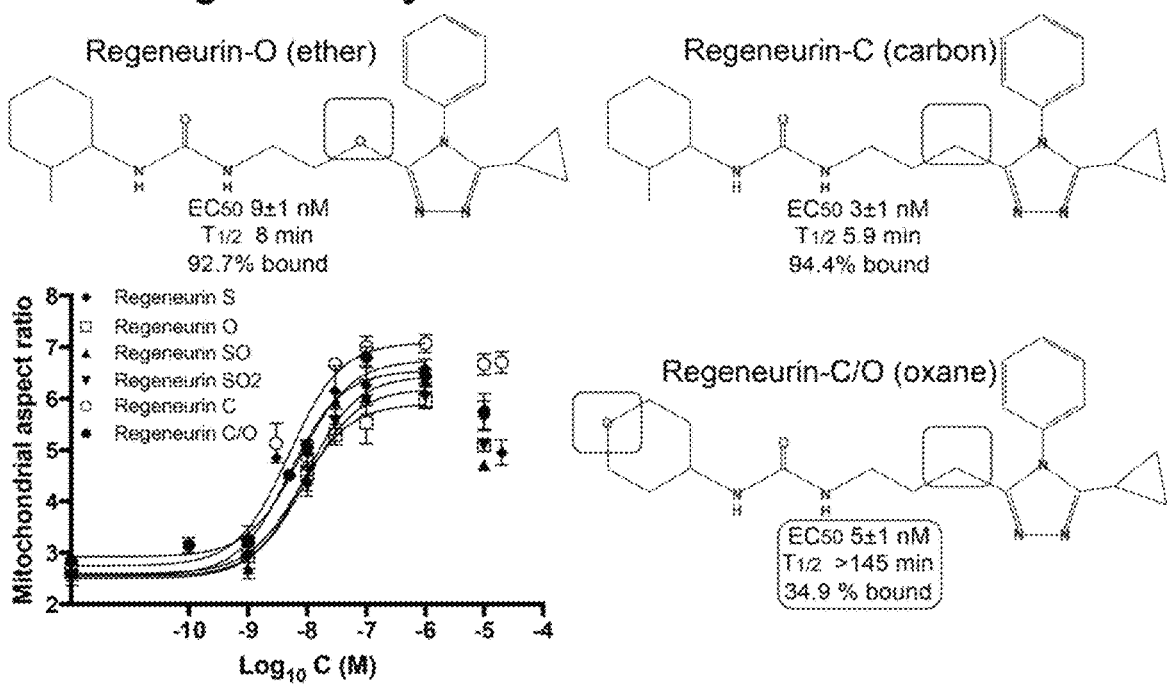

FIG. 47 is a series of structures and a graph showing backbone sulfur modifications or substitutions do not alter Regeneurin mitofusin agonist efficacy or affect its degradation by liver microsomes. The backbone sulfur of the parent thioether was oxidized using hydrogen peroxide to generate the sulfoxide and sulfone, which are potential metabolites (top). The ether and carbon variants and carbon variant with tetrahydropyran substituted for methylated cyclohexane were synthesized de novo (bottom). Red rectangles show substitutions. T % is for human liver microsomes, % bound is for human plasma. (All PK studies were not performed on all backbone variants.) Dose-response curves for mitochondrial elongation (bottom left) are similar for all compounds.

Figure 48A:
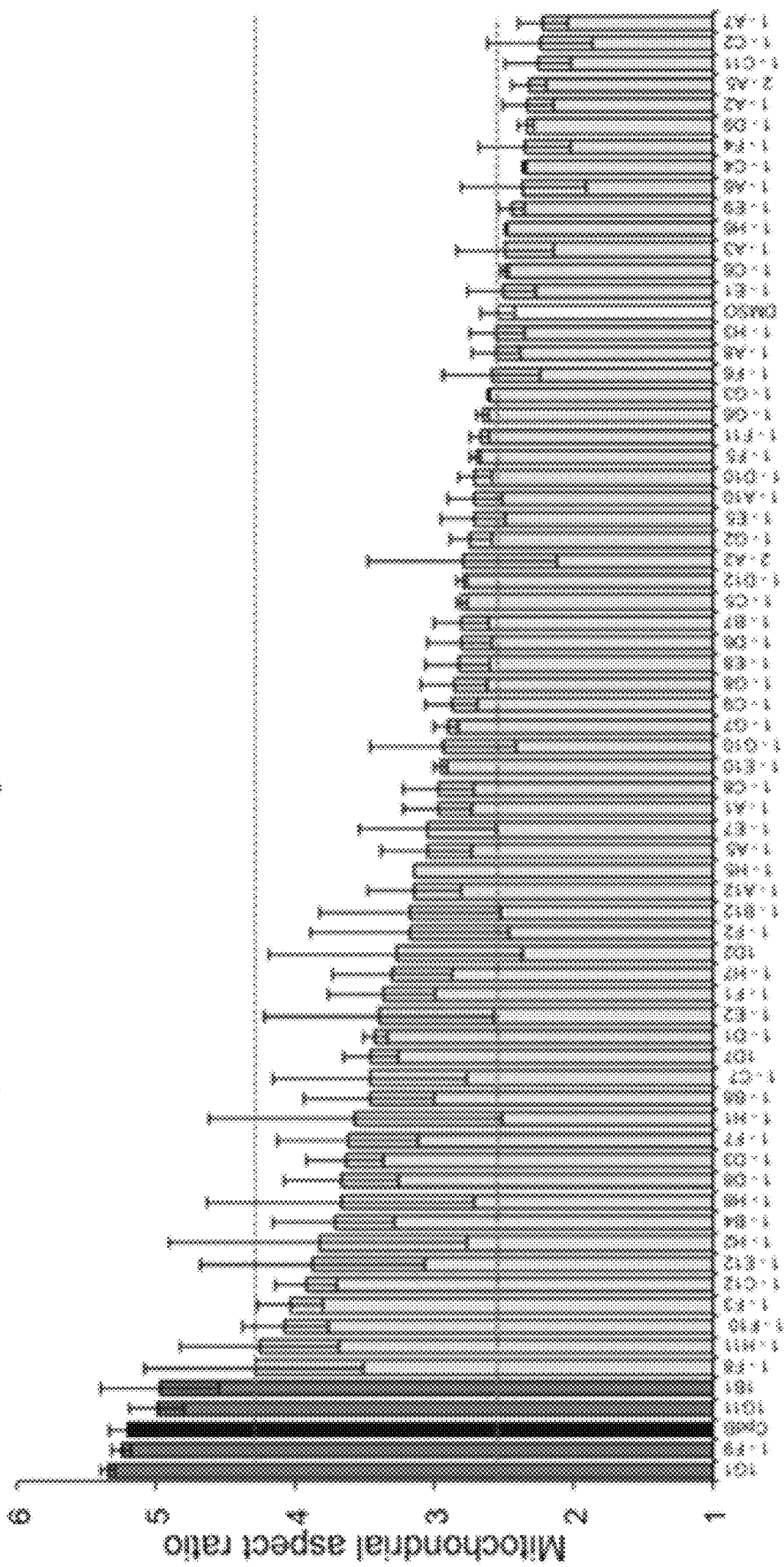
Figure 48B:
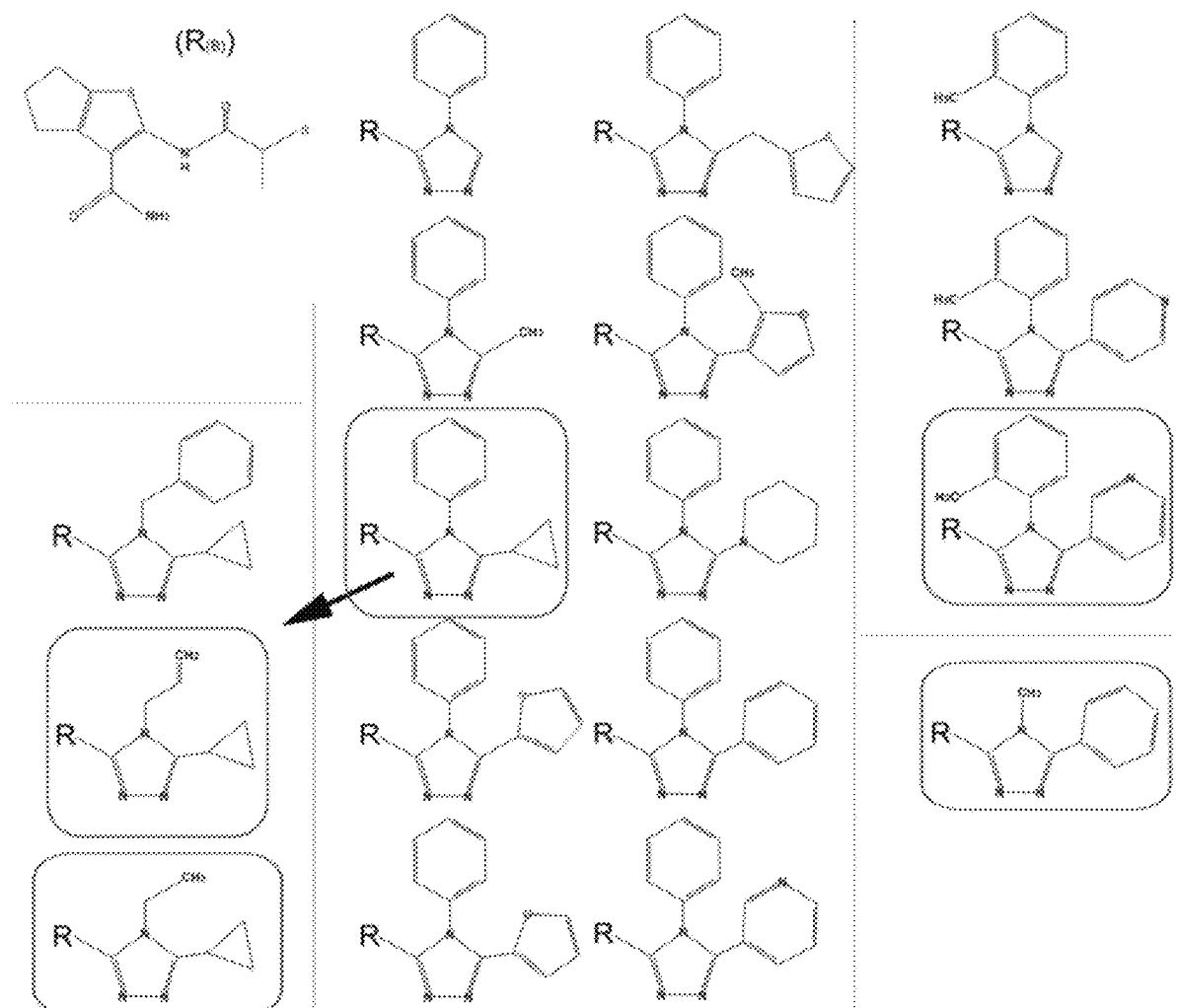

FIG. 48 is a bar graph and a series of structures showing functional screening of commercially available Cpd B tri-azol ring substitution variants. Top: Rank order of fusogenicity (increase in mitochondrial aspect ratio of Mfn2 null MEFs in response to 1 mM compound overnight) provoked by compounds in Supplemental dataset 1. Red dashed line indicates baseline aspect ratio (DMSO-treated MEFs, negative control); green dashed line shows aspect ratio in response to Cpd B (positive control). Bottom: Triazol ring substitutions of 17 compounds otherwise having the common structure $R_{(B)}$. Cpd B is indicated with red rectangle; the other four fusogenic compounds are indicated with green rectangles. Results of detailed studies of these compounds are in FIG. 49.

Figure 49:
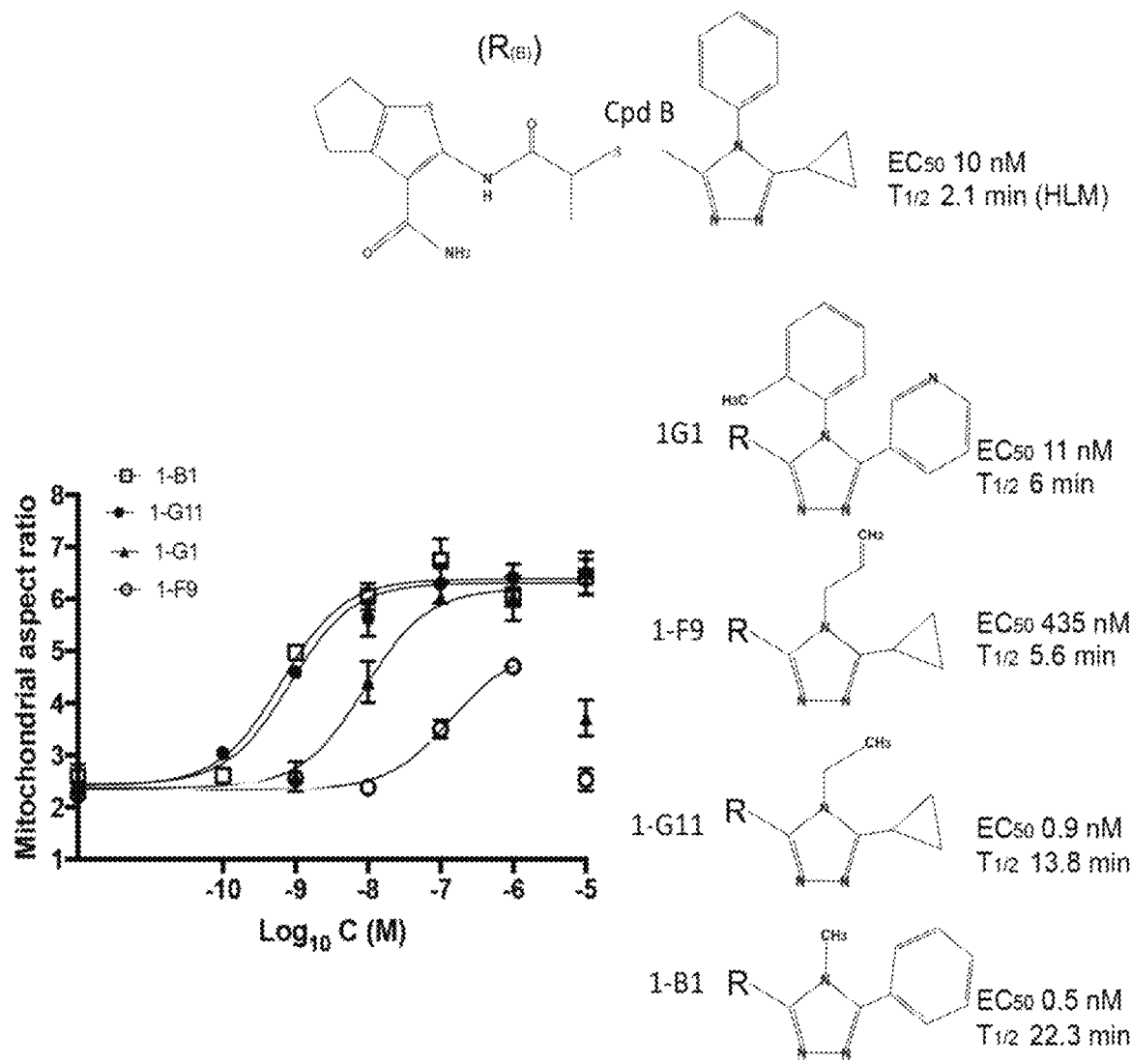

FIG. 49 is a series of structures and a graph showing dose-response and human liver microsomal stability data for fusogenic compounds from FIG. 22. $EC_{50}$ values are mean±SEM of 3 independent experiments assessing mitochondrial aspect ratio in Mfn2 null MEFs; Group data dose-response curves are on the left. $T_{1/2}$ values are from human liver microsome stability assay.

Figure 50:
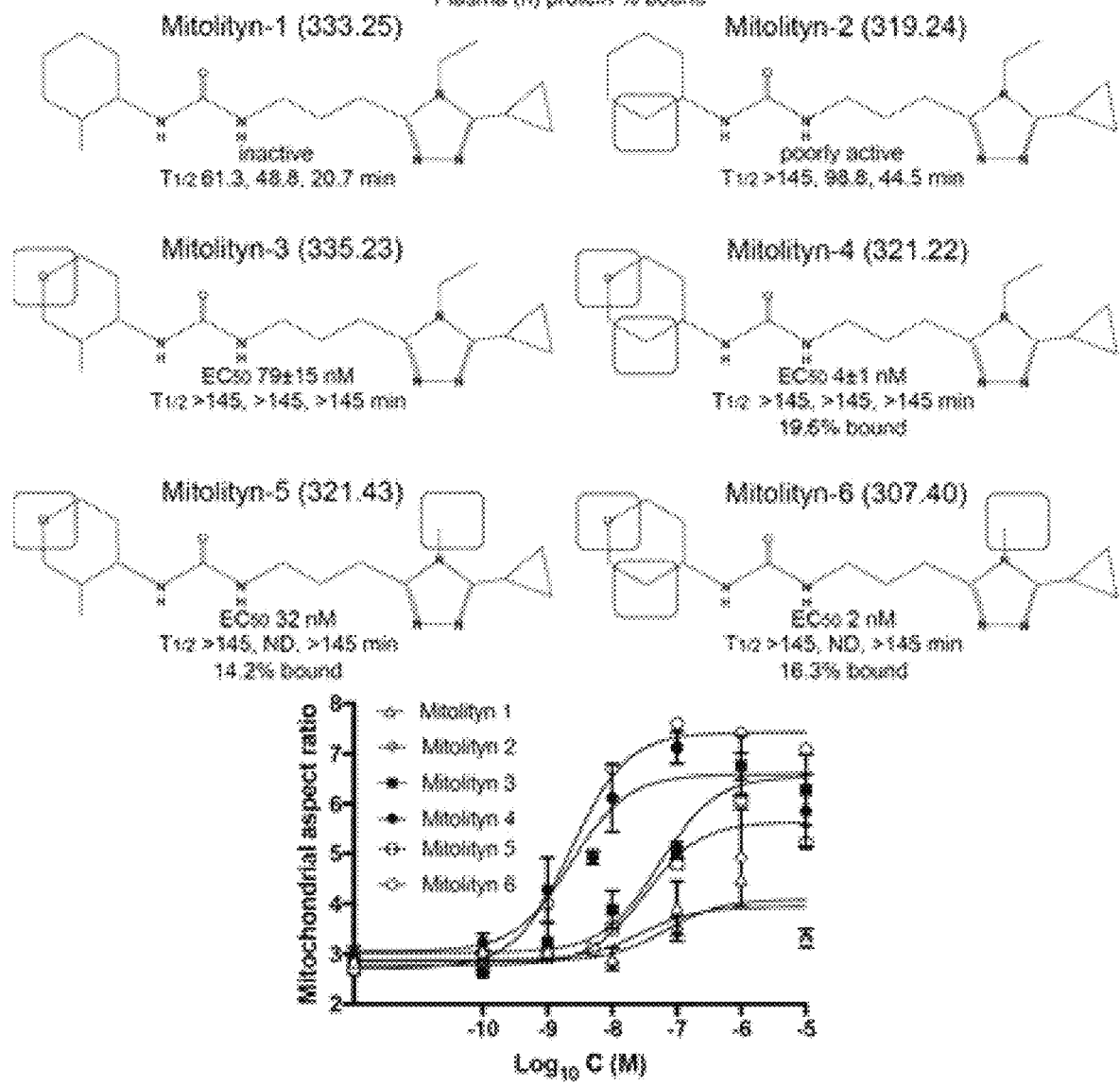

FIG. 50 is a series of structures and a graph showing a mitolityn series of mitofusin agonists. The feature that distinguishes Mitolityns from Regeneurins is replacement of the 2-phenyl group on the 2,4,5 triazol ring with ethyl or methyl groups. Mitolityns 1 and 2 are 2-ethyl cyclohexane variants and Mitolityns 3 and 4 are 2-ethyl tetrahydropyran variants; Mitolityns 5 and 6 are like 3 and 4 with 2-methyl rather than 2-ethyl groups off the 2,4,5 triazol ring. Chemical differences from Mitolityn-1 are shown in red rectangles; molecular weights are in parentheses. $EC_{50}$ values are for stimulated increase in mitochondrial aspect ratio in Mfn2 null MEFs (n=3 each, mean±SEM); $T_{1/2}$ values are for human, rat, and mouse liver microsome stability assay, in that order. % bound is for human plasma. Group mitochondrial aspect ratio dose response data are shown at the bottom. Mitolityns-4 and -6 exhibited highest potency in the fusogenicity assay, stability in the liver microsome assay, and low plasma protein binding.

Figure 51A:
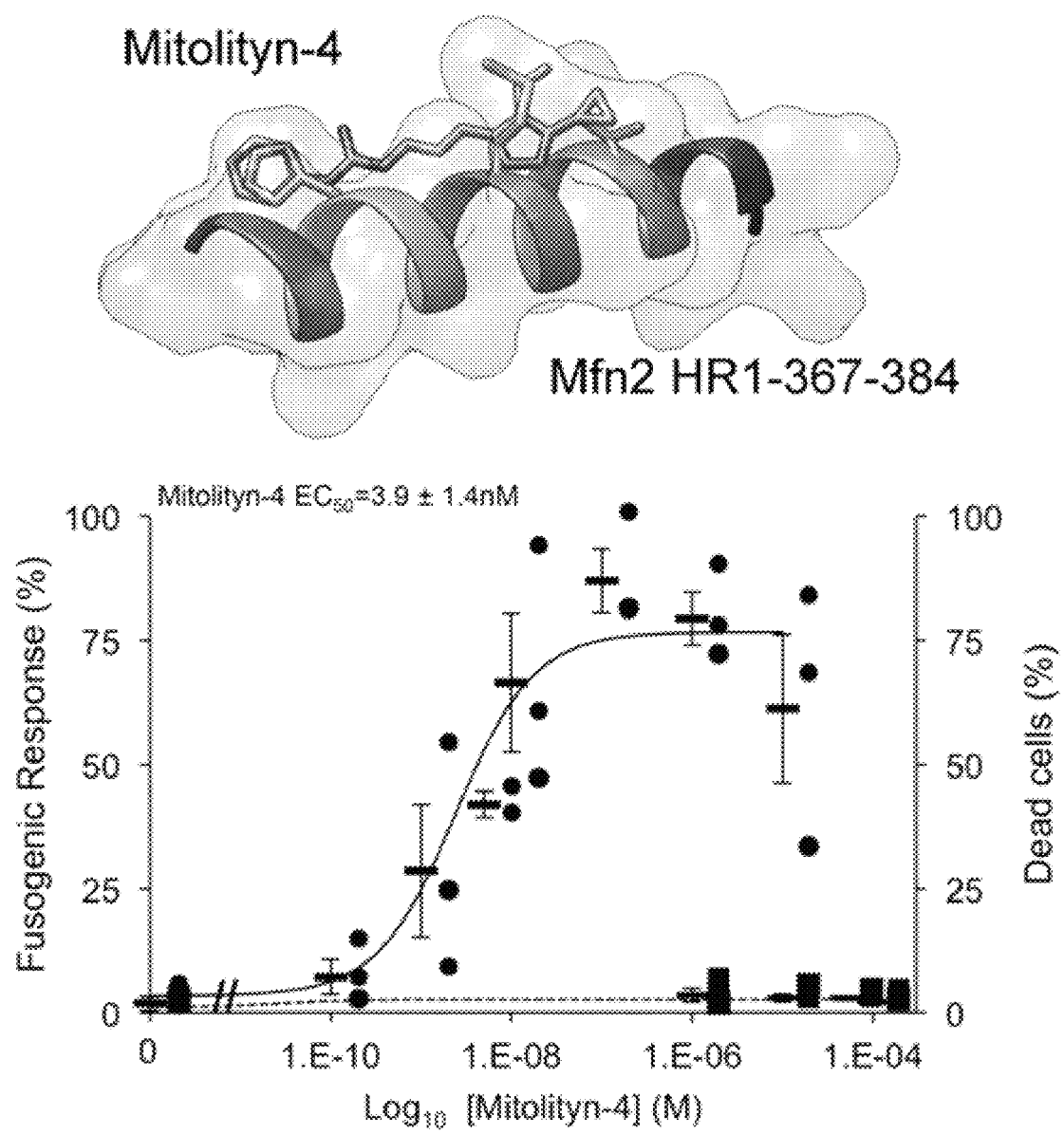
Figure 51B:
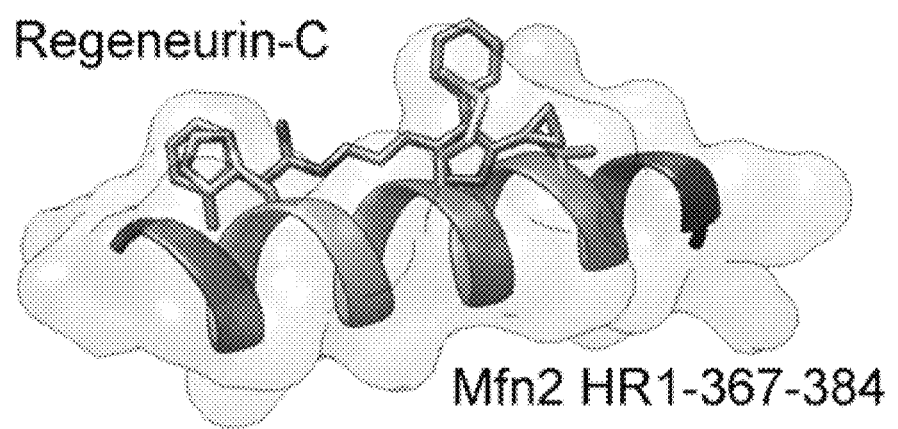
Figure 51B:
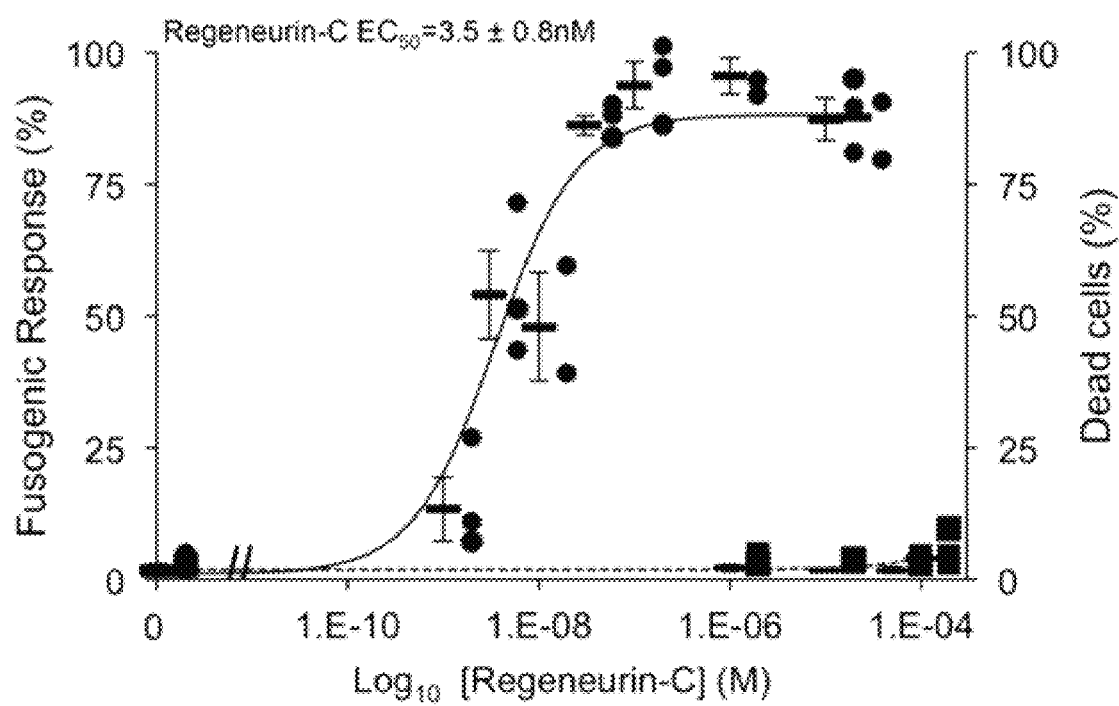

FIG. 51 shows dose-dependent mitochondrial fusion without cytotoxicity of structurally diverse mitofusin agonists. At the top are depictions of Mitolityn-4 (left) and Regeneurin-C (right) mimicry of function-critical side chains of parent agonist peptide Mfn2 HR1 367-384. At the bottom are dose-response relations for each agonist: circles/solid lines show fusogenic responses (mitochondrial elongation assay); squares/dashed lines show % dead cells assayed using the Live-Dead stain. Mfn2 null MEFs were treated with compounds overnight. Indicated $EC_{50}$ values are mean±SEM, n=3 each.

Figure 52:
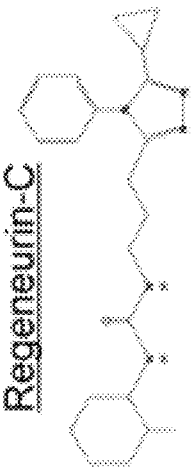

FIG. 52 shows the results of in vitro pharmacokinetic studies of Regeneurin-C, Regeneurin-C/O, and Mitolityn-4 mitofusin agonists.

Figure 53A:
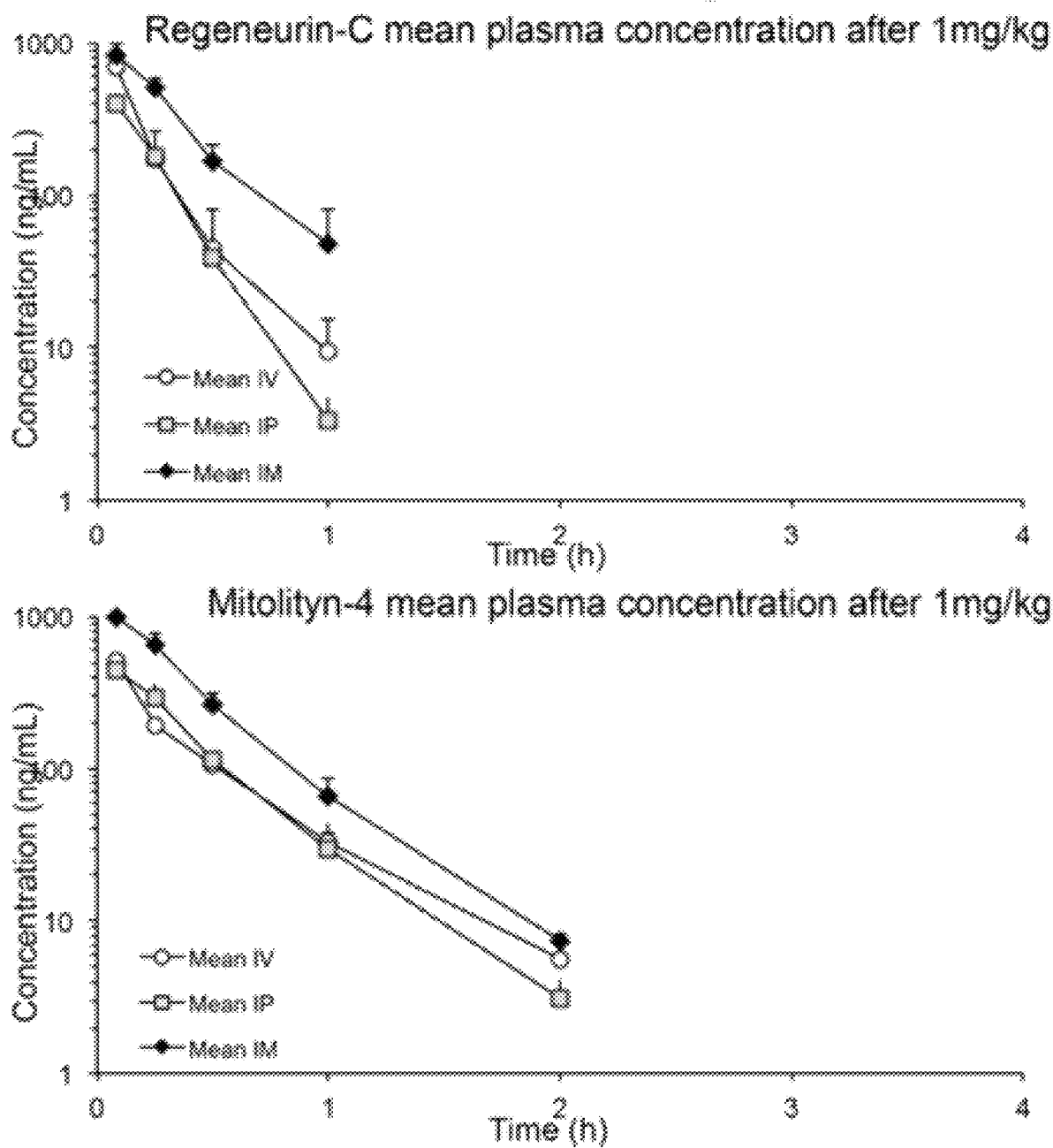
Figure 53B:
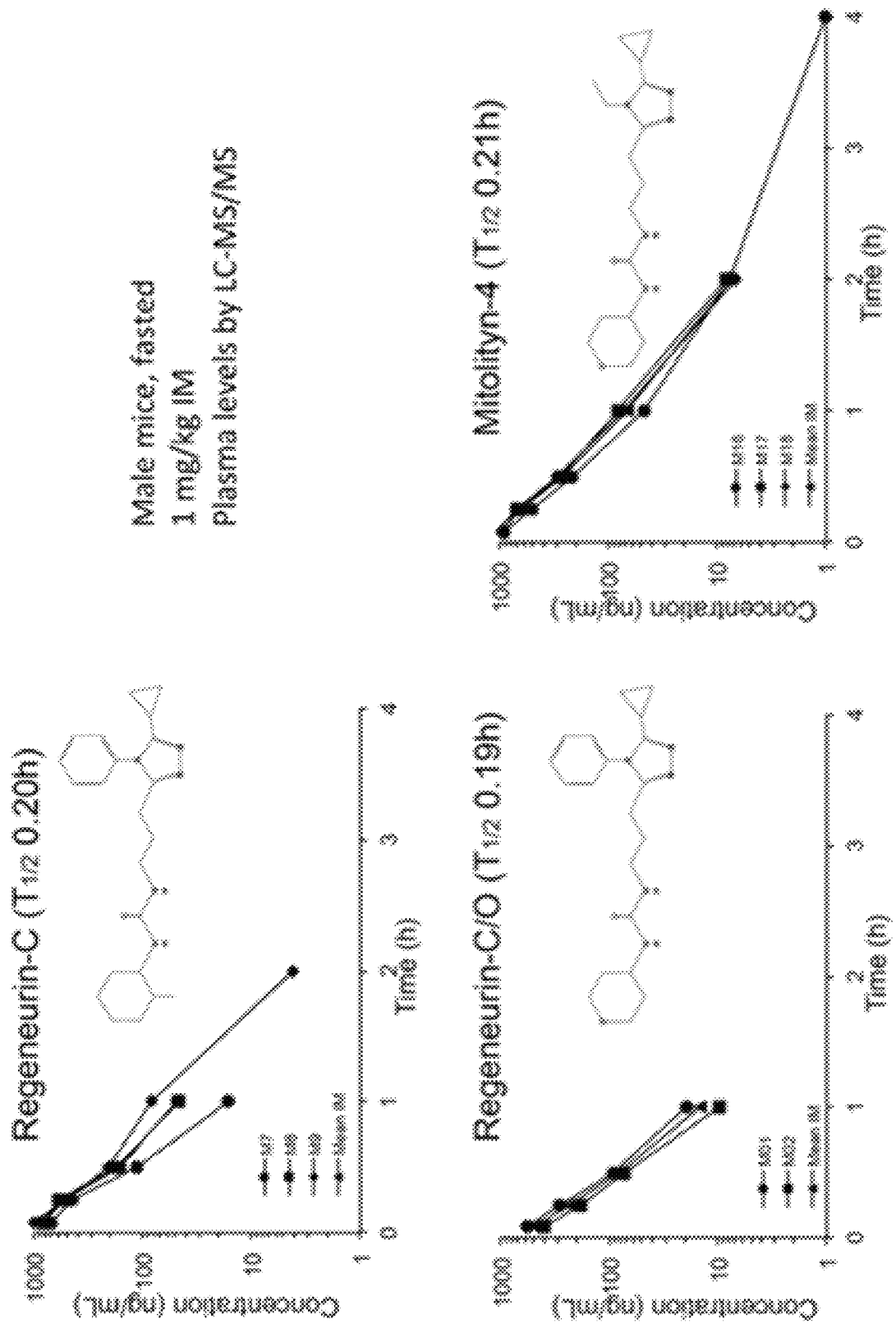

FIG. 53A and FIG. 53B are a series of graphs and corresponding structures showing in vivo pharmacokinetics of Regeneurin-C, Regeneurin C/O and Mitolityn-4. (A) Three mice each were administered 1 mg/kg agonist IV, IP, or IM. Graphs are mean plasma concentration for each administration route. (B) Results for individual mice were administered 1 mg/kg indicated agonist IM.

Figure 54:
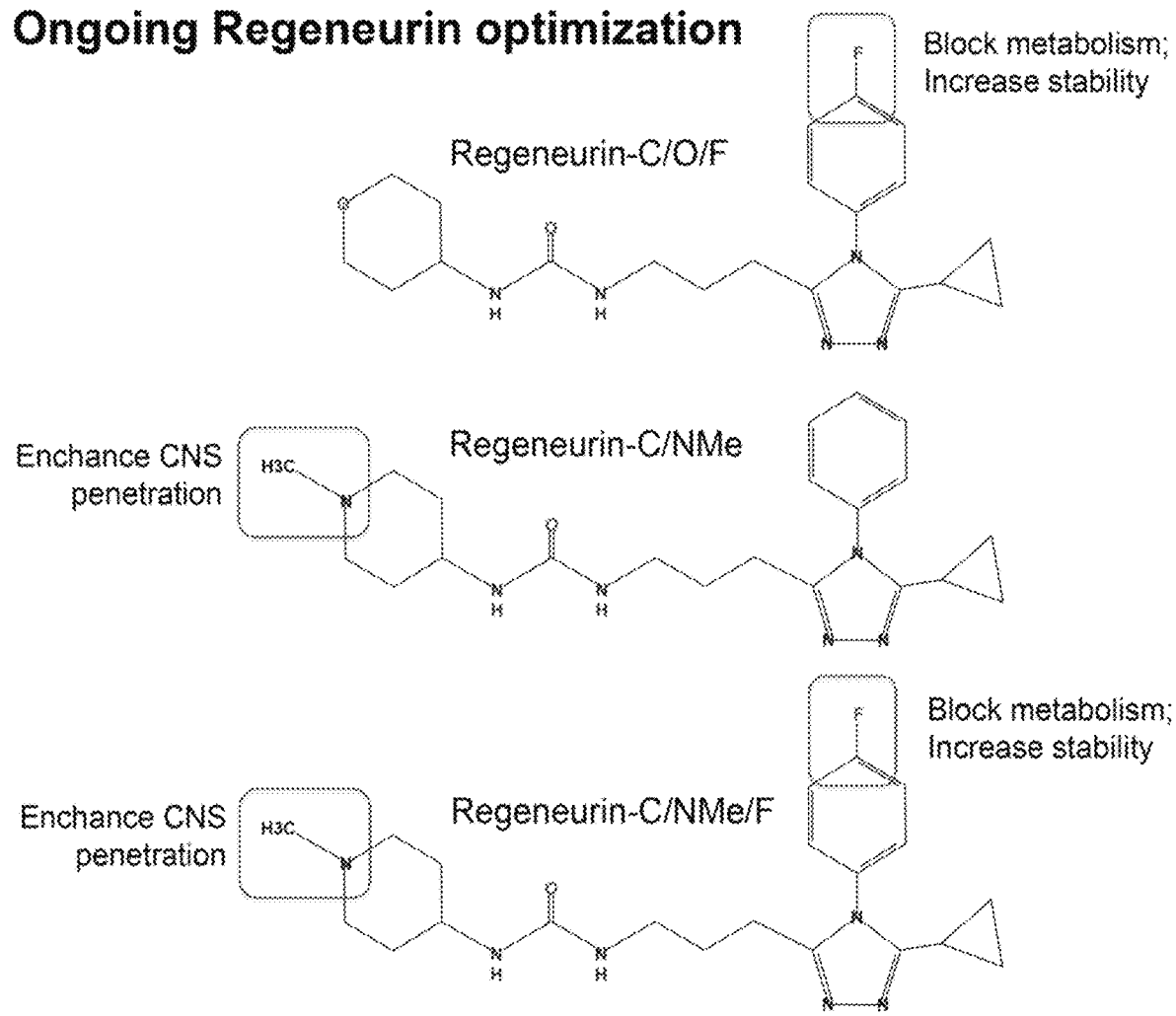
Figure 56A:
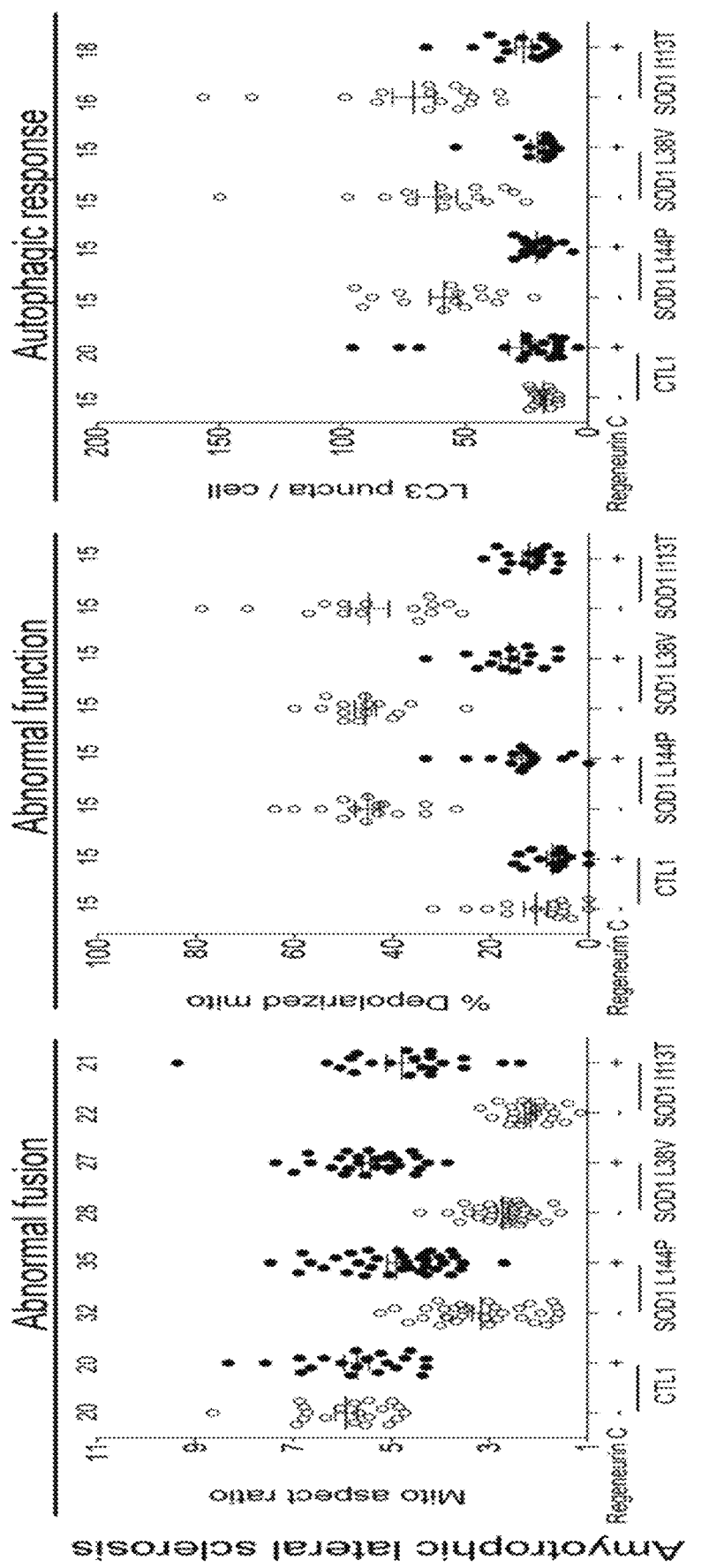
Figure 56B:
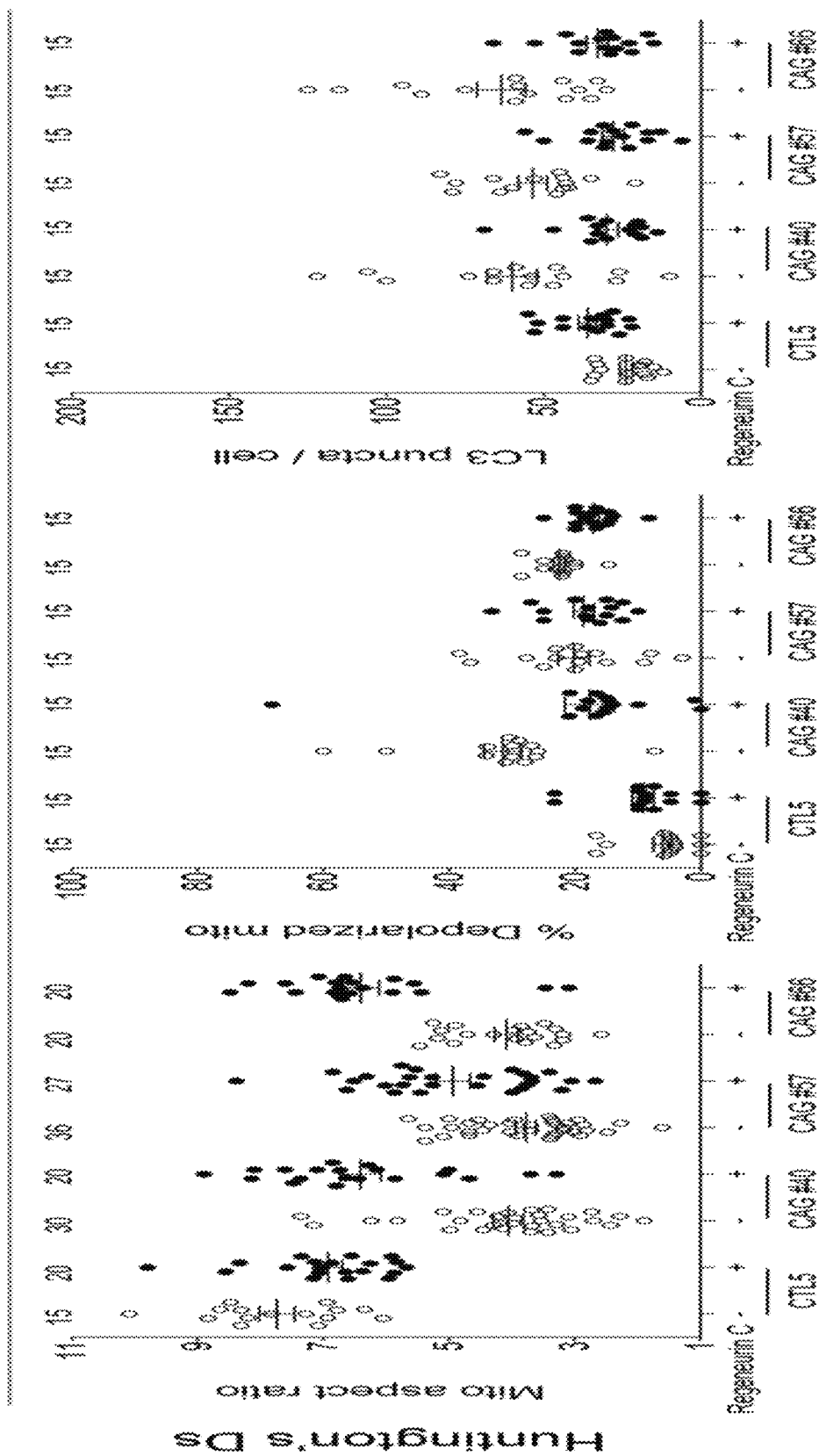
Figure 56C:
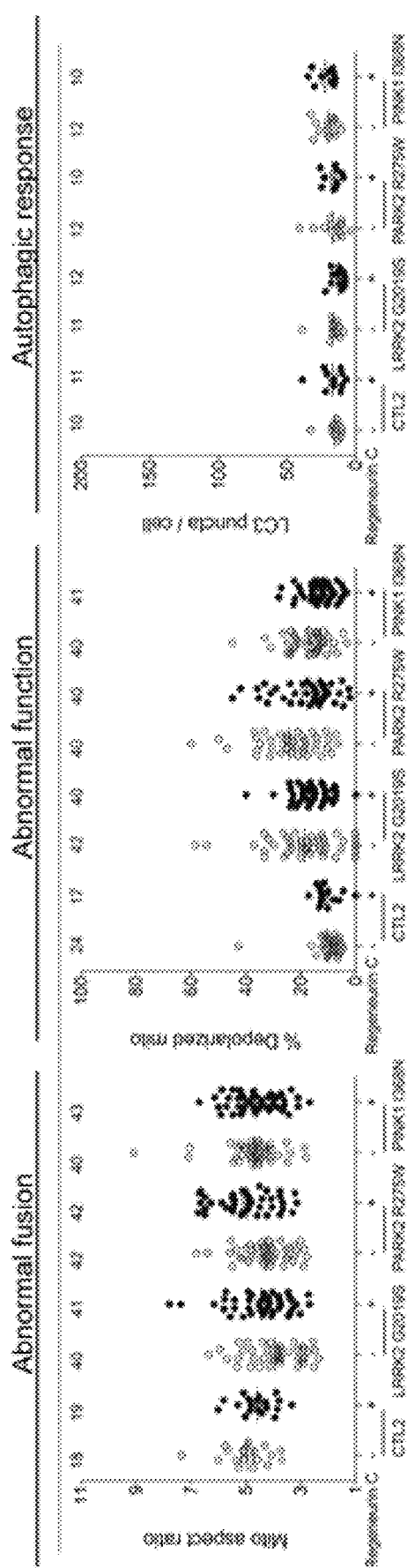
Figure 56D:
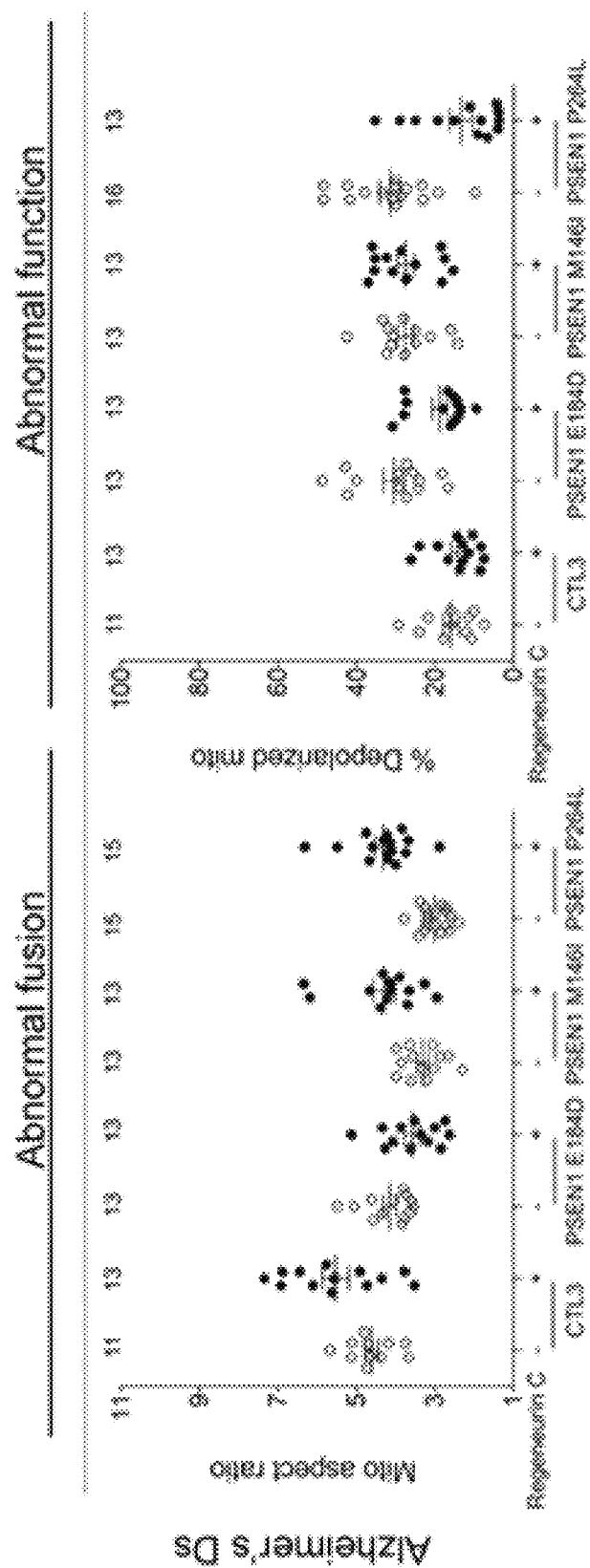
Figure 57A:
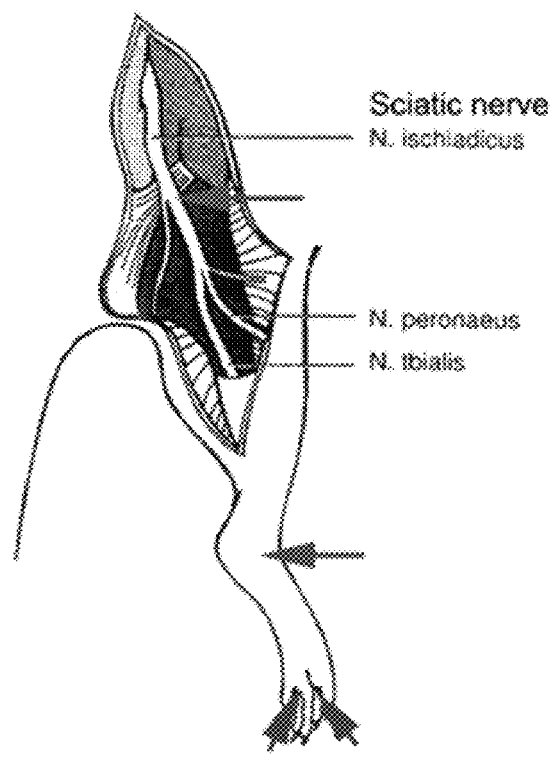
Figure 57B:
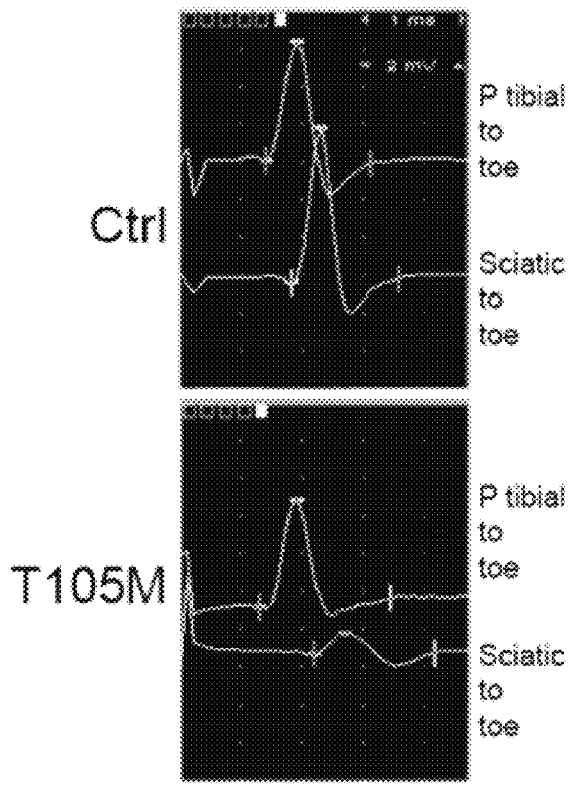
Figure 57C:
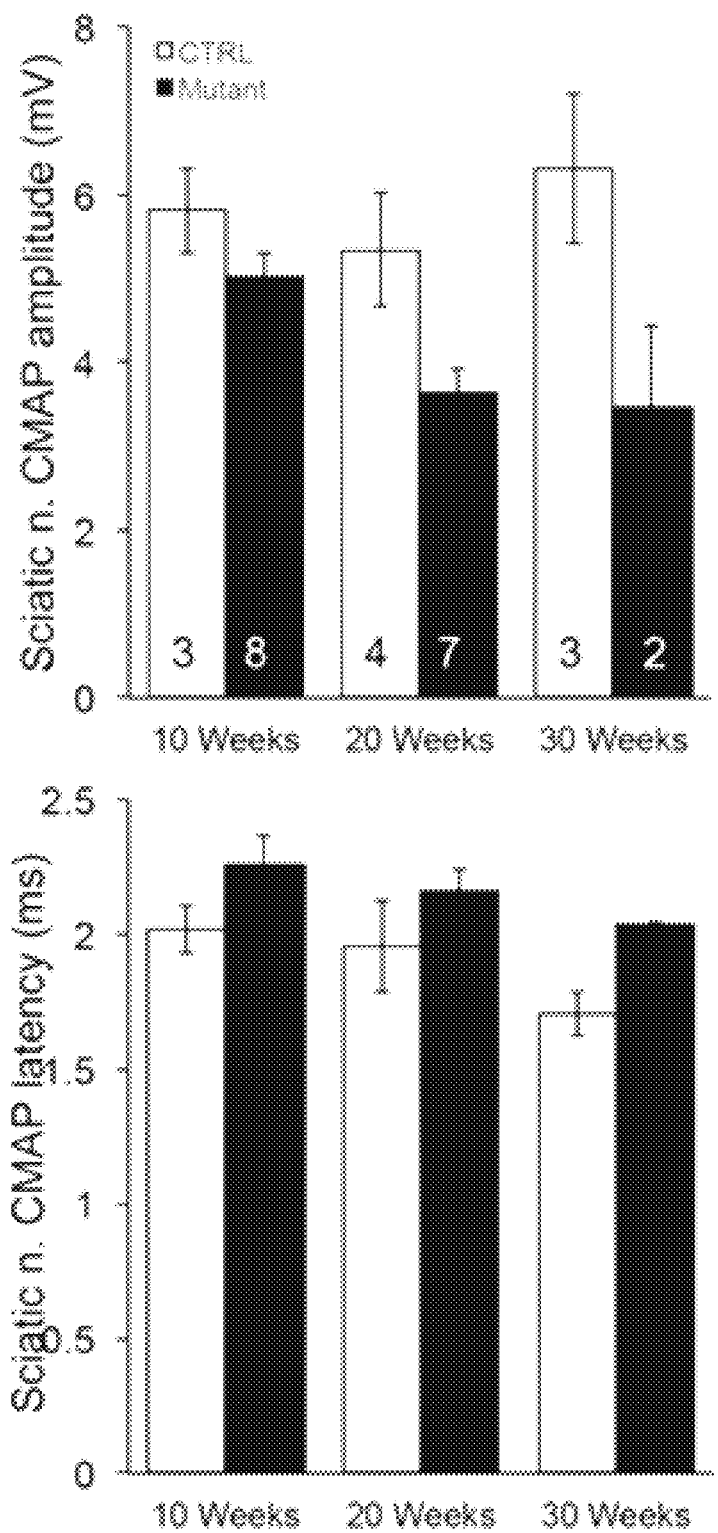
Figure 57D:
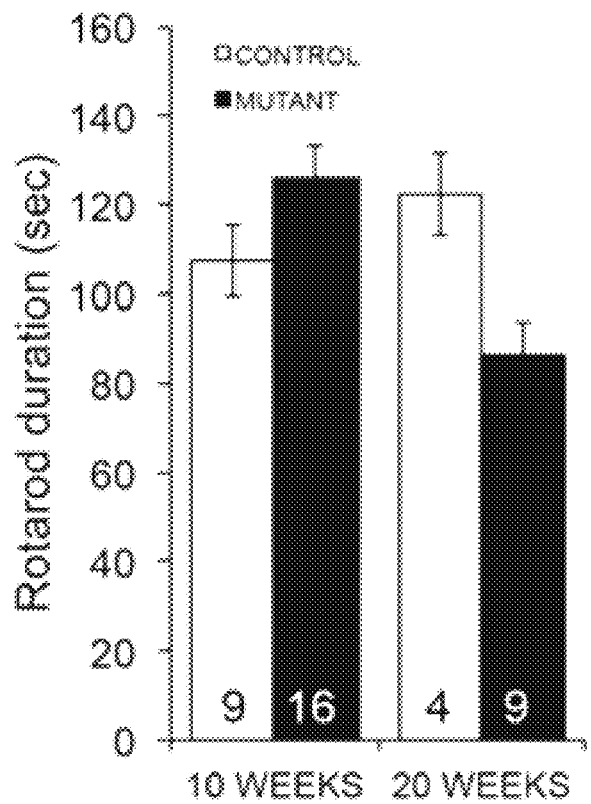

FIG. 54 is a series of structures describing the ongoing chemical modifications and optimizations of Regeneurin C/O.

FIG. 55 is a series of structures of the Fusogenin series of Mfn agonists currently being synthesized.

FIG. 56 is a series of graphs describing Regeneurin-C (100 nM overnight) treatment of primary fibroblasts from human patients with genetically diverse neurodegenerative diseases. FCCP treatment shows effects of complete mitochondrial uncoupling. Ctrl are control primary human fibroblasts.

FIG. 57A, FIG. 57B, FIG. 57C and FIG. 57D are an illustration, traces, and bar graphs describing the initial phenotyping studies of CMT2A mouse (Mfn2 T105M flox-stop×H9B Cre). (A) Schematic depiction of nerve conduction studies; red arrows show positions of stimulating electrodes, blue arrows of sensing electrodes. (B) Representative CMAP tracings from normal control (top) and CMT2A Mfn2 T105M (bottom) mice. Posterior tibial tracings control for CMAP sensing, and are no different as expected. Note marked decrease in amplitude of Sciatic nerve tracing in T105M mouse. (C) Group data from ongoing CMAP studies; each n is a mouse. CMAP amplitude, but not conduction velocity (latency/length) is diminished after 20 weeks in CMT2A mice. (D) Group data from ongoing Rotarod studies suggest functional decline between 10 and 20 weeks.

Figure 58:
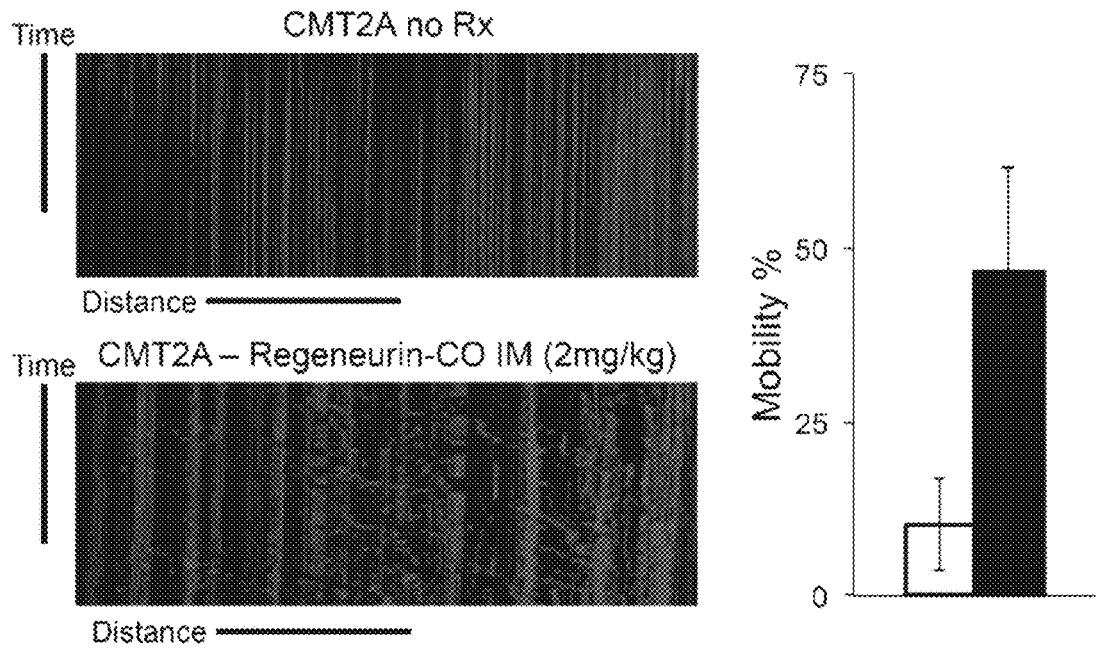

FIG. 58 is a series of images and a graph showing Regeneurin-C/O corrects CMT2A neuronal mitochondrial dymotility in vivo. 10 week old CMT2A MFN2 T105M mice were injected IM with Mfn agonist Regeneurin-C/O 2 mg/kg twice, or vehicle. Sciatic nerve mitochondrial motility was measured 4 hours later. Results for 2 CMT2A mice per group.

DETAILED DESCRIPTION OF THE INVENTION

The present disclosure is based, at least in part, on the discovery that modeling mini peptides can provide small molecule regulators of mitochondrial fusion for use in treating mitochondrial associated diseases, disorders, and conditions. As shown herein, the present disclosure provides new compositions, uses, and techniques for regulating mitochondrial function, including mitochondrial tracking and fusion. These compositions and methods can be useful to correct cell and organ dysfunction caused by primary abnormalities in mitochondrial fission, fusion and subcellular motility/distribution.

As described herein, novel small molecules were designed that incorporated functional features (e.g., potency, specificity) of two mitofusin agonist peptidomimetic compounds identified from a functional screen (Cpds A and B) which were functionally synergistic because they acted on different phosphorylated forms of MFN (see e.g., Example 2).

As described herein, the discovery that "super-activating"/"turbocharging" the endogenous normal mitofusins to overwhelm dominant inhibition by mutant mitofusins constitutes a novel approach to treating diseases caused by loss of function MFN2 mutations. Not only was (1) a way to pharmacologically stimulate mitofusin activity (e.g., fusion and trafficking) discovered, but (2) a therapeutic approach was also designed that bypasses effects of the mutant Mfn2 in CMT2A. This makes the approach applicable no matter the nature of a patient's individual mutation. As such, this approach is better than "personalized medicine"; this approach can be used to treat any individual with any mitofusin mutation.

Conventional wisdom is that unopposed mitochondrial fission (resulting in small mitochondrial size) is primarily responsible for disease (e.g., as in Charcot Marie Tooth Disease). But the present disclosure provides for the surprising discovery that, mitochondrial transport, not mitochondria size, is a more important causative factor in disease state and progression. As described herein, it was discovered that mitochondrial trafficking (e.g., the ability for mitochondria to get from point A to point B) is responsible (see e.g., Example 5).

The present disclosure shows that pharmacological disruption of intramolecular restraints in MFN2 enhances mitochondrial fusion and trafficking in CMT2A neurons. Mitofusins (MFNs) promote fusion-mediated mitochondrial content exchange and subcellular trafficking. Damaging Mfn2 gene mutations cause neurodegenerative Charcot Marie Tooth Disease type 2A (CMT2A). Here it has been shown that Mfn2 activity is determined by Met376 and His380 interactions with Asp725 and Leu727 and controlled by PINK1 kinase-mediated phosphorylation of adjacent Mfn2 Ser378. Also shown here, are small molecule mimics of the peptide-peptide interface disrupted this interaction, allosterically activating Mfn2 and promoting mitochondrial fusion. These first-in-class mitofusin agonists overcame dominant mitochondrial defects provoked in cultured neurons by CMT2A mutants Mfn2 Arg94Gln and Thr105Met, as evidenced by improved mitochondrial dysmotility, fragmentation, depolarization, and clumping. Mitofusin agonists normalized axonal mitochondrial trafficking within sciatic nerves of Mfn2 Thr105Met mice, promising a therapeutic approach for CMT2A and other untreatable diseases of impaired neuronal mitochondrial dynamism or trafficking.

As described herein (see e.g., Example 5), based on molecular modeling and a detailed structural and functional interrogation of MFN2-derived minipeptides encompassing Met$^{376}$, Ser$^{378}$, and His$^{380}$ small molecule mitofusin agonists were developed that reversed mitochondrial dysmorphometry and normalized impaired mobility evoked by 2 CMT2A MFN2 mutants. CMT2A is the prototypical clinical disorder of defective mitochondrial fusion, but impaired mitochondrial trafficking may play as great a role as mitochondrial fragmentation in CMT2A axonal degeneration. Individuals with CMT2A express one mutant MFN2 allele in combination with one normal MFN2 allele and harbor two normal MFN1 alleles. As such, it has been shown herein that it is possible that a therapeutic substrate for agonists to "supercharge" normal mitofusins and overcome dominant inhibition by MFN2 mutants. As shown herein, in vivo mitochondrial dysmotility (provoked by CMT2A mutants), normalized by mitofusin agonists, mechanistically links abnormal mitochondrial trafficking in CMT2A to MFN2 dysfunction. Mitofusin agonists may also have therapeutic potential for neurological conditions other than CMT2A, such as Alzheimer's, Parkinson's, and Huntington's diseases, wherein mitochondrial dysmotility and fragmentation are contributing factors.

Mitofusin Modulating Agent

The present disclosure provides for small molecule mimics of a Mfn2 peptide-peptide interface. As described herein, a composition for the treatment of a mitochondria-associated disease, disorder, or condition, can comprise a mitofusin modulating agent, such as a peptide mimetic (e.g., a small-molecule peptide mimetic). A peptide mimetic can be a chemical peptide mimetic. For example, the peptide mimetic can mimic a mitofusin peptide.

As described herein, chemical peptido-mimetics were identified, and second generation small molecules were designed, based on structural modeling of functionally-critical amino acid side chains of mitofusin (Mfn)-derived mini-peptides (mini-peptides described in Franco et al. Nature 2016). These peptide mimetic compounds activate mitochondrial fusion by directing Mfn1 and Mfn2 to different conformational states. It is believed that these are the first small molecules to target Mfn1 or Mfn2. Specific combinations of small molecules that activate mitochondrial trafficking and mitochondrial fusion, and their use to correct mitochondrial and cellular dysfunction, are described herein.

As described herein, mitofusin modulating agents (e.g., mitofusin agonists) can reverse mitochondrial defects. For example, mitofusin modulating agents can also have mitochondria transport activity. As another example, a mitofusin modulating agent can modulate or enhance the transport (e.g., trafficking, mobility, or movement) of mitochondria, in for example, a nerve. Example 5 shows that mitofusin agonists restore axonal mitochondrial trafficking (see e.g., FIG. 28). Also described herein, mitofusin agonists enhance mitochondrial elongation or mitochondrial elongation aspect ratio. Examples further show, pharmacological disruption of intramolecular restraints in Mfn2 by mitofusin modulating agents promotes mitochondrial fusion and trafficking in neurons.

As described herein, the mitofusin modulating agents can increase mitochondrial trafficking without affecting or substantially affecting mitochondrial fusion or fission.

Mitofusin Mini Peptide

As described herein, a peptide mimetic can be a mitofusin mini-peptide as described in U.S. Provisional Patent Application 62/397,110 (incorporated herein by reference) filed Sep. 20, 2016 and Franco et al. Nature 2016.

Mfn Agonist (Fusion-Promoting) Peptido-Mimetic

As described herein, a peptide mimetic can be a Mfn agonist (fusion-promoting) peptido-mimetic that competes with endogenous HR1-HR2 binding.

The Mfn agonist was designed based on the discovery that Mfn1 and Mfn2 share a common domain structure and structural homology with human Mfn1 and *Arabidopsis thaliana* dynamin-related protein. As described herein, Mfn1 and Mfn2 share a common domain structure that was modeled with I-TASSER and structural homology with bacterial dynamin-like protein, human Mfn1 and *Arabidopsis thaliana* dynamin-related protein (see e.g., FIG. 1). The model shows how the first heptad repeat domain (HR1) interacts in an anti-parallel manner with the carboxyl terminal second heptad repeat (HR2) domain to restrain it and prevent its extension into the cytosol, which is currently believed to be necessary for mitochondrial tethering and fusion (see e.g., Example 1).

As described herein, an Mfn agonist can inhibit or block HR1-HR2 binding or interaction. For example, Met376, Ser378, His380, or Met 381 amino acids were discovered to be necessary for the HR1-HR2 interaction. Amino acids implicated in HR1-HR2 binding or interactions were identified by first defining a minimal HR1-derived mini-peptide that competes with endogenous HR1-HR2 binding (see e.g., FIG. 2A-FIG. 2B), followed by functional analyses of a complete series of alanine substituted peptides (see e.g., FIG. 2C). Based on these results chemical peptido-mimetics were derived that, by mimicking the 3-dimensional spatial and charge characteristics of these critical amino acid side chains, have similar modulatory activity on mitochondrial fusion as the N-terminal mini-peptide (see e.g., Example 1).

Novel Regeneurin agonists (see Example 6, TABLE 8) are described below.

| Compound ID | IUPAC Name | Structure | M.W. (g/mol) | Formula |
|---|---|---|---|---|
| Regeneurin-C | 1-(3-(5-cyclopropyl-4-phenyl-4H-1,2,4-triazol-3-methylcyclohexyl)urea | 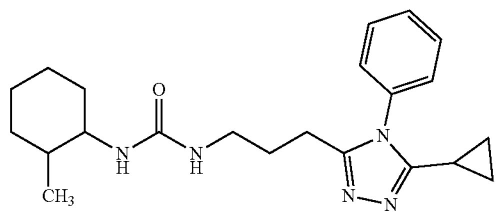 [SMILES: CC1CCCCC1NC(=O)NCCCc1nnc(C2CC2)n1-c1ccccc1] | 381.52 | $C_{22}H_{31}N_5O$ |
| Regeneurin-O | 1-(2-((5-cyclopropyl-4-phenyl-4H-1,2,4-triazol-3-yl)oxy)ethyl)-3-(2-methylcyclohexyl)urea | 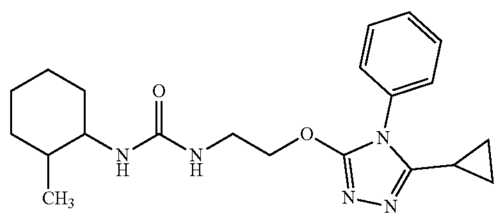 | 383.49 | $C_{21}H_{29}N_5O_2$ |
| Regeneurin-C/O | 1-(3-(5-cyclopropyl-4-phenyl-4H-1,2,4-triazol-3-yl)propyl)-3-(tetrahydro-2H-pyran-4-yl)urea | 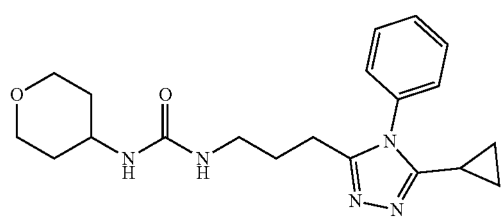 [SMILES: O=C(NCCCc1nnc(C2CC2)n1-c1ccccc1)NC1CCOCC1] | 369.47 | $C_{20}H_{27}N_5O_2$ |
| Regeneurin-SO | 1-(2-((5-cyclopropyl-4-phenyl-4H-1,2,4-triazol-3-yl)sulfinyl)ethyl)-3-(2-methylcyclohexyl)urea | 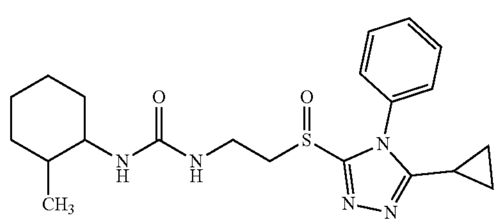 [SMILES: CC1CCCCC1NC(=O)NCCS(=O)c1nnc(C2CC2)n1-c1ccccc1] | 415.55 | $C_{21}H_{29}N_5O_2S$ |
| Regeneurin-SO$_2$ | 1-(2-((5-cyclopropyl-4-phenyl-4H-1,2,4-triazol-3-yl)sulfonyl)ethyl)-3-(2-methylcyclohexyl)urea | 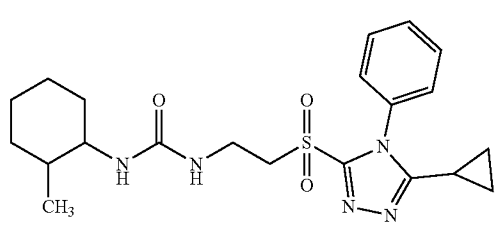 [SMILES: CC1CCCCC1NC(=O)NCCS(=O)(=O)c1nnc(C2CC2)n1-c1ccccc1] | 431.56 | $C_{21}H_{29}N_5O_3S$ |

Novel Mitolityn agonists (see Example 6, TABLE 9) are described below.

| Compound ID | IUPAC Name | Structure | M.W. (g/mol) | Formula |
|---|---|---|---|---|
| Mitolityn-1 | 1-(3-(5-cyclopropyl-4-ethyl-4H-1,2,4-triazol-3-yl)propyl)-3-(2-methylcyclohexyl)urea | 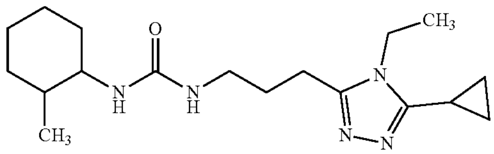 [SMILES: CCn1c(CCCNC(=O)NC2CCCCC2C)nnc1C1CC1] | 333.47 | $C_{18}H_{31}N_5O$ |
| Mitolityn-2 | 1-cyclohexyl-3-(3-(5-cyclopropyl)-4-ethyl-4H-1,2,4-triazol-3-yl)propyl)urea | 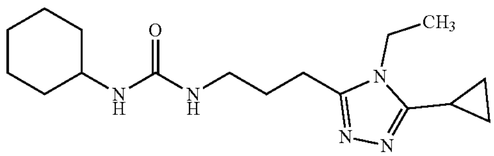 [SMILES: CCn1c(CCCNC(=O)NC2CCCCC2)nnc1C1CC1] | 319.45 | $C_{17}H_{29}N_5O$ |
| Mitolityn-3 | 1-(3-(5-cyclopropyl-4-ethyl-4H-1,2,4-triazol-3-yl)propyl)-3-(3-methyltetrahydro-2H-pyran-4-yl)urea | 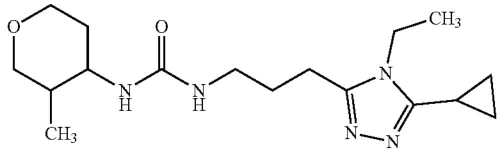 [SMILES: CCn1c(CCCNC(=O)NC2CCOCC2C)nnc1C1CC1] | 335.44 | $C_{17}H_{29}N_5O_2$ |
| Mitolityn-4 | 1-(3-(5-cyclopropyl-4-ethyl-4H-1,2,4-triazol-3-yl)propyl)-3-(tetrahydro-2H-pyran-4-yl)urea | 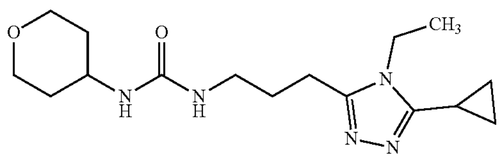 [SMILES: CCn1c(CCCNC(=O)NC2CCOCC2)nnc1C1CC1] | 321.42 | $C_{16}H_{27}N_5O_2$ |
| Mitolityn-5 (Renamed Fusogenin-4a) | 1-(3-(5-cyclopropyl-4-methyl-4H-1,2,4-triazol-3-yl)propyl)-3-(3-methyltetrahydro-2H-pyran-4-yl)urea | 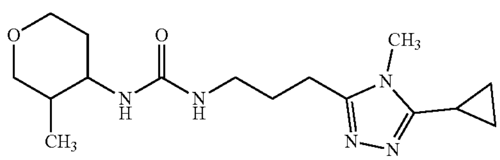 [SMILES: CC1COCCC1NC(=O)NCCCc1nnc(C2CC2)n1C] | 321.43 | $C_{16}H_{27}N_5O_2$ |
| Mitolityn-6 (Renamed after Fusogenin-3a) | 1-(3-(5-cyclopropyl-4-methyl-4H-1,2,4-triazol-3-yl)propyl)-3-(tetrahydro-2H-pyran-4-yl)urea | 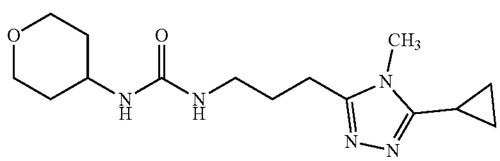 [SMILES: Cn1c(CCCNC(=O)NC2CCOCC2)nnc1C1CC1] | 307.4 | $C_{15}H_{25}N_5O_2$ |

Novel Fusogenin agonists (see Example 6, TABLE 10) are described below.

| Compound ID | IUPAC Name | Structure | M.W. (g/mol) | Formula |
|---|---|---|---|---|
| Fusogenin-1 | 1-(3-(4-methyl-5-phenyl-4H-1,2,4-triazol-3-yl)propyl)-3-(2-methylcyclohexyl)urea | 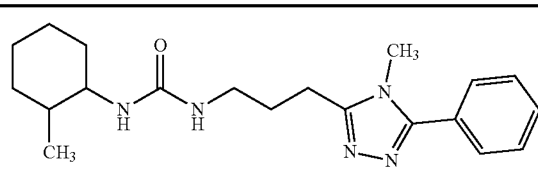 | 355.49 | $C_{20}H_{29}N_5O$ |
| Fusogenin-3 | 1-(3-(4-methyl-5-phenyl-4H-1,2,4-triazol-3-yl)propyl)-3-(tetrahydro-2H-pyran-4-yl)urea | 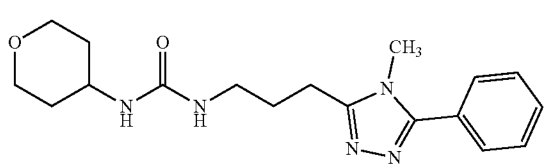 [SMILES: Cn1c(CCCNC(=O)NC2CCOCC2)nnc1-c1ccccc1] | 343.43 | $C_{18}H_{25}N_5O_2$ |

| Compound ID | IUPAC Name | Structure | M.W. (g/mol) | Formula |
|---|---|---|---|---|
| Fusogenin-4 | 1-(3-(4-methyl-5-phenyl-4H-1,2,4-triazol-3-yl)propyl)-3-(3-methyltetrahydro-2H-pyran-4-yl)urea | 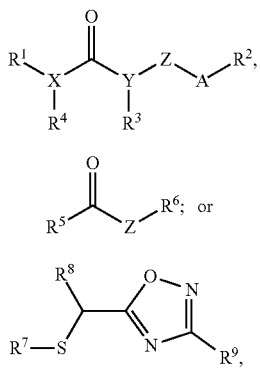 | 357.46 | $C_{19}H_{27}N_5O_2$ |

Mitofusin Modulating Agents: Small Molecules to Target Mfn1 and/or Mfn2

The small molecule Mfn regulators as described herein are allosteric agonists. An agonist can be a substance that fully activates the receptor that it binds to, and an antagonist can be a substance that binds to a receptor but does not activate and can block the activity of other agonists.

Examples of mitofusin modulating agents are described herein (see e.g., Example 2). Mitofusin modulating agents can be, of the formula:

$$R^1\underset{R^4}{\overset{X}{|}}\overset{O}{\underset{}{\|}}\underset{R^3}{\overset{Y}{|}}Z\,A\,R^2, \quad (I)$$

$$R^5\overset{O}{\underset{}{\|}}Z\,R^6; \text{ or} \quad (II)$$

$$R^7-S\underset{}{\overset{R^8}{|}}\overset{O}{\underset{N}{\diagup}}\underset{N}{\diagdown}R^9, \quad (III)$$

or a pharmaceutically acceptable salt, tautomer, or stereoisomer thereof wherein, $R^1$ is selected from the group consisting of $C_{1-8}$ alkyl, $C_{1-8}$ alkyl substituted with S, S, thiophene, $C_{3-8}$ cycloalkyl, $C_{3-8}$ heteroaryl, $C_{3-8}$ heterocyclyl, thiophene, and thiophene carboxamide;

$R^2$ is selected from the group consisting of $C_{3-8}$ cycloalkyl, $C_{3-8}$ heteroaryl, $C_{3-8}$ heterocyclyl, imidazole, thiophene, thiophene carboxamide, and triazole;

$R^3$ is selected from the group consisting of hydrogen (H) and $C_{1-8}$ alkyl;

$R^4$ is selected form the group consisting of hydrogen (H) and $C_{1-8}$ alkyl;

$R^5$ is selected from the group consisting of $C_{1-8}$ alkyl, $C_{1-8}$ alkyl substituted with S, S, thiophene, $C_{3-8}$ cycloalkyl, $C_{3-8}$ heteroaryl, $C_{3-8}$ heterocyclyl, thiophene, thiophene carboxamide, and triazole;

$R^6$ is selected from the group consisting of bicyclononanone, pyrrole, benzimidizole, pyrrole substituted pyrrole, and substituted benzimidizole;

$R^7$ is selected from the group consisting of $C_{1-8}$ alkyl, pyrrole, pyrrole substituted pyrrole, benzimidizole, and substituted benzimidizole;

$R^8$ is selected from the group consisting of hydrogen (H);

$R^9$ is selected from the group consisting of $C_{1-8}$ alkyl; pyrrole, substituted pyrrole, pyrrole substituted pyrrole, benzimidizole, and substituted benzimidizole;

X is selected from the group consisting of O, C, and N;

Y is selected from the group consisting of O, C, and N; and

Z is a linker group selected from the group consisting of a bond or $C_{1-6}$ alkyl; and optionally, $R^1$ and $R^2$ form a cyclic group, $R^1$ and $R^4$ form a cyclic group, $R^2$ and $R^3$ form a cyclic group, $R^4$ and $R^3$ form a cyclic group; or $R^8$ and $R^7$ form a cyclic group, wherein, the bicyclononanone optionally comprises one or more N atoms.

Optionally, the compound of formula (I), (II), or (III) is not a compound of TABLE 4, TABLE 5, TABLE 7, or the commercially sourced compositions in TABLE 1 or TABLE 2.

Furthermore, $R^1$, $R^2$, $R^3$, $R^4$, $R^5$, $R^6$, $R^7$, $R^8$, or $R^9$ can be optionally substituted by one or more of acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene and optionally further substituted with acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene and the alkyl, cycloalkyl, heteroaryl, heterocyclyl, indole, or phenyl is optionally further substituted with one or more selected from the group consisting of acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, or thiophene.

The $R^1$, $R^2$, $R^3$, $R^4$, $R^5$, $R^6$, $R^7$, $R^8$, or $R^9$ groups can be optionally substituted or further substituted with one or more groups independently selected from the group consisting of hydroxyl; $C_{1-10}$ alkyl hydroxyl; amine; $C_{1-10}$ carboxylic acid; $C_{1-10}$ carboxyl; straight chain or branched $C_{1-10}$ alkyl, optionally containing unsaturation; a $C_{2-8}$ cycloalkyl optionally containing unsaturation or one oxygen or nitrogen atom; straight chain or branched $C_{1-10}$ alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring can be optionally substituted with one or more groups independently selected from the group consisting of hydroxyl; $C_{1-10}$ alkyl hydroxyl; amine; $C_{1-10}$ carboxylic acid; $C_{1-10}$ carboxyl; straight chain or branched $C_{1-10}$ alkyl, optionally containing unsaturation; straight chain or branched $C_{1-10}$ alkyl amine, optionally containing unsaturation; a $C_{2-10}$ cycloalkyl optionally containing unsaturation or one oxygen or nitrogen atom; straight chain or branched $C_{1-10}$ alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of hydroxyl; $C_{1-10}$ alkyl hydroxyl; amine; $C_{1-10}$ carboxylic acid; $C_{1-10}$ carboxyl; straight chain or branched $C_{1-10}$ alkyl, optionally containing unsaturation; straight chain or branched $C_{1-10}$ alkyl amine, optionally containing unsaturation; a $C_{2-8}$ cycloalkyl optionally containing unsaturation or one oxygen or nitrogen atom; heterocyclyl; straight chain or branched $C_{1-10}$ alkyl amine; heterocyclic amine; and aryl comprising a phenyl; and heteroaryl containing from 1 to 4 N, O, or S atoms. Any of the above can be further optionally substituted.

In some embodiments, $R^1$, $R^2$, $R^3$, $R^4$, $R^5$, $R^6$, $R^7$, $R^8$, or $R^9$ are optionally substituted by one or more of: acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene; and optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene; wherein the alkyl, cycloalkyl, heteroaryl, heterocyclyl, indole, or phenyl, is optionally further substituted with one or more of acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, or thiophene.

In some embodiments, mitofusin modulating agent or agonists can be selected from the compounds below or the $R^1$, $R^2$, $R^3$, $R^4$, or $R^5$ groups or X or Y comprised in the below compounds can be selected independently and placed into formula (I), (II), or (III) (see e.g., TABLE 7, 70 commercially available compounds):

TABLE 7

70 commercially available compounds

| % long compare to B | 1-A01 Position | Structure | Name |
|---|---|---|---|
| 202 | 1-F9 | 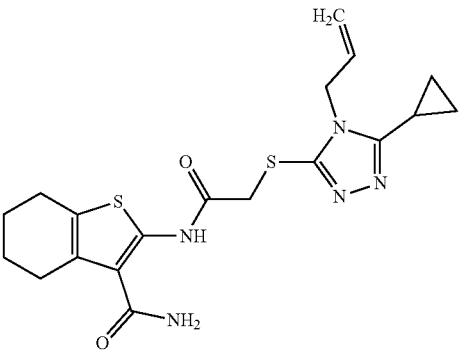 [SMILES: C=CCn1c(SCC(=O)Nc2sc3c(c2C(N)=O)CCCC3)nnc1C1CC1] | 2-(2-{[5-cyclopropyl-4-(prop-2-en-1-yl)-4H-1,2,4-triazol-3-yl]sulfanyl}acetamido)-4,5,6,7-tetrahydro-1-benzothiophene-3-carboxamide |
| 141 | 1-G1 | 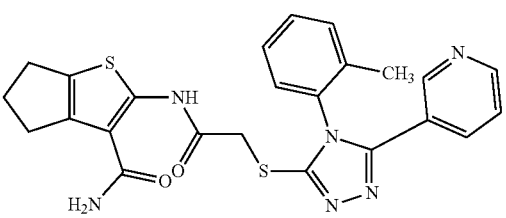 [SMILES: Cc1ccccc1-n1c(SCC(=O)Nc2sc3c(c2C(N)=O)CCC3)nnc1-c1cccnc1] | 2-(2-{[4-(2-methylphenyl)-5-(pyridin-3-yl)-4H-1,2,4-triazol-3-yl]sulfanyl}acetamido)-4H,5H,6H-cyclopenta[b]thiophene-3-carboxamide |
| 128 | 1-D2 | 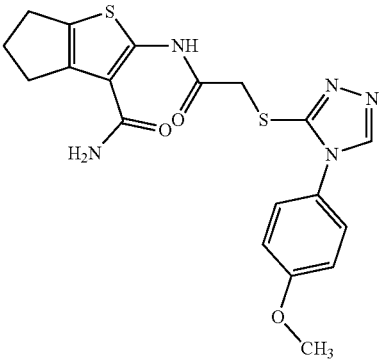 [SMILES: COc1ccc(-n2cnnc2SCC(=O)Nc2sc3c(c2C(N)=O)CCC3)cc1] | 2-(2-{[4-(4-methoxyphenyl)-4H-1,2,4-triazol-3-yl]sulfanyl}acetamido)-4H,5H,6H-cyclopenta[b]thiophene-3-carboxamide |

TABLE 7-continued

70 commercially available compounds

| % long compare to B | 1-A01 Position | Structure | Name |
|---|---|---|---|
| 114 | D08 | 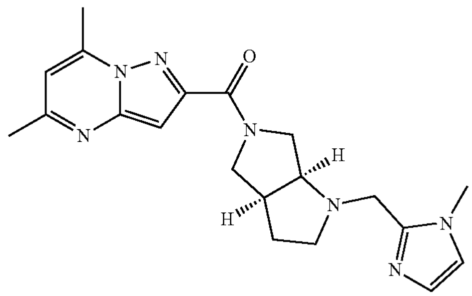 | 2-{[(3aS,6aS)-5-{5,7-dimethylpyrazolo[1,5-a]pyrimidine-2-carbonyl}-octahydropyrrolo[3,4-b]pyrrol-1-yl]methyl}-1-methyl-1H-imidazole |
| 107 | 1-B1 | 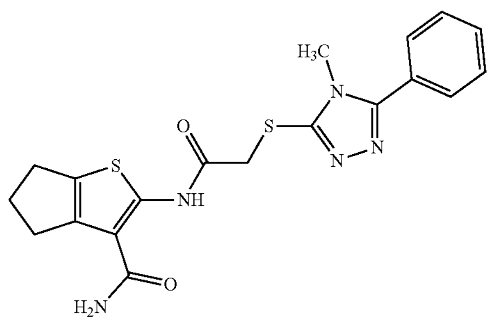 [SMILES: Cn1c(SCC(=O)Nc2sc3c(c2C(N)=O)CCC3)nnc1-c1ccccc1] | 2-{2-[(4-methyl-5-phenyl-4H-1,2,4-triazol-3-yl)sulfanyl]acetamido}-4H,5H,6H-cyclopenta[b]thiophene-3-carboxamide |
| 105 | 1-D4 | 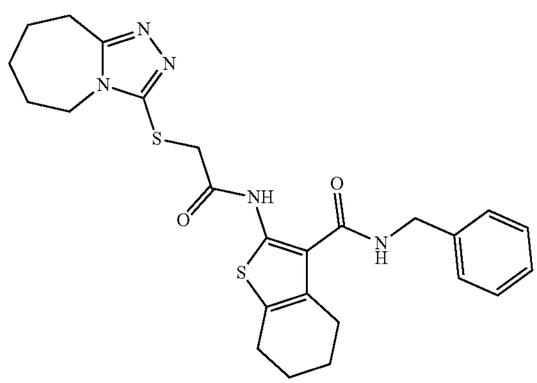 [SMILES: O=C(CSc1nnc2n1CCCCC2)Nc1sc2c(c1C(=O)NCc1ccccc1)CCCC2] | N-benzyl-2-(2-{5H,6H,7H,8H,9H-[1,2,4]triazolo[4,3-a]azepin-3-ylsulfanyl}acetamido)-4,5,6,7-tetrahydro-1-benzothiophene-3-carboxamide |
| 100 | B01 | 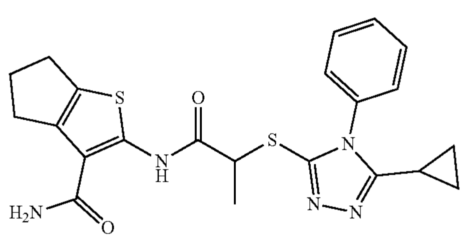 [SMILES: CC(Sc1nnc(C2CC2)n1-c1ccccc1)C(=O)Nc1sc2c(c1C(N)=O)CCC2] | 2-{2-[(5-cyclopropyl-4-phenyl-4H-1,2,4-triazol-3-yl)sulfanyl]propanamido}-4H,5H,6H-cyclopenta[b]thiophene-3-carboxamide |

TABLE 7-continued

| | | 70 commercially available compounds | |
|---|---|---|---|
| % long compare to B | 1-A01 Position | Structure | Name |
| 99 | 1-G11 | | 2-{2-[(5-cyclopropyl-4-ethyl-4H-1,2,4-triazol-3-yl)sulfanyl]acetamido}-4H,5H,6H-cyclopenta[b]thiophene-3-carboxamide |
| 92 | 1-D7 | | 2-[2-({4-[(furan-2-yl)methyl]-5-phenyl-4H-1,2,4-triazol-3-yl}sulfanyl)propanamido]-4H,5H,6H-cyclopenta[b]thiophene-3-carboxamide |
| 90 | 1-B3 | | 2-{2-[(5-cyclopropyl-4-phenyl-4H-1,2,4-triazol-3-yl)sulfanyl]acetamido}-4H,5H,6H-cyclopenta[b]thiophene-3-carboxamide |
| 75 | A4 | | 3-(4-methylphenyl)-1-(4-phenylbutyl)urea |

TABLE 7-continued

70 commercially available compounds

| % long compare to B | 1-A01 Position | Structure | Name |
|---|---|---|---|
| 73 | D09 | 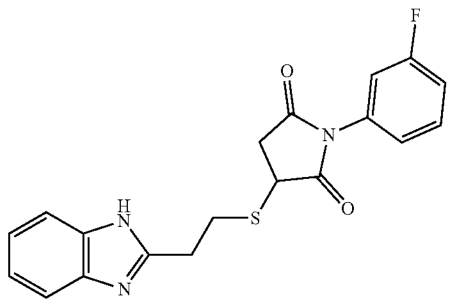 [SMILES: O=C1CC(SCCc2nc3ccccc3[nH]2)C(=O)N1c1cccc(F)c1] | 3-{[2-(1H-1,3-benzodiazol-2-yl)ethyl]sulfanyl}-1-(3-fluorophenyl)pyrrolidine-2,5-dione |
| 71 | A10 | 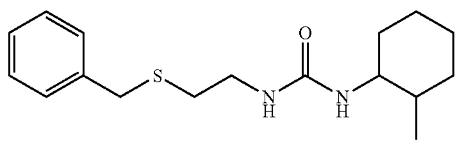 [SMILES: CC1CCCCC1NC(=O)NCCSCc1ccccc1] | 1-[2-(benzylsulfanyl)ethyl]-3-(2-methylcyclohexyl)urea |
| 68 | 1-B6 | 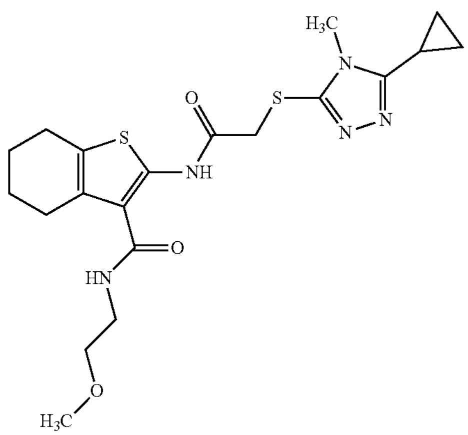 [SMILES: COCCNC(=O)c1c(NC(=O)CSc2nnc(C3CC3)n2C)sc2c1CCCC2] | 2-{2-[(5-cyclopropyl-4-methyl-4H-1,2,4-triazol-3-yl)sulfanyl]acetamido}-N-(2-methoxyethyl)-4,5,6,7-tetrahydro-1-benzothiophene-3-carboxamide |
| 64 | B07 | 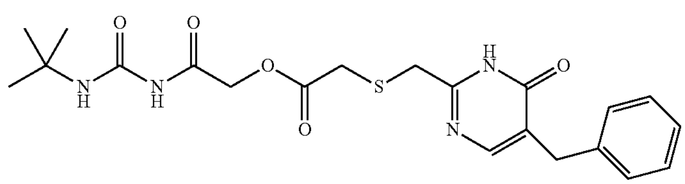 [SMILES: CC(C)(C)NC(=O)NC(=O)COC(=O)CSCc1ncc(Cc2ccccc2)c(=O)[nH]1] | 2-[(tert-butylcarbamoyl)amino]-2-oxoethyl 2-[({4-oxo-5-phenyl-3H,4H-thieno[2,3-d]pyrimidin-2-yl}methyl)sulfanyl]acetate |
| 59 | pA | 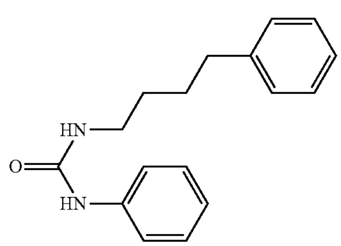 [SMILES: O=C(NCCCCc1ccccc1)Nc1ccccc1] | 3-phenyl-1-(4-phenylbutyl)urea |
| 55 | A09 | 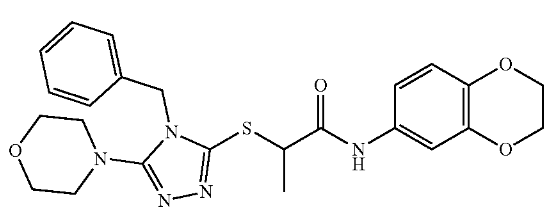 [SMILES: CC(Sc1nnc(N2CCOCC2)n1Cc1ccccc1)C(=O)Nc1ccc2c(c1)OCCO2] | 2-{[4-benzyl-5-(morpholin-4-yl)-4H-1,2,4-triazol-3-yl]sulfanyl}-N-(2,3-dihydro-1,4-benzodioxin-6-yl)propanamide |

TABLE 7-continued

| | | 70 commercially available compounds | |
|---|---|---|---|
| % long compare to B | 1-A01 Position | Structure | Name |
| 47 | A08 | | 2-({2-[(morpholin-4-yl)methyl]quinazolin-4-yl}sulfanyl)-N-[3-(trifluoromethyl)-phenyl]propanamide |
| 47 | 1-A8 | | 2-{2-[(5-benzyl-4-ethyl-4H-1,2,4-triazol-3-yl)sulfanyl]propana-mido}-4H,5H,6H-cyclopenta[b]thiophene-3-carboxamide |
| 45 | 1-A10 | | 2-(2-{5H,6H,7H,8H,9H-[1,2,4]triazolo[4,3-a]azepin-3-ylsulfanyl}acetamido)-4H,5H,6H-cyclopenta[b]thiophene-3-carboxamide |
| 41 | 1-B7 | | 2-[2-({4-methyl-5-[(thiophen-2-yl)methyl]-4H-1,2,4-triazol-3-yl}sulfanyl)propana-mido]-4H,5H,6H-cyclopenta[b]thiophene-3-carboxamide |

TABLE 7-continued 70 commercially available compounds

| % long compare to B | 1-A01 Position | Structure | Name |
|---|---|---|---|
| 39 | 1-C10 | | methyl 2-{2-[(5-methyl-4-phenyl-4H-1,2,4-triazol-3-yl)sulfanyl]acetamido}-4H,5H,6H-cyclopenta[b]thiophene-3-carboxylate |
| 39 | B03 | | 2-{[4-benzyl-5-(morpholin-4-yl)-4H-1,2,4-triazol-3-yl]sulfanyl}-N-(2-oxo-2,3-dihydro-1H-1,3-benzodiazol-5-yl)propanamide |
| 38 | 1-E1 | 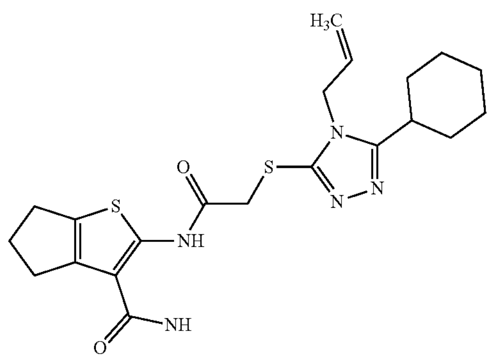 [SMILES: C=CCn1c(SCC(=O)Nc2sc3c(c2C(N)=O)CCC3)nnc1C1CCCCC1] | 2-(2-{[5-cyclohexyl-4-(prop-2-en-1-yl)-4H-1,2,4-triazol-3-yl]sulfanyl}acetamido)-4H,5H,6H-cyclopenta[b]thiophene-3-carboxamide |
| 36 | B09 | 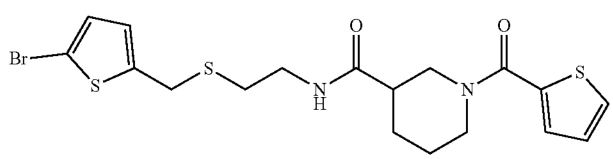 [SMILES: O=C(NCCSCc1ccc(Br)s1)C1CCCN(C(=O)c2cccs2)C1] | N-(2-{[(5-bromothiophen-2-yl)methyl]sulfanyl}-ethyl)-1-(thiophene-2-carbonyl)piperidine-3-carboxamide |
| 35 | 1-C8 | 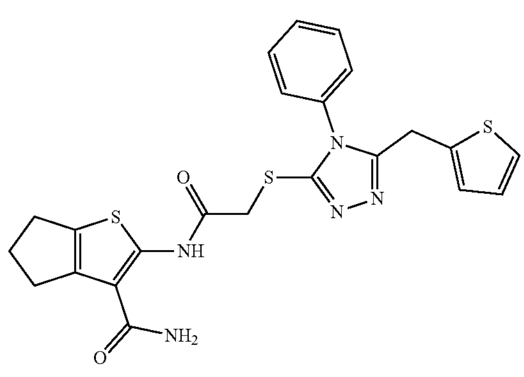 [SMILES: NC(=O)c1c(NC(=O)CSc2nnc(Cc3cccs3)n2-c2ccccc2)sc2c1CCC2] | 2-[2-({4-phenyl-5-[(thiophen-2-yl)methyl]-4H-1,2,4-triazol-3-yl}sulfanyl)acetamido]-4H,5H,6H-cyclopenta[b]thiophene-3-carboxamide |

TABLE 7-continued

| | | 70 commercially available compounds | |
|---|---|---|---|
| % long compare to B | 1-A01 Position | Structure | Name |
| 32 | A3 | 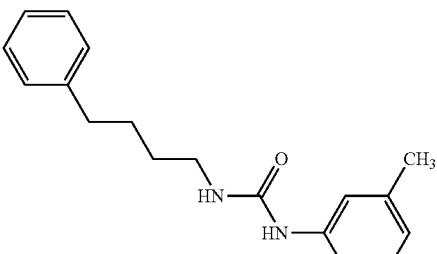 | 3-(3-methylphenyl)-1-(4-phenylbutyl)urea |
| 31 | A12 | 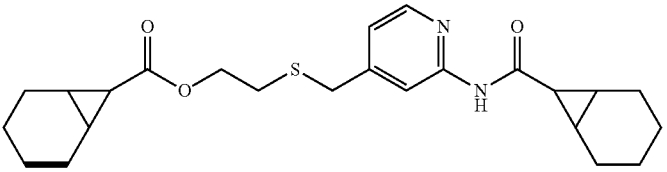 | 2-{[(2-{bicyclo[4.1.0]heptane-7-amido}pyridin-4-yl)methyl]sulfanyl}ethyl bicyclo[4.1.0]heptane-7-carboxylate |
| 30 | 1-F6 | 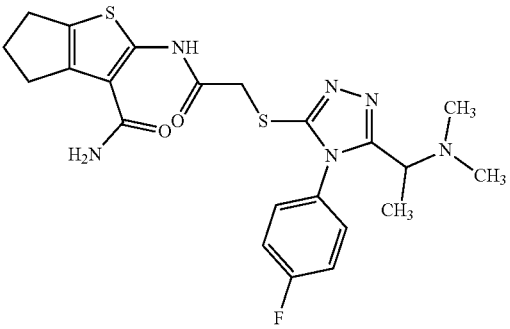 [SMILES: CC(c1nnc(SCC(=O)Nc2sc3c(c2C(N)=O)CCC3)n1-c1ccc(F)cc1)N(C)C] | 2-[2-({5-[1-(dimethylamino)ethyl]-4-(4-fluorophenyl)-4H-1,2,4-triazol-3-yl}sulfanyl)acetamido]-4H,5H,6H-cyclopenta[b]thiophene-3-carboxamide |
| 29 | 1-F10 | 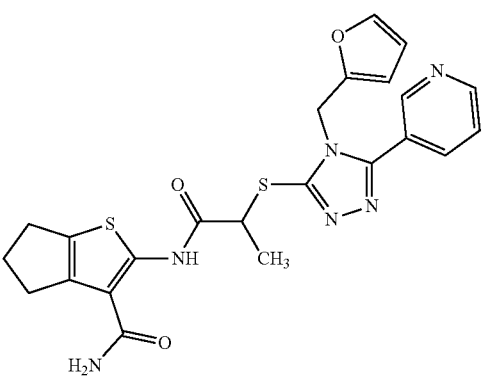 [SMILES: CC(Sc1nnc(-c2cccnc2)n1Cc1ccco1)C(=O)Nc1sc2c(c1C(N)=O)CCC2] | 2-[2-({4-[(furan-2-yl)methyl]-5-(pyridin-3-yl)-4H-1,2,4-triazol-3-yl}sulfanyl)propanamido]-4H,5H,6H-cyclopenta[b]thiophene-3-carboxamide |

TABLE 7-continued

| 70 commercially available compounds | | | |
|---|---|---|---|
| % long compare to B | 1-A01 Position | Structure | Name |
| 29 | C07 | | 1-[1-(4-chlorophenyl)-1H,2H,3H,4H,9H-pyrido[3.4-b]indol-2-yl]-2-{[(4-fluorophenyl)methyl]sulfanyl}ethan-1-one |
| 29 | 1-H9 | | 1-[2-(benzylsulfanyl)ethyl]-3-cyclopentylurea |
| 26 | 2-A1 (also B5 on screen 2) | | N-benzyl-2-[2-({4-methyl-5-[(phenylcarbamoyl)methyl]-4H-1,2,4-triazol-3-yl}sulfanyl)acetamido]-4,5,6,7-tetrahydro-1-benzothiophene-3-carboxamide |
| 26 | B12 | | N-{[4-(dimethylamino)phenyl]methyl}-2-({[(3-methylphenyl)carbamoyl]methyl}sulfanyl)-N-(propan-2-yl)acetamide |

TABLE 7-continued

| | | 70 commercially available compounds | |
|---|---|---|---|
| % long compare to B | 1-A01 Position | Structure | Name |
| 24 | D04 | | ethyl 4-methyl-2-(2-{5H-[1,2,4]triazino[5,6-b]indol-3-ylsulfanyl}butanamido)-1,3-thiazole-5-carboxylate |
| 23 | 1-D1 | | 2-[2-({4-benzyl-5-[1-(dimethylamino)propyl]-4H-1,2,4-triazol-3-yl}sulfanyl)acetamido]-4H,5H,6H-cyclopenta[b]thiophene-3-carboxamide |
| 23 | 1-H5 | | 2-(2-{[4-(4-fluorophenyl)-5-(pyridin-4-yl)-4H-1,2,4-triazol-3-yl]sulfanyl}acetamido)-4H,5H,6H-cyclopenta[b]thiophene-3-carboxamide |
| 23 | B11 | | 9-oxo-N-(2-{[(thiophen-3-yl)methyl]sulfanyl}-ethyl)bicyclo[3.3.1]-nonane-3-carboxamide |
| 23 | 1-C6 | | 2-[2-({5-[(1,1-dioxo-1$\lambda^6$-thiolan-3-yl)methyl]-4-methyl-4H-1,2,4-triazol-3-yl}sulfanyl)acetamido]-4,5,6,7-tetrahydro-1-benzothiophene-3-carboxamide |

TABLE 7-continued

| | | 70 commercially available compounds | |
|---|---|---|---|
| % long compare to B | 1-A01 Position | Structure | Name |
| 22 | 1-F4 | | 2-(2-{[4-(2-methoxyphenyl)-5-methyl-4H-1,2,4-triazol-3-yl]sulfanyl}acetamido)-4,5,6,7-tetrahydro-1-benzothiophene-3-carboxamide |
| 21 | 1-F1 | | 2-(2-{[5-(furan-2-yl)-4-phenyl-4H-1,2,4-triazol-3-yl]sulfanyl}acetamido)-4H,5H,6H-cyclopenta[b]thiophene-3-carboxamide |
| 21 | 1-E10 | | 2-(2-{[1-(2,3-dimethylphenyl)-1H-imidazol-2-yl]sulfanyl}propanamido)-4H,5H,6H-cyclopenta[b]thiophene-3-carboxamide |
| 20 | 1-G2 | | 2-{2-[(diphenyl-4H-1,2,4-triazol-3-yl)sulfanyl]acetamido}-4,5,6,7-tetrahydro-1-benzothiophene-3-carboxamide |

TABLE 7-continued

| 70 commercially available compounds | | | | |
|---|---|---|---|---|
| % long compare to B | 1-A01 Position | Structure | | Name |
| 20 | 1-B8 | 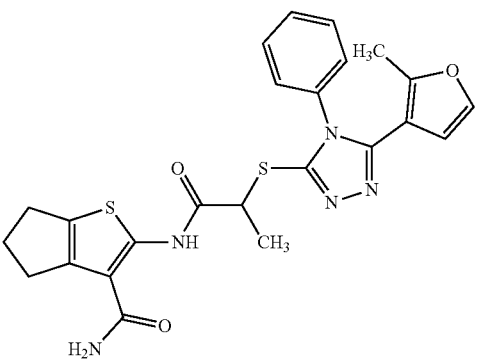 [SMILES: Cc1occc1-c1nnc(SC(C)C(=O)Nc2sc3c(c2C(N)=O)CCC3)n1-c1ccccc1] | | 2-(2-{[5-(2-methylfuran-3-yl)-4-phenyl-4H-1,2,4-triazol-3-yl]sulfanyl}propana-mido)-4H,5H,6H-cyclopenta[b]thiophene-3-carboxamide |
| 19 | 1-C1 | 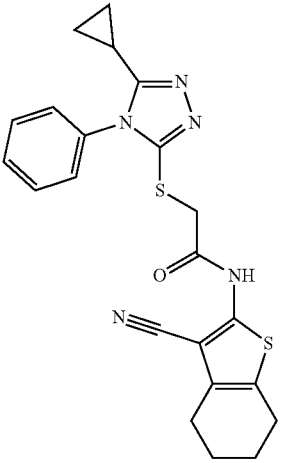 [SMILES: N#Cc1c(NC(=O)CSc2nnc(C3CC3)n2-c2ccccc2)sc2c1CCCC2] | | N-(3-cyano-4,5,6,7-tetrahydro-1-benzothiophen-2-yl)-2-[(5-cyclopropyl-4-phenyl-4H-1,2,4-triazol-3-yl)sulfanyl]acetamide |
| 18 | 1-D12 | 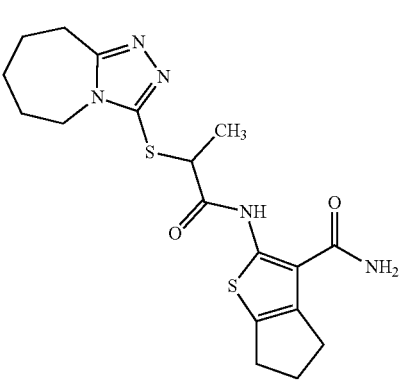 [SMILES: CC(Sc1nnc2n1CCCCC2)C(=O)Nc1sc2c(c1C(N)=O)CCC2] | | 2-(2-{5H,6H,7H,8H,9H-[1,2,4]triazolo[4,3-a]azepin-3-ylsulfanyl}propan-amido)-4H,5H,6H-cyclopenta[b]thiophene-3-carboxamide |

TABLE 7-continued 70 commercially available compounds

| % long compare to B | 1-A01 Position | Structure | Name |
|---|---|---|---|
| 18 | 1-B9 | 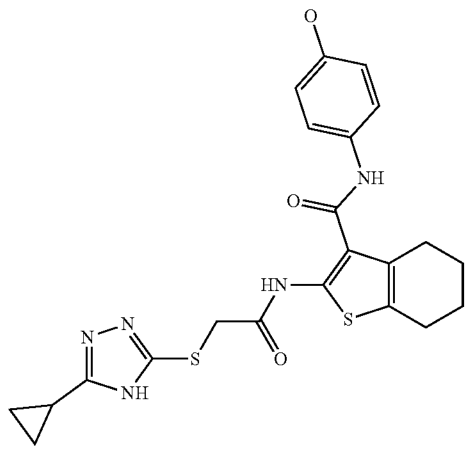 [SMILES: O=C(CSc1nnc(C2CC2)[nH]1)Nc1sc2c(c1C(=O)Nc1ccc(O)cc1)CCCC2] | N-(4-chlorophenyl)-2-{2-[(5-cyclopropyl-4H-1,2,4-triazol-3-yl)sulfanyl]acetamido}-4,5,6,7-tetrahydro-1-benzothiophene-3-carboxamide |
| 17 | 1-E4 | | 2-{2-[(5-cyclopropyl-4-methyl-4H-1,2,4-triazol-3-yl)sulfanyl]acetamido}-N-(4-methoxyphenyl)-4,5,6,7-tetrahydro-1-benzothiophene-3-carboxamide |
| 17 | 1-E2 | | 2-(2-{[4-(2-methoxyphenyl)-4H-1,2,4-triazol-3-yl]sulfanyl}acetamido)-4H,5H,6H-cyclopenta[b]thiophene-3-carboxamide |
| 17 | 1-D10 | | 2-(2-{[5-(2-methylfuran-3-yl)-4-phenyl-4H-1,2,4-triazol-3-yl]sulfanyl}acetamido)-4H,5H,6H-cyclopenta[b]thiophene-3-carboxamide |

TABLE 7-continued

| | | 70 commercially available compounds | |
|---|---|---|---|
| % long compare to B | 1-A01 Position | Structure | Name |
| 16 | C01 | | 2-{[4-(4-methylphenyl)-5-(morpholin-4-yl)-4H-1,2,4-triazol-3-yl]sulfanyl}-N-[1-(propan-2-yl)-1H-pyrazol-5-yl]propanamide |
| 15 | B05 | | N-(2-{[(2-cyanophenyl)methyl]sulfanyl}ethyl)-2-{methyl[1-(3-nitrophenyl)ethyl]amino}acetamide |
| 15 | 1-H11 | | 2-{2-[(4-benzyl-5-cyclopropyl-4H-1,2,4-triazol-3-yl)sulfanyl]acetamido}-4,5,6,7-tetrahydro-1-benzothiophene-3-carboxamide |
| 14 | 1-G8 | | 2-{2-[(4-phenyl-4H-1,2,4-triazol-3-yl)sulfanyl]propanamido}-4H,5H,6H-cyclopenta[b]thiophene-3-carboxamide |

TABLE 7-continued

| 70 commercially available compounds | | | |
|---|---|---|---|
| % long compare to B | 1-A01 Position | Structure | Name |
| 14 | A07 | | 6-methyl-N-{[6-(4-methyl-1,4-diazepan-1-yl)pyridin-3-yl]methyl}-2,3-dihydro-1-benzothiophene-2-carboxamide |
| 14 | C02 | | 5-methyl-2-{[1-(3-propyl-1,2,4-oxadiazol-5-yl)ethyl]sulfanyl}-1H-1,3-benzodiazole |
| 13 | 1-C12 | | 2-(2-{[4-cyclopropyl-5-(thiophen-2-yl)-4H-1,2,4-triazol-3-yl]sulfanyl}propanamido)-4H,5H,6H-cyclopenta[b]thiophene-3-carboxamide |
| 13 | 1-F11 | | 2-(2-{[4-phenyl-5-(pyridin-3-yl)-4H-1,2,4-triazol-3-yl]sulfanyl}acetamido)-4H,5H,6H-cyclopenta[b]thiophene-3-carboxamide |
| 13 | D02 | | 7-(3,4-dimethylphenyl)-3-{[1-(3,4-dimethylphenyl)-1-oxopropan-2-yl]sulfanyl}-7H,8H-[1,2,4]triazolo[4,3-a]pyrazin-8-one |

TABLE 7-continued 70 commercially available compounds

| % long compare to B | 1-A01 Position | Structure | Name |
|---|---|---|---|
| 13 | 1-F3 | 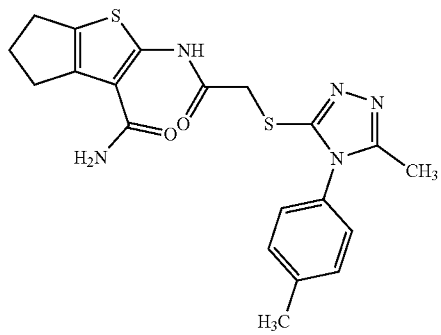 [SMILES: Cc1ccc(-n2c(C)nnc2SCC(=O)Nc2sc3c(c2C(N)=O)CCC3)cc1] | 2-(2-{[5-methyl-4-(4-methylphenyl)-4H-1,2,4-triazol-3-yl]sulfanyl}acetamido)-4H,5H,6H-cyclopenta[b]thiophene-3-carboxamide |
| 12 | B2 | | 2-[2-(phenylsulfanyl)acetamido]-4H,5H,6H-cyclopenta[b]thiophene-3-carboxamide |
| 12 | 1-C5 | | 2-(2-{[4-(2-methylphenyl)-4H-1,2,4-triazol-3-yl]sulfanyl}acetamido)-4H,5H,6H-cyclopenta[b]thiophene-3-carboxamide |
| 12 | B08 | | N-(2,6-dimethylphenyl)-4-({[3-(3-fluoro-4-methylphenyl)-1,2,4-oxadiazol-5-yl]methyl}sulfanyl)-butanamide |
| 11 | 1-A1 | 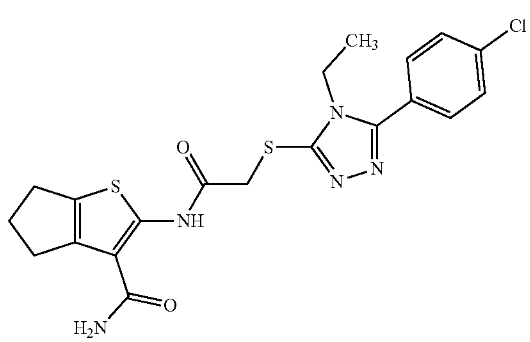 [SMILES: CCn1c(SCC(=O)Nc2sc3c(c2C(N)=O)CCC3)nnc1-c1ccc(Cl)cc1] | 2-(2-{[5-(4-chlorophenyl)-4-ethyl-4H-1,2,4-triazol-3-yl]sulfanyl}acetamido)-4H,5H,6H-cyclopenta[b]thiophene-3-carboxamide |

TABLE 7-continued

| 70 commercially available compounds ||||
|---|---|---|---|
| % long compare to B | 1-A01 Position | Structure | Name |
| 11 | E02 | | 2-({[4-oxo-6-(propan-2-yl)-3H,4H,4aH,7aH-thieno[2,3-d]pyrimidin-2-yl]methyl}sulfanyl)-N-[(pyridin-2-yl)methyl]acetamide |
| 11 | 1-E3 | | 2-{2-[(4-benzyl-5-cyclopropyl-4H-1,2,4-triazol-3-yl)sulfanyl]acetamido}-6-methyl-4,5,6,7-tetrahydro-1-benzothiophene-3-carboxamide |
| 10 | 1-E6 | | N-benzyl-2-{2-[(5-cyclopropyl-4-ethyl-4H-1,2,4-triazol-3-yl)sulfanyl]acetamido}-4,5,6,7-tetrahydro-1-benzothiophene-3-carboxamide |
| 10 | 1-H3 | | 2-{2-[(5-methyl-4-phenyl-4H-1,2,4-triazol-3-yl)sulfanyl]acetamido}-4H,5H,6H-cyclopenta[b]thiophene-3-carboxamide |

TABLE 7-continued 70 commercially available compounds

| % long compare to B | 1-A01 Position | Structure | Name |
|---|---|---|---|
| 10 | 1-06 | | 2-(2-{[5-(furan-2-yl)-4-phenyl-4H-1,2,4-triazol-3-yl]sulfanyl}propanamido)-4H,5H,6H-cyclopenta[b]thiophene-3-carboxamide |
| 10 | 1-B4 | | 2-(2-{[4-methyl-5-(trifluoromethyl)-4H-1,2,4-triazol-3-yl]sulfanyl}acetamido)-4H,5H,6H-cyclopenta[b]thiophene-3-carboxamide |
| 10 | C03 | | 2-[(4-methoxyphenyl)sulfanyl]-N-(1H-pyrazol-3-yl)propanamide |
| 9 | 1-E7 | | 2-(2-{[4-methyl-5-(2-methylphenyl)-4H-1,2,4-triazol-3-yl]sulfanyl}acetamido)-4H,5H,6H-cyclopenta[b]thiophene-3-carboxamide |
| 9 | 1-G6 | | 2-[2-({4-cyclopropyl-5-[(thiophen-2-yl)methyl]-4H-1,2,4-triazol-3-yl}sulfanyl)propanamido]-4H,5H,6H-cyclopenta[b]thiophene-3-carboxamide |

TABLE 7-continued 70 commercially available compounds

| % long compare to B | 1-A01 Position | Structure | Name |
|---|---|---|---|
| 9 | B04 | | 1-{bicyclo[2.2.1]heptan-2-yl}-3-(2-{[(furan-2-yl)methyl]sulfanyl}ethyl)thiourea |
| 9 | D01 | | 2-{[(7,8-dimethyl-4-oxo-1,4-dihydroquinolin-2-yl)methyl]sulfanyl}-N-(2-ethoxyphenyl)acetamide |
| 8 | 1-H6 | 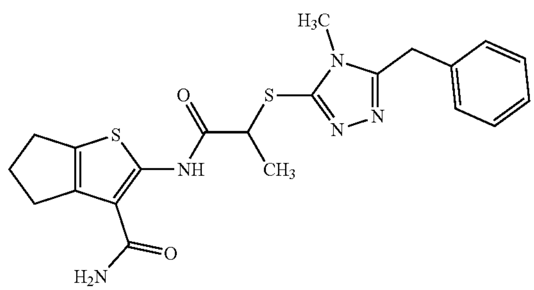 [SMILES: CC(Sc1nnc(Cc2ccccc2)n1C)C(=O)Nc1sc2c(c1C(N)=O)CCC2] | 2-{2-[(5-benzyl-4-methyl-4H-1,2,4-triazol-3-yl)sulfanyl]propanamidoMH,5H,6H-cyclopenta[b]thiophene-3-carboxamide |
| 7 | 1-G5 | | N-{3-cyano-4H,5H,6H,7H,8H-cyclohepta[b]thiophen-2-yl}-2-[(5-cyclopropyl-4-phenyl-4H-1,2,4-triazol-3-yl)sulfanyl]propanamide |
| 7 | A5 | | 3-(2-methylphenyl)-1-(4-phenylbutyl)urea |

TABLE 7-continued 70 commercially available compounds

| % long compare to B | 1-A01 Position | Structure | Name |
|---|---|---|---|
| 6 | pB | | 2-(4-phenylbutanamido)-4H,5H,6H-cyclopenta[b]thiophene-3-carboxamide |
| 6 | B10 | | N-(2,6-dimethylphenyl)-4-({[5-(propan-2-yl)-1,3-oxazol-2-yl]methyl}sulfanyl)-butanamide |
| 6 | 1-H7 | | 2-{2-[(5-benzyl-4-methyl-4H-1,2,4-triazol-3-yl)sulfanyl]acetamido}-4H,5H,6H-cyclopenta[b]thiophene-3-carboxamide |
| 6 | 1-A11 | | 2-{2-[(5-cyclopropyl-4-methyl-4H-1,2,4-triazol-3-yl)sulfanyl]acetamido}-6-methyl-4,5,6,7-tetrahydro-1-benzothiophene-3-carboxamide |
| 6 | 1-D11 | | 2-{2-[(5-cyclopropyl-4-ethyl-4H-1,2,4-triazol-3-yl)sulfanyl]acetamido}-6-methyl-4,5,6,7-tetrahydro-1-benzothiophene-3-carboxamide |
| 6 | 1-B10 | | 1-cyclohexyl-3-(2-{[(2-fluorophenyl)methyl]sulfanyl}ethyl)urea |

TABLE 7-continued 70 commercially available compounds

| % long compare to B | 1-A01 Position | Structure | Name |
|---|---|---|---|
| 5 | 1-D9 | | 2-(2-({5-[(1,1-dioxo-1λ⁶-thiolan-3-yl)methyl]-4-methyl-4H-1,2,4-triazol-3-yl}sulfanyl)acetamido]-4H,5H,6H-cyclopenta[b]thiophene-3-carboxamide |
| 5 | 1-E8 | | 2-(2-{[1-(3-fluorophenyl)-1H-imidazol-2-yl]sulfanyl}propanamido)-4H,5H,6H-cyclopenta[b]thiophene-3-carboxamide |
| 4 | 1-G3 | | 2-(2-{[4-phenyl-5-(pyridin-3-yl)-4H-1,2,4-triazol-3-yl]sulfanyl}acetamido)-4,5,6,7-tetrahydro-1-benzothiophene-3-carboxamide |
| 4 | 2-A2 | | 2-{2-[(dicyclopropyl-4H-1,2,4-triazol-3-yl)sulfanyl]acetamido}-4,5,6,7-tetrahydro-1-benzothiophene-3-carboxamide |
| 4 | B4 | | 2-{2-[(4-benzyl-5-cyclopropyl-4H-1,2,4-triazol-3-yl)sulfanyl]propanamido}thiophene-3-carboxamide |

TABLE 7-continued

| 70 commercially available compounds | | | | |
|---|---|---|---|---|
| % long compare to B | 1-A01 Position | Structure | | Name |
| 4 | D05 | 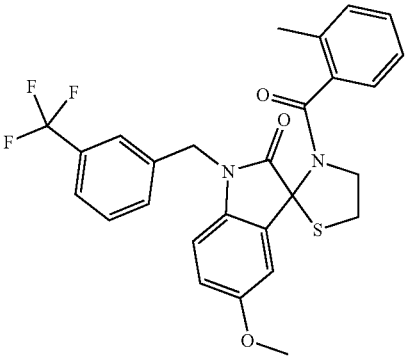 [SMILES: COc1ccc2c(c1)C1(SCCN1C(=O)c1ccccc1C)C(=O)N2Cc1cccc(C(F)(F)F)c1] | | 5-methoxy-3'-(2-methylbenzoyl)-1-{[3-(trifluoromethyl)-phenyl]methyl}-1,2-dihydrospiro[indole-3,2'-[1,3]thiazolidine]-2-one |
| 4 | A11 | 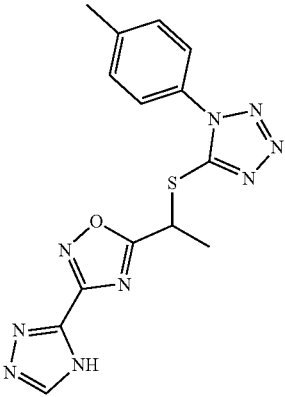 [SMILES: Cc1ccc(-n2nnnc2SC(C)c2nc(-c3nnc[nH]3)no2)cc1] | | 1-(4-methylphenyl)-5-({1-[3-(4H-1,2,4-triazol-3-yl)-1,2,4-oxadiazol-5-yl]ethyl}sulfanyl)-1H-1,2,3,4-tetrazole |
| 4 | E07 | 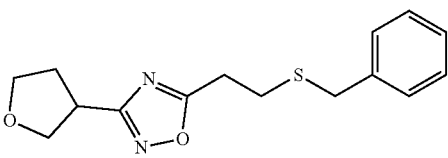 [SMILES: c1ccc(CSCCc2nc(C3CCOC3)no2)cc1] | | 5-[2-(benzylsulfanyl)ethyl]-3-(oxolan-3-yl)-1,2,4-oxadiazole |
| 3 | 1-G7 | 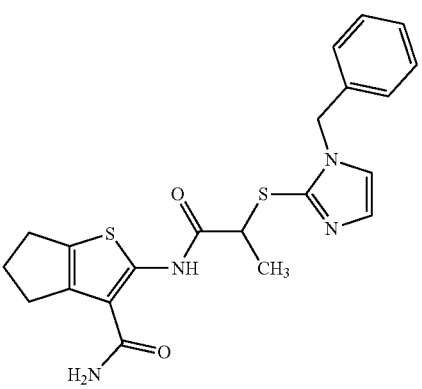 [SMILES: CC(Sc1nccn1Cc1ccccc1)C(=O)Nc1sc2c(c1C(N)=O)CCC2] | | 2-{2-[(1-benzyl-1H-imidazol-2-yl)sulfanyl]propanamido}-4H,5H,6H-cyclopenta[b]thiophene-3-carboxamide |

TABLE 7-continued 70 commercially available compounds

| % long compare to B | 1-A01 Position | Structure | Name |
|---|---|---|---|
| 3 | 2-A4 | 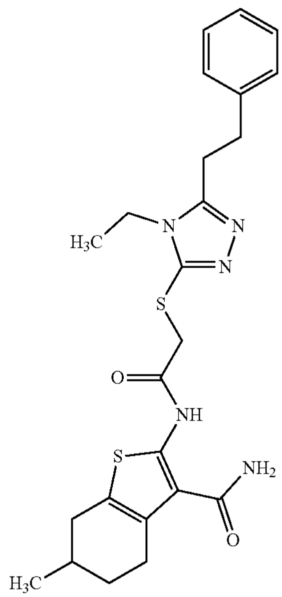 [SMILES: CCn1c(CCc2ccccc2)nnc1SCC(=O)Nc1sc2c(c1C(N)=O)CCC(C)C2] | 2-(2-{[4-ethyl-5-(2-phenylethyl)-4H-1,2,4-triazol-3-yl]sulfanyl}acetamido)-6-methyl-4,5,6,7-tetrahydro-1-benzothiophene-3-carboxamide |
| 2 | 2-A5 | | 2-{2-[(dimethyl-4H-1,2,4-triazol-3-yl)sulfanyl]acetamido}-4H,5H,6H-cyclopenta[b]thiophene-3-carboxamide |
| 2 | 1-A4 | | 6-methyl-2-(2-{5H,6H,7H,8H,9H-[1,2,4]triazolo[4,3-a]azepin-3-ylsulfanyl}acetamido)-4,5,6,7-tetrahydro-1-benzothiophene-3-carboxamide |
| 2 | 1-F8 | | 2-(2-{[4-cyclopropyl-5-(1H-indol-3-yl)-4H-1,2,4-triazol-3-yl]sulfanyl}propanamido)-4H,5H,6H-cyclopenta[b]thiophene-3-carboxamide |

TABLE 7-continued

| | | 70 commercially available compounds | |
|---|---|---|---|
| % long compare to B | 1-A01 Position | Structure | Name |
| 2 | 1-D5 | | 2-{2-[(5-cyclopropyl-4-phenyl-4H-1,2,4-triazol-3-yl)sulfanyl]acetamido}-6-methyl-4,5,6,7-tetrahydro-1-benzothiophene-3-carboxamide |
| 1 | 1-D3 | | 2-(2-{[5-methyl-4-(4-methylphenyl)-4H-1,2,4-triazol-3-yl]sulfanyl}acetamido)-4,5,6,7-tetrahydro-1-benzothiophene-3-carboxamide |
| 1 | E05 | | N-[2-(benzyl-sulfanyl)ethyl]oxane-2-carboxamide |
| 1 | E04 | | N-(butan-2-yl)-2-{2-[(4-methyl-phenyl)sulfanyl]pro-panamido}benzamide |
| 1 | 1-C11 | | 2-[2-({4-methyl-5-[(thiophen-2-yl)methyl]-4H-1,2,4-triazol-3-yl}sulfanyl)acelamido]-4H,5H,6H-cyclopenta[b]thiophene-3-carboxamide |

TABLE 7-continued

70 commercially available compounds

| % long compare to B | 1-A01 Position | Structure | Name |
|---|---|---|---|
| 0 | 1-H2 | | 2-(2-{[5-(4-chlorophenyl)-4-methyl-4H-1,2,4-triazol-3-yl]sulfanyl}acetamido)-4H,5H,6H-cyclopenta[b]thiophene-3-carboxamide |
| 0 | 1-E9 | | 2-[2-({5-[(1,1-dioxo-1$\lambda^6$-thiolan-3-yl)methyl]-4-methyl-4H-1,2,4-triazol-3-yl}sulfanyl)propanamido]-4H,5H,6H-cyclopenta[b]thiophene-3-carboxamide |
| 0 | C10 | | 3-(2,5-dioxo-3-{[(E)-N-[(1-phenylethyl)imino]carbamimidoyl]sulfanyl}pyrrolidin-1-yl)benzoic acid |
| −1 | C04 | | 2-{[2-(butan-2-yl)-3-oxo-2H,3H-imidazo[1,2-c]quinazolin-5-yl]sulfanyl}-N-(3,5-dimethoxyphenyl)propanamide |
| −1 | D8 | | 2-[2-({5-[(4-methoxyphenoxy)methyl]-4-methyl-4H-1,2,4-triazol-3-yl}sulfanyl)propanamido]-4H,5H,6H-cyclopenta[b]thiophene-3-carboxamide |

TABLE 7-continued 70 commercially available compounds

| % long compare to B | 1-A01 Position | Structure | Name |
|---|---|---|---|
| −1 | B12 | 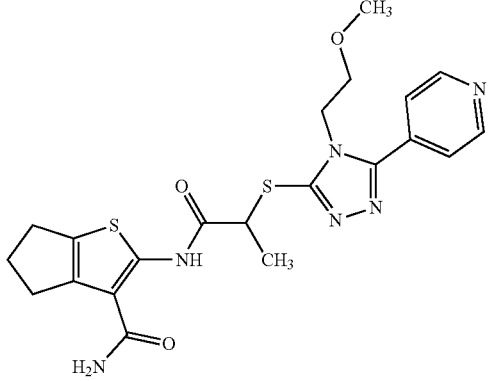 [SMILES: COCCn1c(SC(C)C(=O)Nc2sc3c(c2C(N)=O)CCC3)nnc1-c1ccncc1] | 2-(2-{[4-(2-methoxyethyl)-5-(pyridin-4-yl)-4H-1,2,4-triazol-3-yl]sulfanyl}propanamido)-4H,5H,6H-cyclopenta[b]thiophene-3-carboxamide |
| −2 | A05 | 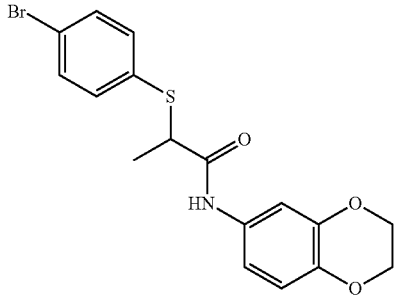 | 2-[(4-bromophenyl)sulfanyl]-N-(2,3-dihydro-1,4-benzodioxin-6-yl)propanamide |
| −3 | B3 | 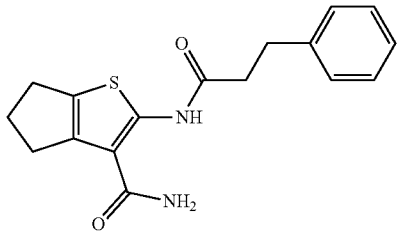 [SMILES: NC(=O)c1c(NC(=O)CCc2ccccc2)sc2c1CCC2] | 2-(3-phenylpropanamido)-4H,5H,6H-cyclopenta[b]thiophene-3-carboxamide |
| −3 | 1-H1 | 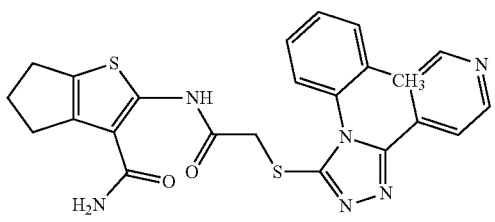 [SMILES: NC(=O)c1c(NC(=O)CSc2nnc3c4ccncc4c4ccccc4n23)sc2c1CCC2] | 2-(2-{[4-(2-methylphenyl)-5-(pyridin-4-yl)-4H-1,2,4-triazol-3-yl]sulfanyl}acetamido)-4H,5H,6H-cyclopenta[b]thiophene-3-carboxamide |
| −3 | 1-G10 | 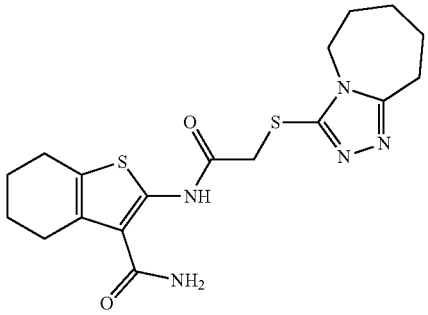 [SMILES: NC(=O)c1c(NC(=O)CSc2nnc3n2CCCCC3)sc2c1CCCC2] | 2-(2-{5H,6H,7H,8H,9H-f[1,2,4]triazolo[4,3-a]azepin-3-ylsulfanyl}acetamido)-4,5,6,7-tetrahydro-1-benzothiophene-3-carboxamide |

TABLE 7-continued 70 commercially available compounds

| % long compare to B | 1-A01 Position | Structure | Name |
|---|---|---|---|
| −3 | 1-C9 | | 2-(2-{[4-methyl-5-(2-methylfuran-3-yl)-4H-1,2,4-triazol-3-yl]sulfanyl}propanamido)-4H,5H,6H-cyclopenta[b]thiophene-3-carboxamide |
| −3 | E06 | | 5-methyl-N-{3-[(5-methyl-1,3,4-thiadiazol-2-yl)sulfanyl]propyl}-1H,4H,5H,6H,7H-pyrazolo[4,3-c]pyridine-3-carboxamide |
| −3 | 1-E12 | | 2-(2-{[4-(2-methylphenyl)-5-(pyridin-3-yl)-4H-1,2,4-triazol-3-yl]sulfanyl}acetamido)-4,5,6,7-tetrahydro-1-benzothiophene-3-carboxamide |
| −3 | 1-E5 | | 2-{2-[(5-cyclopropyl-4-phenyl-4H-1,2,4-triazol-3-yl)sulfanyl]acetamido}-4,5,6,7-tetrahydro-1-benzothiophene-3-carboxamide |
| −4 | A2 | 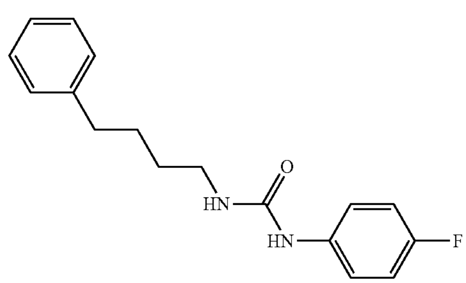 [SMILES: O=C(NCCCCc1ccccc1)Nc1ccc(F)cc1] | 3-(4-fluorophenyl)-1-(4-phenylbutyl)urea |

TABLE 7-continued

| 70 commercially available compounds | | | |
|---|---|---|---|
| % long compare to B | 1-A01 Position | Structure | Name |
| −4 | D12 | | (1S,5R)-3-(6-methylpyridazin-3-yl)-6-[(pyridin-2-yl)methyl]-3,6-diazabicyclo[3.2.2]nonan-7-one |
| −4 | C11 | | N-(2,4-dimethylphenyl)-2-(2-{[(6-hydroxy-2,4-dioxo-1,2,3,4-tetrahydropyrimidin-5-yl)[4-(propan-2-yl)phenyl]methyl]amino}-4-oxo-4,5-dihydro-1,3-thiazol-5-yl)acetamide |
| −4 | 1-H8 | | 2-{2-[(diphenyl-4H-1,2,4-triazol-3-yl)sulfanyl]propanamido}-4H,5H,6H-cyclopenta[b]thiophene-3-carboxamide |
| −5 | C09 | | 2-[({3-[5-methyl-2-(propan-2-yl)phenoxy]propyl}sulfanyl)methyl]-1H-1,3-benzodiazole |
| −6 | 1-A5 | | 2-{2-[(5-cyclopropyl-1-phenyl-1H-1,2,4-triazol-3-yl)sulfanyl]acetamido}-4H,5H,6H-cyclopenta[b]thiophene-3-carboxamide |

TABLE 7-continued

| 70 commercially available compounds | | | |
|---|---|---|---|
| % long compare to B | 1-A01 Position | Structure | Name |
| −6 | D07 | | N-(2-{[(3-chlorophenyl)methyl]-sulfanyl}ethyl)-5H,6H,7H,8H,9H-[1,2,3,4]tetrazolo[1,5-a]azepine-9-carboxamide |
| −7 | 1-F5 | | 2-{2-[(5-cyclopropyl-4-ethyl-4H-1,2,4-triazol-3-yl)sulfanyl]acetamido}-4,5,6,7-tetrahydro-1-benzothiophene-3-carboxamide |
| −7 | D10 | | 4-[(4-methylphenyl)sulfanyl]-1-({4H,5H,6H,7H-pyrazolo[1,5-a]pyrazin-2-yl}methyl)piperidine |
| −8 | C06 | | N-(3,4-dichlorophenyl)-2-{[2-(pyridin-2-yl)ethyl]sulfanyl}-acetamide |
| −8 | D11 | | 1-cyclobutanecarbonyl-N-(2-{[(4-methyl-1H-imidazol-5-yl)methyl]sulfanyl}-ethyl)piperidine-4-carboxamide |

TABLE 7-continued

| | | 70 commercially available compounds | |
|---|---|---|---|
| % long compare to B | 1-A01 Position | Structure | Name |
| −8 | 1-A12 | | 2-(2-{[4-phenyl-5-(piperidin-1-yl)-4H-1,2,4-triazol-3-yl]sulfanyl}propana-mido)-4H,5H,6H-cyclopenta[b]thiophene-3-carboxamide |
| −9 | 1-C3 | | 6-methyl-2-{2-[(4-phenyl-4H-1,2,4-triazol-3-yl)sulfanyl]acetamido}-4,5,6,7-tetrahydro-1-benzothiophene-3-carboxamide |
| −9 | 1-C7 | | 2-{2-[(4-benzyl-5-cyclopropyl-4H-1,2,4-triazol-3-yl)sulfanyl]propana-mido}-4H,5H,6H-cyclopenta[b]thiophene-3-carboxamide |
| −10 | 1-F2 | | 2-(2-{[5-phenyl-4-(prop-2-en-1-yl)-4H-1,2,4-triazol-3-yl]sulfanyl}acetamido)-4H,5H,6H-cyclopenta[b]thiophene-3-carboxamide |

TABLE 7-continued

| 70 commercially available compounds | | | |
|---|---|---|---|
| % long compare to B | 1-A01 Position | Structure | Name |
| −10 | 1-A3 | | 2-(2-{[5-(4-fluorophenyl)-4-methyl-4H-1,2,4-triazol-3-yl]sulfanyl}acetamido)-4H,5H,6H-cyclopenta[b]thiophene-3-carboxamide |
| −10 | E03 | | 2-methyl-6-(2-{[(4-methyl-1H-imidazol-5-yl)methyl]sulfanyl}-ethyl)-2H,6H,7H-pyrazolo[4,3-d]pyrimidin-7-one |
| −11 | 1-B2 | | N-(3-cyano-6-methyl-4,5,6,7-tetrahydro-1-benzothiophen-2-yl)-2-[(5-cyclopropyl-4-phenyl-4H-1,2,4-triazol-3-yl)sulfanyl]acetamide |
| −12 | 1-B11 | | 2-{2-[(5-cyclopropyl-1-phenyl-1H-1,2,4-triazol-3-yl)sulfanyl]acetamido}-6-methyl-4,5,6,7-tetrahydro-1-benzothiophene-3-carboxamide |
| −13 | 1-C4 | | 2-{2-[(4-phenyl-4H-1,2,4-triazol-3-yl)sulfanyl]acetamido}-4H,5H,6H-cyclopenta[b]thiophene-3-carboxamide |

TABLE 7-continued

| 70 commercially available compounds ||||
|---|---|---|---|
| % long compare to B | 1-A01 Position | Structure | Name |
| −14 | A01 | | N-(2H-1,3-benzodioxol-5-yl)-2-{[4-benzyl-5-(morpholin-4-yl)-4H-1,2,4-triazol-3-yl]sulfanyl)propanamide |
| −17 | D03 | | 2-{[2-oxo-2-(1,2,3,4-tetrahydroquinolin-1-yl)ethyl]sulfanyl}-N-phenylacetamide |
| −18 | 1-C2 | | 2-{2-[(4-benzyl-5-methyl-4H-1,2,4-triazol-3-yl)sulfanyl]acetamido}-4H,5H,6H-cyclopenta[b]thiophene-3-carboxamide |
| −23 | 1-A2 | | 2-(2-{[4-cyclopropyl-5-(2-fluorophenyl)-4H-1,2,4-triazol-3-yl]sulfanyl}acetamido)-4H,5H,6H-cyclopenta[b]thiophene-3-carboxamide |

TABLE 7-continued 70 commercially available compounds

| % long compare to B | 1-A01 Position | Structure | Name |
|---|---|---|---|
| −24 | 1-A7 | 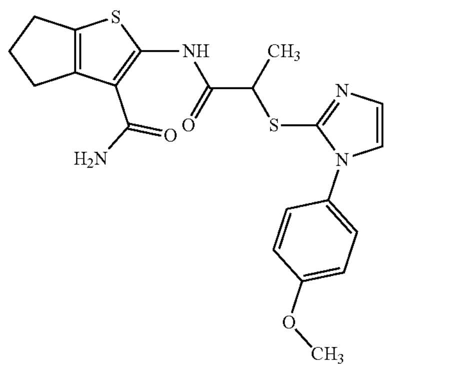 [SMILES: COc1ccc(-n2ccnc2SC(C)C(=O)Nc2sc3c(c2C(N)=O)CCC3)cc1] | 2-(2-{[1-(4-methoxyphenyl)-1H-imidazol-2-yl]sulfanyl}propanamido)-4H,5H,6H-cyclopenta[b]thiophene-3-carboxamide |
| −26 | 1-F7 | 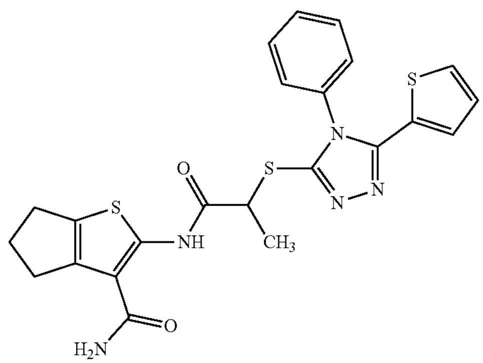 | 2-(2-{[4-phenyl-5-(thiophen-2-yl)-4H-1,2,4-triazol-3-yl]sulfanyl}propanamido)-4H,5H,6H-cyclopenta[b]thiophene-3-carboxamide |
| −31 | 1-A6 | | 2-(2-{[4-ethyl-5-(2-methylfuran-3-yl)-4H-1,2,4-triazol-3-yl]sulfanyl}propanamido)-4H,5H,6H-cyclopenta[b]thiophene-3-carboxamide |
| −31 | 1-B5 | | N-benzyl-2-{2-[(5-cyclopropyl-4-methyl-4H-1,2,4-triazol-3-yl)sulfanyl]acetamido}-4,5,6,7-tetrahydro-1-benzothiophene-3-carboxamide |

In some embodiments, the mitofusin modulating agent can comprise a methylated cyclohexy, a backbone, and a substituted triazole ring (see e.g., FIG. 46).

In some embodiments, the mitofusin modulating agent can comprise one of the following compounds:

The term "acetamide", as used herein, is an organic compound with the formula $CH_3CONH_2$. The "acetamide" can be optionally substituted.

The term "aryl", as used herein, unless otherwise indicated, include a carbocyclic aromatic group. Examples of

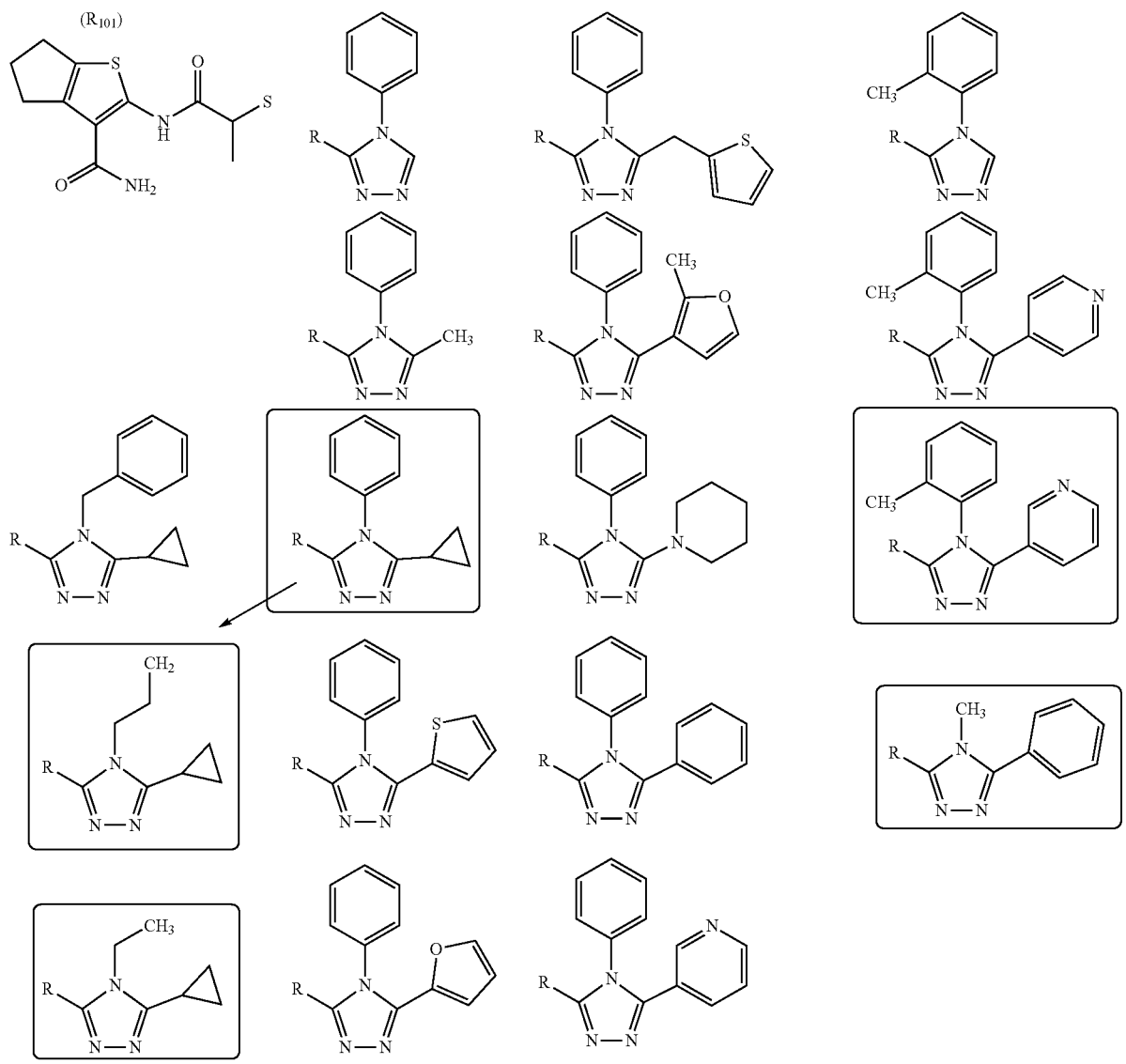

(see e.g., FIG. 48).

The term "imine" or "imino", as used herein, unless otherwise indicated, includes a functional group or chemical compound containing a carbon-nitrogen double bond. The expression "imino compound", as used herein, unless otherwise indicated, refers to a compound that includes an "imine" or an "imino" group as defined herein. The "imine" or "imino" group can be optionally substituted.

The term "hydroxyl", as used herein, unless otherwise indicated, includes —OH. The "hydroxyl" can be optionally substituted.

The terms "halogen" and "halo", as used herein, unless otherwise indicated, include a chlorine, chloro, Cl; fluorine, fluoro, F; bromine, bromo, Br; or iodine, iodo, or I.

aryl groups include, but are not limited to, phenyl, benzyl, naphthyl, or anthracenyl. The "aryl" can be optionally substituted.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group can be optionally substituted.

The term "alkyl", as used herein, unless otherwise indicated, includes saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_{1-8}$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, or -3-methyl-1 butynyl. An alkyl can be saturated, partially saturated, or unsaturated. The "alkyl" can be optionally substituted.

The term "carboxyl", as used herein, unless otherwise indicated, includes a functional group consisting of a carbon atom double bonded to an oxygen atom and single bonded to a hydroxyl group (—COOH). The "carboxyl" can be optionally substituted.

The term "alkenyl", as used herein, unless otherwise indicated, includes alkyl moieties having at least one carbon-carbon double bond wherein alkyl is as defined above and including E and Z isomers of said alkenyl moiety. An alkenyl can be partially saturated or unsaturated. The "alkenyl" can be optionally substituted.

The term "alkynyl", as used herein, unless otherwise indicated, includes alkyl moieties having at least one carbon-carbon triple bond wherein alkyl is as defined above. An alkynyl can be partially saturated or unsaturated. The "alkynyl" can be optionally substituted.

The term "acyl", as used herein, unless otherwise indicated, includes a functional group derived from an aliphatic carboxylic acid, by removal of the hydroxyl (—OH) group. The "acyl" can be optionally substituted.

The term "alkoxyl", as used herein, unless otherwise indicated, includes O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl, —O-3-methyl-1-butynyl, —O— cyclopropyl, —O-cyclobutyl, —O-cyclopentyl, —O-cyclohexyl, —O-cycloheptyl, —O—cyclooctyl, —O-cyclononyl, —O-cyclodecyl, —O—CH$_2$-cyclopropyl, —O—CH$_2$-cyclobutyl, —O—CH$_2$-cyclopentyl, —O—CH$_2$-cyclohexyl, —O—CH$_2$-cycloheptyl, —O—CH$_2$-cyclooctyl, —O—CH$_2$-cyclononyl, —O—CH$_2$-cyclodecyl, —O—(CH$_2$)$_n$-cyclopropyl, —O—(CH$_2$)$_n$-cyclobutyl, —O—(CH$_2$)$_n$-cyclopentyl, —O—(CH$_2$)$_n$-cyclohexyl, —O—(CH$_2$)$_n$-cycloheptyl, —O—(CH$_2$)$_n$-cyclooctyl, —O—(CH$_2$)$_n$-cyclononyl, or —O—(CH$_2$)$_n$-cyclodecyl. An alkoxyl can be saturated, partially saturated, or unsaturated. The "alkoxyl" can be optionally substituted. n can be between 1 and 20.

The term "cycloalkyl", as used herein, unless otherwise indicated, includes a non-aromatic, saturated, partially saturated, or unsaturated, monocyclic or fused, spiro or unfused bicyclic or tricyclic hydrocarbon referred to herein containing a total of from 3 to 10 carbon atoms. Examples of cycloalkyls include, but are not limited to, $C_{3-10}$ cycloalkyl groups include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. The term "cycloalkyl" also includes -lower alkyl-cycloalkyl, wherein lower alkyl and cycloalkyl are as defined herein. Examples of -lower alkyl-cycloalkyl groups include, but are not limited to, —CH$_2$-cyclopropyl, —CH$_2$-cyclobutyl, —CH$_2$-cyclopentyl, —CH$_2$-cyclopentadienyl, —CH$_2$— cyclohexyl, —CH$_2$-cycloheptyl, or —CH$_2$-cyclooctyl. The "cycloalkyl" can be optionally substituted.

The term "heterocyclyl" (e.g., a "heteroaryl"), as used herein, unless otherwise indicated, includes an aromatic or non-aromatic cycloalkyl in which one to four of the ring carbon atoms are independently replaced with a heteroatom from the group consisting of O, S and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated. The "heterocyclic" can be optionally substituted.

The term "indole", as used herein, is an aromatic heterocyclic organic compound with formula $C_8H_7N$. It has a bicyclic structure, consisting of a six-membered benzene ring fused to a five-membered nitrogen-containing pyrrole ring. The "indole" can be optionally substituted.

The term "cyano", as used herein, unless otherwise indicated, includes a —CN group. The "cyano" can be optionally substituted.

The term "alcohol", as used herein, unless otherwise indicated, includes a compound in which the hydroxyl functional group (—OH) is bound to a carbon atom. In particular, this carbon center should be saturated, having single bonds to three other atoms. The "alcohol" can be optionally substituted.

The term "solvate" is intended to mean a solvate form of a specified compound that retains the effectiveness of such compound. Examples of solvates include compounds of the invention in combination with, for example: water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "μg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

MFN1 or MFN2

Mitochondria generate ATP that fuels neuronal activity. Mitochondria must fuse in order to exchange genomes and promote mutual repair. The initial stages of mitochondrial fusion proceed through the physiochemical actions of two closely related dynamin family GTPases, mitofusins (Mfn) 1 and 2. The obligatory first step leading to mitochondrial fusion is molecular tethering of two mitochondria via homo- or hetero-oligomerization (in trans) of extended Mfn1 or Mfn2 carboxyl termini. Subsequently, GTP binding to and hydrolysis by Mfn1 or Mfn2 promotes irreversible physical fusion of the organellar outer membranes.

Mitofusins (Mfn) belong to a class of highly conserved GTPases which are located on the outer membrane of mitochondria in mammals, flies, the worm and budding yeast. Each of Mfn1 and Mfn2, the mitofusins present in mammals, are anchored to the outer membrane by two transmembrane domains such that their N-terminus and C-terminus are exposed to the cytoplasm. Mitofusins on different organelles undergo transdimerization through anti-parallel binding of their extended carboxy terminal α-helical domains to form mitochondria-mitochondria tethers—the obligate initial step in mitochondrial fusion (Koshiba et al., 2004, Science, 305:858-861). Conventional wisdom is that mitofusins exist constitutively in this "active" extended molecular conformation which supports mitochondrial tethering, although other possible conformations and the likelihood of functionally relevant molecular plasticity have not been rigorously tested. The components involved in mitochondrial tethering involve intermolecular and possibly intramolecular interactions of particular Mfn1 and Mfn2 domains. These interactions were further studied and exploited in the design and testing of compositions which affect the interactions and the resultant mitochondrial function.

Mfn1 and Mfn2 share a common domain structure. The amino terminal GTPase domain is followed by a coiled-coiled heptad repeat region (HR1), two adjacent small transmembrane domains, and a carboxyl terminal coiled heptad repeat region (HR2). Amino acid conservation between Mfn1 and Mfn2 varies by domain, being most highly conserved in the GTPase, transmembrane, and HR2 domains. HR2 domains extending from Mfn1 molecules located on different mitochondria can bind to each other, forming inter-molecular HR2-HR2 interactions that link the molecules and tether the organelles (Koshiba et al. ibid). HR2 can also bind to HR1 (Huang et al., 2011, PLoS One, 6:e20655), although there has been no determination of whether this is an inter- or intra-molecular interaction.

The crystal structure of bacterial dynamin-like protein (OLP) (Low and Lowe, 2006, Nature, 444:766-769; Protein Data Bank (PDB) ID No. 2J69) was used to model Mfn2 structure. The domain sequences of the OLP and Mfn2 proteins were aligned. The alignment and modeling of Mfn2 based on the OLP structure provided a template for the expansion and refining of the identities of HR2 amino acids that mediate inter-molecular HR2-HR2 tethering (Koshiba et al., 2004, Science, 305:858-861). This analysis led to the novel conception that these same amino acids mediate inter-molecular antiparallel binding of HR2 to HR2 (see e.g., FIG. 2A) and intra-molecular antiparallel binding of HR2 to HR1.

Mitochondria-Associated Diseases, Disorders, or Conditions

The present disclosure provides for compositions and methods of treatment for treating mitochondria-related diseases, disorders, or conditions such as diseases or disorders associated with mitofusin 1 (Mfn1) and/or mitofusin 2 (Mfn2) and mitochondrial dysfunction. A mitochondria-associated disease, disorder, or condition can be a disease associated with mitochondrial dysfunction, fragmentation, or fusion or associated with dysfunction in Mfn1 or Mfn2 unfolding. Mitochondria dysfunction can be caused by mutations.

Mitochondria transit within cells and undergo fusion to exchange genomes and promote mutual repair. Mitochondrial fusion and subcellular trafficking are mediated in part by mitofusins (Mfn) 1 and 2. Genetic mutations in Mfn2 that suppress mitochondrial fusion and motility cause Charcot Marie Tooth Disease 2A (CMT2A), the most common heritable axonal neuropathy. Mitochondrial fragmentation, dysfunction, and dysmotility are also central features of other genetic neurodegenerative syndromes, such as amyotrophic lateral sclerosis, Huntington's disease, Parkinson's disease, and Alzheimer's disease. Because no therapeutics exist that directly enhance mitochondrial fusion or trafficking, these diseases are unrelenting and irreversible.

As described herein, mitochondria-related diseases, disorders, or conditions can be any disease disorder or condition that is related to mitochondrial dysfunction. Mitochondrial dysfunction is implicated in chronic degenerative neurological conditions such as Alzheimer's, Parkinson's, and Huntington's diseases. For example, the genetic neurodegenerative condition, Charcot Marie Tooth Disease (type 2A) (CMT) or Hereditary motor and sensory neuropathy, is caused by multiple loss-of-function mutations of Mfn2. The underlying mechanism that causes this debilitating neuropathy is impaired mitochondrial fusion. Currently, because there are no pharmacological Mfn agonists, there is no treatment for CMT.

Mitochondria-associated diseases, disorders, or conditions can be Alzheimer's disease, Parkinson's disease, Huntington's disease, Charcot Marie Tooth Disease (type 2A) (CMT), hereditary motor and sensory neuropathy, autism, autosomal dominant optic atrophy (ADOA), muscular dystrophy, Lou Gehrig's disease, cancer, mitochondrial myopathy, Diabetes mellitus and deafness (DAD), Leber's hereditary optic neuropathy (LHON), Leigh syndrome, subacute sclerosing encephalopathy, Neuropathy, ataxia, retinitis pigmentosa, and ptosis (NARP), Myoneurogenic gastrointestinal encephalopathy (MNGIE), Myoclonic Epilepsy with Ragged Red Fibers (MERRF), Mitochondrial myopathy, encephalomyopathy, lactic acidosis, stroke-like symptoms (MELAS), mtDNA depletion, mitochondrial neurogastrointestinal encephalomyopathy (MNGIE), Dysautonomic Mitochondrial Myopathy, Mitochondrial Channelopathy, or pyruvate dehydrogenase complex deficiency (PDCD/PDH).

Symptoms that can be treated with the methods as described herein can include poor growth, loss of muscle coordination, muscle weakness, visual problems, hearing problems, learning disabilities, heart disease, liver disease, kidney disease, gastrointestinal disorders, respiratory disorders, neurological problems, autonomic dysfunction, and dementia.

Neurodeqenerative Disease

As described herein, mitofusin agonists (e.g., chimera B-A/I) rapidly reverse mitochondrial dysmotility in sciatic nerve axons of a mouse model of Charcot Marie Tooth disease. Because impaired mitochondrial fusion, fitness, and/or trafficking also contribute to neuronal degeneration in various neurodegenerative diseases (e.g., in Charcot Marie Tooth disease (CMT2A), Huntington's disease, Parkinson's disease, and Alzheimer's disease, and especially in Amyotrophic Lateral Sclerosis (ALS)), the present disclosure provides for compositions (e.g., mitofusin agonists) and methods to treat such neurodegenerative diseases, disorders, or conditions.

For example, a neurodegenerative disease, disorder or condition can be a disease of impaired neuronal mitochondrial dynamism or trafficking, such as a hereditary motor and sensory neuropathy (HMSN) (e.g., Charcot Marie Tooth (CMT) disease), CMT1 (a dominantly inherited, hypertrophic, predominantly demyelinating form), CMT2 (a dominantly inherited predominantly axonal form), Dejerine-Sottas (severe form with onset in infancy), CMTX (inherited in an X-linked manner), CMT4 (includes the various demyelinating autosomal recessive forms of Charcot-Marie-Tooth disease), hereditary sensory and autonomic neuropathy type IE, hereditary sensory and autonomic neuropathy type II, hereditary sensory and autonomic neuropathy type V, HMSN types 1A and 1B (e.g., dominantly inherited hypertrophic demyelinating neuropathies), HMSN type 2 (e.g., dominantly inherited neuronal neuropathies), HMSN type 3 (e.g., hypertrophic neuropathy of infancy [Dejerine-Sottas]), HMSN type 4 (e.g., hypertrophic neuropathy [Refsum] associated with phytanic acid excess), HMSN type 5 (associated with spastic paraplegia), or HMSN type 6 (e.g., with optic atrophy).

As another example, a neurodegenerative disease, disorder or condition can be Alzheimer's disease, amyotrophic lateral sclerosis (ALS), Alexander disease, Alpers' disease, Alpers-Huttenlocher syndrome, alpha-methylacyl-CoA racemase deficiency, Andermann syndrome, Arts syndrome, ataxia neuropathy spectrum, ataxia (E.g., with oculomotor apraxia, autosomal dominant cerebellar ataxia, deafness, and narcolepsy), autosomal recessive spastic ataxia of Charlevoix-Saguenay, Batten disease, beta-propeller protein-associated neurodegeneration, Cerebro-Oculo-Facio-Skeletal Syndrome (COFS), Corticobasal Degeneration, CLN1 disease, CLN10 disease, CLN2 disease, CLN3 disease, CLN4 disease, CLN6 disease, CLN7 disease, CLN8 disease, cognitive dysfunction, congenital insensitivity to pain with anhidrosis, dementia, familial encephalopathy with neuroserpin inclusion bodies, familial British dementia, familial Danish dementia, fatty acid hydroxylase-associated neurodegeneration, Gerstmann-Straussler-Scheinker Disease, GM2-gangliosidosis (e.g., AB variant), HMSN type 7 (e.g., with retinitis pigmentosa), Huntington's disease, infantile neuroaxonal dystrophy, infantile-onset ascending hereditary spastic paralysis, Huntington's disease (HD), infantile-onset spinocerebellar ataxia, juvenile primary lateral sclerosis, Kennedy's disease, Kuru, Leigh's Disease, Marinesco-Sjögren syndrome, Mild Cognitive Impairment (MCI), mitochondrial membrane protein-associated neurodegeneration, Motor neuron disease, Monomelic Amyotrophy, Motor neuron diseases (MND), Multiple System Atrophy, Multiple System Atrophy with Orthostatic Hypotension (Shy-Drager Syndrome), multiple sclerosis, multiple system atrophy, neurodegeneration in Down's syndrome (NDS), neurodegeneration of aging, Neurodegeneration with brain iron accumulation, neuromyelitis optica, pantothenate kinase-associated neurodegeneration, Opsoclonus Myoclonus, prion disease, Progressive Multifocal Leukoencephalopathy, Parkinson's disease (PD), PD-related disorders, polycystic lipomembranous osteodysplasia with sclerosing leukoencephalopathy, prion disease, progressive external ophthalmoplegia, riboflavin transporter deficiency neuronopathy, Sandhoff disease, Spinal muscular atrophy (SMA), Spinocerebellar ataxia (SCA), Striatonigral degeneration, Transmissible Spongiform Encephalopathies (prion diseases), or Wallerian-like degeneration.

Charcot Marie Tooth (CMT) Disease.

Charcot Marie Tooth (CMT) disease is an example of a non-curable and currently untreatable neurodegenerative disease, disorder, or condition, which can be characterized by mutations of Mfn2 and/or axonal neuropathy. As described herein, it was discovered that mitochondrial transport, not the conventional wisdom that mitochondria size, is implicated in CMT disease progression. It is shown here that the ability of mitochondria to get from point A to point B is the cause of progression. CMT is a progressive disease, caused by mutation in Mfn2, and characterized by neuronal neuropathy. The disease affects the legs at 8 to 10 years of age, then upper limbs, muscle wasting, skeletal deformities, and results in being wheelchair bound. The present disclosure provides for the discovery that the progression of CMT was not due to small mitochondria size but the length of mitochondrial travel. As such, this disclosure provides for the evaluation of mitochondrial trafficking as a route of therapy in the first mouse model of disease. It was discovered that the mitochondria in the legs do not move, but in the arm, there is mitochondria movement. As such, it was discovered that Mfn2 pays a role in mitochondria trafficking. Data showed that administration of a mitofusin modulating agent allowed for the mitochondria to move in a mouse model where mitochondria were not previously moving, which is applicable in any neuropathy (e.g., Huntington's disease, amyotrophic lateral sclerosis (ALS) or ALS-like sclerosis, Alzheimer's disease).

Neurological Disease

As described herein, mitofusin agonists (e.g., chimera B-A/I) rapidly reverses mitochondrial dysmotility in sciatic nerve axons of a mouse model of Charcot Marie Tooth disease. It is currently believed that impaired mitochondrial trafficking also contribute to neuronal degeneration in various neurological diseases (e.g., in Huntington's, Parkinson's, and Alzheimer's diseases, and especially in Amyotrophic Lateral Sclerosis (ALS)). As such, the present disclosure provides for methods and compositions to treat neurological diseases, disorders, or conditions. For example, a neurological disease, disorder, or condition can be Abulia; Agraphia; Alcoholism; Alexia; Alien hand syndrome; Allan-Herndon-Dudley syndrome; Alternating hemiplegia of childhood; Alzheimer's disease; Amaurosis fugax; Amnesia; Amyotrophic lateral sclerosis (ALS); Aneurysm; Angelman syndrome; Anosognosia; Aphasia; Apraxia; Arachnoiditis; Arnold-Chiari malformation; Asomatognosia; Asperger syndrome; Ataxia; Attention deficit hyperactivity disorder; ATR-16 syndrome; Auditory processing disorder; Autism spectrum; Behcets disease; Bipolar disorder; Bell's palsy; Brachial plexus injury; Brain damage; Brain injury; Brain tumor; Brody myopathy; Canavan disease; Capgras delusion; Carpal tunnel syndrome; Causalgia; Central pain syndrome; Central pontine myelinolysis; Centronuclear myopathy; Cephalic disorder; Cerebral aneurysm; Cerebral arteriosclerosis; Cerebral atrophy; Cerebral autosomal dominant arteriopathy with subcortical infarcts and leukoencephalopathy (CADASIL); Cerebral dysgenesis-neuropathy-ichthyosis-keratoderma syndrome (CEDNIK syndrome); Cerebral gigantism; Cerebral palsy; Cerebral vasculitis; Cervical spinal stenosis; Charcot-Marie-Tooth disease; Chiari malformation; Chorea; Chronic fatigue syndrome; Chronic inflammatory demyelinating polyneuropathy (CIDP); Chronic pain; Cockayne syndrome; Coffin-Lowry syndrome; Coma; Complex regional pain syndrome; Compression neuropathy; Congenital facial diplegia; Corticobasal degeneration; Cranial arteritis; Craniosynostosis; Creutzfeldt-Jakob disease; Cumulative trauma disorders; Cushing's syndrome; Cyclothymic disorder; Cyclic Vomiting Syndrome (CVS); Cytomegalic inclusion body disease (CIBD); Cytomegalovirus Infection; Dandy-Walker syndrome; Dawson disease; De Morsier's syndrome; Dejerine-Klumpke palsy; Dejerine-Sottas disease; Delayed sleep phase syndrome; Dementia; Dermatomyositis; Developmental coordination disorder; Diabetic neuropathy; Diffuse sclerosis; Diplopia; Disorders of consciousness; Down syndrome; Dravet syndrome; Duchenne muscular dystrophy; Dysarthria; Dysautonomia; Dyscalculia; Dysgraphia; Dyskinesia; Dyslexia; Dystonia; Empty sella syndrome; Encephalitis; Encephalocele; Encephalotrigeminal angiomatosis; Encopresis; Enuresis; Epilepsy; Epilepsy-intellectual disability in females; Erb's palsy; Erythromelalgia; Essential tremor; Exploding head syndrome; Fabry's disease; Fahr's syndrome; Fainting; Familial spastic paralysis; Febrile seizures; Fisher syndrome; Friedreich's ataxia; Fibromyalgia; Foville's syndrome; Fetal alcohol syndrome; Fragile X syndrome; Fragile X-associated tremor/ataxia syndrome (FXTAS); Gaucher's disease; Generalized epilepsy with febrile seizures plus; Gerstmann's syndrome; Giant cell arteritis; Giant cell inclusion disease; Globoid Cell Leukodystrophy; Gray matter heterotopia; Guillain-Barré syndrome; Generalized anxiety disorder; HTLV-1 associated myelopathy; Hallervorden-Spatz syndrome; Head injury; Headache; Hemifacial Spasm; Hereditary Spastic Paraplegia; Heredopathia atactica polyneuritiformis; Herpes zoster oticus; Herpes zoster; Hirayama syndrome; Hirschsprung's disease; Holmes-Adie syndrome; Holoprosencephaly; Huntington's disease; Hydranencephaly; Hydrocephalus; Hypercortisolism; Hypoxia; Immune-Mediated encephalomyelitis; Inclusion body myositis; Incontinentia pigmenti; Infantile Refsum disease; Infantile spasms; Inflammatory myopathy; Intracranial cyst; Intracranial hypertension; Isodicentric 15; Joubert syndrome; Karak syndrome; Kearns-Sayre syndrome; Kinsbourne syndrome; Kleine-Levin syndrome; Klippel Feil syndrome; Krabbe disease; Kufor-Rakeb syndrome; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Leukoencephalopathy with vanishing white matter; Lewy body dementia; Lissencephaly; Locked-in syndrome; Lou Gehrig's disease (amyotrophic lateral sclerosis (ALS)); Lumbar disc disease; Lumbar spinal stenosis; Lyme disease-Neurological Sequelae; Machado-Joseph disease (Spinocerebellar ataxia type 3); Macrencephaly; Macropsia; Mal de debarquement; Megalencephalic leukoencephalopathy with subcortical cysts; Megalencephaly; Melkersson-Rosenthal syndrome; Menieres disease; Meningitis; Menkes disease; Metachromatic leukodystrophy; Microcephaly; Micropsia; Migraine; Miller Fisher syndrome; Mini-stroke (transient ischemic attack); Misophonia; Mitochondrial myopathy; Mobius syndrome; Monomelic amyotrophy; Morvan syndrome; Motor Neurone Disease—see amyotrophic lateral sclerosis; Motor skills disorder; Moyamoya disease; Mucopolysaccharidoses; Multi-infarct dementia; Multifocal motor neuropathy; Multiple sclerosis; Multiple system atrophy; Muscular dystrophy; Myalgic encephalomyelitis; Myasthenia gravis; Myelinoclastic diffuse sclerosis; Myoclonic Encephalopathy of infants; Myoclonus; Myopathy; Myotubular myopathy; Myotonia congenita; Narcolepsy; Neuro-Behçet's disease; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Neuropathy; Neurosis; Niemann-Pick disease; Non-24-hour sleep-wake disorder; Nonverbal learning disorder; O'Sullivan-McLeod syndrome; Occipital Neuralgia; Occult Spinal Dysraphism Sequence; Ohtahara syndrome; Olivopontocerebellar atrophy; Opsoclonus myoclonus syndrome; Optic neuritis; Orthostatic Hypotension; Otosclerosis; Overuse syndrome; Palinopsia; Paresthesia; Parkinson's disease; Paramyotonia congenita; Paraneoplastic diseases; Paroxysmal attacks; Parry-Romberg syndrome; PANDAS; Pelizaeus-Merzbacher disease; Periodic paralyses; Peripheral neuropathy; Pervasive developmental disorders; Phantom limb/Phantom pain; Photic sneeze reflex; Phytanic acid storage disease; Pick's disease; Pinched nerve; Pituitary tumors; PMG; Polyneuropathy; Polio; Polymicrogyria; Polymyositis; Porencephaly; Post-polio syndrome; Postherpetic neuralgia (PHN); Postural hypotension; Prader-Willi syndrome; Primary lateral sclerosis; Prion diseases; Progressive hemifacial atrophy; Progressive multifocal leukoencephalopathy;

Progressive supranuclear palsy; Prosopagnosia; Pseudotumor cerebri; Quadrantanopia; Quadriplegia; Rabies; Radiculopathy; Ramsay Hunt syndrome type I; Ramsay Hunt syndrome type II; Ramsay Hunt syndrome type III—see Ramsay-Hunt syndrome; Rasmussen encephalitis; Reflex neurovascular dystrophy; Refsum disease; REM sleep behavior disorder; Repetitive stress injury; Restless legs syndrome; Retrovirus-associated myelopathy; Rett syndrome; Reye's syndrome; Rhythmic Movement Disorder; Romberg syndrome; Saint Vitus dance; Sandhoff disease; Schilder's disease (two distinct conditions); Schizencephaly; Sensory processing disorder; Septo-optic dysplasia; Shaken baby syndrome; Shingles; Shy-Drager syndrome; Sjögren's syndrome; Sleep apnea; Sleeping sickness; Snatiation; Sotos syndrome; Spasticity; Spina bifida; Spinal cord injury; Spinal cord tumors; Spinal muscular atrophy; Spinal and bulbar muscular atrophy; Spinocerebellar ataxia; Split-brain; Steele-Richardson-Olszewski syndrome; Stiff-person syndrome; Stroke; Sturge-Weber syndrome; Stuttering; Subacute sclerosing panencephalitis; Subcortical arteriosclerotic encephalopathy; Superficial siderosis; Sydenham's chorea; Syncope; Synesthesia; Syringomyelia; Tarsal tunnel syndrome; Tardive dyskinesia; Tardive dysphrenia; Tarlov cyst; Tay-Sachs disease; Temporal arteritis; Temporal lobe epilepsy; Tetanus; Tethered spinal cord syndrome; Thomsen disease; Thoracic outlet syndrome; Tic Douloureux; Todd's paralysis; Tourette syndrome; Toxic encephalopathy; Transient ischemic attack; Transmissible spongiform encephalopathies; Transverse myelitis; Traumatic brain injury; Tremor; Trichotillomania; Trigeminal neuralgia; Tropical spastic paraparesis; Trypanosomiasis; Tuberous sclerosis; 22q13 deletion syndrome; Unverricht-Lundborg disease; Vestibular schwannoma (Acoustic neuroma); Von Hippel-Lindau disease (VHL); Viliuisk Encephalomyelitis (VE); Wallenberg's syndrome; West syndrome; Whiplash; Williams syndrome; Wilson's disease; Y-Linked Hearing Impairment; or Zellweger syndrome.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

A nucleic acid sequence or amino acid sequence (e.g., DNA, RNA, a genetic sequence, polynucleotide, oligonucleotide, primer, protein, polypeptide, peptide) can have about 80%; about 81%; about 82%; about 83%; about 84%; about 85%; about 86%; about 87%; about 88%; about 89%; about 90%; about 91%; about 92%; about 93%; about 94%; about 95%; about 96%; about 97%; about 98%; or about 99% sequence identity to a reference sequence or a naturally occurring sequence or contain at least one substitution modification to the reference sequence or naturally occurring sequence. Recitation of each of these discrete values is understood to include ranges between each value.

A nucleic acid sequence or an amino acid sequence can be operably linked to a heterologous promoter.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gin by Asn, Val by lie, Leu by lie, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[Na$^+$])+0.41 (fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a mitochondria-associated disease, disorder, or condition in a subject in need administration of a therapeutically effective amount of mitofusin modulating agent, so as to prevent or treat a mitochondria-associated disease, disorder, or condition.

For example, the compositions and methods described herein can be used as a primary therapy for Charcot Marie Tooth, or adjunctive therapy for Huntington's, Parkinson's, and Alzheimer's diseases or ALS to reverse or retard progression.

Methods described herein are generally performed on a subject in need thereof. A subject in need of the therapeutic methods described herein can be a subject having, diagnosed with, suspected of having, or at risk for developing a mitochondria-associated disease, disorder, or condition. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of a mitofusin modulating agent is, for example, that amount that would cause the desired therapeutic effect in a subject while minimizing undesired side effects. In various embodiments, an effective amount of a mitofusin modulating agent described herein can substantially inhibit mitochondria-associated disease, disorder, or condition, slow the progress of mitochondria-associated disease, disorder, or condition, or limit the development of mitochondria-associated disease, disorder, or condition. For example, a desired therapeutic effect can be a delay in peripheral neuropathy (e.g., over the course of three years) compared to placebo assessed by slower increase in modified composite CMT neuropathy score. As another example, a desired therapeutic effect can be reversal or absence of progression of peripheral neuropathy compared to placebo, as indicated by lower or stable modified composite CMT neuropathy score.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a mitofusin modulating agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to treat, prevent, or slow the progression of mitochondria-associated disease, disorder, or condition.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a mitofusin modulating agent can occur as a single event or over a time course of treatment. For example, a mitofusin modulating agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for treating, preventing, or slowing the progression of mitochondria-associated disease, disorder, or condition.

A mitofusin modulating agent can be administered simultaneously or sequentially with another agent, such as an antibiotic, an anti-inflammatory, or another agent. For example, a mitofusin modulating agent can be administered simultaneously with another agent, such as an antibiotic or an anti-inflammatory. Simultaneous administration can occur through administration of separate compositions, each containing one or more of a mitofusin modulating agent, an antibiotic, an anti-inflammatory, or another agent. Simultaneous administration can occur through administration of one composition containing two or more of mitofusin modulating agent, an antibiotic, an anti-inflammatory, or another agent. A mitofusin modulating agent can be administered sequentially with an antibiotic, an anti-inflammatory, or another agent. For example, a mitofusin modulating agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, transdermal (e.g., a transdermal patch) intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening (see e.g., Example 2, Example 3). As described herein, a FRET method for screening and evaluating small molecular regulators of mitochondrial tethering and fusion is provided. Also provided herein is a binding assay for screening and evaluating small molecular regulators of mitochondrial tethering and fusion.

The term "FRET" as used herein refers to fluorescence resonance energy transfer between molecules. In FRET methods, one fluorophore is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g., on the same, or a neighboring molecule). See for example U.S. Pat. Nos. 5,707,804, 5,728,528, 5,853, 992, and 5,869,255 (for a description of FRET dyes), T Mergny et al., (1994) Nucleic Acid Res. 22:920-928, and Wolf et al., (1988) Proc. Natl. Acad. Sci. USA 85:8790-8794 (for general descriptions and methods for FRET), each of which is hereby incorporated by reference in its entirety.

With the modulating compounds and peptides available which have been shown to activate mitochondrial fusion, assays can be designed and performed to screen candidate agents or molecules for specific compositions which can activate mitochondrial fusion. For example, identification of small molecule activators provides an alternate modulating composition which may be more efficient to synthesize and use. Candidate agents encompass numerous chemical classes, typically synthetic, semi-synthetic, or naturally-occurring inorganic or organic molecules. Candidate agents include those found in large libraries of synthetic or natural compounds. Alternatively, libraries of natural compounds in the form of bacterial, fungal, plant and animal extracts are available from commercial resources or are readily producible. In some embodiments, small molecule activators of mitochondrial fusion identified through these screening assays can become promising therapeutic agents for treating diseases or disorders associated with defects in mitochondrial fusion.

One screening assay can use the HR1 peptide or variant which has been shown to increase mitochondrial aspect ratio. In this assay, the Mfn2 protein or a fragment of the Mfn2 protein which contains the HR2 domain is immobilized to a solid substrate such as nitrocellulose or to the well surface of a high throughput screen plate or array substrate. The immobilized protein or fragment is then incubated with the HR1 peptide or variant in a solution conducive to protein-protein interactions. The HR1 peptide is conjugated to a detectable label such as FITC or other fluorescent dye, generating a signal in each well or array position. Detectable labels are well-known in the art and include isotope, colorimetric, fluorescent, photochromic and electrochemical labels. A candidate agent is assessed for its ability to compete with the HR1 peptide for binding to the solid phase-bound Mfn2 protein or HR2 domain. An agent which can compete with the HR1 peptide for binding to Mfn2 protein or HR2 will reduce or eliminate the signal from the label. A candidate agent able compete with the HR1 peptide is an agent which can activate mitochondrial aspect ratio and/or mitochondrial fusion.

In some embodiments, a method for identifying an agent or compound able to bind to the Mfn2 protein is provided. In these embodiments, the compound competes with the HR1 peptide for binding to Mfn2 or to a fragment of Mfn2 comprising the HR2 domain. A test compound is identified as active it if decreases the binding of the peptide, i.e., its effect on the extent of binding is above a threshold level. More specifically, if the decrease in binding of the labeled HR1 peptide to the solid phase bound Mfn2 protein or HR2 domain is a several-fold different between the control and experimental samples, the compound would be considered as having binding activity. Typically, a 2-fold or 4-fold threshold difference in binding between the test and control samples is sought. In some embodiments, this agent increases the mitochondrial aspect ratio when incubated in a cell.

In some embodiments, an alternative assay is provided to identify a composition able to activate intermolecular binding of the HR2 domains of two Mfn proteins. In this assay, a first population of Mfn2 proteins is labeled with an acceptor fluorophore on its HR2 arm and a second population of Mfn2 proteins is labeled with a donor fluorophore on its HR2 arm. Use of fluorophore donors and complementary acceptor molecules for FRET analysis is well known (see, e.g., Jager et al., 2005, Protein Sci, 14:2059-2068; Jager et al, 2006, Protein Sci, 15:640-646). Accordingly, as described above, when an HR2 arm is liberated from the configuration in which it is interacting with the HR1 domain within the core of the Mfn protein, the free HR2 arm is able to interact with the free HR2 arm of a second Mfn2 to facilitate mitochondrial tethering and subsequent fusion. It follows that provided herein is an assay to screen a population of agents or compounds for those that facilitate mitochondrial tethering and subsequent fusion wherein the population of candidate compounds is added to an array, wherein each well or position in the array contains a test reaction mix which comprises a first population of Mfn2 proteins labeled at or near the HR2 arm with a donor fluorophore and a second population of Mfn2 proteins labeled at or near the HR2 arm with a acceptor fluorophore. The fluorescence is measured in each test reaction mix and compared with a negative control reaction mix containing no HR2-binding peptide and a positive control reaction mix which contains an HR2-binding peptide and no candidate compound. A fluorescence signal which is greater in a test reaction mix containing a candidate compound is identified the candidate compound as an activator of mitochondrial fusion.

In a third screening assay, interaction between the HR1 and HR2 domains of a single Mfn2 protein is assessed. For example, a single Mfn2 protein is labeled with a single FRET donor and acceptor pair, wherein the donor is positioned at or near the HR1 domain and the acceptor is positioned at or near the HR2 domain, or vice versa. Incubation of a peptide which inhibits mitochondrial fusion (decreases mitochondrial aspect ratio) (e.g., the 367-384Gly peptide or variant thereof) will cause the HR2 arm to extend, removing the quenching action of the FRET pair, resulting in fluorescence signal. Accordingly, a library of candidate modulating molecules can be screened by mixing each with the Mfn2 protein labeled with a FRET donor acceptor pair. Any candidate molecule which increases fluorescence of the labeled Mfn2 protein by at least 50%, 60%, 70% compared to the labeled Mfn2 protein in the absence of a candidate molecule will be identified as an activator of mitochondrial fusion.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Fragment-based lead discovery (FBLD) also known as fragment-based drug discovery (FBDD) is a method that can be used for finding lead compounds as part of the drug discovery process. It is based on identifying small chemical fragments, which may bind only weakly to the biological target, and then growing them or combining them to produce a lead with a higher affinity. FBLD can be compared with high-throughput screening (HTS). In HTS, libraries with up to millions of compounds, with molecular weights of around 500 Da, are screened, and nanomolar binding affinities are sought. In contrast, in the early phase of FBLD, libraries with a few thousand compounds with molecular weights of around 200 Da may be screened, and millimolar affinities can be considered useful.

In analogy to the rule of five, it has been proposed that ideal fragments could follow the 'rule of three' (molecular weight <300, ClogP <3, the number of hydrogen bond donors and acceptors each should be <3 and the number of rotatable bonds should be <3). Since the fragments have relatively low affinity for their targets, they should have high water solubility so that they can be screened at higher concentrations.

In fragment-based drug discovery, the low binding affinities of the fragments can pose significant challenges for screening. Many biophysical techniques have been applied to address this issue. In particular, ligand-observe nuclear magnetic resonance (NMR) methods such as water-ligand observed via gradient spectroscopy (waterLOGSY), saturation transfer difference spectroscopy (STD-NMR), 19F NMR spectroscopy and inter-ligand Overhauser effect (ILOE) spectroscopy, protein-observe NMR methods such as 1H-15N heteronuclear single quantum coherence (HSQC) that utilizes isotopically-labelled proteins, surface plasmon resonance (SPR) and isothermal titration calorimetry (ITC) are routinely-used for ligand screening and for the quantification of fragment binding affinity to the target protein.

Once a fragment (or a combination of fragments) have been identified, protein X-ray crystallography can be used to obtain structural models of the protein-fragment(s) complexes. Such information can then be used to guide organic synthesis for high-affinity protein ligands and enzyme inhibitors.

Advantages of screening low molecular weight fragment based libraries over traditional higher molecular weight chemical libraries can include:

(i) More hydrophilic hits in which hydrogen bonding is more likely to contribute to affinity (enthalpically driven binding). It is generally much easier to increase affinity by adding hydrophobic groups (entropically driven binding), starting with a hydrophilic ligand increases the chances that the final optimized ligand will not be too hydrophobic (log P<5).

(ii) Higher ligand efficiency so that the final optimized ligand will more likely be relatively low in molecular weight (MW<500).

(iii) Since two to three fragments in theory can be combined to form an optimized ligand, screening a fragment library of N compounds is equivalent to screening N2-N3 compounds in a traditional library.

Fragments can be less likely to contain sterically blocking groups that interfere with an otherwise favorable ligand-protein interaction, increasing the combinatorial advantage of a fragment library even further.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to Mfn1, Mfn2, antagonist target peptides, agonist target peptides, or mitofusin modulating agents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

Examples

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Identification of Amino Acid Residues in the HR1 Mfn1 and Mfn2 Domain that Influence Conformation The following example shows that Mfn1 and Mfn2 conformation is influenced by a plurality of amino acid residues in the HR1 domain.

Mitochondria generate ATP that fuels neuronal activity. Mitochondrial dysfunction is implicated in chronic degenerative neurological conditions such as Alzheimer's, Parkinson's, and Huntington's diseases. Mitochondria fuse in order to exchange genomes and promote mutual repair. The initial stages of mitochondrial fusion proceed through the physiochemical actions of two closely related dynamin family GTPases, mitofusins (Mfn) 1 and 2. The obligatory first step leading to mitochondrial fusion is molecular tethering of two mitochondria via homo- or hetero-oligomerization (in trans) of extended Mfn1 or Mfn2 carboxyl termini. Subsequently, GTP binding to and hydrolysis by Mfn1 or Mfn2 promotes irreversible physical fusion of the organellar outer membranes. The genetic neurodegenerative condition, Charcot Marie Tooth Disease (type 2A) (CMT) or Hereditary motor and sensory neuropathy, is caused by multiple loss-of-function mutations of Mfn2. The underlying mechanism that causes this debilitating neuropathy is impaired mitochondrial fusion. Currently, because there are no pharmacological Mfn agonists, there is no treatment for CMT.

Figure 1A:
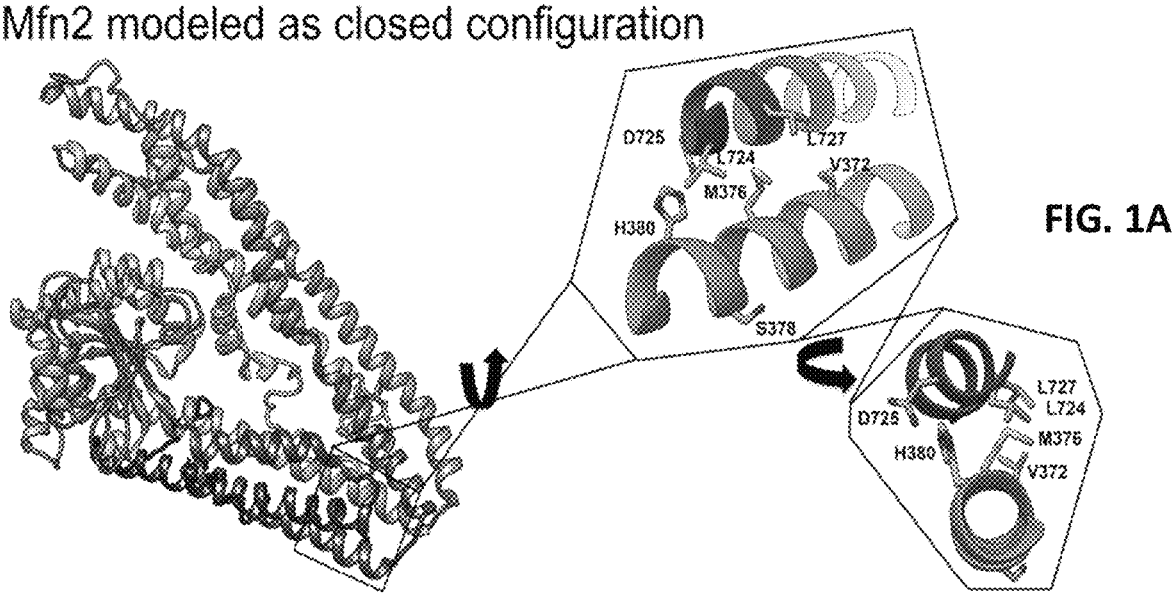
FIG. 1 is a series of hypothetical structures of human MFN2 modeled using I-TASSER. (top) MFN2 modeled in a closed configuration based on structural homology with *Homo sapiens* MFN1 and *Arabidopsis thaliana* dynamin-related protein. (bottom) MFN2 modeled in an open configuration based on structural homology with *Homo sapiens* Opa1. Exploded views show critical HR1 (green)-HR2 (red) interactions in orthogonal views.
Figure 1B:
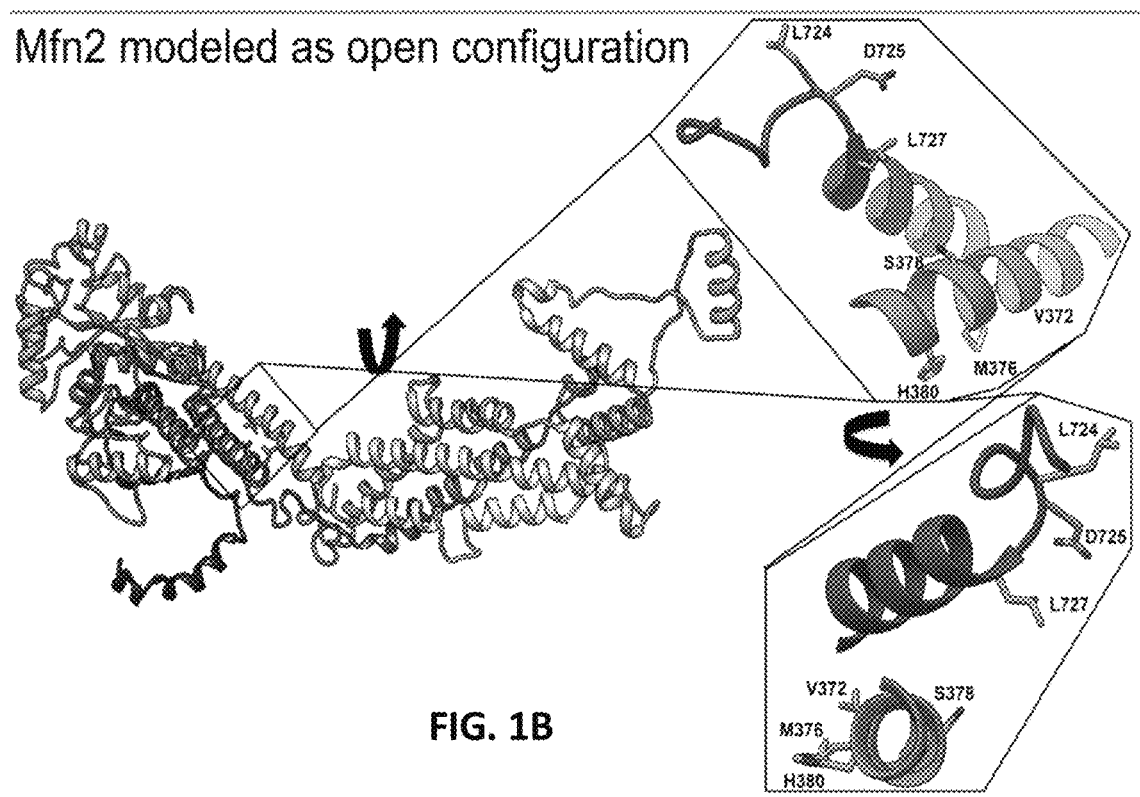

Mfn1 and Mfn2 share a common domain structure, which was modeled using I-TASSER and structural homology with bacterial dynamin-like protein, human Mfn1 and *Arabidopsis thaliana* dynamin-related protein (see e.g., FIG. 1, top panel). The model shows how the first heptad repeat domain (HR1) interacts in an anti-parallel manner with the carboxyl terminal second heptad repeat (HR2) domain to restrain it and prevent its extension into the cytosol, which can be necessary for mitochondrial tethering and fusion (see e.g., FIG. 1, top panel). The amino acids necessary for the HR1-HR2 interaction were identified as Met376, Ser378, His380, and Met 381 by first defining a minimal HR1-derived peptide that competes with endogenous HR1-HR2 binding (see e.g., FIG. 2A-FIG. 2B) and followed by functional analyses of a complete series of alanine substituted peptides (see e.g., FIG. 2C). Based on these results, chemical peptido-mimetics could also mimic the 3-dimensional spatial and charge characteristics of these critical amino acid side chains and would have similar modulatory activity on mitochondrial fusion as the N-terminal mini-peptide (see e.g., Example 2).

Example 2: Peptido-Mimetic Compounds Influence Mfn1 and Mfn2 Conformations

The following example describes peptide-mimetic compounds that influence conformations of Mfn1 and Mfn2.

Mfn Agonist (Fusion-Promoting) Peptido-Mimetics

Figure 4A:
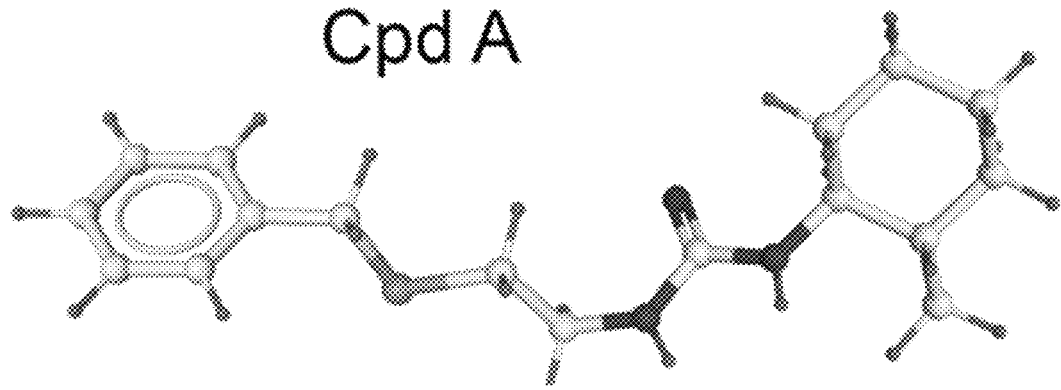
FIG. 4A and FIG. 4B are a series of chemical structures and a bar graph that shows the structure and function of compounds A and B, more specifically, the mitofusin-dependent mitochondrial elongation provoked by prototype Mfn agonist peptide mimetics (compounds A and B).
Figure 4B:
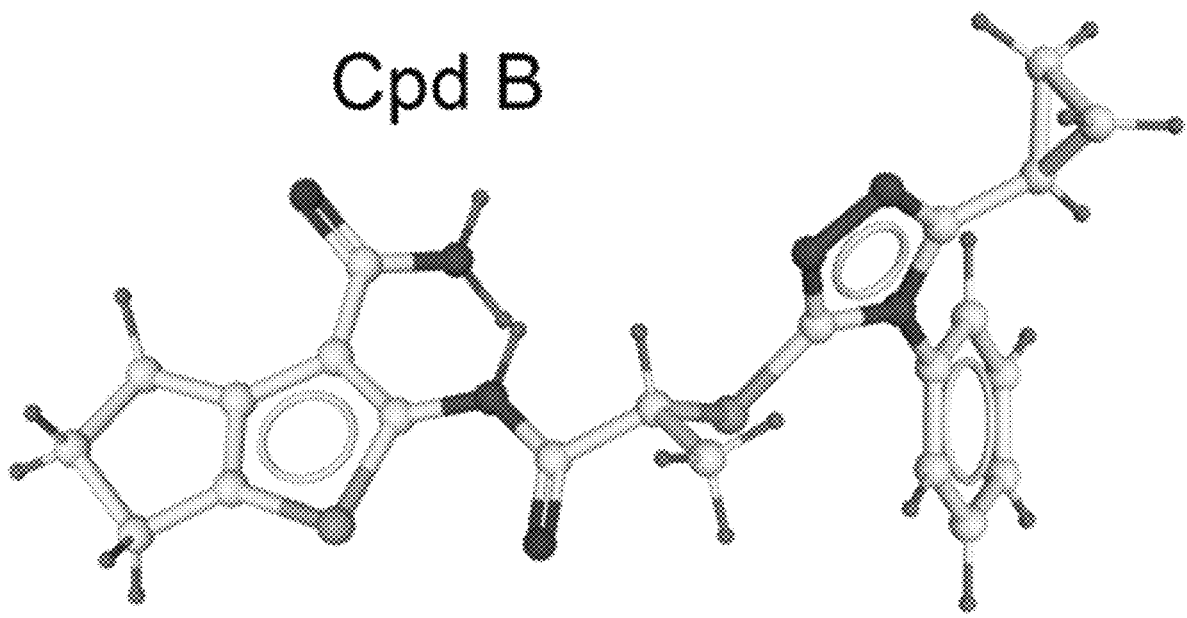
Figure 4C:
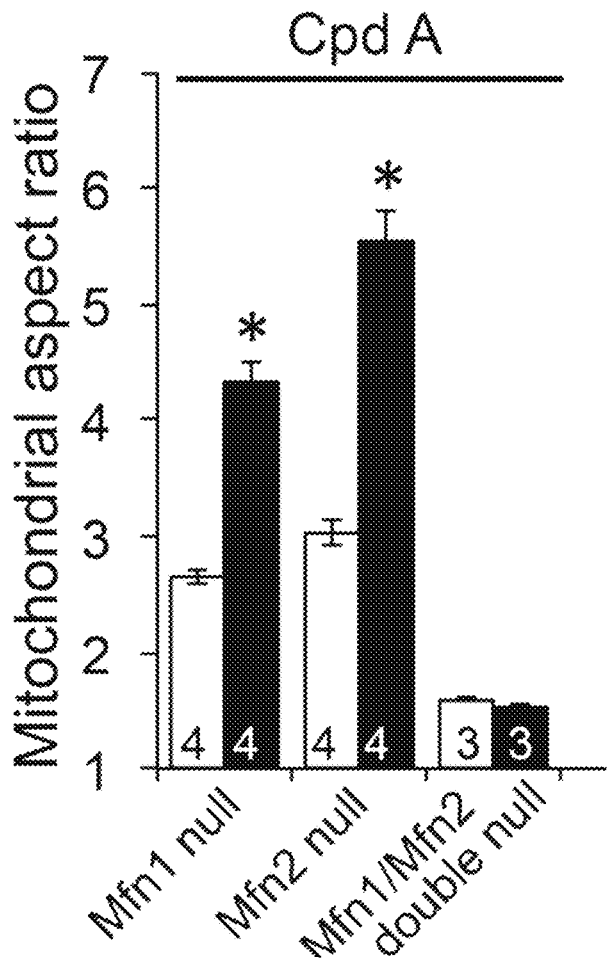
Figure 4D:
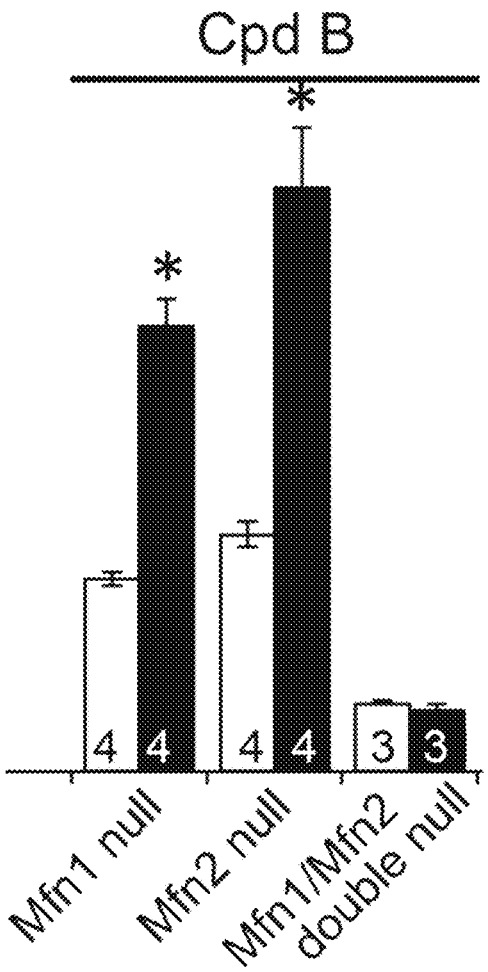
Figure 5A:
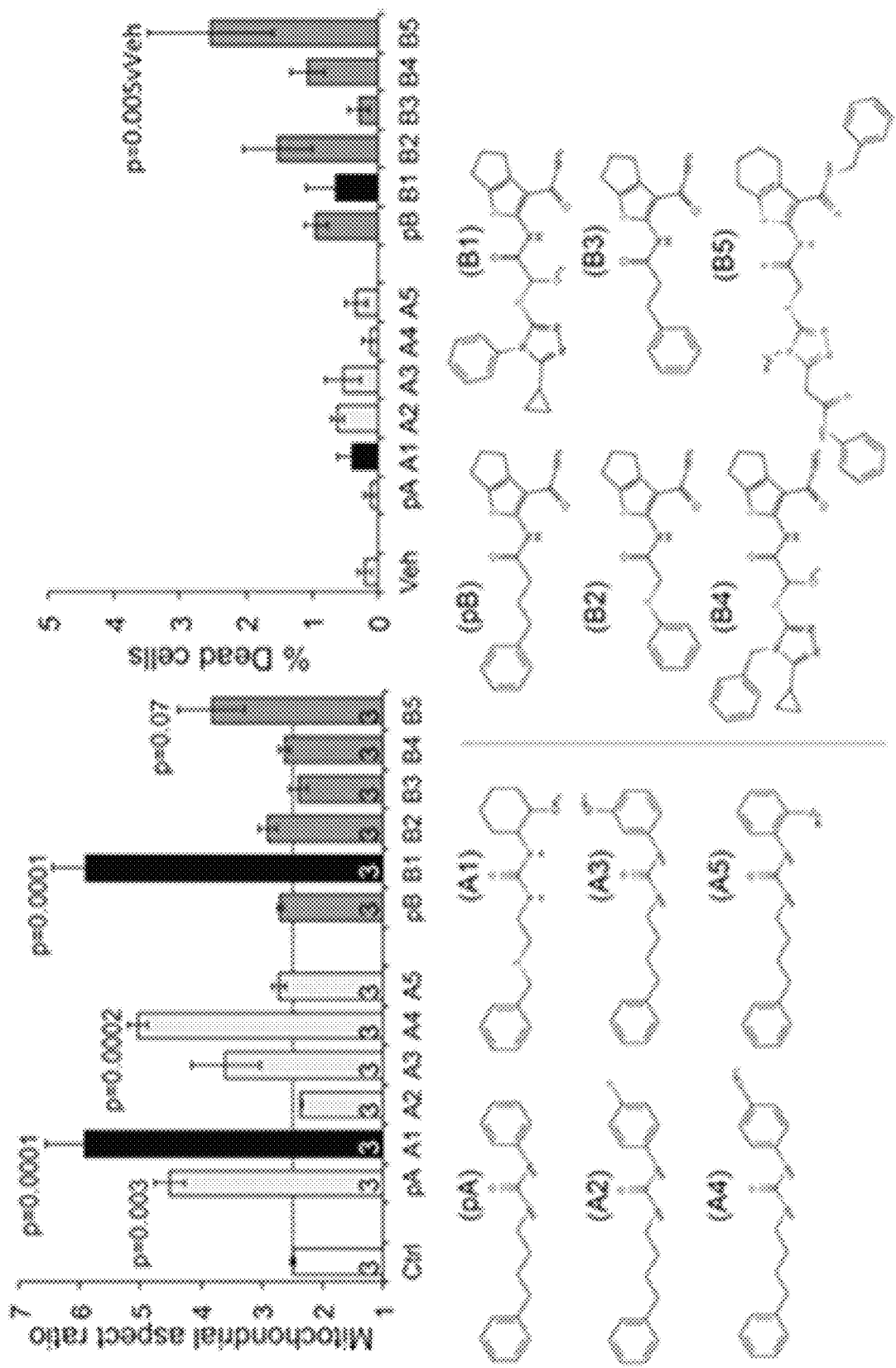
FIG. 5A, FIG. 5B, FIG. 5C, and FIG. 5D are a series of bar graphs, structures, graphs, and images showing that small molecule HR1 MP374-384 mimetics can be mitofusin agonists. (A) Functional screening for class A and B small mitofusin agonists. 1 μM of each candidate compound was added to MFN2-deficient MEFs overnight. Mitochondrial aspect ratio is on left and cell viability on right. Structures of the class A and B chemosimilars are shown below (n=3; p values are by ANOVA with Tukey's post hoc comparison). Black bars indicate class A and B compounds selected for detailed studies. (B) Representative confocal images from studies in (A). Mitochondria were visualized with MitoTracker Orange. Cell viability was assessed simultaneously with mitochondrial aspect ratio—live cells have green cytoplasm (calcein AM) and dead cells lack calcein staining and have purple nuclei (red ethidium homodimer overlying blue Hoechst). Scale bars are 10 μm. (C) Initial dose-response relations of five fusogenic compounds from screening in (A). $EC_{50}$ values (indexed to the 100% maximal response elicited by the most effective compound, B1) are shown for the agonists with strong fusion-promoting activity; mean±SEM of 3 independent studies for each compound. (D) Competition of the HR1 minipeptide at its MFN2 HR2 binding site by five fusogenic compounds from (A). $IC_{50}$ values are shown for agonists with >50% displacement (mean±SEM of 6 independent experiments per compound). Displacement curves for compounds A and B are re-plotted in FIG. 11C.
Figure 5B:
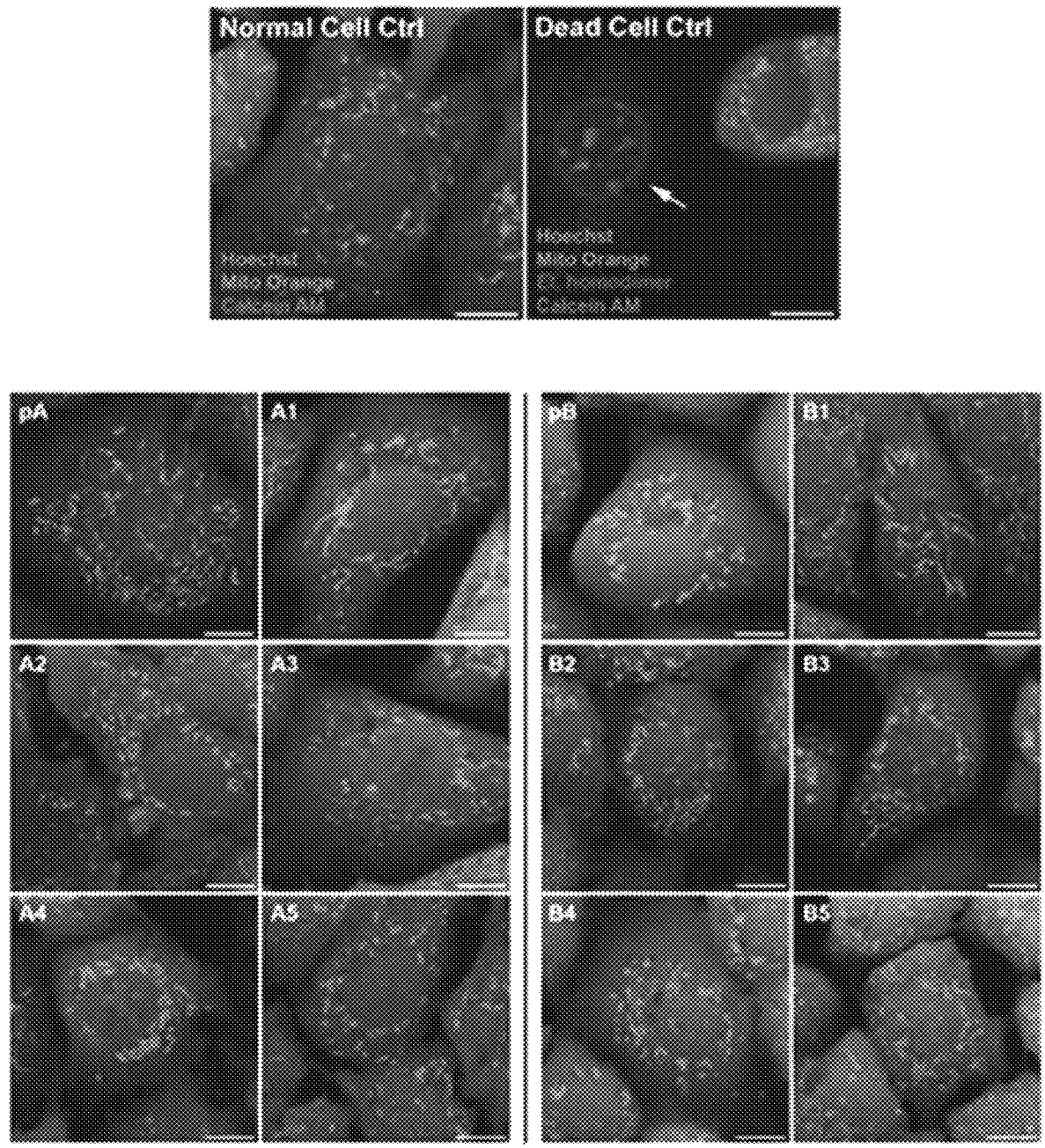
Figure 5C:
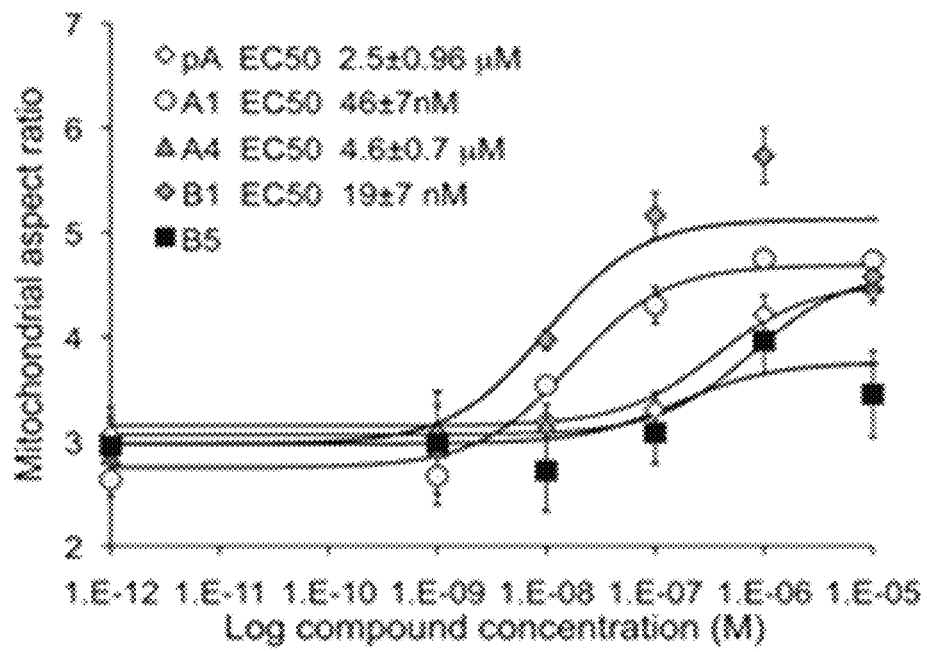
Figure 5D:
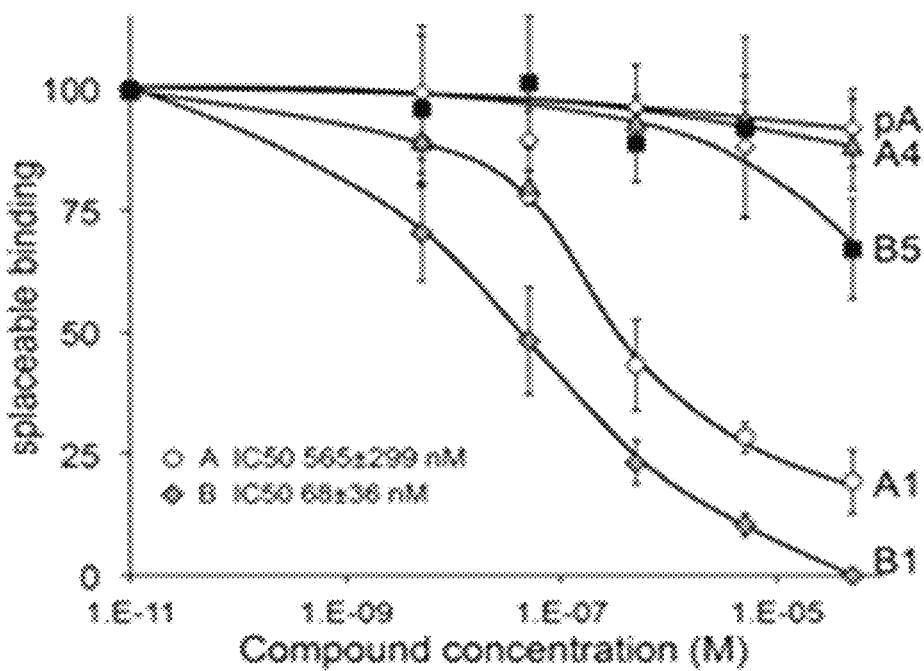

Forty-four candidate compounds were screened, 2 of which (1-[2-(benzylsulfanyl)ethyl]-3-(2-methylcyclohexyl) urea, designated compound A, and 2-{2-[(5-cyclopropyl-4-phenyl-4H-1,2,4-triazol-3yl)sulfanyl] propanamido}-4H, 5H,6H-cyclopenta[b]thiophene-3-carboxamide, designated compound B) induced mitochondrial elongation. Detailed analyses of compounds A and B were performed after purification by silica gel chromatography and structural validation by high performance liquid chromatography (HPLC) and mass spectroscopy (see e.g., FIG. 3). A cultured murine embryonic fibroblast assay system was used in which mitochondrial elongation (an increase in aspect ratio) reflects enhanced mitochondrial fusion. Mitochondrial elongation evoked by compounds A and B (see e.g., FIG. 4A) was similar in cells expressing only Mfn2 (Mfn1 null) or only Mfn1 (Mfn2 null), but did not occur in the absence of both of their mitofusin targets (Mfn1/Mfn2 double null; see e.g., FIG. 4B).

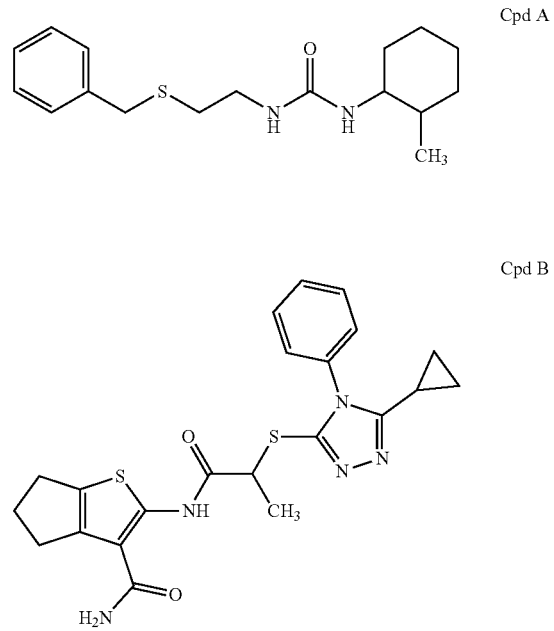

Structure-activity relationships were interrogated to expand the pool of Mfn agonist compounds and to identify chemical analogs with differing potencies for in vitro and in vivo comparative efficacy studies of CMT (see e.g., FIG. 5). Substitutions were evaluated for the cyclopenta[b]thiophene-3-carboxamide (green), sulfanyl-propanamido (purple), and 5-cyclopropyl-4-phenyl-4H-1,2,4-triazol-3-yl (red) moieties of Compound B. These derivatives are described in detail in TABLE 1 and TABLE 2.

TABLE 1

Mitofusin agonist peptido-mimetics

| | | |
|---|---|---|
| 1-[2-(benzylsulfanyl)ethyl]-3-(2-methylcyclohexyl)urea | MolPort-005-680-744 | 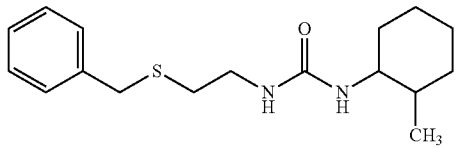 [SMILES: CC1CCCCC1NC(=O)NCCSCc1ccccc1] |
| 3-{2-[(5-cyclopropyl-4-phenyl-4H-1,2,4-triazol-3-yl)sulfanyl]ethyl}-1-(2-methylcyclohexyl)urea | novel | 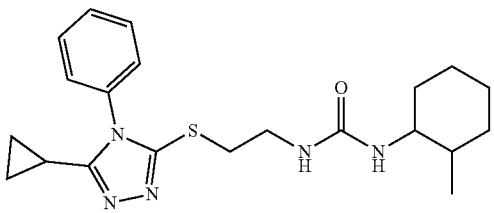 [SMILES: CC1CCCCC1NC(=O)NCCSc1nnc(C2CC2)n1-c1ccccc1] |
| 2-[(5-cyclopropyl-4-phenyl-4H-1,2,4-triazol-3-yl)sulfanyl]-N-(2-methylcyclohexyl)propanamide | novel | 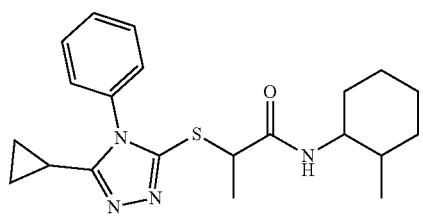 [SMILES: CC(Sc1nnc(C2CC2)n1-c1ccccc1)C(=O)NC1CCCCC1C] |
| 2-({[2-(benzyl-sulfanyl)ethyl]carbamoyl}amino)-4H,5H,6H-cyclopenta[b]thiophene-3-carboxamide | novel | 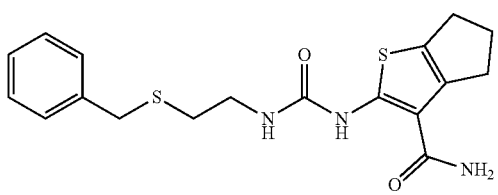 [SMILES: NC(=O)c1c(NC(=O)NCCSCc2ccccc2)sc2c1CCC2] |
| 2-[2-(benzylsulfanyl)propanamido]-4H,5H,6H-cyclopenta[b]thiophene-3-carboxamide | novel | 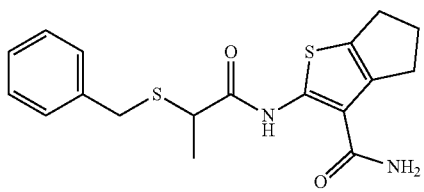 [SMILES: CC(SCc1ccccc1)C(=O)Nc1sc2c(c1C(N)=O)CCC2] |
| 2-{2-[(5-cyclopropyl-4-phenyl-4H-1,2,4-triazol-3-yl)sulfanyl]propanamido}-4H,5H,6H-cyclopenta[b]thiophene-3-carboxamide | MolPort-004-201-234 | 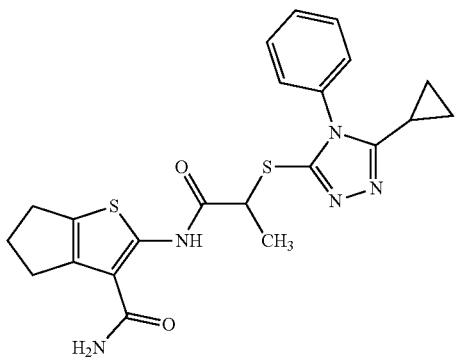 [SMILES: CC(Sc1nnc(C2CC2)n1-c1ccccc1)C(=O)Nc1sc2c(c1C(N)=O)CCC2] |

TABLE 1-continued
Mitofusin agonist peptido-mimetics
2-{2-[(5-cyclopropyl-4-phenyl-4H-1,2,4-triazol-3-yl)sulfanyl]acetamido}-4H,5H,6H-cyclopenta[b]thiophene-3-carboxamide    MolPort-004-059-486
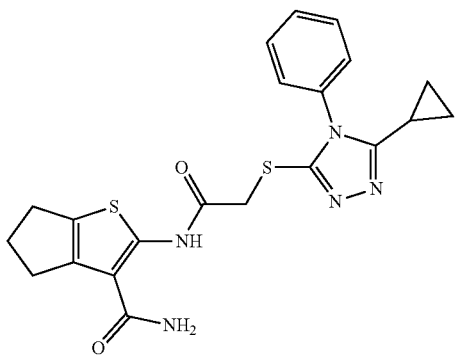 [SMILES: NC(=O)c1c(NC(=O)CSc2nnc(C3CC3)n2-c2ccccc2)sc2c1CCC2]
2-(2-{[4-cyclopropyl-5-(1H-indol-3-yl)-4H-1,2,4-triazol-3-yl]sulfanyl}propanamido)-4H,5H,6H-cyclopenta[b]thiophene-3-carboxamide    MolPort-004-214-844
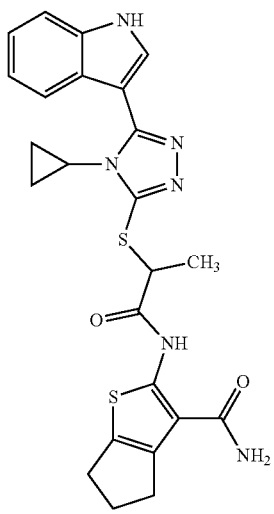 [SMILES: CC(Sc1nnc(-c2c[nH]c3ccccc23)n1C1CC1)C(=O)Nc1sc2c(c1C(N)=O)CCC2]
2-{2-[(diphenyl-4H-1,2,4-triazol-3-yl)sulfanyl]propanamido}-4H,5H,6H-cyclopenta[b]thiophene-3-carboxamide    MolPort-005-522-531
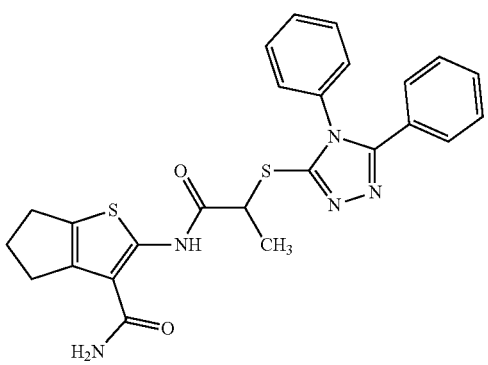 [SMILES: CC(Sc1nnc(-c2ccccc2)n1-c1ccccc1)C(=O)Nc1sc2c(c1C(N)=O)CCC2]

TABLE 1-continued

Mitofusin agonist peptido-mimetics

N-(4-chlorophenyl)-2-{2-[(5-cyclopropyl-4H-1,2,4-triazol-3-yl)sulfanyl]acetamido}-4,5,6,7-tetrahydro-1-benzothiophene-3-carboxamide    MolPort-005-784-050

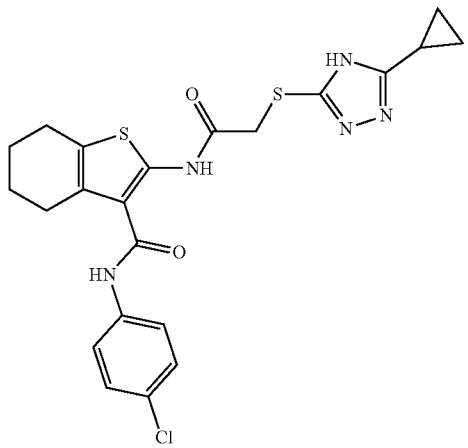 [SMILES: O=C(CSc1nnc(C2CC2)[nH]1)Nc1sc2c(c1C(=O)Nc1ccc(Cl)cc1)CCCC2]

N-benzyl-2-{2-[(5-cyclopropyl-4-ethyl-4H-1,2,4-triazol-3-yl)sulfanyl]acetamido}-4,5,6,7-tetrahydro-1-benzothiophene-3-carboxamide    MolPort-005-803-773

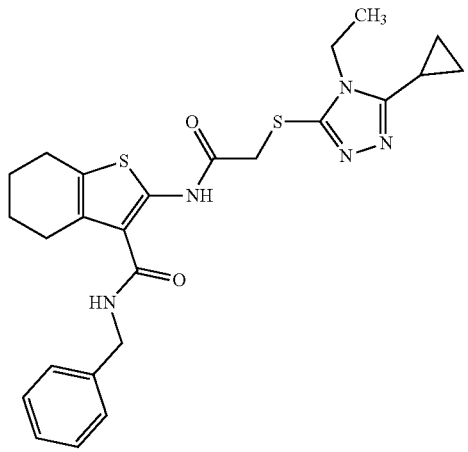 [SMILES: CCn1c(SCC(=O)Nc2sc3c(c2C(=O)NCc2ccccc2)CCCC3)nnc1C1CC1]

2-{2-[(5-cyclopropyl-4-ethyl-4H-1,2,4-triazol-3-yl)sulfanyl]acetamido}-4H,5H,6H-cyclopenta[b]thiophene-3-carboxamide    MolPort-009-869-122

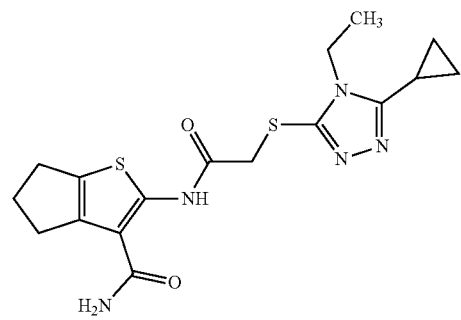 [SMILES: CCn1c(SCC(=O)Nc2sc3c(c2C(N)=O)CCC3)nnc1C1CC1]

N-benzyl-2-[2-({4-methyl-5-[(phenylcarbamoyl)methyl]-4H-1,2,4-triazol-3-yl}sulfanyl)acetamido]-4,5,6,7-tetrahydro-1-benzothiophene-3-carboxamide    MolPort-002-272-952

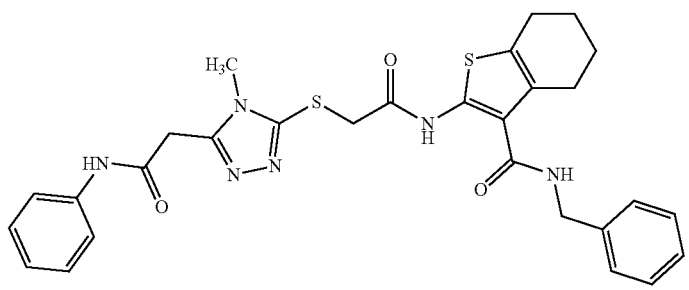 [SMILES: Cn1c(CC(=O)Nc2ccccc2)nnc1SCC(=O)Nc1sc2c(c1C(=O)NCc1ccccc1)CCCC2]

TABLE 1-continued

Mitofusin agonist peptido-mimetics

| | | |
|---|---|---|
| 2-{[(3aS,6aS)-5-{5,7-dimethylpyrazolo[1,5-a]pyrimidine-2-carbonyl}-octahydropyrrolo[3,4-b]pyrrol-1-yl]methyl}-1-methyl-1H-imidazole | MolPort-023-329-196 | 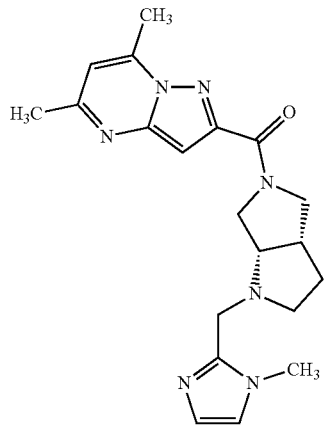 [SMILES: Cc1cc(C)n2nc(C(=O)N3C[C@@H]4CCN(Cc5nccn5C)[C@@H]4C3)cc2n1] |

TABLE 2

Mitofusin agonist lower potency compounds

| | | |
|---|---|---|
| 2-{2-[(4-benzyl-5-cyclopropyl-4H-1,2,4-triazol-3-yl)sulfanyl]propanamido}-4H,5H,6H-cyclopenta[b]thiophene-3-carboxamide | MolPort-004-201-235 | 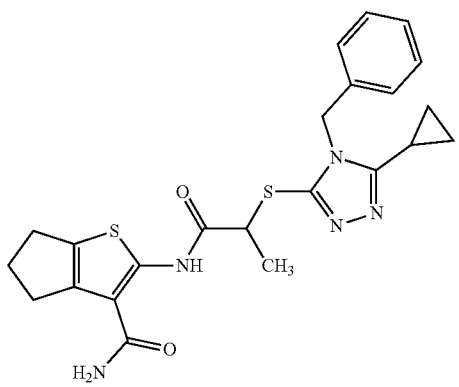 [SMILES: CC(Sc1nnc(C2CC2)n1Cc1ccccc1)C(=O)Nc1sc2c(c1C(N)=O)CCC2] |
| 2-{2-[(4-phenyl-4H-1,2,4-triazol-3-yl)sulfanyl]propanamido}-4H,5H,6H-cyclopenta[b]thiophene-3-carboxamide | MolPort-005-522-674 | 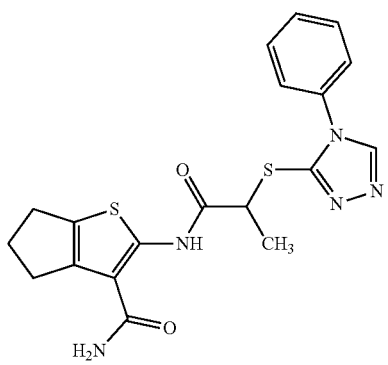 [SMILES: CC(Sc1nncn1-c1ccccc1)C(=O)Nc1sc2c(c1C(N)=O)CCC2] |

Figure 6A:
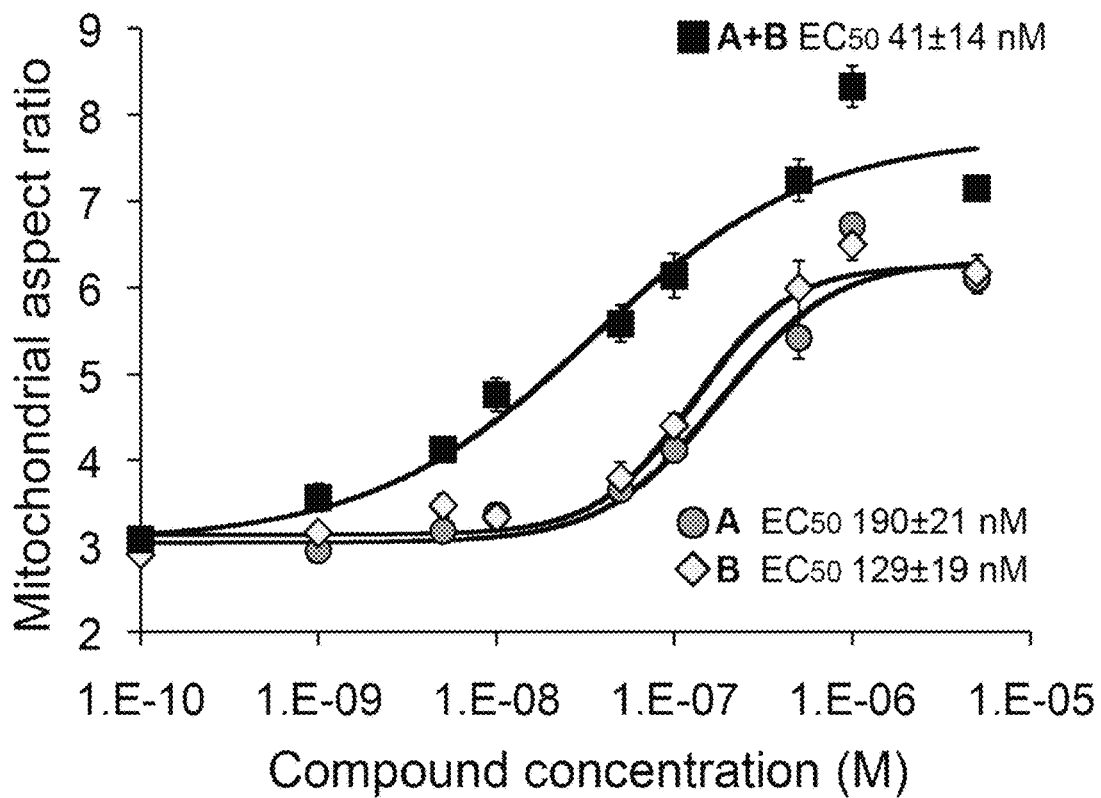
FIG. 6A, FIG. 6B, FIG. 6C and FIG. 6D are a series of line and bar graphs, images, and structures showing compounds A and B synergistically promote mitochondrial fusion by acting upon different mitofusin conformational states and displaying the EC50 values of compounds A and B and a key phosphorylation site in Mfn2.

EC50 values for mitochondrial elongation by compounds A and B were 100-200 nM, which is comparable to the prototype mini-peptide (Franco et al 2016 Nature 540: 74-79). When added in equal amounts, compounds A and B synergistically promoted mitochondrial elongation, with a combined EC50 of ~40 nM and a ~25% greater maximal increase in mitochondrial aspect ratio (P<0.05 vs each compound alone; see e.g., FIG. 6A).

The mechanism for compound synergy was determined to be preferential binding of A and B to different phosphorylated forms of Mfn1 and Mfn2 (see e.g., FIG. 6B, FIG. 6C): When Ser378 is replaced by non-phosphorylatable alanine (A), cysteine (C), asparagine (N), or glycine (G) mini-peptide activity is abrogated because alternate salt-bridge formation provokes α-helix destabilization of replacement of His380 by Leu379 and the HR1-HR2 interface (see e.g., FIG. 6D). Because compound B is hydrophobic (phenyl) at one end and polar (carboxamide) at the other it mimics side chains presented by Val372/Met376/His381 (see e.g., FIG. 1, top panel). By contrast, compound A is hydrophobic (phenyl and cyclohexyl) at both ends, which mimics the side chains presented to the Mfn2 hydrophobic core after the conformational shift to Val372/Met376/Leu379.

Figure 6B:
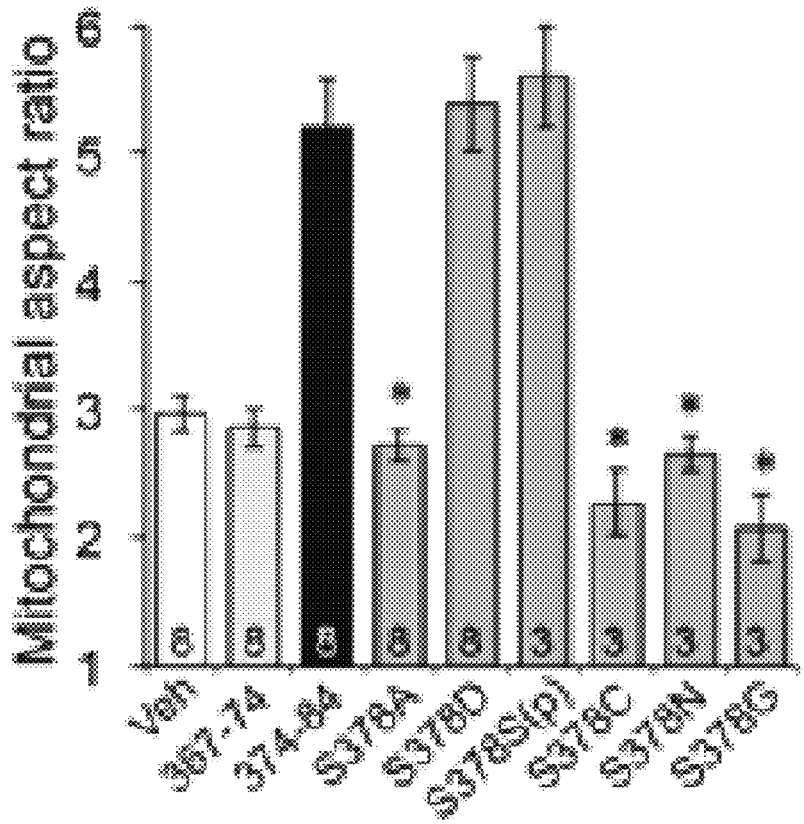
Figure 6C:
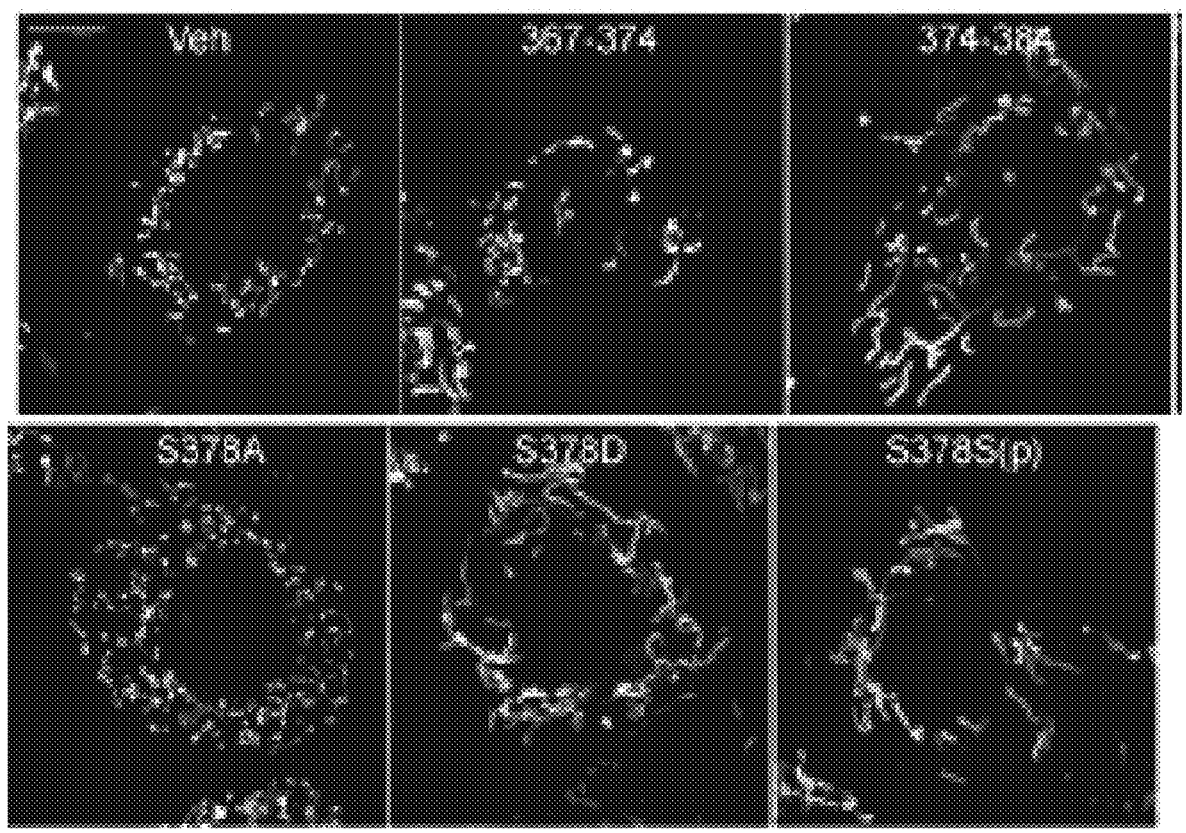
Figure 6D:
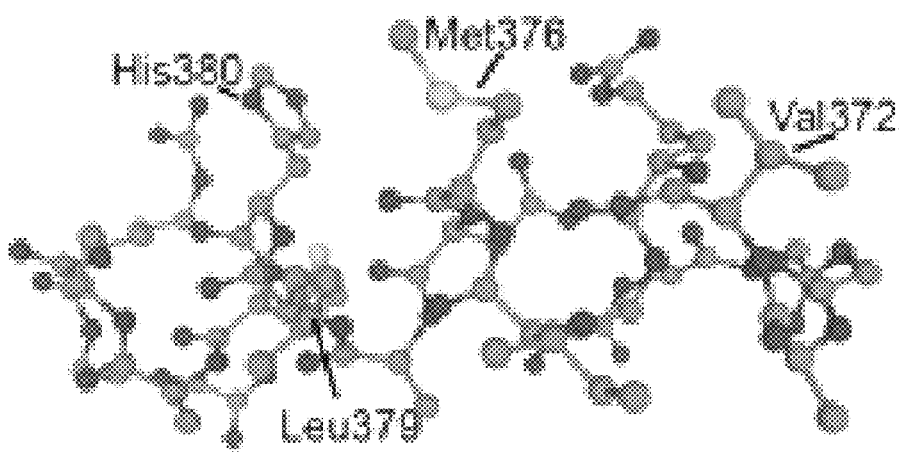
Figure 6E:
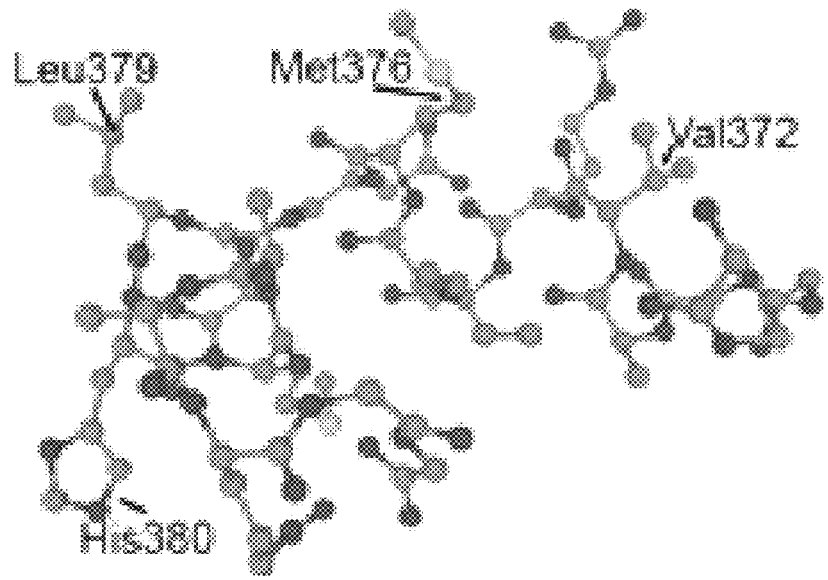

Partial unwinding of the HR1 alpha helix and shifting of Met 380 for His381 at the HR1-HR2 interacting interface is controlled by the phosphorylation status of Ser378 (see e.g., FIG. 6B). Thus, synergistic effects of compounds A and B are likely the consequence of their preferential binding to different phosphorylated forms of Mfn1 and Mfn2.

Figure 7A:
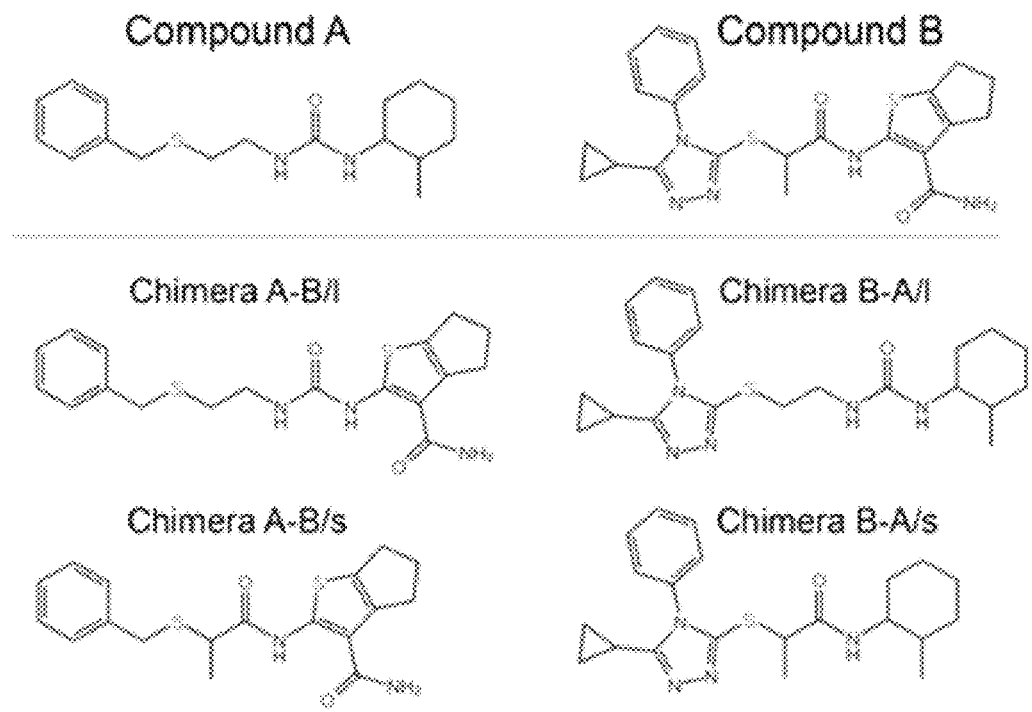
FIG. 7A, FIG. 7B and FIG. 7C are a series of structures and graphs showing the evaluation of chimeric small molecule mitofusin agonists. (A) Structures of compounds A and B and their chimeras. (B) Dose-response of compounds in (A) to promote mitochondrial fusion (increase in aspect ratio) in MFN2-deficient MEFs. Data for compounds A and B and chimera B-A/I in FIG. 11B are re-plotted here for comparison. (C) Comparison of EC50 values calculated from studies in panel B. p values are from ANOVA with Tukey's test.
Figure 7B:
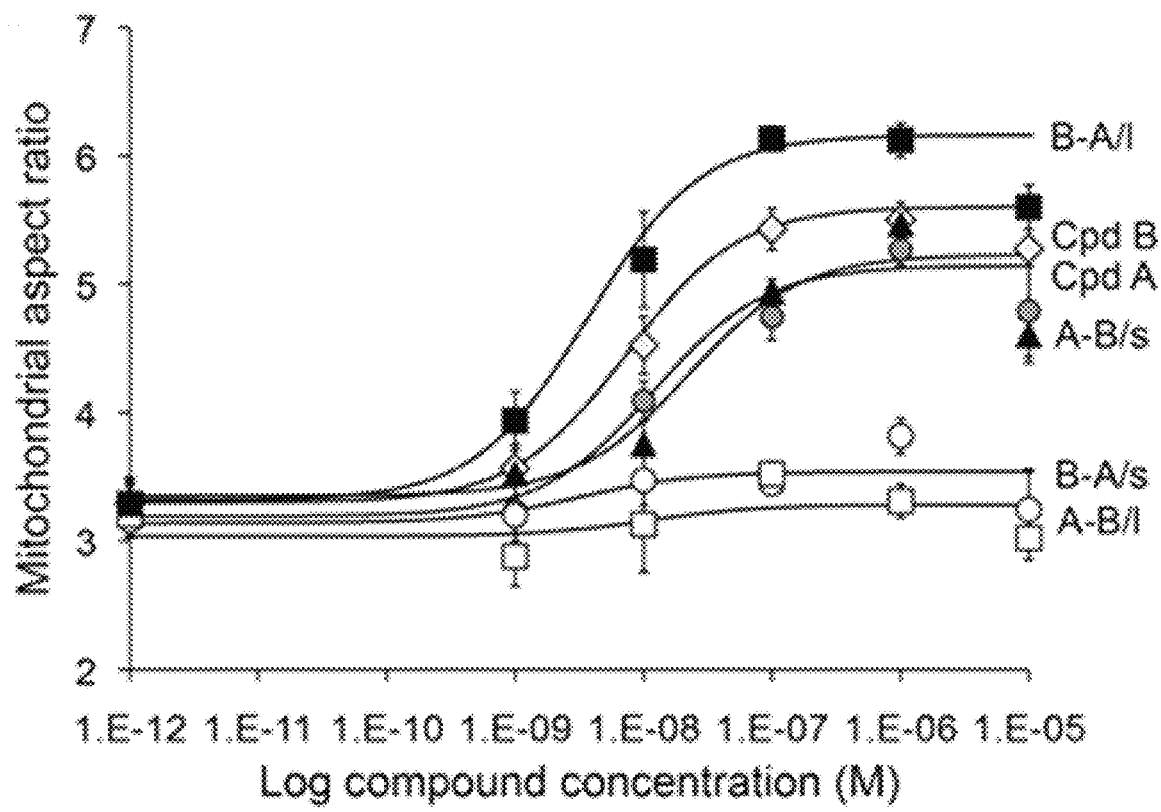
Figure 7C:
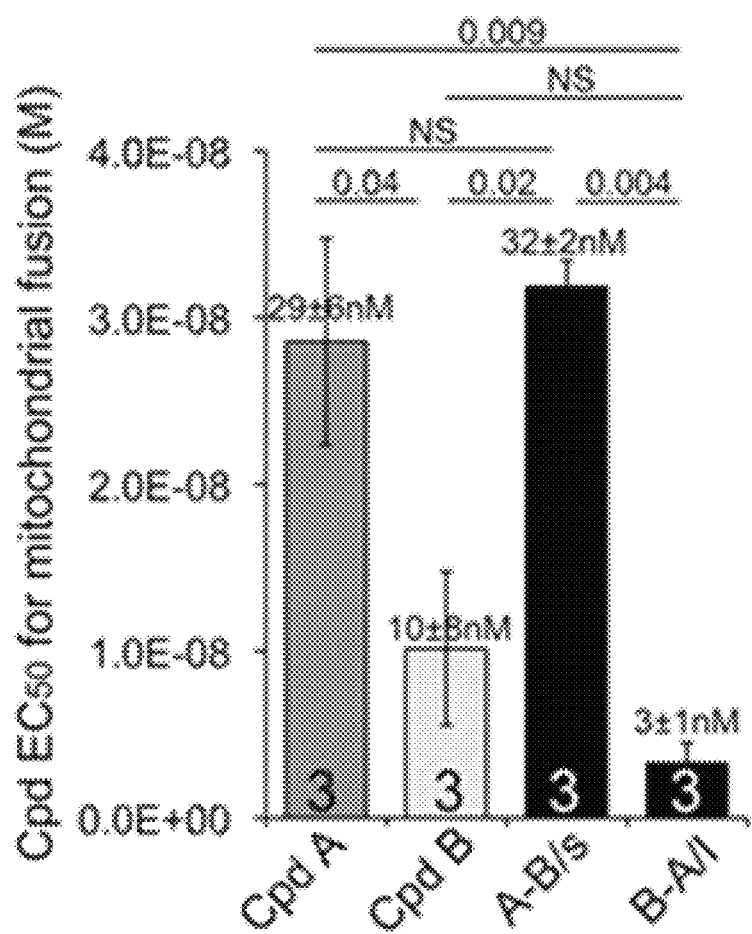
Figure 8A:
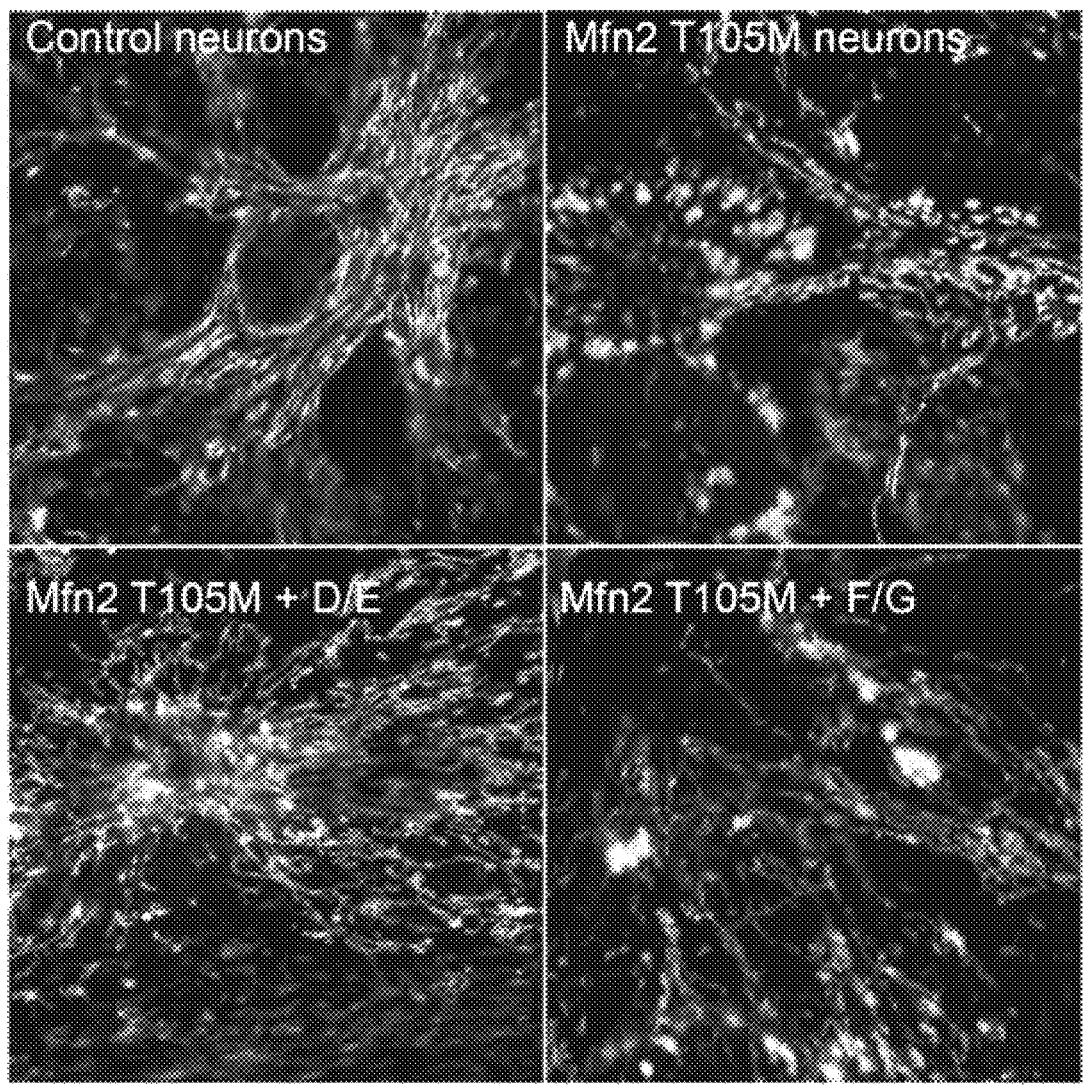
FIG. 8 is a series of immunofluorescence images from cultured mouse neurons. Neurons with the human Charcot Marie Tooth disease mutation, Mfn2 T105M, exhibited increased mitochondrial fragmentation and neuronal pathology compared to control. Note how administration of compounds repaired the defects in mutant neurons (see e.g., Example 2).
Figure 8B:
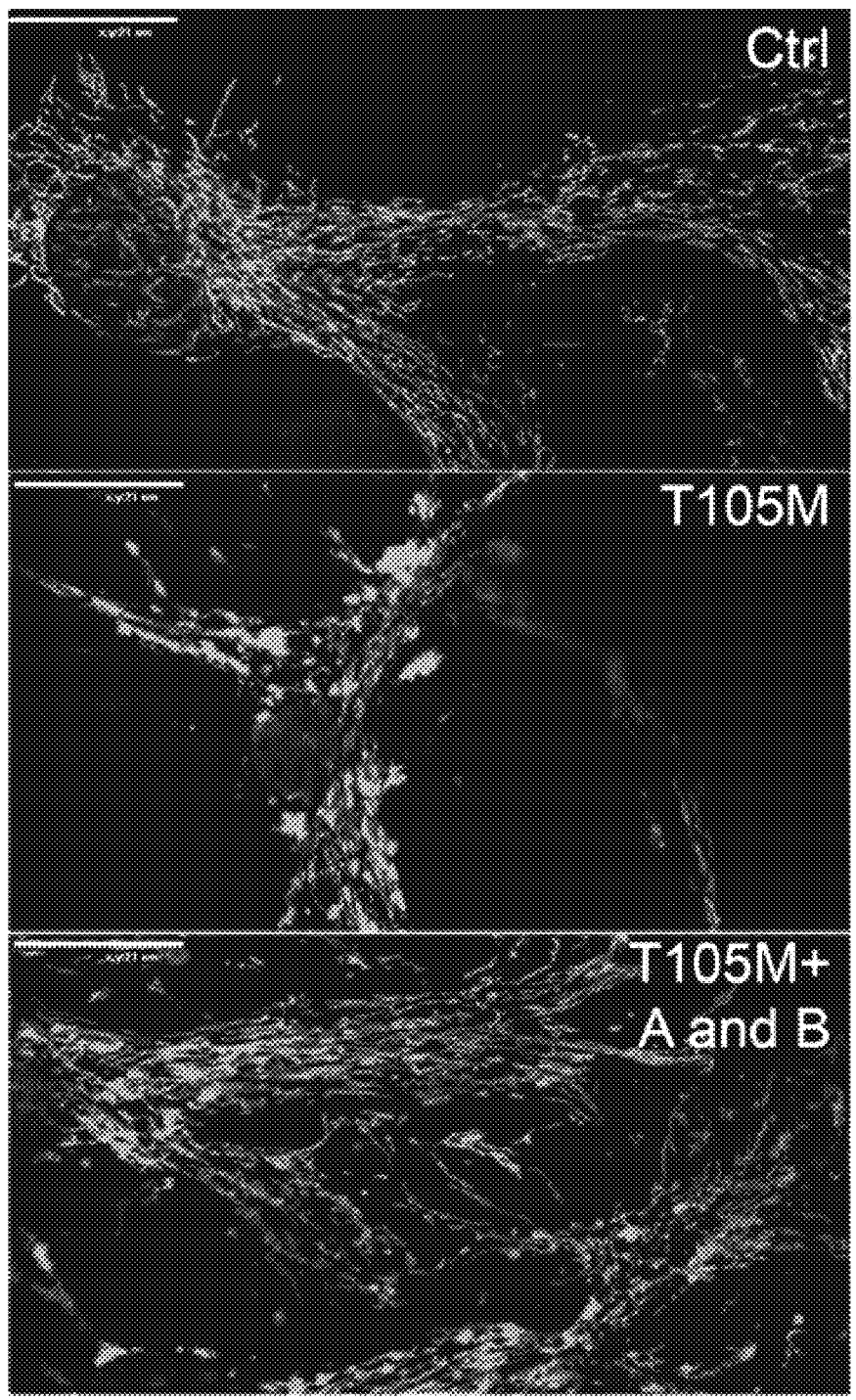
Figure 9A:
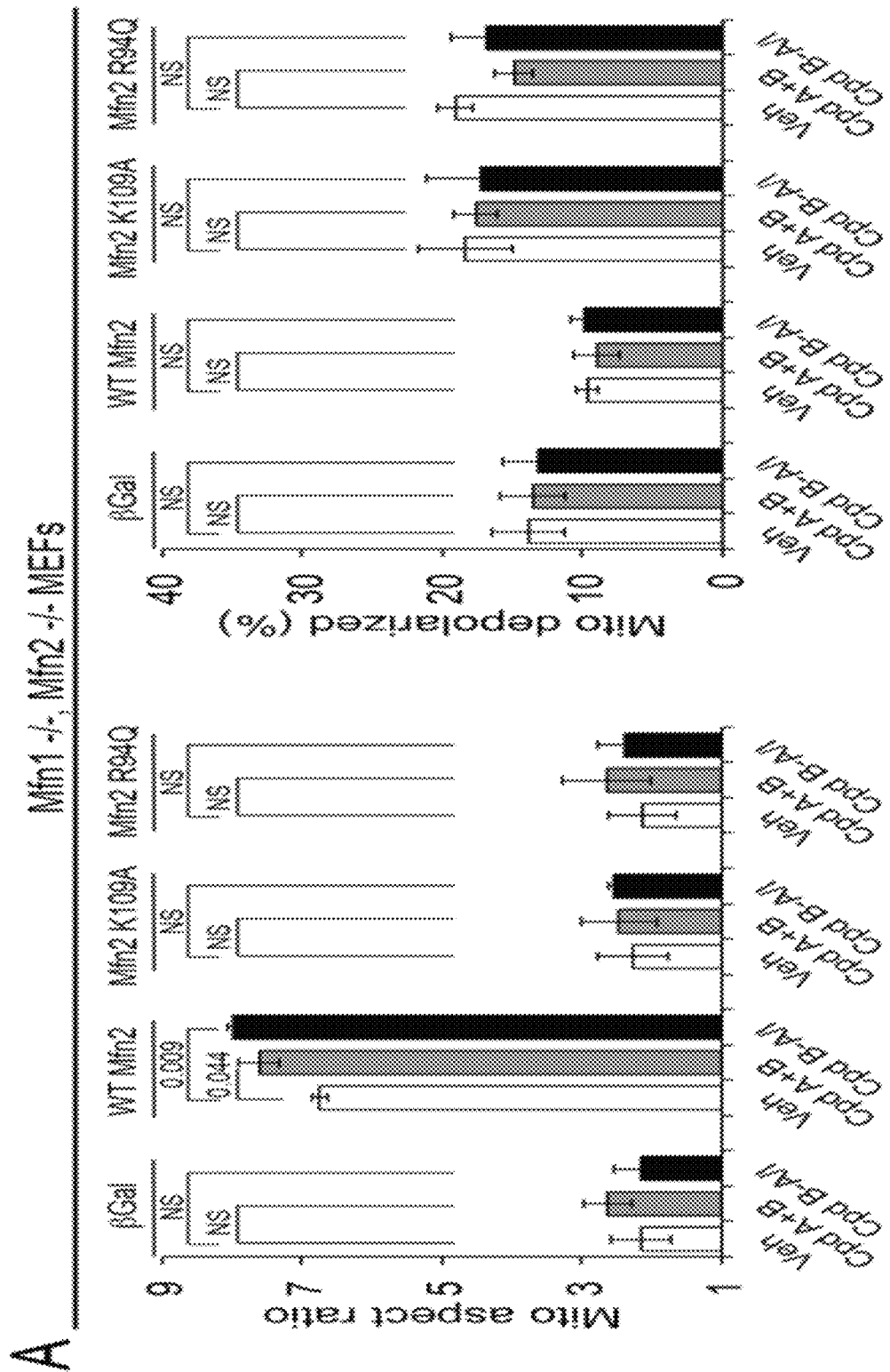
FIG. 9A, FIG. 9B, FIG. 9C, FIG. 9D, and FIG. 9E are a series of bar graphs and images showing mitofusin agonists correct mitochondrial damage induced by nonfunctioning MFN2 mutants by activating endogenous mitofusins. (A) Effects of mitofusin agonists in mitofusin-deficient cells expressing WT or mutant MFN2 (n=3 each). (B) Same as (A) in $MFN1^{+/+}$, $MFN2^{-/-}$ cells. (C) Representative mitochondrial pathology in cultured neonatal mouse neurons expressing MFN2 R94Q and correction by mitofusin agonists. Immunoblot showing MFN2R94Q expression in individual mouse pups is above. Scale bars are 21 mm; expanded views are from white squares. (D) Group data for studies in (C). (E) Results of similar studies in cultured neonatal mouse neurons expressing MFN2 T105M.
Figure 9B:
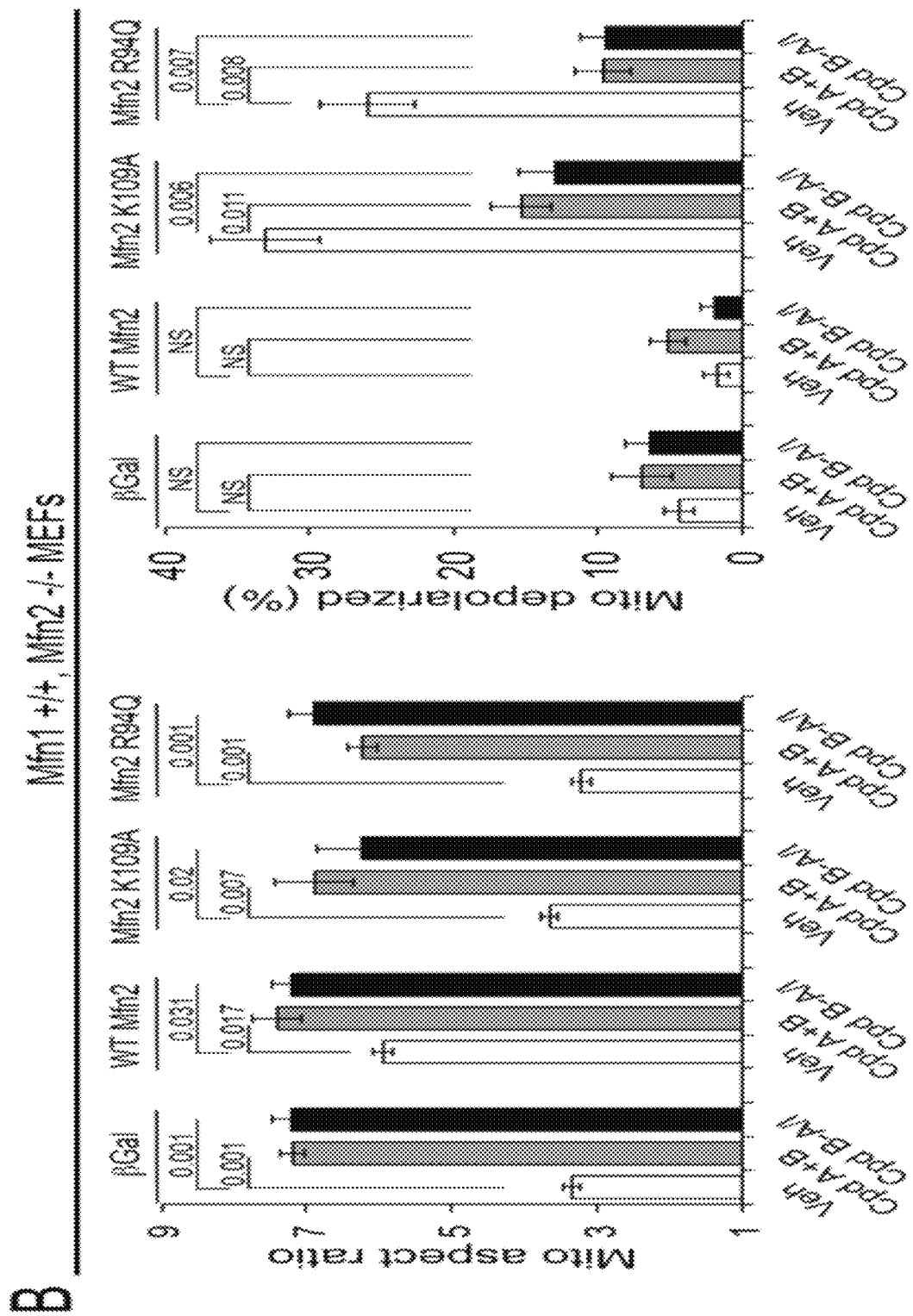
Figure 9C:
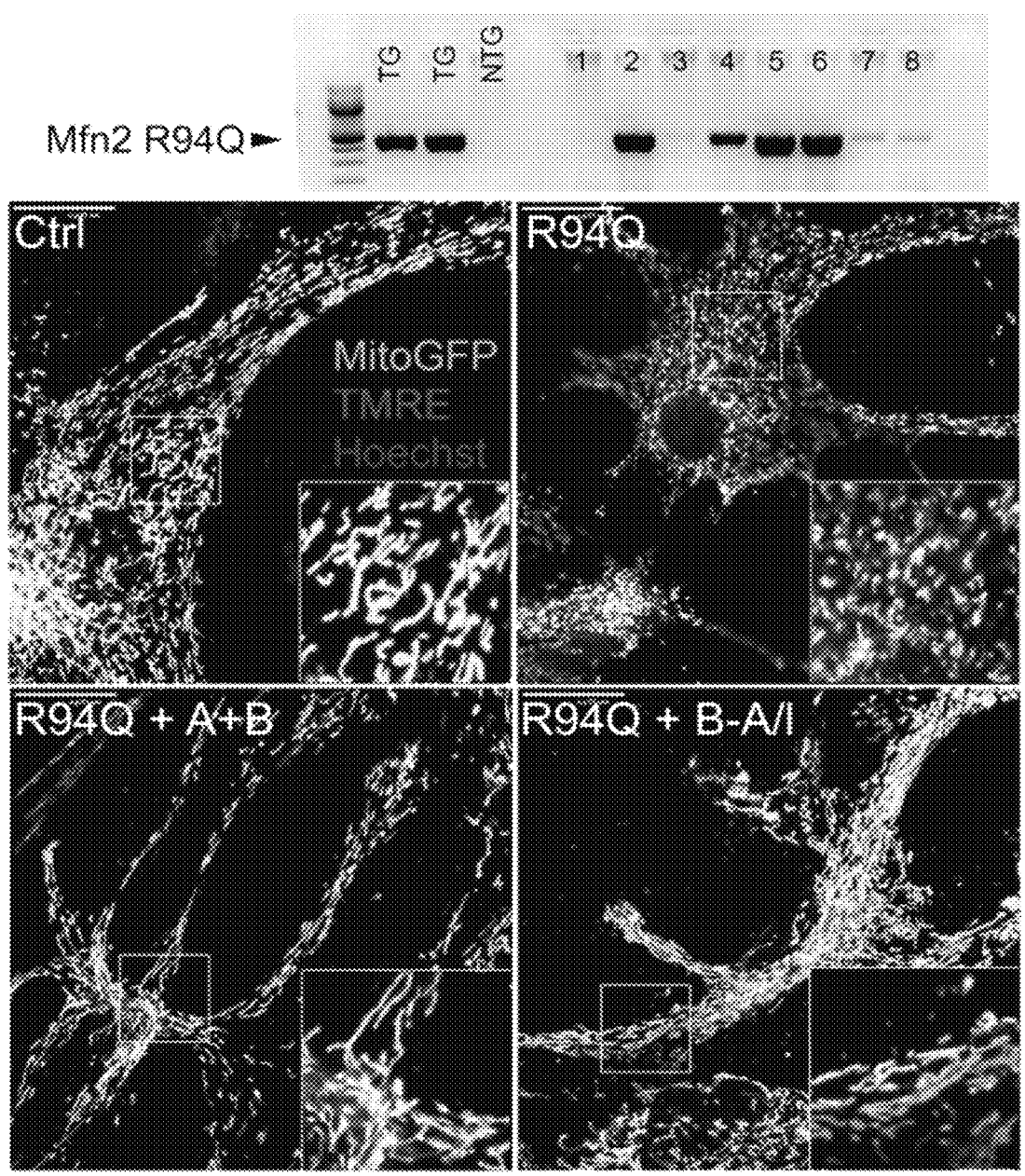
Figure 9D:
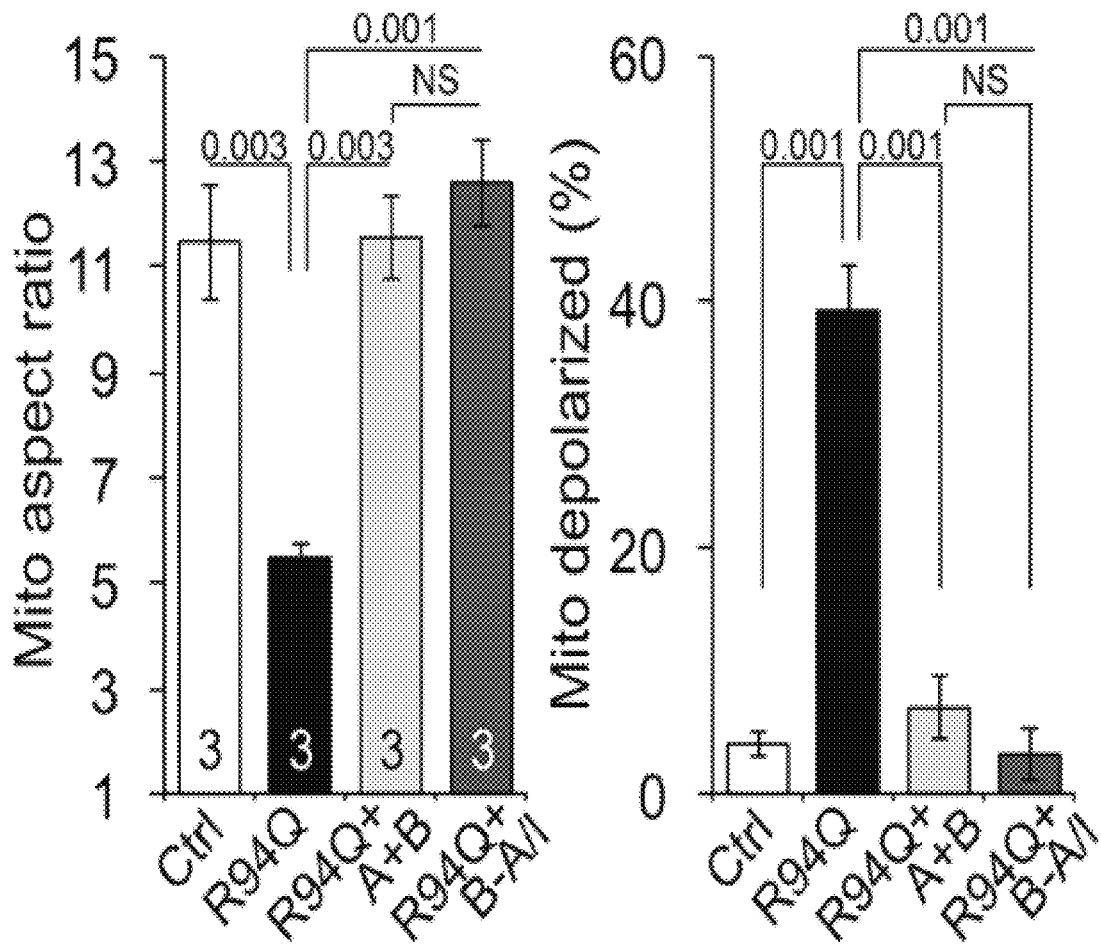
Figure 9E:
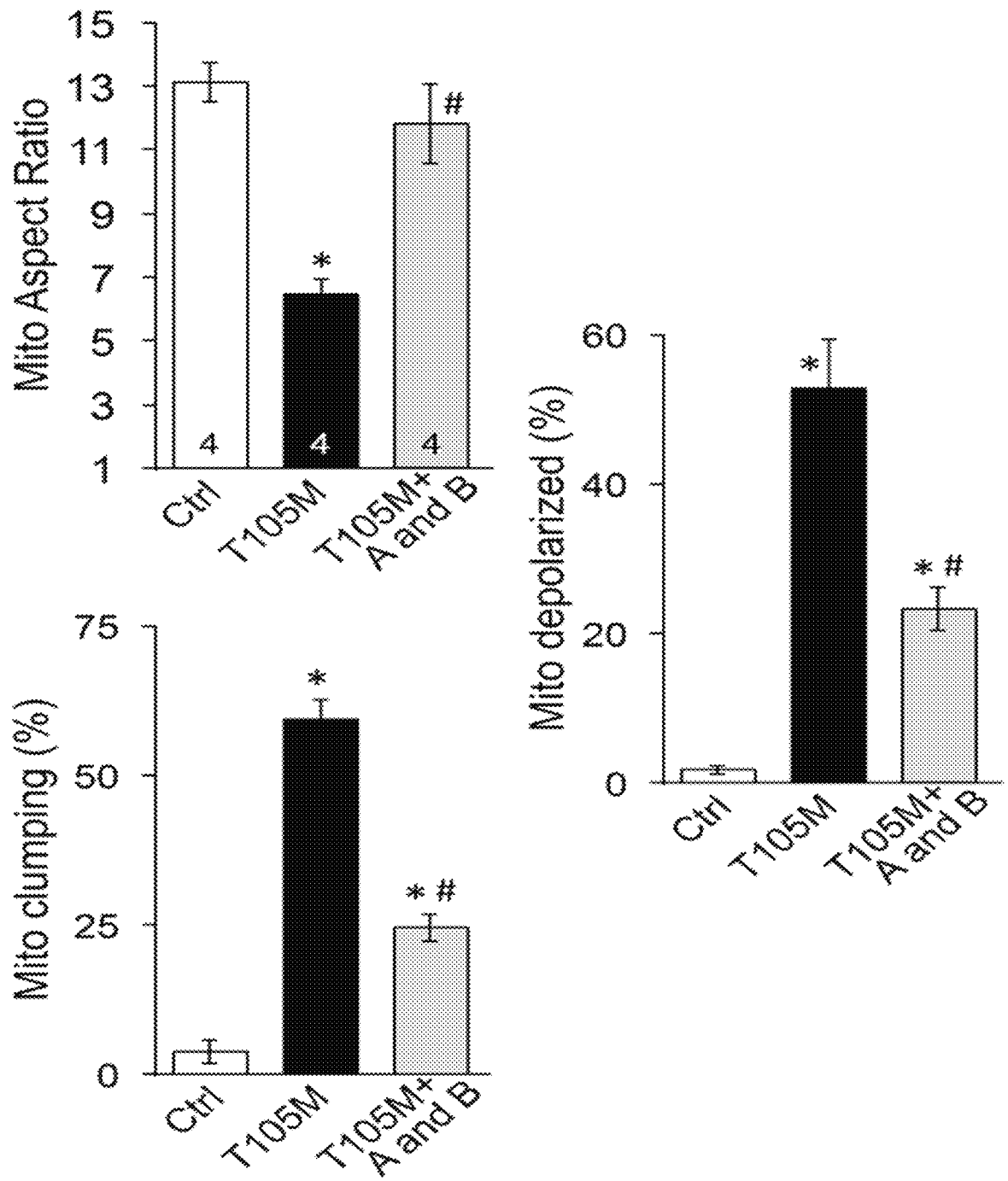

The efficacy and synergy of the prototype Mfn agonist peptido-mimetics (small molecule mitochondrial fusion activators) were enhanced and their specificity modified by engineering novel chimeric compounds combining optimal features of the parental molecules (see e.g., FIG. 7, TABLE 1, TABLE 2). The ability of these compounds to repair mitochondrial fragmentation and neuronal pathology conditionally expressing a human Charcot Marie Tooth disease mutation, Mfn2 T105M, was demonstrated (see e.g., FIG. 8, FIG. 9).

Example 3: HR1-HR2 Competition Binding Assay for Screening and Evaluating Mfn Peptido-Mimetic Targeting and Binding Affinity The following example describes a HR1-HR2 competition binding assay for screening and evaluating Mfn peptido-mimetic targeting and binding affinity.

Figure 10:
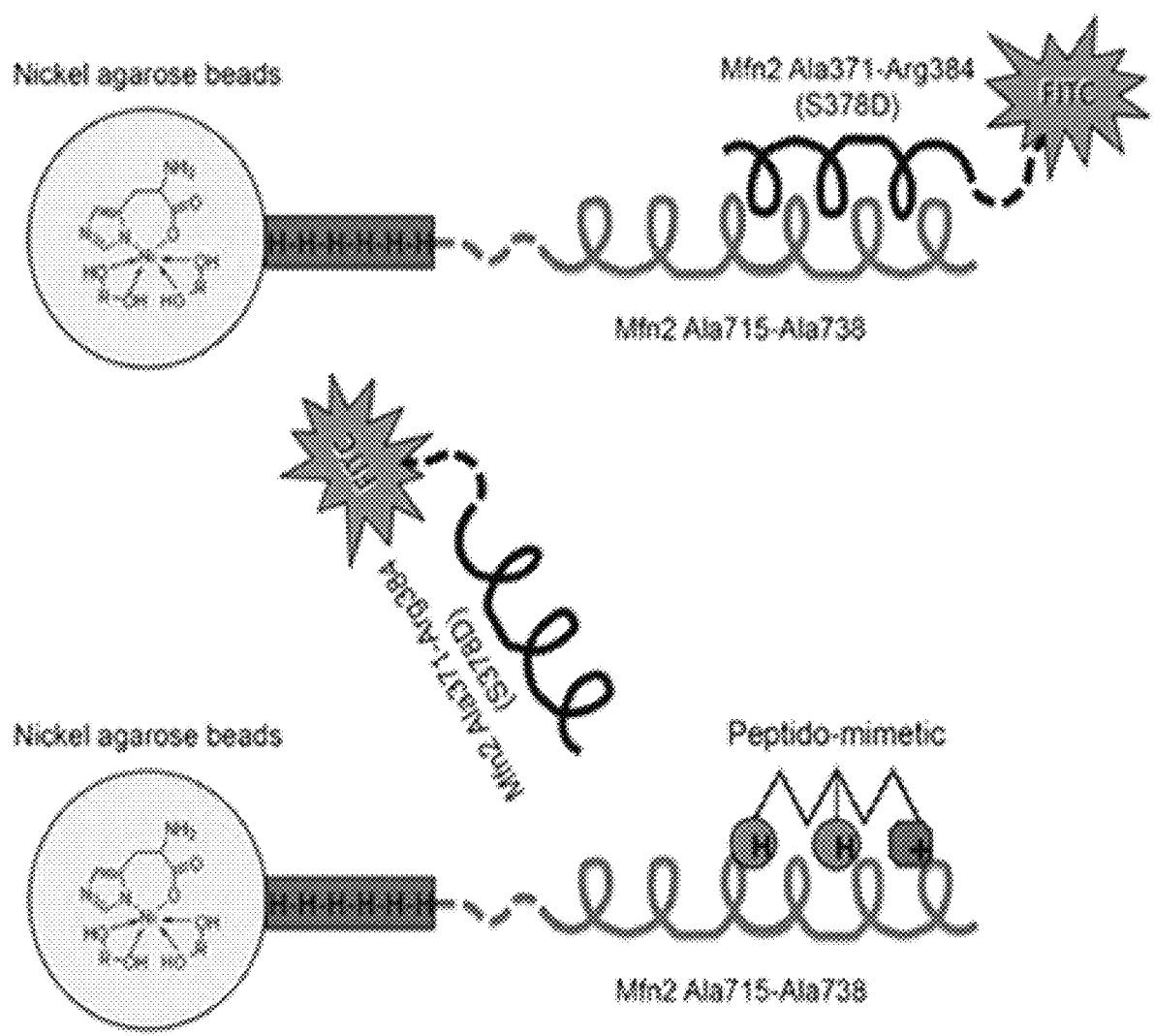
FIG. 10 is illustration showing Mfn agonist peptide binding and its displacement by compounds A and B. The schematic demonstrates components of the system, depicting FITC labeled peptide binding to its immobilized target (top) and displacement of the FITC peptide by competing small molecule.
Figure 11A:
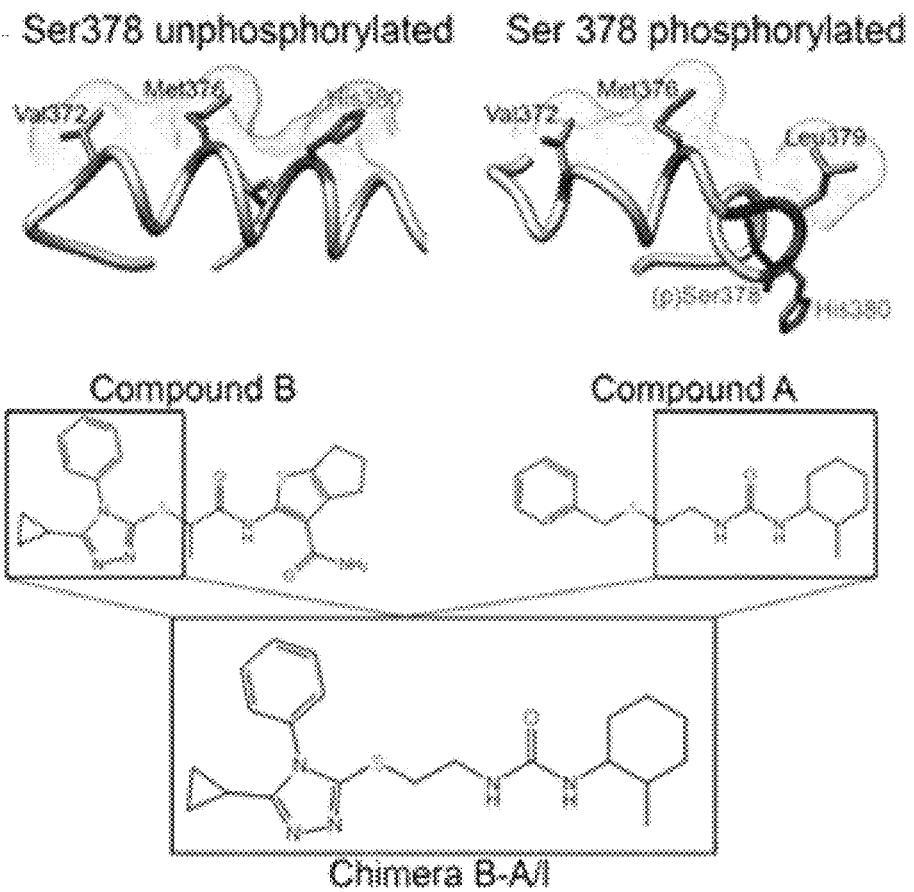
Figure 11B:
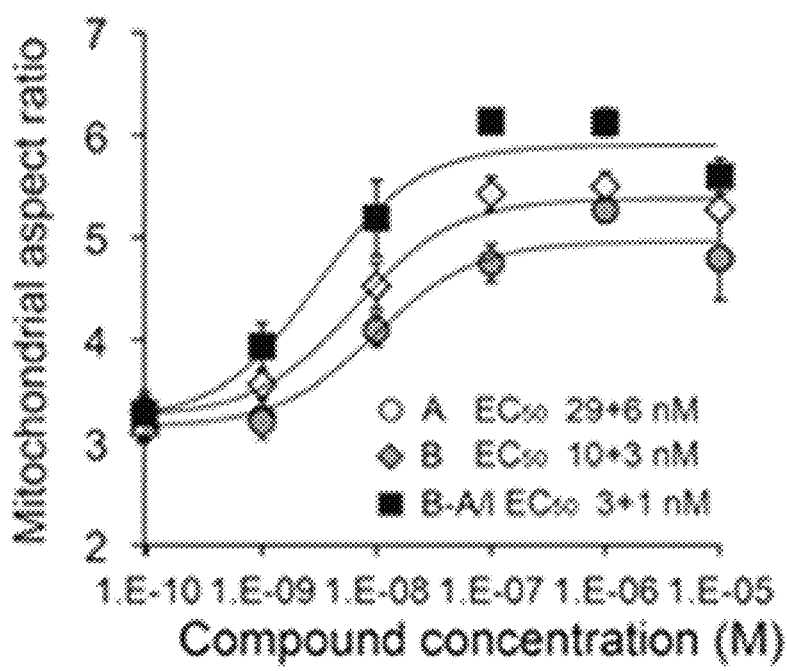
Figure 11C:
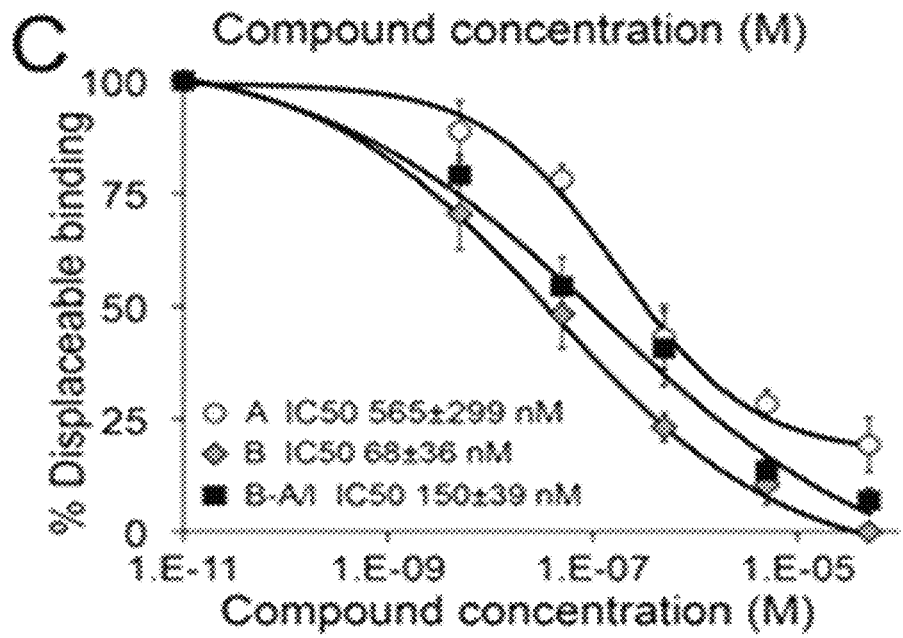
Figure 11D:
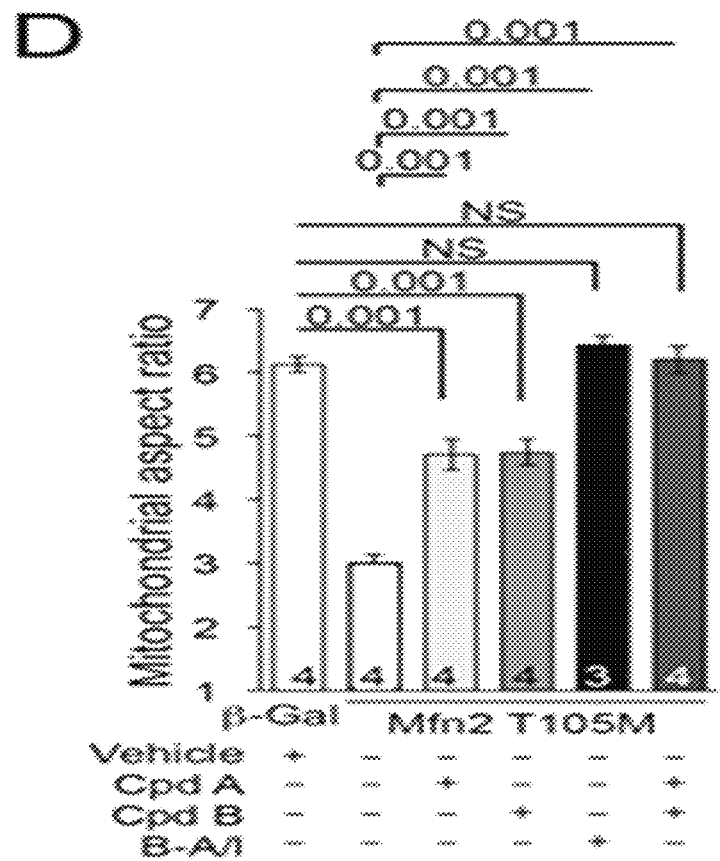
Figure 11E:
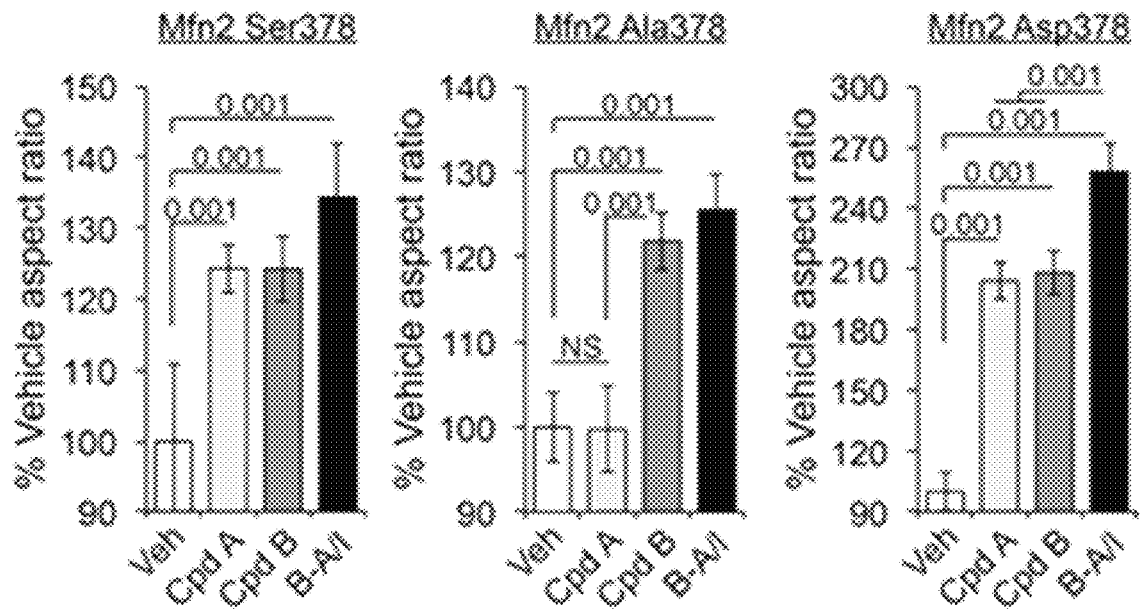
Figure 11F:
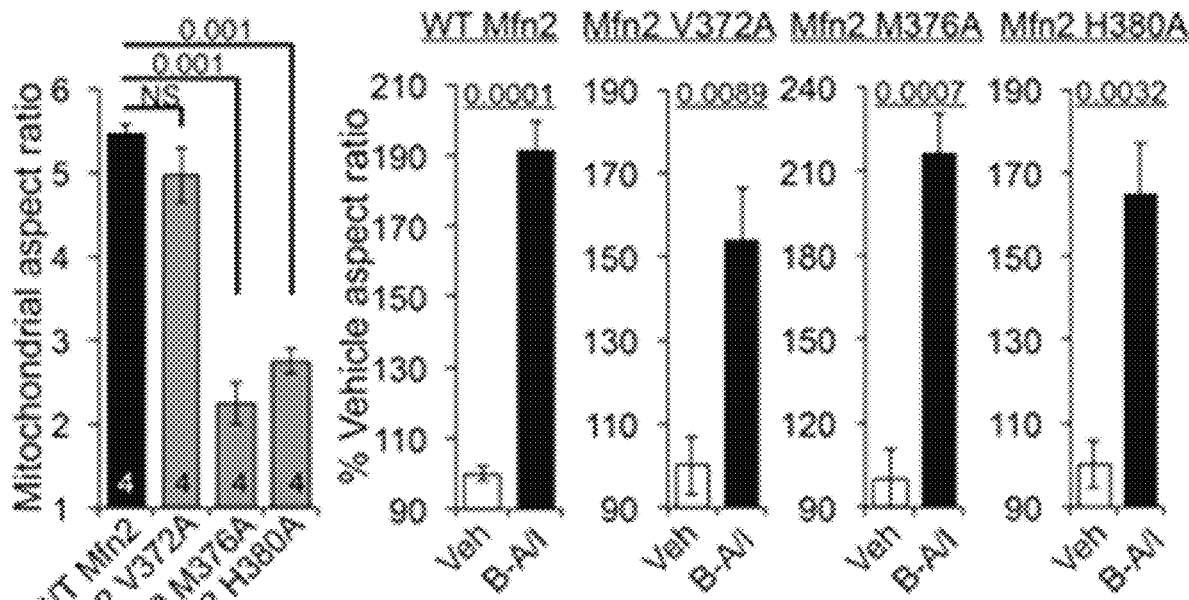

The Mfn-derived fusion-promoting and -inhibiting mini-peptides (simulated to obtain the chemical Mfn agonists in TABLE 1 and TABLE 2) were modified from amino acid heptad repeats (HR) in the HR1 domain and predicted to interact with their counterparts in the carboxyl terminus HR2 domain within the Mfn stalk region (see e.g., FIG. 1, top panel). A high-throughput binding assay was designed whereby the target HR2 peptide sequences, modified to include amino terminal 6×His tags and Gly linkers, were bonded to Ni-chelate resin (20 µg/ml) and used as immobilized "receptor" for amino-FITC-tagged Mfn2 374-384 (agonist ligand) in which the Ser analogous to Ser378 was replaced with Asp to confer the negative charge essential for activity. For antagonist studies the ligand was amino-FITC-tagged Mfn2 406-418. The FITC peptide ligands are suspended at 1 mM in 30% DMSO, 70% water (to minimize spontaneous aggregation) and diluted into binding buffer (de-ionized water) to a final concentration of 25 µM in the presence or absence of competing compound. Dose-dependent loss of resin-bound FITC signal (485 nm excitation/538 nm emission) measured in a 96 well spectrofluorometer represents binding of compound to its HR2 target (see e.g., FIG. 10, FIG. 11). Either the ligand peptide or the receptor peptide can be modified to represent mutations, variations, or posttranslational modifications of Mfn2. Target peptide-bound resin pre-incubated with FITC ligand in column form can be used for high throughput screening by monitoring FITC in the eluate.

Amino acid sequences for Mfn agonist peptido-mimetic binding assay components:

SEQ ID NO: 1: (NH3) HHHHHH-GGGG-AAMNKKI-EVLDSLQSKAKLLRNKA-GG (COOH) (receptor)

SEQ ID NO: 2: (NH3) FITC-GGGG-AVRGIMDDLH-MAAR-GG (COOH) (amino FITC labeled ligand) Amino acid sequences for Mfn antagonist peptido-mimetic binding assay:

SEQ ID NO: 3: (NH3) HHHHHH-GGGG-LHAFTG-SLEQQVQHSCNSG-GG (COOH) (receptor)

SEQ ID NO: 4: (NH3) FITC-GGGG-KQLEL-LAQDYKLRIKQ-GG (COOH) (amino FITC labeled ligand)

The system can be modified to contain the respective Mfn1 sequences if specific interrogation of both Mfn isoforms is desired.

Example 4: A Fret Assay for Screening and Evaluating Mfn Peptido-Mimetic Effects on Mfn Conformation The following examples describe a FRET assay for screening and evaluating Mfn peptido-mimetic effects on Mfn conformation.

Figure 12A:
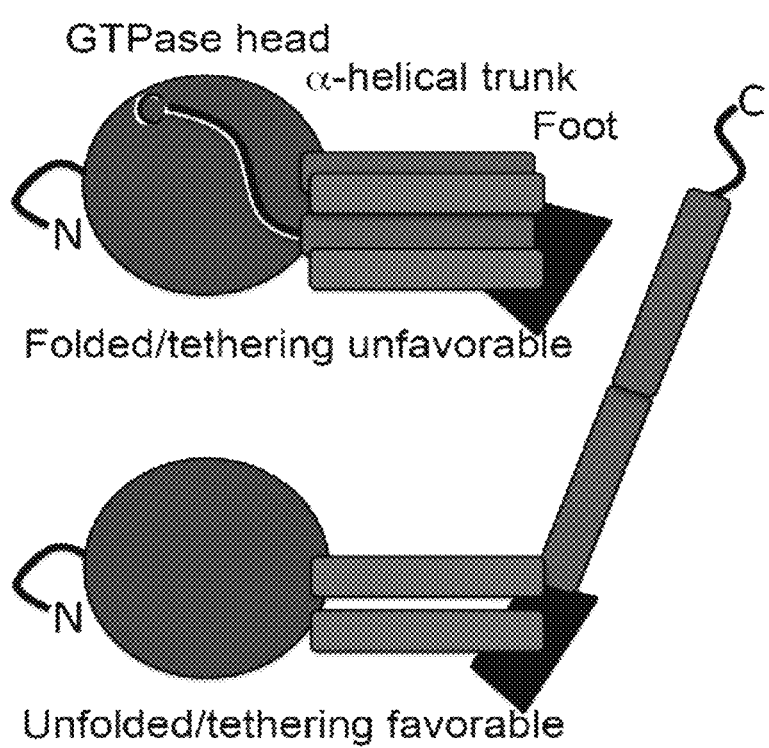
FIG. 12A, FIG. 12B and FIG. 12C are a series of drawings that diagram the working model of Mfn2 conformation and function and Mfn folding/unfolding measured by FRET.
Figure 12B:
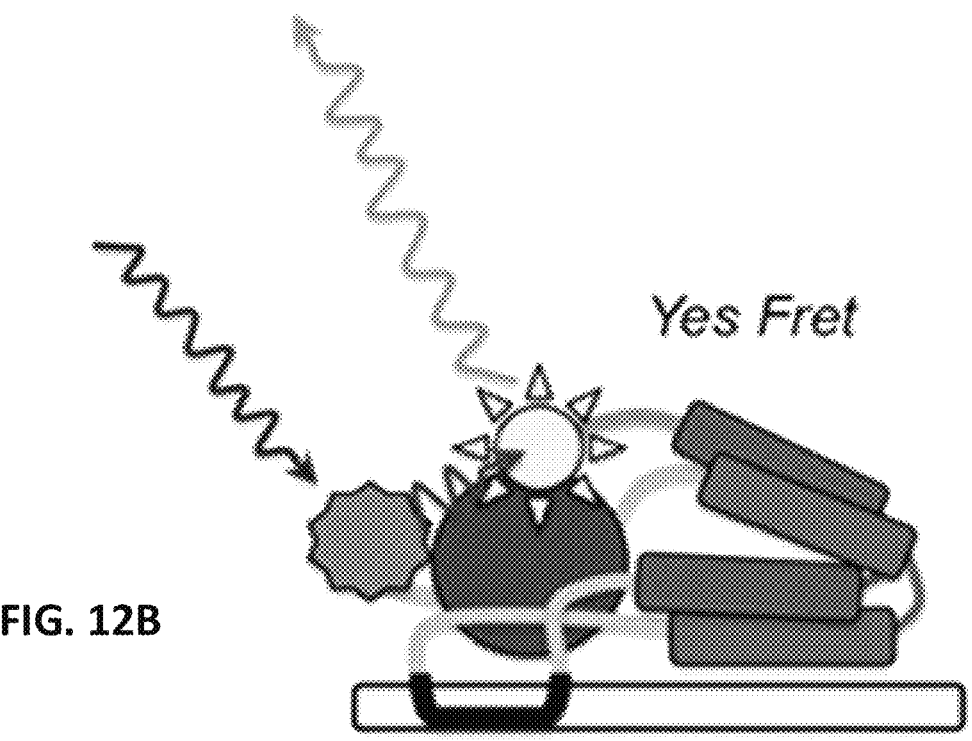

The small molecules described herein enhance mitochondrial fusion by destabilizing the folded conformation of Mfn1 or Mfn2, thus promoting extension of HR2 carboxyl termini that mediate mitochondrial tethering by interacting in trans with similarly extended carboxyl termini of Mfn1 or Mfn2 on neighboring mitochondria (see e.g., FIG. 12A). The Forster resonance energy transfer (FRET) assay was designed to screen for and evaluate candidate agents of any chemical class, or molecules with specific alternate compositions, including large libraries of synthetic or natural compounds.

The mechanism by which Mfn2 HR1 mini-peptides regulate Mfn1 and Mfn2 activity is by directing Mfns into either an unfolded active or folded inactive conformation, as demonstrated by a change in FRET signal of Mfn2 labeled with amino-terminal mCerulean and carboxyl terminal mVenus. This FRET system was limited by low transfection efficiency as a plasmid, an unacceptably poor signal to noise ratio, and the confounding influences of Mfn GTPase activity.

Figure 12C:
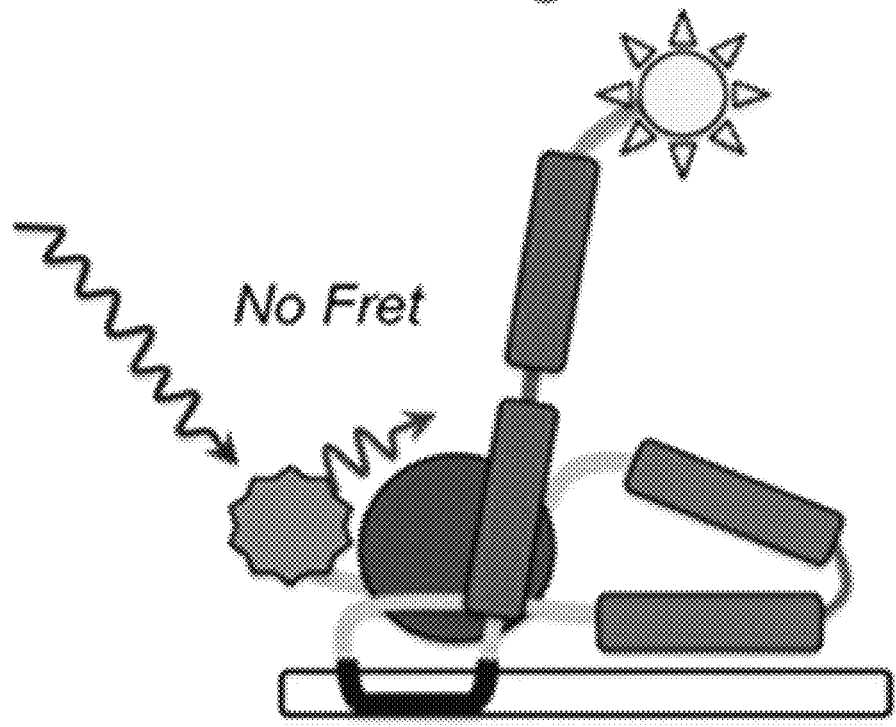
Figure 12D:
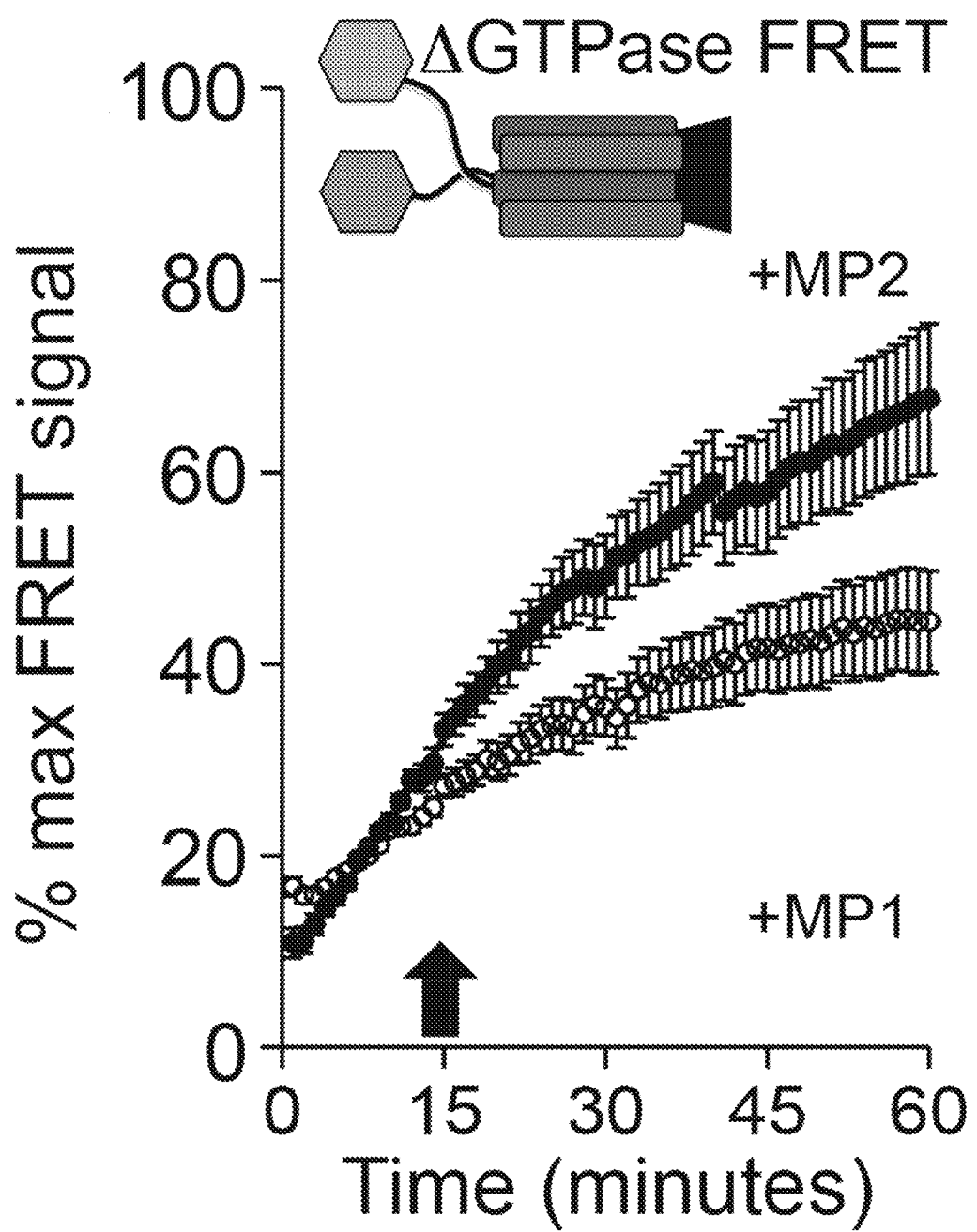
Figure 13A:
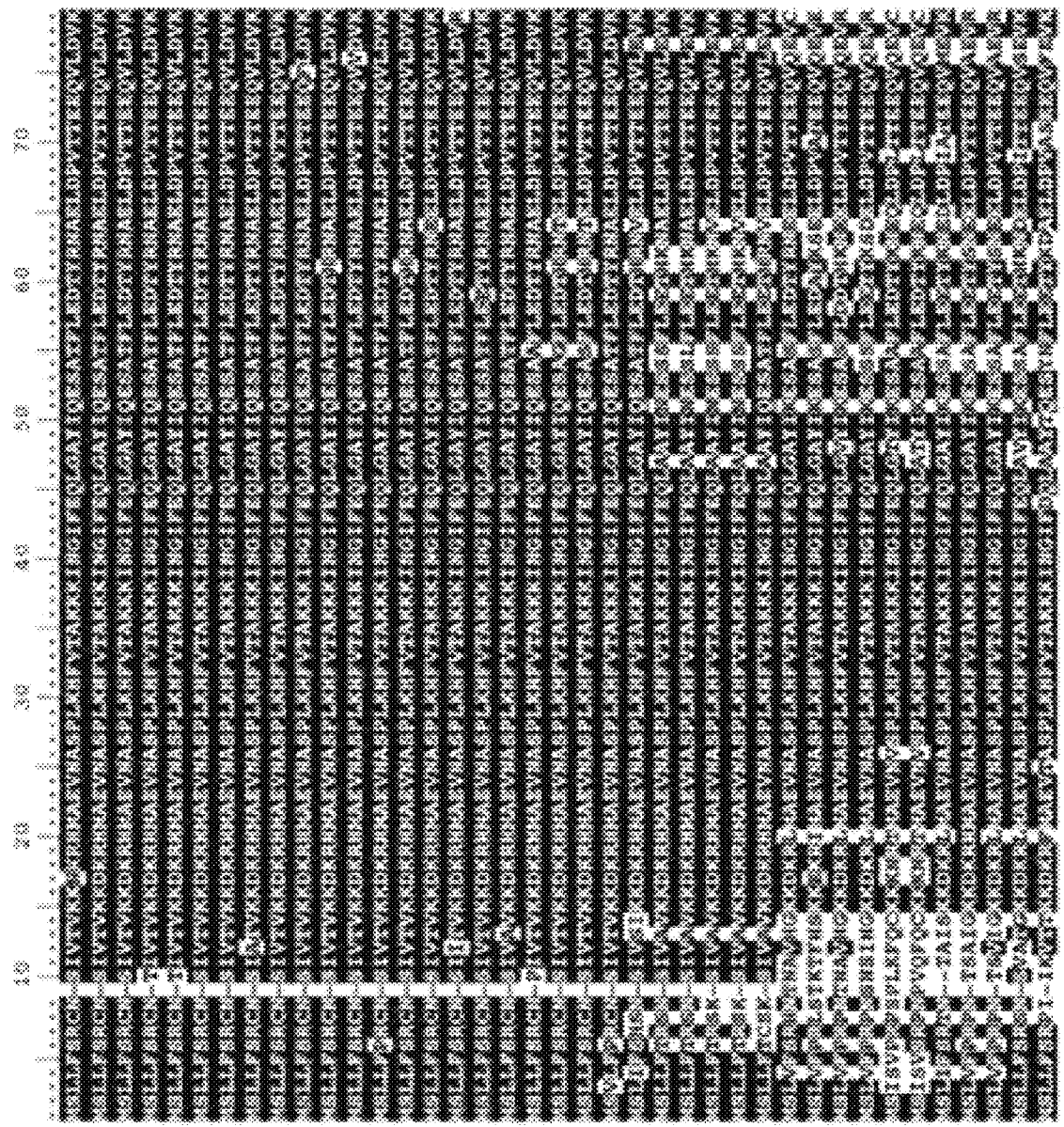
FIG. 13 shows a multi-species alignment of MFN2 amino acid sequence. Black highlighting shows identity with human MFN2 protein.
Figure 13B:
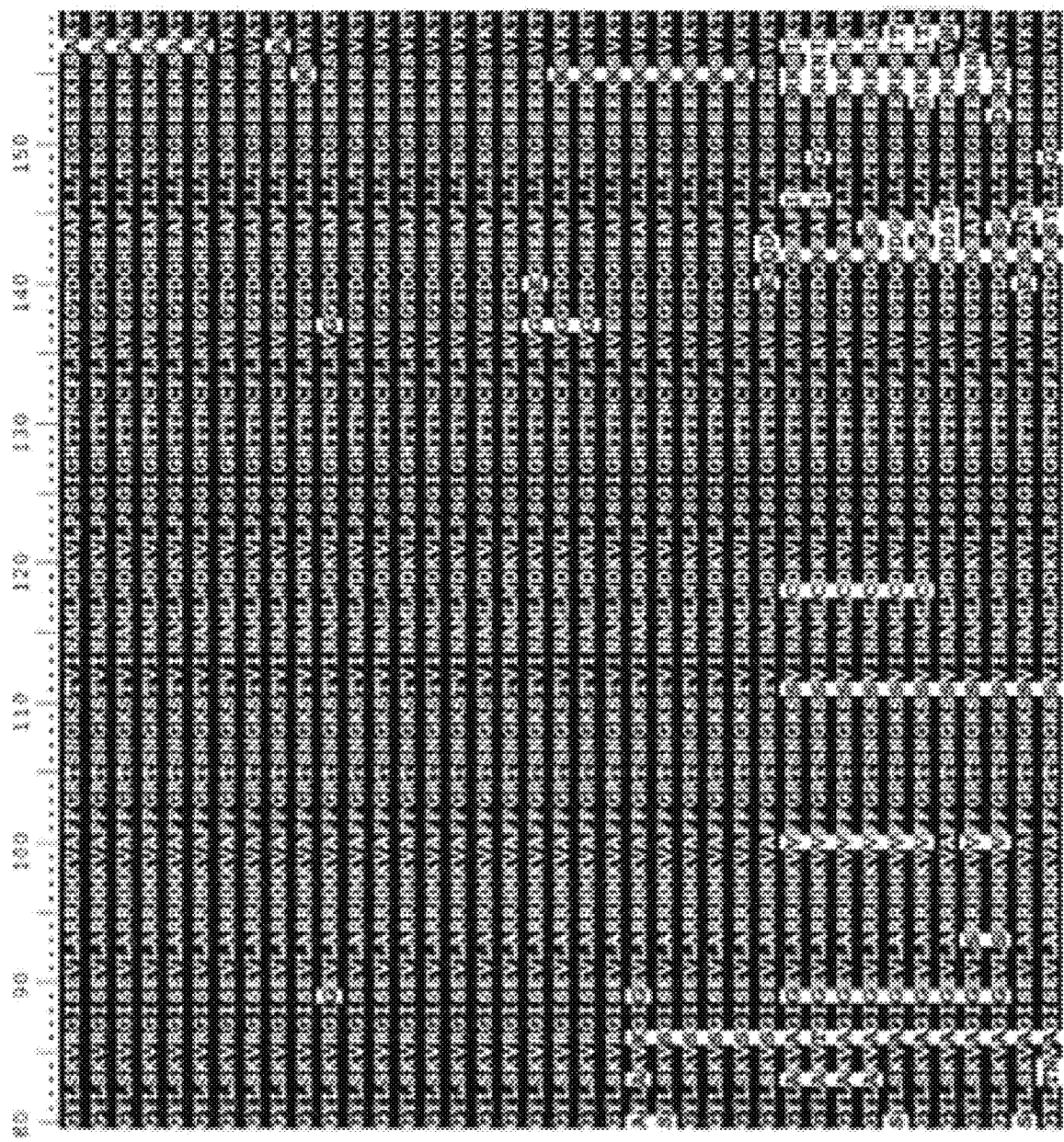
Figure 13C:
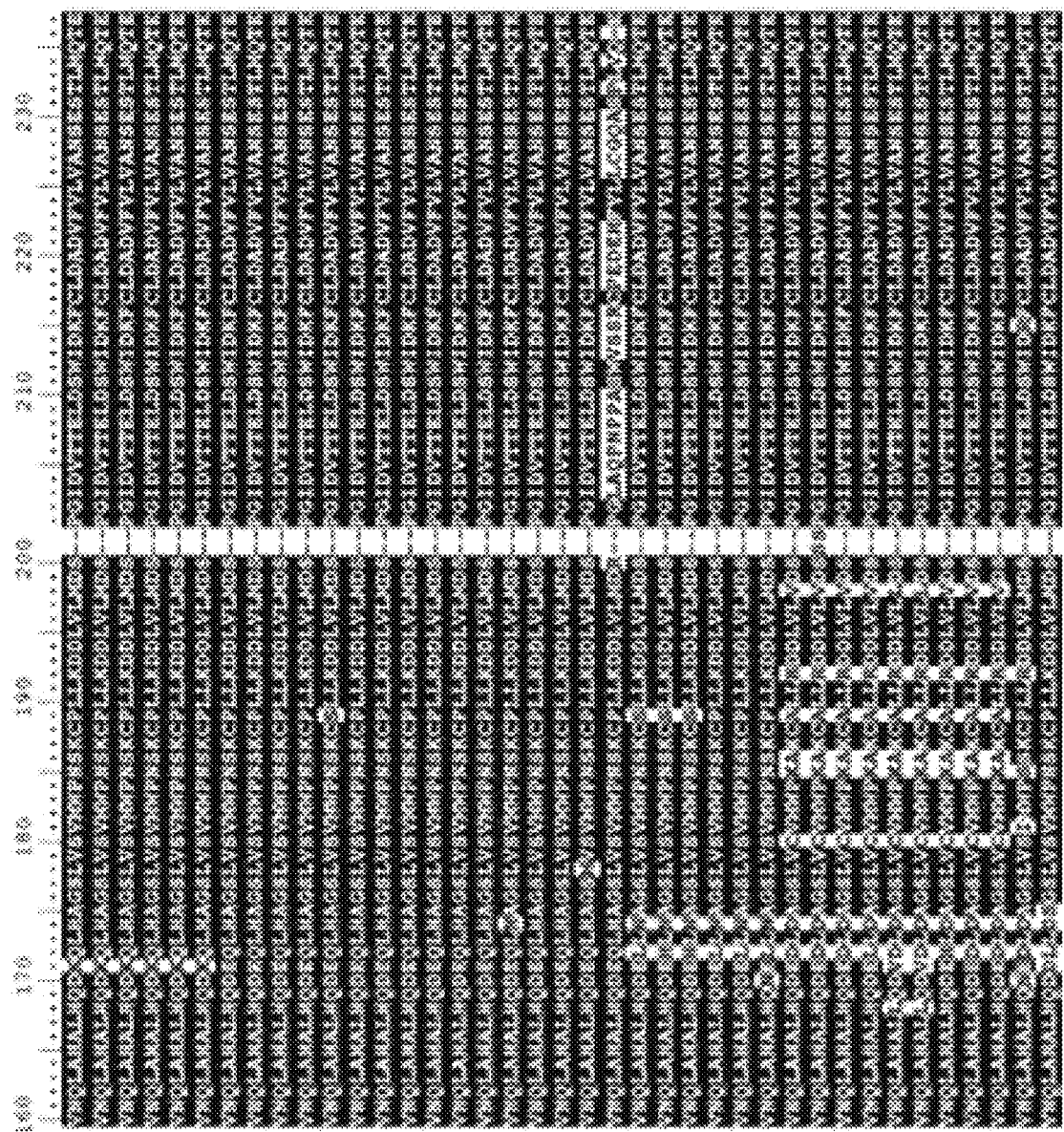
Figure 13D:
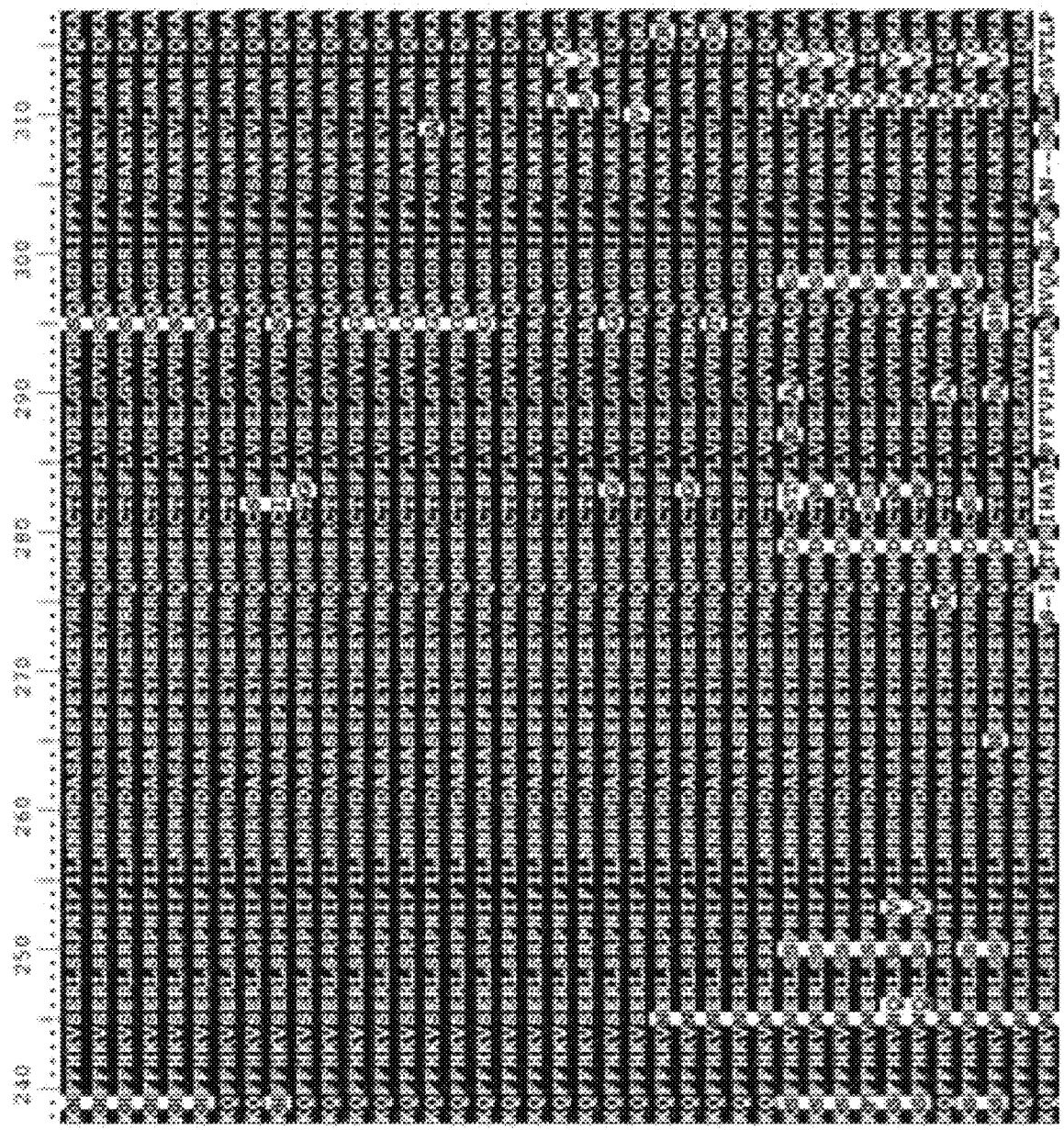
Figure 13E:
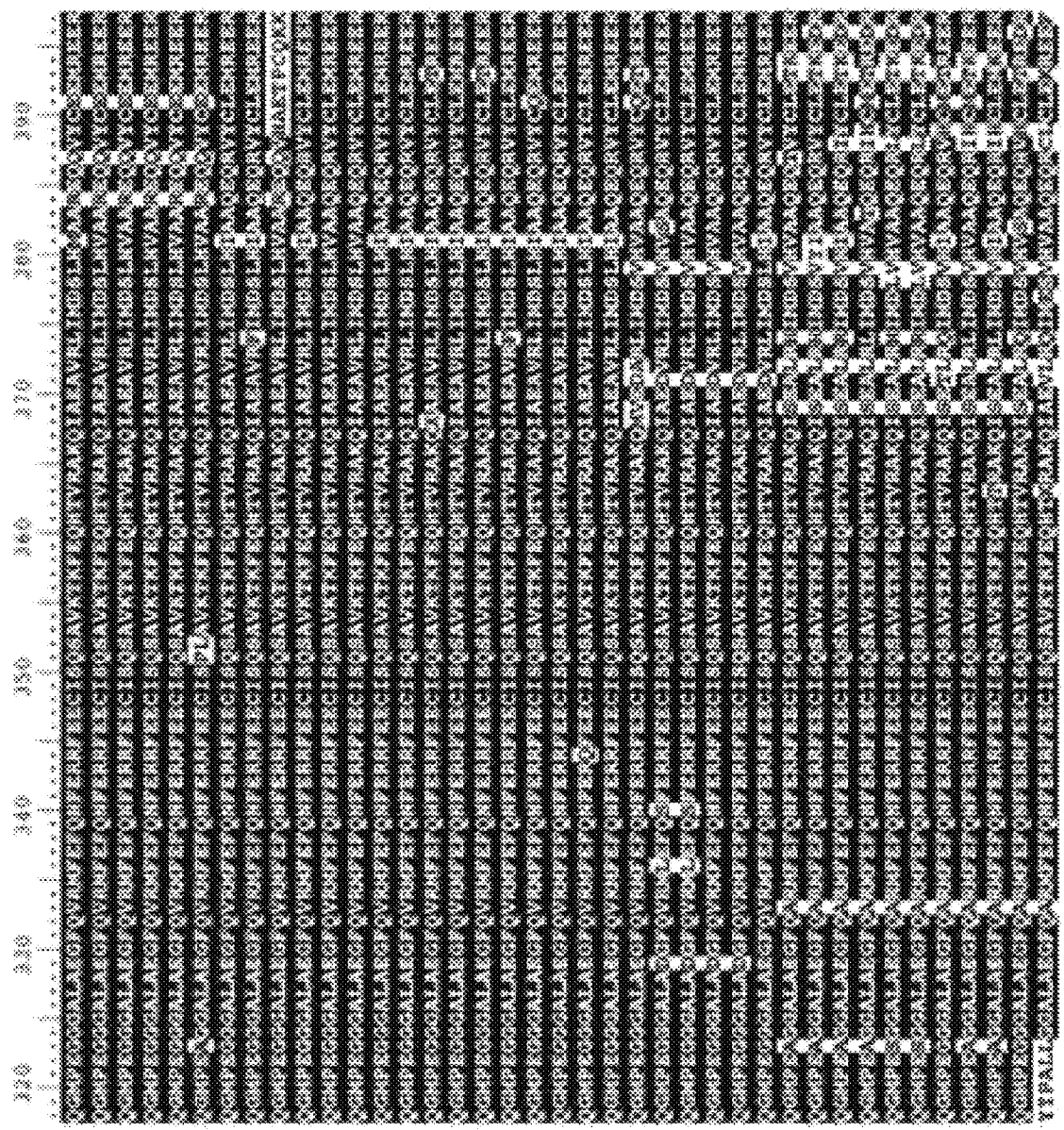
Figure 13F:
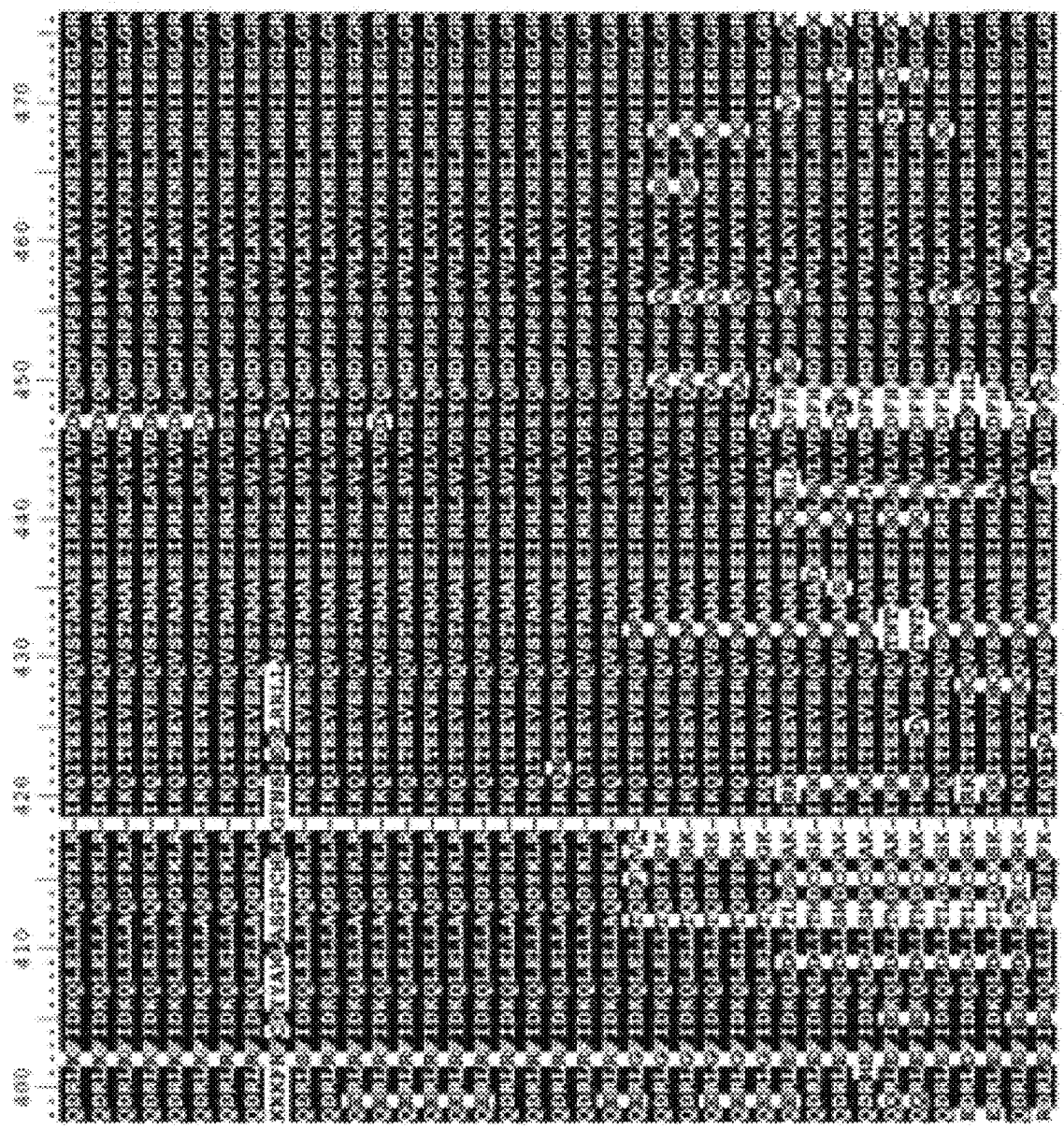
Figure 13H:
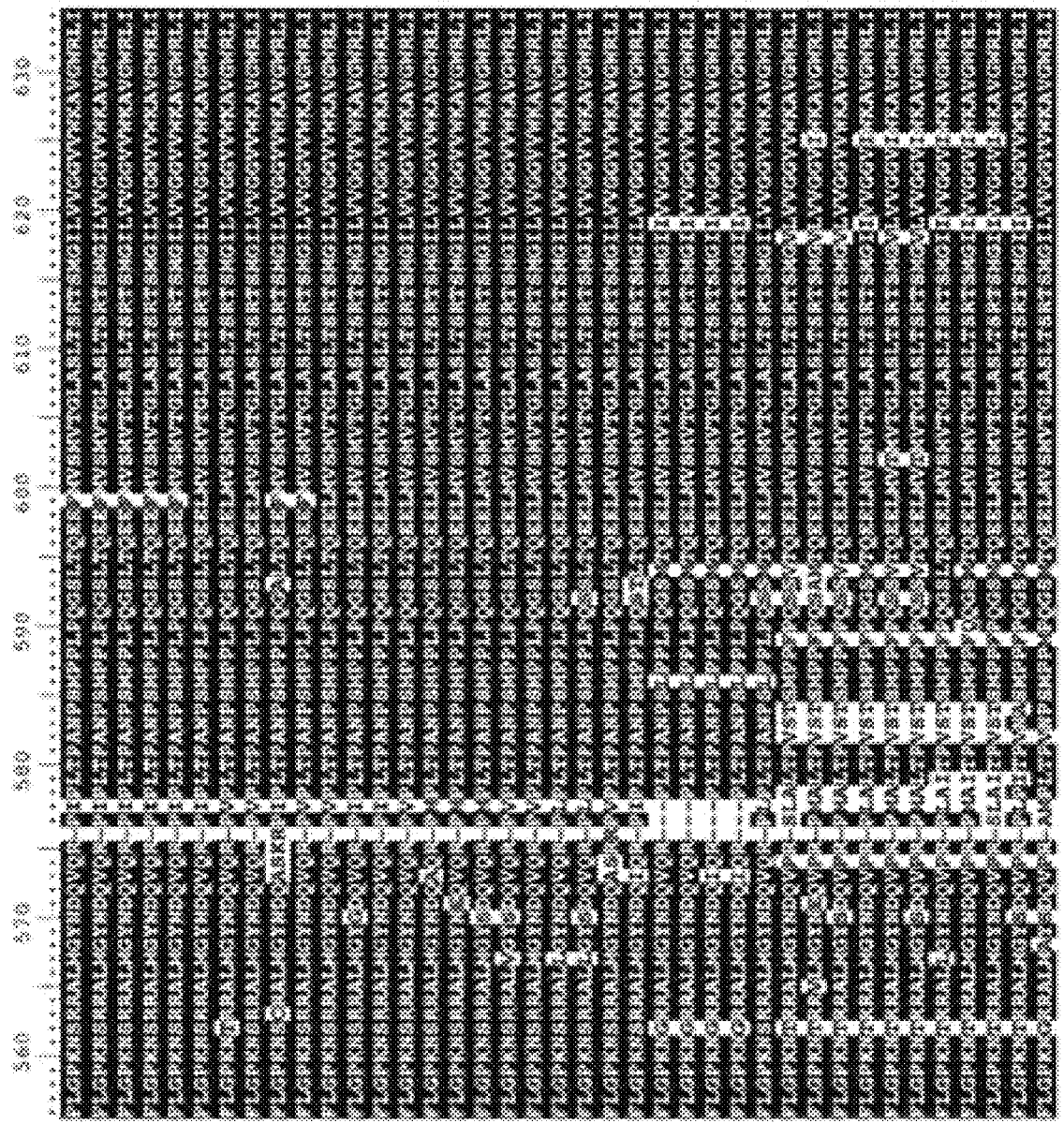
Figure 13I:
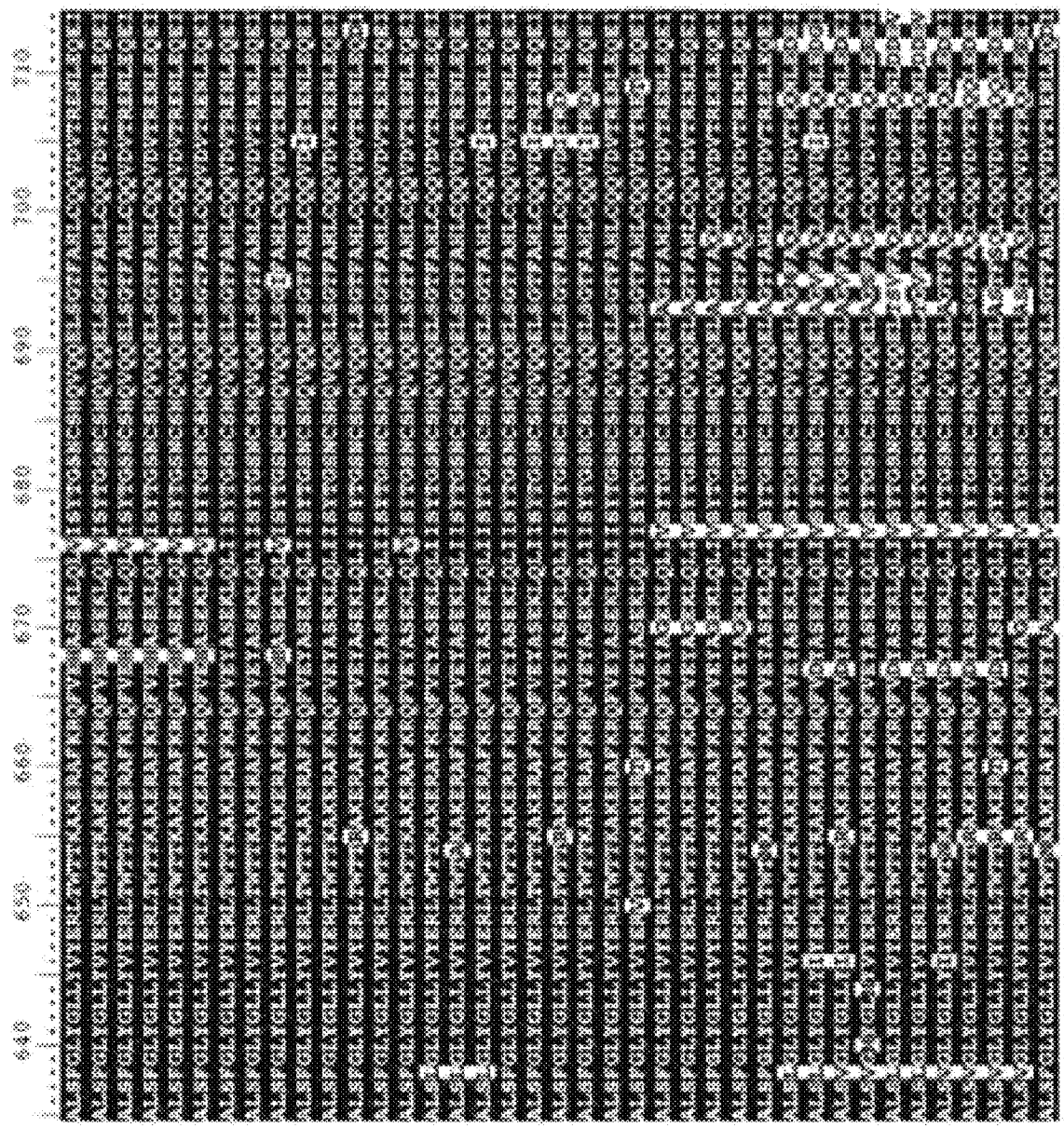

These problems were solved by re-engineering the Mfn2 FRET probe after deleting the GTPase domain (A80-275) (which is dispensable to Mfn folding/unfolding) and cloning it into an adenoviral vector for high efficiency expression. Briefly, mCerulean1 and mVenus were cloned onto the 5' and 3' ends of a hMfn2 cDNA from which the entire GTPase domain (amino acids 80-275) was deleted (see e.g., FIG. 12C, top). Removal of the GTPase domain eliminates the need for adding GTPase inhibitors such as GTPγS in the assay and increases the FRET signal to noise ratio. The sequence-confirmed construct was sub-cloned into an adenoviral vector for expression in murine embryonic fibroblasts having different mitofusin expression profiles (wild-type, Mfn1 null, Mfn2 null, Mfn1/Mfn2 double null) or other cell types. Forty-eight hours after adenoviral transduction cells were pre-treated with the anti-fusion mini-peptide MP2 to increase FRET (1 µM, 1 hour; see e.g., FIG. 12C). Cells were then exposed to screening compound(s) for 1 hour in a 96 well format fluorescence plate reader or on the stage of a confocal microscope. FRET was analyzed as follows: mCerulean was excited at 436 nm with emission at 480 nm. mVenus was excited at 500 nm with emission at 535 nm. FRET was imaged with excitation at 436 nm and emission at 535 nm. Data are represented as FRET signal/mCerulean signal. Increased FRET reflects folded Mfn2; loss of FRET reflects Mfn2 unfolding that favors mitochondrial tethering and fusion.

The adeno-Mfn2 FRET A80-275 is expressed at near 100% efficiency at 50 MOI in cultured murine embryonic fibroblasts (the cell of choice for functional screening of Mfn activity), and exhibits 5-fold greater signal/noise that the original Mfn2 FRET probe. This system is useful in 96 or 384 well formats for high-throughput screening of Mfn agonists (extinguishing of HR1 398-418 induced FRET) and antagonists (stimulation of baseline FRET or reversal of HR1 374-384 FRET suppression; see e.g., FIG. 12).

Example 5: Rationally Designed Mitofusin Agonists Reverse In Vitro and In Vivo CMT2A Mitochondrial Defects This example describes the reversal mitochondrial defects in preclinical models of Charcot Marie Tooth disease type 2A with MFN2 agonists and that pharmacological disruption of intramolecular restraints in MFN2 promotes mitochondrial fusion and trafficking in CMT2A neurons.

Mitofusins (MFNs) promote fusion-mediated mitochondrial content exchange and subcellular trafficking. Mutations in MFN2 cause neurodegenerative Charcot Marie Tooth Disease type 2A (CMT2A). Here, it has been shown that MFN2 activity is determined by $Met^{376}$ and $His^{380}$ interactions with $Asp^{725}$ and $Leu^{727}$ and controlled by PINK1 kinase-mediated phosphorylation of adjacent MFN2 $Ser^{378}$.

Also shown here is that small molecule mimics of the peptide-peptide interface of MFN2 disrupted this interaction, allosterically activating MFN2 and promoting mitochondrial fusion. These first-in-class mitofusin agonists overcame dominant mitochondrial defects provoked in cultured neurons by CMT2A mutants MFN2 $Arg^{94} \rightarrow Gln^{94}$ and $Thr^{105} \rightarrow Met^{105}$, as demonstrated by amelioration of mitochondrial dysmotility, fragmentation, depolarization, and clumping. A mitofusin agonist normalized axonal mitochondrial trafficking within sciatic nerves of MFN2 $Thr^{105s} \rightarrow Met^{105}$ mice, promising a therapeutic approach for CMT2A and other untreatable diseases of impaired neuronal mitochondrial dynamism and/or trafficking.

Mitochondria are organelles that generate a rich energy source for cells, which require their continuous subcellular redistribution via mitochondrial trafficking and mutual repair via mitochondrial fusion. Mitochondrial fusion and subcellular trafficking are mediated in part by mitofusin 1 (MFN1) and MFN2. Genetic mutations in MFN2 that suppress mitochondrial fusion and motility cause Charcot Marie Tooth Disease 2A (CMT2A), the most common heritable axonal neuropathy. Because no therapeutics exist that directly enhance mitochondrial fusion or trafficking, this disease is unrelenting and irreversible.

Figure 14A:
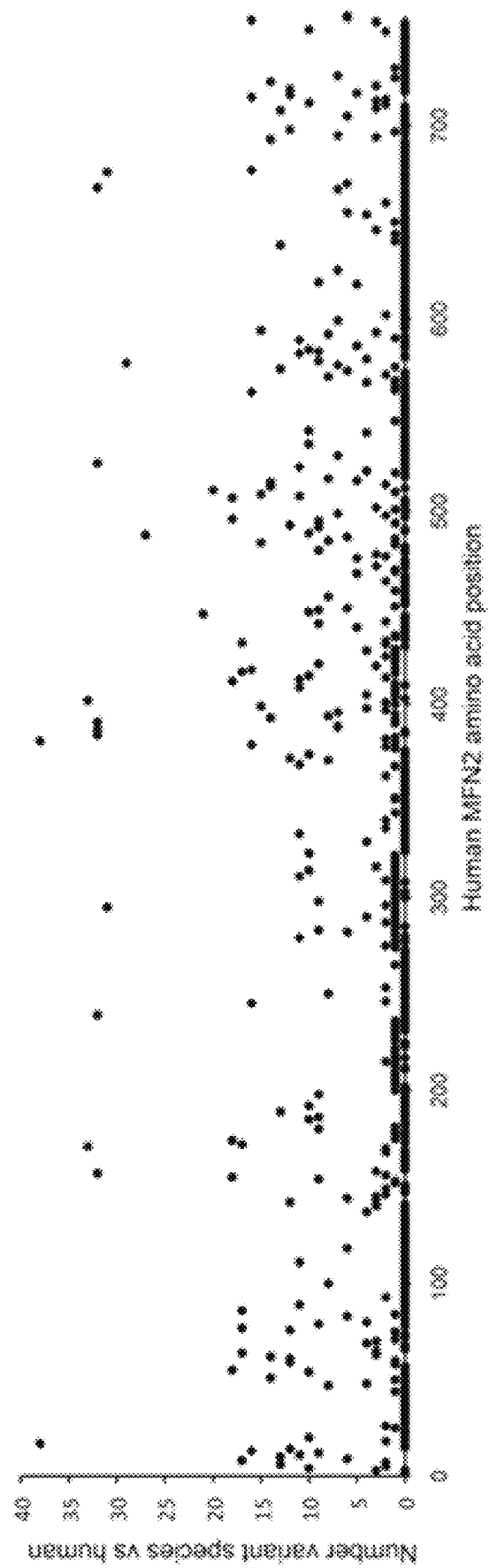
FIG. 14 is a homology plot of MFN2 amino acid sequence by functional domain. Positions of HR1 MP374-384 ("fuse") and its HR2 interacting site ("Binding") are shown on exploded views below.

Computational modeling based on the closed structure of bacterial dynamin-related protein (BDRP) and the more open structure of optic atrophy-1 suggested that MFN2 can change conformation according to how closely the first and second heptad repeat (HR) domains interact (see e.g., FIG. 1). A closed conformation is fusion incompetent, whereas an open conformation favoring mitochondrial fusion can be induced by a competing peptide analogous to amino acids 367 to 384 within the MFN2 HR1 domain. Amino acids controlling these events were identified, first by truncation analysis to define the smallest fusion promoting minipeptide (residues 374 to 384) (see e.g., FIG. 2A-FIG. 2B), and then through functional investigation of this minimal peptide by alanine (Ala) scanning. Substitution of Ala for $Met^{376}$, $Ser^{378}$, $His^{380}$, and $Met^{381}$ which are highly conserved across vertebrate species (see e.g., FIG. 13, FIG. 14) impaired minipeptide-stimulated mitochondrial fusion, as measured by an increase in the mitochondrial length/width (aspect ratio) (see e.g., FIG. 2C). The structural model of human MFN2 in a closed conformation on the basis of homology with BDRP predicted a helical interaction between HR1 and HR2 domains, with alignment of $Met^{376}$ and $His^{380}$ side chains in the HR1 domain with $Leu^{727}$ and Asp725 in the HR2 domain (see e.g., FIG. 1). This arrangement suggested that $Met^{376}$ and $His^{380}$ stabilize the MFN2 HR1-HR2 interaction, potentially explaining their critical function as defined by minipeptide Ala scanning. By contrast, $Ser^{378}$ was modeled as extending from the noninteracting surface of the HR1 α helix (see e.g., FIG. 1), implying a different mechanism for its involvement in mitochondrial fusion.

To address whether $Ser^{378}$ might be phosphorylated, $Ser^{378}$ was substituted (with Ala, Cys, Asn or Gly) in the mini-peptide and it was found that phosphorylation and fusion activity were abrogated. Functionality was restored by substituting Asp to mimic phosphorylated Ser, or by inserting phospho-Ser [(p)Ser]itself (see e.g., FIG. 2D, FIG. 15). Moreover, in an in vitro binding assay devoid of cellular kinases the $Asp^{378}$-substituted minipeptide bound to its putative HR2 interacting domain, whereas $Ser^{378}$ and $Ala^{378}$ minipeptides did not (see e.g., FIG. 2E). Elimination of minipeptide binding by replacement of HR2 $Leu^{724}$, $Asp^{725}$, and $Leu^{727}$ with Ala confirmed the HR1-HR2 interaction model (see e.g., FIG. 2F).

Nuclear magnetic resonance spectrometry of the minipeptides showed low conformational stability with a propensity to form helical structures. $Ser^{378}$ phosphorylation reduced the peptide dynamics most visibly for residues $Leu^{379}$ to $Met^{381}$, potentially changing amino acid side chains presented to HR2 (see e.g., FIG. 16, FIG. 17). Indeed, recombinant MFN2 mutations that replaced $Ser^{378}$ with Asp (mimicking MFN2 $Ser^{378}$ phosphorylation) or substituted Ala for $Met^{376}$ or $His^{380}$ (disrupting the putative HR1-HR2 interaction controlled by $Ser^{378}$ phosphorylation) impaired MFN2-stimulated mitochondrial fusion (see e.g., FIG. 18). By contrast, replacing MFN2 $Ser^{378}$ with Ala (to prevent its phosphorylation), or substitution Ala for neighboring $Val^{372}$, which was not important for HR1-HR2 interactions, did not depress MFN2-mediated fusion (see e.g., FIG. 18).

MFN2 can be phosphorylated by mitochondrial PTEN-induced putative kinase 1 (PINK1). Targeted mass spectrometry demonstrated phosphorylation of MFN2 $Ser^{378}$ as well as MFN2 $Thr^{111}$ and $Ser^{442}$ by PINK1 kinase (see e.g., FIG. 2G; FIG. 19 and FIG. 20; TABLE 3), but not by software-nominated G-protein receptor kinase 2 (see e.g., FIG. 21). MFN2 $Ser^{378}$ mutants were expressed with or without PINK1 in MFN1 and MFN2 doubly deficient (MFN1$^{-/-}$, MFN2$^{-/-}$) cells. Fusion-defective mitochondria in these cells were abnormally short at baseline, but forced expression of wild-type ($Ser^{378}$) MFN2 resulted in elongation from restoration of fusion (see e.g., FIG. 2H, FIG. 22). Co-expression of PINK1 with MFN2, or mutational replacement of MFN2 $Ser^{378}$ with Asp (which mimics PINK1-mediated $Ser^{378}$ phosphorylation) restrained MFN2-stimulated elongation (see e.g., FIG. 2H, FIG. 22). By contrast, MFN2 $Ala^{378}$ (which cannot be phosphorylated) promoted mitochondrial fusion resistant to PINK1 suppression (see e.g., FIG. 2H, FIG. 22). The effects of MFN2 $Ser^{378}$ mutants were recapitulated in assays of fusion-mediated mitochondrial content exchange (see e.g., FIG. 23).

TABLE 3

Fragmentation ions from tandem MS of MFN phosphopeptides.

LIMDsLHMAAR[1] (m/z = 446.543)

| ion | m/z (Theoretical) | m/z (Observed) | ppm |
|---|---|---|---|
| $y_1$ | 175.119 | 175.120 | 3.7 |
| $y_3$ | 317.193 | 317.194 | 1.4 |
| $y_4$ | 448.234 | 448.230 | −9.0 |
| $y_5$ | 585.293 | 585.290 | −3.6 |
| $y_6$ | 698.377 | 698.380 | 5.0 |
| $y_7\text{-}H_3PO_4^{+2}$ | $384.203^{+2}$ | 384.203 | 0.7 |
| $y_8\text{-}H_3PO_4$ | 882.425 | 882.427 | 2.3 |

LIMDsLHMAAR-[$^{13}C_6$][$^{15}N_4$] (m/z = 449.880)

| ion | m/z (Theoretical) | m/z (Observed) | ppm |
|---|---|---|---|
| $y_1$ | 185.127 | 185.127 | 0.2 |
| $y_2$ | 256.164 | 256.163 | −4.3 |
| $y_3$ | 327.201 | 327.200 | −3.1 |
| $y_4$ | 458.242 | 458.242 | −0.7 |
| $y_5$ | 595.301 | 595.300 | −1.0 |
| $y_6$ | 708.385 | 708.382 | −4.6 |
| $y_7\text{-}H_3PO_4$ | 777.406 | 777.404 | −3.7 |
| $y_8\text{-}H_3PO_4$ | 892.433 | 892.431 | −2.1 |
| $y_9\text{-}H_3PO_4$ | 1023.474 | 1023.472 | −1.7 |
| $y_{10}\text{-}H_3PO_4$ | 1136.558 | 1136.549 | −8.0 |

[1]The lower case single amino acid abbreviation indicates the phosphorylated residue.

Identification and De Novo Design of Small Molecule Mitofusin Agonists

A pharmacophore model was generated based on the interactions of HR1 and HR2 domains in the calculated structural model of Mfn2 in the closed conformation. The key features included hydrophobic interactions involving Mfn2 HR1: Val372 and Met376, and aromatic interactions and hydrogen bonding involving Mfn2 HR1 His380. Although the pharmacophore model did not structurally model mitofusin agonist minipeptide HR1 (367-384), it was noted that peptide residues Val6, Met10, and His14 correspond to Mfn2 HR1: Val372, Met376 and His380. A library comprising ~14 million commercially available compounds was prepared in silico and evaluated using PHASE to fit these criteria. Top ranked hits were clustered, and filtered based on pharmacological properties using Qikprop. The top 55 (see TABLE 4) commercially available small molecules conforming to the model were selected for functional screening and purchased in 1 mg aliquots. Each compound was dissolved to a stock concentration of 10 mM in DMSO and applied to Mfn2 null MEFs overnight at a final concentration of 1 mM. Eleven of the library members were not soluble in DMSO at the required concentration. The 44 fully soluble compounds were screened in groups of 6 at a time for cytotoxicity (calcein AM/ethidium homodimer staining; ThermoFisher LIVE/DEAD Assay cat #L3224) and fusogenicity (increase in mitochondrial aspect ratio; MitoTracker Orange staining) compared to cells treated overnight with 5 mM of the parent HR1 367-384 mitofusin agonist peptide (positive control) or vehicle (DMSO). Images were acquired by confocal microscopy. Each compound was scored for fusogenicity (see e.g., FIG. 24A) and % cell death (see e.g., FIG. 24B). Pharmacophore model fit generally correlated with actual fusogenic activity (Pearson correlation coefficient r=0.214; see e.g., FIG. 24A, inset; TABLE 4).

TABLE 4

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 1 | 2-{[(3aS,6aS)-5-{5,7-dimethylpyrazolo[1,5-a]pyrimidine-2-carbonyl}-octahydropyrrolo[3,4-b]pyrrol-1-yl]methyl}-1-methyl-1H-imidazole | 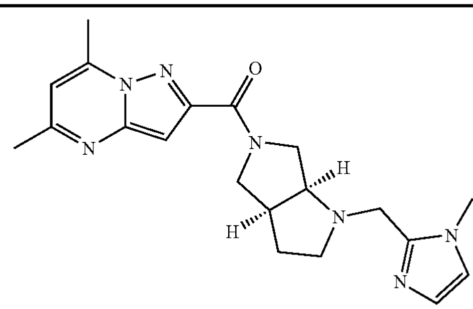 | 9.0 ± 3.1 | 1 |
| 2 | 3-{[2-(1H-1,3-benzodiazol-2-yl)ethyl]sulfanyl}-1-(3-fluorophenyl)pyrrolidine-2,5-dione | 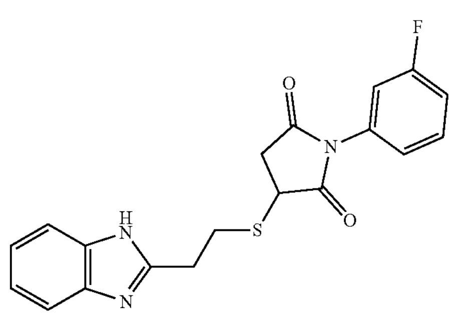 [SMILES: O=C1CC(SCCc2nc3ccccc3[nH]2)C(=O)N1c1cccc(F)c1] | 6.9 ± 0.8 | 3 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 3 | 2-[({3-[5-methyl-2-(propan-2-yl)phenoxy]propyl}sulfanyl)methyl]-1H-1,3-benzodiazole | 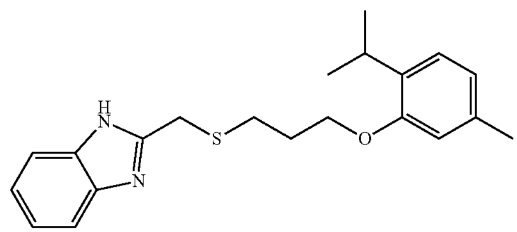 [SMILES: Cc1ccc(C(C)C)c(OCCCSCc2nc3ccccc3[nH]2)c1] | 3.0 ± 0.4 | 37 |
| 4 | 2-[(4-methoxyphenyl)sulfanyl]-N-(1H-pyrazol-3-yl)propanamide | 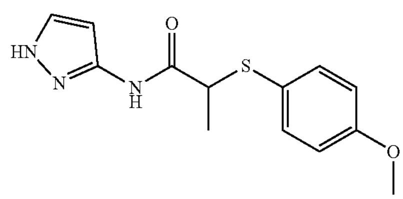 [SMILES: COc1ccc(SC(C)C(=O)Nc2cc[nH]n2)cc1] | 3.8 ± 0.4 | 22 |
| 5 | 1-[1-(4-chlorophenyl)-1H,2H,3H,4H,9H-pyrido[3,4-b]indol-2-yl]-2-{[(4-fluorophenyl)methyl]sulfanyl}ethan-1-one | 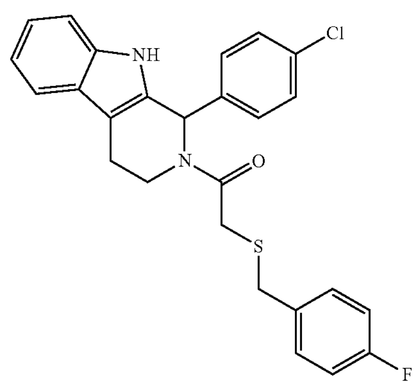 [SMILES: O=C(CSCc1ccc(F)cc1)N1CCc2c([nH]c3ccccc23)C1c1ccc(Cl)cc1] | 4.7 ± 0.9 | 11 |
| 6 | ethyl 4-methyl-2-(2-{5H-[1,2,4]triazino[5,6-b]indol-3-ylsulfanyl}butanamido)-1,3-thiazole-5-carboxylate | 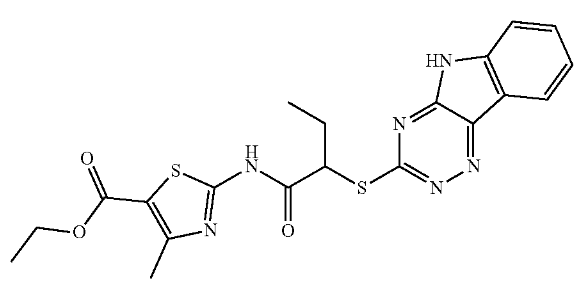 [SMILES: CCOC(=O)c1sc(NC(=O)C(CC)Sc2nnc3c(n2)[nH]c2ccccc23)nc1C] | 4.5 ± 0.5 | 13 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 7 | 2-({[4-oxo-6-(propan-2-yl)-3H,4H,4aH,7aH-thieno[2,3-d]pyrimidin-2-yl]methyl}sulfanyl)-N-[(pyridin-2-yl)methyl]acetamide | 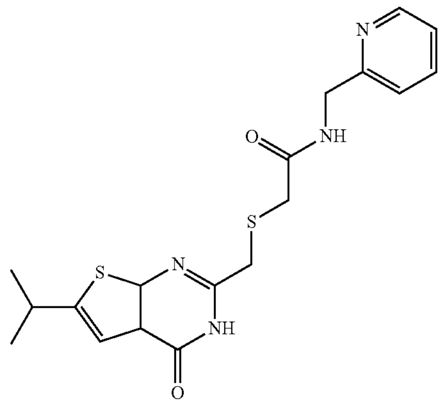 [SMILES: CC(C)C1=CC2C(=O)NC(CSCC(=O)NCc3ccccn3)=NC2S1] | 3.8 ± 0.6 | 21 |
| 8 | N-(3,4-dichlorophenyl)-2-{[2-(pyridin-2-yl)ethyl]sulfanyl}acetamide | 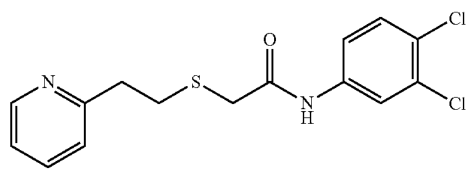 [SMILES: O=C(CSCCc1ccccn1)Nc1ccc(Cl)c(Cl)c1] | 2.8 ± 0.1 | 41 |
| 9 | 2-methyl-6-(2-{[(4-methyl-1H-imidazol-5-yl)methyl]sulfanyl}ethyl)-2H,6H,7H-pyrazolo[4,3-d]pyrimidin-7-one | 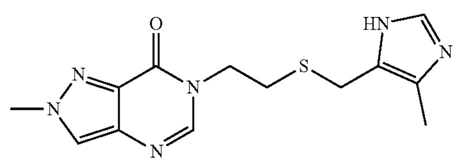 [SMILES: Cc1nc[nH]c1CSCCn1cnc2cn(C)nc2c1=O] | 2.8 ± 0.2 | 42 |
| 10 | 3-acetamido-N-(2-{[(4-methylphenyl)methyl]sulfanyl}ethyl)adamantane-1-carboxamide | 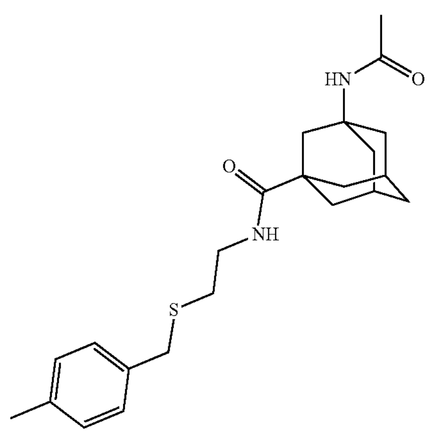 [SMILES: CC(=O)NC12CC3CC(C1)CC(C(=O)NCCSCc1ccc(C)cc1)(C3)C2] | Not obtained | Insoluble |
| 11 | N-(2-{[(2-cyanophenyl)methyl]sulfanyl}ethyl)-2-{methyl[1-(3-nitrophenyl)ethyl]amino}-acetamide | 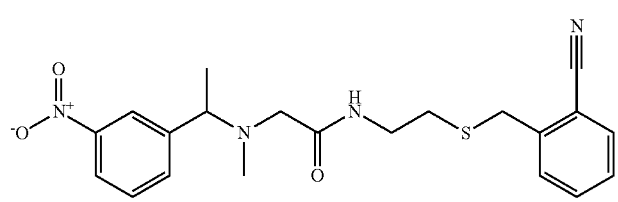 | 4.0 ± 0.5 | 16 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 12 | N-(2,6-dimethylphenyl)-4-({[3-(3-fluoro-4-methylphenyl)-1,2,4-oxadiazol-5-yl]methyl}sulfanyl)butanamide | 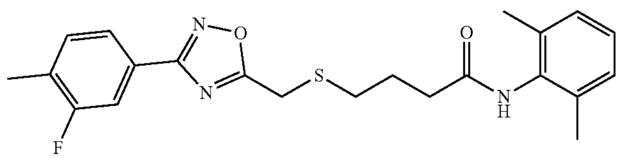 [SMILES: Cc1ccc(-c2noc(CSCCCC(=O)Nc3c(C)cccc3C)n2)cc1F] | 3.9 ± 0.5 | 20 |
| 13 | 5-methoxy-3'-(2-methylbenzoyl)-1-{[3-(trifluoromethyl)phenyl]methyl}-1,2-dihydrospiro[indole-3,2'-[1,3]thiazolidine]-2-one | 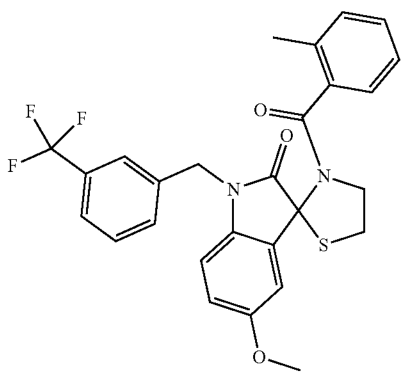 [SMILES: COc1ccc2c(c1)C1(SCCN1C(=O)c1ccccc1C)C(=O)N2Cc1cccc(C(F)(F)F)c1] | 3.5 ± 0.6 | 26 |
| 14 | N-(2,6-dimethylphenyl)-4-({[5-(propan-2-yl)-1,3-oxazol-2-yl]methyl}sulfanyl)butanamide | 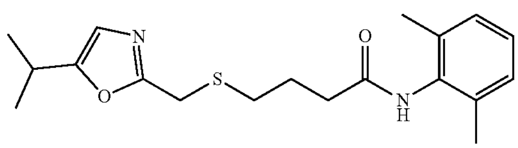 [SMILES: Cc1cccc(C)c1NC(=O)CCCSCc1ncc(C(C)C)o1] | 3.5 ± 0.1 | 25 |
| 15 | 6-methyl-N-{[6-(4-methyl-1,4-diazepan-1-yl)pyridin-3-yl]methyl}-2,3-dihydro-1-benzothiophene-2-carboxamide | 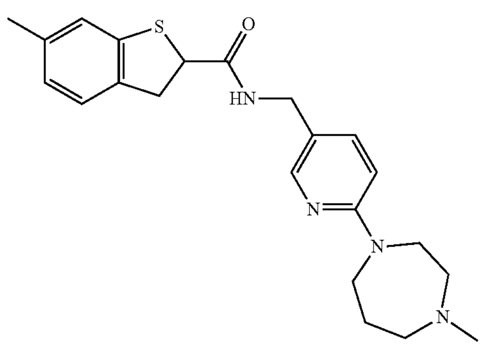 | 4.0 ± 0.3 | 18 |
| 16 | N-(2-{[(5-bromothiophen-2-yl)methyl]sulfanyl}ethyl)-1-(thiophene-2-carbonyl)piperidine-3-carboxamide | 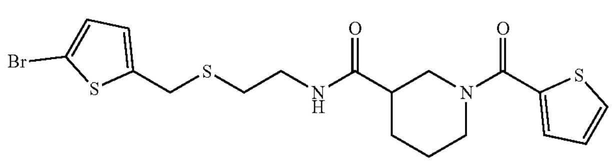 [SMILES: O=C(NCCSCc1ccc(Br)s1)C1CCCN(C(=O)c2cccs2)C1] | 5.1 ± 0.2 | 9 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 17 | 3-{[1-(3,4-dimethylphenyl)-1-oxopropan-2-yl]sulfanyl}-7-phenyl-7H,8H-[1,2,4]triazolo[4,3-a]pyrazin-8-one | 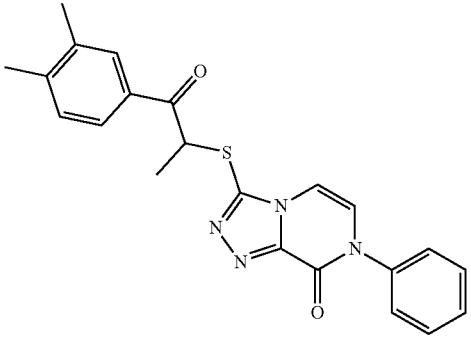 [SMILES: Cc1ccc(C(=O)C(C)Sc2nnc3c(=O)n(-c4ccccc4)ccn23)cc1C] | Not obtained | Insoluble |
| 18 | 1-(4-methylphenyl)-5-({1-[3-(4H-1,2,4-triazol-3-yl)-1,2,4-oxadiazol-5-yl]ethyl}sulfanyl)-1H-1,2,3,4-tetrazole | 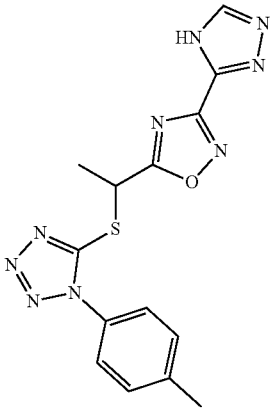 [SMILES: Cc1ccc(-n2nnnc2SC(C)c2nc(-c3nnc[nH]3)no2)cc1] | 3.4 ± 0.3 | 27 |
| 19 | 5-methyl-N-{3-[(5-methyl-1,3,4-thiadiazol-2-yl)sulfanyl]propyl}-1H,4H,5H,6H,7H-pyrazolo[4,3-c]pyridine-3-carboxamide | 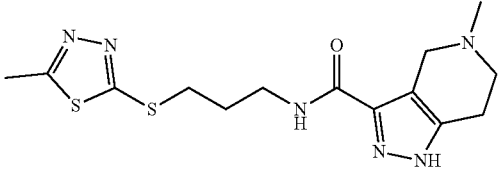 [SMILES: Cc1nnc(SCCCNC(=O)c2n[nH]c3c2CN(C)CC3)s1] | 3.1 ± 0.3 | 34 |
| 20 | 7-(4-bromophenyl)-3-{[1-(3,4-dimethylphenyl)-1-oxopropan-2-yl]sulfanyl}-7H,8H-[1,2,4]triazolo[4,3-a]pyrazin-8-one | 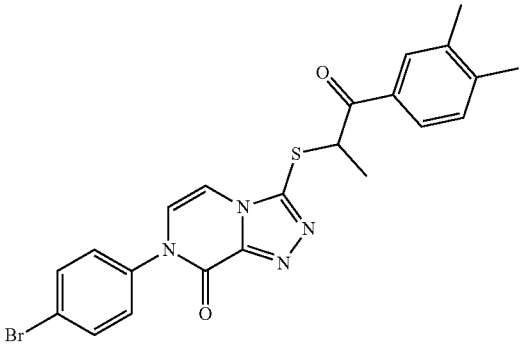 [SMILES: Cc1ccc(C(=O)C(C)Sc2nnc3c(=O)n(-c4ccc(Br)cc4)ccn23)cc1C] | Not obtained | Insoluble |
| 21 | N-[2-(benzylsulfanyl)ethyl]oxane-2-carboxamide | 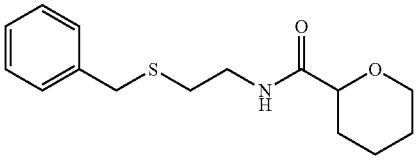 [SMILES: O=C(NCCSCc1ccccc1)C1CCCCO1] | 3.3 ± 0.4 | 30 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 22 | N-(2-{[(4-methylphenyl)methyl]sulfanyl}ethyl)-1-[3-(trifluoromethyl)-[1,2,4]triazolo[4,3-b]pyridazin-6-yl]piperidine-4-carboxamide | 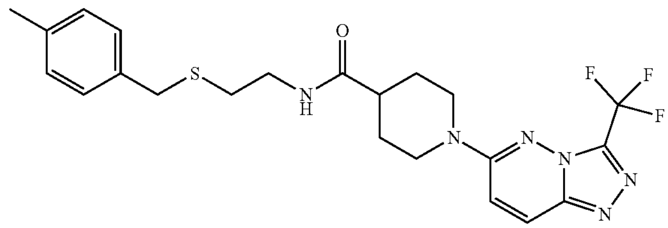 [SMILES: Cc1ccc(CSCCNC(=O)C2CCN(c3ccc4nnc(C(F)(F)F)n4n3)CC2)cc1] | Not obtained | Insoluble |
| 23 | 1-cyclobutanecarbonyl-N-(2-{[(4-methyl-1H-imidazol-5-yl)methyl]sulfanyl}ethyl)-piperidine-4-carboxamide | 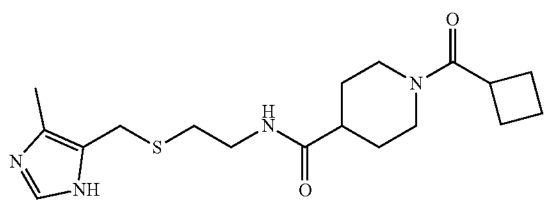 [SMILES: Cc1nc[nH]c1CSCCNC(=O)C1CCN(C(=O)C2CCC2)CC1] | 2.9 ± 0.5 | 40 |
| 24 | 2-{[(2-{bicyclo[4.1.0]heptane-7-amido}pyridin-4-yl)methyl]sulfanyl}ethyl bicyclo[4.1.0]heptane-7-carboxylate | 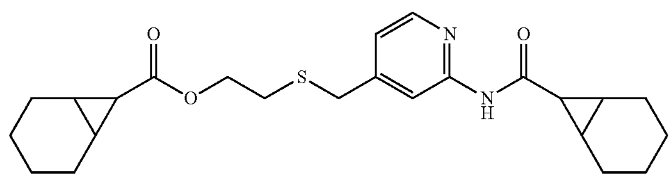 [SMILES: O=C(Nc1cc(CSCCOC(=O)C2C3CCCCC32)ccn1)C1C2CCCCC21] | 4.8 ± 1.0 | 10 |
| 25 | N-(2-{[(3-chlorophenyl)methyl]sulfanyl}ethyl)-5H,6H,7H,8H,9H-[1,2,3,4]tetrazolo[1,5-a]azepine-9-carboxamide | 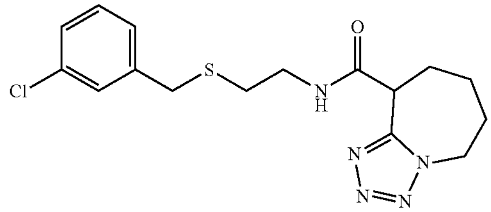 [SMILES: O=C(NCCSCc1cccc(Cl)c1)C1CCCCn2nnnc21] | 2.9 ± 0.2 | 38 |
| 26 | 2-{[4-benzyl-5-(morpholin-4-yl)-4H-1,2,4-triazol-3-yl]sulfanyl}-N-(2-oxo-2,3-dihydro-1H-1,3-benzodiazol-5-yl)propanamide | 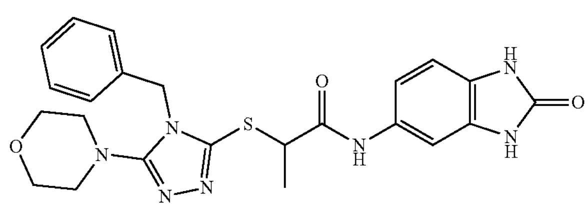 [SMILES: CC(Sc1nnc(N2CCOCC2)n1Cc1ccccc1)C(=O)Nc1ccc2[nH]c(=O)[nH]c2c1] | 5.2 ± 0.2 | 8 |
| 27 | 1-[2-(benzylsulfanyl)ethyl]-3-(2-methylcyclohexyl)urea | 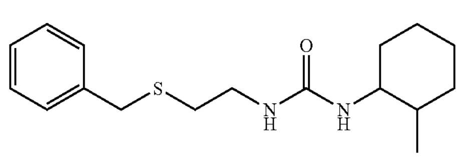 [SMILES: CC1CCCCC1NC(=O)NCCSCc1ccccc1] | 6.8 ± 0.6 | 4 |
| 28 | 1-{bicyclo[2.2.1]heptan-2-yl}-3-(2-{[(furan-2-yl)methyl]sulfanyl}ethyl)thiourea | 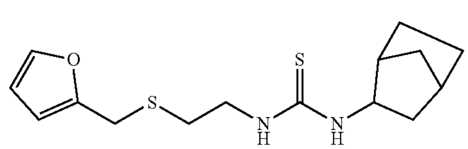 [SMILES: S=C(NCCSCc1ccco1)NC1CC2CCC1C2] | 3.7 ± 0.9 | 23 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 29 | 2-{[4-benzyl-5-(morpholin-4-yl)-4H-1,2,4-triazol-3-yl]sulfanyl}-N-(2,3-dihydro-1,4-benzodioxin-6-yl)propanamide | 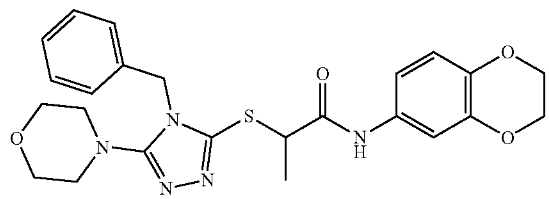 [SMILES: CC(Sc1nnc(N2CCOCC2)n1Cc1ccccc1)C(=O)Nc1ccc2c(c1)OCCO2] | 6.0 ± 0.1 | 6 |
| 30 | 2-({2-[(morpholin-4-yl)methyl]quinazolin-4-yl}sulfanyl)-N-[3-(trifluoromethyl)phenyl]-propanamide | 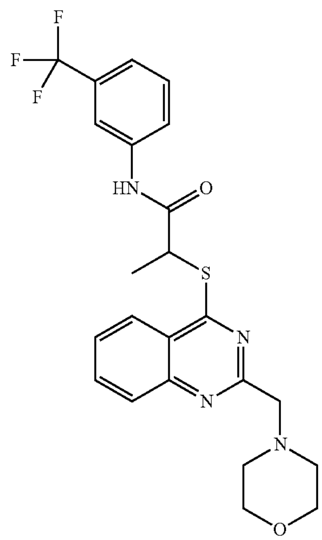 [SMILES: CC(Sc1nc(CN2CCOCC2)nc2ccccc12)C(=O)Nc1cccc(C(F)(F)F)c1] | 5.6 ± 0.6 | 7 |
| 31 | 2-{2-[(5-cyclopropyl-4-phenyl-4H-1,2,4-triazol-3-yl)sulfanyl]propanamido}-4H,5H,6H-cyclopenta[b]thiophene-3-carboxamide | 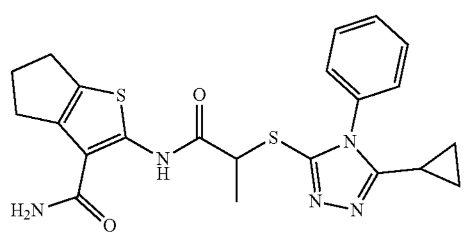 [SMILES: CC(Sc1nnc(C2CC2)n1-c1ccccc1)C(=O)Nc1sc2c(c1C(N)=O)CCC2] | 8.3 ± 2.3 | 2 |
| 32 | 2-{[4-(4-methylphenyl)-5-(morpholin-4-yl)-4H-1,2,4-triazol-3-yl]sulfanyl}-N-[1-(propan-2-yl)-1H-pyrazol-5-yl]propanamide | 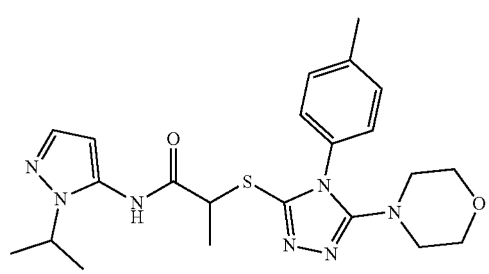 [SMILES: Cc1ccc(-n2c(SC(C)C(=O)Nc3ccnn3C(C)C)nnc2N2CCOCC2)cc1] | 4.1 ± 0.9 | 15 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 33 | N-[4-(3,4-dihydro-2H-1,5-benzodioxepine-7-sulfonamido)phenyl]-2-[(4-methylphenyl)sulfanyl]-propanamide | 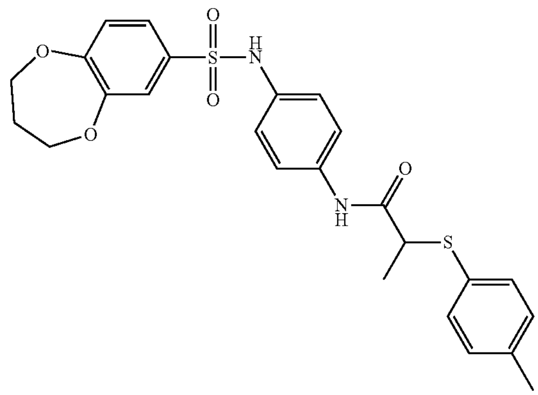 [SMILES: Cc1ccc(SC(C)C(=O)Nc2ccc(NS(=O)(=O)c3ccc4c(c3)OCCCO4)cc2)cc1] | Not obtained | Insoluble |
| 34 | 5-methyl-2-{[1-(3-propyl-1,2,4-oxadiazol-5-yl)ethyl]sulfanyl}-1H-1,3-benzodiazole | 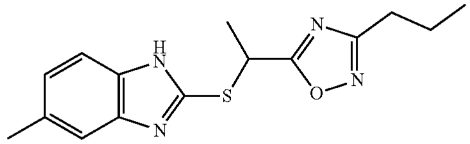 [SMILES: CCCc1noc(C(C)Sc2nc3cc(C)ccc3[nH]2)n1] | 4.0 ± 1.0 | 17 |
| 35 | (1S,4S)-2-(4-chloro-2-methoxy-5-methylphenyl)-5-{[1-(pyrimidin-2-yl)-1H-pyrrol-2-yl]methyl}-2,5-diazabicyclo[2.2.1]heptan-3-one | 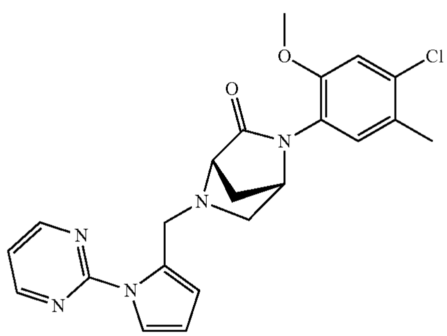 [SMILES: COc1cc(Cl)c(C)cc1N1C(=O)[C@@H]2C[C@H]1CN2Cc1cccn1-c1ncccn1] | Not obtained | Insoluble |
| 36 | 1-(7-{3-[(4,6-dimethylpyrimidin-2-yl)sulfanyl]-2-methylpropyl}-3-methyl-2,6-dioxo-2,3,6,7-tetrahydro-1H-purin-8-yl)piperidine-4-carboxamide | 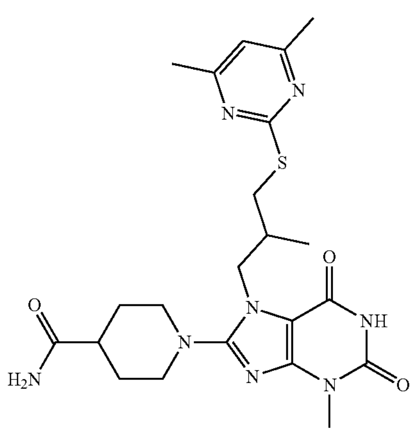 [SMILES: Cc1cc(C)nc(SCC(C)Cn2c(N3CCC(C(N)=O)CC3)nc3c2c(=O)[nH]c(=O)n3C)n1] | Not obtained | Insoluble |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 37 | 2-{[2-(butan-2-yl)-3-oxo-2H,3H-imidazo[1,2-c]quinazolin-5-yl]sulfanyl}-N-(3,5-dimethoxyphenyl)propanamide | 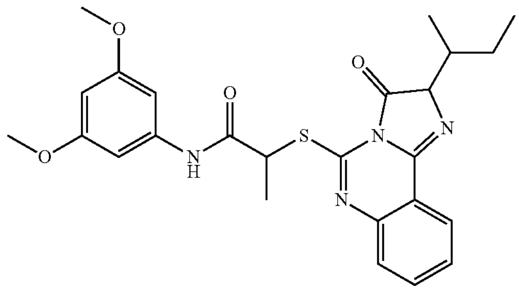 [SMILES: CCC(C)C1N=C2c3ccccc3N=C(SC(C)C(=O)Nc3cc(OC)cc(OC)c3)N2C1=O] | 3.2 ± 0.3 | 32 |
| 38 | N-(5-methyl-1,2-oxazol-3-yl)-2-{[({4-[(1-phenylethyl)amino]phenyl}carbamoyl)methyl]sulfanyl}propanamide | 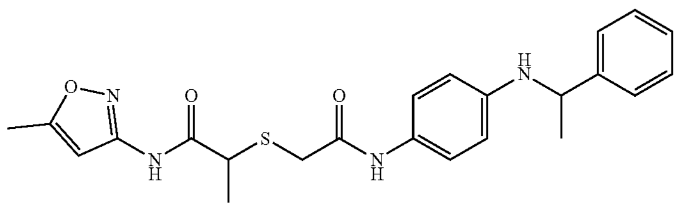 [SMILES: Cc1cc(NC(=O)C(C)SCC(=O)Nc2ccc(NC(C)c3ccccc3)cc2)no1] | Not obtained | Insoluble |
| 39 | N-(butan-2-yl)-2-{2-[(4-methylphenyl)sulfanyl]propanamido}benzamide | 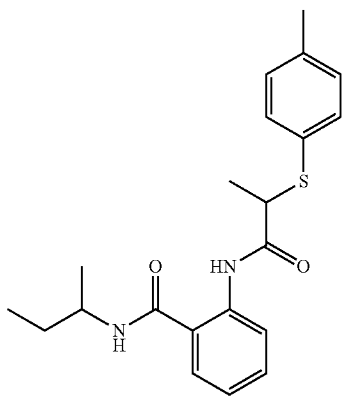 [SMILES: CCC(C)NC(=O)c1ccccc1NC(=O)C(C)Sc1ccc(C)cc1] | 3.3 ± 0.4 | 29 |
| 40 | N-ethyl-2-({12-ethyl-5-oxa-1,10,11-triazatricyclo[6.4.0.0²,⁶]dodeca-2(6),3,7,9,11-pentaen-9-yl}sulfanyl)-N-(3-methylphenyl)butanamide | 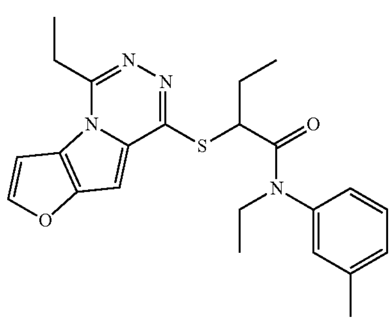 [SMILES: CCc1nnc(SC(CC)C(=O)N(CC)c2cccc(C)c2)c2cc3occc3n12] | Not obtained | Insoluble |
| 41 | 5-[2-(benzylsulfanyl)ethyl]-3-(oxolan-3-yl)-1,2,4-oxadiazole | 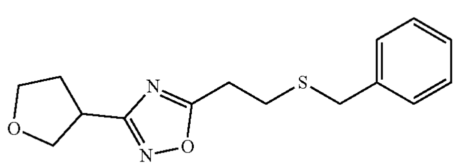 [SMILES: c1ccc(CSCCc2nc(C3CCOC3)no2)cc1] | 3.4 ± 0.6 | 28 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 42 | 2-[(4-bromophenyl)sulfanyl]-N-(2,3-dihydro-1,4-benzodioxin-6-yl)propanamide | 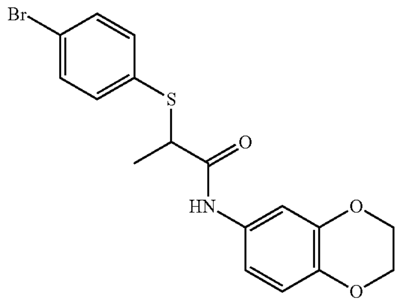 [SMILES: CC(Sc1ccc(Br)cc1)C(=O)Nc1ccc2c(c1)OCCO2] | 3.2 ± 0.5 | 33 |
| 43 | 7-(3,4-dimethylphenyl)-3-{[1-(3,4-dimethylphenyl)-1-oxopropan-2-yl]sulfanyl}-7H,8H-[1,2,4]triazolo[4,3-a]pyrazin-8-one | 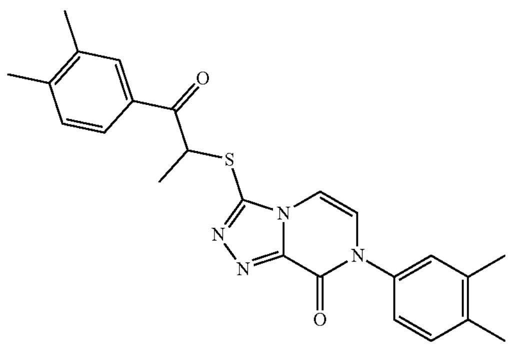 | 3.9 ± 0.8 | 19 |
| 44 | 9-oxo-N-(2-{[(thiophen-3-yl)methyl]sulfanyl}ethyl)-bicyclo[3.3.1]nonane-3-carboxamide | 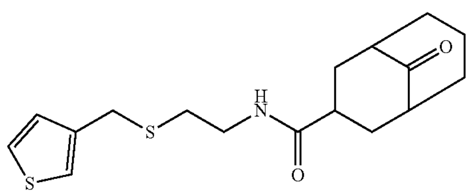 [SMILES: O=C(NCCSCc1ccsc1)C1CC2CCCC(C1)C2=O] | 4.4 ± 0.6 | 14 |
| 45 | N-(2H-1,3-benzodioxol-5-yl)-2-{[4-benzyl-5-(morpholin-4-yl)-4H-1,2,4-triazol-3-yl]sulfanyl}propanamide | 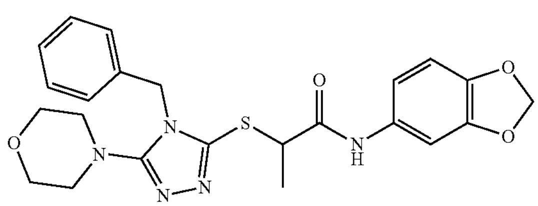 [SMILES: CC(Sc1nnc(N2CCOCC2)n1Cc1ccccc1)C(=O)Nc1ccc2c(c1)OCO2] | 2.5 ± 0.6 | 43 |
| 46 | N-(cyclohexylmethyl)-2-({2,8-dicyclopropyl-5,7-dioxo-5H,6H,7H,8H-pyrimido[4,5-d][1,3]diazin-4-yl}sulfanyl)propanamide | 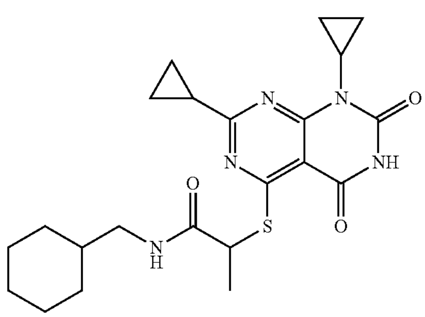 [SMILES: CC(Sc1nc(C2CC2)nc2c1c(=O)[nH]c(=O)n2C1CC1)C(=O)NCC1CCCCC1] | Not obtained | Insoluble |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 47 | N-{[4-(dimethylamino)phenyl]-methyl}-2-({[(3-methylphenyl)carbamoyl]-methyl}sulfanyl)-N-(propan-2-yl)acetamide | 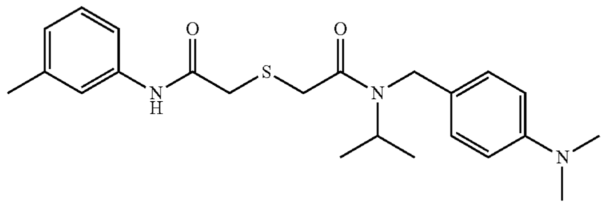 | 4.6 ± 0.2 | 12 |
| 48 | (1S,5R)-3-(6-methylpyridazin-3-yl)-6-[(pyridin-2-yl)methyl]-3,6-diazabicyclo[3.2.2]nonan-7-one | 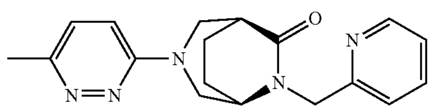 [SMILES: Cc1ccc(N2C[C@@H]3CC[C@H](C2)N(Cc2ccccn2)C3=O)nn1] | 3.0 ± 0.4 | 36 |
| 49 | 4-[(4-methylphenyl)sulfanyl]-1-({4H,5H,6H,7H-pyrazolo[1,5-a]pyrazin-2-yl}methyl)piperidine | 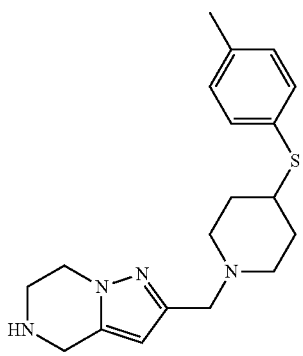 [SMILES: Cc1ccc(SC2CCN(Cc3cc4n(n3)CCNC4)CC2)cc1] | 2.9 ± 0.2 | 39 |
| 50 | 3-(2,5-dioxo-3-{[(E)-N-[(1-phenylethyl)imino]carbamimidoyl]sulfanyl}pyrrolidin-1-yl)benzoic acid | 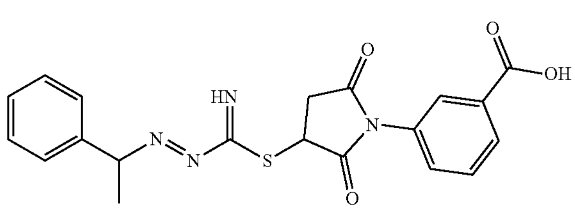 [SMILES: CC(/N=N/C(=N)SC1CC(=O)N(c2cccc(C(=O)O)c2)C1=O)c1ccccc1] | 3.3 ± 0.0 | 31 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 51 | 2-{[(7,8-dimethyl-4-oxo-1,4-dihydroquinolin-2-yl)methyl]sulfanyl}-N-(2-ethoxyphenyl)acetamide | 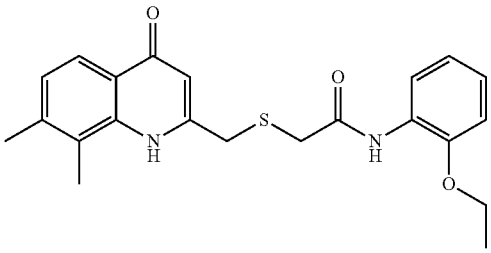 [SMILES: CCOc1ccccc1NC(=O)CSCc1cc(=O)c2ccc(C)c(C)c2[nH]1] | 3.7 ± 0.6 | 24 |
| 52 | 2-{[2-oxo-2-(1,2,3,4-tetrahydroquinolin-1-yl)ethyl]sulfanyl}-N-phenylacetamide | 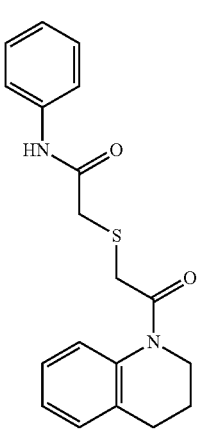 [SMILES: O=C(CSCC(=O)N1CCCc2ccccc21)Nc1ccccc1] | 2.4 ± 0.4 | 44 |
| 53 | 2-[(tert-butylcarbamoyl)amino]-2-oxoethyl 2-[({4-oxo-5-phenyl-3H,4H-thieno[2,3-d]pyrimidin-2-yl}methyl)sulfanyl]acetate | 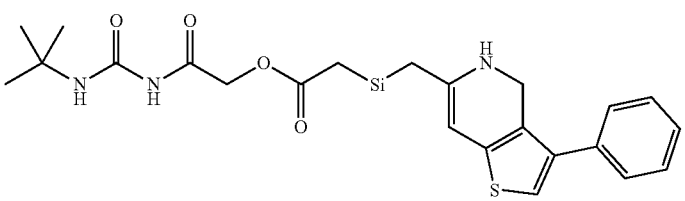 | 6.5 ± 0.4 | 5 |

TABLE 4-continued

Fusogenicity screening results and characteristics of 55 candidate mitofusin agonists (commercially sourced).

| Goodness of fit Rank | IUPAC Name | Structure | Aspect ratio (MEAN ± SEM)* | Fusogenicity Rank |
|---|---|---|---|---|
| 54 | 2-({2-[2-(3,5-dimethyl-1H-pyrazol-1-yl)ethyl]-8,9-dimethoxy-[1,2,4]triazolo[1,5-c]quinazolin-5-yl]sulfanyl)-N-(4-fluorophenyl)butanamide | 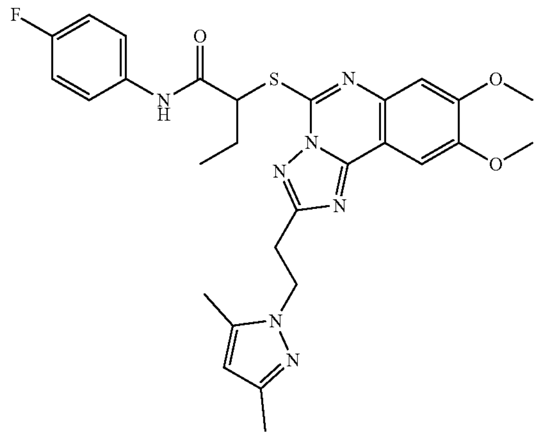 [SMILES: CCC(Sc1nc2cc(OC)c(OC)cc2c2nc(CCn3nc(C)cc3C)nn12)C(=O)Nc1ccc(F)cc1] | Not obtained | Insoluble |
| 55 | N-(2,4-dimethylphenyl)-2-(2-{[(6-hydroxy-2,4-dioxo-1,2,3,4-tetrahydropyrimidin-5-yl)[4-(propan-2-yl)phenyl]methyl]amino}-4-oxo-4,5-dihydro-1,3-thiazol-5-yl)acetamide | 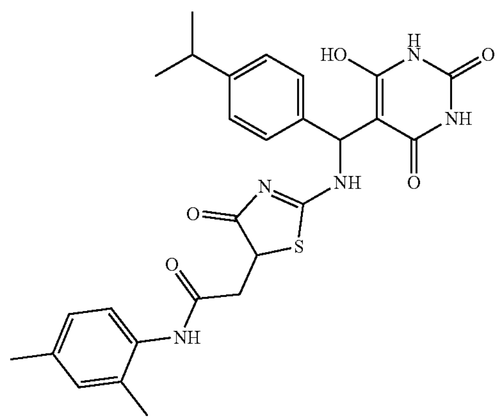 [SMILES: Cc1ccc(NC(=O)CC2SC(NC(c3ccc(C(C)C)cc3)c3c(O)[nH]c(=O)[nH]c3=O)=NC2=O)c(C)c1] | 3.1 ± 0.3 | 35 |

*Treatment with 1 µM compound.

Of nine compounds exhibiting apparent fusogenic activity on the initial screen (defined as an increase in mitochondrial aspect ratio to >5 after 24 h exposure to 1 mM compound), one (A8) was mildly cytotoxic and therefore did not undergo further evaluation. The remaining eight candidate fusogenic compounds were evaluated in a second series of experiments for their ability to provoke dose-dependent mitochondrial elongation. Fusogenicity of six compounds was confirmed, with $EC_{50}$ values between ~25 nM and 150 nM (see e.g., FIG. 25, TABLE 4). Two compounds (D9 and A9) failed validation in the secondary screen.

The present results defining a minimal fusogenic HR1 peptide (see e.g., FIG. 2B), identifying function-critical amino acids within the minipeptide (see e.g., FIG. 2C), and defining HR1-HR2 interacting amino acids through binding assays (see e.g., FIG. 2E and FIG. 2F) suggested that the Mfn2 HR1-HR2 interaction model (see e.g., Example 1) was imperfect, thus providing a likely reason for the poor correlation between in silico pharmacophore model fit of compounds B1 and A10 and their actual fusogenicity: Val372 was proven to be functionally dispensable and His380 paired with Asp725 rather than Lys720 as indicated in the original model. Moreover, the present studies revealed that phosphorylation of Ser378 in both the mitofusin agonist peptide and intact Mfn2 protein can change amino acids presented to the HR1-HR2 interface (see e.g., FIG. 11A); this key transitional feature was not part of the initial model. Compounds A10 and B1 (which ranked $4^{th}$ and $2^{nd}$ in fusogenicity, but $27^{th}$ and $31^{st}$ in fit to the pharmacophore model) and their chemosimilars conformed well to an Mfn2 HR1-HR2 interaction model incorporating these biological findings, as depicted in FIG. 1. These two compounds were therefore purified (see e.g., FIG. 3) and used in subsequent studies.

The ultimate goal was to design mitofusin agonists having optimal activity profiles. (Here, a "fusogenic compound" is defined as promoting mitochondrial elongation without a clearly defined mechanism, while a "mitofusin agonist" is a fusogenic compound that binds to the Mfn2 HR2 minipeptide target domain, promotes Mfn2 opening, and loses its fusogenic activity when endogenous mitofusin proteins are not present). Molecular modeling of class A and B agonists assumed that the minipeptide a-helix is comprised of 3.6 amino acids per turn with a 1.4 A pitch advance per amino acid, resulting in a distance of ~5.4 A between amino acids of adjacent turns. Aliphatic backbones assumed a distance between single bonded carbons of 1.54 A. Structures were created or edited using Marvin JS at the MolPort website and available chemical analogs (chemosimilars; TABLE 5) identified using the search function and a similarity parameter of 0.5.

TABLE 5

Characteristics of 12 (6 each) class A and class B mitofusin agonists (commercially sourced).

| ID | IUPAC Name | Stucture |
|---|---|---|
| pA | 3-phenyl-1-(4-phenylbutyl) urea | |
| A1 | 1-[2-(benzylsulfanyl)ethyl]-3-(2-methylcyclohexyl)urea | |
| A2 | 3-(4-fluorophenyl)-1-(4-phenylbutyl) urea | |
| A3 | 3-(3-methylphenyl)-1-(4-phenylbutyl) urea | |
| A4 | 3-(4-methylphenyl)-1-(4-phenylbutyl) urea | |

TABLE 5-continued

Characteristics of 12 (6 each) class A and class B mitofusin agonists (commercially sourced).

| ID | IUPAC Name | Structure |
|---|---|---|
| A5 | 3-(2-methyl-phenyl)-1-(4-phenylbutyl) urea | |
| pB | 2-(4-phenylbutan-amido)-4H,5H,6H-cyclopenta[b]-thiophene-3-carboxamide | |
| B1 | 2-{2-[(5-cyclopropyl-4-phenyl-4H-1,2,4-triazol-3-yl)sulfanyl]pro-panamido}-4H,5H,6H-cyclopenta[b]-thiophene-3-carboxamide | |
| B2 | 2-[2-(phenylsulfa-nyl)acetamido]-4H,5H,6H-cyclopenta[b]-thiophene-3-carboxamide | |
| B3 | 3-acetamido-N-(2-{[(4-methylphen-yl)methyl]sul-fanyl}ethyl)ada-mantane-1-carboxamide | |

TABLE 5-continued

Characteristics of 12 (6 each) class A and class B mitofusin agonists (commercially sourced).

| ID | IUPAC Name | Structure |
|---|---|---|
| B4 | 2-{2-[(4-benzyl-5-cyclopropyl-4H-1,2,4-triazol-3-yl)sulfanyl]pro-panamido}-thiophene-3-carboxamide | |
| B5 | N-benzyl-2-[2-({4-methyl-5-[(phenylcarb-amoyl)meth-yl]-4H-1,2,4-triazol-3-yl}sulfanyl)-acetamido]-4,5,6,7-tetrahydro-1-benzothio-phene-3-carboxamide | |

Fusogenic activity of commercially available small-molecule candidate pharmacophores (TABLE 4), focusing on those having structures that mimicked $Ser^{378}$-phosphorylated (class A) and -unphosphorylated (class B) minipeptide amino acid side chains were assessed (see e.g., FIG. 5, TABLE 5). It was reasoned that simultaneous application of class A and B agonists could enhance mitofusin by acting on both MFN2 $Ser^{378}$ phosphorylation states. Indeed, lead compounds (Cpd) A and B acted synergistically to promote mitochondrial fusion (see e.g., FIG. 26; compare to FIG. 5C). Therefore, Cpd A and B functionality were assimilated into a single molecule by creating Cpd A-B chimeras (see e.g., FIG. 11, FIG. 7, TABLE 6). The novel chimeric compounds incorporated functional features (e.g., potency, specificity) of both Cpds A and B which were functionally synergistic because they acted on different phosphorylated forms of MFN (see e.g., Example 2). Chimera B-A/long (B-A/l) potently stimulated mitochondrial fusion in MFN2-deficient cells (see e.g., FIG. 11B), competed for minipeptide binding at the MFN2 HR2 interaction site (see e.g., FIG. 11C), and was as effective as the combination of Cpds A+B in reversing mitochondrial dysmorphology provoked by the CMT2A mutant, MFN2 $Thr^{105}{\rightarrow}Met^{105}$ (MFN2 T105M) (see e.g., FIG. 11D). Fusogenic effects of Cpd A were specific for the $Asp^{378}$ mutant of MFN2 that mimicked $Ser^{378}$-phosphorylation, whereas Cpd B and chimera B-A/l were non-selective for the phosphomimic $Asp^{378}$ and non-phosphorylatable $Ala^{378}$ mutants (see e.g., FIG. 11E). Because they mimic WT MFN2 HR1 sequence and interact with HR2, mitofusin agonists evoked fusion to proportionally similar degrees in mitochondria expressing mutants of HR1 that are fusion deficient (see e.g., FIG. 11F; compare to FIG. 2H and FIG. 18). Small molecule mitofusin agonists required endogenous MFN1 or MFN2 to promote mitochondrial fusion, exhibited no promiscuous activity for structurally related dynamin, and did not compromise cell viability (see e.g., FIG. 27). On the basis of fluorescence resonance energy transfer (FRET) analysis of MFN2 labeled at the N and C termini, mitofusin agonists promoted an open MFN2 conformation favoring mitochondrial fusion, with a rank order paralleling that for HR2 binding and mitochondrial fusion (see e.g., FIG. 11G; compare to FIG. 11B and FIG. 11C), supporting allosteric activation.

Small molecule mitofusin agonists efficacy was shown in CMT2A model of neuronal degeneration. In CMT2A, MFN2 mutants produce mitochondrial "fragmentation" (decreased aspect ratio) and loss of normal membrane polarization through dominant inhibition of normal mitofusins. Experiments using $MFN1^{-/-}$, $MFN2^{-/-}$ deficient murine embryonic fibroblasts (MEFs) showed that in the absence of normal mitofusins, small-molecule mitofusin agonists did not improve mitochondria of cells expressing the guanosine triphosphatase (GTPase)-crippled MFN2 $Arg^{94}{\rightarrow}Gln^{94}$ (R94Q) or $Lys^{109}{\rightarrow}Ala^{109}$ (K109A) mutant (see e.g., FIG. 9A). However, mitofusin agonists corrected mitochondrial dysmorphology and reversed mitochondrial hypopolarization induced by these MFN2 mutants when MFN1 was present ($MFN1^{+/+}$, $MFN2^{-/-}$ MEFs) (see e.g., FIG. 9B). Mitofusin agonists also reversed mitochondrial fragmentation and hypopolarization in cultured neurons expressing (in addition to endogenous mitofusins) CMT2A mutants MFN2 R94Q (see e.g., FIG. 9C, FIG. 9D) or MFN2 T105M (see e.g., FIG. 9E). Thus, mitofusin agonists do not restore function of CMT2A MFN2 GTPase domain mutants. Rather, by destabilizing the fusion-permissive open conformation of endogenous MFN1 or MFN2, mitofusin agonists can overcome dominant suppression of mitochondrial fusion by these disease-causing dysfunctional proteins.

Clinical CMT2A classically affects long nerves innervating the lower and upper limbs. It is unclear how a principal defect in mitochondrial fusion would cause length-dependent neuronal disease. Conversely, disruption of axonal mitochondrial transport would be predicted to preferentially impact cells requiring mitochondrial transport over the greatest physical distance, such as the sciatic nerves originating in the spine and terminating in the foot. MFN2 interacts with Miro/Milton to promote mitochondrial trafficking in neurons, so the effects of mitofusin agonism on murine neuronal mitochondrial trafficking were tested. Chimera B-A/I reversed mitochondrial "clumping" (formation of static mitochondrial aggregates) and restored mitochondrial motility in cultured neurons expressing the CMT2A mutant MFN2 T105M (see e.g., FIG. 28A, FIG. 29). Mitochondrial hypopolarization and increased autophagy (see e.g., FIG. 28B, FIG. 30) and mitochondrial dysmorphology (see e.g., FIG. 28C, FIG. 30) were concomitantly corrected. Thus, a small molecule mitofusin agonist enhanced organelle and cell fitness in CMT2A neurons by promoting mitochondrial fusion and subcellular transport.

The concept of activating mitofusins to stimulate axonal mitochondrial trafficking was evaluated in sciatic nerves of mice expressing the CMT2A mutant MFN2 T105M in vivo. In normal sciatic nerves ~30% of axonal mitochondria exhibited robust bidirectional transport (see e.g., FIG. 28, FIG. 31). Mitochondria of MFN2 T105M sciatic nerves were severely hypomotile (see e.g., FIG. 28E, FIG. 32), but application of chimera B-A/I to MFN2 T105M sciatic nerves restored mitochondrial motility to within normal levels (see e.g., FIG. 28F, FIG. 32). Mobile mitochondria in WT and B-A/I-treated MFN2 T105M axons were smaller (see e.g., FIG. 28G), supporting in vitro observations distinguishing between MFN2-mediated mitochondrial dysmotility and defective fusion in CMT2A.

Improvement in mitochondrial factors in ALS and HD patient-derived fibroblasts treated with B-A/I was shown. Here, B-A/I enhances mitochondrial structural defects, reduces mitochondrial ROS levels, and improves mitochondrial membrane potential in ALS and HD patient-derived fibroblasts and has no effect on fibroblasts from control subjects (see e.g., FIG. 28).

Here, it was found that PINK1 phosphorylation of MFN2 at $Ser^{378}$ can alter the positions of $Met^{376}$ and $His^{380}$ (in the HR1 domain), which normally interact with HR2 domain amino acids to orchestrate MFN2 toggling between conformations that modulate mitochondrial fusion. MFN2 $Ser^{378}$ phosphorylation (by PINK1 or other kinases) regulated the positions of $Met^{376}$ and $His^{380}$ that interact with HR2 amino acids, thus directing MFN2 conformation and governing fusion. These findings establish a mechanistic basis for clinical observations that MFN2 $Met^{376}$ mutations to Ile, Thr, and Val can cause CMT2A.

Based on molecular modeling and a detailed structural and functional interrogation of MFN2-derived minipeptides encompassing $Met^{376}$, $Ser^{378}$, and $His^{380}$ small molecule mitofusin agonists were developed that reversed mitochondrial dysmorphometry and normalized impaired mobility evoked by 2 CMT2A MFN2 mutants. CMT2A is the prototypical clinical disorder of defective mitochondrial fusion, but impaired mitochondrial trafficking may play as great a role as mitochondrial fragmentation in CMT2A axonal degeneration. Individuals with CMT2A express one mutant MFN2 allele in combination with one normal MFN2 allele and harbor two normal MFN1 alleles. It is therefore possible that a therapeutic substrate for agonists to "supercharge" normal mitofusins and overcome dominant inhibition by MFN2 mutants. The observation that in vivo mitochondrial dysmotility provoked by CMT2A mutants can be normalized by mitofusin agonists mechanistically links abnormal mitochondrial trafficking in CMT2A to MFN2 dysfunction. Mitofusin agonists may also have therapeutic potential for neurological conditions other than CMT2A, such as Alzheimer's, Parkinson's, and Huntington's diseases, wherein mitochondrial dysmotility and fragmentation are contributing factors.

Materials and Methods

Cell Lines and Adenoviral Constructs

Wild-type MEFs were prepared from E10.5 c57/bl6 mouse embryos. SV-40 T antigen-immortalized Mfn1 null (CRL-2992), Mfn2 null (CRL-2993) and Mfn1/Mfn2 double null MEFs (CRL-2994) were purchased from ATCC. MEFs were subcultured in DMEM (4.5 g/L glucose) plus 10% fetal bovine serum, 1×nonessential amino acids, 2 mM L-glutamine, 100 U/ml penicillin and 100 ug/ml streptomycin.

Human Mfn2 Ser378 was mutated to Ala or Asp by site-directed mutagenesis using the QuikChange Lightning kit (Agilent Technologies Inc.) and primers:

Mfn2-S378D-fw 5'-cgactcatcatggacgacctgcacatggcggc-3' (SEQ ID NO: 7)

Mfn2-S378D-rv 5'-gccgccatgtgcaggtcgtccatgatgagtcg-3' (SEQ ID NO: 8)

Mfn2-S378A-fw 5'-gactcatcatggacgccctgcacatggcg-3' (SEQ ID NO: 9)

Mfn2-S378A-rv 5'-cgccatgtgcagggcgtccatgatgagtc-3' (SEQ ID NO: 10)

Mfn2 and its mutants were sub-cloned into adenoviral vector Type 5 (dE1/E3) with RGD-fiber modification (Vector Biolabs) using BamHI/XhoI. All constructs were verified by Sanger DNA sequencing. Adeno-viral PINK1 was purchased from Vector Biolabs. Immunoblotting used mouse anti-Mfn2 (Abcam #ab56889, 1: 1000), anti-PINK1 (Sigma #P0076, 1: 500), and beta-actin (Santa Cruz Biotechnology #sc-81178, 1:1000). Protein detection and digital acquisition used peroxidase-conjugated anti mouse secondary antibody (Cell Signaling #7076S, 1:2500) and Western Lightning PLUS ECL substrate (Perkin Elmer 105001EA) on a Li—COR Odyssey instrument.

Peptide Studies

The C-terminal and N-terminal Mfn2 367-384Gly peptides and Ala substituted variants of Mfn2 374-384 were chemically synthesized and introduced into cells using TAT47-57 conjugation (ThermoFisher Scientific). Except when indicated, 1 mM stocks in sterile water were diluted into culture media 1:1000 to achieve a final concentration of 1 µM. Cells were treated overnight.

For Alanine scanning the following peptides were synthesized:

(NH3) GIADSLHMAARGGYGRKKRRQRRR (COOH) (SEQ ID NO: 11)

(NH3) GIMASLHMAARGGYGRKKRRQRRR (COOH) (SEQ ID NO: 12)

(NH3) GIMDALHMAARGGYGRKKRRQRRR (COOH) (SEQ ID NO: 13)

(NH3) GIMDSAHMAARGGYGRKKRRQRRR (COOH) (SEQ ID NO: 14)

(NH3) GIMDSLAMAARGGYGRKKRRQRRR (COOH) (SEQ ID NO: 15)

The following peptides were synthesized for Ser378 substitution studies:

(NH3) GIMDSLHAAARGGYGRKKRRQRRR (COOH) (SEQ ID NO: 16)

(NH3) GIMDDLHMAARGGYGRKKRRQRRR (COOH) (SEQ ID NO: 17)

(NH3) GIMDS(p)LHMAARGGYGRKKRRQRRR (COOH) (SEQ ID NO: 18)

(NH3) GIMDGLHMAARGGYGRKKRRQRRR (COOH) (SEQ ID NO: 19)

(NH3) GIMDCLHMAARGGYGRKKRRQRRR (COOH) (SEQ ID NO: 20)

(NH3) GIMDNLHMAARGGYGRKKRRQRRR (COOH) (SEQ ID NO: 21)

Nuclear Magnetic Resonance (NMR) of HR1 Peptide Structure

Carboxyl terminal-amidated S378 parent and substituted peptide were synthesized for NMR studies:

Mfn2-371-384 (378S)-AVRGIMDSLHMAAR (SEQ ID NO: 22)

Mfn2-371-384 (378S(p))-AVRGIMD[S(p)]LHMAAR (SEQ ID NO: 23)

Proton 2D NOESY and $^{15}$N-$^1$H heteronuclear single quantum coherence overlay spectra of the above peptides were recorded on 600 MHz Bruker Avance III spectrometer equipped with cryoprobe, at 15° C., pH 6, 50 mM NaCl, with each peptide at 2 mM concentration. Distance restraints were derived from observed NOE interactions between hydrogens within each peptide, and torsion angle restraints (φ and ψ) were derived from the observed chemical shifts (for C, H and N nuclei). The calculations used only experimental data; no theoretical molecular dynamics simulations/refinements were applied.

The helical structures/propensities in these peptides were not inferred or assumed from any single type of data. "Diagnostic" NOEs, in particular dNN and dab(i, i+3), were present in 200 ms and 500 ms mixing time H-H NOESY experiments, wherever signals could be resolved. The structural ensemble calculations used only restraints derived from NMR experiments. Distance restraints were derived from observed NOE interactions between hydrogens within each peptide, and torsion angle restraints (f and y) were derived from the observed chemical shifts (for C, H and N nuclei).

Both ensembles show preponderance of helical conformation between 378-383. These are more regular in phosphopeptide ensemble (see e.g., FIG. 16C). Both ensembles show no regular conformation between 371-376, consistent with a lack of observed NOEs and values of chemical shifts characteristic for unstructured sequences. At the current level of precision, there is little difference between two ensembles in positions of side chains for residues 379-383. The almost identical 13C/1H chemical shifts of these methyl groups also suggest the similarity of their positions and local environments. However, the backbone amide (N—H) and Ca signals clearly show differences, beyond the obvious one caused by phosphate esterification of serine. The amide signals shifted down-field (to higher values), a characteristic observed when amides form (or strengthen) hydrogen bonds within peptides. In general, the helical secondary structure is often stabilized by a negatively charged group "capping" the positive N-terminal end of the helix dipole. Here, a phosphorylation of Ser 378 can produce H-bonding for the amide of Leu-379 and the negative phosphate can additionally stabilize the helical turns following 379, providing an explanation for observed down-field shifts (i.e., H-bonding induced) in amides of 380, 381 and 382. MFN2 FRET for conformational studies Mfn2 FRET probes contained N-termini-ceruleum and C-termini-mVenus fused to the human (h) mitofusin protein as previously described. FRET analyses were performed either on mitochondria isolated from Mfn1/Mfn2 null MEFs expressing the WT hMfn2 FRET-hMfn2 protein or intact Mfn1/Mfn2 null MEFs expressing WT or mutant Mfn2 FRET proteins (50 MOI). For isolated mitochondria studies 65 μg of organelle protein was used for each reaction in a total volume of 100 μl diluted in 10 mM Tris-MOPS (pH 7.4), 10 mM EGTA/Tris, and 200 mM sucrose. 1 μM of mitofusin agonist in DMSO was added simultaneously with 2 μM mitofusin antagonist peptide, incubated in dark at room-temperature for 30 minutes, and FRET signal corrected for Cerulean signal analyzed using a Tecan Safire II multi-mode plate reader in polystyrene 96 well assay plate (Costar 3916). Data acquisition was: FRET—Excitation 433/8 nm, Emission 528/8 nm; Cerulean—Excitation 433/8 nm, Emission—475/8 nm. Isolated mitochondria of non-infected cells were used to subtract background, and FRET signals were normalized to respective cerulean signals. The % changes in FRET/Cerulean provoked by mitofusin antagonist peptide and reversed by different mitofusin agonist small molecules were compared to Mfn2-FRET mitochondria treated with water and DMSO, the vehicles for Mfn antagonist peptide and mitofusin agonist, respectively.

For FRET in intact cells, Mfn1/Mfn2 double null MEFs at 70% confluence were infected with adenoviri expressing FRET-hMfn2, FRET-hMfn2 (S378A) or FRET hMfn2 (S378D) at 50 MOI. Two-days after transduction and 1 hour after application of 1 μM Mfn2 antagonist mini-peptide MP2 to promote the closed/inactive Mfn conformation, cells were released from tissue culture substrate with trypsin/EDTA, washed, and transferred to a polystyrene 96 well assay plate (Costar 3916; 20,000 cells/50 ml/well). Fifty-microliters of modified Krebs-Henseleit buffer containing DMSO (vehicle) or 1 μM mitofusin agonist was added with gentle agitation for 10 min at room temperature. FRET and cerulean signals were assayed in a 96-well plate reader (TriStar 2S LB 942, Berthold Technologies) with 1 sec reading times at low sensitivity. Filters combinations are as follows: FRET—Excitation 430/10, Emission 535/25; Cerulean—Excitation 430/10, Emission—475/20. Signals from non-infected cells were used for background correction. FRET was normalized to the respective cerulean signal for each well.

MFN2 Amino Terminal FLAG Epitope Unmasking Assay

HEK293 cells were transfected with wild-type or mutant MFN2 having an amino terminal FLAG epitope tag using Lipofectamine 3000 (Invitrogen) per the manufacturer's instructions. After 48 hours cells mitofusin agonists or DMSO vehicle were added at the indicated concentrations for 1 hour (37° C.). Cells were harvested and proteins extracted using Invitrogen cell extraction buffer supplemented with protease and phosphatase inhibitors (Roche). Proteins were quantified using the Bradford assay (Biorad). Two mg aliquots of protein extract were incubated in a final volume of 500 μl with 50 μl (bed volume) of ANTI-FLAG M2 Affinity Gel (Sigma) with gentle agitation for 2 hours at 4° C. Beads were washed twice with 1 ml of cold PBS buffer and proteins were eluted by adding 100 μl of reducing SDS sample buffer. Samples of input extract and immunoprecipitated proteins were size-separated on SDS-PAGE mini-gels and immunoblotted for MFN2.

HR1 Peptide-HR2 Target Binding Assay

Target HR2 peptide sequence modified to include amino terminal 6×His tags and Gly linkers, were bonded to Ni-NTA resin (4.4 μg/ml) (Quiagen) and used as immobilized "receptor" for amino-FITC-tagged Mfn2 374-384 (ligand) in which the Ser analogous to Ser378 was replaced with Asp to confer the negative charge essential for activity. FITC peptide ligands were suspended at 1 mM in 30% DMSO, 70% water (to minimize spontaneous aggregation) and diluted into binding buffer (de-ionized water). For the displacement binding, 2.5 nmol of FITC labeled agonist peptide was used in the presence or absence of different amounts of competing compounds. Resin-bound FITC signal (485 nm excitation/538 nm emission) measured in a 96 well spectrofluorometer (Spectramax M5e, Molecular Devices)

represented binding to HR2 target. Competition binding isotherms were plotted and $IC_{50}$ values calculated using Prism 7 (GraphPad).

Sequences for binding assay components are:

(NH3) HHHHHH-GGGG-AAMNKKIEVLD-SLQSKAKLLRNKA-GG (COOH) (target) (SEQ ID NO: 24)

(NH3) HHHHHH-GGGG-AAMNKKI-EVAASAQSKAKLLRNKA-GG (COOH) (target mutant) (SEQ ID NO: 25)

(NH3) FITC-GGGG-AVRGIMDSLHMAAR-GG (COOH) (FITC labeled Ser peptide) (SEQ ID NO: 26)

(NH3) FITC-GGGG-AVRGIMDDLHMAAR-GG (COOH) (FITC labeled Asp peptide) (SEQ ID NO: 27)

(NH3) FITC-GGGG-AVRGIMDALHMAAR-GG (COOH) (FITC labeled Ala peptide) (SEQ ID NO: 28)

Protein and Peptide Modeling

The hypothetical structures of human Mfn2 were developed using the I-TASSER Suite package. The putative closed conformation is based on structural homology with bacterial dynamin-like protein (PDB: 2J69), human Mfn1 (PDB:5GNS), and *Arabidopsis thaliana* dynamin-related protein (PDB: 3T34). The putative open conformation was based on structural homology with human Opa1, retrieved from the following structures: rat dynamin (PDB: 3ZVR), human dynamin 1-like protein (PDB: 4BEJ), and human myxovirus resistance protein 2 (PDB: 4WHJ). Minipeptide and protein modeling used PEP-FOLD3 (http://bioserv.rpbs.univ-paris-diderot.fr/services/PEP-FOLD3/) and UCSF Chimera, respectively.

Protein Alignment and Phylogenetic Analysis

Mfn2 orthologous sequences were retrieved from the Ensembl project database. Protein alignments were performed using Clustal Omega.

In Vitro PINK1-Mfn2 Phosphorylation Assay

In silico prediction of kinases that might phosphorylate Mfn2 Ser378 in the peptide sequence AVRLIMDSLHMAARE used GPS 3.0 (http://gps.biocuckoo.org). GRK2/bARK1 was the top hit (score of 31.595), and GRK isoforms comprised 5 of the top 7 hits; ROCK kinase (score 15.919) and PKCa (score 11.48) were the other two hits. PINK1 kinase is not represented at this site, and no other sites reported any likely kinases for Mfn2 Ser378.

In vitro phosphorylation of Mfn2 by PINK1 and GRK kinases used a modified published protocol. Briefly, 20 mg of recombinant human Mfn2 (expressed in HEK293 cells; OriGene: TP326143) plus 10-20 mg *Tribolium castaneum* PINK1 (expressed in *E. coli*; Ubiquigent: 66-0043-050) or 10 mg human GRK2 (Invitrogen: PV3361) were combined in kinase buffer (20 mM Hepes pH 7.4, 10 mM DTT, 0.1 mM EGTA, 0.1 mM ATP and 10 mM MgCl2) and the reactions allowed to proceed at 37° C. for 4 hours or overnight.

Mass Spectrometric Analysis of Mfn2 Phosphopeptides

Preparation of Peptides for Nano-LC-MS.

The in vitro kinase solution that contained 10 μg of Mfn2 was spiked (10 μL) with a mixture of five carrier proteins (10 μg each). The mixture consisted of human apo-transferrin (Sigma, T4382), bovine α-casein (Sigma, C6780), bovine β-casein (Sigma, C6905), bovine ribonuclease (Sigma, R7884), and bovine albumin (Sigma A7030) in 100 mM Tris buffer, pH 7.6 with 4% SDS and 100 mM DTT. The sample was lyophilized overnight in a VirTis AdVantage Lyophilizer (SP Scientific).

Peptides were prepared using a modified filter-aided sample preparation method: dried sample was dissolved in 60 μL of Tris buffer, pH 7.6 that contained 4% SDS and 100 mM DTT and denatured by heating (95° C.) for 5 min. The sample was then alkylated with 50 mM iodoacetamide (Sigma, A3221) for 1 h at room temperature in the dark. After the addition of 1 ml of 50 mM ammonium bicarbonate buffer (pH 8.5) containing 8M urea (UA) and vortexing, equal volumes of the samples were transferred to two YM-30 filter units (Millipore, Ref No. MRCF0R030) and spun for 14 min at 10,000 rcf (Eppendorf, Model No. 5424). Filters were washed with 200 μl of UA and the spin-wash cycle was repeated twice. The sample was then exchanged into digest buffer with the addition of 200 μl of ammonium bicarbonate buffer, pH 8.5 (ABC) and centrifugation (11,000 rcf) for 10 min. After transferring the upper filter unit to a new collection tube, 80 μL of the ABC buffer was added and the sample was digested with trypsin (1 μg) for 4 h at 37° C. The digestion was continued overnight after another addition of trypsin. Filter units were then spun at 11,000 rcf for 10 min with a subsequent filter washing step with 0.5 M NaCl (50 μL) followed by centrifugation (14,000 rcf for 10 min). The digest was then extracted three times with 1 ml of ethyl acetate and acidified with trifluoroacetic acid (TFA) (50%) to a final concentration of 1%. The pH was <2.0 using pH paper. Solid phase extraction of the peptides was performed using sequential, robotic pipetting with C4 and porous graphite carbon micro-tips (Glygen). The peptides were eluted with 60% acetonitrile in 0.1% TFA and pooled for drying in a Speed-Vac (Thermo Scientific, Model No. Savant DNA 120 concentrator) after adding TFA to 5%. The peptides were dissolved in 20 μL of 1% acetonitrile in water. An aliquot (10%) was removed for quantification using the Pierce Quantitative Fluorometric Peptide Assay kit (Thermo Scientific, Cat. No. 23290). The remaining sample was transferred to an autosampler vial (Sun-Sri, Cat. No. 200046), dried in the SpeedVac and dissolved in 2.7 μL of 0.1% TFA.

Nano-LC-MS/MS Analysis of Phosphopeptides—

The samples were loaded (2.5 μL) at a constant pressure of 700 bar at 100% of mobile phase solvent A (0.1% FA) onto a 75 μm i.d.×50 cm Acclaim® PepMap 100 C18 RSLC column (Thermo-Fisher Scientific) using an EASY nanoLC (Thermo Fisher Scientific). Before sample loading the column was equilibrated with 100% A using 20 μL at 700 bar. Peptide chromatography was initiated with A containing 2% B (100% ACN, 0.1% FA) for 5 min, then linear increased to 20% B over 100 min, to 32% B over 20 min, to 95% B over 1 min and held at 95% B for 7 min, at a flow rate of 300 nL/min. The data dependent mode analysis was performed with in the Orbitrap mass analyzer (Thermo-Fisher Scientific Q-Exactive™ Plus Hybrid Quadrupole-Orbitrap™ mass spectrometer) with a scan range of m/z=375 to 1500 and a mass resolving power set to 70,000. Ten data-dependent high-energy collisional dissociations were performed with a mass resolving power set to 17,500, a fixed lower value of m/z=100, an isolation width of 2 Da, and a normalized collision energy of 27. The maximum injection time was 60 ms for parent-ion accumulations and 60 ms for product-ion analysis. The parent ions that were selected for MS2 were dynamically excluded for 20 sec. The automatic gain control was set at a target ion value of 1e6 for MS1 scans and 1e5 for MS2 acquisition. Peptide ions with charge states of one or >8 were excluded for CID acquisition.

Phosphopeptide data from the PINK kinase reactions were also acquired in targeted mode. The full-scan mass spectra were acquired by the Orbitrap mass analyzer with a scan range of m/z=350-2000 and a mass resolving power set to 70,000. The CID spectra were acquired at resolving power of 17,500 with maximum table time of 120 ms. The loop count was set to 4 and the isolation width was 2 Da. The acquisition of CID spectra were triggered by an inclusion list of four m/z values for the +2 and +3 charge state of the natural abundance phosphorylated and non-phosphorylated peptide (see e.g., TABLE 3, above, for values). An AGC target value of 3e6 was used for MS scans and 2e5 for MS/MS scans. The unprocessed LC-MS data were analyzed using SKYLINE (version 3.6.9).

The high-resolution ion chromatograms for the y ion series from the CID phosphopeptide spectra shown in FIG. 2G were acquired during the LC-MS analysis of the tryptic digest of human recombinant Mfn2 after phosphorylation with PINK1. The corresponding chromatograms from the synthetic, isotope-labeled phosphopeptide co-eluted with the PINK1 product and all ions were observed with the same proportional intensities in the CID spectra as shown in the adjacent stacked bar charts, confirming the sequence identity and phosphorylated residue location. The expected mass increment of 10 Da from the Arg-[13C6] [15N4] residue was observed for all y ions in the CID spectra of the synthetic phosphopeptide. The spectra from the PINK1 phosphopeptide product and the synthetic phosphopeptide were acquired from the triply charged parent ions at m/z=446.543 and m/z=449.880, respectively. The site of phosphorylation was confirmed from the series of y ions with neutral losses of the phosphate moiety ($H_3PO_4$) that were observed as y8-H3PO4 (m/z=882.427), and y7-H3PO4+2 (m/z=384.203). The same ion series was observed in the CID spectrum of the synthetic peptide with the expected 10 Da mass increment, y8-$H_3PO_4$ (m/z=892.432) and y7-$H_3PO_4$ (m/z=777.404). Using the synthetic phosphorylated and non-phosphorylated peptides, it was determined that the phosphopeptide consistently eluted 9.5-10.5 min later in all LC-MS analyses. All tandem spectra that were acquired from a precursor ion were also analyzed at m/z=446.543 for any evidence of phosphorylation at Ser-378 in replicate PINK1 experiments, GRK phosphorylation experiments, and in a digest of the recombinant Mfn2 protein without added kinase. Phosphopeptides with the Ser-378 site were only observed from the PINK1 phosphorylation experiments.

Dextran Uptake Assays of Dynamin Function

Wild-type MEFs (100,000 cells) were grown on cover slips. When they reached 60% confluency they were washed with serum-free DMEM. Subsequently, cells were incubated in serum-free DMEM containing either 1 µM compound A; B; B/A-L; dynasore (Calbiochem) or DMSO only (vehicle) for 30 min at 37° C. AF594-labelled 10,000 MW Dextran (Invitrogen) was then added to a final concentration of 0.5 mg/ml and incubated for additional 10 min. at 37° C. Internalization was stopped by washing three-times with ice-cold PBS. Residual dextran was removed by washing with 0.1 M Na acetate, 0.05 M NaCl for 10 min. Samples were fixed in 4% PFA followed by confocal microscopy analysis.

Confocal Live Cell Studies of Mitochondria

Confocal imaging used a Nikon Ti Confocal microscope equipped with a 60×1.3NA oil immersion objective. All live cells were grown on cover slips loaded onto a chamber (Warner instrument, RC-40LP) in modified Krebs-Henseleit buffer (138 mM NaCl, 3.7 mM KCl, 1.2 mM KH2PO4, 15 mM Glucose, 20 mM HEPES and 1 mM CaCl2) at room temperature.

Cells were excited with 408 nm (Hoechst), 561 nm (MitoTracker Green and Calcein AM, GFP), or 637 nm (TMRE, MitoTracker Orange, Ethidium homodimer-1, and AF594-Dextran) laser diodes. For mitochondrial elongation studies mitochondrial aspect ratio (long axis/short axis) was calculated using automated edge detection and Image J software. Mitochondrial depolarization was calculated as % of green mitochondria visualized on MitoTracker Green and TMRE merged images, expressed as green/(green+yellow mitochondria)×100.

Chemical Synthesis, Purification and Analyses of Novel Small Molecule Mitofusin Agonists Four A-B chimeric molecules designed to incorporate different characteristics of Cpds A and B (TABLE 6) were synthesized de novo:

TABLE 6

Characteristics of 4 novel, newly synthesized chimeric class A/B mitofusin agonists (chimeras)

| Compound ID | IUPAC Name | Structure | M.W. | Formula | Purity |
|---|---|---|---|---|---|
| A-B/s | 2-[2-(benzylsulfanyl)propanamido]-4H,5H,6H-cyclopenta[b]thiophene-3-carboxamide | 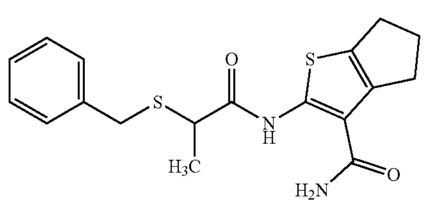 [SMILES: CC(SCc1ccccc1)C(=O)Nc1sc2c(c1C(N)=O)CCC2] | 360.4936 | C18H20N2O2S2 | 98.8% |
| B-A/s | 2-[(5-cyclopropyl-4-phenyl-4H-1,2,4-triazol-3-yl)sulfanyl]-N-(2-methylcyclohexyl)-propanamide | 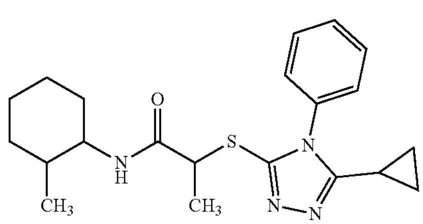 [SMILES: CC(Sc1nnc(C2CC2)n1-c1ccccc1)C(=O)NC1CCCCC1C] | 384.53822 | C21H28N4OS | 99.9% |

TABLE 6-continued

Characteristics of 4 novel, newly synthesized chimeric class A/B mitofusin agonists (chimeras)

| Compound ID | IUPAC Name | Structure | M.W. | Formula | Purity |
|---|---|---|---|---|---|
| A-B/1 | 2-(3-(2-(benzyl-thio)ethyl)ureido)-5,6-dihydro-4H-cyclopenta[b]thiophene-3-carboxamide | | 375.50824 | C18H21N3O2S2 | 97.6% |
| B-A/1 | 1-(2-((5-cyclopropyl-4-phenyl-4H-1,2,4-triazol-3-yl)thio)ethyl)-3-(2-methylcyclohexyl)-urea | | 399.55286 | C21H29N5OS | 99.9% |

Chimera B-A/l-(1-(2-((5-cyclopropyl-4-phenyl-4H-1,2,4-triazol-3-yl)thio)ethyl)-3-(2-methylcyclohexyl)urea) was synthesized by Enamine Ltd as a racemic mixture (see e.g., FIG. 33). Step A: 5-Cyclopropyl-4-phenyl-4H-1,2,4-triazole-3-thiol (1) (1 mmol) was dissolved in 1 mL of $CH_3OH/H_2O$ (50:50), then NaOH (1 mmol) was added, stirred for 10 min, and 2-(boc-amino)ethyl bromide (2) (1 mmol) was added at 25° C. The reaction was allowed to stir for 3 hours then poured into 10 mL water. The precipitate was filtered and dried to get a solid. The crude product was dissolved in 10 ml of trifluoroacetic acid (TFA), and heated at 50° C. for 10 h to remove the solvent and 10 ml of water and NaOH (1 mmol) were added. The mixture was stirred at room temperature for 1 h, filtered, and washed with water (50 ml). The residue was purified using reversed phase high-performance liquid chromatography RP-HPLC. Yield: 52%. Step B: 2-((5-Cyclopropyl-4-phenyl-4H-1,2,4-triazol-3-yl)thio)ethan-1-amine (3) (0.5 mmol) and 1,1'-carbonyldiimidazole (CDI) (1 mmol) were dissolved in 0.6 ml $CH_3CN$, the mixture was kept at a temperature of 70° C. for 1 h, and then the 2-methyl-cyclohexylamine (4) (0.5 mmol) was added. The mixture was heated for 2 hours at 70° C., then filtered, and evaporated. The residue was purified using RP-HPLC to give the desired product as a white solid; Purity: 99.99% (see e.g., FIG. 34A); Yield: 32%; C21H29N5OS; MW 399.5. Liquid chromatography with high-resolution mass spectrometry using electrospray ionization LC-HRMS (ESI) with expected m/z 399.25 showed exact mass found 400.2 $[M+H]^+$ (see e.g., FIG. 34B). Chemical structure was confirmed by proton nuclear magnetic resonance ($^1H$ NMR) and carbon-13 nuclear magnetic resonance ($^{13}C$ NMR) (see e.g., FIG. 35). $^1H$ NMR (400 MHz, DMSO-d6) δ 7.60 (m, 3H), 7.48 (m, 2H), 5.95 (dt, 1H), 5.81 (dd, 1H), 3.26 (q, 2H), 3.07 (t, 2H), 3.00 (m, 1H), 1.62 (m, 4H), 0.99 (m, 10H), 0.81 (d, 2H), 0.75* (d, 1H). $^{13}C$ NMR (126 MHz, $CDCl_3$) δ 157.45, 156.97, 149.14, 133.14, 129.74, 127.34, 53.83, 48.83, 39.00, 34.12, 33.92, 32.69, 25.39, 25.30, 19.20, 7.15, 5.67.

Chimera B-A/s (2-((5-cyclopropyl-4-phenyl-4H-1,2,4-triazol-3-yl)thio)-N-(2-methylcyclohexyl)propanamide) was synthesized by Enamine as a racemic mixture (see e.g., FIG. 36): 5-Cyclopropyl-4-phenyl-4H-1,2,4-triazole-3-thiol (1) (0.5 mmol) was dissolved in 1 mL of $CH_3OH$, then KOH (0.5 mmol) was added, stirred for 10 min, and then 2-chloro-N-(2-methylcyclohexyl)propanamide (2) (0.5 mmol), was added at room temperature. The reaction was allowed to stir for 3 hours then poured into 10 mL water. The precipitate was filtered and dried, then was purified using RP-HPLC to give the title compound as a light brown solid; Purity: 99.99% (see e.g., FIG. 37A); Yield: 43%; C21H28N4OS; MW 384.54. LC-HRMS (ESI): expected m/z 384.24, exact mass found 385.2 $[M+H]^+$ (see e.g., FIG. 37B). Chemical structure was confirmed by $^1H$ NMR and $^{13}C$ NMR (see e.g., FIG. 38): $^1H$ NMR (500 MHz, DMSO-$d_6$) δ 8.01 (dd, 1H), 7.60 (m, 3H), 7.45 (m, 2H), 4.27 (qd, 1H), 3.14 (qd, 1H), 1.65 (m, 3H), 1.57 (m, 2H), 1.44 (d, 2H), 1.40 (d, 1H), 1.16 (m, 4H), 0.93 (m, 3H), 0.86 (m, 2H), 0.78 (d, 2H), 0.71* (d, 1H). $^{13}C$ NMR (126 MHz, DMSO-$d_6$) δ 158.01, 139.15, 129.31, 128.75, 127.18, 54.27, 49.26, 39.36, 38.56, 35.24, 34.61, 34.48, 31.88, 31.83, 25.88, 25.79, 19.70.

Chimera A-B/I: (2-(3-(2-(benzylthio)ethyl)ureido)-5,6-dihydro-4H-cyclopenta[b]thiophene-3-carboxamide) was synthesized by Enamine Ltd (see e.g., FIG. 39). Step A: Under an argon atmosphere, into a reaction vessel of 2-amino-5,6-dihydro-4H-cyclopenta[b]thiophene-3-carboxamide (1) (1.0 mmol), potassium iodide (0.8 mmol), potassium carbonate (1.0 mmol), N,N-dimethylformamide (DMF) 1 mL and 2,2,2-trifluoroethyl chloroformate (2) (1.0 mmol) were added. The reaction vessel was heated to 80° C., and the mixture was stirred for 12 hours. The reaction vessel was cooled to room temperature, and ethyl acetate 100 mL was added. The organic layer was washed with water (50 mL), saturated brine (50 mL), and dried over sodium sulfate. The sodium sulfate and the solvent were distilled off. Compound 3 was purified using RP-HPLC. Yield: 54%. Step B: To a solution of 2 mmol of a 2,2,2-trifluoroethyl (3-carbamoyl-5,6-dihydro-4H-cyclopenta[b]thiophen-2-yl) carbamate (3) and 2 mmol of an 2-(benzylthio)ethan-1-amine (4) in 2 mL of acetonitrile, 0.2 mmol of 1,8-diazabicyclo[5.4.0]undec-7-ene (DBU) was added. The reaction mixture was heated at 80° C. for 4 h. Then 0.5-2 mL of water was added to the hot reaction mixture. The product precipitated from the solution upon cooling to room temperature then filtered and concentrated in vacuum. The residue was purified using RP-HPLC to give the title compound as a brown solid. Purity: 97.56% (see e.g., FIG. 40A); Yield: 51%; C18H21N3O2S2; MW 375.51; LC-HRMS (ESI): expected m/z 375.13, exact mass found 376.0 $[M+H]^+$ (see e.g., FIG. 40B); Structure was confirmed by $^1H$ NMR and $^{13}$C NMR (see e.g., FIG. 41): $^1$H NMR (400 MHz, DMSO-d$_6$) δ 10.87 (s, 1H), 7.88 (s, 1H), 7.31 (m, 6H), 6.47 (s, 1H), 3.76 (s, 2H), 3.25 (q, 2H), 2.86 (t, 2H), 2.73 (t, 2H), 2.48 (m, 2H), 2.31 (p, 2H). $^{13}$C NMR (126 MHz, DMSO-d$_6$) δ 167.20, 153.47, 151.94, 138.52, 128.88, 128.84, 128.32, 107.82, 34.74, 30.66, 29.30, 28.22, 27.52.

Chimera A-B/s: (2-(2-(benzylthio)propanamido)-5,6-dihydro-4H-cyclopenta[b]thiophene-3-carboxamide) was synthesized by Enamine Ltd as a racemic mixture (see e.g., FIG. 42): Phenylmethanethiol (1) (0.5 mmol) was dissolved in 1 mL of CH$_3$OH, then ethylbis(propan-2-yl)amine (0.55 mmol) was added, stirred for 10 min, and then 2-(2-chloropropanamido)-4H,5H,6H-cyclopenta[b]thiophene-3-carboxamide (2) (0.5 mmol) was added. The reaction was allowed to stir at room temperature for 3 hours, and then poured into 10 mL water. The precipitate was filtered and dried, then was purified using RP-HPLC to give the title compound as a yellow solid; Purity: 98.76% (see e.g., FIG. 43A); Yield: 37%; C18H20N2O2S2; MW 360.49; LC-HRMS (ESI): expected m/z 360.12, exact mass found 361.2 [M+H]+(see e.g., FIG. 43B); Structure was confirmed by 1H NMR and 13C NMR (see e.g., FIG. 44): $^1$H NMR (500 MHz, DMSO-d$_6$) δ 12.49 (s, 1H), 7.64 (s, 1H), 7.33 (d, 2H), 7.28 (t, 2H), 7.22 (t, 1H), 6.70 (s, 1H), 3.83 (AB-system, 2H), 3.63 (q, 1H), 2.92 (t, 2H), 2.79 (t, 2H), 2.36 (q, 2H), 1.40 (d, 3H). $^{13}$C NMR (126 MHz, DMSO-d$_6$) δ 168.77, 167.06, 148.07, 139.07, 137.35, 131.71, 128.91, 128.37, 126.99, 111.30, 42.52, 34.88, 29.03, 28.22, 27.68, 17.57.

Purification Methods
Preparative HPLC

Purification was performed using HPLC (H$_2$O-MeOH; Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm) The material was dissolved in 0.7 mL DMSO. Flow: 30 mL/min. Purity of the obtained fractions was checked via the analytical LCMS. Spectra were recorded for each fraction as it was obtained straight after chromatography in the solution form. The solvent was evaporated in the flow of N$_2$ at 80° C. On the basis of post-chromatography LCMS analysis fractions were united. Solid fractions were dissolved in 0.5 mL MeOH and transferred into pre-weighted marked vials. Obtained solutions were again evaporated in the flow of N$_2$ at 80° C. After drying, products were finally characterized by LCMS and $^1$H NMR and 13C NMR.

Analytical Methods
HPLC/HRMS (ESI)

LC/MS analysis was carried out using Agilent 1100 Series LC/MSD system with DAD\ELSD and Agilent LC\MSD VL (G1956A), SL (G1956B) mass-spectrometer or Agilent 1200 Series LC/MSD system with DAD\ELSD and Agilent LC\MSD SL (G6130A), SL (G6140A) mass-spectrometer. All the LC/MS data were obtained using positive/negative mode switching. The compounds were separated using a Zorbax SB-C18 1.8 μm 4.6×15 mm Rapid Resolution cartridge (PN 821975-932) under a mobile phase (A—acetonitrile, 0.1% formic acid; B—water (0.1% formic acid)). Flow rate: 3 ml/min; Gradient 0 min—100% B; 0.01 min—100% B; 1.5 min—0% B; 1.8 min—0% B; 1.81 min—100% B; Injection volume 1 μl; Ionization mode atmospheric pressure chemical ionization (APCI); Scan range m/z 80-1000.

NMR $^1$H and $^{13}$C NMR spectra were recorded at ambient temperature using Bruker AVANCE DRX 500; Varian UNITYplus 400 spectrometers.

Mouse Hippocampal Neuron Preparation, Culture, and Live Cell Imaging

Neonatal mouse hippocampal neurons were cultured from brains of one day old Mfn2 T105M or non-transgenic sibling mouse pups as described. After 10 days of differentiating culture neurons were infected with Adeno-Cre to induce Mfn2 T105M expression or Adeno-βgal as a control (50 MOI). After an additional 72 hours mitofusin agonists or DMSO vehicle were added. For static confocal imaging neuronal mitochondria were labeled with adenoviral-expressed mitoGFP plus TMRE. Autophagy was measured by LC3 aggregation in neurons infected with adenoviral LC3-GFP. For time-lapse studies of mitochondrial trafficking bi-cistronic Adeno-Cre/GFP marked Cre expression and mitochondria were labeled with adeno-mitoDsRed. Confocal live cell images were acquired with a time-lapse of 1 frame every 90 seconds for 1 hour.

HB9-Cre/Mfn2 T105M Mouse Creation and Sciatic Nerve Studies

All mouse procedures were approved by the Institutional Animal Care and Use Committee of Washington University in St. Louis. C57BL/6-Gt(ROSA)26Sortm1(CAG-MFN2*T105M)Dple/J (stock no. 025322 donated by David Pleasure, University of California Davis) and B6.129S1-Mn×1tm4(cre)Tmj/J (here referred to as HB9-Cre; stock no. 006600 donated by Thomas Jessel of Columbia University) were purchased from The Jackson Laboratory. The HB9-Cre driver was bred onto the ROSA26 flox-stop Mfn2 T105 transgene to induce Mfn2 T105M expression in motor neurons. Age- and sex-matched C57/b6 mice or mice carrying the MFN2 T105 flox-stop transgene in the absence of Cre were studied as normal controls.

Sciatic nerves of 12-18 week old male or female MFN2 T105M mice were removed en bloc with the lumbar spine and axotomy at the tibial nerve, stained with TMEM (200 mM) for 30 minutes in prewarmed Neurobasal Medium without phenol red (Thermo Fisher Scientific) at room temperature, washed, and maintained on the stage of a Nikon A1Rsi Confocal Microscope at 37 degrees C. for time-lapse confocal studies. Images were acquired with a 40×oil immersion objective at 1 frame every 5 or 10 seconds for sequential 10 minute periods. Mitofusin agonist chimera B-A/I was added after the first 10 minute imaging period (final concentrations of 1 or 5 mM) and nerve axons imaged for another 40 minutes. Because there was no difference in mitochondrial trafficking or response to mitofusin agonist between male and female mice, the data were combined.

Statistical Methods

All data are reported as mean±SEM. Statistical comparisons (two-sided) used one-way ANOVA and Tukey's tests for multiple groups or Student's t-test for paired comparisons. p<0.05 was considered significant.

Cell Culture.

HD patient-derived fibroblast cell lines (GM04693 from 33-year-old male patient and GM05539 from 10-year-old male patient) were purchased from Invitrogen. ALS patient-derived fibroblasts (ALS 1: ND29509 from 55-year old male patient having SOD1 mutation; ALS 2: ND30327 having FUS1 mutation) and fibroblasts of control healthy individuals were purchased from Coriell Institute, USA. All fibroblast cultures were maintained in MEM supplemented with 15% (v/v) FBS and 1% (v/v) penicillin/streptomycin at 37° C. in 5% CO2-95% air. Galactose media was used, to increase mitochondria-dependent metabolism oxidative phosphorylation. Human fibroblasts were switched to grow for 48 h in DMEM deprived of glucose and containing galactose (4.5 g/l), 1% FBS, 5 mM sodium pyruvate and 2 mM L-glutamine for the studies.

Immunofluorescence.

Cells cultured in 8-well chamber slides were washed with cold PBS, fixed in 4% formaldehyde, and permeabilized with 0.1% Triton X-100. After incubation with 2% normal goat serum (to block nonspecific staining), fixed cells were incubated overnight at 4° C. with TOM20 antibody (1:500)

(Santa Cruz, USA). Cells were washed with PBS and incubated for 60 minutes with FITC-conjugated goat anti-rabbit IgG (1:500 dilution). The cells were then washed gently with PBS and counterstained with Hoechst 33342 (1:10,000 dilution, Molecular Probes) to visualize nuclei. The coverslips were mounted with Slow-fade anti-fade reagent (Invitrogen), and images were acquired at 60×using an All-in-One Fluorescence Microscope BZ-X700 (Keyence).

Mitochondrial Health Assays.

Cells were incubated with tetra-methyl-rhodamine methyl ester (TMRM, 25 nM, Invitrogen) in HBSS (Hank's balanced salt solution) for 30 min at 37° C., per the manufacture's protocol, and the fluorescence was analyzed to measure mitochondrial membrane potential. All data were normalized with respect to the fluorescence intensity of control cells. To determine mitochondrial ROS production, cells were treated with 5 µM MitoSOX™ Red, a mitochondrial superoxide indicator (Invitrogen) for 20 min at 37° C., according to the manufacturer's protocol, and fluorescence was analyzed using SpectraMax M2e (Molecular devices).

Autophagy Assay.

Activation of autophagy was measured using the autophagy assay kit (Sigma Aldrich) according to the manufacturer's protocol, using SpectraMax M2e (Molecular devices) (λex=333/λem=518 nm).

Example 6: Evolutionary Design of Small Molecule Mitofusin Agonists for In Vivo Use In vitro pharmacokinetic studies performed on the presently disclosed prototype small molecule mitofusin agonist, Regeneurin-S(S for the backbone sulfur; chimera B-A/I from Example 5), revealed it to be soluble, highly protein bound, stable in plasma, but rapidly degraded by liver microsomes (see e.g., FIG. 45). The solubility of 1, 20, and 200 mM solutions of compound in 50 mM phosphate buffer (pH 7.4) was assessed after 24 shaking. Plasma protein binding was measured using equilibrium dialysis; % bound= (1-[free compound in dialysate]/[total compound in retentate])×100. Plasma stability of 2 mM compound in clarified freeze-thawed plasma was assessed by LC-MS/MS of supernatants after protein precipitation; 120 min data are reported for studies including 0, 10, 30, 60, and 120 min. Microsome stability of 1 mM compound in liver microsomes (0.5 mg/ml) after 0, 5, 10, 20, 30, 60 min. incubation was assessed by LC/MS/MS of reaction extracts.

Regeneurin-S was considered to have three functional domains corresponding to amino acid side chains of the prototype mitofusin agonist minipeptide it was designed to mimic: the methylated cyclohexane group corresponds to Mfn2 His380, the phenyl- and cyclopropyl-substituted triazol ring corresponds to Met376 and Val372, and the thioether backbone provides proper spacing (see Example 5) (see e.g., FIG. 46). According to this concept, a step-wise modification was performed of these functional domains to engineer subsequent generations of agonists having different functional and pharmacokinetic properties.

It was initially posited that oxidation of the backbone sulfur contributed to instability in the liver microsome assay. It was asked: (1) how does oxidation of this sulfur affect function (e.g., Regeneurin-S fusogenic function)? and (2) could replacing the backbone sulfur increase stability in the liver microsome test? Thus, the sulfoxide and sulfone by chemical oxidation of the parent thioether was generated (see e.g., FIG. 47 top), and the ether and carbon backbone variants were synthesized de novo (see e.g., FIG. 47 bottom). As illustrated in FIG. 47, neither oxidation nor substitution of the backbone sulfur altered fusogenicity, consistent with the backbone acting simply as a spacer to properly position the active terminal groups that mimic amino acid side chains of the prototype agonist peptide. Nor did any of the chemical changes greatly increase molecular stability in the microsome test. However, Regeneurin-C/O, having the carbon backbone and with tetrahydropyran substituted for the cyclohexyl group, exhibited enhanced microsomal stability and improved (decreased) plasma protein binding.

These results showed that the backbone sulfur of Renegeurin-S was neither function-critical, nor the basis for microsomal instability. The results also revealed a solution to microsomal instability evoked by the methylated cyclohexyl group. Recognizing that liver cytochrome P450 enzymes oxidize aromatic rings, such as the phenyl group on the triazol ring of the Regeneurin series of agonists, the structure-function relations of triazol ring group substitutions were next evaluated. In the pharmacophore model, the phenyl, cyclopropyl-substituted triazol ring mimics the hydrophobic side chains of Mfn2 Met376 and Val372 (see e.g., FIG. 46). Thus, the mitochondrial fusogenicity of 70 commercially available chemical variants were compared, 17 of which differed exclusively in their triazol ring substitutions (see e.g., TABLE 7). Five compounds, all of which had a common chemical structure except for triazol ring substitutions, were fusogenic (see e.g., FIG. 48); one of these was previously described (designated as "Cpd B" above).

TABLE 7

70 commercially available compounds evaluated.

| ID | IUPAC Name | Structure |
|---|---|---|
| Cpd B | 2-{2-[(5-cyclopropyl-4-phenyl-4H-1,2,4-triazol-3-yl)sulfanyl]-propanamido}-4H,5H,6H-cyclopenta[b]-thiophene-3-carboxamide | 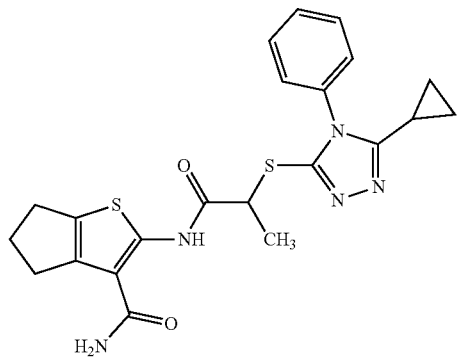 [SMILES: CC(Sc1nnc(C2CC2)n1-c1ccccc1)C(=O)Nc1sc2c(c1C(N)=O)CCC2] |

TABLE 7-continued 70 commercially available compounds evaluated.

| ID | IUPAC Name | Structure |
|---|---|---|
| 1-G1 | 2-(2-{[4-(2-methylphenyl)-5-(pyridin-3-yl)-4H-1,2,4-triazol-3-yl]sulfanyl}acetamido)-4H,5H,6H-cyclopenta[b]thiophene-3-carboxamide | 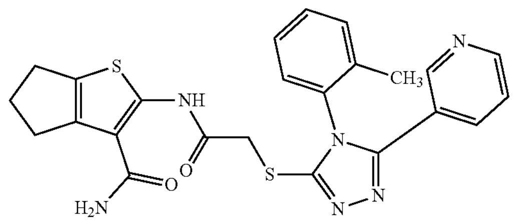 [SMILES: Cc1ccccc1-n1c(SCC(=O)Nc2sc3c(c2C(N)=O)CCC3)nnc1-c1cccnc1] |
| 1-F9 | 2-(2-{[5-cyclopropyl-4-(prop-2-en-1-yl)-4H-1,2,4-triazol-3-yl]sulfanyl}acetamido)-4,5,6,7-tetrahydro-1-benzothiophene-3-carboxamide | 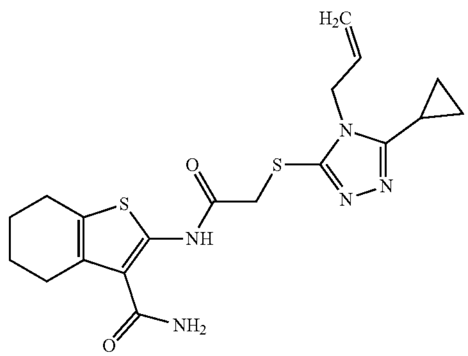 [SMILES: C=CCn1c(SCC(=O)Nc2sc3c(c2C(N)=O)CCCC3)nnc1C1CC1] |
| 1-G11 | 2-{2-[(5-cyclopropyl-4-ethyl-4H-1,2,4-triazol-3-yl)sulfanyl]acetamido}-4H,5H,6H-cyclopenta[b]thiophene-3-carboxamide | 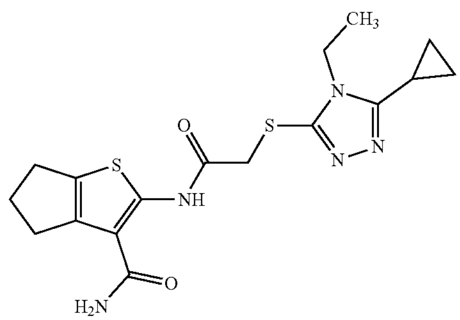 [SMILES: CCn1c(SCC(=O)Nc2sc3c(c2C(N)=O)CCC3)nnc1C1CC1] |
| 1-B1 | 2-{2-[(4-methyl-5-phenyl-4H-1,2,4-triazol-3-yl)sulfanyl]acetamido}-4H,5H,6H-cyclopenta[b]thiophene-3-carboxamide | 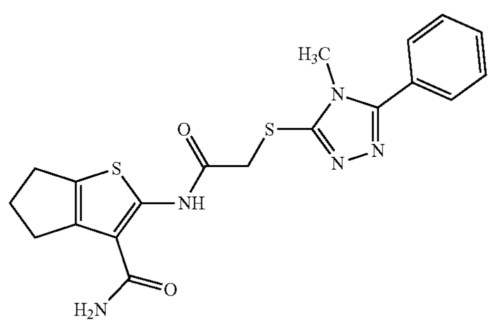 [SMILES: Cn1c(SCC(=O)Nc2sc3c(c2C(N)=O)CCC3)nnc1-c1ccccc1] |
| 1-F8 | 2-(2-{[4-cyclopropyl-5-(1H-indol-3-yl)-4H-1,2,4-triazol-3-yl]sulfanyl}propanamido)-4H,5H,6H-cyclopenta[b]thiophene-3-carboxamide | 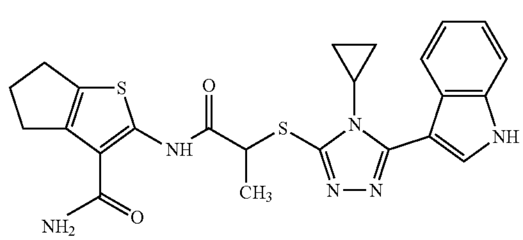 [SMILES: CC(Sc1nnc(-c2c[nH]c3ccccc23)n1C1CC1)C(=O)Nc1sc2c(c1C(N)=O)CCC2] |

TABLE 7-continued 70 commercially available compounds evaluated.

| ID | IUPAC Name | Structure |
| --- | --- | --- |
| 1-H11 | 2-{2-[(4-benzyl-5-cyclopropyl-4H-1,2,4-triazol-3-yl)-sulfanyl]acetamido}-4,5,6,7-tetrahydro-1-benzothiophene-3-carboxamide | 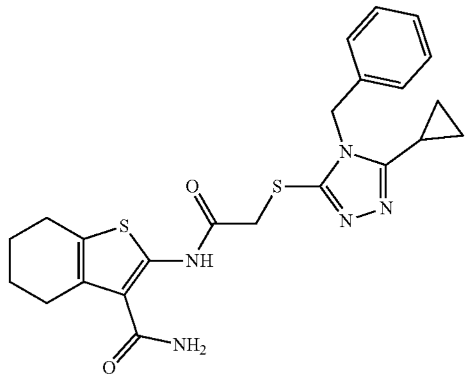 [SMILES: NC(=O)c1c(NC(=O)CSc2nnc(C3CC3)n2Cc2ccccc2)sc2c1CCCC2] |
| 1-F10 | 2-[2-({4-[(furan-2-yl)methyl]-5-(pyridin-3-yl)-4H-1,2,4-triazol-3-yl}sulfanyl)propanamido]-4H,5H,6H-cyclopenta[b]-thiophene-3-carboxamide | 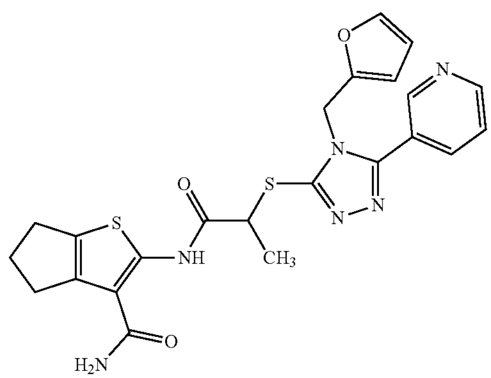 [SMILES: CC(Sc1nnc(-c2cccnc2)n1Cc1ccco1)C(=O)Nc1sc2c(c1C(N)=O)CCC2] |
| 1-F3 | 2-(2-{[5-methyl-4-(4-methylphenyl)-4H-1,2,4-triazol-3-yl]sulfanyl}acetamido)-4H,5H,6H-cyclopenta[b]-thiophene-3-carboxamide | 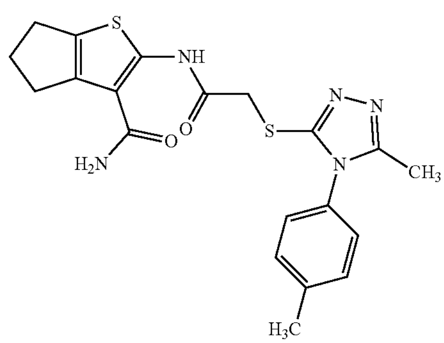 [SMILES: Cc1ccc(-n2c(C)nnc2SCC(=O)Nc2sc3c(c2C(N)=O)CCC3)cc1] |
| 1-C12 | 2-(2-{[4-cyclopropyl-5-(thiophen-2-yl)-4H-1,2,4-triazol-3-yl]sulfanyl}propanamido)-4H,5H,6H-cyclopenta[b]-thiophene-3-carboxamide | 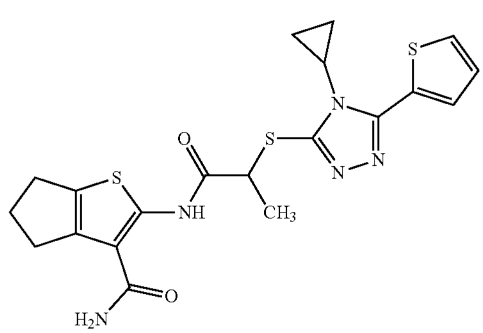 [SMILES: CC(Sc1nnc(-c2cccs2)n1C1CC1)C(=O)Nc1sc2c(c1C(N)=O)CCC2] |

TABLE 7-continued 70 commercially available compounds evaluated.

| ID | IUPAC Name | Structure |
|---|---|---|
| 1-E12 | 2-(2-{[4-(2-methylphenyl)-5-(pyridin-3-yl)-4H-1,2,4-triazol-3-yl]sulfanyl}acetamido)-4,5,6,7-tetrahydro-1-benzothiophene-3-carboxamide | 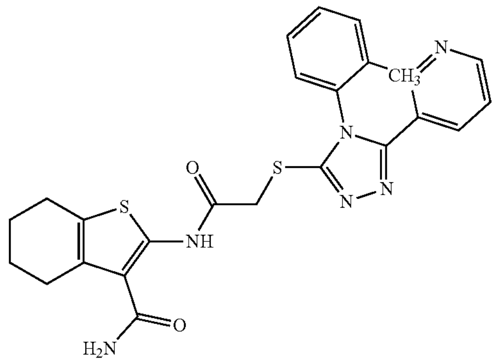 [SMILES: NC(=O)c1c(NC(=O)CSc2nnc3c4cccnc4c4ccccc4n23)sc2c1CCCC2] |
| 1-H2 | 2-(2-{[5-(4-chlorophenyl)-4-methyl-4H-1,2,4-triazol-3-yl]-sulfanyl]acetamido)-4H,5H,6H-cyclopenta[b]thiophene-3-carboxamide | 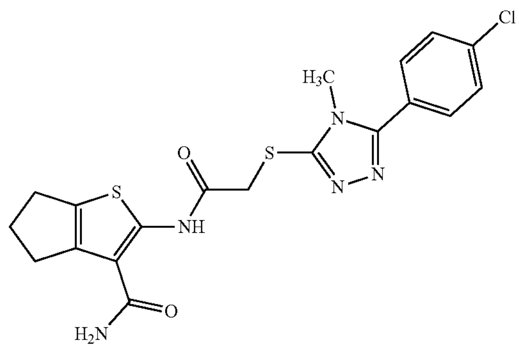 [SMILES: Cn1c(SCC(=O)Nc2sc3c(c2C(N)=O)CCC3)nnc1-c1ccc(Cl)cc1] |
| 1-B4 | 2-(2-{[4-methyl-5-(trifluoromethyl)-4H-1,2,4-triazol-3-yl]sulfanyl}acetamido)-4H,5H,6H-cyclopenta[b]-thiophene-3-carboxamide | 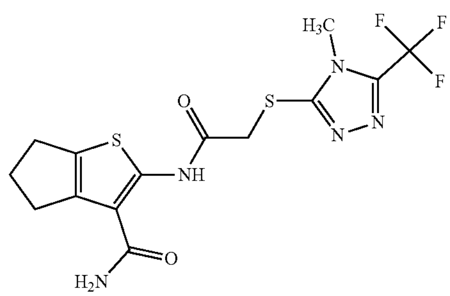 [SMILES: Cn1c(SCC(=O)Nc2sc3c(c2C(N)=O)CCC3)nnc1C(F)(F)F] |
| 1-H8 | 2-{2-[(diphenyl-4H-1,2,4-triazol-3-yl)sulfanyl]propanamido}-4H,5H,6H-cyclopenta[b]thiophene-3-carboxamide | 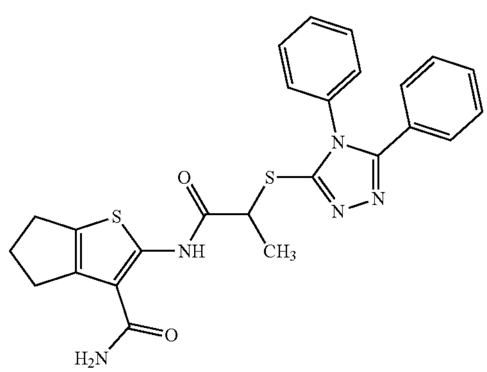 [SMILES: CC(Sc1nnc(-c2ccccc2)n1-c1ccccc1)C(=O)Nc1sc2c(c1C(N)=O)CCC2] |

TABLE 7-continued 70 commercially available compounds evaluated.

| ID | IUPAC Name | Structure |
|---|---|---|
| 1-D8 | 2-[2-({5-[(4-methoxyphenoxy)-methyl]-4-methyl-4H-1,2,4-triazol-3-yl}sulfanyl)propan-amido]-4H,5H,6H-cyclopenta-[b]thiophene-3-carboxamide | 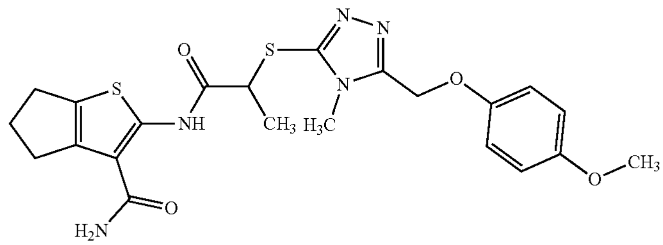 [SMILES: COc1ccc(OCc2nnc(SC(C)C(=O)Nc3sc4c(c3C(N)=O)CCC4)n2C)cc1] |
| 1-D3 | 2-(2-{[5-methyl-4-(4-methyl-phenyl)-4H-1,2,4-triazol-3-yl]sulfanyl]acetamido)-4,5,6,7-tetrahydro-1-benzothiophene-3-carboxamide | 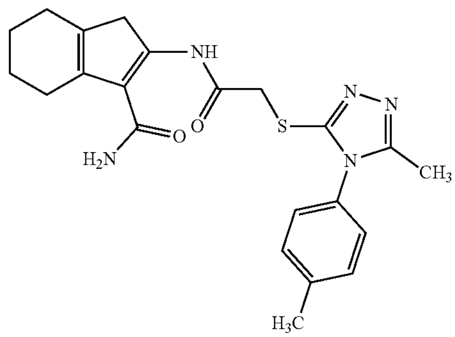 [SMILES: Cc1ccc(-n2c(C)nnc2SCC(=O)NC2=C(C(N)=O)C3=C(CCCC3)C2)cc1] |
| 1-F7 | 2-(2-{[4-phenyl-5-(thiophen-2-yl)-4H-1,2,4-triazol-3-yl]sulfanyl}propanamido)-4H,5H,6H-cyclopenta[b]thiophene-3-carboxamide | 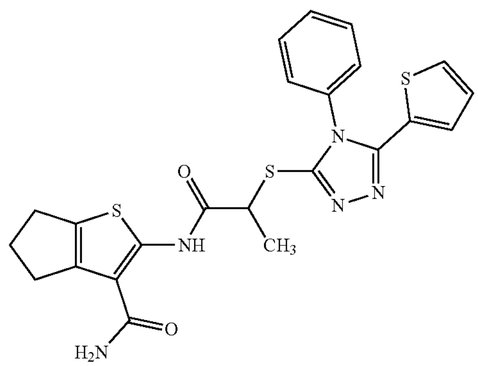 [SMILES: CC(Sc1nnc(-c2cccs2)n1-c1ccccc1)C(=O)Nc1sc2c(c1C(N)=O)CCC2] |
| 1-H1 | 2-(2-{[4-(2-methylphenyl)-5-(pyridin-4-yl)-4H-1,2,4-triazol-3-yl}sulfanyl]acetamido-4H,5H,6H-cyclopenta[b]thio-phene-3-carboxamide | 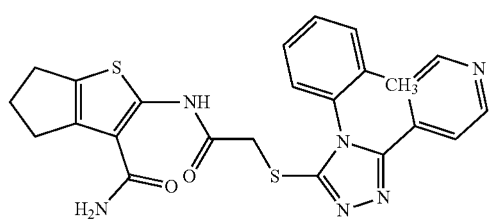 [SMILES: NC(=O)c1c(NC(=O)CSc2nnc3c4ccncc4c4ccccc4n23)sc2c1CCC2] |
| 1-B8 | 2-(2-{[5-(2-methylfuran-3-yl)-4-phenyl-4H-1,2,4-triazol-3-yl]sulfanyl}propanamido)-4H,5H,6H-cyclopenta[b]thio-phene-3-carboxamide | 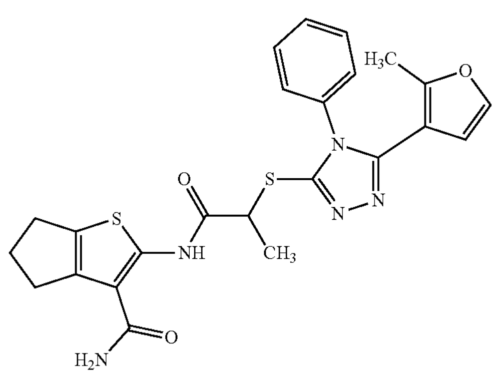 [SMILES: Cc1occc1-c1nnc(SC(C)C(=O)Nc2sc3c(c2C(N)=O)CCC3)n1-c1ccccc1] |

TABLE 7-continued 70 commercially available compounds evaluated.

| ID | IUPAC Name | Structure |
|---|---|---|
| 1-C7 | 2-{2-[(4-benzyl-5-cyclopropyl-4H-1,2,4-triazol-3-yl)sulfanyl]-propanamido}-4H,5H,6H-cyclopenta[b]thiophene-3-carboxamide | 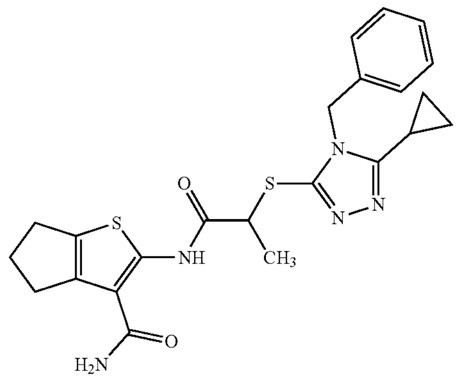 [SMILES: CC(Sc1nnc(C2CC2)n1Cc1ccccc1)C(=O)Nc1sc2c(c1C(N)=O)CCC2] |
| 1-D7 | 2-[2-({4-[(furan-2-yl)methyl]-5-phenyl-4H-1,2,4-triazol-3-yl}sulfanyl)propanamido]-4H,5H,6H-cyclopenta[b]thiophene-3-carboxamide | 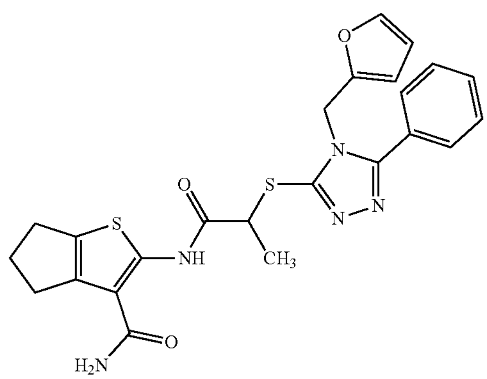 [SMILES: CC(Sc1nnc(-c2ccccc2)n1Cc1ccco1)C(=O)Nc1sc2c(c1C(N)=O)CCC2] |
| 1-D1 | 2-[2-({4-benzyl-5-[1-(dimethylamino)propyl]-4H-1,2,4-triazol-3-yl}sulfanyl)acetamido]-4H,5H,6H-cyclopenta[b]thiophene-3-carboxamide | 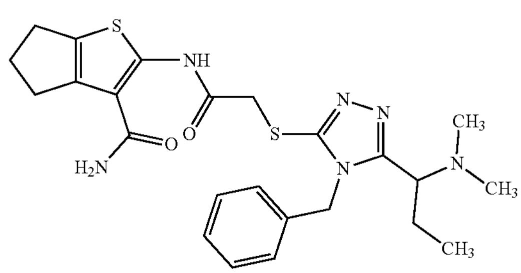 [SMILES: CCC(c1nnc(SCC(=O)Nc2sc3c(c2C(N)=O)CCC3)n1Cc1ccccc1)N(C)C] |
| 1-E2 | 2-(2-{[4-(2-methoxyphenyl)-4H-1,2,4-triazol-3-yl]sulfanyl}acetamido)-4H,5H,6H-cyclopenta[b]thiophene-3-carboxamide | 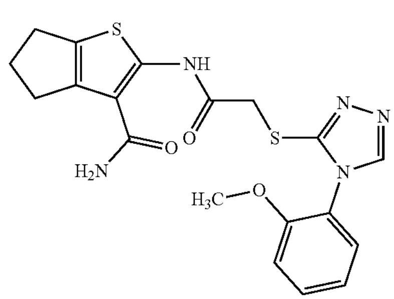 [SMILES: COc1ccccc1-n1cnnc1SCC(=O)Nc1sc2c(c1C(N)=O)CCC2] |

TABLE 7-continued 70 commercially available compounds evaluated.

| ID | IUPAC Name | Structure |
|---|---|---|
| 1-F1 | 2-(2-{[5-(furan-2-yl)-4-phenyl-4H-1,2,4-triazol-3-yl]sulfanyl}-acetamido)-4H,5H,6H-cyclopenta[b]thiophene-3-carboxamide | 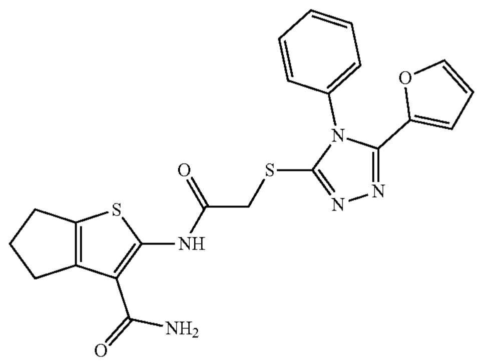 [SMILES: NC(=O)c1c(NC(=O)CSc2nnc(-c3ccco3)n2-c2ccccc2)sc2c1CCC2] |
| 1-H7 | 2-{2-[(5-benzyl-4-methyl-4H-1,2,4-triazol-3-yl)sulfanyl]-acetamido}-4H,5H,6H-cyclopenta[b]thiophene-3-carboxamide | 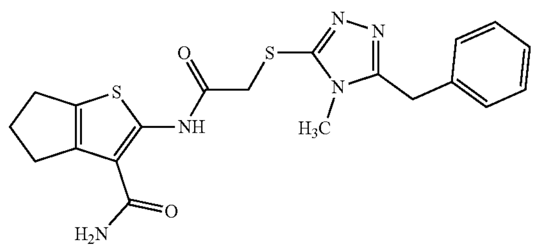 [SMILES: Cn1c(Cc2ccccc2)nnc1SCC(=O)Nc1sc2c(c1C(N)=O)CCC2] |
| 1-D2 | 2-(2-{[4-(4-methoxyphenyl)-4H-1,2,4-triazol-3-yl]sulfanyl}acetamido)-4H,5H,6H-cyclopenta[b]thiophene-3-carboxamide | 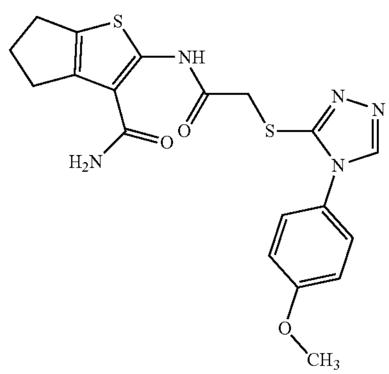 [SMILES: COc1ccc(-n2cnnc2SCC(=O)Nc2sc3c(c2C(N)=O)CCC3)cc1] |
| 1-F2 | 2-(2-{[5-phenyl-4-(prop-2-en-1-yl)-4H-1,2,4-triazol-3-yl]sulfanyl}acetamido)-4H,5H,6H-cyclopenta[b]thiophene-3-carboxamide | 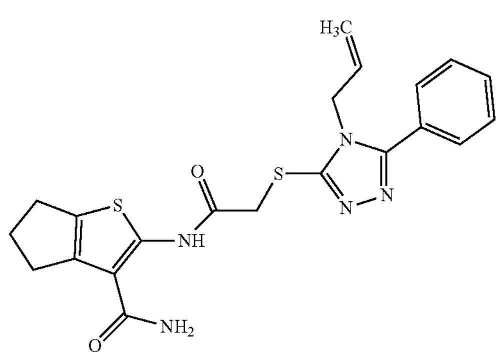 [SMILES: C=CCn1c(SCC(=O)Nc2sc3c(c2C(N)=O)CCC3)nnc1-c1ccccc1] |

TABLE 7-continued 70 commercially available compounds evaluated.

| ID | IUPAC Name | Structure |
|---|---|---|
| 1-B12 | 2-(2-{[4-(2-methoxyethyl)-5-(pyridin-4-yl)-4H-1,2,4-triazol-3-yl]sulfanyl}propanamido)-4H,5H,6H-cyclopenta[b]thiophene-3-carboxamide | 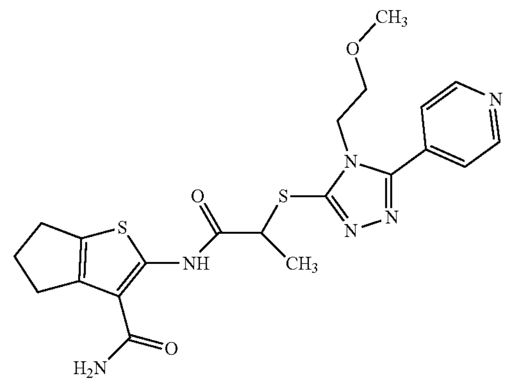 [SMILES: COCCn1c(SC(C)C(=O)Nc2sc3c(c2C(N)=O)CCC3)nnc1-c1ccncc1] |
| 1-A12 | 2-(2-{[4-phenyl-5-(piperidin-1-yl)-4H-1,2,4-triazol-3-yl]sulfanyl]propanamido)-4H,5H,6H-cyclopenta[b]thiophene-3-carboxamide | 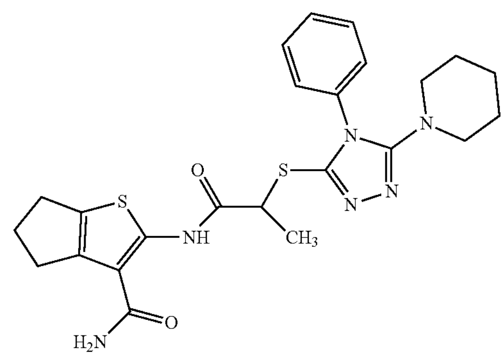 [SMILES: CC(Sc1nnc(N2CCCCC2)n1-c1ccccc1)C(=O)Nc1sc2c(c1C(N)=O)CCC2] |
| 1-H5 | 2-(2-{[4-(4-fluorophenyl)-5-(pyridin-4-yl)-4H-1,2,4-triazol-3-yl]sulfanyl]acetamido)-4H,5H,6H-cyclopenta[b]thiophene-3-carboxamide | 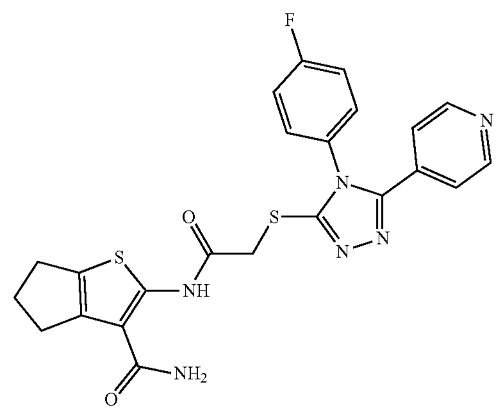 [SMILES: NC(=O)c1c(NC(=O)CSc2nnc(-c3ccncc3)n2-c2ccc(F)cc2)sc2c1CCC2] |
| 2-A5 | 2-{2-[(dimethyl-4H-1,2,4-triazol-3-yl)sulfanyl]acetamido}-4H,5H,6H-cyclopenta[b]thiophene-3-carboxamide | 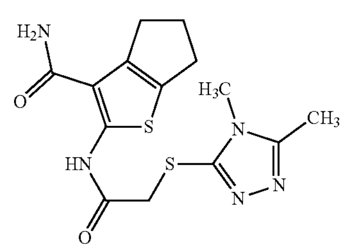 [SMILES: Cc1nnc(SCC(=O)Nc2sc3c(c2C(N)=O)CCC3)n1C] |

TABLE 7-continued 70 commercially available compounds evaluated.

| ID | IUPAC Name | Structure |
|---|---|---|
| 1-E7 | 2-(2-{[4-methyl-5-(2-methyl-phenyl)-4H-1,2,4-triazol-3-yl]sulfanyl}acetamido)-4H,5H,6H-cyclopenta[b]-thiophene-3-carboxamide | 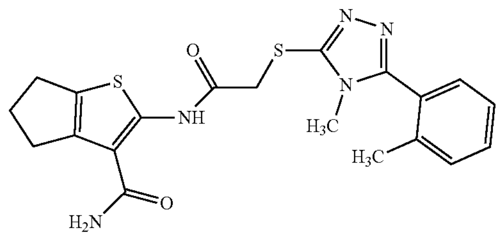 [SMILES: Cc1ccccc1-c1nnc(SCC(=O)Nc2sc3c(c2C(N)=O)CCC3)n1C] |
| 1-A1 | 2-(2-{[5-(4-chlorophenyl)-4-ethyl-4H-1,2,4-triazol-3-yl]sulfanyl}acetamido)-4H,5H,6H-cyclopenta[b]thiophene-3-carboxamide | 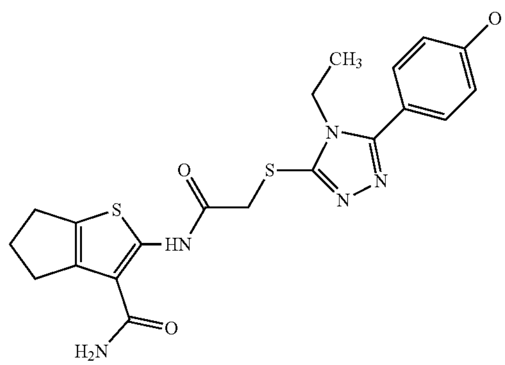 [SMILES: CCn1c(SCC(=O)Nc2sc3c(c2C(N)=O)CCC3)nnc1-c1ccc(O)cc1] |
| 1-C8 | 2-[2-({4-phenyl-5-[(thiophen-2-yl)methyl]-4H-1,2,4-triazol-3-yl}sulfanyl)acetamido]-4H,5H,6H-cyclopenta[b]thiophene-3-carboxamide | 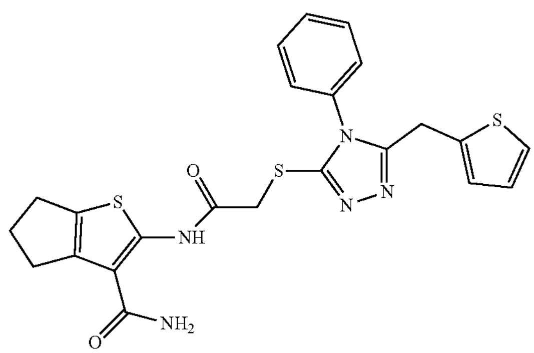 [SMILES: NC(=O)c1c(NC(=O)CSc2nnc(Cc3cccs3)n2-c2ccccc2)sc2c1CCC2] |
| 1-E10 | 2-(2-{[1-(2,3-dimethylphenyl)-1H-imidazol-2-yl]sulfanyl}propanamido)-4H,5H,6H-cyclopenta[b]thiophene-3-carboxamide | 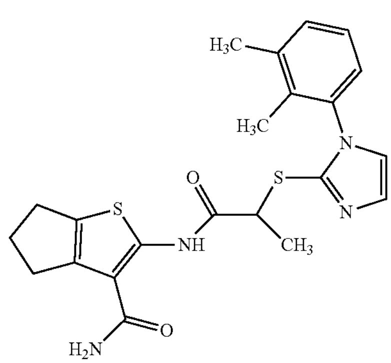 [SMILES: Cc1cccc(-n2ccnc2SC(C)C(=O)Nc2sc3c(c2C(N)=O)CCC3)c1C] |

TABLE 7-continued 70 commercially available compounds evaluated.

| ID | IUPAC Name | Structure |
|---|---|---|
| 1-G10 | 2-(2-{5H,6H,7H,8H,9H-[1,2,4]triazolo[4,3-a]azepin-3-ylsulfanyl}acetamido)-4,5,6,7-tetrahydro-1-benzothiophene-3-carboxamide | 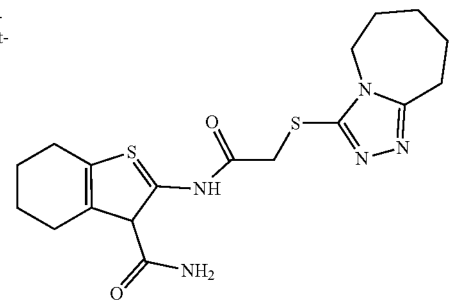 |
| 1-G7 | 2-{2-[(1-benzyl-1H-imidazol-2-yl)sulfanyl]propanamido}-4H,5H,6H-cyclopenta[b]thiophene-3-carboxamide | 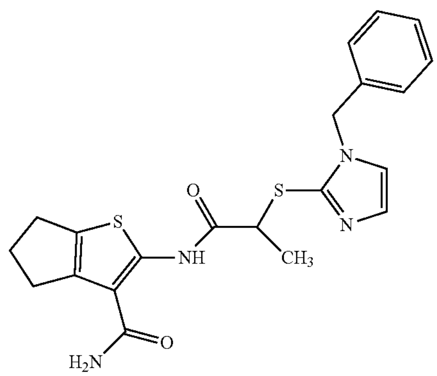 [SMILES: CC(Sc1nccn1Cc1ccccc1)C(=O)Nc1sc2c(c1C(N)=O)CCC2] |
| 1-C9 | 2-(2-{[4-methyl-5-(2-methylfuran-3-yl)-4H-1,2,4-triazol-3-yl]sulfanyl}propanamido)-4H,5H,6H-cyclopenta[b]thiophene-3-carboxamide | 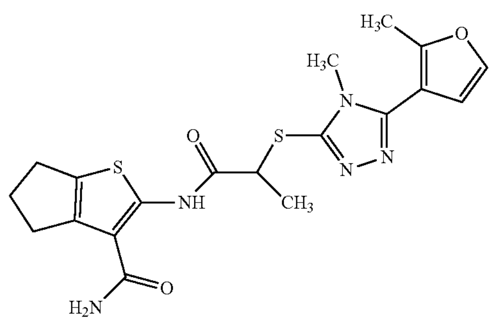 [SMILES: Cc1occc1-c1nnc(SC(C)C(=O)Nc2sc3c(c2C(N)=O)CCC3)n1C] |
| 1-G8 | 2-{2-[(4-phenyl-4H-1,2,4-triazol-3-yl)sulfanyl]propanamido}-4H,5H,6H-cyclopenta[b]thiophene-3-carboxamide | 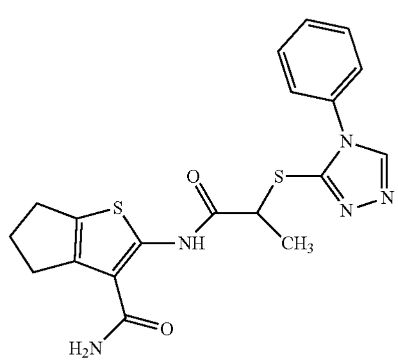 [SMILES: CC(Sc1nncn1-c1ccccc1)C(=O)Nc1sc2c(c1C(N)=O)CCC2] |

TABLE 7-continued 70 commercially available compounds evaluated.

| ID | IUPAC Name | Structure |
|---|---|---|
| 1-E8 | 2-(2-{[1-(3-fluorophenyl)-1H-imidazol-2-yl]sulfanyl}pro-panamido)-4H,5H,6H-cyclo-penta[b]thiophene-3-carboxamide | 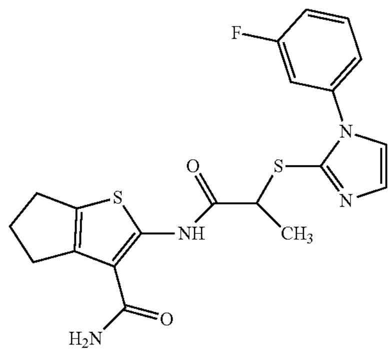 [SMILES: CC(Sc1nccn1-c1cccc(F)c1)C(=O)Nc1sc2c(c1C(N)=O)CCC2] |
| 1-D6 | 2-(2-{[5-(furan-2-yl)-4-phenyl-4H-1,2,4-triazol-3-yl]sulfanyl]-propanamido)-4H,5H,6H-cyclopenta[b]thiophene-3-carboxamide | 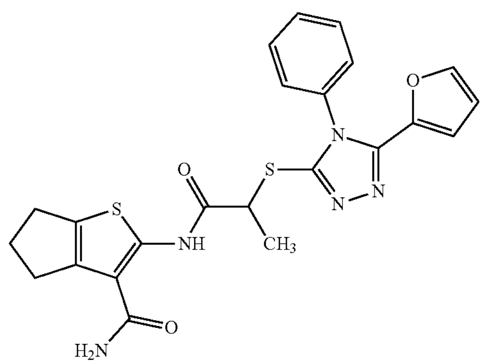 |
| 1-B7 | 2-[2-({4-methyl-5-[(thiophen-2-yl)methyl]-4H-1,2,4-triazol-3-yl}sulfanyl)propanamido]-4H,5H,6H-cyclopenta[b]thio-phene-3-carboxamide | 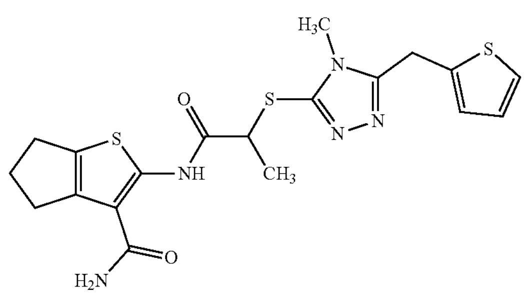 [SMILES: CC(Sc1nnc(Cc2cccs2)n1C)C(=O)Nc1sc2c(c1C(N)=O)CCC2] |
| 1-C5 | 2-(2-{[4-(2-methylphenyl)-4H-1,2,4-triazol-3-yl]sulfanyl}acet-amido)-4H,5H,6H-cyclopenta-[b]thiophene-3-carboxamide | 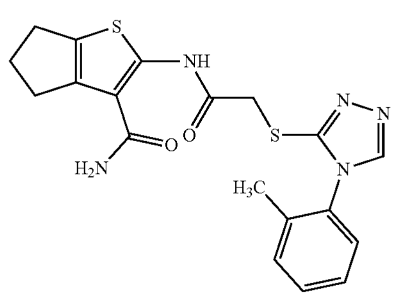 [SMILES: Cc1ccccc1-n1cnnc1SCC(=O)Nc1sc2c(c1C(N)=O)CCC2] |

TABLE 7-continued 70 commercially available compounds evaluated.

| ID | IUPAC Name | Structure |
|---|---|---|
| 1-D12 | 2-(2-{5H,6H,7H,8H,9H-[1,2,4]triazolo[4,3-a]azepin-3-ylsulfanyl}propanamido)-4H,5H,6H-cyclopenta[b]-thiophene-3-carboxamide | 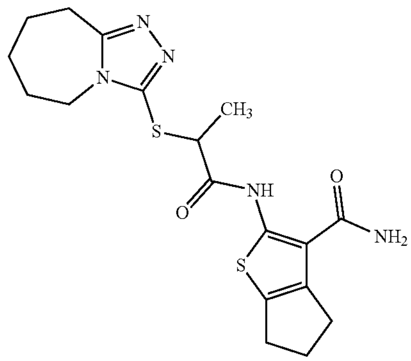 [SMILES: CC(Sc1nnc2n1CCCCC2)C(=O)Nc1sc2c(c1C(N)=O)CCC2] |
| 2-A2 | 2-{2-[(dicyclopropyl-4H-1,2,4-triazol-3-yl)sulfanyl]acetamido}-4,5,6,7-tetrahydro-1-benzothiophene-3-carboxamide | 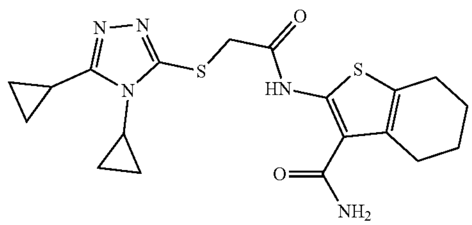 [SMILES: NC(=O)c1c(NC(=O)CSc2nnc(C3CC3)n2C2CC2)sc2c1CCCC2] |
| 1-G2 | 2-{2-[(diphenyl-4H-1,2,4-triazol-3-yl)sulfanyl]acetamido}-4,5,6,7-tetrahydro-1-benzothiophene-3-carboxamide | 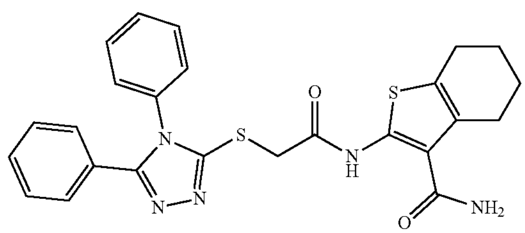 [SMILES: NC(=O)c1c(NC(=O)CSc2nnc(-c3ccccc3)n2-c2ccccc2)sc2c1CCCC2] |
| 1-E5 | 2-{2-[(5-cyclopropyl-4-phenyl-4H-1,2,4-triazol-3-yl)sulfanyl]-acetamido}-4,5,6,7-tetrahydro-1-benzothiophene-3-carboxamide | 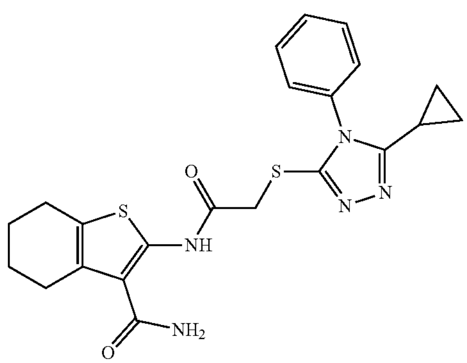 [SMILES: NC(=O)c1c(NC(=O)CSc2nnc(C3CC3)n2-c2ccccc2)sc2c1CCCC2] |
| 1-A10 | 2-(2-{5H,6H,7H,8H,9H-[1,2,4]triazolo[4,3-a]azepin-3-ylsulfanyl}acetamido)-4H,5H,6H-cyclopenta[b]thiophene-3-carboxamide | 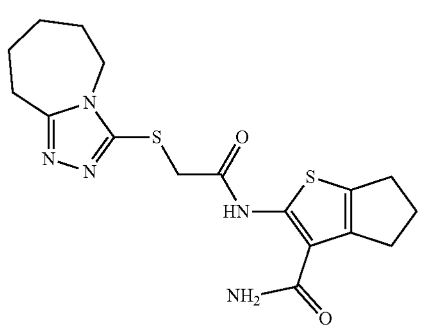 [SMILES: NC(=O)c1c(NC(=O)CSc2nnc3n2CCCCC3)sc2c1CCC2] |

TABLE 7-continued 70 commercially available compounds evaluated.

| ID | IUPAC Name | Structure |
|---|---|---|
| 1-D10 | 2-(2-{[5-(2-methylfuran-3-yl)-4-phenyl-4H-1,2,4-triazol-3-yl]sulfanyl}acetamido)-4H,5H,6H-cyclopenta[b]thiophene-3-carboxamide | 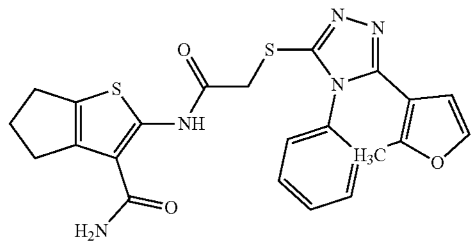 [SMILES: NC(=O)c1c(NC(=O)CSc2nnc3c4ccoc4c4ccccc4n23)sc2c1CCC2] |
| 1-F5 | 2-{2-[(5-cyclopropyl-4-ethyl-4H-1,2,4-triazol-3-yl)sulfanyl]acetamido}-4,5,6,7-tetrahydro-1-benzothiophene-3-carboxamide | 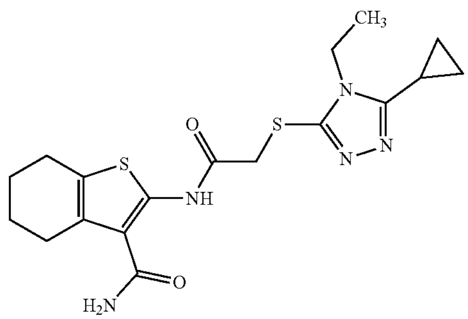 [SMILES: CCn1c(SCC(=O)Nc2sc3c(c2C(N)=O)CCCC3)nnc1C1CC1] |
| 1-F11 | 2-(2-{[4-phenyl-5-(pyridin-3-yl)-4H-1,2,4-triazol-3-yl]sulfanyl]acetamido)-4H,5H,6H-cyclopenta[b]thiophene-3-carboxamide | 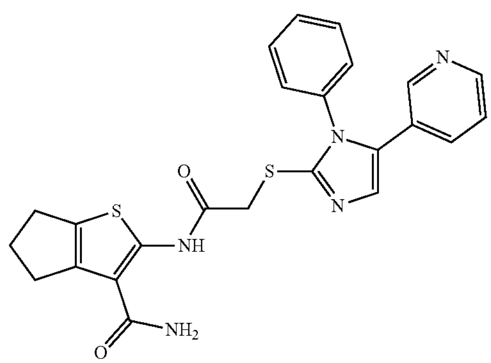 |
| 1-G6 | 2-[2-({4-cyclopropyl-5-[(thiophen-2-yl)methyl]-4H-1,2,4-triazol-3-yl}sulfanyl)propanamido]-4H,5H,6H-cyclopenta[b]thiophene-3-carboxamide | 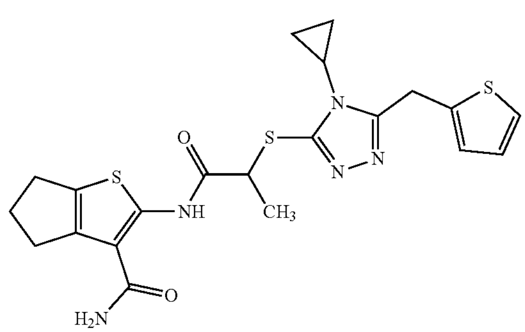 [SMILES: CC(Sc1nnc(Cc2cccs2)n1C1CC1)C(=O)Nc1sc2c(c1C(N)=O)CCC2] |
| 1-G3 | 2-(2-{[4-phenyl-5-(pyridin-3-yl)-4H-1,2,4-triazol-3-yl]sulfanyl}acetamido)-4,5,6,7-tetrahydro-1-benzothiophene-3-carboxamide | 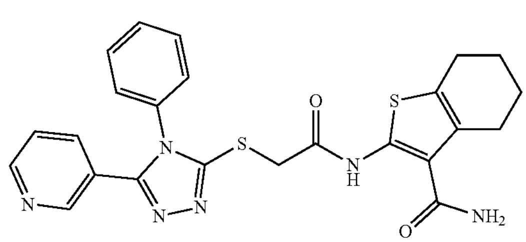 |

TABLE 7-continued 70 commercially available compounds evaluated.

| ID | IUPAC Name | Structure |
|---|---|---|
| 1-F6 | 2-[2-({5-[1-(dimethylamino)ethyl]-4-(4-fluorophenyl)-4H-1,2,4-triazol-3-yl}sulfanyl)acetamido]-4H,5H,6H-cyclopenta[b]thiophene-3-carboxamide | 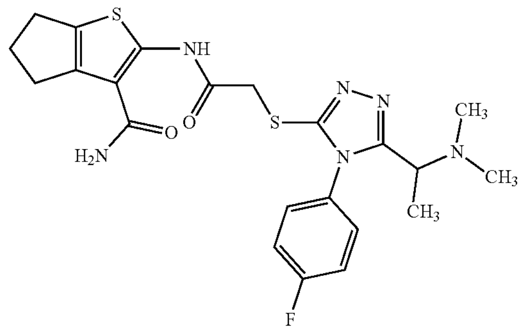 [SMILES: CC(c1nnc(SCC(=O)Nc2sc3c(c2C(N)=O)CCC3)n1-c1ccc(F)cc1)N(C)C] |
| 1-A8 | 2-{2-[(5-benzyl-4-ethyl-4H-1,2,4-triazol-3-yl)sulfanyl]-propanamido}-4H,5H,6H-cyclopenta[b]thiophene-3-carboxamide | 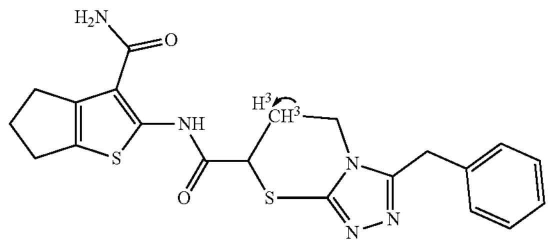 |
| 1-H3 | 2-{2-[(5-methyl-4-phenyl-4H-1,2,4-triazol-3-yl)sulfanyl]acetamido}-4H,5H,6H-cyclopenta[b]thiophene-3-carboxamide | 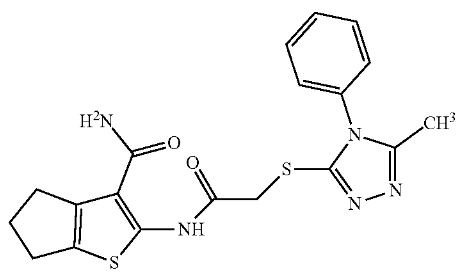 [SMILES: Cc1nnc(SCC(=O)Nc2sc3c(c2C([2NH2])=O)CCC3)n1-c1ccccc1] |
| 1-E1 | 2-(2-{[5-cyclohexyl-4-(prop-2-en-1-yl)-4H-1,2,4-triazol-3-yl]sulfanyl}acetamido)-4H,5H,6H-cyclopenta[b]thiophene-3-carboxamide | 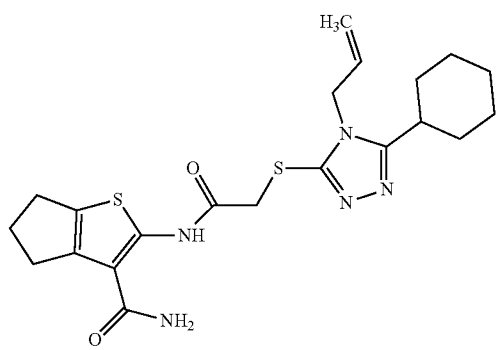 [SMILES: C=CCn1c(SCC(=O)Nc2sc3c(c2C(N)=O)CCC3)nnc1C1CCCCC1] |
| 1-C6 | 2-[2-({5-[(1,1-dioxo-1$\lambda^6$-thiolan-3-yl)methyl]-4-methyl-4H-1,2,4-triazol-3-yl}sulfanyl)-acetamido]-4,5,6,7-tetrahydro-1-benzothiophene-3-carboxamide | 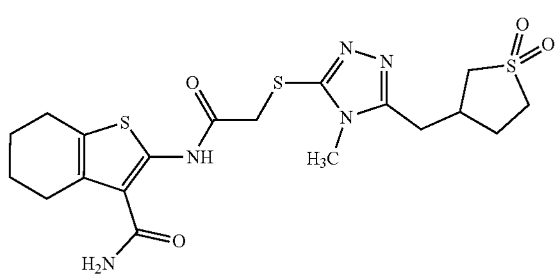 [SMILES: Cn1c(CC2CCS(=O)(=O)C2)nnc1SCC(=O)Nc1sc2c(c1C(N)=O)CCCC2] |

TABLE 7-continued 70 commercially available compounds evaluated.

| ID | IUPAC Name | Structure |
|---|---|---|
| 1-A3 | 2-(2-{[5-(4-fluorophenyl)-4-methyl-4H-1,2,4-triazol-3-yl]sulfanyl}acetamido)-4H,5H,6H-cyclopenta[b]-thiophene-3-carboxamide | 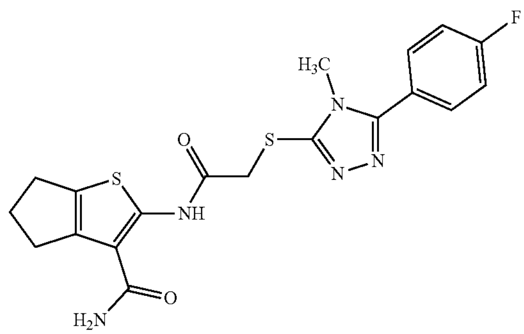 [SMILES: Cn1c(SCC(=O)Nc2sc3c(c2C(N)=O)CCC3)nnc1-c1ccc(F)cc1] |
| 1-H6 | 2-{2-[(5-benzyl-4-methyl-4H-1,2,4-triazol-3-yl)sulfanyl]propanamido}-4H,5H,6H-cyclopenta[b]-thiophene-3-carboxamide | 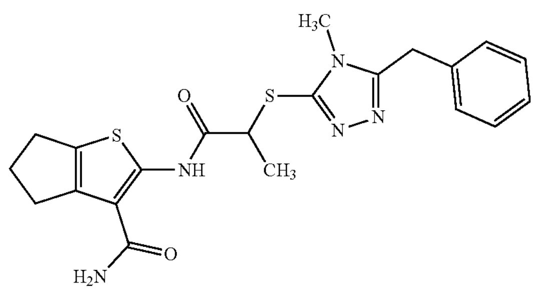 [SMILES: CC(Sc1nnc(Cc2ccccc2)n1C)C(=O)Nc1sc2c(c1C(N)=O)CCC2] |
| 1-E9 | 2-[2-({5-[(1,1-dioxo-1$\lambda^6$-thiolan-3-yl)methyl]-4-methyl-4H-1,2,4-triazol-3-yl}sulfanyl)propanamido]-4H,5H,6H-cyclopenta[b]thiophene-3-carboxamide | 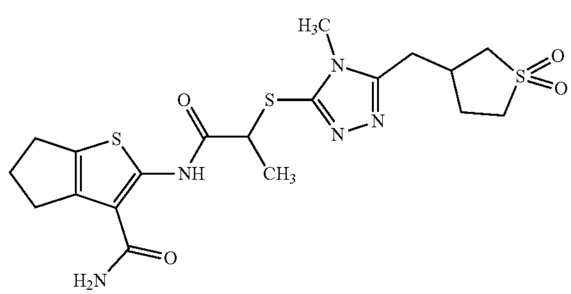 [SMILES: CC(Sc1nnc(CC2CCS(=O)(=O)C2)n1C)C(=O)Nc1sc2c(c1C(N)=O)CCC2] |
| 1-A6 | 2-(2-{[4-ethyl-5-(2-methylfuran-3-yl)-4H-1,2,4-triazol-3-yl]sulfanyl}propanamido)-4H,5H,6H-cyclopenta[b]thiophene-3-carboxamide | 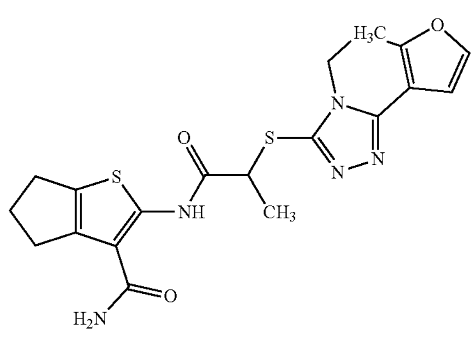 [SMILES: CC(Sc1nnc2n1CCc1occc1-2)C(=O)Nc1sc2c(c1C(N)=O)CCC2] |

TABLE 7-continued 70 commercially available compounds evaluated.

| ID | IUPAC Name | Structure |
|---|---|---|
| 1-C4 | 2-{2-[(4-phenyl-4H-1,2,4-triazol-3-yl)sulfanyl]acetamido}-4H,5H,6H-cyclopenta[b]thiophene-3-carboxamide | 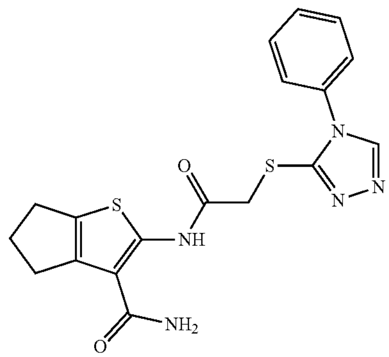 [SMILES: NC(=O)c1c(NC(=O)CSc2nncn2-c2ccccc2)sc2c1CCC2] |
| 1-F4 | 2-(2-{[4-(2-methoxyphenyl)-5-methyl-4H-1,2,4-triazol-3-yl]sulfanyl}acetamido)-4,5,6,7-tetrahydro-1-benzothiophene-3-carboxamide | 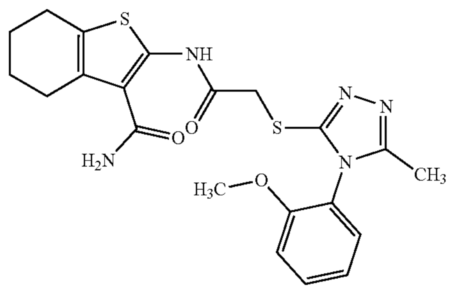 [SMILES: COc1ccccc1-n1c(C)nnc1SCC(=O)Nc1sc2c(c1C(N)=O)CCCC2] |
| 1-D9 | 2-[2-({5-[(1,1-dioxo-1$\lambda^6$-thiolan-3-yl)methyl]-4-methyl-4H-1,2,4-triazol-3-yl}sulfanyl)acetamido]-4H,5H,6H-cyclopenta[b]thiophene-3-carboxamide | 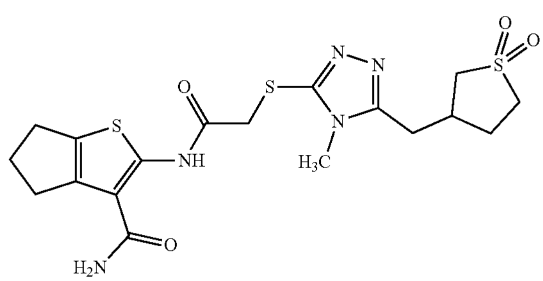 [SMILES: Cn1c(CC2CCS(=O)(=O)C2)nnc1SCC(=O)Nc1sc2c(c1C(N)=O)CCC2] |
| 1-A2 | 2-(2-{[4-cyclopropyl-5-(2-fluorophenyl)-4H-1,2,4-triazol-3-yl]sulfanyl}acetamido)-4H,5H,6H-cyclopenta[b]thiophene-3-carboxamide | 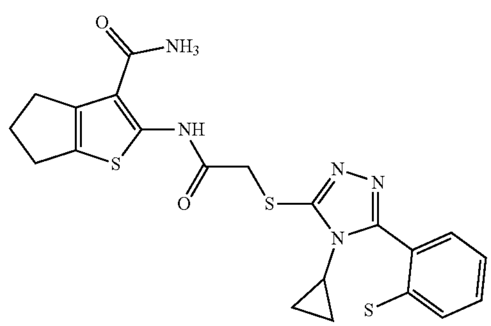 [SMILES: NC(=O)c1c(NC(=O)CSc2nnc(-c3ccccc3S)n2C2CC2)sc2c1CCC2] |
| 2-A5 | 2-{2-[(dimethyl-4H-1,2,4-triazol-3-yl)sulfanyl]acetamido}-4H,5H,6H-cyclopenta[b]thiophene-3-carboxamide | 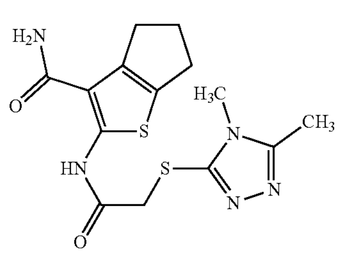 [SMILES: Cc1nnc(SCC(=O)Nc2sc3c(c2C(N)=O)CCC3)n1C] |

TABLE 7-continued

70 commercially available compounds evaluated.

| ID | IUPAC Name | Structure |
|---|---|---|
| 1-C11 | 2-[2-({4-methyl-5-[(thiophen-2-yl)methyl]-4H-1,2,4-triazol-3-yl}sulfanyl)acetamido]-4H,5H,6H-cyclopenta[b]thiophene-3-carboxamide | 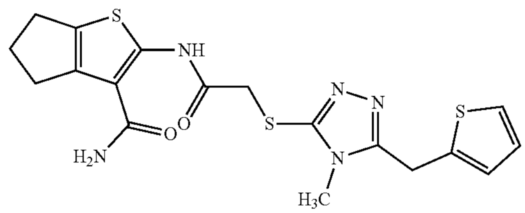 [SMILES: Cn1c(Cc2cccs2)nnc1SCC(=O)Nc1sc2c(c1C(N)=O)CCC2] |
| 1-C2 | 2-{2-[(4-benzyl-5-methyl-4H-1,2,4-triazol-3-yl)sulfanyl]acetamido}-4H,5H,6H-cyclopenta[b]thiophene-3-carboxamide | 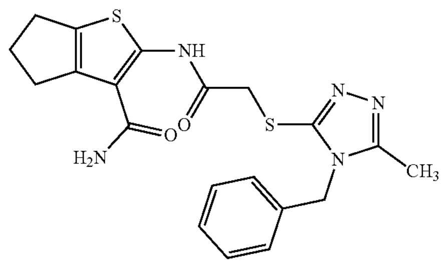 [SMILES: Cc1nnc(SCC(=O)Nc2sc3c(c2C(N)=O)CCC3)n1Cc1ccccc1] |
| 1-A7 | 2-(2-{[1-(4-methoxyphenyl)-1H-imidazol-2-yl]sulfanyl}propanamido)-4H,5H,6H-cyclopenta[b]thiophene-3-carboxamide | 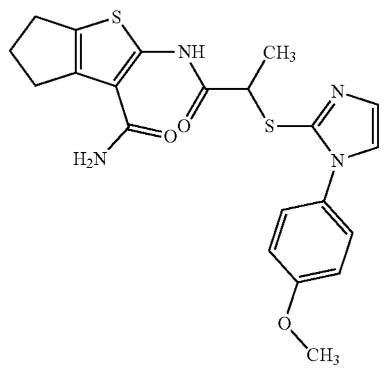 [SMILES: COc1ccc(-n2ccnc2SC(C)C(=O)Nc2sc3c(c2C(N)=O)CCC3)cc1] |

Two Cpd B chemosimilars, 1-G11 and 1-B1, were more potent and had greater resistance to liver microsomal degradation than their parent, Cpd B (see e.g., FIG. 49, TABLE 7). Because compound 1-G11 lacked aromatic groups on the triazol ring, having replaced an ethyl group for the phenyl group in Cpd B, the next series of chemical modifications introduced this configuration; this series of agonists were designated Mitolityns. Mitolityn-1 simply substituted an ethyl group for the phenyl group of the triazol ring in Regeneurin-C, retaining the rest of its structure (see e.g., FIG. 50).

Because it was reasoned that the methylated cyclohexane group might also be susceptible to oxidation by liver cytochrome P450, additional modifications were engineered to remove the cyclohexane methyl group (Mitolityn-2), replace the methylated cyclohexane ring with a methylated tetrahydropyran ring (Mitolityn-3), and replace the methylated cyclohexane with an unmethylated tetrahydropyran ring (Mitolityn-4; corresponding to replacing the triazol phenyl group of Regeneurin C/O with an ethyl group. Finally Mitolityn-3 and -4 with methyl rather than ethyl groups on the triazol ring were synthesized (see e.g., FIG. 50). The Mitolityn series of compounds were then assayed for fusogenicity (increase in aspect ratio) and liver microsome stability (see e.g., FIG. 50).

Neither of the lead compounds in the presently disclosed structurally distinct series of mitofusin agonists, Mitolityn-4 or Regeneurin-C, exhibited cytotoxicity up to drug concentrations of 100 mM, which is more than 4 orders of magnitude greater concentration than their EC50 to stimulate mitochondrial fusion (see e.g., FIG. 51).

Notwithstanding similar fusogenic efficacies and lack of cytotoxicity, in vitro pharmacokinetic studies of the lead compounds revealed marked differences in plasma protein binding, liver microsome stability, and parallel artificial membrane permeability assay (PAMPA) (see e.g., FIG. 52). Like prototypical Regeneurin-S (see e.g., FIG. 2), Regeneurin-C was highly bound to plasma proteins, but rapidly degraded by liver microsomes, showed excellent passive diffusion across a lipid-infused artificial membrane (PAMPA), but was actively transported by P-gp/MDR1. These features suggested that this compound might not be effectively delivered to the central and peripheral nervous systems in vivo. Mitolityn-4 exhibited the reciprocal of these features, with low plasma protein binding, stability in the liver microsome assay, no passive diffusion across lipid membrane and therefore no reverse transport by P-gp. These features were also not conducive to central and peripheral nervous system delivery. Regeneurin C/O, however, had intermediate features, being modestly bound to plasma proteins, stable in the liver microsome assay, and exhibiting intermediate passive permeability and P-gp mediated reverse transport.

Preliminary in vivo pharmacokinetic studies revealed that the presently disclosed mitofusin agonists compounds are eliminated from the circulation within 2 hours of IV, IP, or IM administration (see e.g., FIG. 53); IM administration provided the longest plasma half-time and bioavailability. For Regeneurin-C that is ~90% plasma protein bound (see e.g., FIG. 52), drug was undetectable 2 hours after IM administration, reflecting virtual absence of free drug. However, for Mitolityn-4 that is only 11.2% plasma protein bound in the mouse (see e.g., FIG. 52), total plasma drug concentration 2 hours after IM administration was 7.5 ng/ml, or ~6.66 ng/ml (~20 nM) free drug concentration, which is still several-fold greater than its EC50 of ~3 nM (see e.g., FIG. 53). Thus, in vivo efficacy for Mitolityn-4 was expected, but not Regeneurin-C, for at least 2 hours after a single IM injection.

The presently disclosed step-wise chemical evolution from first generation mitofusin agonists, Regeneurin-S (aka chimera B-A/I), Regeneurin-C, and Regeneurin-C/O, to second generation Mitolityns-4 and -6 revealed that the oxygen atom in the tetrahydropyran ring improved in vitro microsomal instability and reduced plasma protein binding relative to the parent 2-methylcyclohexyl group. Moreover, the structure-activity relationships of members of the Regeneurin and Mitolityn series of compounds refined the understanding of how these molecules mimic the prototype mitofusin agonist peptide: the cyclopropyl group extending from the triazol ring of Mitolityn-4 provides a hydrophobic interaction like that of Val372, whereas the tetrahydropyran ring on the opposite end of the molecule mimics both a ringed structure and hydrogen bond acceptor activity of His380.

Here, the optimization of Regeneurin C/O is shown, enhancing its stability and introducing features that will help it cross the BBB, by modifying it as shown in FIG. 54; these methods can be used to further synthesize optimized Regeneurins. Moreover, it is presently thought that substitution of the 3-cyclopropyl group on the 2,4,5 triazol ring with a structurally distinct moiety having similar hydrophobic characteristics should preserve the functional activity of the molecule, retain low plasma protein binding and microsomal stability, but have greater lipophilicity for blood- and nerve-brain barrier permeability. This approach was tested by synthesizing three additional mitofusin agonist candidates having a 3-phenyl replacing the 3-cyclopropyl group in the Mitolityn 2,4,5 triazol ring structure; this new series of Mfn agonists are called Fusogenins (see e.g., FIG. 55).

TABLE 8

Novel Regeneurin agonists.

| Compound ID | IUPAC Name | Structure | M.W. (g/mol) | Formula |
|---|---|---|---|---|
| Regeneurin-C | 1-(3-(5-cyclopropyl-4-phenyl-4H-1,2,4-triazol-3-yl)propyl)-3-(2-methylcyclohexyl)urea | 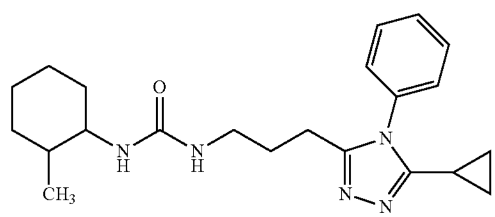 [SMILES: CC1CCCCC1NC(=O)NCCCc1nnc(C2CC2)n1-c1ccccc1] | 381.52 | C22H31N5O |
| Regeneurin-O | 1-(2-((5-cyclopropyl-4-phenyl-4H-1,2,4-triazol-3-yl)oxy)ethyl)-3-(2-methylcyclohexyl)urea | 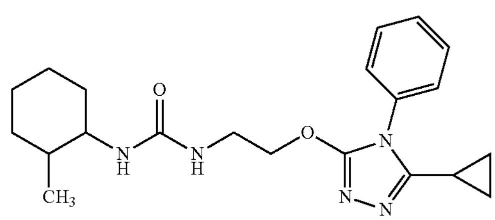 [SMILES: CC1CCCCC1NC(=O)NCCOc1nnc(C2CC2)n1-c1ccccc1] | 383.49 | C21H29N5O2 |
| Regeneurin-C/O | 1-(3-(5-cyclopropyl-4-phenyl-4H-1,2,4-triazol-3-yl)propyl)-3-(tetrahydro-2H-pyran-4-yl)urea | 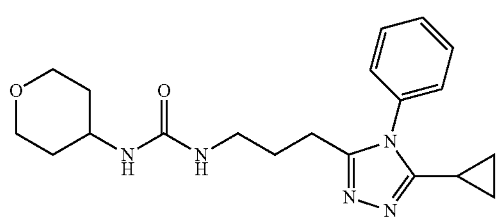 [SMILES: O=C(NCCCc1nnc(C2CC2)n1-c1ccccc1)NC1CCOCC1] | 369.47 | C20H27N5O2 |
| Regeneurin-SO | 1-(2-((5-cyclopropyl-4-phenyl-4H-1,2,4-triazol-3-yl)sulfinyl)ethyl)-3-(2-methylcyclohexyl)urea | 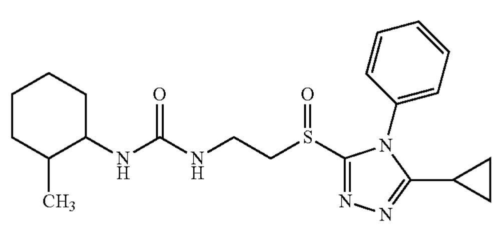 [SMILES: CC1CCCCC1NC(=O)NCCS(=O)c1nnc(C2CC2)n1-c1ccccc1] | 415.55 | C21H29N5O2S |

TABLE 8-continued

Novel Regeneurin agonists.

| Compound ID | IUPAC Name | Structure | M.W. (g/mol) | Formula |
|---|---|---|---|---|
| Regeneurin-SO2 | 1-(2-((5-cyclopropyl-4-phenyl-4H-1,2,4-triazol-3-yl)sulfonyl)ethyl)-3-(2-methylcyclohexyl)urea | 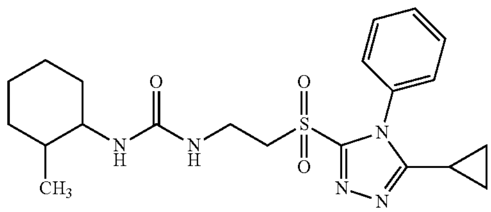 [SMILES: CC1CCCCC1NC(=O)NCCS(=O)(=O)c1nnc(C2CC2)n1-c1ccccc1] | 431.56 | C21H29N5O3S |

TABLE 9

Novel Mitolityn agonists.

| Compound ID | IUPAC Name | Structure | M.W. (g/mol) | Formula |
|---|---|---|---|---|
| Mitolityn-1 | 1-(3-(5-cyclopropyl-4-ethyl-4H-1,2,4-triazol-3-yl)propyl)-3-(2-methylcyclohexyl)urea | 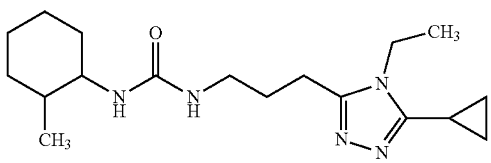 [SMILES: CCn1c(CCCNC(=O)NC2CCCCC2C)nnc1C1CC1] | 333.47 | C18H31N5O |
| Mitolityn-2 | 1-cyclohexyl-3-(3-(5-cyclopropyl)-4-ethyl-4H-1,2,4-triazol-3-yl)propyl)urea | 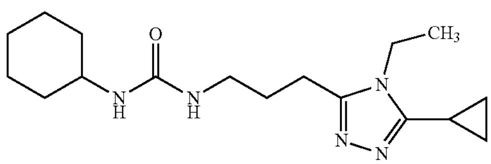 [SMILES: CCn1c(CCCNC(=O)NC2CCCCC2)nnc1C1CC1] | 319.45 | C17H29N5O |
| Mitolityn-3 | 1-(3-(5-cyclopropyl-4-ethyl-4H-1,2,4-triazol-3-yl)propyl)-3-(3-methyltetrahydro-2H-pyran-4-yl)urea | 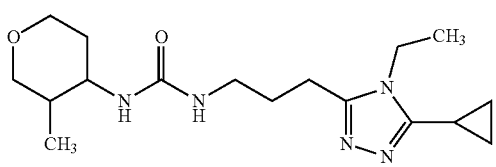 [SMILES: CCn1c(CCCNC(=O)NC2CCOCC2C)nnc1C1CC1] | 335.44 | C17H29N5O2 |
| Mitolityn-4 | 1-(3-(5-cyclopropyl-4-ethyl-4H-1,2,4-triazol-3-yl)propyl)-3-(tetrahydro-2H-pyran-4-yl)urea | 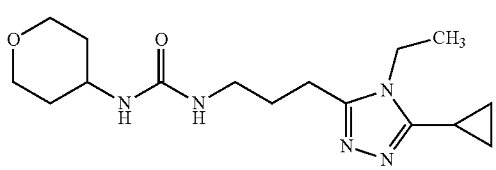 [SMILES: CCn1c(CCCNC(=O)NC2CCOCC2)nnc1C1CC1] | 321.42 | C16H27N5O2 |
| Mitolityn-5 (Renamed after Fusogenin-4a) | 1-(3-(5-cyclopropyl-4-methyl-4H-1,2,4-triazol-3-yl)propyl)-3-(3-methyltetrahydro-2H-pyran-4-yl)urea | 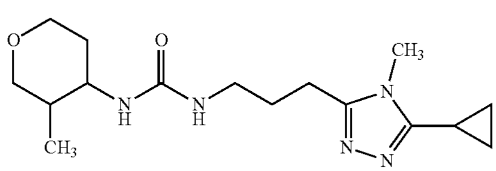 [SMILES: CC1COCCC1NC(=O)NCCCc1nnc(C2CC2)n1C] | 321.43 | C16H27N5O2 |
| Mitolityn-6 (Renamed after Fusogenin-3a) | 1-(3-(5-cyclopropyl-4-methyl-4H-1,2,4-triazol-3-yl)propyl)-3-(tetrahydro-2H-pyran-4-yl)urea | 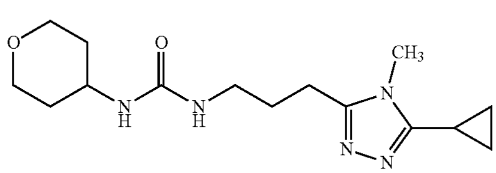 [SMILES: Cn1c(CCCNC(=O)NC2CCOCC2)nnc1C1CC1] | 307.4 | C15H25N5O2 |

TABLE 10

Novel Fusogenin agonists.

| Compound ID | IUPAC Name | Structure | M.W. (g/mol) | Formula |
|---|---|---|---|---|
| Fusogenin-1 | 1-(3-(4-methyl-5-phenyl-4H-1,2,4-triazol-3-yl)propyl)-3-(2-methylcyclohexyl)urea | [structure] | 355.49 | C20H29N5O |
| Fusogenin-3 | 1-(3-(4-methyl-5-phenyl-4H-1,2,4-triazol-3-yl)propyl)-3-(tetrahydro-2H-pyran-4-yl)urea | [structure] | 343.43 | C18H25N5O2 |
| Fusogenin-4 | 1-(3-(4-methyl-5-phenyl-4H-1,2,4-triazol-3-yl)propyl)-3-(3-methyltetrahydro-2H-pyran-4-yl)urea | [structure] | 357.46 | C19H27N5O2 |

Example 7: Pre-Clinical Studies Evaluating the Potential Efficacy of Mitofusin Agonists in CMT2A and Other Chronic Neurodegenerative Syndromes The following example shows mitofusin agonist effects on mitochondrial pathology in primary fibroblasts from human neurodegenerative disease patients.

High neuronal metabolic activity makes the neurological system uniquely susceptible to genetic mitochondrial damage. Oxidative stress is frequently invoked as the mechanism linking mitochondrial dysfunction to neurological diseases, but defective mitochondrial transport in long peripheral axons may contribute to neuronal vulnerability. For example, bioenergetic support of neuronal maintenance, repair and regeneration requires mitochondrial redistribution to sites of degeneration. Accordingly, it was examined whether the facilitory effects of the presently disclosed small molecule mitofusin agonist, Regeneurin-C, on mitochondrial trafficking, fusion, and polarization status would improve mitochondria fitness in primary fibroblasts from human patients with a variety of mutations causing Amyotrophic lateral sclerosis (3 SOD1 gene mutations) Huntington's (HD gene CAG repeat numbers 40, 57, and 66), Parkinson's (Parkin, PINK, and LRRK2 gene mutations), and Alzheimer's diseases (3 PSEN1 gene mutations), as well as CMT2A (3 Mfn2 gene mutations). These studies show evidence that mitofusin agonists markedly enhance or improve mitochondrial function (e.g., trafficking) in ALS and confer a modest benefit in Huntington's disease (see e.g., FIG. 56, TABLE 11). FCCP treatment shows effects of complete mitochondrial uncoupling.

TABLE 11

Primary patient-derived fibroblasts used for Regeneurin-C studies

| Subject ID | Fibrob ID | Diseases | Gender | Age | Genes | Mutation | Source | P |
|---|---|---|---|---|---|---|---|---|
| NDS00108 | ND34730 | Alzheimer's | M | — | PSEN1 | GLU184ASP | NIH | 4 |
| NDS00114 | ND34732 | Alzheimer's | F | — | PSEN1 | MET146ILE | NIH | 4 |
| NDS00115 | ND34733 | Alzheimer's | M | — | PSEN1 | PRO264LEU | NIH | 4 |
| NDS00125 | ND29415 | ALS | M | 51 | SOD1 | LEU144PRO | NIH | 2 |
| NDS00129 | ND29523 | ALS | M | 47 | SOD1 | LEU38VAL | NIH | 2 |
| NDS00211 | ND32969 | ALS | M | 59 | SOD1 | ILE113THR | NIH | 6 |
| NDS00090 | ND33392 | Huntington's | F | 29 | HD | CAG:57 | NIH | 2 |
| NDS00093 | ND29970 | Huntington's | M | 65 | HD | CAG:40 | NIH | 2 |
| NDS00189 | ND40536 | Huntington's | F | — | HD | CAG:66 | NIH | 2 |
| NDS00009 | ND33879 | Parkinson's | F | 66 | LRRK2 | GLY2019SER | NIH | 2 |
| NDS00012 | ND29969 | Parkinson's | F | 61 | PARK2 | ARG275TRP | NIH | 2 |
| NDS00228 | ND40066 | Parkinson's | M | 64 | PINK1 | ILE368ASN | NIH | 6 |
| NDS00035 | ND34769 | Control | F | 68 | — | — | NIH | 2 |
| NDS00047 | ND36320 | Control | F | 71 | — | — | NIH | 2 |
| NDS00126 | ND29510 | Control | F | 55 | — | — | NIH | 2 |
| NDS00085 | ND29178 | Control | M | 66 | — | — | NIH | 7 |
| NDS00036 | ND34770 | Control | M | 72 | — | — | NIH | 2 |
| NDS00059 | ND38530 | Control | M | 55 | — | — | NIH | 5 |
| | | CMT2A | | | MFN2 | HIS361TYR | Baloh | |
| | | CMT2A | | | MFN2 | THR105MET | Baloh | |
| | | CMT2A | | | MFN2 | ARG274TRP | Barbara | 2 |

Development of a Preclinical Mouse Model of CMT2A

Multiple mouse knock-ins of human CMT2A Mfn2 mutations have not developed typical CMT2A neuropathology. High-level transgenic expression of human CMT2A Mfn2 mutants can cause pathology, but the phenotypes are not limited to the neurological system as in human disease. Because a suitable animal model of CMT2A did not exist a mouse was developed having conditional, motor-neuron-specific expression of human Mfn2 T105M (one of the CMT2A mutants used in the presently described in vitro and ex vivo studies (see e.g., Example 5)). Initial studies of these mice indicate that they develop progressive sciatic nerve CMAP (compound motor action potential) abnormalities (decreased CMAP amplitude) accompanied by impaired neuromuscular function (Rotarod latency) (see e.g., FIG. 57). These features are characteristic of the human condition. Moreover, the efficacy of Regeneurin-S was already demonstrated to rapidly correct mitochondrial dysmotility in sciatic nerves of these mice (see e.g., Example 5). It was planned to use this model for in vivo assessment of mitofusin agonist efficacy for CMT2A. Standard mouse models for ALS suitable for in vivo efficacy studies are available from Jackson Labs (JAX). A target product profile is shown in TABLE 12, below.

TABLE 12

Preliminary target product profile for mitofusin agonists to treat CMT2A.

| Product targets | Minimal acceptable result | Ideal result |
| --- | --- | --- |
| Primary indication | Chronic therapy that retards progression of axonal neuropathy in CMT2A | Chronic therapy that reverses axonal neuropathy in CMT2A |
| Patient population | Children with a new genetic diagnosis of CMT2A and patients of all ages with genetically diagnosed mild to moderate CMT2A | Patients of all ages with mild to moderate genetically diagnosed CMT2A CMT Neuropathy Score ≤20 |
| Treatment duration | Chronic | Chronic |
| Delivery mode | IM injection | Transdermal |
| Dosage form | Prefilled vials | Transdermal patch |
| Regimen | Once a week | Once a week |
| Efficacy | Delay in peripheral neuropathy progression over 3 years compared to placebo, assessed by slower increase in modified composite CMT Neuropathy Score* | Reversal or absence of progression of peripheral neuropathy compared to placebo, as indicated by lower or stable modified composite CMT Neuropathy Score* |
| Risk/side effect | Devoid of local injection effect and clinically meaningful CNS, cardiac or muscular side effects | Devoid of local patch effect and any systemic side effects |
| Therapeutic modality | Small molecule peptidomimetic | Small molecule peptidomimetic |

*Mannil M et al Neuromuscul Disord 24:1003-17, 2014

Example 8: In Vivo Administration of Regeneurin-C/O Reverses the Characteristic Mitochondrial Immobility in Sciatic Nerve Axons The following example describes in vivo administration of Regeneurin-C/O to CMT2A mice (IM, 2 mg/kg) reverses the characteristic mitochondrial immobility in sciatic nerve axons (assessed 4 hours later).

10 week old CMT2A MFN2 T105M mice were injected IM with Mfn agonist Regeneurin-C/O 2 mg/kg twice, or vehicle. Sciatic nerve mitochondrial motility was measured 4 hours later. Results described in FIG. 58 are for 2 CMT2A mice per group. As demonstrated herein, these mitofusin agonists can correct mitochondrial motility.

What is claimed is:

1. A compound of formula (I):

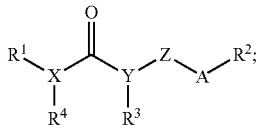

wherein, $R^1$ is selected from the group consisting of

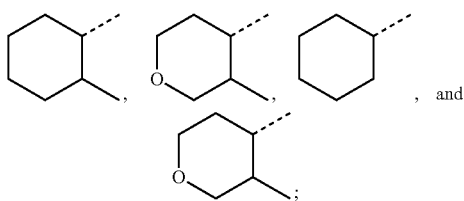

$R^2$ is selected from the group consisting of

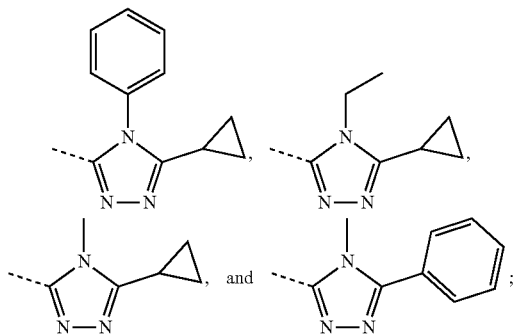

$R^3$ is selected from the group consisting of hydrogen (H) and $C_{1-8}$ alkyl;
$R^4$ is selected form the group consisting of hydrogen (H) and $C_{1-8}$ alkyl;
A is SO or $SO_2$;
X is N;
Y is N; and
Z is a linker group selected from the group consisting of a bond and $C_{1-6}$ alkyl;
wherein, $R^1$ or $R^2$ are optionally substituted by one or more of:
acetamide, $C_{1-8}$alkoxy, amino, azo, Br, $C_{1-8}$alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, nitrile, phenyl, or thiophene; and
optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, nitrile, phenyl, or thiophene;
wherein,
the alkyl, cycloalkyl, heteroaryl, heterocyclyl, indole, or phenyl, is optionally further substituted with one or more selected from the group consisting of acetamide, alkoxy, amino, azo, Br, $C_{1-8}$alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, nitrile, phenyl, and thiophene.

2. The compound of claim 1, wherein, $R^3$ or $R^4$ are substituted by one or more of:
acetamide, $C_{1-8}$alkoxy, amino, azo, Br, $C_{1-8}$alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, nitrile, phenyl, or thiophene; and
optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, nitrile, phenyl, or thiophene;
wherein,
the alkyl, cycloalkyl, heteroaryl, heterocyclyl, indole, or phenyl, is optionally further substituted with one or more selected from the group consisting of acetamide, alkoxy, amino, azo, Br, $C_{1-8}$alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, nitrile, phenyl and thiophene.

3. The compound of claim 1, selected from the group consisting of:

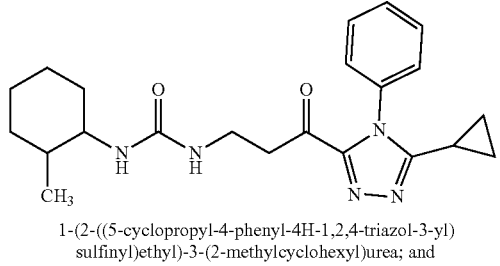

1-(2-((5-cyclopropyl-4-phenyl-4H-1,2,4-triazol-3-yl)sulfinyl)ethyl)-3-(2-methylcyclohexyl)urea; and

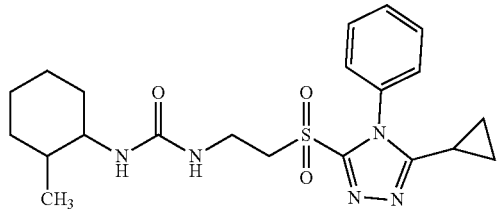

1-(2-((5-cyclopropyl-4-phenyl-4H-1,2,4-triazol-3-yl)sulfonyl)ethyl)-3-(2-methylcyclohexyl)urea.

4. A pharmaceutical composition comprising the compound of claim 1.

* * * * *